(12) United States Patent
Yoshikawa et al.

(10) Patent No.: US 11,236,106 B2
(45) Date of Patent: Feb. 1, 2022

(54) CYCLOALKANE-1,3-DIAMINE DERIVATIVE

(71) Applicant: Daiichi Sankyo Company, Limited, Tokyo (JP)

(72) Inventors: Kenji Yoshikawa, Chuo-ku (JP); Noriyasu Haginoya, Chuo-ku (JP); Tomoaki Hamada, Chuo-ku (JP); Ryutaro Kanada, Chuo-ku (JP); Jun Watanabe, Chuo-ku (JP); Yoshiko Kagoshima, Chuo-ku (JP); Eri Tokumaru, Chuo-ku (JP); Kenji Murata, Chuo-ku (JP); Takayuki Baba, Chuo-ku (JP); Mayumi Kitagawa, Chuo-ku (JP); Akiko Kurimoto, Chuo-ku (JP); Masashi Numata, Chuo-ku (JP); Machiko Shiroishi, Chuo-ku (JP); Taeko Shinozaki, Chuo-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 17/243,360

(22) Filed: Apr. 28, 2021

(65) Prior Publication Data
US 2021/0269454 A1 Sep. 2, 2021

Related U.S. Application Data

(63) Continuation of application No. PCT/JP2019/048834, filed on Dec. 5, 2019.

(30) Foreign Application Priority Data

Dec. 6, 2018 (JP) .............................. JP2018-229397

(51) Int. Cl.
C07D 495/04 (2006.01)
A61P 35/02 (2006.01)
A61K 45/06 (2006.01)

(52) U.S. Cl.
CPC ............ *C07D 495/04* (2013.01); *A61K 45/06* (2013.01); *A61P 35/02* (2018.01); *C07B 2200/13* (2013.01)

(58) Field of Classification Search
CPC ....... C07D 495/04; A61P 35/02; A61K 45/06; C07B 2200/13
See application file for complete search history.

(56) References Cited

U.S. PATENT DOCUMENTS

2018/0105531 A1  4/2018  Grembecka et al.
2018/0208578 A1  7/2018  Ciblat et al.

FOREIGN PATENT DOCUMENTS

JP  2017510651 A  4/2017
JP  2018516888 A  6/2018
(Continued)

OTHER PUBLICATIONS

Montero, Why do BCL-2 inhibitors work and where should we use them in the clinic?, 2018, Cell Death and Differentiation, 25, pp. 56-64 (Year: 2018).*

(Continued)

*Primary Examiner* — Savitha M Rao
*Assistant Examiner* — Andrew P Lee
(74) *Attorney, Agent, or Firm* — Christensen O'Connor Johnson Kindness PLLC

(57) ABSTRACT

The present invention provides a compound or a pharmaceutically acceptable salt thereof having an inhibitory action on the interaction between menin and an MLL protein. The compound represented by the formula (1) or a pharmaceutically acceptable salt thereof.

(Continued)

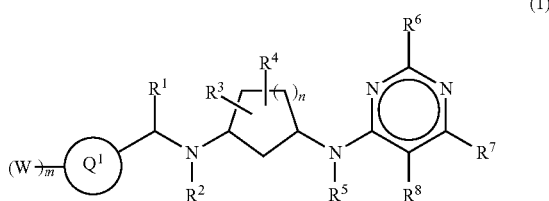

(1)

wherein, in the formula (1), the dotted circle, $R^1$, $R^2$, $R^3$, $R^4$, $R^5$, $R^6$, $R^7$, $R^8$, Ring $Q^1$, W, m and n are each as defined in the description.

17 Claims, 9 Drawing Sheets

(56) References Cited

FOREIGN PATENT DOCUMENTS

| WO | 2004007491 A1 | 1/2004 |
|---|---|---|
| WO | 2004108690 A1 | 12/2004 |
| WO | 2005032488 A2 | 4/2005 |
| WO | 2005108399 A1 | 11/2005 |
| WO | 2007013673 A1 | 2/2007 |
| WO | 2007118041 A1 | 10/2007 |
| WO | 2010141796 A2 | 12/2010 |
| WO | 2011109267 A1 | 9/2011 |
| WO | 2012097013 A1 | 7/2012 |
| WO | 2013013503 A1 | 1/2013 |
| WO | 2013093849 A1 | 6/2013 |
| WO | 2014078813 A1 | 5/2014 |
| WO | 2014114186 A1 | 7/2014 |
| WO | 2014164749 A1 | 10/2014 |
| WO | 2016195776 A1 | 12/2016 |
| WO | 2017100668 A1 | 6/2017 |
| WO | 2017161002 A1 | 9/2017 |
| WO | 2017161028 A1 | 9/2017 |
| WO | 2017214367 A1 | 12/2017 |
| WO | 2018024602 A1 | 2/2018 |
| WO | 2018053267 A1 | 3/2018 |
| WO | 2018109088 A1 | 6/2018 |

OTHER PUBLICATIONS

Atzrodt, J et al., "The Renaissance of H/D Exchange", Angew. Chem. Int. Ed., 46, 7744-7765, 2007.
Baumgartner, C., et al., "Structure-Based Design and Synthesis of the First Weak Non-Phosphate Inhibitors for IspF, an Enzyme in the Non-Mevalonate Pathway of Isoprenoid Biosynthesis", Helvetica Chimica Acta, 90, 1043-1068, 2007.
Beaulieu, P., et al., "Improved replicon cellular activity of non-nucleoside allosteric inhibitors of HCV NS5B polymerase: From benzimidazole to indole scaffolds", Bioorganic & Medicinal Chemistry Letters, 16, 4987-4993, 2006.
Blaise, E., et al., "Access to 4-Alkylaminopyridazine Derivatives via Nitrogen-Assisted Regioselective Pd-Catalyzed Reactions", J. Org. Chem., 79, 10311-10322, 2014.
Borkin, D., et al., "Pharmacologic Inhibition of the Menin-MLL Interaction Blocks Progression of MLL Leukemia in Vivo", Cancer Cell, 27, 589-602, Apr. 13, 2015.
Borkin, D., et al., "Property Focused Structure-Based Optimization of Small Molecule Inhibitors of the Protein-Protein Interaction between Menin and Mixed Lineage Leukemia (MLL)", J. Med Chem., 59, 892-913, 2016.
Büuldt, L., et al., "Photoredox Properties of Homoleptic $d^6$ Metal Complexes with the Electron-Rich 4,4', 5,5'-Tetramethoxy-2,2'—bipyridine Ligand", Eur. J. Inorg. Chem., 4666-4677, 2015.

Cai, C., et al., "Chiral aminocyclopentene-based cycloaddition strategies to bicyclic [3.3.0] rings", Tetrahedron Asymmetry, 24, 651-656, 2013.
Chamberlain, C., et al., "Menin determines K-RAS proliferative outputs in endocrine cells", J Clin. Invest., 124(9), 4093-4101, 2014.
Chen, W., et al., "Chemoselective hydrogenation of nitrobenzyl ethers to aminobenzyl ethers catalyzed by palladium-nickel bimetallic nanoparticles", Tetrahedron, 71, 9240-9244, 2015.
Chen, Y., "The tumor suppressor menin regulates hematopoiesis and myeloid transformation by influencing Hox gene expression", PNAS, 103(4), 1018-1023, Jan. 24, 2006.
Cierpicki, T., et al., "Challenges and opportunities in targeting the menin-MLL interaction", Future Med. Chem., 6(4), 447-462, 2014.
Decrane, L., et al., "Metalation of Bromodiazines. Diazines XL", J. Heterocyclic Chem., 42, 509-513, 2005.
Dreijerink, K., et al., "Menin Links Estrogen Receptor Activation to Histone H3K4 Trimethylation", Cancer Res, 66(9), 4929-4935, 2006.
Funato, K., et al., "Use of human embryonic stem cells to model pediatric gliomas with H3.3K27M histone mutation", Science, vol. 346, Issue 6216, 1529-1533, Dec. 19, 2014.
Grembecka, J., et al., "Menin-MLL inhibitors reverse oncogenic activity of MLL fusion proteins in leukemia", Nature Chemical Biology, vol. 8, 277-284, 2012.
Gu, Q., et al., "Enantioselective Synthesis of (+)—Mitomycin K by a Palladium-Catalyzed Oxidative Tandem Cyclization", Angew. Chem. Int. Ed., 56, 5886-5889, 2017.
Haesler, J., et al., "Absolute configuration of chirally deuterated neopentane", Nature, vol. 446, 526-529, Mar. 29, 2007.
Imachi, H., et al., "Menin, a product of the MENI gene, binds to estrogen receptor to enhance its activity in breast cancer cells: possibility of a novel predictive factor for tamoxifen resistance", Breast Cancer Res. Treat, 122, 395-407, 2010.
Jöst, C., et al., "Promiscuity and Selectivity in Covalent Enzyme Inhibition: A Systematic Study of Electrophilic Fragments", J. Med. Chem., 57, 7590-7599, 2014.
Kühn, M, et al., "Targeting Chromatin Regulators Inhibits Leukemogenic Gene Expression in NPM1 Mutant Leukemia", Cancer Discovery, 1166-1181, Oct. 2016.
Lloyd, R., et al., "Use of hydrolases for the synthesis of cyclic amino acids", Tetrahedron, 60, 717-728, 2004.
Malik, R., et al., "Targeting the MLL complex in castration-resistant prostate cancer", Nature Medicine, 21(4), 344-352, Apr. 2015.
Maltais, F., et al., "In Vitro and in Vivo Isotope Effects with Hepatitis C Protease Inhibitors: Enhanced Plasma Exposure of Deuterated Telaprevir versus Telaprevir in Rats", J. Med. Chem. 52, 7993-8001, 2009.
Mylari, B., et al., "Sorbitol Dehydrogenase Inhibitors (SDIs): A New Potent, Enantiomeric SDI, 4-[2-1 R-Hydroxy-ethyl)-pyrimidin-4-yl]-piperazine-1-sulfonic Acid Dimethylamide", J. Med. Chem. 44, 2695-2700, 2001.
Panteleev, J., et al., "Alkylation of Nitrogen-Containing Heterocycles via in Situ Sulfonyl Transfer", Synlett, 26, A-G, 2015.
Rodríguez-Vázquez, N., et al., "Synthesis of Cyclic γ-Amino Acids for Foldamers and Peptide Nanotubes", Eur. J. Org. Chem., 3477-3493, 2013.
Sagong, H., et al., "Phenyl Substituted 4-Hydroxypyridazin-3(2H)-ones and 5-Hydroxypyrimidin-4(3H)-ones: Inhibitors of Influenza A Endonuclease", J. Med. Chem., 57, 8086-8098, 2014.
Sanderson, K., "Big interest in heavy drugs", Nature, 269, 2009.
Shaw, M., et al., "Native functionality in triple catalytic cross-coupling: $sp^3$ C—H bonds as latent nucleophiles", Science, vol. 352, Issue 6291, 1304-1308, Jun. 10, 2016.
Shi, A., et al., "Structural insights into inhibition of the bivalent menin-MLL interaction by small molecules in leukemia", Blood, 120(23), 4461-4469, Nov. 29, 2012.
Wang, X., et al., "An efficient stereoselective synthesis of six stereoisomers of 3, 4-diaminocyclohexane carboxamide as key intermediates for the synthesis of factor Xa inhibitors", Tetrahedron, 73, 1381-1386, 2017.
Wang, M., et al., "Selective Synthesis of Seven- and Eight-Membered Ring Sultams via Two Tandem Reaction Protocols from One Starting Material", Org Lett., 14(14), 3700-3703, 2012.

(56) References Cited

OTHER PUBLICATIONS

Wang, Z., et al., "Syntheses and evaluation of fluorinated conformationally restricted analogues of GABA as potential inhibitors of GABA aminotransferase", Bioorg Med. Chem., 14, 2242-2252, 2006.

Welin, E., et al., "Enantioselective α-Alkylation of Aldehydes by Photoredox Organocatalysis: Rapid Access to Pharmacophore Fragments from β-Cyanoaldehydes", Angew. Chem. Int. Ed., 54, 9668-9672, 2015.

Wu, X., et al., "Menin, Histone H3 Methyltransferases, and Regulation of Cell Proliferation: Current Knowledge and Perspective", Current Molecular Medicine, 8, 805-815, 2008.

Xu, B., et al., "Menin promotes hepatocellular carcinogenesis and epigenetically up-regulates Yap1 transcription", PNAS, 110(43), 17480-17485, Oct. 22, 2013.

Yang, E., et al., "Design and Synthesis of Janus Kinase 2 (JAK2) and Histone Deacetlyase (HDAC) Bispecific Inhibitors Based on Pacritinib and Evidence of Dual Pathway Inhibition in Hematological Cell Lines", J. Med. Chem., 59, 8233-8262, 2016.

Yang, Y., et al., "Reversal of preexisting hyperglycemia in diabetic mice by acute deletion of the Men1 gene", PNAS, 107(47), 20358-20363, Nov. 23, 2010.

Yokoyama, A., et al., "The Menin Tumor Suppressor Protein Is an Essential Oncogenic Cofactor for MLL-Associated Leukemogenesis", Cell, vol. 123, 207-218, Oct. 21, 2005.

Zhu, J., et al., "Gain-of-function $p^{53}$ mutants co-opt chromatin pathways to drive cancer growth", Nature, 525, 206-211, Sep. 10, 2015.

International Search Report dated Feb. 18, 2020, issued in corresponding International Application No. PCT/JP2019/048834, filed Dec. 5, 2019, 2 pages.

\* cited by examiner

CYCLOALKANE-1,3-DIAMINE DERIVATIVE

CROSS REFERENCE TO RELATED APPLICATIONS

This application is a continuation of International Application No. PCT/JP2019/048834, filed Dec. 5, 2019, which claims priority to Japanese Application No. 2018-229397, filed Dec. 6, 2018, each expressly incorporated herein by reference in its entirety.

TECHNICAL FIELD

The present invention relates to low-molecular compounds or a pharmaceutically acceptable salt thereof that inhibit the interaction between menin and an MLL protein.

BACKGROUND ART

Chromosomal translocation of MLL (Mixed-Lineage Leukemia) gene is observed in infant leukemia and some poor-prognosis leukemia cases. As a result of chromosomal translocation, MLL fuses with 70 or more various translocation partner genes at its amino-terminus to express an MLL fusion protein. Wild-type MLL constitutes a transcriptional regulatory complex that modifies the chromatin structure, specifically methylates lysine at the 4th position of histone H3, and plays an extremely important role in the transcriptional regulation of gene cluster (e.g., HOX gene cluster, etc.) involved in hematopoiesis and development. Meanwhile, the MLL fusion protein, whose expression is induced by chromosomal translocation, has lost the histone methylase activity, but permanently activates gene cluster (e.g., HOX and MEIS1 genes, etc.) involved in cell differentiation control. As a result, abnormal cell growth and inhibition of differentiation induction of hematopoietic cells are triggered, which leads to onset of leukemia. Leukemia with MLL gene mutation has poor prognosis, and the standard treatment methods currently used for leukemia treatment have not been sufficiently effective. For this reason, development of a new treatment method is strongly desired.

Menin is a tumor-suppressor protein identified as a causal factor of multiple endocrine neoplasia type 1 (MEN1), which is one of autosomal dominant hereditary tumor syndromes, and characterized by tumorigenesis in multiple endocrine organs. Menin is an ubiquitously expressed nucleoprotein that interacts with a wide variety of proteins and is involved in various cellular processes. It is considered that the biological functions of menin can be tumor-suppressing or tumor-promoting, and dependent on the cell context. Menin interacts with the amide-terminus of MLL1, and functions as a carcinogenic cofactor that increases the transcription of gene cluster such as HOX and MEIS1. It is known that the interaction between menin and an MLL fusion protein is essential for abnormal activation of a series of gene cluster caused by the MLL fusion protein, and onset of leukemia (Non-Patent Documents 1 and 2). Thus, it is expected that inhibition of the interaction between menin and an MLL fusion protein contributes to the treatment and/or prophylaxis of leukemias involving chromosomal translocations of MLL gene and other leukemia/blood cancers accompanied with constant expression of HOX and MEIS1 genes. Accordingly, for example, the creation of a drug that inhibits the interaction between menin and an MLL fusion protein is extremely significant in terms of providing a new option for cancer treatment.

A plurality of compounds having an inhibitory activity on the interaction between menin and an MLL protein have been already known (Patent Documents 1 to 4, Non-Patent Documents 3 to 5).

DOCUMENT LIST

Patent Document

Patent Document 1: WO 2017/161028 pamphlet
Patent Document 2: WO 2018/053267 pamphlet
Patent Document 3: WO 2018/109088 pamphlet
Patent Document 4: WO 2018/024602 pamphlet Non-Patent Document Non-Patent Document 1: Chen et al., Proc. Natl. Acad. Sci., 2006, 103, 1018-1023.
Non-Patent Document 2: Yokoyama et al., Cell, 2005, 123, 207-218.
Non-Patent Document 3: Grembecka et al., Nat. Chem. Biol., 2012, 8, 277-284.
Non-Patent Document 4: Shi et al., Blood, 2012, 120, 4461-4469.
Non-Patent Document 5: Borkin et al., Cancer Cell, 2015, 27, 589-602.

SUMMARY OF THE INVENTION

Problem to be Solved by the Invention

The present invention provides a novel low-molecular compound having an inhibitory action on the interaction between menin and an MLL protein (hereinafter, sometimes to be referred to as a menin-MLL inhibitory action), which is useful as a medicament for the treatment and/or prophylaxis of diseases dependent on the interaction between menin and an MLL protein.

Means of Solving the Problems

The present inventors have conducted research on novel low-molecular compounds with the aim of developing a menin-MLL inhibitor, and have found that a compound having a specific structure or a pharmaceutically acceptable salt thereof disclosed in the present invention has a menin-MLL inhibitory action, and is useful as a medicament for the treatment and/or prophylaxis of diseases (e.g., cancer or diabetes) dependent on the interaction between menin and an MLL protein, and completed the present invention based on these findings. The compounds or pharmaceutically acceptable salts thereof disclosed in the present invention have not been known so far, and their pharmacological activities are also unknown.

The present invention relates to the following [1] to [92].

[1] A compound represented by the following general formula (1) or a pharmaceutically acceptable salt thereof:

[Formula 1]

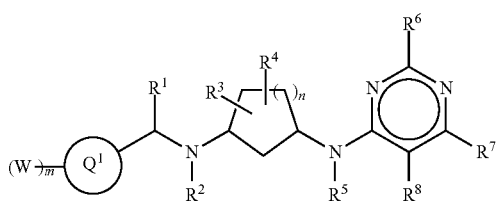

(1)

wherein
the dotted circle indicates that the ring is aromatic, $R^1$ and $R^2$ are each independently a hydrogen atom or a $C_{1-6}$ alkyl group,
one of $R^3$ and $R^4$ is a hydrogen atom, a hydroxy group, a halogen atom, a $C_{1-6}$ alkoxy group, a di($C_{1-6}$ alkyl)carbamoyl group, or an oxazolyl group, and
the other of $R^3$ and $R^4$ is a hydrogen atom, a hydroxy group, a halogen atom, or a $C_{1-6}$ alkoxy group,
$R^5$ is a hydrogen atom, a $C_{1-6}$ alkyl group, or a hydroxy $C_{1-6}$ alkyl group,
$R^6$ is a hydrogen atom, a $C_{1-6}$ alkyl group, a halogen atom, a $C_{1-6}$ alkoxy group, an amino group, or a $C_{1-6}$ alkylamino group,
$R^7$ and $R^8$ are taken together with the carbon atom to which $R^7$ is bonded and the carbon atom to which $R^8$ is bonded to form any of the following formulas (2A) to (2C):

[Formula 2]

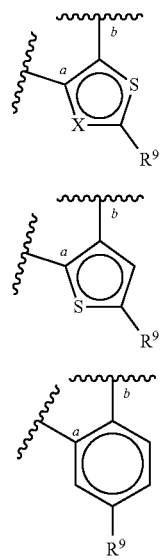

wherein
the dotted circle indicates that the ring is aromatic,
the carbon atom marked with a is the carbon atom to which $R^8$ is bonded,
the carbon atom marked with b is the carbon atom to which $R^7$ is bonded,
X is CH or a nitrogen atom, and $R^9$ is a halogeno $C_{1-6}$ alkyl group, a $C_{3-8}$ cycloalkyl group, a $C_{3-8}$ cycloalkyl $C_{1-6}$ alkyl group, a $C_{1-6}$ alkoxy $C_{1-6}$ alkyl group, or an oxetanyl group, or
$R^7$ is a hydrogen atom, and $R^8$ is the following formula (3):

[Formula 3]

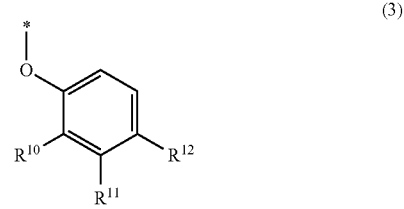

(3)

wherein
* indicates a bonding site,
$R^{10}$ is a di($C_{1-6}$ alkyl) carbamoyl group, a ($C_{1-6}$ alkyl) pyrimidinyl group, a ($C_{1-6}$ alkyl)phenyl group, or a ($C_{1-6}$ alkyl)pyrazolyl group,
$R^{11}$ is a hydrogen atom or a halogen atom, and
$R^{12}$ is a halogen atom,
m is 1 or 0,
n is 1 or 2,
Ring $Q^1$ is a 6-membered aromatic ring optionally containing one nitrogen atom in the ring (the aromatic ring optionally has one or two substituents independently selected from the following Group A), a 5-membered aromatic heterocycle containing, in the ring, one or two heteroatoms independently selected from the group consisting of a nitrogen atom and a sulfur atom (the aromatic heterocycle optionally has one substituent independently selected from the following Group A), a $C_{3-8}$ cycloalkane ring optionally having one substituent independently selected from the following Group A, a $C_{4-8}$ cycloalkene ring optionally having one substituent independently selected from the following Group A, a 4- to 8-membered saturated heterocycle containing one nitrogen atom in the ring (the saturated heterocycle optionally has one substituent independently selected from the following Group A), or a 9-membered bicyclic aromatic heterocycle containing one nitrogen atom in the ring (the bicyclic aromatic heterocycle optionally has one or two substituents independently selected from the following Group B), and
W is the following formula (4A) or (4B):

[Formula 4]

(4A)

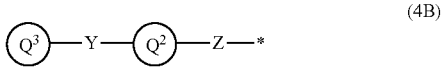

(4B)

wherein
* indicates a bonding site,
Ring $Q^2$ is a 6-membered aromatic ring optionally containing one nitrogen atom in the ring (the aromatic ring optionally has one to three substituents independently selected from the following Group C), a 6-membered aromatic heterocycle containing two nitrogen atoms in the ring (the aromatic heterocycle optionally has one to three substituents independently selected from the following Group C), a 5-membered aromatic heterocycle containing, in the ring, one to three heteroatoms independently selected from the group consisting of a nitrogen atom, an oxygen atom and a sulfur atom (the aromatic heterocycle optionally has one substituent independently selected from the following Group C), a 9- or 10-membered bicyclic aromatic or partially unsaturated heterocycle containing, in the ring, one to three heteroatoms independently selected from the group consisting of a nitrogen atom and an oxygen atom (the bicyclic aromatic or partially unsaturated heterocycle optionally has one or two substituents independently selected from the following Group D), a 5- to 8-membered saturated heterocycle containing, in the ring, one or two heteroatoms independently selected from the group consisting of an oxygen atom and a nitrogen atom (the saturated heterocycle optionally has one substituent independently selected from the following Group E), or a $C_{3-8}$ cycloalkane ring optionally having one substituent independently selected from the following Group E, Ring $Q^3$ is a 4- to 8-membered saturated heterocycle containing one nitrogen atom or one oxygen atom in the ring (the saturated heterocycle optionally has one $C_{1-6}$ alkylsulfonyl group), or a 6-membered aromatic ring optionally containing one nitrogen atom in the ring (the aromatic ring optionally has one substituent independently selected from the following Group F), Y is a single bond or an oxygen atom, and Z is a single bond, an oxygen atom, —NH—, —SO$_2$—, a $C_{1-6}$ alkylene group, *—R$^{13}$—NHC(=O)—**, *—R$^{14}$—O—**, or *—R$^{15}$—NH—**, wherein * is bonded to Ring Q$^2$, ** is bonded to Ring Q$^1$, and R$^{13}$, R$^{14}$ and R$^{15}$ are each independently a $C_{1-6}$ alkylene group, Group A: a halogen atom, a hydroxy group, a $C_{1-6}$ alkyl group, a $C_{1-6}$ alkoxy group, a hydroxy $C_{1-6}$ alkoxy group, a vinylsulfonylamino($C_{1-6}$ alkyl)carbamoyl group, and a prop-2-enoylamino($C_{1-6}$ alkyl)carbamoyl group, Group B: a cyano group, a $C_{1-6}$ alkyl group, a halogen atom, and a $C_{1-6}$ alkoxy group, Group C: a halogen atom, a $C_{1-6}$ alkyl group, a $C_{1-6}$ alkoxy group, a $C_{1-6}$ alkyl($C_{1-6}$ alkylsulfonyl)amino group, a cyano group, a $C_{1-6}$ alkylsulfonyl group, a $C_{1-6}$ alkylamino group, a di($C_{1-6}$ alkyl)amino group, a halogeno $C_{1-6}$ alkyl group, a $C_{1-6}$ alkoxy $C_{1-6}$ alkoxy group, a halogeno $C_{1-6}$ alkoxy group, a $C_{1-6}$ alkylsulfonyl $C_{1-6}$ alkyl group, a di($C_{1-6}$ alkyl)sulfamoyl group, a $C_{1-6}$ alkylenedioxy group, a ($C_{1-6}$ alkyl)carbamoyl group, a hydroxy $C_{1-6}$ alkyl group, a 2-$C_{3-6}$ alkenoylamino group, a $C_{1-6}$ alkyl (2-$C_{3-6}$ alkenoyl)amino group, a hydroxy group, an oxo group, a ($^2$H$_3$)methoxy group, and a bis[($^2$H$_3$)methyl]amino group, Group D: a halogen atom, a $C_{1-6}$ alkyl group, and a $C_{1-6}$ alkylsulfonyl group, Group E: an oxo group, a hydroxy group, and a $C_{1-6}$ alkoxy group, and Group F: a halogen atom, and a $C_{1-6}$ alkoxy group.

[2] The compound according to [1], or a pharmaceutically acceptable salt thereof, wherein R$^1$ is a hydrogen atom or a methyl group.

[3] The compound according to [1], or a pharmaceutically acceptable salt thereof, wherein R$^1$ is a hydrogen atom.

[4] The compound according to any one of [1] to [3], or a pharmaceutically acceptable salt thereof, wherein R$^2$ is a hydrogen atom or a methyl group.

[5] The compound according to any one of [1] to [3], or a pharmaceutically acceptable salt thereof, wherein R$^2$ is a hydrogen atom.

[6] The compound according to any one of [1] to [5], or a pharmaceutically acceptable salt thereof, wherein the moiety represented by the following formula (5) in the formula (1) is the following formula (5A) or (5B):

[Formula 5]

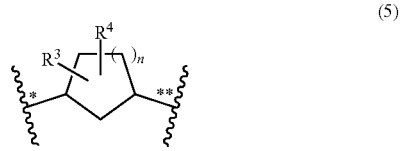

(5)

[Formula 6]

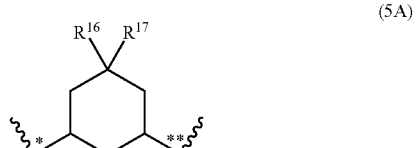

(5A)

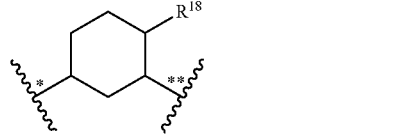

(5B)

wherein

* is bonded to the nitrogen atom to which R$^2$ is bonded,

** is bonded to the nitrogen atom to which R$^5$ is bonded,

R$^{16}$ is a hydrogen atom, a halogen atom, a hydroxy group, a di($C_{1-6}$ alkyl)carbamoyl group, an oxazol-2-yl group, or a $C_{1-6}$ alkoxy group, R$^{17}$ is a hydrogen atom or a halogen atom, and R$^{18}$ is a $C_{1-6}$ alkoxy group.

[7] The compound according to any one of [1] to [5], or a pharmaceutically acceptable salt thereof, wherein the moiety represented by the following formula (5) in the formula (1) is the following formula (6A) or (6B):

[Formula 7]

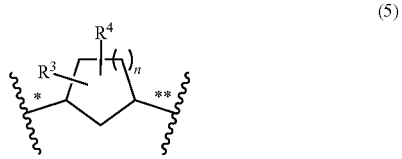

(5)

[Formula 8]

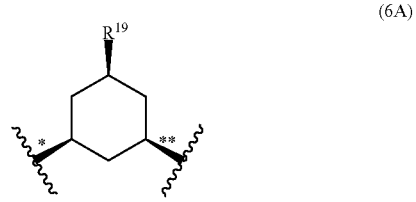

(6A)

-continued (6B)
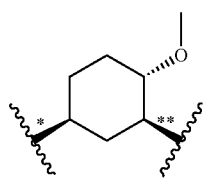

wherein
* is bonded to the nitrogen atom to which $R^2$ is bonded,
** is bonded to the nitrogen atom to which $R^5$ is bonded, and
$R^{19}$ is a hydrogen atom, a hydroxy group, a dimethylcarbamoyl group, an oxazol-2-yl group, or a methoxy group.

[8] The compound according to any one of [1] to [5], or a pharmaceutically acceptable salt thereof, wherein the moiety represented by the following formula (5) in the formula (1) is the following formula (7A):

[Formula 9]

(5)
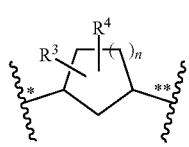

[Formula 10]

(7A)
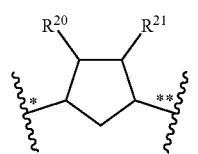

wherein
* is bonded to the nitrogen atom to which $R^2$ is bonded,
** is bonded to the nitrogen atom to which $R^5$ is bonded,
$R^{20}$ is a hydrogen atom or a hydroxy group, and
$R^{21}$ is a hydrogen atom, a hydroxy group, or a $C_{1-6}$ alkoxy group.

[9] The compound according to any one of [1] to [5], or a pharmaceutically acceptable salt thereof, wherein the moiety represented by the following formula (5) in the formula (1) is any of the following formulas (8A) to (8E):

[Formula 11]

(5)
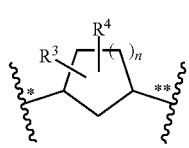

[Formula 12]

(8A)
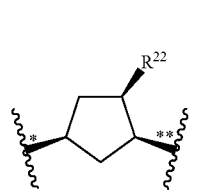

-continued (8B)
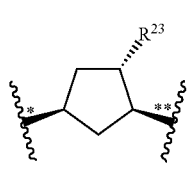

(8C)
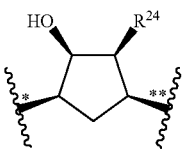

(8D)
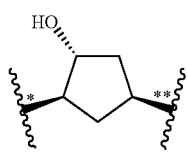

(eE)
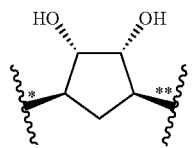

wherein
* is bonded to the nitrogen atom to which $R^2$ is bonded,
** is bonded to the nitrogen atom to which $R^5$ is bonded,
$R^{22}$ is a hydrogen atom, a hydroxy group or a methoxy group,
$R^{23}$ is a hydroxy group or a methoxy group, and
$R^{24}$ is a hydrogen atom or a hydroxy group.

[10] The compound according to any one of [1] to [5], or a pharmaceutically acceptable salt thereof, wherein the moiety represented by the following formula (5) in the formula (1) is any of the following formulas (9A) to (9C):

[Formula 13]

(5)
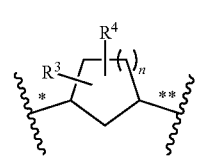

[Formula 14]

(9A)
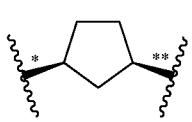

(9B)
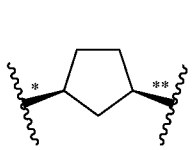

-continued

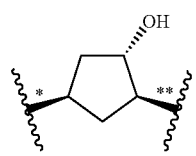
(9C)

wherein

* is bonded to the nitrogen atom to which $R^2$ is bonded, and

** is bonded to the nitrogen atom to which $R^5$ is bonded.

[11] The compound according to any one of [1] to [10], or a pharmaceutically acceptable salt thereof, wherein $R^5$ is a hydrogen atom, a methyl group, an ethyl group, or a 2-hydroxyethyl group.

[12] The compound according to any one of [1] to [10], or a pharmaceutically acceptable salt thereof, wherein $R^5$ is a methyl group.

[13] The compound according to any one of [1] to [12], or a pharmaceutically acceptable salt thereof, wherein $R^6$ is a hydrogen atom, a methyl group, a chlorine atom, a methoxy group, an amino group, or a methylamino group.

[14] The compound according to any one of [1] to [13], or a pharmaceutically acceptable salt thereof, wherein $R^7$ and $R^8$ are taken together with the carbon atom to which $R^7$ is bonded and the carbon atom to which $R^8$ is bonded to form the following formula (10A):

[Formula 15]

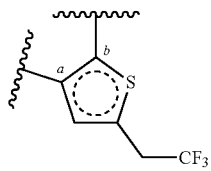
(10A)

wherein the dotted circle indicates that the ring is aromatic, the carbon atom marked with a is the carbon atom to which $R^8$ is bonded, and the carbon atom marked with b is the carbon atom to which $R^7$ is bonded.

[15] The compound according to any one of [1] to [13], or a pharmaceutically acceptable salt thereof, wherein $R^7$ is a hydrogen atom, and $R^8$ is the following formula (11A) or (11B):

[Formula 16]

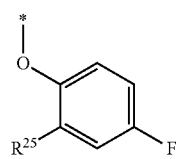
(11A)

-continued

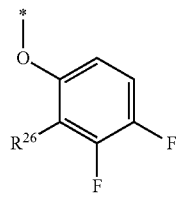
(11B)

wherein

* indicates a bonding site, $R^{25}$ is a diisopropylcarbamoyl group, a 4-isopropylpyrimidin-5-yl group, a 2-isopropylphenyl group, or a 1-isopropylpyrazol-5-yl group, and $R^{26}$ is a diisopropylcarbamoyl group.

[16] The compound according to any one of [1] to [15], or a pharmaceutically acceptable salt thereof, wherein Ring $Q^1$ is any of the following (i) to (vii):

(i) a benzene ring optionally having one or two substituents independently selected from the above Group A;

(ii) a pyridine ring optionally having one or two substituents independently selected from the above Group A;

(iii) a 1,3-thiazole ring or a pyrazole ring (the 1,3-thiazole ring or pyrazole ring optionally has one substituent independently selected from the above Group A);

(iv) a cyclohexane ring optionally having one substituent independently selected from the above Group A;

(v) a cyclohexene ring optionally having one substituent independently selected from the above Group A;

(vi) a piperidine ring optionally having one substituent independently selected from the above Group A; or (vii) an indole ring optionally has one or two substituents independently selected from the above Group B.

[17] The compound according to any one of [1] to [15], or a pharmaceutically acceptable salt thereof, wherein m is 1, and Ring $Q^1$ is any of the following formulas (12A) to (12H):

[Formula 17]

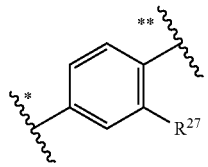
(12A)

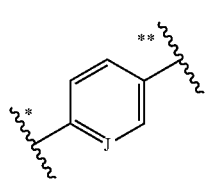
(12B)

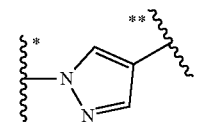
(12C)

-continued

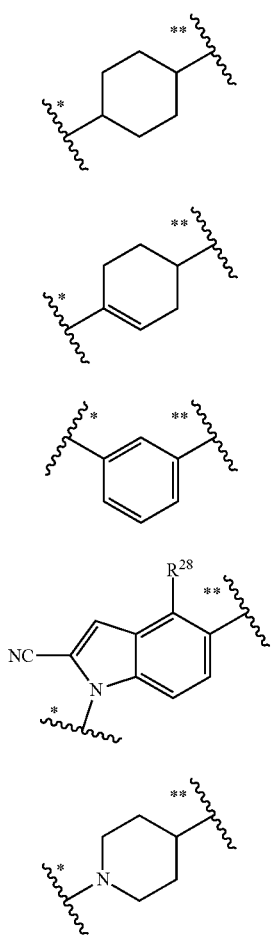

(12D)
(12E)
(12F)
(12G)
(12H)

wherein

* is bonded to Z,

** is bonded to the carbon atom to which $R^1$ is bonded, $R^{27}$ is a hydrogen atom, a halogen atom, a $C_{1-6}$ alkoxy group, or a $C_{1-6}$ alkyl group, J is a nitrogen atom or $CR^{29}$, $R^{29}$ is a halogen atom, and $R^{28}$ is a hydrogen atom or a $C_{1-6}$ alkyl group.

[18] The compound according to any one of [1] to [15], or a pharmaceutically acceptable salt thereof, wherein m is 1, and Ring $Q^1$ is the following formula (13A) or (13B):

[Formula 18]

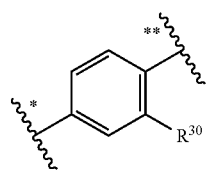

(13A)

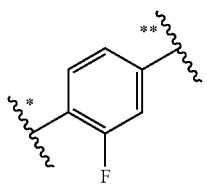

(13B)

wherein
*is bonded to Z,
** is bonded to the carbon atom to which $R^1$ is bonded, and
$R^{30}$ is a hydrogen atom, a fluorine atom, a methyl group, or a methoxy group.

[19] The compound according to any one of [1] to [18], or a pharmaceutically acceptable salt thereof, wherein Ring $Q^2$ is any of the following (i) to (vii):

(i) a benzene ring optionally having one to three substituents independently selected from the above Group C;

(ii) a pyridine ring optionally having one to three substituents independently selected from the above Group C;

(iii) a pyridazine ring, a pyrazine ring or a pyrimidine ring (the pyridazine ring, pyrazine ring or pyrimidine ring optionally has one to three substituents independently selected from the above Group C);

(iv) a pyrazole ring, an imidazole ring, a 1,3-thiazole ring, a 1,3-oxazole ring or a 4H-1,2,4-triazole ring (the pyrazole ring, imidazole ring, 1,3-thiazole ring, 1,3-oxazole ring or 4H-1,2,4-triazole ring optionally has one substituent independently selected from the above Group C);

(v) an isoquinoline ring, an indazole ring, a benzimidazole ring, a 1H-pyrrolo[2,3-c]pyridine ring, a 1H-pyrrolo[3,2-c]pyridine ring, a furo[3,2-b]pyridine ring, a 1H-pyrazolo[3,4-c]pyridine ring or an indoline ring (the isoquinoline ring, indazole ring, benzimidazole ring, 1H-pyrrolo[2,3-c]pyridine ring, 1H-pyrrolo[3,2-c]pyridine ring, furo[3,2-b]pyridine ring, 1H-pyrazolo[3,4-c]pyridine ring or indoline ring optionally has one or two substituents independently selected from the above Group D);

(vi) a pyrrolidine ring, a piperidine ring, a morpholine ring or an azepane ring (the pyrrolidine ring, piperidine ring, morpholine ring or azepane ring optionally has one substituent independently selected from the above Group E); or (vii) a cyclohexane ring optionally having one substituent independently selected from the above Group E.

[20] The compound according to any one of [1] to [18], or a pharmaceutically acceptable salt thereof, wherein W is the above formula (4A); and Ring $Q^2$ is any of the following formulas (14A) to (14F):

[Formula 19]

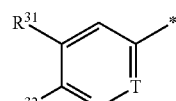

(14A)

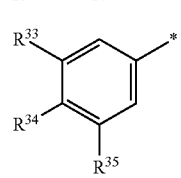

(14B)

-continued

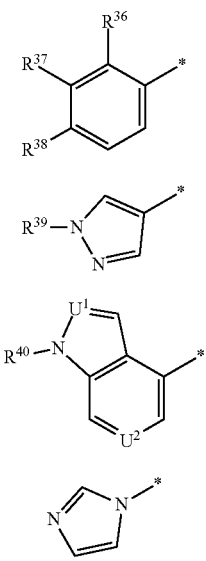

(14C)

(14D)

(14E)

(14F)

wherein
* indicates a bonding site,
T is CH or a nitrogen atom,
$R^{31}$ is a hydrogen atom, a $C_{1-6}$ alkoxy group, a halogeno $C_{1-6}$ alkoxy group, or a $(^2H_3)$methoxy group,
$R^{32}$ is a hydrogen atom, a $C_{1-6}$ alkyl group, a halogen atom, a $C_{1-6}$ alkoxy group, a cyano group, a di($C_{1-6}$ alkyl)amino group, a halogeno $C_{1-6}$ alkyl group, a $C_{1-6}$ alkylamino group, a $C_{1-6}$ alkylsulfonyl group, a $C_{1-6}$ alkoxy $C_{1-6}$ alkoxy group, a halogeno $C_{1-6}$ alkoxy group, a hydroxy $C_{1-6}$ alkyl group, a $C_{1-6}$ alkyl (2-$C_{3-6}$ alkenoyl)amino group, a $(^2H_3)$methoxy group, or a bis[$(^2H_3)$methyl]amino group, or
$R^{31}$ and $R^{32}$ are taken together to form an ethylenedioxy group,
$R^{33}$ and $R^{35}$ are each independently a hydrogen atom, a halogen atom, a $C_{1-6}$ alkoxy group, a $C_{1-6}$ alkyl($C_{1-6}$ alkylsulfonyl)amino group, a ($C_{1-6}$ alkyl)carbamoyl group, a di($C_{1-6}$ alkyl)sulfamoyl group, a 2-$C_{3-6}$ alkenoylamino group, or a $C_{1-6}$ alkylsulfonyl $C_{1-6}$ alkyl group,
$R^{34}$ is a hydrogen atom or a halogen atom,
$R^{36}$ is a halogen atom,
$R^{37}$ is a $C_{1-6}$ alkoxy group,
$R^{38}$ is a halogen atom,
$R^{39}$ is a $C_{1-6}$ alkyl group or a $C_{1-6}$ alkylsulfonyl group,
$R^{40}$ is a $C_{1-6}$ alkyl group or a $C_{1-6}$ alkylsulfonyl group,
$U^1$ is CH or a nitrogen atom,
$U^2$ is $CR^{41}$ or a nitrogen atom, and
$R^{41}$ is a hydrogen atom or a halogen atom.
[21] The compound according to any one of [1] to [18], or a pharmaceutically acceptable salt thereof, wherein
W is the above formula (4A); and
Ring $Q^2$ is any of the following formulas (15A) to (15C):

[Formula 20]

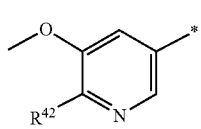

(15A)

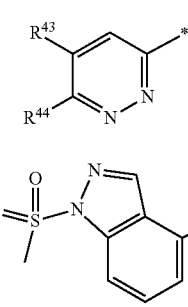

(15B)

(15C)

wherein
* indicates a bonding site,
$R^{42}$ is a methyl group, a chlorine atom, a methoxy group, a cyano group, a dimethylamino group, or a bis[$(^2H_3)$methyl]amino group,
$R^{43}$ is a methoxy group or a $(^2H_3)$methoxy group, and
$R^{44}$ is a chlorine atom, a methoxy group, a methoxyethoxy group, a dimethylamino group, a difluoromethoxy group, or a $(^2H_3)$methoxy group.
[22] The compound according to any one of [1] to [18], or a pharmaceutically acceptable salt thereof, wherein
W is the above formula (4A); and
Ring $Q^2$ is any of the following formulas (16A) to (16G):

[Formula 21]

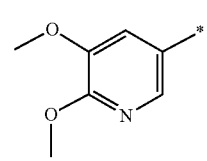

(16A)

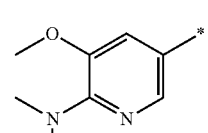

(16B)

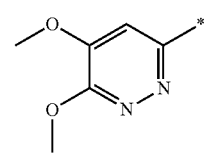

(16C)

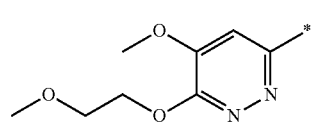

(16D)

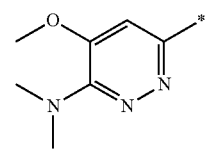

(16E)

-continued (16F)
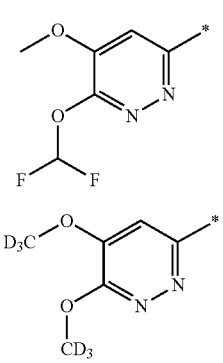

(16G)

wherein * indicates a bonding site.

[23] The compound according to any one of [1] to [18], or a pharmaceutically acceptable salt thereof, wherein
W is the above formula (4B); and
Ring $Q^2$ is the following formula (17A) or (17B):

[Formula 22]

(17A)
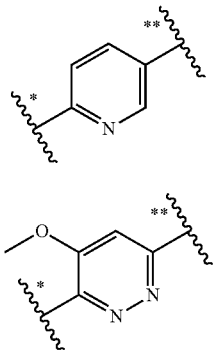

(17B)

wherein
* is bonded to Y, and
** is bonded to Z.

[24] The compound according to any one of [1] to [19] and [23], or a pharmaceutically acceptable salt thereof, wherein
W is the above formula (4B); and
Ring $Q^3$ is any of the following formulas (18A) to (18D):

[Formula 23]

(18A)
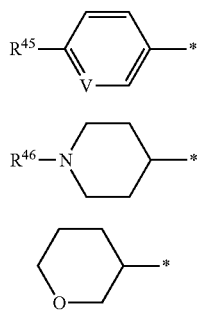

(18B)

(18C)

-continued (18D)

wherein
* indicates a bonding site,
$R^{45}$ is a hydrogen atom or a halogen atom,
$R^{46}$ is a $C_{1-6}$ alkylsulfonyl group, and
V is a nitrogen atom or CH.

[25] The compound according to any one of [1] to [19] and [23], or a pharmaceutically acceptable salt thereof, wherein
W is the above formula (4B); and
Ring $Q^3$ is a phenyl group, an azetidin-1-yl group, a 3-pyridyl group, a 6-chloro-3-pyridyl group, a tetrahydropyran-3-yl group, or a 1-methylsulfonyl-4-piperidyl group.

[26] The compound according to any one of [1] to [19] and [23] to [25], or a pharmaceutically acceptable salt thereof, wherein
W is the above formula (4B); and
Y is a single bond or an oxygen atom.

[27] The compound according to any one of [1] to [26], or a pharmaceutically acceptable salt thereof, wherein Z is a single bond, —NH—, an oxygen atom, —SO$_2$—, —CH$_2$—, *—CH$_2$—NHC(=O)—**, *—CH$_2$CH$_2$—O—**, or *—CH$_2$—NH—**, wherein * is bonded to Ring $Q^2$, and ** is bonded to Ring $Q^1$.

[28] The compound according to any one of [1] to [26], or a pharmaceutically acceptable salt thereof, wherein Z is a single bond.

[29] The compound according to [1], or a pharmaceutically acceptable salt thereof, wherein
$R^1$ is a hydrogen atom;
$R^2$ is a hydrogen atom;
the moiety represented by the following formula (5) is any of the following formulas (9A) to (9C):

[Formula 24]

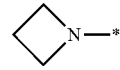
(5)

[Formula 25]

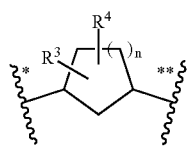
(9A)

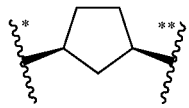
(9B)

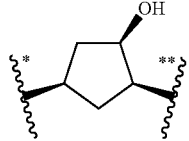
(9C)

wherein

* is bonded to the nitrogen atom to which $R^2$ is bonded, and

** is bonded to the nitrogen atom to which $R^5$ is bonded;

$R^5$ is a methyl group;

$R^6$ is a hydrogen atom, a methyl group, a chlorine atom, a methoxy group, an amino group, or a methylamino group;

$R^7$ and $R^8$ are taken together with the carbon atom to which $R^7$ is bonded and the carbon atom to which $R^8$ is bonded to form the following formula (10A):

[Formula 26]

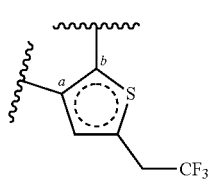

(10A)

wherein the dotted circle indicates that the ring is aromatic, the carbon atom marked with a is the carbon atom to which $R^8$ is bonded, and the carbon atom marked with b is the carbon atom to which $R^7$ is bonded, or $R^7$ is a hydrogen atom, and $R^8$ is the following formula (11A) or (11B):

[Formula 27]

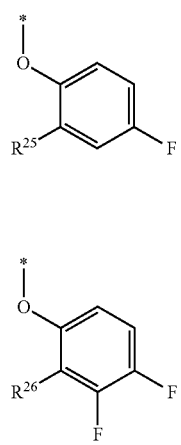

wherein

* indicates a bonding site, $R^{25}$ is a diisopropylcarbamoyl group, a 4-isopropylpyrimidin-5-yl group, a 2-isopropylphenyl group, or a 1-isopropylpyrazol-5-yl group, and $R^{26}$ is a diisopropylcarbamoyl group;

m is 1;

Ring $Q^1$ is the following formula (13A) or (13B):

[Formula 28]

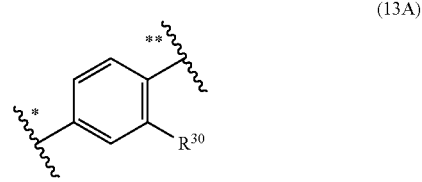

(13A)

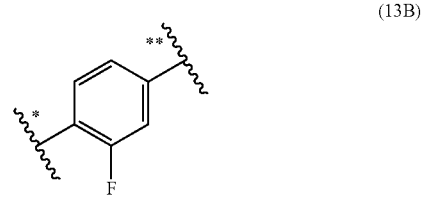

(13B)

wherein

* is bonded to Z,

** is bonded to the carbon atom to which $R^1$ is bonded, and $R^{30}$ is a hydrogen atom, a fluorine atom, a methyl group, or a methoxy group;

W is the above formula (4A), and

Ring $Q^2$ is any of the following formulas (15A) to (15C):

[Formula 29]

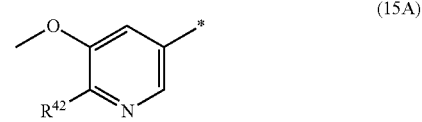

(15A)

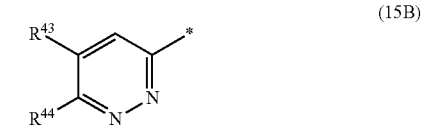

(15B)

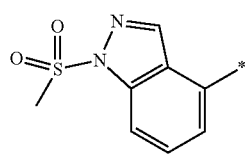

(15C)

wherein

* indicates a bonding site, $R^{42}$ is a methyl group, a chlorine atom, a methoxy group, a cyano group, a dimethylamino group, or a bis[($^2H_3$) methyl]amino group, $R^{43}$ is a methoxy group or a ($^2H_3$)methoxy group, and $R^{44}$ is a chlorine atom, a methoxy group, a methoxyethoxy group, a dimethylamino group, a difluoromethoxy group, or a ($^2H_3$)methoxy group, or W is the above formula (4B), Ring $Q^2$ is the following formula (17A) or (17B):

[Formula 30]

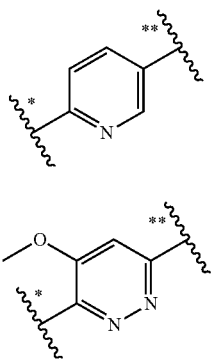

(17A)

(17B)

wherein

* is bonded to Y, and

** is bonded to Z,

Ring $Q^3$ is a phenyl group, an azetidin-1-yl group, a 3-pyridyl group, a 6-chloro-3-pyridyl group, a tetrahydropyran-3-yl group, or a 1-methylsulfonyl-4-piperidyl group, and Y is a single bond or an oxygen atom; and Z is a single bond.

[30] The compound according to [1], or a pharmaceutically acceptable salt thereof, wherein $R^1$ is a hydrogen atom;

$R^2$ is a hydrogen atom;

the moiety represented by the following formula (5) is any of the following formulas (9A) to (9C):

[Formula 31]

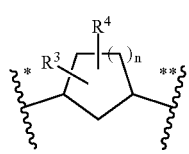

(5)

[Formula 32]

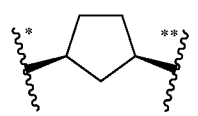

(9A)

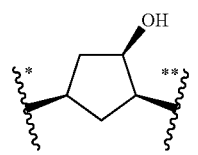

(9B)

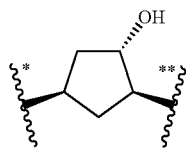

(9C)

wherein

* is bonded to the nitrogen atom to which $R^2$ is bonded, and

** is bonded to the nitrogen atom to which $R^5$ is bonded;

$R^5$ is a methyl group;

$R^6$ is a hydrogen atom, a methyl group, a chlorine atom, a methoxy group, an amino group, or a methylamino group;

$R^7$ and $R^8$ are taken together with the carbon atom to which $R^7$ is bonded and the carbon atom to which $R^8$ is bonded to form the following formula (10A):

[Formula 33]

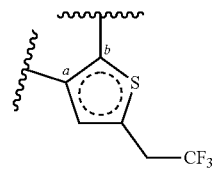

(10A)

wherein the dotted circle indicates that the ring is aromatic, the carbon atom marked with a is the carbon atom to which $R^8$ is bonded, and the carbon atom marked with b is the carbon atom to which $R^7$ is bonded;

m is 1;

Ring $Q^1$ is the following formula (13A) or (13B):

[Formula 34]

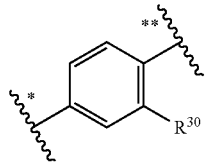

(13A)

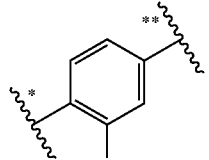

(13B)

wherein

* is bonded to Z,

** is bonded to the carbon atom to which $R^1$ is bonded, and $R^{30}$ is a hydrogen atom, a fluorine atom, a methyl group, or a methoxy group;
W is the above formula (4A); and
Ring $Q^2$ is any of the following formulas (16A) to (16G):

[Formula 35]

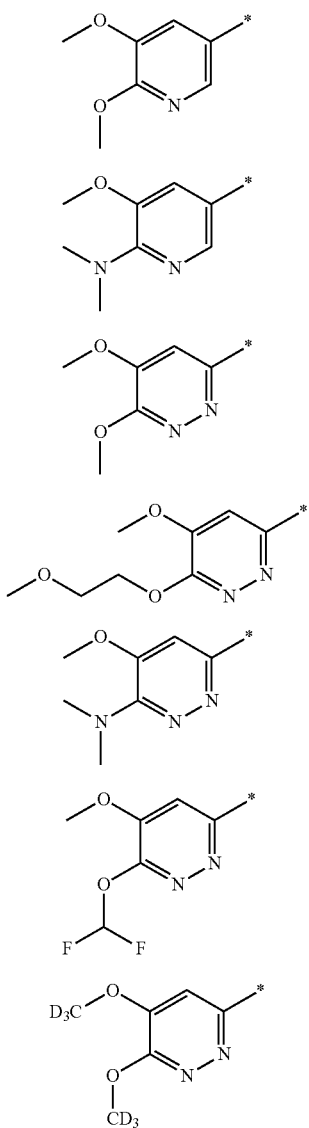

wherein * indicates a bonding site; and
Z is a single bond.

[31] Any compound selected from the following group, or a pharmaceutically acceptable salt thereof:

5-[4-({[(1R,3R,4S)-3-hydroxy-4-{methyl[6-(2,2,2-trifluoroethyl)thieno[2,3-d]pyrimidin-4-yl]amino}cyclopentyl]amino}methyl)phenyl]-3-methoxypyridine-2-carbonitrile, (1R,2S,4R)-4-[({4-[1-(methanesulfonyl)-1H-indazol-4-yl]phenyl}methyl)amino]-2-{methyl[6-(2,2,2-trifluoroethyl)thieno[2,3-d]pyrimidin-4-yl]amino}cyclopentan-1-ol, (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-[({4-[6-(dimethylamino)-5-methoxypyridin-3-yl]phenyl}methyl)amino]-2-{methyl[6-(2,2,2-trifluoroethyl)thieno[2,3-d]pyrimidin-4-yl]amino}cyclopentan-1-ol, (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol, (1R,2S,4R)-4-({[4-(5-methoxy-6-methylpyridin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-({[4-(1H-imidazol-1-yl)phenyl]methyl}amino)-2-{methyl[2-(methylamino)-6-(2,2,2-trifluoroethyl)thieno[2,3-d]pyrimidin-4-yl]amino}cyclopentan-1-ol, (1R,2S,4R)-4-({[4-(6-chloro-5-methoxypyridin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-({[4-(5,6-dimethoxypyridin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-({[4-(6-fluoro-5-methoxypyridin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-({[4-(5,6-dimethoxypyridin-3-yl)phenyl]methyl}amino)-2-{methyl[2-(methylamino)-6-(2,2,2-trifluoroethyl)thieno[2,3-d]pyrimidin-4-yl]amino}cyclopentan-1-ol, (1R,2S,4R)-4-({[4-(5,6-dimethoxypyridin-3-yl)phenyl]methyl}amino)-2-{[2-methoxy-6-(2,2,2-trifluoroethyl)thieno[2,3-d]pyrimidin-4-yl](methyl)amino}cyclopentan-1-ol, (1R,2S,4R)-4-({[4-(6-chloro-5-methoxypyridazin-3-yl)phenyl]methyl}amino)-2-{methyl[6-(2,2,2-trifluoroethyl)thieno[2,3-d]pyrimidin-4-yl]amino}cyclopentan-1-ol, 2-[(4-{[(1S,2R,4R)-4-({[4-(5,6-dimethoxypyridazin-3-yl)phenyl]methyl}amino)-2-hydroxycyclopentyl](methyl)amino}pyrimidin-5-yl)oxy]-5-fluoro-N,N-di(propan-2-yl)benzamide, (1R,2S,4R)-2-{[2-chloro-6-(2,2,2-trifluoroethyl)thieno[2,3-d]pyrimidin-4-yl](methyl)amino}-4-({[4-(5,6-dimethoxypyridazin-3-yl)phenyl]methyl}amino)cyclopentan-1-ol, (1R,3S)—N³-{[4-(5,6-dimethoxypyridazin-3-yl)phenyl]methyl}-N'-methyl-N'-[6-(2,2,2-trifluoroethyl)thieno[2,3-d]pyrimidin-4-yl]cyclopentane-1,3-diamine, (1R,2S,4R)-4-[({4-[6-(dimethylamino)-5-methoxypyridazin-3-yl]phenyl}methyl)amino]-2-{methyl[6-(2,2,2-trifluoroethyl)thieno[2,3-d]pyrimidin-4-yl]amino}cyclopentan-1-ol, 6-[4-({[(1R,3R,4S)-3-hydroxy-4-{methyl[6-(2,2,2-trifluoroethyl)thieno[2,3-d]pyrimidin-4-yl]amino}cyclopentyl]amino}methyl)phenyl]-4-methoxypyridazine-3-carbonitrile, (1S,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-[({4-[5-methoxy-6-(2-methoxyethoxy)pyridazin-3-yl]phenyl}methyl)amino]-2-{[2-methoxy-6-(2,2,2-trifluoroethyl)thieno[2,3-d]pyrimidin-4-yl](methyl)amino}cyclopentan-1-ol, (1R,2S,4R)-4-({[4-(4,5-dimethoxypyridin-2-yl)phenyl]methyl}amino)-2-{[2-methoxy-6-(2,2,2-trifluoroethyl)thieno[2,3-d]pyrimidin-4-yl](methyl)amino}cyclopentan-1-ol, (1R,2S,4R)-4-[({4-[6-(dimethylamino)-5-methoxypyridin-3-yl]phenyl}methyl)amino]-2-{[2-methoxy-6-(2,2,2-trifluoroethyl)thieno[2,3-d]pyrimidin-4-yl](methyl)amino}cyclopentan-1-ol, (1R,2S,4R)-4-[({4-[6-(difluoromethoxy)-5-methoxypyridazin-3-yl]phenyl}methyl)amino]-2-{[2-methoxy-6-

(2,2,2-trifluoroethyl)thieno[2,3-d]pyrimidin-4-yl] (methyl)amino}cyclopentan-1-ol,
(1R,2S,4R)-4-{[(4-{5,6-bis[($^2$H$_3$)methyloxy]pyridazin-3-yl}phenyl)methyl]amino}-2-{methyl[6-(2,2,2-trifluoroethyl)thieno[2,3-d]pyrimidin-4-yl]amino}cyclopentan-1-ol,
(1R,2S,4R)-4-({[4-(6-{bis[($^2$H$_3$)methyl]amino}-5-methoxypyridin-3-yl)phenyl]methyl}amino)-2-{methyl[6-(2,2,2-trifluoroethyl)thieno[2,3-d]pyrimidin-4-yl]amino}cyclopentan-1-ol, and
(1R,2S,4R)-4-{[(4-{5,6-bis[($^2$H$_3$)methyloxy]pyridazin-3-yl}phenyl)methyl]amino}-2-{[2-methoxy-6-(2,2,2-trifluoroethyl)thieno[2,3-d]pyrimidin-4-yl](methyl)amino}cyclopentan-1-ol.

[32] An inhibitor of the interaction between menin and one or more proteins selected from the group consisting of MLL1, MLL2, a MLL fusion protein and a MLL partial tandem duplication protein, which comprises, as an active ingredient, the compound according to any one of [1] to [31], or a pharmaceutically acceptable salt thereof.

[33] A pharmaceutical composition comprising the compound according to any one of [1] to [31], or a pharmaceutically acceptable salt thereof and a pharmaceutically acceptable carrier.

[34] The pharmaceutical composition according to [33], for the treatment and/or prophylaxis of diseases that can be treated and/or prevented by inhibiting the interaction between menin and one or more proteins selected from the group consisting of MLL1, MLL2, a MLL fusion protein and a MLL partial tandem duplication protein.

[35] The pharmaceutical composition according to [33], for the treatment and/or prophylaxis of diabetes.

[36] The pharmaceutical composition according to [33], for the treatment and/or prophylaxis of cancer.

[37] The pharmaceutical composition according to [36], wherein the cancer is blood cancer, prostate cancer, breast cancer, hepatoma or pediatric glioma.

[38] The pharmaceutical composition according to [36], wherein the cancer is blood cancer.

[39] The pharmaceutical composition according to [38], wherein the blood cancer is acute myelogenous leukemia (AML) or acute lymphocytic leukemia (ALL).

[40] A method for treating and/or preventing diabetes, comprising administering the compound according to any one of [1] to [31], or a pharmaceutically acceptable salt thereof.

[41] A method for treating and/or preventing cancer, comprising administering the compound according to any one of [1] to [31], or a pharmaceutically acceptable salt thereof.

[42] The compound according to any one of [1] to [31], or a pharmaceutically acceptable salt thereof, for use in the treatment and/or prophylaxis of cancer.

[43] Use of the compound according to any one of [1] to [31], or a pharmaceutically acceptable salt thereof, for the manufacture of a medicament for the treatment and/or prophylaxis of cancer.

[44] The compound according to [1], which is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol, or a pharmaceutically acceptable salt thereof.

[45] The compound according to [1], which is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol succinate.

[46] The compound according to [1], which is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol benzenesulfonate.

[47] The compound according to [1], which is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol maleate.

[48] The compound according to [1], which is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol fumarate.

[49] The compound according to [1], which is (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol, or a pharmaceutically acceptable salt thereof.

[50] The compound according to [1], which is (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol fumarate.

[51] The compound according to [1], which is (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol mucate.

[52] The compound according to [1], which is (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol adipate.

[53] The compound according to [1], which is (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol succinate.

[54] A crystal of the compound according to [1], wherein the compound is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol succinate, having at least five peaks at diffraction angles (2θ) selected from 4.66±0.2, 7.02±0.2, 14.10±0.2, 16.68±0.2, 17.46±0.2, 18.68±0.2, 21.34±0.2, 24.52±0.2, 25.54±0.2 and 28.22±0.2 in a powder X-ray diffraction diagram obtained through irradiation with copper Kα line (λ=1.54 angstroms).

[55] A crystal of the compound according to [1], wherein the compound is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol benzenesulfonate, having at least five peaks at diffraction angles (2θ) selected from 10.92±0.2, 11.70±0.2, 12.40±0.2, 15.00±0.2, 17.38±0.2, 18.16±0.2, 22.18±0.2, 22.62±0.2, 23.86±0.2 and 24.20±0.2 in a powder X-ray diffraction diagram obtained through irradiation with copper Kα line (λ=1.54 angstroms).

[56] A crystal of the compound according to [1], wherein the compound is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol maleate, having at least five peaks at diffraction angles (2θ) selected from 4.64±0.2, 7.02±0.2, 7.46±0.2, 11.14±0.2, 14.04±0.2, 16.76±0.2, 18.54±0.2, 19.76±0.2, 21.26±0.2 and 22.62±0.2 in a powder X-ray diffraction diagram obtained through irradiation with copper Kα line (λ=1.54 angstroms).

[57] A crystal of the compound according to [1], wherein the compound is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol fumarate, having at least five peaks at diffraction angles (2θ) selected from 4.80±0.2, 7.94±0.2, 9.66±0.2, 11.56±0.2, 14.56±0.2, 17.62±0.2, 18.14±0.2, 20.46±0.2, 21.36±0.2 and 24.46±0.2 in a powder X-ray diffraction diagram obtained through irradiation with copper Kα line (λ=1.54 angstroms).

[58] A crystal of the compound according to [1], wherein the compound is (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol, having at least five peaks at diffraction angles (2θ) selected from 7.14±0.2, 8.76±0.2, 12.26±0.2, 14.30±0.2, 17.52±0.2, 23.40±0.2, 24.40±0.2, 24.86±0.2, 25.34±0.2 and 25.90±0.2 in a powder X-ray diffraction diagram obtained through irradiation with copper Kα line (λ=1.54 angstroms).

[59] A crystal of the compound according to [1], wherein the compound is (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol fumarate, having at least five peaks at diffraction angles (2θ) selected from 8.06±0.2, 12.22±0.2, 12.52±0.2, 15.14±0.2, 17.54±0.2, 18.56±0.2, 20.08±0.2, 23.48±0.2, 24.28±0.2 and 25.00±0.2 in a powder X-ray diffraction diagram obtained through irradiation with copper Kα line (λ=1.54 angstroms).

[60] A crystal of the compound according to [1], wherein the compound is (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol mucate, having at least five peaks at diffraction angles (2θ) selected from 6.56±0.2, 9.44±0.2, 9.94±0.2, 13.20±0.2, 18.22±0.2, 18.86±0.2, 19.60±0.2, 22.68±0.2, 25.10±0.2 and 28.70±0.2 in a powder X-ray diffraction diagram obtained through irradiation with copper Kα line (λ=1.54 angstroms).

[61] A crystal of the compound according to [1], wherein the compound is (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol adipate, having at least five peaks at diffraction angles (2θ) selected from 5.88±0.2, 6.20±0.2, 9.18±0.2, 10.34±0.2, 12.50±0.2, 13.70±0.2, 15.66±0.2, 17.82±0.2, 18.48±0.2 and 22.16±0.2 in a powder X-ray diffraction diagram obtained through irradiation with copper Kα line (λ=1.54 angstroms).

[62] A crystal of the compound according to [1], wherein the compound is (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol succinate, having at least five peaks at diffraction angles (2θ) selected from 4.60±0.2, 6.60±0.2, 7.74±0.2, 8.02±0.2, 9.26±0.2, 11.16±0.2, 12.00±0.2, 12.44±0.2, 13.22±0.2 and 19.66±0.2 in a powder X-ray diffraction diagram obtained through irradiation with copper Kα line (λ=1.54 angstroms).

[63] An inhibitor of the interaction between menin and one or more proteins selected from the group consisting of MLL1, MLL2, a MLL fusion protein and a MLL partial tandem duplication protein, which comprises, as an active ingredient, the compound according to any one of [1] to [31] and [44] to [53], or a pharmaceutically acceptable salt thereof, or the crystal according to any one of [54] to [62].

[64] A pharmaceutical composition comprising the compound according to any one of [1] to [31] and [44] to [53], or a pharmaceutically acceptable salt thereof, or the crystal according to any one of [54] to [62], and a pharmaceutically acceptable carrier.

[65] The pharmaceutical composition according to [64], for the treatment and/or prophylaxis of diseases that can be treated and/or prevented by inhibiting the interaction between menin and one or more proteins selected from the group consisting of MLL1, MLL2, a MLL fusion protein and a MLL partial tandem duplication protein.

[66] The pharmaceutical composition according to [64], for the treatment and/or prophylaxis of diabetes.

[67] The pharmaceutical composition according to [64], for the treatment of cancer.

[68] The pharmaceutical composition according to [67], wherein the cancer is blood cancer, prostate cancer, breast cancer, hepatoma or pediatric glioma.

[69] The pharmaceutical composition according to [67], wherein the cancer is blood cancer.

[70] The pharmaceutical composition according to [69], wherein the blood cancer is acute myelogenous leukemia (AML) or acute lymphocytic leukemia (ALL).

[71] A method for treating and/or preventing diabetes, comprising administering the compound according to any one of [1] to [31] and [44] to [53], or a pharmaceutically acceptable salt thereof, or the crystal according to any one of [54] to [62].

[72] A method for treating cancer, comprising administering the compound according to any one of [1] to [31] and [44] to [53], or a pharmaceutically acceptable salt thereof, or the crystal according to any one of [54] to [62].

[73] The compound according to any one of [1] to [31] and [44] to [53], or a pharmaceutically acceptable salt thereof, or the crystal according to any one of [54] to [62], for use in the treatment of cancer.

[74] Use of the compound according to any one of [1] to [31] and [44] to [53], or a pharmaceutically acceptable salt thereof, or the crystal according to any one of [54] to [62], for the manufacture of a medicament for the treatment of cancer.

[75] The pharmaceutical composition according to [69], wherein the blood cancer is acute myelogenous leukemia (AML) with NPM1 mutation.

[76] A pharmaceutical composition comprising one drug selected from the group consisting of a Bcl-2 inhibitor, a DNA methyltransferase inhibitor and a pyrimidine antimetabolite, and the compound according to any one of [1] to [31] and [44] to [53], or a pharmaceutically acceptable salt thereof, or the crystal according to any one of [54] to [62], which are administered in combination.

[77] The pharmaceutical composition according to [76], wherein the one drug selected from the group consisting of a Bcl-2 inhibitor, a DNA methyltransferase inhibitor and a pyrimidine antimetabolite, and the compound according to any one of [1] to [31] and [44] to [53], or a pharmaceutically acceptable salt thereof, or the crystal according to any one of [54] to [62] are separately comprised as active ingredients in different formulations and administered at the same time or different times.

[78] The pharmaceutical composition according to [76], wherein the one drug selected from the group consisting of a Bcl-2 inhibitor, a DNA methyltransferase inhibitor and a pyrimidine antimetabolite, and the compound according to any one of [1] to [31] and [44] to [53], or a pharmaceutically acceptable salt thereof, or the crystal according to any one of [54] to [62] are comprised in a single formulation.

[79] The pharmaceutical composition according to any one of [76] to [78], wherein the drug selected from the group consisting of a Bcl-2 inhibitor, a DNA methyltransferase inhibitor and a pyrimidine antimetabolite is Venetoclax.

[80] The pharmaceutical composition according to any one of [76] to [78], wherein the one drug selected from the group consisting of a Bcl-2 inhibitor, a DNA methyltransferase inhibitor and a pyrimidine antimetabolite is Azacitidine.

[81] The pharmaceutical composition according to any one of [76] to [78], wherein the one drug selected from the group consisting of a Bcl-2 inhibitor, a DNA methyltransferase inhibitor and a pyrimidine antimetabolite is Cytarabine.

[82] The method according to [72], wherein the compound according to any one of [1] to [31] and [44] to [53], or a pharmaceutically acceptable salt thereof, or the crystal according to any one of [54] to [62] is administered in combination with one drug selected from the group consisting of a Bcl-2 inhibitor, a DNA methyltransferase inhibitor and a pyrimidine antimetabolite.

[83] The method according to [82], wherein the one drug selected from the group consisting of a Bcl-2 inhibitor, a DNA methyltransferase inhibitor and a pyrimidine antimetabolite, and the compound according to any one of [1] to [31] and [44] to [53], or a pharmaceutically acceptable salt thereof, or the crystal according to any one of [54] to [62] are separately comprised as active ingredients in different formulations and administered at the same time or different times.

[84] The method according to [82], wherein the one drug selected from the group consisting of a Bcl-2 inhibitor, a DNA methyltransferase inhibitor and a pyrimidine antimetabolite, and the compound according to any one of [1] to [31] and [44] to [53], or a pharmaceutically acceptable salt thereof, or the crystal according to any one of [54] to [62] are comprised in a single formulation.

[85] The compound according to any one of [1] to [31] and [44] to [53], or a pharmaceutically acceptable salt thereof, or the crystal according to any one of [54] to [62], which is administered in combination with one drug selected from the group consisting of a Bcl-2 inhibitor, a DNA methyltransferase inhibitor and a pyrimidine antimetabolite.

[86] The compound or pharmaceutically acceptable salt thereof or crystal according to [85], wherein the one drug selected from the group consisting of a Bcl-2 inhibitor, a DNA methyltransferase inhibitor and a pyrimidine antimetabolite, and the compound according to any one of [1] to [31] and [44] to [53], or a pharmaceutically acceptable salt thereof, or the crystal according to any one of [54] to [62] are separately comprised as active ingredients in different formulations and administered at the same time or different times.

[87] The compound or pharmaceutically acceptable salt thereof or crystal according to [85], wherein the one drug selected from the group consisting of a Bcl-2 inhibitor, a DNA methyltransferase inhibitor and a pyrimidine antimetabolite, and the compound according to any one of [1] to [31] and [44] to [53], or a pharmaceutically acceptable salt thereof, or the crystal according to any one of [54] to [62] are comprised in a single formulation.

[88] The compound or pharmaceutically acceptable salt thereof or crystal according to any one of [85] to [87], wherein the one drug selected from the group consisting of a Bcl-2 inhibitor, a DNA methyltransferase inhibitor and a pyrimidine antimetabolite is Venetoclax.

[89] The compound or pharmaceutically acceptable salt thereof or crystal according to any one of [85] to [87], wherein the one drug selected from the group consisting of a Bcl-2 inhibitor, a DNA methyltransferase inhibitor and a pyrimidine antimetabolite is Azacitidine.

[90] The compound or pharmaceutically acceptable salt thereof or crystal according to any one of [85] to [87], wherein the one drug selected from the group consisting of a Bcl-2 inhibitor, a DNA methyltransferase inhibitor and a pyrimidine antimetabolite is Cytarabine.

[91] A composition for inducing differentiation of leukemia cells, comprising the compound according to any one of [1] to [31] and [44] to [53], or a pharmaceutically acceptable salt thereof, or the crystal according to any one of [54] to [62].

[92] A method for inducing differentiation of leukemia cells, comprising administering the compound according to any one of [1] to [31] and [44] to [53], or a pharmaceutically acceptable salt thereof, or the crystal according to any one of [54] to [62].

Effect of the Invention

The compound of the present invention or a pharmaceutically acceptable salt thereof exhibits an inhibitory action on the interaction between menin and an MLL protein. Specifically, administration of the pharmaceutical composition comprising the compound of the present invention or a pharmaceutically acceptable salt thereof and a pharmaceutically acceptable carrier to a mammal (human, bovine, horse, swine, etc.) or a bird (chicken, etc.) can be employed for the treatment and/or prophylaxis of diseases dependent on the interaction between menin and an MLL protein. Examples of the disease dependent on the interaction between menin and an MLL protein include cancers and diabetes. Examples of the cancer include blood cancer, myelodysplastic syndrome, prostate cancer, breast cancer, hepatoma and pediatric glioma, preferred is blood cancer, and more preferred are acute myelogenous leukemia (AML) and acute lymphocytic leukemia (ALL).

DESCRIPTION OF EMBODIMENTS

Figure 1:
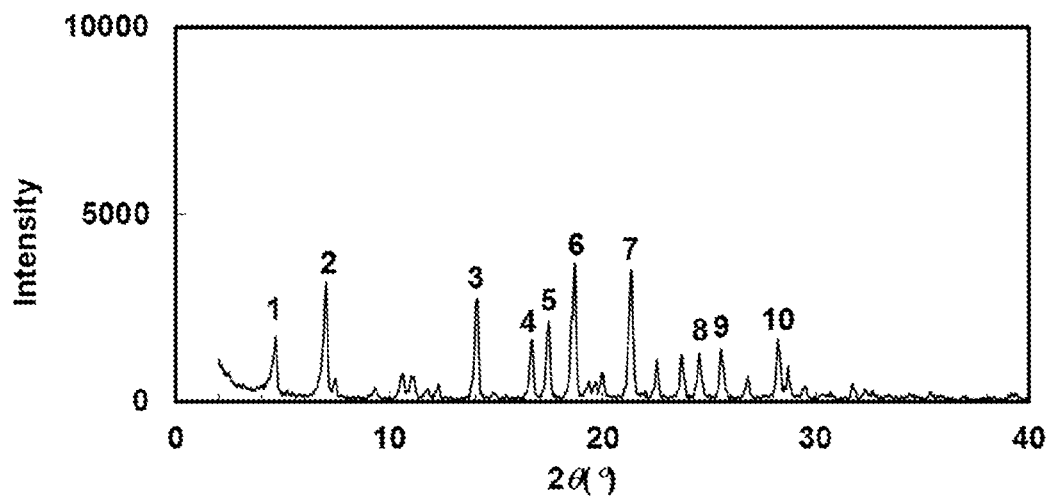
FIG. 1 is a powder X-ray diffraction diagram of the crystal obtained in Example 131. The vertical axis indicates the diffraction intensity (Intensity) in count/sec (cps) unit, and the horizontal axis indicates the value of the diffraction angle 2θ.

Unless defined otherwise, all technical and scientific terms used herein have the same meaning as is commonly understood by one of skill in the art to which this invention belongs.

In the present invention, the "halogen atom" refers to a fluorine atom, a chlorine atom, a bromine atom or an iodine atom.

In the present invention, the "$C_{1-6}$ alkyl group" refers to a linear or branched alkyl group having 1 to 6 carbon atoms. Examples thereof include a methyl group, an ethyl group, a n-propyl group, an isopropyl group, a n-butyl group, a sec-butyl group, a tert-butyl group, a n-pentyl group, an isopentyl group, a 2-methylbutyl group, a neo-pentyl group, a 1-ethylpropyl group, a n-hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group and the like.

In the present invention, the "$C_{1-6}$ alkoxy group" refers to a group in which the above "$C_{1-6}$ alkyl group" is bonded to an oxygen atom. Examples thereof include a methoxy group, an ethoxy group, a n-propoxy group, an isopropoxy group, a n-butoxy group, a sec-butoxy group, a tert-butoxy group, a n-pentoxy group, an isopentoxy group, a 2-methylbutoxy group, a n-hexyloxy group and the like.

In the present invention, the ($C_{1-6}$ alkyl)carbamoyl group refers to a group in which one hydrogen atom of a carbamoyl group is substituted with the above "$C_{1-6}$ alkyl group". Examples thereof include a methylcarbamoyl group, an ethylcarbamoyl group, a propylcarbamoyl group, an isopropylcarbamoyl group, a sec-butylcarbamoyl group, a 1-ethylpropylcarbamoyl group and the like.

In the present invention, the "di($C_{1-6}$ alkyl)carbamoyl group" refers to a group in which two hydrogen atoms of a carbamoyl group are substituted with the same or different two of the above "$C_{1-6}$ alkyl groups". Examples thereof include a dimethylcarbamoyl group, an ethyl(methyl)carbamoyl group, a methyl(propyl)carbamoyl group, a diethylcarbamoyl group, a dipropylcarbamoyl group, a diisopropylcarbamoyl group, a sec-butyl(pentyl)carbamoyl group and the like.

In the present invention, the "hydroxy $C_{1-6}$ alkyl group" refers to a group in which one hydrogen atom of the above "$C_{1-6}$ alkyl group" is substituted with a hydroxy group. Examples thereof include a hydroxymethyl group, a 1-hydroxyethyl group, a 2-hydroxyethyl group, a 1-hydroxypropyl group, a 2-hydroxypropyl group, a 1-hydroxyisopropyl group, a 1-hydroxybutyl group, a 2-hydroxybutyl group, a 1-hydroxypentyl group, a 2-hydroxypentyl group, a 1-hydroxyhexyl group and the like.

In the present invention, the "hydroxy $C_{1-6}$ alkoxy group" refers to a group in which one hydrogen atom of the above "$C_{1-6}$ alkoxy group" is substituted with a hydroxy group. Examples thereof include a hydroxymethoxy group, a 2-hydroxyethoxy group, a 2-hydroxypropoxy group, a 3-hydroxypropoxy group, a 2-hydroxy-1-methyl-ethoxy group, a 3-hydroxybutoxy group, a 2-hydroxybutoxy group, a 2-hydroxypentoxy group, a 5-hydroxypentoxy group, a 4-hydroxyhexoxy group and the like.

In the present invention, the "$C_{1-6}$ alkylamino group" refers to a group in which one hydrogen atom of an amino group is substituted with the above "$C_{1-6}$ alkyl group". Examples thereof include a methylamino group, an ethylamino group, a n-propylamino group, an isopropylamino group, a n-butylamino group, a sec-butylamino group, a tert-butylamino group, a n-pentylamino group and the like.

In the present invention, the "di($C_{1-6}$ alkyl)amino group" refers to a group in which two hydrogen atoms of an amino group are substituted with the same or different two of the above "$C_{1-6}$ alkyl groups". Examples thereof include a dimethylamino group, a methyl(ethyl)amino group, a methyl(propyl)amino group [e.g., a N-methyl-N-(1-propyl)amino group etc.], a methyl(butyl)amino group [e.g., a N-(1-butyl)-N-methylamino group etc.], a methyl(pentyl)amino group, a methyl(hexyl)amino group, a diethylamino group, an ethyl(propyl)amino group [e.g., a N-ethyl-N-(1-propyl)amino group etc.], an ethyl(butyl)amino group, a dipropylamino group, a propyl(butyl)amino group, a dibutylamino group, a dipentylamino group, a dihexylamino group and the like.

In the present invention, the "halogeno $C_{1-6}$ alkyl group" refers to a group in which one to three hydrogen atoms of the above "$C_{1-6}$ alkyl group" are substituted with the above "halogen atoms". Examples thereof include a fluoromethyl group, a difluoromethyl group, a trifluoromethyl group, a chloromethyl group, a dichloromethyl group, a trichloromethyl group, a 1-fluoroethyl group, a 1-chloroethyl group, a 2-fluoroethyl group, a 1,2-difluoropropyl group, a 2,2,2-trifluoroethyl group and the like.

In the present invention, the "$C_{3-8}$ cycloalkyl group" refers to a 3- to 8-membered monocyclic saturated hydrocarbon group (ring). Examples thereof include a cyclopropyl group, a cyclobutyl group, a cyclopentyl group, a cyclohexyl group, a cycloheptyl group and a cyclooctyl group.

In the present invention, the "$C_{3-8}$ cycloalkyl $C_{1-6}$ alkyl group" refers to a group in which one hydrogen atom of the above "$C_{1-6}$ alkyl group" is substituted with the above "$C_{3-8}$ cycloalkyl group". Examples thereof include a cyclopropylmethyl group, a 2-cyclobutylethyl group, a 3-cyclopentylbutyl group, a 3-cycloheptyl-2-methyl-butyl group and the like.

In the present invention, the "$C_{1-6}$ alkoxy $C_{1-6}$ alkyl group" refers to a group in which one hydrogen atom of the above "$C_{1-6}$ alkyl group" is substituted with the above "$C_{1-6}$ alkoxy group". Examples thereof include a methoxymethyl group, an ethoxymethyl group, a n-propoxymethyl group, an isopropoxymethyl group, a 2-methoxyethyl group, a 2-ethoxyethyl group, a 1-propoxyethyl group, a 1-isopropoxyethyl group and the like.

In the present invention, the "oxetanyl group" refers to an oxetan-3-yl group or an oxetan-2-yl group.

In the present invention, the "($C_{1-6}$ alkyl)pyrimidinyl group" refers to a group in which one hydrogen atom of a pyrimidinyl group is substituted with the above "$C_{1-6}$ alkyl group". Examples thereof include a 4-isopropylpyrimidin-5-yl group, a 5-methylpyrimidin-2-yl group, a 5-sec-butylpyrimidin-4-yl group, a 4-pentylpyrimidin-5-yl group and the like.

In the present invention, the "($C_{1-6}$ alkyl)phenyl group" refers to a group in which one hydrogen atom of a phenyl group is substituted with the above "$C_{1-6}$ alkyl group". Examples thereof include a 3-tolyl group, a 2-ethylphenyl group, a 2-isopropylphenyl group, a 4-(2,3-dimethylbutyl)phenyl group and the like.

In the present invention, the "($C_{1-6}$ alkyl)pyrazolyl group" refers to a group in which one hydrogen atom of a pyrazolyl group is substituted with the above "$C_{1-6}$ alkyl group". Examples thereof include a 3-methyl-1H-pyrazol-4-yl group, a 2-isopropylpyrazol-3-yl group, a 4-isopentyl-1H-pyrazol-5-yl group, a 3-hexylpyrazol-1-yl group and the like.

In the present invention, the "$C_{1-6}$ alkylsulfonyl group" refers to a group in which the above "$C_{1-6}$ alkyl group" is bonded to a sulfur atom of a sulfonyl group. Examples thereof include a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group and the like.

In the present invention, the "$C_{1-6}$ alkylene group" refers to a linear or branched alkylene group having 1 to 6 carbon atoms. Examples thereof include a methylene group, an ethylene group [—$(CH_2)_2$—], a trimethylene group [—$(CH_2)_3$—], a tetramethylene group, a pentamethylene group, a hexamethylene group, a methylmethylene group [—CH(CH$_3$)—], a methylethylene group [—CH(CH$_3$)CH$_2$— or —CH$_2$CH(CH$_3$)—], an ethylethylene group [—CH(CH$_2$CH$_3$)CH$_2$— or —CH$_2$CH(CH$_2$CH$_3$)—], a 1,2-dimethylethylene group [—CH(CH$_3$)CH(CH$_3$)—], a 1,1,2,2-tetramethylethylene group [—C(CH$_3$)$_2$C(CH$_3$)$_2$—] and the like.

In the present invention, the "vinylsulfonylamino($C_{1-6}$ alkyl)carbamoyl group" refers to a group in which one hydrogen atom of a carbamoyl group is substituted with the following "vinylsulfonylamino($C_{1-6}$ alkyl) group". Examples thereof include a (vinylsulfonylamino)methylcarbamoyl group, a 2-(vinylsulfonylamino)ethylcarbamoyl group, a 3-(vinylsulfonylamino)propylcarbamoyl group, a 2-[(vinylsulfonylamino)methyl]butylcarbamoyl group and the like.

In the present invention, the "vinylsulfonylamino($C_{1-6}$ alkyl) group" refers to a group in which one hydrogen atom of the above "$C_{1-6}$ alkyl group" is substituted with the following "vinylsulfonylamino group". Examples thereof include a (vinylsulfonylamino)methyl group, a 1-(vinylsulfonylamino)ethyl group, a 3-(vinylsulfonylamino)propyl group, a 3-methyl-4-(vinylsulfonylamino)butyl group and the like.

In the present invention, the "vinylsulfonylamino group" refers to a group in which one hydrogen atom of an amino group is substituted with the following "vinylsulfonyl group".

In the present invention, the "vinylsulfonyl group" refers to a group in which a vinyl group is bonded to a sulfur atom of a sulfonyl group.

In the present invention, the "prop-2-enoylamino($C_{1-6}$ alkyl)carbamoyl group" refers to one hydrogen atom of a carbamoyl group is substituted with the following "prop-2-enoylamino($C_{1-6}$ alkyl) group". Examples thereof include a (prop-2-enoylamino)methylcarbamoyl group, a 2-(prop-2-enoylamino)ethylcarbamoyl group, a 3-(prop-2-enoylamino)propylcarbamoyl group, a [2-methyl-3-(prop-2-enoylamino)propyl]carbamoyl group, a 2-(prop-2-enoylamino)pentylcarbamoyl group and the like.

In the present invention, the "prop-2-enoylamino($C_{1-6}$ alkyl) group" refers to a group in which one hydrogen atom of the above "$C_{1-6}$ alkyl group" is substituted with the following "prop-2-enoylamino group". Examples thereof include a (prop-2-enoylamino)methyl group, a 2-(prop-2-enoylamino)ethyl group, a 3-(prop-2-enoylamino)propyl group, a 2-methyl-3-(prop-2-enoylamino)propyl group, a 4-(prop-2-enoylamino)butyl group, a 6-(prop-2-enoylamino)hexyl group and the like.

In the present invention, the "prop-2-enoylamino group" refers to a group in which one hydrogen atom of an amino group is substituted with the following "prop-2-enoyl group".

In the present invention, the "prop-2-enoyl group" refers to a group in which a vinyl group is bonded to a carbon atom of a carbonyl group.

In the present invention, the "$C_{1-6}$ alkyl ($C_{1-6}$ alkylsulfonyl)amino group" refers to a group in which two hydrogen atoms of an amino group are substituted with the above "$C_{1-6}$ alkyl group" and the above "$C_{1-6}$ alkylsulfonyl". Examples thereof include a methyl(methylsulfonyl)amino group, an ethyl(isopropylsulfonyl)amino group, a butylsulfonyl(propyl)amino group, a hexylsulfonyl(isobutyl)amino group and the like.

In the present invention, the "$C_{1-6}$ alkoxy $C_{1-6}$ alkoxy group" refers to a group in which one hydrogen atom of the above "$C_{1-6}$ alkoxy group" is substituted with the above "$C_{1-6}$ alkoxy group". Examples thereof include a methoxymethoxy group, an ethoxymethoxy group, a n-propoxymethoxy group, an isopropoxymethoxy group, a methoxyethoxy group, an ethoxyethoxy group, a n-propoxyethoxy group, an isopropoxyethoxy group and the like.

In the present invention, the "halogeno $C_{1-6}$ alkoxy group" refers to a group in which one or two hydrogen atoms of the above "$C_{1-6}$ alkoxy group" are substituted with the above "halogen atoms". Examples thereof include a fluoromethoxy group, a difluoromethoxy group, a chloromethoxy group, a dichloromethoxy group, a 1-fluoroethoxy group, a 1-chloroethoxy group, a 2-fluoroethoxy group, a 1,2-difluoropropoxy group and the like.

In the present invention, the "$C_{1-6}$ alkylsulfonyl $C_{1-6}$ alkyl group" refers to a group in which one hydrogen atom of the above "$C_{1-6}$ alkyl group" is substituted with the above "$C_{1-6}$ alkylsulfonyl group". Examples thereof include a methylsulfonylmethyl group, a methylsulfonylethyl group, an ethylsulfonylmethyl group, a n-propylsulfonylmethyl group, an isopropylsulfonylmethyl group, a n-butylsulfonylmethyl group, a sec-butylsulfonylmethyl group, a tert-butylsulfonylmethyl group, a tert-butylsulfonylethyl group, a n-pentylsulfonylmethyl group and the like.

In the present invention, the "di($C_{1-6}$ alkyl)sulfamoyl group" refers to a group in which two hydrogen atoms of the following "sulfamoyl group" are substituted with the same or different two of the above "$C_{1-6}$ alkyl groups". Examples thereof include a dimethylsulfamoyl group, an ethyl(methyl)sulfamoyl group, an ethyl(isopropyl)sulfamoyl group, a dibutylsulfamoyl group, a hexyl(isopentyl)sulfamoyl group and the like.

In the present invention, the "sulfamoyl group" refers to an amino group is bonded to a sulfur atom of a sulfonyl group.

In the present invention, the "$C_{1-6}$ alkylenedioxy group" refers to a group in which two hydrogen atoms of the above "$C_{1-6}$ alkyl group" are substituted with oxy groups (—O—). Examples thereof include a methylenedioxy group (—OCH$_2$O—), an ethylenedioxy group [—O(CH$_2$)$_2$O—], a trimethylenedioxy group [—O(CH$_2$)$_3$O—], a methylethylenedioxy group [—OCH(CH$_3$)CH$_2$O— or —OCH$_2$CH(CH$_3$)O—] and the like.

In the present invention, the "2-$C_{3-6}$ alkenoylamino group" refers to a group in which one hydrogen atom of an amino group is substituted with the following "2-$C_{3-6}$ alkenoyl group". Examples thereof include a prop-2-enoylamino group, a 2-methylprop-2-enoylamino group, a 3-methylbuta-2-enoylamino group, an [(E)-penta-2-enoyl]amino group, an [(E)-3-methylpenta-2-enoyl]amino group and the like.

In the present invention, the "2-$C_{3-6}$ alkenoyl group" refers to a group in which the following "1-$C_{2-5}$ alkenyl group" is bonded to a carbon atom of a carbonyl group. Examples thereof include a prop-2-enoyl group, an (E)-buta-2-enoyl group, a 3-methylbuta-2-enoyl group, an (E)-hexa-2-enoyl group, a 2-methylprop-2-enoyl group, a 3-methyl-2-methylene-butanoyl group and the like.

In the present invention, the "1-$C_{2-5}$ alkenyl group" refers to a linear or branched alkenyl group having 2 to 5 carbon atoms (the bonding site of the alkenyl group is present on the unsaturated carbon atom). Examples thereof include an (E)-prop-1-enyl group, a 2-methylprop-1-enyl group, an (E)-pent-1-enyl group, an isopropenyl group, a 1-methylenebutyl group, a (Z)-1-ethylprop-1-enyl group and the like.

In the present invention, the "$C_{1-6}$ alkyl (2-$C_{3-6}$ alkenoyl)amino group" refers to a group in which two hydrogen atoms of an amino group are substituted with the above "$C_{1-6}$ alkyl group" and the above "2-$C_{3-6}$ alkenoyl group". Examples thereof include a methyl(prop-2-enoyl)amino group, an ethyl(2-methylprop-2-enoyl)amino group, a 3-methylbuta-2-enoyl(propyl)amino group, an isopropyl-[(E)-penta-2-enoyl]amino group and the like.

In the present invention, the "($^2$H$_3$)methoxy group" refers to a group in which three hydrogen atoms of a methoxy group are all substituted with deuteriums ($^2$H; D).

In the present invention, the "bis[($^2$H$_3$)methyl]amino group" refers to a group in which six hydrogen atoms of a dimethylamino group are all substituted with deuteriums ($^2$H; D).

In the present invention, the "when a ring has a oxo group" refers to a case where an oxo group is bonded to a ring-constituting atom. For example, when a pyridine ring has an oxo group, examples thereof include a 1H-pyridin-2-one ring, a 4H-pyridin-3-one and the like, and when a pyridazine ring has an oxo group, examples thereof include a 1H-pyridazin-6-one ring and the like.

In the present invention, the "6-membered aromatic ring optionally containing one nitrogen atom in the ring" refers to a 6-membered monocyclic aromatic ring optionally containing one nitrogen atom as a ring-constituting atom, besides a carbon atom. Examples thereof include a benzene ring and a pyridine ring. The "6-membered aromatic ring optionally containing one nitrogen atom in the ring" for Ring $Q^1$ is preferably a benzene ring or a pyridine ring, more preferably a benzene ring. The "6-membered aromatic ring optionally containing one nitrogen atom in the ring" for Ring $Q^2$ is preferably a benzene ring or a pyridine ring, more preferably a pyridine ring. The "6-membered aromatic ring optionally containing one nitrogen atom in the ring" for Ring $Q^3$ is preferably a benzene ring or a pyridine ring, more preferably a pyridine ring.

In the present invention, the "5-membered aromatic heterocycle containing, in the ring, one or two heteroatoms independently selected from the group consisting of a nitrogen atom and a sulfur atom" refers to a 5-membered monocyclic aromatic ring containing one or two heteroatoms (a nitrogen atom or a sulfur atom) as a ring-constituting atom, besides a carbon atom. Examples thereof include a thiophene ring, a 1,2-thiazole ring, a 1,3-thiazole ring, a pyrrole ring, a pyrazole ring and an imidazole ring. The "5-membered aromatic heterocycle containing, in the ring, one or two heteroatoms independently selected from the group consisting of a nitrogen atom and a sulfur atom" for Ring $Q^1$ is preferably a 1,3-thiazole ring or a pyrazole ring.

In the present invention, the "$C_{3-8}$ cycloalkane ring" refers to a 3- to 8-membered monocyclic saturated hydrocarbon ring. Examples thereof include a cyclopropane ring, a cyclobutane ring, a cyclopentane ring, a cyclohexane ring, a cycloheptane ring and a cyclooctane ring. The "$C_{3-8}$ cycloalkane ring" for Ring $Q^1$ is preferably a cyclohexane ring. The "$C_{3-8}$ cycloalkane ring" for Ring $Q^2$ is preferably a cyclohexane ring.

In the present invention, the "$C_{4-8}$ cycloalkene ring" refers to a 4- to 8-membered monocyclic unsaturated hydrocarbon ring having one double bond in the ring. Examples thereof include a cyclobutene ring, a cyclopentene ring, a cyclohexene ring, a cycloheptene ring and a cyclooctene ring. The "$C_{4-8}$ cycloalkene ring" for Ring $Q^1$ is preferably a cyclohexene ring.

In the present invention, the "4- to 8-membered saturated heterocycle containing one nitrogen atom in the ring" refers to a 4- to 8-membered monocyclic saturated ring containing one nitrogen atom as a ring-constituting atom, besides a carbon atom. Examples thereof include an azetidine ring, a pyrrolidine ring, a piperidine ring, an azepane ring and an azocane ring. The "4- to 8-membered saturated heterocycle containing one nitrogen atom in the ring" for Ring $Q^1$ is preferably a piperidine ring.

In the present invention, the "9-membered bicyclic aromatic heterocycle containing one nitrogen atom in the ring" refers to a 9-membered bicyclic fused aromatic ring containing one nitrogen atom as a ring-constituting atom, besides a carbon atom. Examples thereof include an indole ring, an isoindole ring, an indolizine ring and the like. The "9-membered bicyclic aromatic heterocycle containing one nitrogen atom in the ring" for Ring $Q^1$ is preferably an indole ring.

In the present invention, the "6-membered aromatic heterocycle containing two nitrogen atoms in the ring" refers to a 6-membered monocyclic aromatic ring containing two nitrogen atoms as a ring-constituting atom, besides a carbon atom. Examples thereof include a pyridazine ring, a pyrazine ring and a pyrimidine ring. The "6-membered aromatic heterocycle containing two nitrogen atoms in the ring" for Ring $Q^2$ is preferably a pyridazine ring, a pyrazine ring or a pyrimidine ring.

In the present invention, the "5-membered aromatic heterocycle containing, in the ring, one to three heteroatoms independently selected from the group consisting of a nitrogen atom, an oxygen atom and a sulfur atom" refers to a 5-membered monocyclic aromatic ring containing one to three heteroatoms (a nitrogen atom, an oxygen atom or a sulfur atom) as a ring-constituting atom, besides a carbon atom. Examples thereof include a pyrrole ring, a furan ring, a thiophene ring, an imidazole ring, a pyrazole ring, a 1,2-oxazole ring, a 1,3-oxazole ring, a 1,2-thiazole ring, a 1,3-thiazole ring, a 4H-1,2,4-triazole ring, a 1H-1,2,3-triazole ring, a 1,2,4-oxadiazole ring, a 1,3,4-thiadiazole ring and the like. The "5-membered aromatic heterocycle containing, in the ring, one to three heteroatoms independently selected from the group consisting of a nitrogen atom, an oxygen atom and a sulfur atom" for Ring $Q^2$ is preferably an imidazole ring, a pyrazole ring, a 1,3-thiazole ring, a 1,3-oxazole ring or a 4H-1,2,4-triazole ring.

In the present invention, the "9- or 10-membered bicyclic aromatic or partially unsaturated heterocycle containing, in the ring, one to three heteroatoms independently selected from the group consisting of a nitrogen atom and an oxygen atom" refers to a ring derived from a 9- or 10-membered bicyclic fused aromatic ring containing one to three heteroatoms (a nitrogen atom or an oxygen atom) as a ring-constituting atom, besides a carbon atom, which optionally having a saturated bond in a part of the bicyclic ring. Examples thereof include an indole ring, a benzofuran ring, an indazole ring, a benzimidazole ring, a 1H-pyrrolo[2,3-c]pyridine ring, a 1H-pyrrolo[3,2-c]pyridine ring, a furo[3,2-b]pyridine ring, a 1H-pyrazolo[3,4-c]pyridine ring, a quinoline ring, an isoquinoline ring, a 1,8-naphthyridine ring, an indoline ring and the like. The "9- or 10-membered bicyclic aromatic or partially unsaturated heterocycle containing, in the ring, one to three heteroatoms independently selected from the group consisting of a nitrogen atom and an oxygen atom" for Ring $Q^2$ is preferably an isoquinoline ring, an indazole ring, a benzimidazole ring, a 1H-pyrrolo[2,3-c]pyridine ring, a 1H-pyrrolo[3,2-c]pyridine ring, a furo[3,2-b]pyridine ring, a 1H-pyrazolo[3,4-c]pyridine ring or an indoline ring.

In the present invention, the "5- to 8-membered saturated heterocycle containing, in the ring, one or two heteroatoms independently selected from the group consisting of an oxygen atom and a nitrogen atom" refers to a 5- to 8-membered monocyclic saturated ring containing one or two heteroatoms (a nitrogen atom or an oxygen atom) as a ring-constituting atom, besides a carbon atom. Examples thereof include a pyrrolidine ring, a piperidine ring, a piperazine ring, a morpholine ring, an azepane ring, an oxazepane ring, a 1,4-oxazepane ring, a 1,4-diazocane ring and the like. The "5- to 8-membered saturated heterocycle containing, in the ring, one or two heteroatoms independently selected from the group consisting of an oxygen atom and a nitrogen atom" for Ring $Q^2$ is preferably a pyrrolidine ring, a piperidine ring, a morpholine ring or an azepane ring.

In the present invention, the "4- to 8-membered saturated heterocycle containing one nitrogen atom or one oxygen atom in the ring" refers to a 4- to 8-membered monocyclic saturated ring containing one heteroatom (a nitrogen atom or an oxygen atom) as a ring-constituting atom, besides a carbon atom. Examples thereof include an azetidine ring, an oxetane ring, a pyrrolidine ring, a tetrahydrofuran ring, a piperidine ring, a tetrahydropyran ring, an azepane ring and the like. The "4- to 8-membered saturated heterocycle containing one nitrogen atom or one oxygen atom in the ring" for Ring $Q^3$ is preferably an azetidine ring, a tetrahydropyran ring or a piperidine ring.

In the present invention, the "heterocycle containing a nitrogen atom in the ring" refers to a heterocycle containing a nitrogen atom as a ring-constituting atom, besides a carbon atom. Examples thereof include a piperidine ring, an azepane ring and the like.

In the present invention, the borono group refers to a group in which two hydrogen atoms of a boranyl group are both substituted with hydroxy groups.

In the present invention, the dialkoxyboranyl group refers to a group in which two hydrogen atoms of a boranyl group are both substituted with alkoxy groups (e.g., a methoxy group, an ethoxy group, etc.). Examples thereof include a dimethoxyboranyl group, a diethoxyboranyl group and the like.

In the present invention, the dioxaborolanyl group refers to a group derived from a ring formed by two alkoxy groups bonded to the boron atom of the above dialkoxyboranyl group taken together with the boron atom. Examples thereof include a 4,4,5,5-tetramethyl-1,3,2-dioxaborolan-2-yl group and the like.

In the present invention, menin refers to a tumor-suppressor protein identified as a causal factor of multiple endocrine neoplasia type 1 (MEN1), which is an ubiquitously expressed nucleoprotein that is involved in DNA processing, modified proteins, protein-modifying chromatin, and interactions with numerous transcription factors (Agarwal, et al.; Horm Metab Res, 2005, 37(6):369-374).

In the present invention, the MLL protein refers to MLL1, MLL2, a MLL fusion protein or a MLL partial tandem duplication protein.

In the present invention, the MLL1 refers to MLL1 (also known as KMT2A) protein, which is one of methyltransferases belonging to MLL (mixed lineage leukemia) family. In the present invention, the term MLL1 gene indicates a gene encoding the protein.

In the present invention, the MLL2 refers to MLL2 (also known as KMT2D) protein, which is one of methyltransferases belonging to MLL (mixed lineage leukemia) family. In the present invention, the term MLL2 gene indicates a gene encoding the protein.

In the present invention, the MLL fusion protein refers to a chimeric protein produced by transcription and expression of a chimeric gene caused by chromosomal translocation of a MLL gene.

In the present invention, the MLL partial tandem duplication (PTD) protein refers to an abnormal protein produced by transcription and expression of an abnormal gene caused by chromosomal duplication of a MLL gene.

In the present invention, the interaction between menin and one or more proteins selected from the group consisting of MLL1, MLL2, a MLL fusion protein and a MLL partial tandem duplication protein refers to an interaction between protein molecules formed by menin and MLL1, MLL2, a MLL fusion proteins or a MLL partial tandem duplication protein. When two or more types of MLL proteins are present in the same system, two or more interactions between protein molecules formed independently by menin and each MLL protein may coexist.

In the present invention, the terms "tumor" and "cancer" are used interchangeably. Furthermore, in the present invention, tumor, malignant tumor, cancer, malignant neoplasm, carcinoma, sarcoma and the like may be collectively referred to as "tumor" or "cancer". Moreover, the terms "tumor" and "cancer" also include pathological conditions categorized into a premalignant stage in some cases, such as myelodysplastic syndrome.

As used herein, the term "treat" and its derivatives mean remission, alleviation or delay of exacerbation of clinical symptoms of diseases, illnesses, disorders and the like (hereinafter referred to as "diseases and the like") in a patient who develops the diseases and the like.

As used herein, the term "prevent" and its derivatives mean inhibiting, suppressing, controlling, slowing or stopping the onset of clinical symptoms of the diseases and the like in a mammal who may develop the diseases and the like, but have not yet developed, or are concerned about recurrence of the diseases and the like after treatment.

In the present invention, the "Bcl-2 inhibitor" refers to a drug that binds to Bcl-2, which is a protein having an anti-apoptotic action, to inhibit the anti-apoptotic action, and as a result, induces apoptosis to exert an anti-cancer action. In the present invention, the "Bcl-2 inhibitor" is preferably Venetoclax.

In the present invention, the "pyrimidine antimetabolite" refers to a drug that has a partial structure similar to that of a pyrimidine base, and inhibits nucleic acid biosynthesis to prevent the growth and division of tumor cells, and as a result, exerts an anti-cancer action.

In the present invention, the "pyrimidine antimetabolite" is preferably Cytarabine.

In the present invention, the "DNA methyltransferase inhibitor" refers to a drug that inhibits an enzyme that catalyzes transmethylation of DNA, and as a result, exerts an anti-cancer action.

In the present invention, the "DNA methyltransferase inhibitor" is preferably Azacitidine.

In the present invention, Venetoclax is 4-(4-{[2-(4-chlorophenyl)-4,4-dimethylcyclohex-1-en-1-yl]methyl}piperazin-1-yl)-N-[(3-nitro-4-{[(oxan-4-yl)methyl]amino}phenyl)sulfonyl]-2-[(1H-pyrrolo[2,3-b]pyridin-5-yl)oxy]benzamide (CAS registry number: 1257044-40-8), and is also referred to as VENCLEXTA (registered trademark), VENCLYXTO (registered trademark) or Venetoclax. It is readily available as a commercial product.

In the present invention, Azacitidine is 4-amino-1-β-D-ribofuranosyl-1,3,5-triazin-2(1H)-one (CAS registry number: 320-67-2), and is also referred to as 5-Azacitidine or 5Aza, or as Vidaza (registered trademark). It is readily available as a commercial product.

In the present invention, Cytarabine is 1-β-D-arabinofuranosylcytosine (CAS registry number: 147-94-4), and is also referred to as Ara-C or AraC, or as CYLOCIDE (registered trademark). It is readily available as a commercial product.

In the present invention, Venetoclax, Azacitidine or Cytarabine may be a free form, a solvate, any of various pharmaceutically acceptable salts, or in the form of a pharmaceutical composition contained with various pharmaceutically acceptable carriers, and the like.

In the present invention, the term "administered in combination" means that both drugs are taken into the body of the subject to be administered for a certain period of time. Both drugs may be administered in a single formulation, or each may be formulated separately and administered separately. When they are formulated separately, the timing of their administrations is not particularly limited, and they may be administered at the same time, at different times at intervals, or on different days.

When they are administered at different times or on different days, the order of their administrations is not particularly limited. Generally, their formulations are administered according to their respective administration methods, so that the formulations may be administered in the same number of doses or in a different number of doses. In addition, when they are formulated separately, the respective administration methods (administration routes) of the formulations may be the same as each other, or the formulations may be administered by different administration methods (administration routes). Moreover, both drugs do not have to exist in the body at the same time, and may be taken into the body for a certain period of time (e.g., one month, preferably one week, more preferably several days, even more preferably one day). One of the active ingredients may have disappeared from the body at the time of administration of the other active ingredient.

Suitable substituents in the compound of the present invention will be described below.

$R^1$ is preferably a hydrogen atom or a methyl group. $R^1$ is more preferably a hydrogen atom.

$R^2$ is preferably a hydrogen atom or a methyl group. $R^2$ is more preferably a hydrogen atom.

One of $R^3$ and $R^4$ is preferably a hydrogen atom, a hydroxy group, a fluorine atom, a methoxy group, a dimethylcarbamoyl group, or an oxazol-2-yl group, more preferably a hydrogen atom or a hydroxy group. The other of $R^3$ and $R^4$ is preferably a hydrogen atom, a hydroxy group, a fluorine atom, or a methoxy group, more preferably a hydrogen atom or a hydroxy group.

The moiety represented by the following formula (5) in the formula (1) is preferably the following formula (5A) or (5B).

[Formula 36]

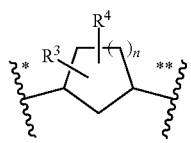
(5)

[Formula 37]

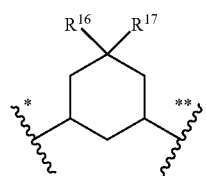
(5A)

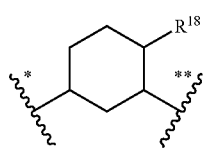
(5B)

wherein * is bonded to the nitrogen atom to which $R^2$ is bonded, ** is bonded to the nitrogen atom to which $R^5$ is bonded, $R^{16}$ is a hydrogen atom, a halogen atom, a hydroxy group, a di($C_{1-6}$ alkyl)carbamoyl group, an oxazol-2-yl group, or a $C_{1-6}$ alkoxy group, $R^{17}$ is a hydrogen atom or a halogen atom, and $R^{18}$ is a $C_{1-6}$ alkoxy group.

The moiety represented by the following formula (5) in the formula (1) is more preferably any of the following formulas (6A) to (6D), still more preferably (6A) or (6B).

[Formula 38]

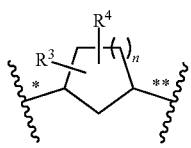
(5)

[Formula 39]

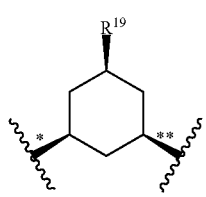
(6A)

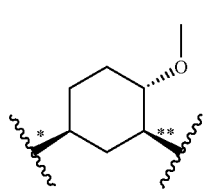
(6B)

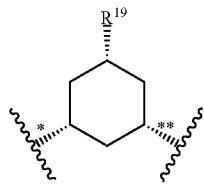
(6C)

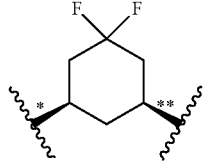
(6D)

wherein * is bonded to the nitrogen atom to which $R^2$ is bonded, ** is bonded to the nitrogen atom to which $R^5$ is bonded, and $R^{19}$ is a hydrogen atom, a hydroxy group, a dimethylcarbamoyl group, an oxazol-2-yl group, or a methoxy group.

The moiety represented by the following formula (5) in the formula (1) is preferably the following formula (7A).

[Formula 40]

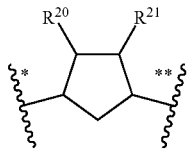
(5)

[Formula 41]

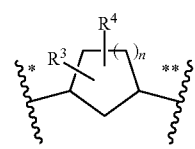
(7A)

wherein * is bonded to the nitrogen atom to which $R^2$ is bonded, ** is bonded to the nitrogen atom to which $R^5$ is bonded, $R^{20}$ is a hydrogen atom or a hydroxy group, and $R^{21}$ is a hydrogen atom, a hydroxy group, or a $C_{1-6}$ alkoxy group.

The moiety represented by the following formula (5) in the formula (1) is more preferably any of the following formulas (8A) to (8F), still more preferably any of (8A) to (8E).

[Formula 42]

(5)

-continued

[Formula 43]

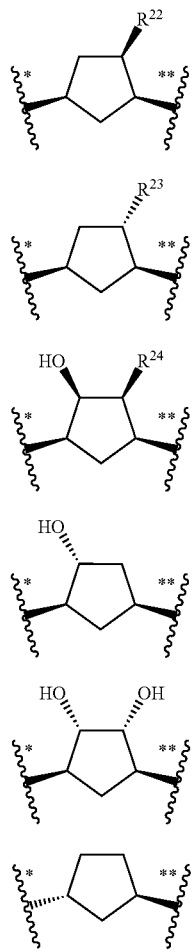

(8A)

(8B)

(8C)

(8D)

(8E)

(8F)

wherein * is bonded to the nitrogen atom to which $R^2$ is bonded, ** is bonded to the nitrogen atom to which $R^5$ is bonded, $R^{22}$ is a hydrogen atom, a hydroxy group or a methoxy group, $R^{23}$ is a hydroxy group or a methoxy group, and $R^{24}$ is a hydrogen atom or a hydroxy group.

The moiety represented by the following formula (5) in the formula (1) is most preferably any of the following formulas (9A) to (9C). Among the following formulas (9A) to (9C), it is preferably (9B) or (9C), more preferably (9B).

[Formula 44]

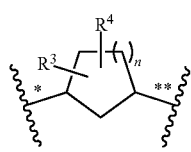

(5)

[Formula 45]

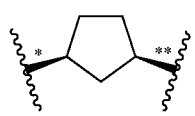

(9A)

-continued

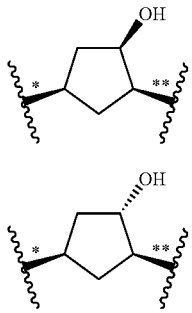

(9B)

(9C)

wherein * is bonded to the nitrogen atom to which $R^2$ is bonded, and ** is bonded to the nitrogen atom to which $R^5$ is bonded.

$R^5$ is preferably a hydrogen atom, a methyl group, an ethyl group, or a 2-hydroxyethyl group. $R^5$ is more preferably a methyl group.

$R^6$ is preferably a hydrogen atom, a methyl group, a chlorine atom, a methoxy group, an amino group, or a methylamino group. $R^6$ is more preferably a hydrogen atom, a chlorine atom, a methoxy group, an amino group, or a methylamino group. $R^6$ is still more preferably a hydrogen atom, a chlorine atom, a methoxy group, or a methylamino group.

As to $R^7$ and $R^8$, preferably, $R^7$ and $R^8$ are taken together with the carbon atom to which $R^7$ is bonded and the carbon atom to which $R^8$ is bonded to form the following formula (2A) or (2B).

[Formula 46]

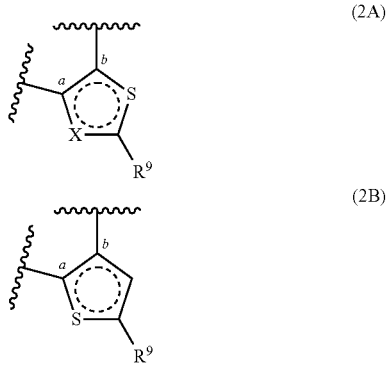

(2A)

(2B)

wherein the dotted circle indicates that the ring is aromatic, the carbon atom marked with a is the carbon atom to which $R^8$ is bonded, the carbon atom marked with b is the carbon atom to which $R^7$ is bonded, X is CH or a nitrogen atom, and $R^9$ is a halogeno $C_{1-6}$ alkyl group, a $C_{3-8}$ cycloalkyl group, a $C_{3-8}$ cycloalkyl $C_{1-6}$ alkyl group, a $C_{1-6}$ alkoxy $C_{1-6}$ alkyl group, or an oxetanyl group.

$R^9$ is preferably a 2,2,2-trifluoroethyl group, a cyclopropyl group, a cyclopropylmethyl group, a methoxymethyl group, or an oxetan-3-yl group. $R^9$ is more preferably a 2,2,2-trifluoroethyl group, a cyclopropyl group, or a cyclopropylmethyl group. $R^9$ is still more preferably a 2,2,2-trifluoroethyl group.

As to $R^7$ and $R^8$, more preferably, $R^7$ and $R^8$ are taken together with the carbon atom to which $R^7$ is bonded and the carbon atom to which $R^8$ is bonded to form form the following formula (10A).

[Formula 47]

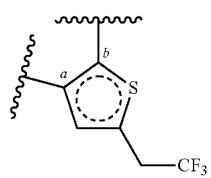

(10A)

wherein the dotted circle indicates that the ring is aromatic, the carbon atom marked with a is the carbon atom to which $R^8$ is bonded, and the carbon atom marked with b is the carbon atom to which $R^7$ is bonded.

As to $R^7$ and $R^8$, preferably, $R^7$ is a hydrogen atom, and $R^8$ is the following formula (3).

[Formula 48]

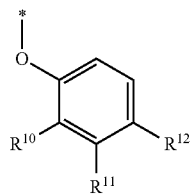

(3)

wherein * indicates a bonding site, $R^{10}$ is a di($C_{1-6}$ alkyl) carbamoyl group, a ($C_{1-6}$ alkyl)pyrimidinyl group, a ($C_{1-6}$ alkyl)phenyl group, or a ($C_{1-6}$ alkyl)pyrazolyl group, $R^{11}$ is a hydrogen atom or a halogen atom, and $R^{12}$ is a halogen atom.

$R^{10}$ is preferably a diisopropylcarbamoyl group, a 4-isopropylpyrimidin-5-yl group, a 2-isopropylphenyl group, or a 1-isopropylpyrazol-5-yl group. $R^{11}$ is preferably a hydrogen atom or a fluorine atom. $R^{12}$ is preferably a fluorine atom.

As to $R^7$ and $R^8$, more preferably $R^7$ is a hydrogen atom, and $R^8$ is the following formula (11A) or (11B).

[Formula 49]

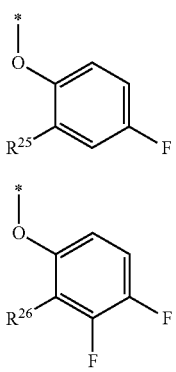

(11A)

(11B)

wherein * indicates a bonding site, $R^{25}$ is a diisopropylcarbamoyl group, a 4-isopropylpyrimidin-5-yl group, a 2-isopropylphenyl group, or a 1-isopropylpyrazol-5-yl group, and $R^{26}$ is a diisopropylcarbamoyl group.

m is preferably 1.

n is preferably 1.

Ring $Q^1$ is preferably any of the following (i) to (vii).

(i) a benzene ring optionally having one or two substituents independently selected from the above Group A;

(ii) a pyridine ring optionally having one or two substituents independently selected from the above Group A;

(iii) a 1,3-thiazole ring or a pyrazole ring (the 1,3-thiazole ring or pyrazole ring optionally has one substituent independently selected from the above Group A);

(iv) a cyclohexane ring optionally having one substituent independently selected from the above Group A;

(v) a cyclohexene ring optionally having one substituent independently selected from the above Group A;

(vi) a piperidine ring optionally having one substituent independently selected from the above Group A; or (vii) an indole ring optionally has one or two substituents independently selected from the above Group B.

When m is 0, then Ring $Q^1$ is more preferably any of the following (i) to (iv).

(i) a benzene ring optionally having one or two substituents independently selected from the above Group A;

(ii) a 1,3-thiazole ring or a pyrazole ring, each optionally having one substituent independently selected from the above Group A;

(iii) a cyclohexane ring optionally having one substituent independently selected from the above Group A; or (iv) an indole ring optionally having one substituent independently selected from the above Group B.

When m is 0, then Ring $Q^1$ is still more preferably a phenyl group, a 4-hydroxyphenyl group, a 4-[3-(prop-2-enoylamino)propylcarbamoyl]phenyl group, a 4-[3-(vinylsulfonylamino)propylcarbamoyl]phenyl group, a 3-fluoro-4-(2-hydroxyethoxy)phenyl group, a thiazol-5-yl group, a cyclohexyl group, or a 2-cyano-1H-indol-5-yl group.

When m is 1, then Ring $Q^1$ is more preferably any of the following (i) to (vii).

(i) a benzene ring optionally having one substituent independently selected from the above Group A;

(ii) a pyridine ring optionally having one substituent independently selected from the above Group A;

(iii) a pyrazole ring optionally having one substituent independently selected from the above Group A;

(iv) a cyclohexane ring optionally having one substituent independently selected from the above Group A;

(v) a cyclohexene ring optionally having one substituent independently selected from the above Group A;

(vi) a piperidine ring optionally having one substituent independently selected from the above Group A; or (vii) an indole ring optionally has one or two substituents independently selected from the above Group B.

When m is 1, then Ring $Q^1$ is still more preferably any of the following formulas (12A) to (12H).

[Formula 50]

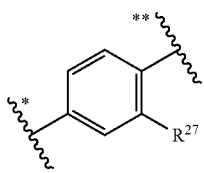

(12A)

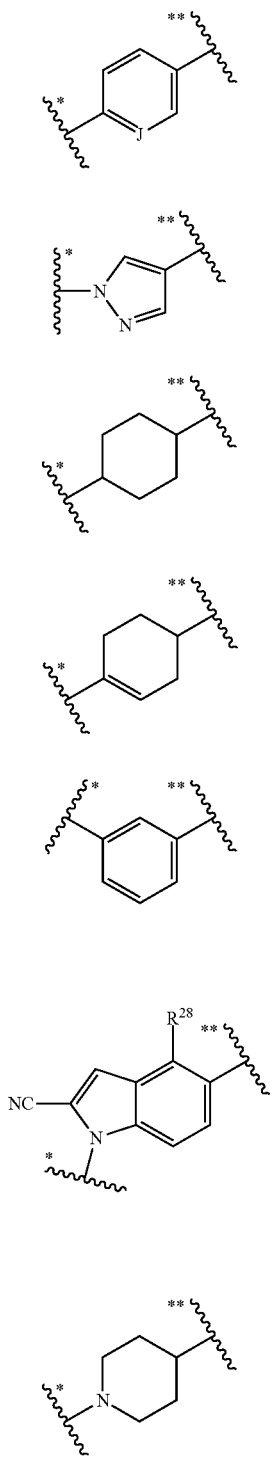

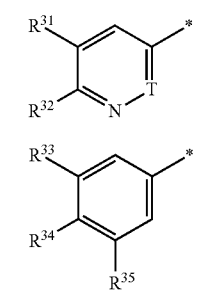

wherein * is bonded to Z, ** is bonded to the carbon atom to which R¹ is bonded, R²⁷ is a hydrogen atom, a halogen atom, a $C_{1-6}$ alkoxy group, or a $C_{1-6}$ alkyl group, J is a nitrogen atom or CR²⁹, R²⁹ is a halogen atom, and R²⁸ is a hydrogen atom or a $C_{1-6}$ alkyl group.

When m is 1, then Ring Q¹ is most preferably the following formula (13A) or (13B).

[Formula 51]

(13A)

(13B)

wherein * is bonded to Z, ** is bonded to the carbon atom to which R¹ is bonded, and R³⁰ is a hydrogen atom, a fluorine atom, a methyl group, or a methoxy group.

Ring Q² is preferably any of the following (i) to (vii).

(i) a benzene ring optionally having one to three substituents independently selected from the above Group C;
(ii) a pyridine ring optionally having one to three substituents independently selected from the above Group C;
(iii) a pyridazine ring, a pyrazine ring or a pyrimidine ring (the pyridazine ring, pyrazine ring or pyrimidine ring optionally has one to three substituents independently selected from the above Group C);
(iv) a pyrazole ring, an imidazole ring, a 1,3-thiazole ring, a 1,3-oxazole ring or a 4H-1,2,4-triazole ring (the pyrazole ring, imidazole ring, 1,3-thiazole ring, 1,3-oxazole ring or 4H-1,2,4-triazole ring optionally has one substituent independently selected from the above Group C);
(v) an isoquinoline ring, an indazole ring, a benzimidazole ring, a 1H-pyrrolo[2,3-c]pyridine ring, a 1H-pyrrolo[3,2-c]pyridine ring, a furo[3,2-b]pyridine ring, a 1H-pyrazolo[3,4-c]pyridine ring or an indoline ring (the isoquinoline ring, indazole ring, benzimidazole ring, 1H-pyrrolo[2,3-c]pyridine ring, 1H-pyrrolo[3,2-c]pyridine ring, furo[3,2-b]pyridine ring, 1H-pyrazolo[3,4-c]pyridine ring or indoline ring optionally has one or two substituents independently selected from the above Group D);
(vi) a pyrrolidine ring, a piperidine ring, a morpholine ring or an azepane ring (the pyrrolidine ring, piperidine ring, morpholine ring or azepane ring optionally has one substituent independently selected from the above Group E); or
(vii) a cyclohexane ring optionally having one substituent independently selected from the above Group E.

When W is the above formula (4A), then Ring Q² is more preferably any of the following formulas (14A) to (14F).

[Formula 52]

(14A)

(14B)

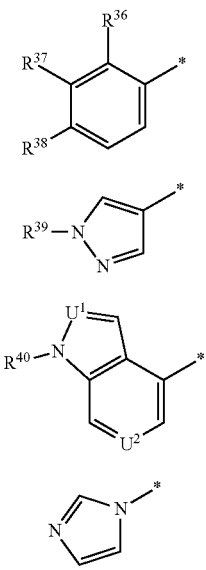

(14C)

(14D)

(14E)

(14F)

wherein * indicates a bonding site, T is CH or a nitrogen atom, $R^{31}$ is a hydrogen atom, a $C_{1-6}$ alkoxy group, a halogeno $C_{1-6}$ alkoxy group, or a ($^2H_3$)methoxy group, $R^{32}$ is a hydrogen atom, a $C_{1-6}$ alkyl group, a halogen atom, a $C_{1-6}$ alkoxy group, a cyano group, a di($C_{1-6}$ alkyl)amino group, a halogeno $C_{1-6}$ alkyl group, a $C_{1-6}$ alkylamino group, a $C_{1-6}$ alkylsulfonyl group, a $C_{1-6}$ alkoxy $C_{1-6}$ alkoxy group, a halogeno $C_{1-6}$ alkoxy group, a hydroxy $C_{1-6}$ alkyl group, a $C_{1-6}$ alkyl (2-$C_{3-6}$ alkenoyl)amino group, a ($^2H_3$)methoxy group, or a bis[($^2H_3$)methyl]amino group, or $R^{31}$ and $R^{32}$ are taken together to form an ethylenedioxy group, $R^{33}$ and $R^{35}$ are each independently a hydrogen atom, a halogen atom, a $C_{1-6}$ alkoxy group, a $C_{1-6}$ alkyl($C_{1-6}$ alkylsulfonyl)amino group, a ($C_{1-6}$ alkyl)carbamoyl group, a di($C_{1-6}$ alkyl)sulfamoyl group, a 2-$C_{3-6}$ alkenoylamino group, or a $C_{1-6}$ alkylsulfonyl $C_{1-6}$ alkyl group, $R^{34}$ is a hydrogen atom or a halogen atom, $R^{36}$ is a halogen atom, $R^{37}$ is a $C_{1-6}$ alkoxy group, $R^{38}$ is a halogen atom, $R^{39}$ is a $C_{1-6}$ alkyl group or a $C_{1-6}$ alkylsulfonyl group, $R^{40}$ is a $C_{1-6}$ alkyl group or a $C_{1-6}$ alkylsulfonyl group, $U^1$ is CH or a nitrogen atom, $U^2$ is $CR^{41}$ or a nitrogen atom, and $R^{41}$ is a hydrogen atom or a halogen atom.

$R^{31}$ is preferably a hydrogen atom, a methoxy group, a difluoromethoxy group, or a ($^2H_3$)methoxy group.

$R^{32}$ is preferably a hydrogen atom, a methyl group, a fluorine atom, a chlorine atom, a methoxy group, a cyano group, a dimethylamino group, a trifluoromethyl group, a methylamino group, a methylsulfonyl group, a methoxyethoxy group, a difluoromethoxy group, a hydroxymethyl group, a methyl(prop-2-enoyl)amino group, a ($^2H_3$)methoxy group, or a bis[($^2H_3$)methyl]amino group.

$R^{33}$ and $R^{35}$ are each independently preferably a hydrogen atom, a fluorine atom, a methoxy group, a prop-2-enoylamino group, a methyl(methylsulfonyl)amino group, a methylcarbamoyl group, a dimethylsulfamoyl group, or a methylsulfonylmethyl group.

$R^{34}$ is preferably a hydrogen atom or a fluorine atom.

$R^{36}$ is preferably a fluorine atom.

$R^{37}$ is preferably a methoxy group.

$R^{38}$ is preferably a fluorine atom.

$R^{39}$ is preferably a methyl group or a methylsulfonyl group.

$R^{40}$ is preferably a methyl group or a methylsulfonyl group.

$R^{41}$ is preferably a hydrogen atom or a fluorine atom.

When W is the above formula (4A), then Ring $Q^2$ is more preferably a 5,6-dimethoxypyrazin-2-yl group, a 4,5-dimethoxypyrimidin-2-yl group, a 4-pyridyl group, a 2,4-difluoro-3-methoxy-phenyl group, a 4,5-dimethoxy-2-pyridyl group, a morpholino group, an oxazol-2-yl group, a 4H-1,2,4-triazol-3-yl group, a 5-oxopyrrolidin-2-yl group, a 2-oxopyrrolidin-1-yl group, a cyclohexyl group, a 2-methoxythiazol-5-yl group, a furo[3,2-b]pyridin-6-yl group, an indolin-1-yl group, a 3-hydroxy-1-piperidyl group, an azepan-1-yl group, a 4-chloro-1H-pyrrolo[3,2-c]pyridin-7-yl group, a 1-methylpyrazolo[3,4-c]pyridin-4-yl group, a benzimidazol-1-yl group, a 4-isoquinolyl group, a 1-(difluoromethyl)-4-methoxy-6-oxo-pyridazin-3-yl group, or a 6-oxo-1H-pyridin-3-yl group.

When W is the above formula (4A), then Ring $Q^2$ is still more preferably any of the following formulas (15A) to (15C).

[Formula 53]

(15A)

(15B)

(15C)

wherein * indicates a bonding site, $R^{42}$ is a methyl group, a chlorine atom, a methoxy group, a cyano group, a dimethylamino group, or a bis[($^2H_3$)methyl]amino group, $R^{43}$ is a methoxy group or a ($^2H_3$)methoxy group, and $R^{44}$ is a chlorine atom, a methoxy group, a methoxyethoxy group, a dimethylamino group, a difluoromethoxy group, or a ($^2H_3$) methoxy group.

When W is the above formula (4A), then Ring $Q^2$ is most preferably any of the following formulas (16A) to (16G).

[Formula 54]

(16A)

(16B)

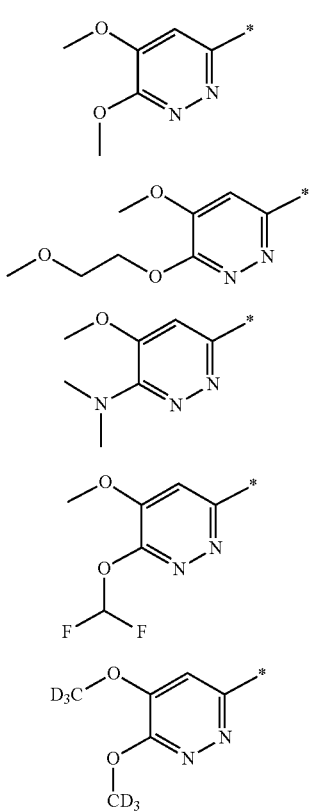

wherein * indicates a bonding site.

When W is the above formula (4B), then Ring Q² is more preferably the following formula (17A) or (17B).

[Formula 55]

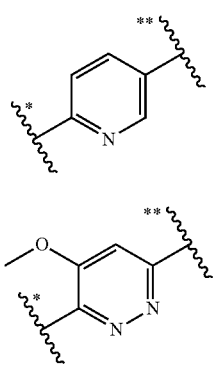

wherein * is bonded to Y, and ** is bonded to Z.

When W is the above formula (4B), then Ring Q³ is preferably any of the following formulas (18A) to (18D).

[Formula 56]

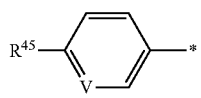

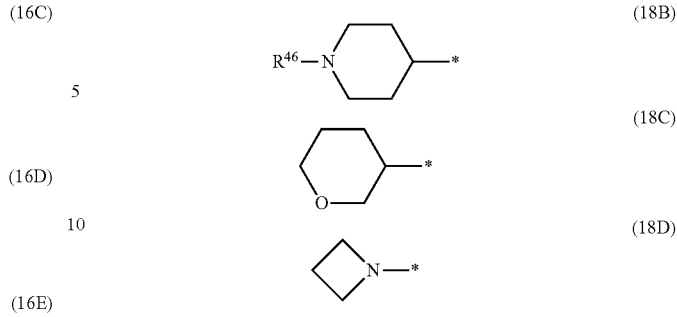

wherein * indicates a bonding site, $R^{45}$ is a hydrogen atom or a halogen atom, $R^{46}$ is a $C_{1-6}$ alkylsulfonyl group, and V is a nitrogen atom or CH.

When W is the above formula (4B), then Ring Q³ is more preferably a phenyl group, an azetidin-1-yl group, a 3-pyridyl group, a 6-chloro-3-pyridyl group, a tetrahydropyran-3-yl group, or a 1-methylsulfonyl-4-piperidyl group.

When W is the above formula (4B), then Y is preferably a single bond or an oxygen atom.

Z is preferably a single bond, —NH—, an oxygen atom, —SO₂—, —CH₂—, *—CH₂—NHC(=O)—**, *—CH₂CH₂—O—**, or *—CH₂—NH—**, wherein * is bonded to Ring Q², and ** is bonded to Ring Q¹.

Z is more preferably a single bond.

W is preferably the above formula (4A).

The compound of the present invention is preferably one selected from the following compounds or pharmaceutically acceptable salts thereof (preferably hydrochloride, succinate, benzenesulfonate, maleate, fumarate, mucate, or adipate, more preferably succinate, benzenesulfonate, maleate, fumarate, mucate, or adipate):

5-[4-({[(1R,3R,4S)-3-hydroxy-4-{methyl[6-(2,2,2-trifluoroethyl)thieno[2,3-d]pyrimidin-4-yl]amino}cyclopentyl]amino}methyl)phenyl]-3-methoxypyridine-2-carbonitrile, (1R,2S,4R)-4-[({4-[1-(methanesulfonyl)-1H-indazol-4-yl]phenyl}methyl)amino]-2-{methyl[6-(2,2,2-trifluoroethyl)thieno[2,3-d]pyrimidin-4-yl]amino}cyclopentan-1-ol, (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-[({4-[6-(dimethylamino)-5-methoxypyridin-3-yl]phenyl}methyl)amino]-2-{methyl[6-(2,2,2-trifluoroethyl)thieno[2,3-d]pyrimidin-4-yl]amino}cyclopentan-1-ol, (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol, (1R,2S,4R)-4-({[4-(5-methoxy-6-methylpyridin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-({[4-(1H-imidazol-1-yl)phenyl]methyl}amino)-2-{methyl[2-(methylamino)-6-(2,2,2-trifluoroethyl)thieno[2,3-d]pyrimidin-4-yl]amino}cyclopentan-1-ol, (1R,2S,4R)-4-({[4-(6-chloro-5-methoxypyridin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-({[4-(5,6-dimethoxypyridin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-({[4-(6-fluoro-5-methoxypyridin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-({[4-(5,6-dimethoxypyridin-3-yl)phenyl]methyl}amino)-2-{methyl[2-(methylamino)-6-(2,2,2-trifluoroethyl)thieno[2,3-d]pyrimidin-4-yl]amino}cyclopentan-1-ol, (1R,2S,4R)-4-({[4-(5,6-dimethoxypyridin-3-yl)phenyl]methyl}amino)-2-{[2-methoxy-6-(2,2,2-trifluoroethyl)thieno[2,3-d]pyrimidin-4-yl](methyl)amino}cyclopentan-1-ol, (1R,2S,4R)-4-({[4-(6-chloro-5-methoxypyridazin-3-yl)phenyl]methyl}amino)-2-{methyl[6-(2,2,2-trifluoroethyl)thieno[2,3-d]pyrimidin-4-yl]amino}cyclopentan-1-ol, 2-[(4-{[(1S,2R,4R)-4-({[4-(5,6-dimethoxypyridazin-3-yl)phenyl]methyl}amino)-2-hydroxycyclopentyl](methyl)amino}pyrimidin-5-yl)oxy]-5-fluoro-N,N-di(propan-2-yl)benzamide, (1R,2S,4R)-2-{[2-chloro-6-(2,2,2-trifluoroethyl)thieno[2,3-d]pyrimidin-4-yl](methyl)amino}-4-({[4-(5,6-dimethoxypyridazin-3-yl)phenyl]methyl}amino)cyclopentan-1-ol, (1R,3S)—N³-{[4-(5,6-dimethoxypyridazin-3-yl)phenyl]methyl}-N'-methyl-N'-[6-(2,2,2-trifluoroethyl)thieno[2,3-d]pyrimidin-4-yl]cyclopentane-1,3-diamine, (1R,2S,4R)-4-[({4-[6-(dimethylamino)-5-methoxypyridazin-3-yl]phenyl}methyl)amino]-2-{methyl[6-(2,2,2-trifluoroethyl)thieno[2,3-d]pyrimidin-4-yl]amino}cyclopentan-1-ol, 6-[4-({[(1R,3R,4S)-3-hydroxy-4-{methyl[6-(2,2,2-trifluoroethyl)thieno[2,3-d]pyrimidin-4-yl]amino}cyclopentyl]amino}methyl)phenyl]-4-methoxypyridazine-3-carbonitrile, (1S,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol, (1R,2S,4R)-4-[({4-[5-methoxy-6-(2-methoxyethoxy)pyridazin-3-yl]phenyl}methyl)amino]-2-{[2-methoxy-6-(2,2,2-trifluoroethyl)thieno[2,3-d]pyrimidin-4-yl](methyl)amino}cyclopentan-1-ol, (1R,2S,4R)-4-({[4-(4,5-dimethoxypyridin-2-yl)phenyl]methyl}amino)-2-{[2-methoxy-6-(2,2,2-trifluoroethyl)thieno[2,3-d]pyrimidin-4-yl](methyl)amino}cyclopentan-1-ol, (1R,2S,4R)-4-[({4-[6-(dimethylamino)-5-methoxypyridin-3-yl]phenyl}methyl)amino]-2-{[2-methoxy-6-(2,2,2-trifluoroethyl)thieno[2,3-d]pyrimidin-4-yl](methyl)amino}cyclopentan-1-ol, (1R,2S,4R)-4-[({4-[6-(difluoromethoxy)-5-methoxypyridazin-3-yl]phenyl}methyl)amino]-2-{[2-methoxy-6-(2,2,2-trifluoroethyl)thieno[2,3-d]pyrimidin-4-yl](methyl)amino}cyclopentan-1-ol, (1R,2S,4R)-4-{[(4-{5,6-bis[($^2$H$_3$)methyloxy]pyridazin-3-yl}phenyl)methyl]amino}-2-{methyl[6-(2,2,2-trifluoroethyl)thieno[2,3-d]pyrimidin-4-yl]amino}cyclopentan-1-ol, (1R,2S,4R)-4-({[4-(6-{bis[($^2$H$_3$)methyl]amino}-5-methoxypyridin-3-yl)phenyl]methyl}amino)-2-{methyl[6-(2,2,2-trifluoroethyl)thieno[2,3-d]pyrimidin-4-yl]amino}cyclopentan-1-ol, and (1R,2S,4R)-4-{[(4-{5,6-bis[($^2$H$_3$)methyloxy]pyridazin-3-yl}phenyl)methyl]amino}-2-{[2-methoxy-6-(2,2,2-trifluoroethyl)thieno[2,3-d]pyrimidin-4-yl](methyl)amino}cyclopentan-1-ol.

The compound of the present invention is more preferably one selected from the following compounds or pharmaceutically acceptable salts thereof (preferably hydrochloride, succinate, benzenesulfonate, maleate, fumarate, mucate, or adipate, more preferably succinate, benzenesulfonate, maleate, fumarate, mucate, or adipate):

(1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol, and (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol.

The compound of the present invention or a pharmaceutically acceptable salt thereof or the crystal of the present invention has excellent properties in terms of menin-MLL inhibitory action, solubility, cell membrane permeability, oral absorption, blood concentration, metabolic stability, tissue transferability, bioavailability, in vitro activity, in vivo activity, rapid onset of drug effect, sustainability of drug effect, physical stability, drug interaction, toxicity, and the like, and is useful as a drug.

In one embodiment, the present invention relates to a pharmaceutical composition comprising, as an active ingredient, the compound represented by the general formula (1) or a pharmaceutically acceptable salt thereof or the crystal of the present invention, for the treatment and/or prophylaxis of diseases that can be treated and/or prevented by inhibiting the interaction between an MLL protein and menin.

In another embodiment, the present invention relates to a method for treating and/or preventing diabetes, comprising administering the compound represented by the general formula (1) or a pharmaceutically acceptable salt thereof or the crystal of the present invention.

In another embodiment, the present invention relates to a method for treating and/or preventing cancer, comprising administering the compound represented by the general formula (1) or a pharmaceutically acceptable salt thereof or the crystal of the present invention.

The disease to be treated is not particularly limited as long as it depends on the interaction between menin and an MLL protein, and examples thereof include cancers and diabetes (preferably cancer).

The type of cancer to be treated is not particularly limited as long as it is confirmed to be sensitive to the compound of the present invention. Examples thereof include blood cancer, brain tumor (e.g., pediatric glioma, etc.), head/neck region cancer, esophageal cancer, stomach cancer, appendix cancer, colon cancer, anus cancer, gallbladder cancer, bile duct cancer, pancreatic cancer, gastrointestinal stromal tumor, lung cancer, liver cancer (e.g., hepatoma, etc.), mesothelioma, thyroid gland cancer, renal cancer, prostate cancer, neuroendocrine tumor, melanoma, breast cancer, endometrial cancer, cervical cancer, ovarian cancer, osteosarcoma, soft tissue sarcoma, Kaposi's sarcoma, myosarcoma, bladder cancer and testicular cancer. Preferred are blood cancer, prostate cancer, breast cancer, hepatoma and pediatric glioma, and more preferred is blood cancer.

Examples of the blood cancer include mixed lineage leukemia (MLL), MLL-related leukemia, MLL-associated leukemia, MLL-positive leukemia, MLL-induced leukemia, rearranged mixed lineage leukemia (MLL-r), leukemia associated with a MLL rearrangement (a rearrangement of the MLL gene, MLL-rearranged leukemias), MLL-amplified leukemias, MLL partial tandem duplication leukemias (MLL-PTD leukemias), other leukemia/blood cancers associated with constant expression of HOX and MEIS1 genes, acute leukemia, chronic leukemia, indolent leukemia, lymphoblastic leukemia, lymphocytic leukemia, myeloid leukemia, myelogenous leukemia, childhood leukemia, acute lymphoblastic leukemia (ALL), acute myeloid leukemia (AML), acute granulocytic leukemia, acute nonlymphocytic leukemia, chronic lymphocytic leukemia (CLL), chronic myelogenous leukemia (CML), therapy related leukemia, myelodysplastic syndrome (MDS), myeloproliferative disease (MPD), myeloproliferative neoplasia (MPN), multiple myeloma, myelodysplasia, plasma cell neoplasm, cutaneous T-cell lymphoma, lymphoid neoplasm, AIDS-related lymphoma, mycosis fungoides (granuloma fungoides), Alibert-Bazin syndrome, Sezary Syndrome, hairy cell leukemia (HCL), T-cell prolymphocytic leukemia (T-PLL), large granular lymphocytic leukemia, meningeal leukemia, Hodgkin's lymphoma, non Hodgkin's lymphoma (malignant lymphoma), Waldenstrom's macroglobulinemia and the like. More preferred are acute myeloid leukemia (AML) and acute lymphoblastic leukemia (ALL).

p53 is one of important factors that suppress carcinogenesis, and deletion or mutation of the p53 gene has been observed in about half of human cancers. It is known that mutations in p53 may promote cancer (gain-of-function p53 mutation), and cell growth is inhibited by allowing the compound having a menin-MLL inhibitory action on a cancer cell line expressing gain-of-function p53 mutation (Zhu et al., Nature, 2015, 525, 206-211.). Since the compound of the present invention or a pharmaceutically acceptable salt thereof has a menin-MLL inhibitory action, it is effective for the treatment and/or prophylaxis of cancer expressing gain-of-function p53 mutation. Examples of the cancer expressing gain-of-function p53 mutation include blood cancer, brain tumor, head/neck region cancer, esophageal cancer, stomach cancer, appendix cancer, colon cancer, anus cancer, gallbladder cancer, bile duct cancer, pancreatic cancer, gastrointestinal stromal tumor, lung cancer, liver cancer, mesothelioma, thyroid gland cancer, renal cancer, prostate cancer, neuroendocrine tumor, melanoma, breast cancer, endometrial cancer, cervical cancer, ovarian cancer, osteosarcoma, soft tissue sarcoma, Kaposi's sarcoma, myosarcoma, bladder cancer and testicular cancer.

The interaction between menin and a MLL fusion protein is known to be essential for the expression of several downstream oncogenes (e.g., leukemia-related genes such as HOX, MEIS1, MYC, etc.) (Borkin et al., Cancer Cell, 2015, 27, 589-602.). Since the compound of the present invention or a pharmaceutically acceptable salt thereof has a menin-MLL inhibitory action, it is effective for leukemia exhibiting expression characteristics of HOX gene, MEIS1 gene, MYC gene etc.

Since the compound of the present invention or a pharmaceutically acceptable salt thereof or the crystal of the present invention has a menin-MLL inhibitory action, it is preferably used for diseases dependent on the interaction between menin and a MLL protein. Examples of the diseases dependent on the interaction between menin and a MLL protein include blood cancer, prostate cancer, breast cancer, hepatoma, pediatric glioma and diabetes (e.g., see the following documents: blood cancer (A1, A2, A3, A4), myelodysplastic syndrome (A1, A3), prostate cancer (B), breast cancer (C1, C2, C3), hepatoma (D), pediatric glioma (E), diabetes (F1, F2, F3)).

A1, Yokoyama et al., Cell, 2005, 123, 207-218.
A2, Borkin et al., Cancer Cell, 2015, 27, 589-602.
A3, Cierpicki and Grembecka. Future Med Chem. 2014, 447-462.
A4, Kuehn M W et al., Cancer Discovery, 2016, 1166-1181.
B, Malik et al., Nat. Med., 2015, 21, 344-352.
C1, Dreijerink et al., Cancer Res., 2006, 66, 4929-4935.
C2, Imachi et al., Breast Cancer Res. Treat., 2010, 122, 395-407.
C3, Zhu et al., Nature, 2015, 525, 206-211.
D, Xu et al., Proc. Natl. Acad. Sci. USA., 2013, 110, 17480-17485.
E, Fumato et al., Science, 2014, 346, 1529-1533.
F1, Wu et al., Curr. Mol. Med., 2008, 8(8), 805-815.
F2, Chamberlain et al., J. Clin. Invest., 2014, 124, 4093-4101.
F3, Yang et al., Proc. Natl. Acad. Sci. USA., 2010, 107, 20358-20363.

In another embodiment, the present invention relates to a pharmaceutical composition comprising one drug selected from the group consisting of a Bcl-2 inhibitor, a DNA methyltransferase inhibitor and a pyrimidine antimetabolite, and the compound of the present invention or a pharmaceutically acceptable salt thereof or the crystal of the present invention, which are administered in combination.

In another embodiment, the present invention relates to a method for treating cancer, comprising administering the compound of the present invention or a pharmaceutically acceptable salt thereof or the crystal of the present invention in combination with one drug selected from the group consisting of a Bcl-2 inhibitor, a DNA methyltransferase inhibitor and a pyrimidine antimetabolite.

In another embodiment, the present invention relates to the compound of the present invention or a pharmaceutically acceptable salt thereof or the crystal of the present invention, which is administered in combination with one drug selected from the group consisting of a Bcl-2 inhibitor, a DNA methyltransferase inhibitor and a pyrimidine antimetabolite.

One drug selected from the group consisting of a Bcl-2 inhibitor, a DNA methyltransferase inhibitor and a pyrimidine antimetabolite, and the compound of the present invention or a pharmaceutically acceptable salt thereof or the crystal of the present invention may be separately comprised as active ingredients in different formulations, or may be comprised in a single formulation. When they are separately comprised as active ingredients in different formulations, their formulations may be administered at the same time or different times.

In another embodiment, the present invention relates to a composition for inducing differentiation of leukemia cells, comprising the compound of the present invention or a pharmaceutically acceptable salt thereof or the crystal of the present invention.

In another embodiment, the present invention relates to a method for inducing differentiation of leukemia cells, comprising administering the compound of the present invention or a pharmaceutically acceptable salt thereof or the crystal of the present invention.

In the compound of the present invention, depending on the type and combination of substituents, geometric isomers such as cis-forms and trans-forms, tautomers, or optical isomers such as l-forms and d-forms (e.g., enantiomers or diastereomers) when the compound of the present invention has an asymmetric carbon atom can be present. The compound of the present invention includes all of these isomers and mixtures thereof in any ratio, unless otherwise specified.

In the present invention, the pharmaceutically acceptable salt includes both pharmaceutically acceptable acid addition salts and pharmaceutically acceptable base addition salts.

When the compound of the present invention has a basic group such as an amino group etc., a pharmacologically acceptable acid addition salt can be generally formed. Examples of the acid addition salt include hydrohalides such as hydrofluoride, hydrochloride, hydrobromide, hydroiodide etc.; inorganic acid salts such as nitrate, perchlorate, sulfurate, phosphate etc.; lower alkanesulfonates such as methanesulfonate, trifluoromethanesulfonate, ethanesulfonate etc.; aryl sulfonates such as benzenesulfonate, p-toluenesulfonate etc.; organic acid salts such as acetate, malate, fumarate, succinate, citrate, tartrate, oxalate, maleic acid, mucic acid, adipate etc.; and amino acid salts such as ornithate, glutamate, aspartate etc., and preferred are hydrohalides, aryl sulfonates and organic acid salts. The acid addition salt of the compound of the present invention is preferably hydrochloride, succinate, benzenesulfonate, maleate, fumarate, mucate or adipate, more preferably succinate, benzenesulfonate, maleate, fumarate, mucate or adipate.

The acid addition salt of the compound of the present invention includes acid additions salt that can be formed by combining the acid to be added to the compound of the present invention with the compound of the present invention in an any ratio. For example, the hydrochloride includes formable salts such as monohydrochloride, dihydrochloride, trihydrochloride etc., the fumarate includes formable salts such as monofumarate, ½ fumarate etc., and the succinate includes formable salts such as monosuccinate, ⅔ succinate, ⅓ succinate etc.

When the compound of the present invention has an acidic group such as a carboxy group etc., a pharmacologically acceptable base addition salt can be generally formed. Examples of the base addition salt include alkali metal salts such as sodium salt, potassium salt, lithium salt etc.; alkaline-earth metal salts such as calcium salt, magnesium salt etc.; inorganic salts such as ammonium salt etc.; and organic amine salts such as dibenzylamine salt, morpholine salt, phenylglycinealkyl ester salt, ethylene diamine salt, N-methylglucamine salt, diethylamine salt, triethylamine salt, cyclohexylamine salt, dicyclohexylamine salt, N,N'-dibenzylethylenediamine salt, diethanolamine salt, N-benzyl-N-(2-phenylethoxy)amine salt, piperazine salt, tetramethylammonium salt, tris(hydroxymethyl)aminomethane salt etc.

The compound of the present invention may be present as a non-solvate or a solvate. The solvate is not particularly limited as long as it is pharmacologically acceptable, and specifically, is preferably a hydrate, an ethanolate or the like. In addition, when a nitrogen atom is present in the compound represented by the general formula (1), the compound may be a N-oxide form. Such solvates and N-oxide forms are encompassed within the scope of the present invention. Moreover, the compound of the present invention can contain one or more isotopes at a non-natural abundance, as a compound-constituting atom. Examples of the isotope include deuterium ($^2H$;D), tritium ($^3H$; T), iodine-125 ($^{125}I$), carbon-14 ($^{14}C$) and the like. Furthermore, the compound of the present invention can be radiolabeled with a radioisotope such as tritium ($^3H$), iodine-125 ($^{125}I$) or carbon-14 ($^{14}C$). The radiolabeled compound is useful as a therapeutic or preventive agent, a research reagent (e.g., an assay reagent), or a diagnostic agent (e.g., an in vivo image diagnostic agent). The compound of the present invention containing any radioactive or non-radioactive isotope in any ratio is encompassed within the scope of the present invention.

It is known that a low-molecular compound containing one or more deuterium atoms ($^2H$;D) as a compound-constituting hydrogen atom can exhibit a profile useful as a medicine (e.g., drug efficacy, safety, etc.) (Sanderson, Nature, 2009, DOI: 10.1038/458269a, Maltais et al, J. Med. Chem., 2009, 52, 7993-8001.). The compound of the present invention into which one or more deuterium atoms are introduced instead of the hydrogen atoms constituting the compound is also expected to exhibit the same effect as above.

In the present invention, a crystal refers to a solid having an internal structure formed by regularly three-dimensionally repeating constituent atoms or molecules, and is distinguished from an amorphous solid or amorphous substance not having such a regular internal structure. It can be confirmed by employing powder X-ray crystal analysis or the like that the compound of the present invention or a salt thereof is in a crystalline state. In general, a peak value in powder X-ray diffraction may inherently vary due to a difference in the measurement apparatus, sample or sample preparation, and hence the diffraction angle (2θ) can be varied in a range of about ±0.2 (degrees). Therefore, it is understood that the value of the diffraction angle of the present invention encompasses numerical values falling in a range of about ±0.2. Accordingly, the scope of the present invention encompasses not only crystals having exactly the same diffraction angle (2θ), but also crystals having the same diffraction angle within the range of ±0.2, in powder X-ray diffraction. Herein, the unit of the diffraction angle (2θ) is degree (also referred to as "°"), and the unit may be omitted in the description of the numerical value of the diffraction angle (2θ).

In the present invention, the crystal includes a crystal of the compound represented by the general formula (1), a hydrate crystal of the compound represented by the general formula (1), a solvate crystal of the compound represented by the general formula (1), a crystal of a pharmaceutically acceptable salt of the compound represented by the general formula (1), a hydrate crystal of a pharmaceutically acceptable salt of the compound represented by the general formula (1), and a solvate crystal of a pharmaceutically acceptable salt of the compound represented by the general formula (1). The hydrate crystal of the present invention may be in the form of, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0 hydrate, and the hydrated water may be increase or decrease depending on the humidity.

The crystal of the present invention (hereinafter, sometimes to be referred to as "the crystal of Example 131 of the present invention", "the crystal of Example 132 of the present invention", "the crystal of Example 133 of the present invention", "the crystal of Example 134 of the present invention", "the crystal of Example 135 of the present invention", "the crystal of Example 136 of the present invention", "the crystal of Example 137 of the present invention", "the crystal of Example 138 of the present invention" or "the crystal of Example 139 of the present invention") can be stably supplied as a crystal of active pharmaceutical ingredient used in the production of pharmaceuticals, and has excellent hygroscopicity or stability. The differences in these crystal forms are particularly distinguished by powder X-ray diffraction.

The crystal of Example 131 of the present invention has peaks at diffraction angles (2θ) of 4.66±0.2, 7.02±0.2, 14.10±0.2, 16.68±0.2, 17.46±0.2, 18.68±0.2, 21.34±0.2, 24.52±0.2, 25.54±0.2 and 28.22±0.2 in a powder X-ray diffraction diagram obtained through irradiation with copper Kα line (λ=1.54 angstroms).

The crystal of Example 131 of the present invention is preferably monosuccinate.

The crystal of Example 131 of the present invention is preferably non-hydrate.

The crystal of Example 132 of the present invention has peaks at diffraction angles (2θ) of 10.92±0.2, 11.70±0.2, 12.40±0.2, 15.00±0.2, 17.38±0.2, 18.16±0.2, 22.18±0.2, 22.62±0.2, 23.86±0.2 and 24.20±0.2 in a powder X-ray diffraction diagram obtained through irradiation with copper Kα line (λ=1.54 angstroms).

The crystal of Example 132 of the present invention is preferably monobenzenesulfonate.

The crystal of Example 132 of the present invention is preferably trihydrate.

The crystal of Example 133 of the present invention has peaks at diffraction angles (2θ) of 4.64±0.2, 7.02±0.2, 7.46±0.2, 11.14±0.2, 14.04±0.2, 16.76±0.2, 18.54±0.2, 19.76±0.2, 21.26±0.2 and 22.62±0.2 in a powder X-ray diffraction diagram obtained through irradiation with copper Kα line (λ=1.54 angstroms).

The crystal of Example 133 of the present invention is preferably monomaleate.

The crystal of Example 133 of the present invention is preferably non-hydrate.

The crystal of Example 134 of the present invention has peaks at diffraction angles (2θ) of 4.80±0.2, 7.94±0.2, 9.66±0.2, 11.56±0.2, 14.56±0.2, 17.62±0.2, 18.14±0.2, 20.46±0.2, 21.36±0.2 and 24.46±0.2 in a powder X-ray diffraction diagram obtained through irradiation with copper Kα line (λ=1.54 angstroms).

The crystal of Example 134 of the present invention is preferably monofumarate.

The crystal of Example 134 of the present invention is preferably tetrahydrate.

The crystal of Example 135 of the present invention has peaks at diffraction angles (2θ) of 7.14±0.2, 8.76±0.2, 12.26±0.2, 14.30±0.2, 17.52±0.2, 23.40±0.2, 24.40±0.2, 24.86±0.2, 25.34±0.2 and 25.90±0.2 in a powder X-ray diffraction diagram obtained through irradiation with copper Kα line (λ=1.54 angstroms).

The crystal of Example 135 of the present invention is preferably trihydrate.

The crystal of Example 136 of the present invention has peaks at diffraction angles (2θ) of 8.06±0.2, 12.22±0.2, 12.52±0.2, 15.14±0.2, 17.54±0.2, 18.56±0.2, 20.08±0.2, 23.48±0.2, 24.28±0.2 and 25.00±0.2 in a powder X-ray diffraction diagram obtained through irradiation with copper Kα line (λ=1.54 angstroms).

The crystal of Example 136 of the present invention is preferably monofumarate.

The crystal of Example 136 of the present invention is preferably dihydrate.

The crystal of Example 137 of the present invention has peaks at diffraction angles (2θ) of 6.56±0.2, 9.44±0.2, 9.94±0.2, 13.20±0.2, 18.22±0.2, 18.86±0.2, 19.60±0.2, 22.68±0.2, 25.10±0.2 and 28.70±0.2 in a powder X-ray diffraction diagram obtained through irradiation with copper Kα line (λ=1.54 angstroms).

The crystal of Example 137 of the present invention is preferably monomucate.

The crystal of Example 137 of the present invention is preferably trihydrate.

The crystal of Example 138 of the present invention has peaks at diffraction angles (2θ) of 5.88±0.2, 6.20±0.2, 9.18±0.2, 10.34±0.2, 12.50±0.2, 13.70±0.2, 15.66±0.2, 17.82±0.2, 18.48±0.2 and 22.16±0.2 in a powder X-ray diffraction diagram obtained through irradiation with copper Kα line (λ=1.54 angstroms).

The crystal of Example 138 of the present invention is preferably monoadipate.

The crystal of Example 138 of the present invention is preferably trihydrate.

The crystal of Example 139 of the present invention has peaks at diffraction angles (2θ) of 4.60±0.2, 6.60±0.2, 7.74±0.2, 8.02±0.2, 9.26±0.2, 11.16±0.2, 12.00±0.2, 12.44±0.2, 13.22±0.2 and 19.66±0.2 in a powder X-ray diffraction diagram obtained through irradiation with copper Kα line (λ=1.54 angstroms).

The crystal of Example 139 of the present invention is preferably monosuccinate.

The crystal of Example 139 of the present invention is preferably 2.5 hydrate.

The present invention encompasses a compound which can be converted to the compound represented by the general formula (1), which is an active ingredient of the pharmaceutical composition of the present invention, with a reaction due to an enzyme, gastric acid and the like under the physiological condition in the living body, that is, a compound which can be converted to the compound represented by the general formula (1) by enzymatic oxidation, reduction, hydrolysis and the like; and a compound which can be converted to the compound represented by the general formula (1) by hydrolysis and the like due to gastric acid and the like, as a "pharmaceutically acceptable prodrug compound".

When the compound represented by the general formula (1) contains an amino group, examples of the prodrug include a compound obtained by subjecting the amino group to acylation, alkylation or phosphorylation (e.g., a compound obtained by subjecting the amino group to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation or tert-butylation) and the like. When the compound represented by the general formula (1) contains a hydroxy group, examples of the prodrug include a compound obtained by subjecting the hydroxy group to acylation, alkylation, phosphorylation or boration (e.g., a compound obtained by subjecting the hydroxy group to acetylation, palmitoylation, propanoylation, pivaloylation, succinylation, fumarylation, alanylation or dimethylaminomethylcarbonylation) and the like. When the compound represented by the general formula (1) contains a carboxyl group, examples of the prodrug include a compound obtained by subjecting the carboxyl group to esterification or amidation (e.g., a compound obtained by subjecting the carboxyl group to ethyl esterification, phenyl esterification, carboxymethyl esterification, dimethylaminomethyl esterification, pivaloyloxymethyl esterification, ethoxycarbonyloxyethyl esterification or methylamidation) and the like.

The prodrug of the present invention can be produced from the compound represented by the general formula (1) according to a method known per se. The prodrug of the present invention also includes a compound which can be converted to the compound represented by the general formula (1) under physiological conditions as described in "IYAKUHIN no KAIHATSU (Development of Pharmaceuticals)", Vol. 7, Design of Molecules, p. 163-198, published by HIROKAWA SHOTEN (1990).

[Production Method]

Next, typical production methods for the compound represented by the general formula (1) will be described. The compound of the present invention can be produced according to various production methods, and the production methods shown below are merely examples, and the present invention should not be construed as limited to these.

The compound represented by the general formula (1), pharmaceutically acceptable salts thereof and synthetic intermediates thereof can be produced by employing various known production methods, with utilizing characteristics based on the basic skeleton or the type of substituent. Examples of the known methods include methods described in "ORGANIC FUNCTIONAL GROUP PREPARATIONS", the 2nd edition, ACADEMIC PRESS, INC., 1989, "Comprehensive Organic Transformations", the 2nd edition, VCH Publishers Inc., 1999, and the like.

In the production, depending on the type of the functional group contained in the compound, it may sometimes be effective in the production technology to protect the functional group with an appropriate protecting group at the stage of a raw material or intermediate, or to substitute with a group that can be easily converted to the functional group.

Examples of the functional group include an amino group, a hydroxy group, a formyl group, a carbonyl group, and carboxy group and the like, and examples of the protecting group include protecting groups described in "Protective Groups in Organic Synthesis", the 5th edition, Wiley, 2014 written by P. G. Wuts.

The protecting group or the group that can be easily converted to the functional group may be appropriately selected in accordance with the reaction conditions of the production method employed for producing the compound.

According to such a method, after introducing the group and carrying out the reaction, the desired compound can be obtained by removing the protecting group or converting the group to a desired group, if necessary.

The prodrug of the compound can be produced by introducing a specific group at the stage of a raw material or intermediate, or by subjecting the obtained compound to introduction of the group, as in the case of the above-mentioned protecting group. The reaction for producing a prodrug can be carried out by employing conventional methods known to those skilled in the art, such as esterification, amidation, dehydration, hydrogenation and the like.

The compound represented by the general formula (1) can be produced, for example, according to the following Methods A to E. The synthetic intermediates used in Method A to Method E can be produced, for example, according to the following Methods F to Y.

When the compound serving as a reaction substrate in the reaction in each step of the following Methods A to Y has a functional group or partial structure that inhibits the desired reaction, such as an amino group, a hydroxy group, a formyl group, a carbonyl group, a carboxy group, a heteroatom on a cyclic compound and the like, a protecting group may be introduced into it or an introduced protecting group may be removed therefrom, appropriately if necessary. Such a protecting group is not particularly limited as long as it is a commonly used protecting group, and may be, for example, the protecting group described in the above-mentioned "Protective Groups in Organic Synthesis (5th edition, 2014)". The reactions for the introduction and removal of these protecting groups can be carried out according to the conventional methods described in the above document.

In each compound of Methods A to Y, depending on the type of the functional group contained in the compound, the functional group can be substituted with a group that can be easily converted to the functional group at the stage of a raw material or intermediate. The conversion to the desired functional group can be performed at an appropriate stage according to a known method. Examples of the known method include methods described in the above-mentioned documents "ORGANIC FUNCTIONAL GROUP PREPARATIONS", "Comprehensive Organic Transformations" and the like.

In each compound in the following Methods A to Y is isolated and purified in the form of a non-solvate, a salt or any of various solvates such as a hydrate. The salt can be produced according to a conventional method. Examples of the salt include hydrochloride, sulfurate and the like; organic amine salts; and sodium salt, potassium salt and the like.

The solvent used in the reaction in each step of the following Methods A to Y is not particularly limited as long as it does not inhibit the reaction but partially dissolves a starting material, and is selected, for example, from the following solvent group. The solvent group includes aliphatic hydrocarbons such as n-hexane, n-pentane, petroleum ether and cyclohexane; aromatic hydrocarbons such as benzene, toluene and xylene; halogenated hydrocarbons such as dichloromethane (methylene chloride), chloroform, carbon tetrachloride, dichloroethane, chlorobenzene and dichlorobenzene; ethers such as diethyl ether, diisopropyl ether, tetrahydrofuran (THF), dioxane, dimethoxyethane and diethylene glycol dimethyl ether; ketones such as acetone, methyl ethyl ketone, methylisobutylketone and cyclohexanone; esters such as ethyl acetate, propyl acetate, butyl acetate; nitriles such as acetonitrile, propionitrile, butyronitrile and isobutyronitrile; carboxylic acids such as acetic acid and propionic acid; alcohols such as methanol, ethanol, 1-propanol, 2-propanol, 1-butanol, 2-butanol, 2-methyl-1-propanol and 2-methyl-2-propanol; amides such as formamide, N,N-dimethylformamide (DMF), N,N-dimethylacetamide, N-methyl-2-pyrrolidone, hexamethylphosphortriamide; sulfoxides such as dimethyl sulfoxide (DMSO) and tetrahydrothiophene 1,1-dioxide; water; and mixture thereof.

The acid used in the reaction in each step of the following Methods A to Y is not particularly limited as long as it does not inhibit the reaction, and is selected from the following acid group. The acid group includes inorganic acids such as hydrochloric acid, hydrobromic acid, hydroiodic acid, phosphoric acid, sulfuric acid and nitric acid; organic acids such as acetic acid, propionic acid, trifluoroacetic acid and pentafluoropropionic acid; organic sulfonic acids such as methanesulfonic acid, trifluoromethanesulfonic acid, p-toluenesulfonic acid and camphorsulfonic acid; and Lewis acids such as boron tribromide, indium(III) bromide, boron trifluoride, aluminium(III) chloride and trimethylsilyl trifluoromethanesulfonate.

The base used in the reaction in each step of the following Methods A to Y is not particularly limited as long as it does not inhibit the reaction, and is selected from the following base group. The base group includes alkali metal carbonates such as lithium carbonate, sodium carbonate, potassium carbonate and cesium carbonate; alkali metal hydrogencarbonates such as lithium hydrogencarbonate, sodium hydrogencarbonate and potassium hydrogencarbonate; alkali metal hydroxides such as lithium hydroxide, sodium hydroxide and potassium hydroxide; alkaline-earth metal hydroxides such as calcium hydroxide and barium hydroxide; alkali metal hydrides such as lithium hydride, sodium hydride and potassium hydride; alkali metal amides such as lithium amide, sodium amide and potassium amide; alkali metal alkoxides such as lithium methoxide, sodium methoxide, sodium ethoxide, sodium tert-butoxide and potassium tert-butoxide; lithium alkylamides such as lithium diisopropylamide; silylamides such as lithium bistrimethylsilylamide and sodium bistrimethylsilylamide; alkyl lithiums such as n-butyllithium, sec-butyllithium and tert-butyllithium;

alkylmagnesium halides such as methylmagnesium chlorides (methylmagnesium chloride), methylmagnesium bromides (methylmagnesium bromide), methylmagnesium iodides (methylmagnesium iodide), ethylmagnesium chlorides (ethylmagnesium chloride), ethylmagnesium bromides (ethylmagnesium bromide), isopropylmagnesium chlorides (isopropylmagnesium chloride), isopropylmagnesium bromides (isopropylmagnesium bromide) and isobutylmagnesium chlorides (isobutylmagnesium chloride); and organic amines such as triethylamine (TEA), tributylamine, N,N-diisopropylethylamine (DIPEA), 1-methylpiperidine, 4-methylmorpholine, 4-ethylmorpholine, pyridine, picoline, 4-dimethylaminopyridine, 4-pyrrolidinopyridine, 2,6-di-tert-butyl-4-methylpyridine, quinoline, N,N-dimethylaniline, N,N-diethylaniline, 1,5-diazabicyclo[4,3,0]-5-nonene (DBN), 1,4-diazabicyclo[2,2,2]octane (DABCO), 1,8-diazabicyclo[5,4,0]-7-undecene (DBU) and imidazole.

In the reaction in each step of the following Methods A to Y, the reaction temperature depends on the solvent, starting material, reagents and the like, and the reaction time depends on the solvent, starting material, reagents, reaction temperature and the like.

In the reaction in each step of the following Methods A to Y, the target compound of each step is isolated from the reaction mixture by a conventional method after completing the reaction. The target compound is obtained, for example, by (i) filtering off an insoluble substance such as a catalyst etc., if necessary, (ii) extracting the target compound by adding water and a solvent immiscible with water (e.g., dichloromethane, diethyl ether, ethyl acetate etc.) to the reaction mixture, (iii) washing the organic layer with water and drying the resultant with a desiccant such as anhydrous calcium sulfate etc., and (iv) evaporating the solvent. The obtained target compound can be further purified, if necessary, by a conventional method, for example, recrystallization, reprecipitation, distillation or column chromatography (including normal phase chromatography and reverse phase chromatography) using silica gel, alumina or the like. The obtained target compound is identified by standard analysis techniques such as elemental analysis, NMR, mass spectroscopy, IR analysis etc., and its composition or purity can be thus analyzed. Alternatively, the target compound obtained in each step can be used directly in the next reaction without purification.

In each step of the following Methods A to Y, an optical isomer can be separated and purified by fractional recrystallization using an optically active amine such as (R)-(+)- or (S)-(−)-1-phenethylamine etc., or an optically active carboxylic acid such as (+)- or (−)-10-camphorsulfonic acid etc., or by separation using an optically active column.

The deuterium ($^2$H;D) substitute of the compound represented by the general formula (1) can be produced, for example, by employing a method commonly used by those skilled in the art at an appropriate stage during the following Methods A to Y. Examples of the method generally used by those skilled in the art include the methods described in Nature, 2007, 446, 526-529., Angew. Chem. Int. Ed., 2007, 46, 7744-7765., J. Med. Chem., 2009, 52, 7993-8001., and the like.

The raw materials and reagents used in Methods A to Y employed for the production of the compound of the present invention may be a known compound, or can be produced from a known compound as a starting material according to a known method or a method analogous thereto. The starting material known compound can also be purchased from commercial suppliers.

Abbreviations Used Herein

Boc: tert-butoxycarbonyl
Cbz: benzyloxycarbonyl
Alloc: allyloxycarbonyl
Ns: 2-nitrobenzenesulfonyl (nosyl)
MOM: methoxymethyl
TMS: trimethylsilyl
OTf: trifluoromethylsulfonyloxy
Tr: triphenylmethyl
PMB: p-methoxybenzyl
BOP: (benzotriazol-1-yloxy)tris(dimethylamino)phosphonium hexafluorophosphate
HATU: 1-[bis(dimethylamino)methylene]-1H-1,2,3-triazolo[4,5-b]pyridinium 3-oxide hexafluorophosphate
COMU: N-[1-(cyano-2-ethoxy-2-oxoethylideneaminooxy)dimethylamino(morpholino)]uronium hexafluorophosphate
EDC: 1-(3-dimethylaminopropyl)-3-ethylcarbodiimide hydrochloride
HOBt: 1-hydroxybenzotriazole
DPPA: diphenylphosphoryl azide The compound represented by the general formula (1) can be produced according to the methods shown below.

Method A

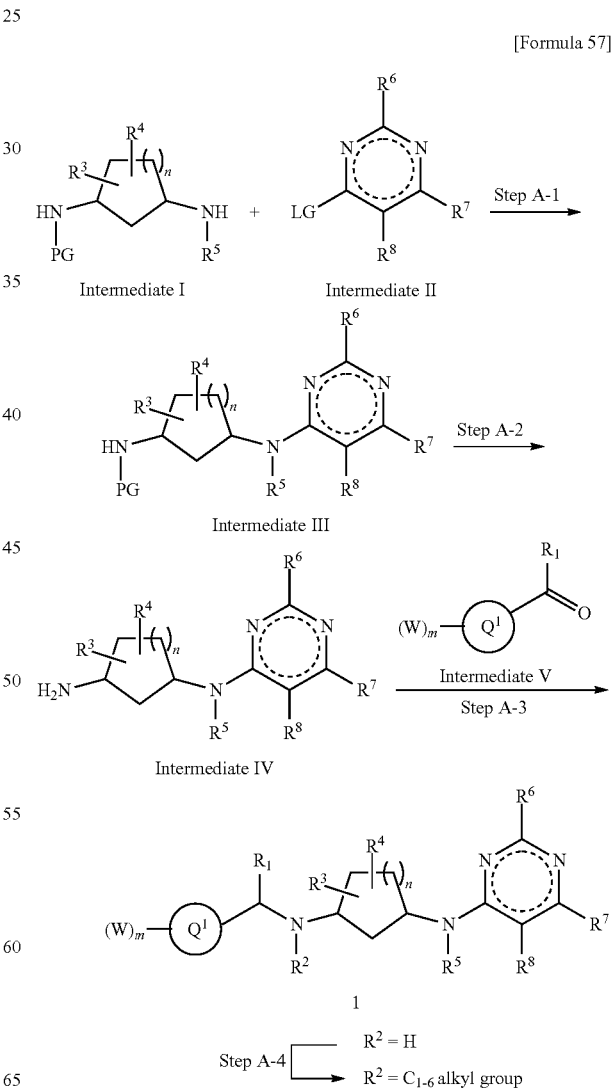

[Formula 57]

In the scheme, PG is a protecting group for an amino group, and examples thereof include a Boc group, a Cbz group, a Ns group, an Alloc group and the like. The protecting groups described in the above-mentioned "Protective Groups in Organic Synthesis", and the like can also be used. LG is a leaving group, and examples thereof include a halogen atom, a p-toluenesulfonyl group and the like.

Step A-1 is a step of obtaining Intermediate III from Intermediate I and Intermediate II. This step can be performed by heating Intermediate I and Intermediate II in the presence of a base (e.g., DIPEA, etc.), in a solvent inert to the reaction (e.g., isopropyl alcohol, etc.).

Step A-2 is a step of removing PG. When PG is a Cbz group, the step can be performed by treating Intermediate III with an acid (e.g., iodotrimethylsilane, etc.) in a solvent inert to the reaction (e.g., acetonitrile, etc.). When PG is a Boc group, the step can be performed by treating Intermediate III with an acid (e.g., hydrochloric acid, etc.) in a solvent inert to the reaction (e.g., dichloromethane, etc.). When PG is a Ns group, the step can be performed by reacting Intermediate III with an thiol (e.g., isopropylbenzenethiol, etc.) and a base (e.g., cesium carbonate, etc.) in a solvent inert to the reaction (e.g., a mixed solvent of THF and methanol, etc.). In addition, the methods described in the above-mentioned "Protective Groups in Organic Synthesis" can also be applied.

Step A-3 is a step of obtaining the compound represented by the general formula (1) wherein $R^2$ is a hydrogen atom, from Intermediate IV and Intermediate V. This step can be performed by reacting Intermediate IV and Intermediate V with a reducing agent (e.g., sodium triacetoxyborohydride, sodium cyanoborohydride, etc.) in a solvent inert to the reaction (e.g., dichloromethane, dichloroethane, etc.). A catalyst such as tetraisopropoxytitanium and the like can also be used to promote the reaction.

Step A-4 is a step of converting $R^2$ of the compound represented by the general formula (1) wherein $R^2$ is a hydrogen atom to a $C_{1-6}$ alkyl group. This step can be performed by reacting the compound with an alkylating agent (e.g., methyl trifluoromethanesulfonate, etc.) and a base (e.g., pyridine, etc.) in a solvent inert to the reaction (e.g., dichloromethane, etc.).

Intermediate III can also be produced using Intermediate I and Intermediate II' (Method B).

Method B

[Formula 58]

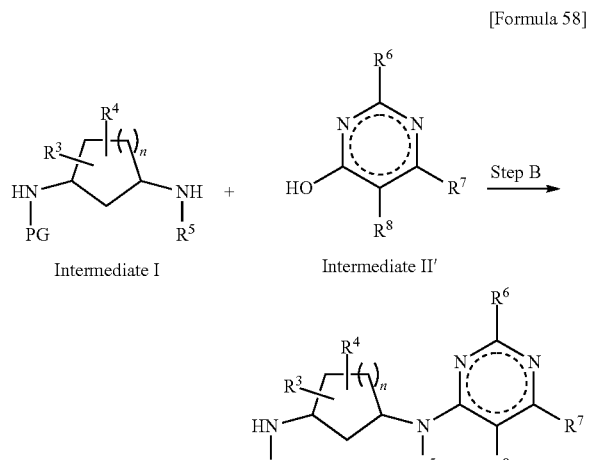

In the scheme, PG is as defined above.

Step B can be performed by reacting Intermediate I and Intermediate II' with a condensing agent (e.g., a BOP reagent, etc.) and a base (e.g., DBU, etc.) in a solvent inert to the reaction (e.g., acetonitrile, etc.), and then heating the mixture.

The compound represented by the general formula (1) can also be produced from Intermediate IV and Intermediate V' (Method C). Intermediate V' can be produced, for example, according to the methods described in CANCER CELL. 2015, 27, 589-602.

Method C

[Formula 59]

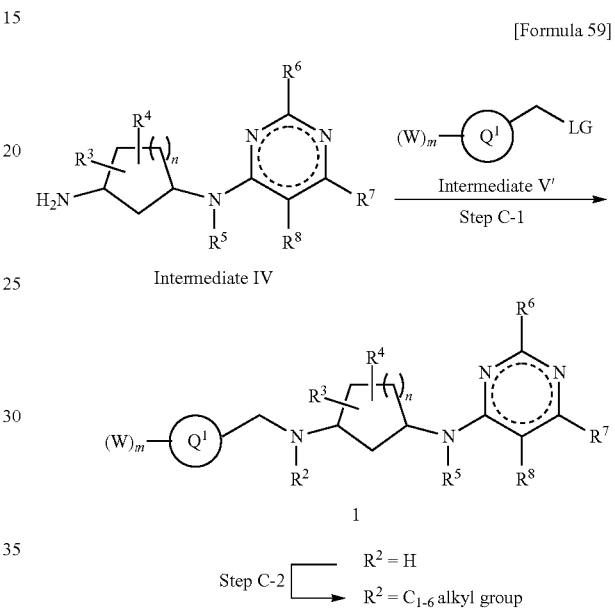

In the scheme, LG is as defined above.

Step C-1 is a step of obtaining the compound represented by the general formula (1) wherein $R^2$ is a hydrogen atom, from Intermediate IV and Intermediate V'. This step can be performed by reacting Intermediate IV and Intermediate V' with a base (e.g., potassium carbonate, etc.) in a solvent inert to the reaction (e.g., DMF, etc.). When a protecting group is present in the structure of Intermediate V', the deprotection can also be performed under a suitable reaction condition (e.g., a method of reacting with tin tetrachloride and the like, in a solvent such as acetonitrile, and the like, in the case of a Boc group as a protecting group) after Step C-1 to convert to the desired structure.

Step C-2 is a step of converting $R^2$ of the compound represented by the general formula (1) wherein $R^2$ is a hydrogen atom to a $C_{1-6}$ alkyl group. This step can be performed in the same manner as in Step A-4. When a protecting group is present in the structure of Intermediate V', the deprotection can also be performed under a suitable reaction condition (e.g., a method of reacting with tin tetrachloride and the like, in a solvent such asacetonitrile, and the like, in the case of a Boc group as a protecting group) after Step C-2 to convert to the desired structure.

Each step shown in the above Methods A to C does not necessarily have to be performed in the same order as long as it does not affect the reaction substrate and the reaction product, and, for example, it may be performed in the following order (Method D).

Method D

[Formula 60]

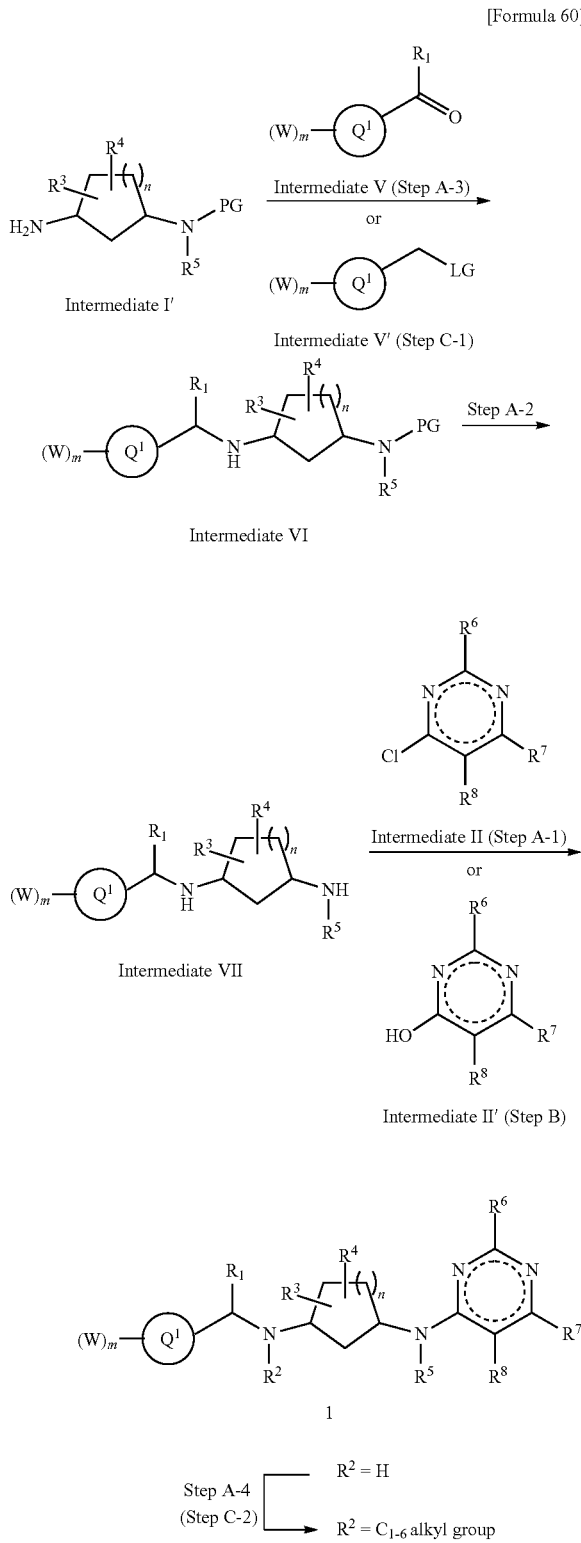

In the scheme, PG and LG are as defined above.

When the compound represented by the general formula (1) is represented by the following compound (1'), it can also be produced via the following Intermediate VIII (Method E).

Method E

[Formula 61]

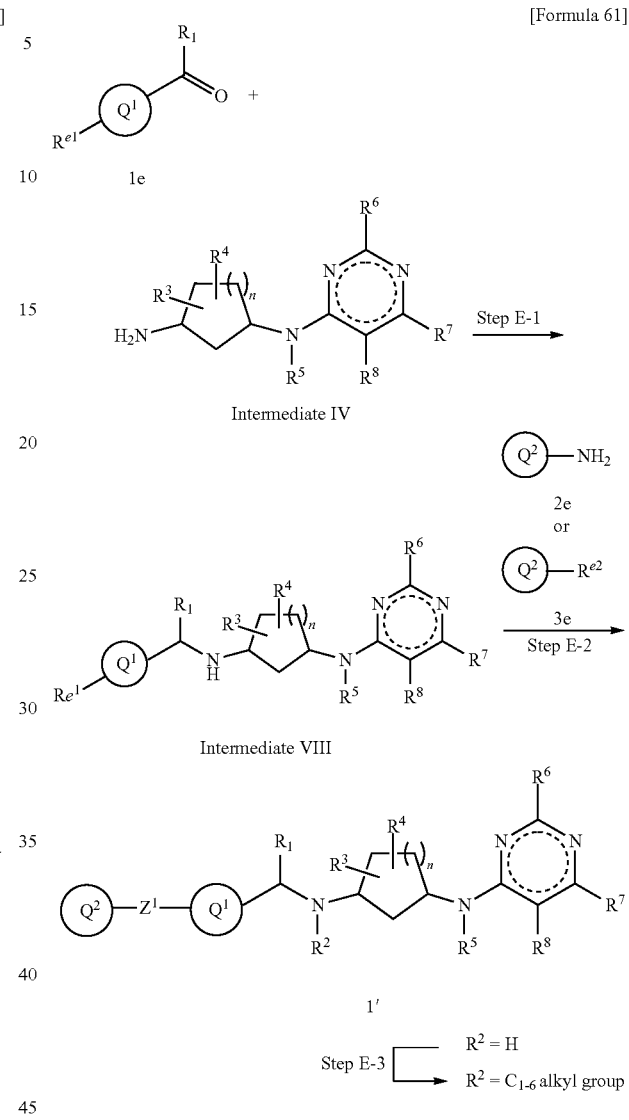

In the scheme, $R^{e1}$ is a substituent that can be reacted in the below-mentioned cross coupling reaction (Step E-2), such as a halogen atom (e.g., bromine, iodine, etc.), a trifluoromethylsulfonyloxy group (OTf group) and the like. $R^{e2}$ is a borono group, a dialkoxyboranyl group (e.g., a dimethoxyboranyl group, etc.), a dioxaborolanyl group (a 4,4,5,5-tetramethyl-1,3,2-dioxaborolan-2-yl group, etc.) or the like. $Z^1$ is —NH— or a single bond.

Step E-1 is a step of producing Intermediate VIII from Intermediate IV and Compound 1e. This step can be performed in the same manner as in Step A-3.

Step E-2 is a step of obtaining the compound represented by the general formula (1') wherein $R^2$ is a hydrogen atom, from Intermediate VIII and any one of Compounds 2e and 3e. This step can be performed by heating Intermediate VIII and any one of Compounds 2e and 3e under nitrogen atmosphere in the presence of a metal catalyst (e.g., bis(triphenylphosphine)palladium dichloride, etc.) and a base (e.g., potassium carbonate, etc.), in a solvent inert to the reaction (e.g., a mixed solvent of dimethoxyethane and water, etc.).

Step E-3 is a step of converting $R^2$ of in the compound represented by the general formula (1') wherein $R^2$ is a hydrogen atom to a $C_{1-6}$ alkyl group. This step can be performed in the same manner as in Step A-4.

The production method of each intermediate will be described below.

The production methods of Intermediate I and Intermediate I' will be described. The production methods shown below are merely examples and should not be construed as limited to these.

[Formula 62]

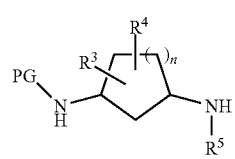

Intermediate I

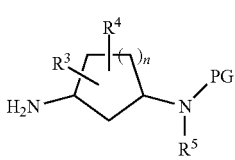

Intermediate I'

In the scheme, PG is as defined above.

Intermediate I or Intermediate I' can also be converted to each other, if necessary, by appropriately combining both steps of (a) introduction of a separate protecting group on the nitrogen atom and (b) removal of an unnecessary protecting group. These steps are general conversion reactions of protecting groups, and can be performed, for example, by employing the method described in the above-mentioned "Protective Groups in Organic Synthesis".

When Intermediate I is represented by the following Compound I-1, I-2, I-3 or I-4, it can be produced, for example, according to Method F or I. Starting Material if is known, or is produced using a known compound as a starting material according to a known method or a method analogous thereto. Known compounds can be purchased from commercial suppliers. Examples of known document include Tetrahedron Asymmetry. 2013, 24, 651-656, Tetrahedron. 2004, 60, 717-728, Bioorg. Med. Chem. 2006, 14, 2242-2252, Tetrahedron. 2017, 73, 1381-1388 and the like. Compound if can also be synthesized according to Method G.

Method F

[Formula 63]

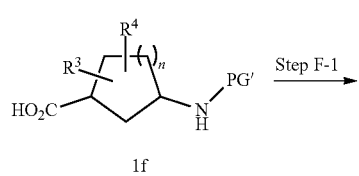

1f

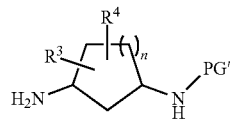

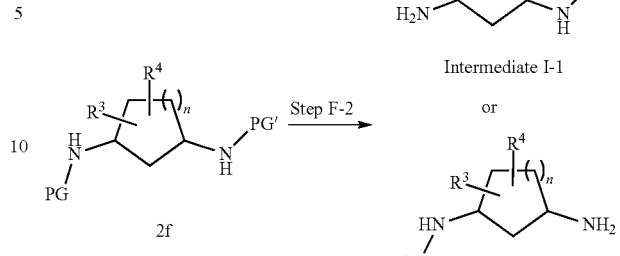

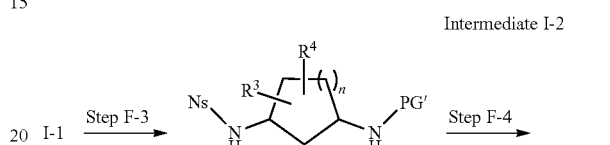

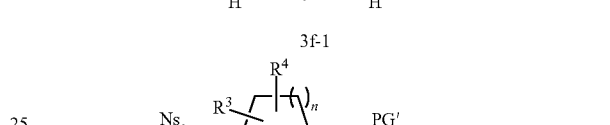

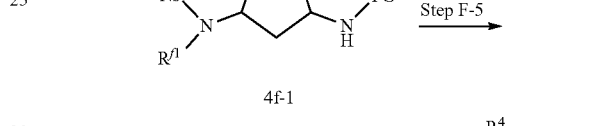

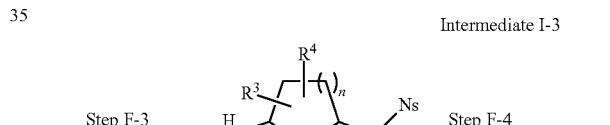

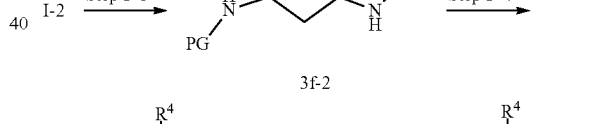

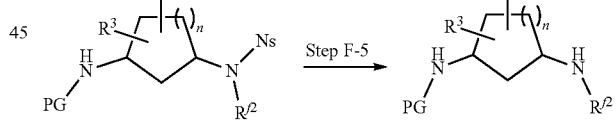

In the scheme, $R^{f1}$ and $R^{f2}$ are each independently a $C_{1-6}$ alkyl group or a protected hydroxy $C_{1-6}$ alkyl group (e.g., a 2-[tert-butyl(dimethyl)silyl]oxyethyl group, etc.). PG and PG' are each independently a protecting group different from each other introduced on the nitrogen atom, and examples thereof include a Boc group, a Cbz group, an Alloc group and the like, and the protecting groups described in the above-mentioned "Protective Groups in Organic Synthesis (the 5th edition, 2014)", and the like can also be used.

Step F-1 is a step of synthesizing Compound 2f from Compound 1f. This step can be performed by heating Compound if together with an azidizing agent (e.g., diphenylphosphoryl azide (DPPA), etc.), a base (e.g., triethylamine, etc.) and an alcohol (e.g., benzyl alcohol, allyl alcohol, etc.) in a solvent inert to the reaction (e.g., toluene, etc.).

Step F-2 is a step of synthesizing Intermediate I-1 or I-2 from Compound 2f (if necessary, the protecting group to be removed may be either PG or PG'). Both steps can be performed under the same conditions as in Step A-2.

When $R^5$ of Intermediate I or I' is $R^{f1}$ or $R^{f2}$, Intermediate I-3 or I-4 can be produced by performing Step F-2, followed by Steps F-3 to F-5.

Step F-3 is a step of synthesizing Compound 3f-1 from Intermediate I-1, or a step of synthesizing Compound 3f-2 from Intermediate I-2. Both steps can be performed, for example, by reacting Intermediate I-1 or Intermediate I-2 with a nosylating agent (e.g., 2-nitrobenzenesulfonyl chloride, etc.) and a base (e.g., DIPEA, etc.) in a solvent inert to the reaction (e.g., dichloromethane, etc.).

Step F-4 is a step of synthesizing Compound 4f-1 from Compound 3f-1, or a step of synthesizing, Compound 4f-2 from Compound 3f-2. Both steps can be performed, for example, by reacting Compound 3f-1 or Compound 3f-2 with an alkylating agent (e.g., iodomethane, etc.) and a base (e.g., potassium carbonate, etc.) in a solvent inert to the reaction (e.g., DMF, etc.).

Step F-5 is a step of synthesizing Intermediate I-3 from Compound 4f-1, or a step of synthesizing Intermediate I-4 from Compound 4f-2. Both steps can be performed, for example, by reacting Compound 4f-1 or Compound 4f-2 with a thiol (e.g., isopropylbenzenethiol, etc.) and a base (e.g., cesium carbonate, etc.) in a solvent inert to the reaction (e.g., a mixed solvent of THF and methanol, etc.).

When a functional group having a protecting group is present in $R^3$ or $R^4$, the protecting group may be removed at the same time as Step F-2 is performed.

Intermediates I-1 to I-4 can also be converted to the desired compounds, which can be used as Intermediate I or a starting material for other steps, if necessary, by appropriately combining both steps of (a) introduction of a separate protecting group on the nitrogen atom and (b) removal of an unnecessary protecting group. These steps are general conversion reactions of protecting groups, and can be performed, for example, by employing the method described in the above-mentioned "Protective Groups in Organic Synthesis".

When the compound represented by the general formula (1f) is represented by the following Compound 1f-1, it can be produced according to Method G. The starting materials are known, or are produced using a known compound as a starting material according to a known method or a method analogous thereto.

Method G

[Formula 64]

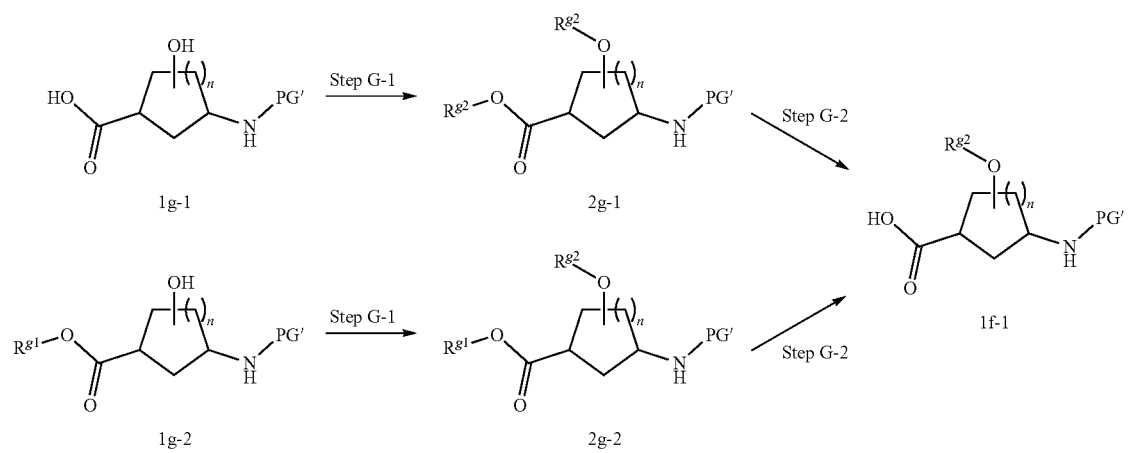

In the scheme, PG' is as defined above. $R^{g1}$ is a protecting group for a carboxy group (e.g., a methyl group, an ethyl group, a MOM group, etc.). $R^{g2}$ is a $C_{1-6}$ alkyl group (e.g., a methyl group, an ethyl group, etc.) or a protecting group for a hydroxy group (e.g., MOM, etc.).

Step G-1 can be performed by reacting Compound 1g-1 or Compound 1g-2 with an alkylating agent (e.g., chloromethyl methyl ether, etc.) and a base (e.g., DIPEA, etc.) in the presence of a reaction promoter (e.g., sodium iodide, etc.), in a solvent inert to the reaction (e.g., dimethoxyethane, etc.), and then heating the mixture. In this step, either Compound 1g-1 or Compound 1g-2 may be used as a raw material. While the reaction conditions of this step depend on the substrate, this step can also be performed by reacting Compound 1g-1 or Compound 1g-2 with an alkylating agent (e.g., iodomethane, etc.) in the presence of a metal catalyst (e.g., silver(I) oxide) and an additive (e.g., molecular sieve, etc.), in a solvent inert to the reaction (e.g., dichloromethane, etc.), and then heating the mixture. The step of converting Compound 1g-1 to Compound 2g-1 can also be performed in two steps: protection of the carboxy group and protection of the hydroxy group.

Step G-2 is a step of synthesizing Compound if-1 from Compound 2g-1 or Compound 2g-2. This step can be performed, for example, by treating Compound 2g-1 or Compound 2g-2 with a base (e.g., aqueous sodium hydroxide solution, etc.) in a solvent inert to the reaction (e.g., a mixed solvent of methanol and THF, etc.).

Intermediate I'-1 can be produced as follows (Method H). The raw material, Compound 1h can be synthesized, for example, according to Method F.

Method H

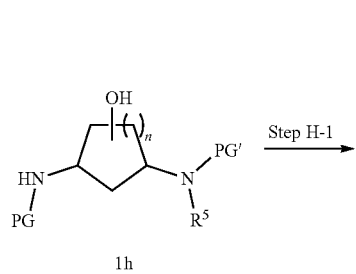

1h

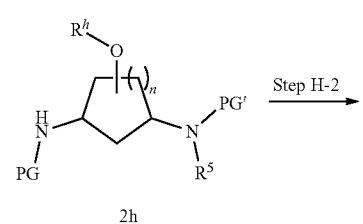

2h

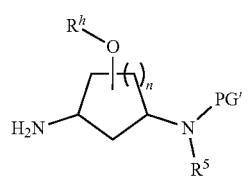

Intermediate I'-1

In the scheme, PG and PG' are as defined above. $R^h$ is $C_{1-6}$ alkyl.

Step H-1 can be performed in the same manner as in Step G-1.

Step H-2 can be performed in the same manner as in Step A-2.

When Intermediate I is represented by the following Compound I-5, it can also be produced as follows (Method I). The raw material, Compound 1i can be synthesized, for example, according to Method G.

Method I

[Formula 66]

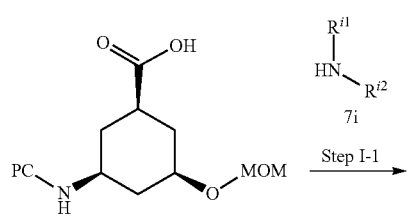

1i

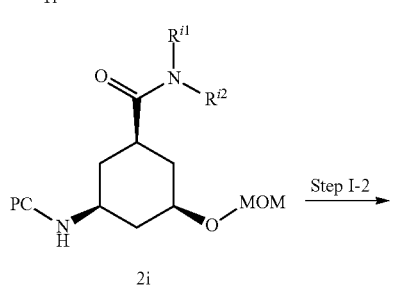

2i

In the scheme, $R^{i1}$ and $R^{i2}$ are each independently a $C_{1-6}$ alkyl group.

Step I-1 is a step of obtaining Compound 2i from Compound 1i. This step can be performed by reacting Compound 1i with Compound 7i in the presence of a condensing agent (e.g., EDC, etc.), a catalyst (e.g., HOBt, etc.) and a base (e.g., triethylamine etc.), in a solvent inert to the reaction (e.g., dichloromethane, etc.)

Step I-2 is a step of obtaining Compound 3i from Compound 2i. This step can be performed by treating Compound 2i with an acid (e.g., hydrochloric acid, etc.) in a solvent inert to the reaction (e.g., 1,4-dioxane, etc.).

Step I-3 is a step of obtaining Compound 4i from Compound 3i. This reaction can be performed by reacting Compound 3i with a carboxylic acid (e.g., 4-nitrobenzoic acid, etc.) in the presence of a phosphine compound (e.g., triphenylphosphine, etc.) and an azodicarboxylate compound (e.g., diisopropyl azodicarboxylate, etc.), in a solvent inert to the reaction (e.g., THF, etc.).

Step I-4 is a step of obtaining Compound 5i from Compound 4i. This step can be performed by treating Compound 4i with a base (e.g., potassium carbonate, etc.) in a solvent inert to the reaction (e.g., ethanol, etc.).

Step I-5 is a step of obtaining Compound 6i from Compound 5i. This step can be performed by reacting Compound 5i with diphenylphosphoryl azide (DPPA) in the presence of an azodicarboxylate compound (e.g., diisopropyl azodicarboxylate (DIAD), etc.) in a solvent inert to the reaction (e.g., THF, etc.).

Step I-6 is a step of obtaining Intermediate I-5 from Compound 6i. This step can be performed by reacting Compound 6i with a reducing agent (e.g., triphenylphosphine, etc.), in a solvent inert to the reaction (e.g., THF, etc.), and then treating the resultant with water, and heating them.

Next, the production methods of Intermediates II and II' will be described. The production methods shown below are merely examples and should not be construed as limited to these.

[Formula 67]

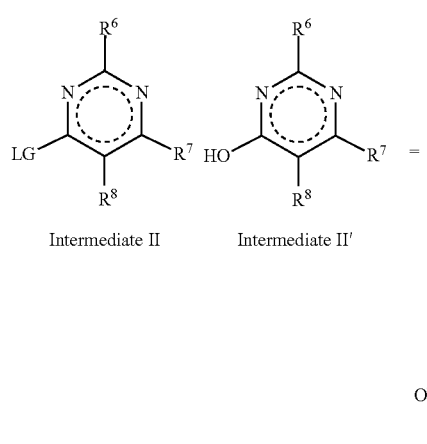

Intermediates II and II' are known, or are produced using a known compound as a starting material according to a known method or a method analogous thereto. Examples of known document include Nat. Chem. Biol. 2012, 8, 277-284., Cancer cell. 2015, 27, 589-602., J. Med. Chem. 2016, 59(3), 892-913., WO 2017/214367, WO 2016/195776, WO 2012/097013, J. Heterocyclic Chem. 2005, 42(4), 509-513., J. Med. Chem. 2001, 44(17), 2695-2700. and the like.

When Intermediate II is represented by the following Compound II-1 or II'-1, it can also be produced according to the following method (Method J). The raw material, Compound 1j is known, or is produced using a known compound as a starting material according to a known method or a method analogous thereto. Examples of known document include WO 2004/007491.

Method J

[Formula 68]

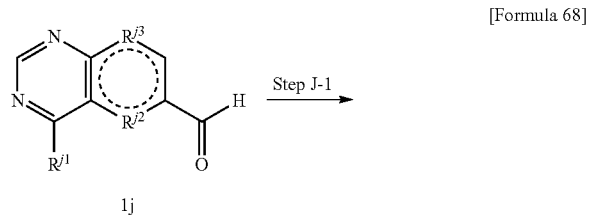

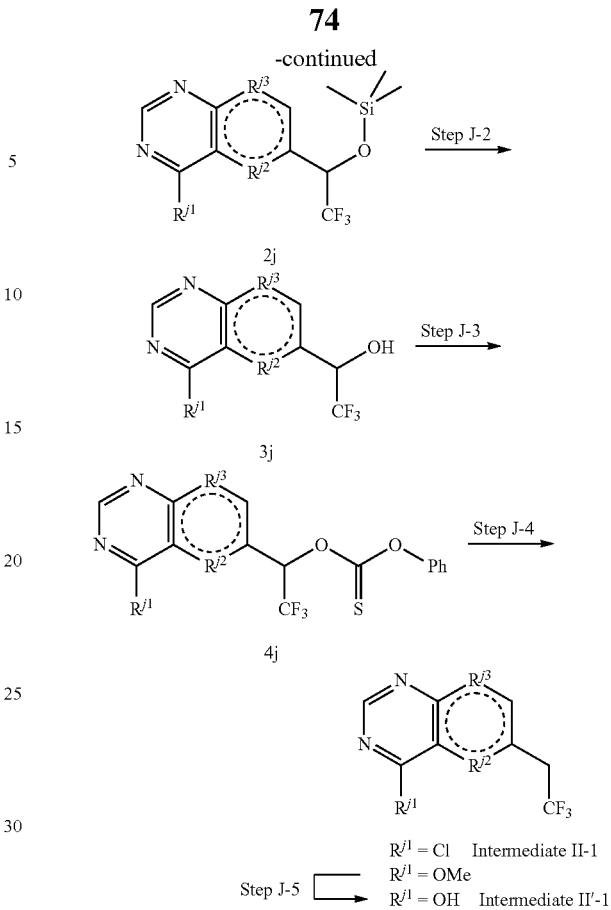

In the scheme, $R^{j1}$ is a chlorine atom or a methoxy group. $R^{j2}$ and $R^{j3}$ are both carbon atoms, or $R^{j2}$ is a sulfur atom and $R^{j3}$ is a bond.

Step J-1 is a step of obtaining Compound 2j from Compound 1j. This step can be performed by reacting Compound 1j with (trifluoromethyl)trimethylsilane (Ruppert reagent) and a reagent to be a fluoride ion source (e.g., tetrabutylammonium fluoride, etc.), in a solvent inert to the reaction (e.g., THF, etc.).

Step J-2 is a step of obtaining Compound 3j from Compound 2j. This step can be performed by treating Compound 2j with an acid (e.g., hydrochloric acid, etc.) in a solvent inert to the reaction (e.g., tetrahydrofuran, etc.).

Step J-3 is a step of obtaining Compound 4j from Compound 3j. This step can be performed by reacting Compound 3j with phenyl chlorothionocarbonate and a base (e.g., TEA, etc.) in a solvent inert to the reaction (e.g., dichloromethane, etc.).

Step J-4 is a step of obtaining Intermediate II-1 from Compound 4j. This step can be performed by reacting Compound 4j with a radical reducing agent (e.g., tributyltin hydride, etc.) and a radical initiator (e.g., azobis(isobutyronitrile), etc.) in a solvent inert to the reaction (e.g., toluene, etc.).

Step J-5 is a step of obtaining Intermediate II'-1 wherein $R^{j1}$ is a hydroxy group from Intermediate II-1 wherein $R^{j1}$ is a methoxy group. This step can be performed by treating Intermediate II-1 wherein $R^{j1}$ is a methoxy group with an acid (e.g., hydrochloric acid, etc.) in a solvent inert to the reaction (e.g., THF, etc.).

When Intermediate III is represented by the following Compound III-1 or III-2, it can also be produced according to the following method (Method K). The raw material, Compound 1k is known, or is produced using a known compound as a starting material according to a known method or a method analogous thereto. Examples of known document include Eur. J. Org. Chem. 2013, 17, 3477-3493.

Method K

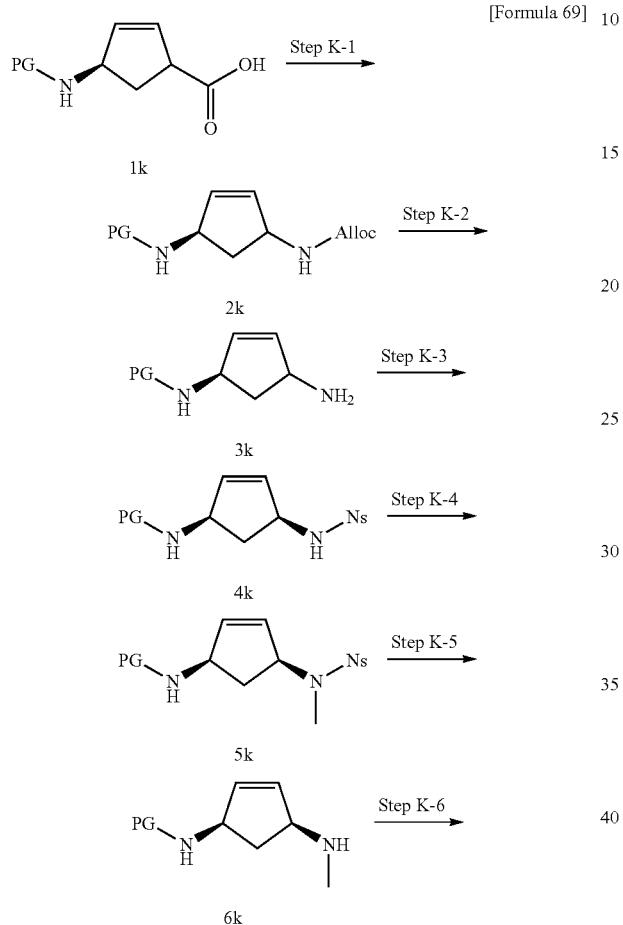

[Formula 69]

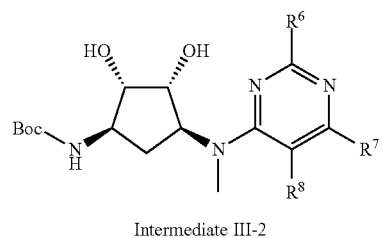

Intermediate III-2

Steps K-1 to K-5 can be performed in the same manner as in Steps F-1 to F-5, and Step K-6 can be performed in the same manner as in Step A-1. In the purification process of Step K-6, various isomers by-produced in a series of steps can also be removed by using an optically active column such as CHIRALPAK (registered trademark, Daicel Co., Ltd.)-IA, IB, IC, ID and the like. As the developing solvent, n-hexane, ethanol, isopropyl alcohol and the like can be used.

Step K-7 is a step of obtaining Intermediates III-1 and III-2 from Compound 7k. This step can be performed by reacting Compound 7k with a catalyst (e.g., osmium tetraoxide, etc.) and an oxidizing agent (e.g., 4-methylmorpholine N-oxide, etc.) in a solvent inert to the reaction (e.g., a mixed solvent of acetone and water, etc.).

When Intermediate III is represented by the following Compound III-3, it can also be produced according to the following method (Method L). The raw material, Compound 1l is known, or is produced using a known compound as a starting material according to a known method or a method analogous thereto. Examples of known document include Bioorg. Med. Chem. 2006, 14, 2242-2252.

Method L

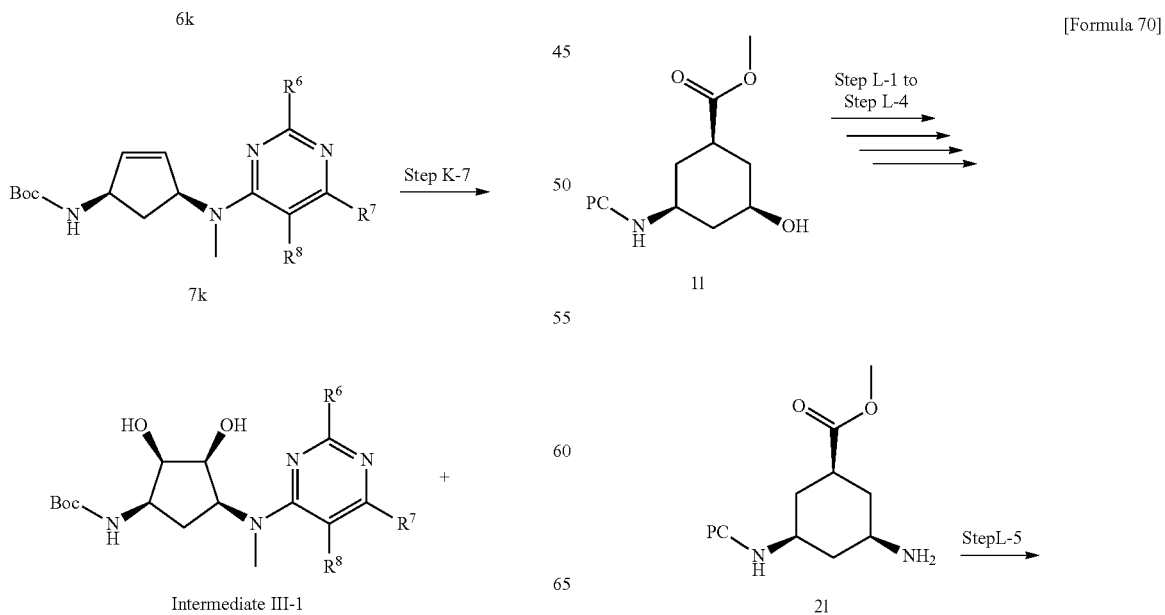

[Formula 70]

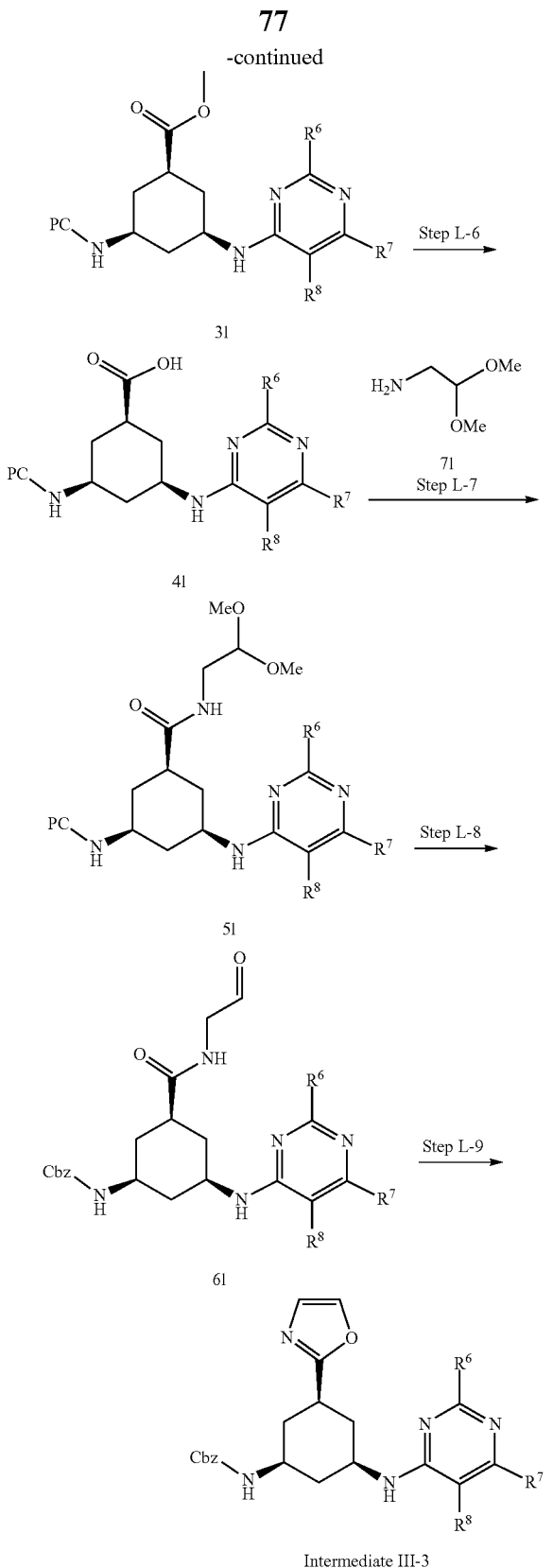

Step L-7 is a step of obtaining Compound 51 from Compound 41. This step can be performed by reacting Compound 41 with Compound 71 in the presence of a condensing agent (e.g., COMU, etc.) and a base (e.g., DIPEA, etc.), in a solvent inert to the reaction (e.g., DMF, etc.).

Step L-8 is a step of obtaining Compound 61 from Compound 51. This step can be performed by treating Compound 51 with an acid (e.g., trifluoroacetic acid, etc.), in a solvent inert to the reaction (e.g., dichloromethane, etc.).

Step L-9 is a step of obtaining Intermediate III-3 from Compound 61. This step can be performed by reacting Compound 61 with a phosphine compound (e.g., triphenylphosphine, etc.), hexachloroethane and a base (e.g., triethylamine, etc.) in a solvent inert to the reaction (e.g., dichloromethane, etc.).

When Intermediate III is represented by the following Compound III-4, it can be produced according to the following method (Method M). Compound 1m can be synthesized according to a known method (WO 2017/214367). The boronic acid (3m) is a known compound, or can be produced using a known compound as a starting material, according to a known method or a method analogous thereto.

Method M

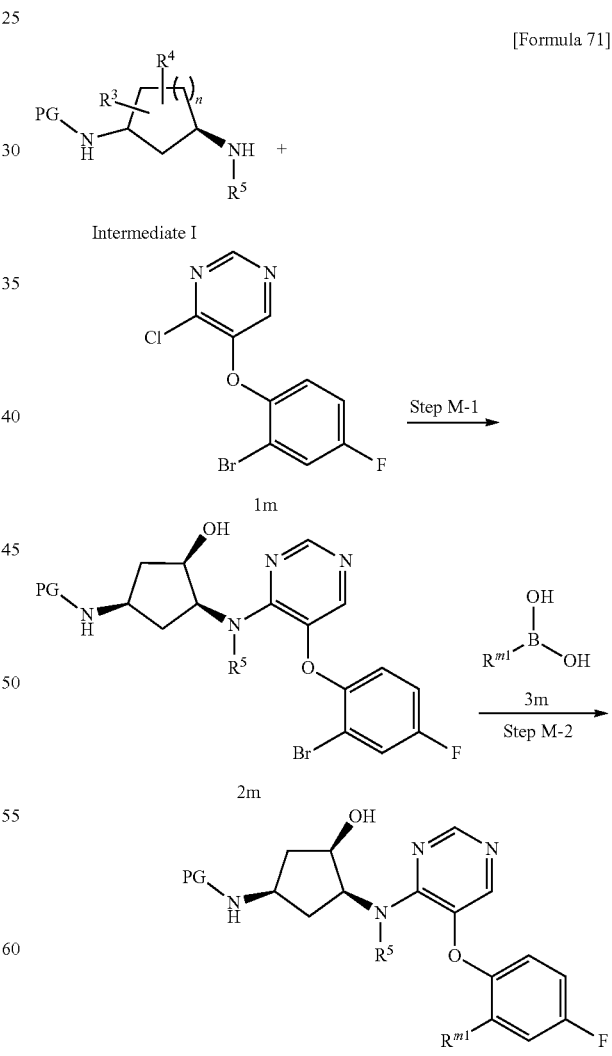

Steps L-1 to Step L-4 can be performed in the same manner as in Steps I-3 to I-6, and Step L-5 can be performed in the same manner as in Step A-1, and Step L-6 can be performed in the same manner as in Step G-2.

In the scheme, $R^{m1}$ is an aromatic ring group.

Step M-1 is a step of obtaining Compound 2m from Intermediate I and Compound 1m. This step can be performed in the same manner as in Step A-1.

Step M-2 is a step of obtaining Intermediate III-4 from Compound 2m. This step can be performed by heating Compound 2m using a metal catalyst (e.g., tetrakis(triphenylphosphine)palladium, etc.) and a base (e.g., sodium carbonate, etc.), under inert gas atmosphere, in a solvent inert to the reaction (e.g., a mixed solvent of dioxane and water, etc.). In this step, a boronate may be used instead of the boronic acid (3m).

When Intermediate III is represented by the following Compound III-5, it can be produced, for example, according to the following method (Method N). Compound 1n can be produced in the same manner as in Step A-1 of Method A.

Method N

[Formula 72]

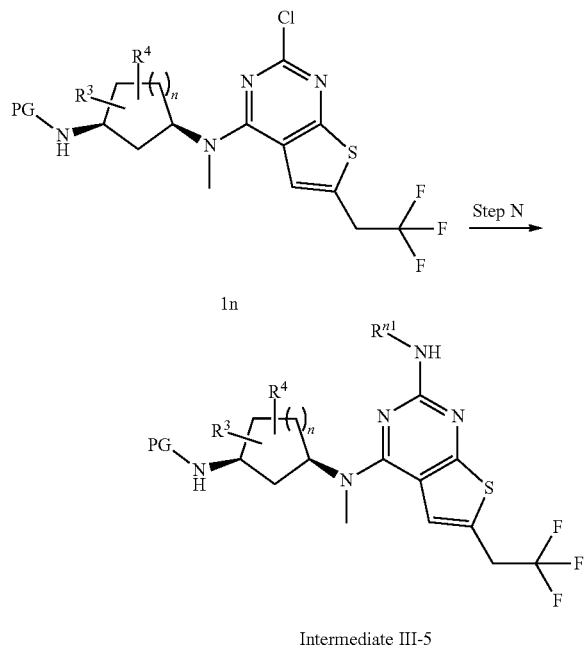

Intermediate III-5

In the scheme, $R^{n1}$ is a $C_{1-6}$ alkyl group, a p-methoxybenzyl group or the like.

Step N is a step of obtaining Intermediate III-5 from Compound 1n. This step can be performed by reacting Compound 1n with an amine (e.g., methylamine, paramethoxybenzylamine, etc.) under heating (desirably, heating above the boiling point of the solvent using a microwave reactor etc.) in a solvent inert to the reaction (e.g., butyronitrile, etc.).

Next, the production methods of Intermediate V will be described. Intermediate V is known, or is produced using a known compound as a starting material according to a known method or a method analogous thereto. Examples of known document include Cancer cell. 2015, 27, 589-602, J. Med. Chem. 2016, 59(3), 892-913, WO 2007/118041, WO 2014/164749 and the like.

Since Intermediate V has a functional group represented by $R^1C(=O)-$ (a formyl group or a $C_{1-6}$ alkylcarbonyl group) on Ring $Q^1$, it can also be derived from a precursor having a group that can be easily converted to the functional group (in the case of a formyl group, examples thereof include a hydroxymethyl group, a $C_{1-6}$ alkoxy carbonyl group, a carboxy group and the like, and in the case of a C1-6 alkylcarbonyl group, examples thereof include an acetyl group, an ethanoyl group and the like).

Intermediate V can also be produced according to Method O to Method Y.

[Formula 73]

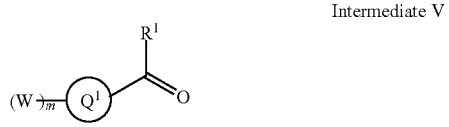

Intermediate V

Intermediate V is represented by the following Compound V-1, it can also be produced, for example, according to Method O.

Method O

[Formula 74]

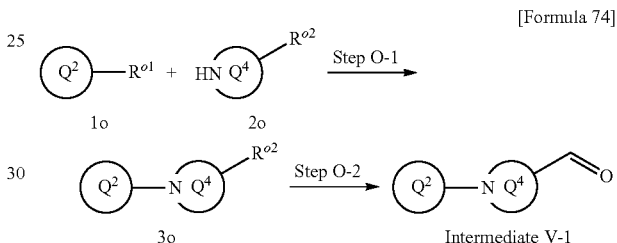

Intermediate V-1

In the scheme, $R^{o1}$ is a halogen atom (e.g., chlorine, bromine, or iodine) or a trifluoromethylsulfonyloxy group. $R^{o2}$ is a functional group that can be easily converted to a formyl group, and examples thereof include a hydroxylmethyl group, a $C_{1-6}$ alkoxy carbonyl group, a carboxy group, an acetal group and the like. Ring $Q^4$ is a heterocycle containing a nitrogen atom in the ring (the heterocycle optionally has substituent(s)), and examples thereof include a piperidine ring and the like.

Step O-1 is a step of obtaining Compound 3o from Compounds 1o and 2o. This step can be performed by heating Compounds 1o and 2o under inert gas atmosphere in the presence of a metal catalyst (e.g., a combination of tris(dibenzylideneacetone)dipalladium(0) and (±)-2,2'-bis (diphenylphosphino)-1,1'-binaphthyl, etc.) and a base (e.g., sodium tert-butoxide, cesium carbonate, triethylamine, etc.), in a solvent inert to the reaction (e.g., toluene, etc.).

Step O-2 is a step of converting Compound 3o to Intermediate V-1. For example, when $R^{o2}$ is a hydroxymethyl group, it can be performed by reacting Compound 3o with an oxidizing agent (pyridinium chlorochromate, Dess-Martin periodinane, manganese(IV) oxide, etc.) in a solvent inert to the reaction (e.g., dichloromethane, chloroform, DMSO, etc.). When $R^{o2}$ is the other functional group (e.g., a $C_{1-6}$ alkoxy carbonyl group, a carboxy group, an acetal group, etc.), the conversion of the functional group to a formyl group can be performed according to the methods described in the above-mentioned "ORGANIC FUNCTIONAL GROUP PREPARATIONS", "Comprehensive Organic Transformations" etc., and the like.

When Intermediate V is represented by the following Compound V-2, it can also be produced, for example, according to Method P.

Method P

[Formula 75]

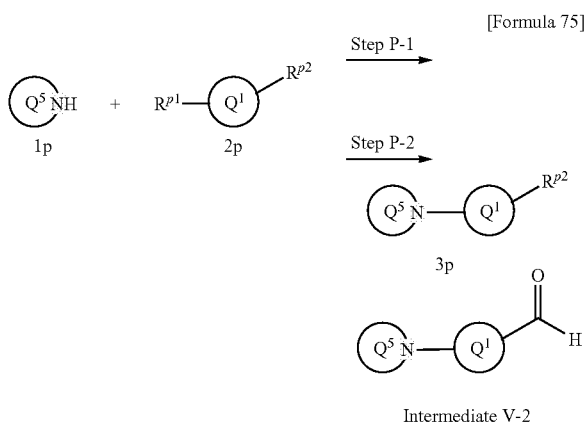

In the scheme, $R^{p1}$ is a halogen atom (e.g., chlorine, bromine, or iodine) or a trifluoromethylsulfonyloxy group. $R^{p2}$ is a functional group that can be easily converted to a formyl group, and examples thereof include a hydroxylmethyl group, a $C_{1-6}$ alkoxy carbonyl group, a carboxy group, an acetal group and the like. Ring $Q^5$ is a heterocycle containing a nitrogen atom in the ring (the heterocycle optionally has substituent(s)), and examples thereof include a dihydroindole ring and the like.

Step P-1 is a step of obtaining Compound 3p from Compound 1p and Compound 2p. This step can be performed in the same manner as in Step O-1.

Step P-2 is a step of obtaining Intermediate V-2 from Compound 3p. For example, when $R^2$ is an acetal group, it can be performed by treating Compound 3p with an acid (e.g., hydrochloric acid, etc.) in a solvent inert to the reaction (e.g., THF, etc.).

Intermediate V is represented by the following Compound V-3, it can also be produced, for example, according to Method Q.

Method Q

[Formula 76]

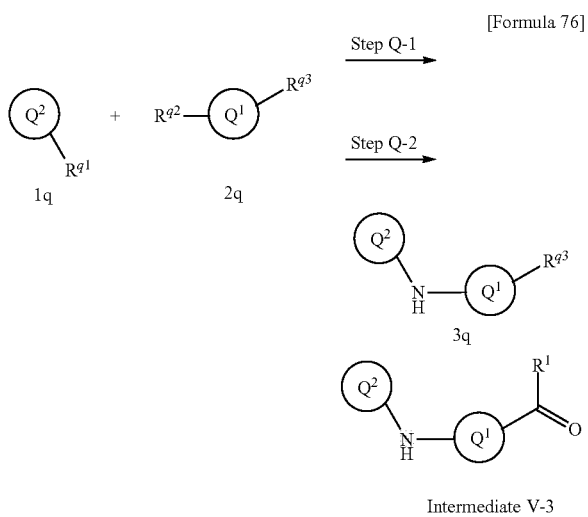

In the scheme, one of $R^{q1}$ and $R^{q2}$ is an amino group, and the other of $R^{q1}$ and $R^{q2}$ is a halogen atom (e.g., chlorine, bromine, or iodine) or a trifluoromethylsulfonyloxy group. $R^{q3}$ is a formyl group or a functional group that can be easily converted to a formyl group, and examples thereof include a hydroxylmethyl group, a $C_{1-6}$ alkoxy carbonyl group, a carboxy group, an acetal group and the like.

Step Q-1 is a step of obtaining Compound 3q from Compound 1q and Compound 2q. This step can be performed by heating Compound 1q and Compound 2q under inert gas atmosphere in the presence of a metal catalyst (e.g., a combination of tris(dibenzylideneacetone)dipalladium(0) and tert-butylphosphine, or tetrakis(triphenylphosphine)palladium(0), etc.) and a base (e.g., sodium tert-butoxide, sodium carbonate, etc.), in a solvent inert to the reaction (e.g., a mixed solvent of toluene, dioxane and water, a mixed solvent of dimethoxyethane and water, etc.).

Step Q-2 is a step of obtaining Intermediate V-3 from Compound 3q. For example, when $R^{q3}$ is an acetal group, it can be performed by treating Compound 3q with an acid (e.g., hydrochloric acid, etc.) in a solvent inert to the reaction (e.g., THF, etc.). When $R^{q3}$ is a formyl group, this step is not required.

Intermediate V is represented by the following Intermediate V-4, it can also be produced, for example, according to Method R.

Method R

[Formula 77]

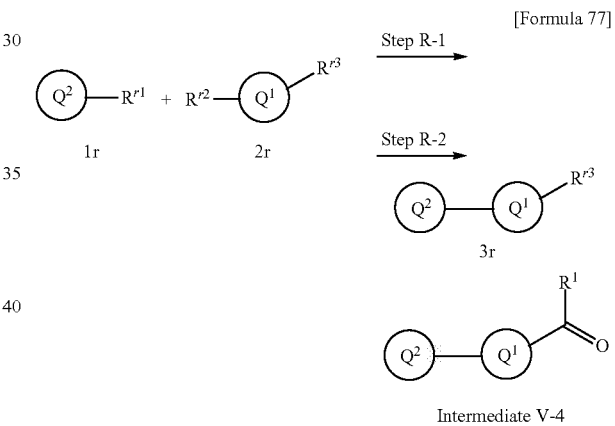

In the scheme, one of $R^{r1}$ and $R^{r2}$ is a halogen atom (e.g., chlorine, bromine, or iodine) or a trifluoromethylsulfonyloxy group, and the other of $R^{r1}$ and $R^{r2}$ is a borono group, a dialkoxyboranyl group (e.g., a dimethoxyboranyl group, etc.), a dioxaborolanyl group (a 4,4,5,5-tetramethyl-1,3,2-dioxaborolan-2-yl group, etc.) and the like. $R^{r3}$ is a formyl group or a functional group that can be easily converted to a formyl group, and examples thereof include a hydroxylmethyl group, a $C_{1-6}$ alkoxy carbonyl group, a carboxy group, an acetal group and the like.

Step R-1 is a step of obtaining Compound 3r from Compound 1r and Compound 2r. This step can be performed by heating Compound 1r and Compound 2r under inert gas atmosphere in the presence of a metal catalyst (e.g., a combination of tris(dibenzylideneacetone)dipalladium(0) and tert-butylphosphine, or tetrakis(triphenylphosphine)palladium(0), etc.) and a base (e.g., sodium tert-butoxide, sodium carbonate, tripotassium phosphate, etc.), in a solvent inert to the reaction (e.g., a mixed solvent of toluene, dioxane and water, a mixed solvent of dimethoxyethane and water, etc.).

Step R-2 is a step of obtaining Intermediate V-4 from Compound 3r. For example, when $R^3$ is a $C_{1-6}$ alkoxy carbonyl group, this step can be performed according to the below Method V. When $R^3$ is a formyl group, this step is not required.

The raw material compounds used in Method O to Method R are known, or are produced using a known compound as a starting material according to a known method or a method analogous thereto. Examples of known document include WO 2014/078813, Synlett. 2015, 26(7), 953-959, J. Med. Chem. 2014, 57(19), 8086-8098, Eur. J. Inorg. Chem. 2015, 28, 4666-4677, WO 2004/108690, WO 2015/0291572, WO 2010/141796, WO 2013/093849, J. Med. Chem. 2014, 57(19), 8086-8098, J. Org. Chem. 2014, 79, 10311-10322, WO 2011/109267, WO 2007/013673, Tetrahedron. 2015, 71(49), 9240-9244, "ORGANIC FUNCTIONAL GROUP PREPARATIONS", the 2nd edition, ACADEMIC PRESS, INC., 1989, "Comprehensive Organic Transformations", VCH Publishers Inc., 1989 and the like.

Compound 1r can also be produced according to the following Method S or Method T.

When Compound 1r is represented by the following Compound 2s or 3s, it can be produced, for example, according to Method S.

Method S

[Formula 78]

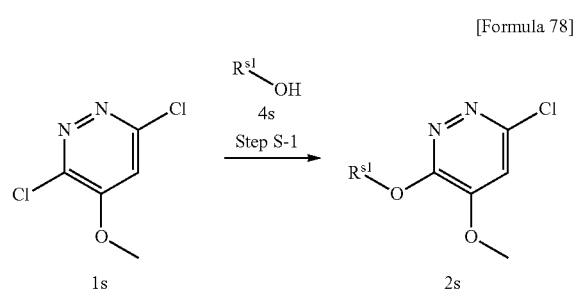

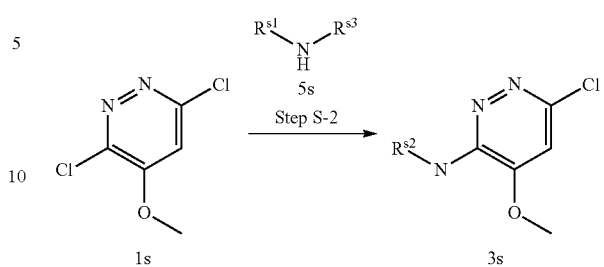

In the scheme, $R^{s1}$, $R^{s2}$ and $R^{s3}$ are each independently a $C_{1-6}$ alkyl group (e.g., a methyl group, an ethyl group, etc.), an aromatic ring group (e.g., pyridyl group, etc.) optionally containing heteroatom(s), or a saturated heterocyclic group (e.g., piperidinyl group, etc.) and the like, or $R^{s2}$ and $R^{s3}$ are optionally taken together with the nitrogen atom to which $R^{s2}$ and $R^{s3}$ are bonded to form a ring.

Step S-1 is a step of obtaining Compound 2s from Compound 1s. This step can be performed by reacting Compound 1s with Compound 4s in the presence of a base (e.g., sodium hydride, potassium carbonate, etc.), in a solvent inert to the reaction (e.g., toluene, DMF, etc.).

Step S-2 is a step of obtaining Compound 3s from Compound 1s. This step can be performed by reacting Compound 1s with Compound 5s in the presence of a base (e.g., diisopropylamine, etc.) in a solvent inert to the reaction (e.g., THF, etc.).

When Compound 1r is represented by any of the following Compounds 3t to 5t, it can also be produced, for example, according to Method T.

Method T

[Formula 79]

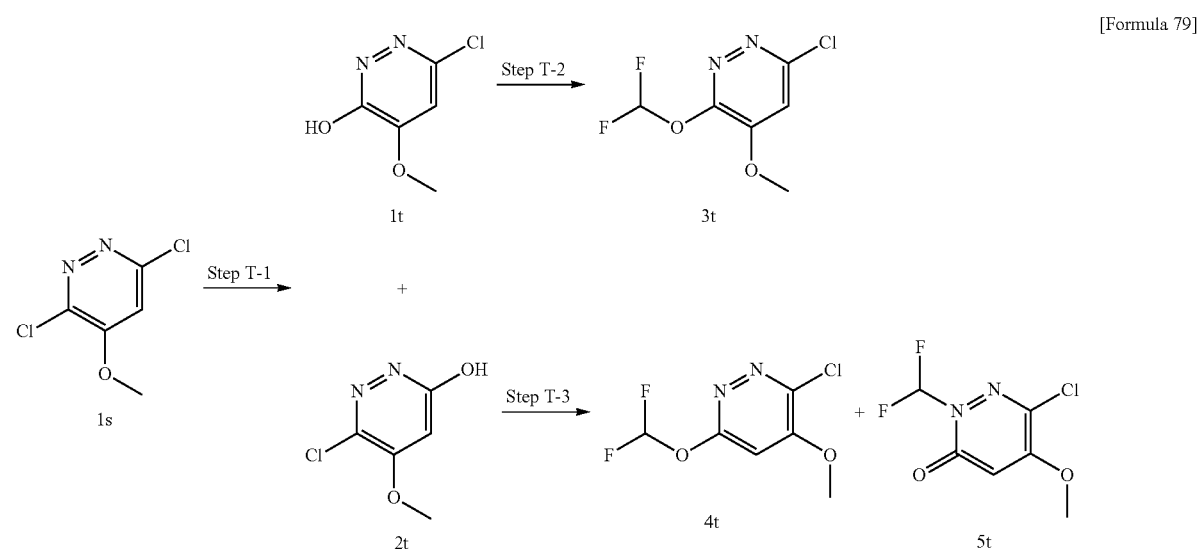

Step T-1 is a step of obtaining Compound 1t and Compound 2t from Compound 1s. This step can be performed by reacting Compound 1s with a base (e.g., potassium acetate, etc.) in a solvent inert to the reaction (e.g., a mixed solvent of acetic acid and water, etc.), and then heating the mixture. The resulting Regioisomers 1t and 2t can be separated from each other, for example, by utilizing the difference in solubility.

Step T-2 is a step of obtaining Compound 3t from Compound 1t. This step can be performed by reacting Compound 1t with a base (e.g., aqueous potassium hydroxide solution, etc.) and a difluoromethylating agent (e.g., difluoromethyltrifluoromethanesulfonic acid, etc.), in a solvent inert to the reaction (e.g., acetonitrile, etc.).

Step T-3 is a step of obtaining Compounds 4t and 5t from Compound 2t. This step can be performed in the same manner as in Step T-2. The resulting Isomers 4t and 5t can be separated from each other, for example, by a method using silica gel column chromatography and the like.

When Intermediate V is represented by the following Compound V-5, it can be produced, for example, according to the following method (Method U).

Method U

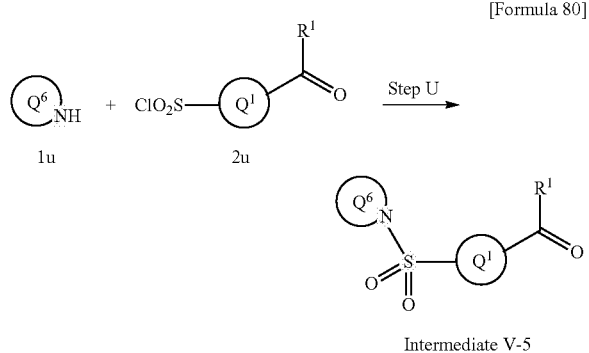

Intermediate V-5

In the scheme, Ring $Q^6$ is a heterocycle containing a nitrogen atom in the ring (the heterocycle optionally has substituent(s)), and examples thereof include a piperidine ring, an azepane ring and the like.

Step U is a step of obtaining Intermediate V-5 from Compound 1u and Compound 2u. This step can be performed by reacting Compound 1u and Compound 2u with an amine (e.g., DIPEA, etc.) in a solvent inert to the reaction (e.g., dichloromethane, etc.).

When Intermediate V is represented by the following Compound V-6, it can also be produced, for example, according to the following method (Method V). The starting material is known, or is produced using a known compound as a starting material according to a known method or a method analogous thereto. Examples of known document include WO 2014/114186, WO 2005/108399, J. Med. Chem. 2016, 59(18), 8233-8262, WO 2005/032488, Science. 2016, 352(6291), 1304-1308, Bioorg. Med. Chem. Let. 2006, 16(19), 4987-4993, Helvetica Chimica Acta. 2007, 90(6), 1043-1068, Tetrahedron. 2015, 71(49), 9240-9244, "ORGANIC FUNCTIONAL GROUP PREPARATIONS", the 2nd edition, ACADEMIC PRESS, INC., 1989, "Comprehensive Organic Transformations", VCH Publishers Inc., 1989, and the like.

Method V

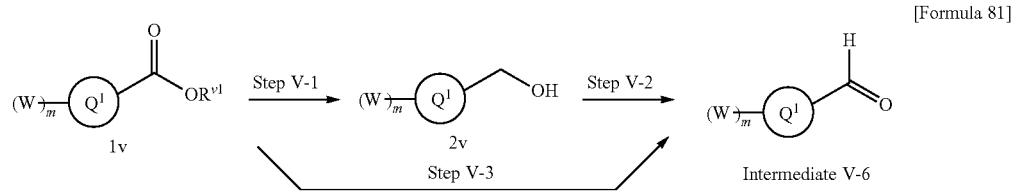

In the scheme, $R^{v1}$ is a hydrogen atom or an alkyl group (e.g., a methyl group, an ethyl group, etc.).

Step V-1 is a step of obtaining Compound 2v from Compound 1v. This step can be performed, for example, by reacting Compound 1v with a reducing agent (e.g., lithium aluminium hydride, lithium borohydride, etc.) in a solvent inert to the reaction (e.g., THF, etc.).

Step V-2 is a step of obtaining Intermediate V-6 from Compound 2v. This step can be performed, for example, by reacting Compound 2v with an oxidizing agent (e.g., pyridinium chlorochromate, Dess-Martin periodinane, manganese(IV) oxide, etc.) in a solvent inert to the reaction (e.g., dichloromethane, chloroform, DMSO, etc.).

Step V-3 is a step of obtaining Intermediate V-6 from Compound 1v. This step can be performed by reacting Compound 1v with a reducing agent (e.g., diisobutylaluminium hydride, etc.) in a solvent inert to the reaction (e.g., dichloromethane, etc.).

When Intermediate V is represented by the following Compound V-7, it can be produced, for example, according to Method W.

Method W

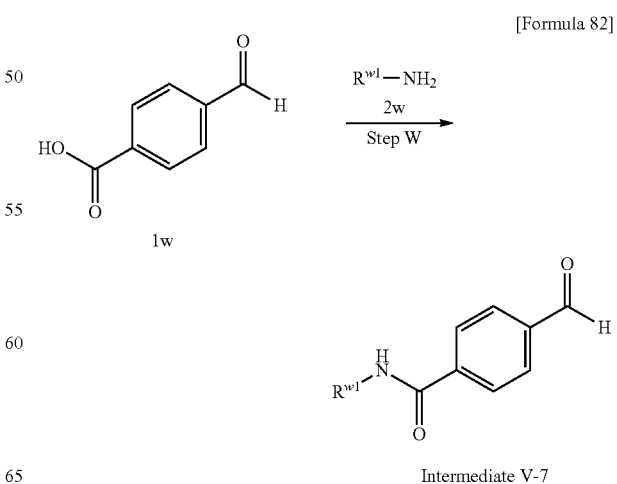

Intermediate V-7

In the scheme, $R^{w1}$ is a $C_{1-6}$ alkyl group optionally having substituent(s) (e.g., a 3-(tert-butoxycarbonylamino)propyl group, a 1-methylpyrazol-4-ylmethyl group, etc.).

Step W is a step of obtaining Intermediate V-7 from Compounds 1w and 2w. This step can be performed in the same manner as in Step I-1.

When Intermediate V has a functional group, Intermediate V can also be used after converting the functional group to a desired functional group by a known method. Examples of known method include the methods described in "ORGANIC FUNCTIONAL GROUP PREPARATIONS", "Comprehensive Organic Transformations" and "Protective Groups in Organic Synthesis (the 5th edition, 2014)", and the methods described in J. Med. Chem. 2014, 57(18), 7590-7599, Synlett. 2015, 26(7), 953-959, WO 2013/013503, Angew. Chem. Int. Ed. 2015, 54(33), 9668-9672, Org. Lett. 2012, 14(14), 3700-3703, WO 2017/100668 and the like, and various reactions such as reduction of a nitro group, acroylation, sulfonylation, methylation, deprotection and the like can be performed.

When the compound represented by the general formula (1) has a functional group, the functional group can also be converted to a desired functional group by a known method. For example, protection or deprotection, conversion or modification of functional groups, and the like can be performed. Examples of known method include the methods described in "ORGANIC FUNCTIONAL GROUP PREPARATIONS", "Comprehensive Organic Transformations" and "Protective Groups in Organic Synthesis (the 5th edition, 2014)", and the methods described in J. Med. Chem. 2014, 57(18), 7590-7599, Angew. Chem. Int. Ed. 2017, 56(21), 5886-5889 and the like.

The compound produced by the above-mentioned method can be isolated and purified by a known method, for example, extraction, precipitation, distillation, chromatography, fractional recrystallization, recrystallization and the like.

The inhibitory activity of the cell-free binding between menin and MLL can be measured by employing the chemiluminescent AlphaLISA (registered trademark, PerkinElmer) method described in the following Experimental Example 1. Alternatively, as general methods for evaluating protein-protein interaction, time-resolved fluorescence resonance energy transfer (TR-FRET) method in which fluorescence energy transfer from a donor-binding protein having long-lived fluorescence to an acceptor-binding protein is detected by FRET (Fluorescence Resonance Energy Transfer), surface plasmon resonance (SPR) method, and the like can be employed.

The cell growth inhibitory activity of the compound of the present invention or a pharmaceutically acceptable salt thereof can be examined by employing a growth inhibitory test method conventionally employed by those skilled in the art. The cell growth inhibitory activity can be examined, for example, as described in the following Experimental Example 2, by comparing the degree of cell growth obtained in the presence of a test compound with that obtained in the absence of the test compound. The degree of growth can be examined, for example, by using a test system for measuring living cells. Examples of method for measuring living cells include a [$^3$H]-thymidine uptake assay, a BrdU method and an MTT assay.

The antitumor activity in vivo can be examined by an antitumor test method conventionally employed by those skilled in the art. For example, as described in the following Experimental Examples 3-1 to 3-4, various tumor cells are transplanted into a mouse, a rat or the like, and after confirming engraftment of the transplanted cells, the compound of the present invention is orally or intravenously administered. After several days or several weeks, the tumor growth in the non-administration group and that in the compound administration group are compared, so that the antitumor activity in vivo according to the present invention can be confirmed.

The compound of the present invention or a pharmacologically acceptable salt thereof can be used together with other antitumor agents. Examples thereof include alkylating agents, antimetabolites, antitumor antibiotics, antitumor plant components, BRMs (biological response modifiers), hormones, vitamins, antitumor antibodies, molecular target drugs, other antitumor agents and the like.

More specifically, examples of the alkylating agent include alkylating agents such as nitrogen mustard, nitrogen mustard N-oxide, chlorambucil etc.; aziridine-based alkylating agents such as carboquone, thiotepa, etc.; epoxide-based alkylating agents such as dibromomannitol, dibromo dulcitol etc.; nitrosourea-based alkylating agents such as carmustine, lomustine, semustine, nimustine hydrochloride, streptozocin, chlorozotocin, ranimustine etc.; and busulfan, improsulfan tosylate, dacarbazine and the like.

Examples of the antimetabolite include purine antimetabolites such as 6-mercaptopurine, 6-thioguanine, thioinosine, etc.; pyrimidine antimetabolites such as fluorouracil, tegafur, tegafur-uracil, carmofur, doxifluridine, broxuridine, cytarabine, enocitabine etc.; folic acid antimetabolites such as methotrexate, trimetrexate etc.; and the like.

Examples of the antitumor antibiotic include mitomycin C, bleomycin, peplomycin, daunorubicin, aclarbicin, doxorubicin, idarubicin, pirarubicin, THP-adriamycin, 4'-epi-doxorubicin or epirubicin, chromomycin A3, and actinomycin D and the like.

Examples of the antitumor plant component include vinca alkaloids such as videsine, vincristine, vinblastine etc.; taxanes such as paclitaxel, docetaxel etc.; and epipodophyllotoxins such as etoposide, teniposide etc.

Examples of the BRM include tumor necrosis factor, indomethacin and the like.

Examples of the hormone include hydrocortisone, dexamethasone, methylprednisolone, prednisolone, prasterone, betamethasone, triamcinolone, oxymetholone, nandrolone, methenolone, fosfestrol, ethinylestradiol, chlormadinone, mepitiostane, medroxyprogesterone and the like Examples of the vitamin include vitamin C, vitamin A and the like.

Examples of the antitumor antibody and molecule target drug include venetoclax, trastuzumab, rituximab, cetuximab, nimotuzumab, denosumab, bevacizumab, infliximab, ipilimumab, nivolumab, pembrolizumab, avelumab, pidilizumab, atezolizumab, ramucirumab, imatinib mesylate, dasatinib, gefitinib, erlotinib, osimertinib, sunitinib, lapatinib, dabrafenib, trametinib, cobimetinib, pazopanib, palbociclib, panobinostat, sorafenib, crizotinib, vemurafenib, quizartinib, bortezomib, carfilzomib, ixazomib, midostaurin, gilteritinib and the like.

Examples of the other antitumor agent include cisplatin, carboplatin, oxaliplatin, tamoxifen, letrozole, anastrozole, exemestane, toremifene citrate, fulvestrant, bicalutamide, flutamide, mitotane, leuprorelin, goserelin acetate, camptothecin, ifosfamide, cyclophosphamide, melphalan, L-asparaginase, aceglatone, schizophyllan, picibanil, procarbazine, pipobroman, neocarzinostatin, hydroxyurea, ubenimex, thalidomide, lenalidomide, pomalidomide, eribulin, tretinoin, krestin and the like.

The pharmaceutical composition of the present invention comprises the compound of the present invention or a pharmaceutically acceptable salt, and a pharmaceutically acceptable carrier, and can be administered as various injections such as intravenous injection, intramuscular injection, subcutaneous injection etc., or by various methods such as oral administration, transdermal administration etc. The pharmaceutically acceptable carrier means a pharmaceutically acceptable material (e.g., an excipient, a diluent, an additive, a solvent, etc.), which is involved in transporting the compound of the present invention or the composition containing the compound of the present invention from one organ to another organ.

A formulation containing the compound of the present invention or a pharmacologically acceptable salt thereof as an active ingredient is prepared by using an additive used in a conventional formulation, such as a carrier, an excipient etc. Administration of the compound of the present invention can be oral administration in the form of a tablet, a pill, a capsule, a granule, a powder, a liquid or the like, or parenteral administration in the form of an injection (such as intravenous injection, intramuscular injection etc.), a suppository, a transdermal agent, a nasal agent, an inhalant or the like. The dose and the number of doses of the compound of the present invention are appropriately determined depending on individual cases in consideration of the symptoms, and the age, the sex or the like of an administration target. The dose is usually 0.001 mg/kg to 100 mg/kg per dose for oral administration to an adult, and usually 0.0001 mg/kg to 10 mg/kg per dose for intravenous administration to an adult. The number of doses is usually once to six times per day, or once per day to once per 7 days.

A solid formulation for oral administration of the present invention can be a tablet, a powder, a granule or the like. Such a formulation can be produced by mixing one or more active substances with an inert excipient, lubricant, disintegrant, dissolution assisting agent and the like, according to a conventional method. The excipient can be, for example, lactose, mannitol or glucose. The lubricant can be, for example, magnesium stearate. The disintegrant can be, for example, sodium carboxymethyl starch. A tablet or pill can be coated with a sugar coating or a gastric-soluble or enteric coating agent if necessary.

A liquid formulation for oral administration can be a pharmaceutically acceptable emulsion, liquid, suspension, syrup, elixir and the like. Such a formulation contains a generally used inert solvent (e.g., purified water, ethanol), and may further contain a solubilizing agent, a wetting agent, a suspending agent, a sweetener, a flavoring agent, an aromatic or a preservative.

An injection for parenteral administration can be an aseptic aqueous or non-aqueous liquid, suspension or emulsion. An aqueous solvent for injection can be, for example, distilled water or a normal saline solution. A non-aqueous solvent for injection can be, for example, propylene glycol, polyethylene glycol, vegetable oils such as olive oil, alcohols such as ethanol, or polysorbate 80 (pharmacopoeia name). Such a formulation may further contain a tonicity agent, a preservative, a wetting agent, an emulsifier, a dispersant, a stabilizer or a dissolution assisting agent. Such a formulation can be sterilized, for example, by filtration through a bacteria retention filter, blending with a bactericide, or radiation exposure. Alternatively, a composition obtained by dissolving or suspending an aseptic solid composition in aseptic water or an injection solvent before use can also be used as a formulation.

EXAMPLE

Hereinafter, the present invention will be described in more detail with reference to Reference Examples and Examples, but the scope of the present invention is not limited to these examples, and these examples are not restrictively interpreted in any sense. In addition, the reagents, solvents and starting materials used herein are readily available from commercially available sources, unless otherwise specified.

The proton nuclear magnetic resonance spectrum ($^1$H-NMR) was measured using 400 MHz nuclear magnetic resonance spectrometer manufactured by JEOL, or 400 MHz nuclear magnetic resonance spectrometer manufactured by Varian. The spectral data indicates significant peaks, showing the chemical shifts (which are shown as relative ppm (δ) from a tetramethylsilane peak), the number of protons, and the multiplicity of peak splitting (which are shown as s: singlet; d: doublet; t: triplet; q: quartet; quint: quintet; m: multiplet; br: broad; br s: broad singlet, etc.), and further, if specified, the coupling constant J value (unit: Hz).

The mass spectrum (MS m/z) was measured using an electrospray ionization method (ESI) or an atmospheric pressure chemical ionization method (APCI). The mass spectral data was shown regarding the maximum ionization peak (corresponding to the maximum UV absorption peak in almost all cases) obtained after passing through a reverse phase high performance liquid chromatography column (Agilent System; column: Develosil Combi-RP-5, 2.0×50 mm, Cadenza CD-C18, 3.0×75 mm, or ZORBAX SB-C18, 1.8 μm, 2.1×50 mm; solvent: 0.1% formic acid-containing acetonitrile/water system, or 0.01% trifluoroacetic acid-containing acetonitrile/water system).

The silica gel column chromatography was performed by using a commercially available packed column and an automatic preparative purification system (e.g., SP1 manufactured by Biotage, EPCLC-W-Prep2XY manufactured by Yamazen, Purif-α2 manufactured by Shoko Science, etc.), and multiple types of solvents used for the mobile phase were merely described. The elution is performed under observation by thin layer chromatography (TLC). As a TLC plate, silica gel 60 $F_{254}$ or 60 $NH_2$ $F_{254}$s manufactured by Merck, $NH_2$ silica gel 60 $F_{254}$ plate manufactured by Wako Pure Chemical Industries, Ltd. or CHROMATOREX NH TLC manufactured by Fuji Silysia Chemical Ltd. was used. As a developing solvent, the mobile phase used in the column chromatography was used. As a detection method, a UV detector or a color-developing reagent was employed. In Reference Examples and Examples, the "amino silica gel" refers to silica gel whose surface is chemically modified by a functional group having an amino group (e.g., Purif-Pack (registered trademark, Shoko Scientific)-EX, NH series etc.).

The preparative thin layer chromatography (PTLC) was performed by using silica gel 60 $F_{254}$ plate manufactured by Merck, or silica gel 70 $PF_{254}$ plate or $NH_2$ silica gel 60 $F_{254}$ plate manufactured by Wako Pure Chemical Industries, Ltd., and multiple types of solvents used for the mobile phase were merely described.

The preparative high-performance liquid chromatography (preparative HPLC) was performed by using reverse-phase column (Develosil Combi-RP-5) manufactured by Nomura Chemical, and 0.1% formic acid-containing acetonitrile/water was used for the mobile phase.

The solvent amount and solvent ratio, the conversion timing and the gradient method used in these chromatographies are not described herein. However, the purification and/or separation method used herein can be reproduced by ordinary knowledge and/or techniques of chemical synthesis.

In Examples, the equipment and measurement conditions in the powder X-RAY diffraction measurement are as follows:
Model: Rigaku Rint TTR-III
Sample holder: non-reflecting sample holder
Sample amount: appropriate amount
X-RAY generation conditions: 50 kV, 300 mA
Wavelength: 1.54 Å (Cu-Kα rays)
Measurement temperature: room temperature
Scanning speed: 20°/min
Scanning range: 2 to 40°
Sampling width: 0.02°
Analytical procedure: Several mg of the test compound was taken with a spatula, placed on a non-reflecting sample holder, and flattened with a medicine wrapping paper. Thereafter, the peak pattern was analyzed under the above conditions.

In the following Reference Examples and Examples, the racemates, optically active substances, geometric isomers, and steric notations are described according to the following criteria for convenience. (1) The steric notation in the structural formula is shown using a wedge-shaped line (bond forwards out of the plain of the page), a broken line (bond backwards out of the plain of the page), a solid line (bond in the plain of the page) or a wavy line (bond not specifying configuration). (2) When "racemate" is described together with the structural formula of the compound, it indicates that the compound represented by the structural formula is a racemate (an equal amount mixture with an enantiomer). When "diastereomeric mixture" is described together with the structural formula of the compound, it indicates that the compound represented by the structural formula is a mixture of diastereomers (derived from the configuration of bonds indicated by the wavy line). When "cis-trans mixture" is described together with the structural formula of the compound, it indicates that the compound represented by the structural formula is a mixture of geometric isomers. In addition, unless otherwise specified in the structural formula and compound name, it indicates that the compound represented by the structural formula is a single stereoisomer (including an optically active substance). (3) When "(racemic)" is attached after the compound name, it indicates that the compound indicated by the compound name is a racemic (an equal amount mixture with an enantiomer). When "(diastereomeric mixture)" is attached after the compound name, it indicates that the compound indicated by the compound name is a mixture of diastereomers (derived from the configuration of the bond indicated by the wavy line). When "(cis-trans mixture)" is attached after the compound name, it indicates that the compound indicated by the compound name is a mixture of geometric isomers.

In the following Reference Examples and Examples, the notations of "HCl" described together with the structural formula of the compound and "hydrochloric acid" attached the compound name indicate that the compound represented by the structural formula or the compound indicated by the compound name and hydrogen chloride can form the hydrochloride in various ratios, not necessarily in a 1:1 ratio (for example, including monohydrochloride, dihydrochloride, trihydrochloride, etc.).

Reference Example A-1

Benzyl [(1R,3R,4S)-3-hydroxy-4-(methylamino)cyclopentyl]carbamate

Step 1 Methyl (1R,4S)-4-aminocyclopent-2-ene-1-carboxylate Hydrochloride

[Formula 83]

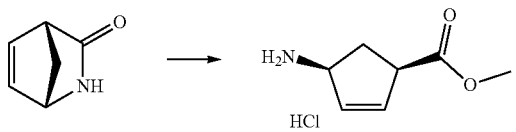

To a mixture of (1S)-(+)-2-azabicyclo[2.2.1]hept-5-en-3-one (CAS: 130931-83-8) (98.6 g) and methanol (300 mL) was added thionyl chloride (CAS: 7719-09-7) (40 mL) over 50 min at 0° C., and the mixture was stirred at 0° C. for 2 hr. The reaction mixture was concentrated under reduced pressure, and the obtained solid was suspended in ethyl acetate, and collected by filtration to give the title compound (158 g) as a solid.

$^1$H-NMR (DMSO-D$_6$) δ: 1.88-1.99 (1H, m), 2.48-2.62 (1H, m), 3.64-3.74 (4H, m), 4.15-4.23 (1H, m), 5.84-5.90 (1H, m), 6.07-6.11 (1H, m), 8.20 (3H, br s).

Step 2 Methyl (1R,4S)-4-[(tert-butoxycarbonyl)amino]cyclopent-2-ene-1-carboxylate

[Formula 84]

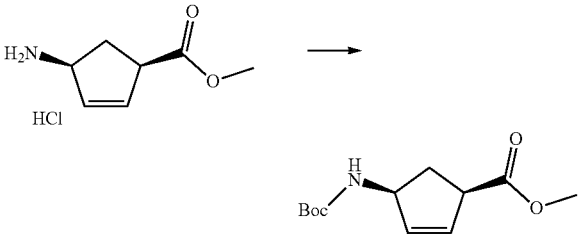

To a mixture of the compound (158 g) obtained in the above Step 1, THF (700 mL) and water (280 mL) were added di-tert-butyl dicarbonate (CAS: 24424-99-5) (194 g) and sodium carbonate (CAS: 497-19-8) (104 g) at 0° C., and the mixture was stirred overnight at room temperature. Water was added to the reaction solution, and the mixture was extracted with ethyl acetate. The organic layer was washed with saturated brine, dried over anhydrous sodium sulfate, and concentrated under reduced pressure to give the title compound (214 g) as an oil.

$^1$H-NMR (CDCl$_3$) δ: 1.44 (9H, s), 1.82-1.91 (1H, m), 2.46-2.57 (1H, m), 3.45-3.52 (1H, m), 3.71 (3H, s), 4.75-4.84 (1H, m), 4.86-4.96 (1H, m), 5.84-5.91 (2H, m).

MS (m/z): 142 (M-Boc+H)$^+$.

Step 3 Methyl (3aS,5S,6S,6aS)-6-bromo-2-oxo-hexahydro-2H-cyclopenta[d][1,3]oxazole-5-carboxylate

[Formula 85]

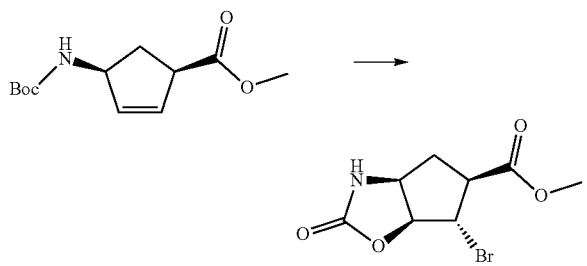

To a mixture of the compound (214 g) obtained in the above Step 2, THF (700 mL) and water (70 mL) was added N-bromosuccinimide (CAS: 128-08-5) (174 g) at 0° C., and the mixture was stirred overnight at room temperature. The reaction solution was concentrated under reduced pressure, and ethyl acetate was added thereto. The organic layer was washed with 1N hydrochloric acid, saturated aqueous sodium hydrogencarbonate solution, saturated aqueous sodium thiosulfate solution and saturated brine, dried over anhydrous sodium sulfate, and concentrated under reduced pressure. The residue was suspended in ethyl acetate/n-hexane, and the solid was collected by filtration. The obtained solid was again suspended in ethyl acetate/n-hexane, and collected by filtration to give the title compound (113 g) as a solid. The filtrate was concentrated under reduced pressure, the residue was suspended in ethyl acetate/n-hexane, and the solid was collected by filtration. The obtained solid was again suspended in ethyl acetate/n-hexane, and collected by filtration. Ethyl acetate/n-hexane and water were added to the obtained solid, and the mixture was subjected to liquid separation. The organic layer was dried over anhydrous sodium sulfate, and concentrated under reduced pressure to give the title compound (11.0 g) as a solid. In total, the title compound (124 g) was obtained as a solid.

$^1$H-NMR (CDCl$_3$) δ: 2.39-2.47 (1H, m), 2.48-2.55 (1H, m), 3.21-3.25 (1H, m), 3.76 (3H, s), 4.42-4.45 (1H, m), 4.79 (1H, s), 5.16 (1H, dd, J=7.6, 1.5 Hz), 5.95 (1H, br s).

MS (m/z): 264, 266 (M+H)$^+$.

Step 4 (3R,4S)-4-[(tert-butoxycarbonyl)amino]-3-hydroxycyclopent-1-ene-1-carboxylic Acid

[Formula 86]

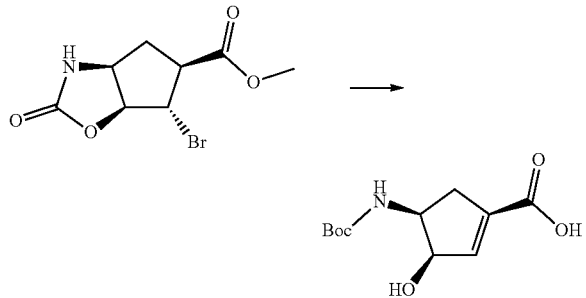

To a mixture of the compound (124 g) obtained in the above Step 3, methanol (580 mL) and water (580 mL) was added potassium hydroxide (CAS: 1310-58-3) (106 g) at 0° C., and the mixture was stirred at 90° C. for 18 hr. The reaction solution was concentrated under reduced pressure, THF (180 mL) and di-tert-butyl dicarbonate (CAS: 24424-99-5) (102 g) were added thereto at 0° C., and the mixture was stirred at room temperature for 4 hr. The mixture was neutralized with 5N hydrochloric acid and 2N hydrochloric acid at 0° C., and extracted five times with ethyl acetate. The combined organic layers were dried over anhydrous sodium sulfate, and the solvent was evaporated under reduced pressure. The obtained solid was suspended in ethyl acetate/n-hexane, collected by filtration, and dried under reduced pressure to give the title compound. The filtrate was concentrated, and the obtained solid was suspended in ethyl acetate/n-hexane, collected by filtration, and dried under reduced pressure to give the title compound. In total, the title compound (96.9 g) was obtained as a solid.

$^1$H-NMR (DMSO-D$_6$) δ: 1.39 (9H, s), 2.30-2.45 (1H, m), 2.53-2.63 (1H, m), 3.91-4.04 (1H, m), 4.47-4.54 (1H, m), 4.97-5.12 (1H, m), 6.35 (1H, d, J=7.9 Hz), 6.52 (1H, d, J=1.8 Hz), 12.53 (1H, br s).

MS (m/z): 242 (M−H)$^-$.

Step 5 (3S,4R)-3-[(tert-butoxycarbonyl)amino]-4-hydroxycyclopentane-1-carboxylic Acid (Diastereomer Mixture)

[Formula 87]

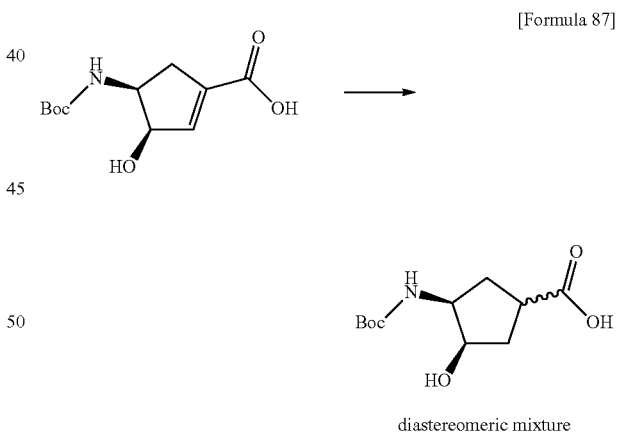

diastereomeric mixture

A mixture of the compound (96.9 g) obtained in the above Step 4, 10% palladium on carbon wet (10.4 g) and methanol (780 mL) was stirred under hydrogen atmosphere for 7.5 hr. The reaction solution was filtered through Celite. The filtrate was concentrated under reduced pressure to give the title compound (105 g) as a solid.

$^1$H-NMR (DMSO-D$_6$) δ: 1.38 (9H, s), 1.69-2.08 (4H, m), 2.59-2.72 (1H, m), 3.52-3.73 (1H, m), 3.84-3.99 (1H, m), 6.15-6.29 (1H, m).

MS (m/z): 146 (M-Boc+H)$^+$.

Step 6 (1R,3S,4R)-3-[(tert-butoxycarbonyl)amino]-4-hydroxycyclopentane-1-carboxylic acid 2-methyl-propan-2-amine Salt

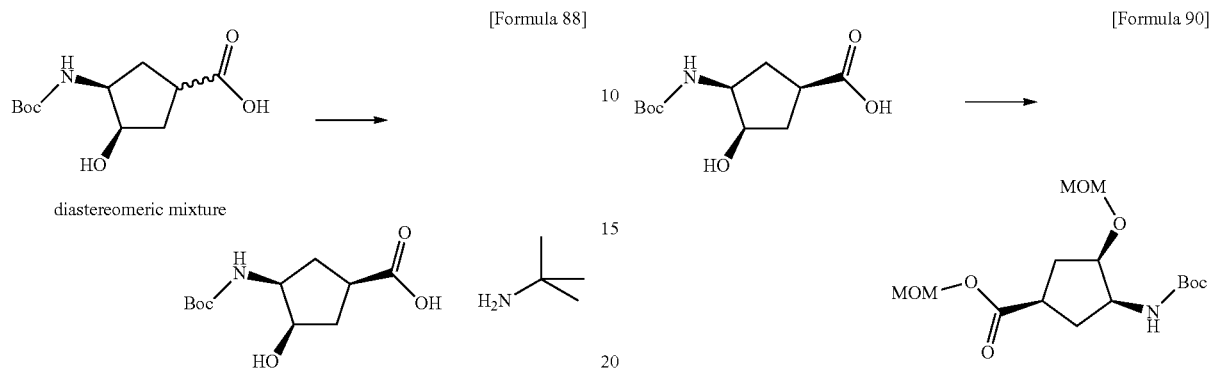

A mixture of the compound (105 g) obtained in the above Step 5, tert-butylamine (42.5 mL), methanol (90 mL) and tert-butyl methyl ether (675 mL) was allowed to stand in the refrigerator for 3 days. The precipitated solid was collected by filtration, and dried under reduced pressure to give the title compound (108 g) as a solid.

$^1$H-NMR (DMSO-D$_6$) δ: 1.18 (9H, s), 1.35 (9H, s), 1.49-1.62 (1H, m), 1.64-1.72 (1H, m), 1.72-1.85 (1H, m), 1.95-2.06 (1H, m), 2.44-2.53 (1H, m), 3.51-3.62 (1H, m), 3.71-3.79 (1H, m), 6.13 (1H, d, J=7.9 Hz).

MS (m/z) 146 (M-Boc+H)$^+$.

Step 7 (1R,3S,4R)-3-[(tert-butoxycarbonyl)amino]-4-hydroxycyclopentane-1-carboxylic Acid A mixture of the compound (108 g) obtained in the above Step 6 and water (200 mL) at 0° C. was adjusted to pH=3 with 2N hydrochloric acid (150 mL). The mixture was extracted three times with dichloromethane/methanol=10/1, and the combined organic layers were dried over anhydrous sodium sulfate, and concentrated under reduced pressure to give the title compound (63.9 g) as a solid.

$^1$H-NMR (DMSO-D$_6$) δ: 1.38 (9H, s), 1.70-1.84 (2H, m), 1.85-1.98 (1H, m), 1.98-2.08 (1H, m), 2.61-2.71 (1H, m), 3.51-3.64 (1H, m), 3.84-3.92 (1H, m), 6.21 (1H, d, J=7.9 Hz).

MS (m/z): 146 (M-Boc+H)$^+$.

Step 8 Methoxymethyl (1R,3S,4R)-3-[(tert-butoxycarbonyl)amino]-4-(methoxymethoxy)cyclopentane-1-carboxylate A mixture of the compound (61.6 g) obtained in the above Step 7, chloromethyl methyl ether (CAS: 107-30-2) (56.7 mL), DIPEA (CAS: 7087-68-5) (262 mL), sodium iodide (75.2 g) and 1,2-dimethoxyethane (1000 mL) was heated under reflux for 1 hr. The reaction solution was allowed to cool to room temperature, saturated brine and water were added thereto, and the mixture was extracted twice with ethyl acetate. The combined organic layers were dried over anhydrous sodium sulfate, and concentrated under reduced pressure. The residue was purified by silica gel column chromatography (n-hexane/ethyl acetate) to give the title compound (66.5 g) as an oil.

$^1$H-NMR (CDCl$_3$) δ: 1.44 (9H, s), 1.87-1.98 (1H, m), 2.04-2.17 (1H, m), 2.17-2.27 (1H, m), 2.27-2.38 (1H, m), 2.81-2.92 (1H, m), 3.37 (3H, s), 3.46 (3H, s), 3.92-4.07 (2H, m), 4.61 (1H, d, J=6.7 Hz), 4.70 (1H, d, J=6.7 Hz), 5.09 (1H, d, J=10.0 Hz), 5.24 (2H, s).

MS (m/z): 234 (M-Boc+H)$^+$.

Step 9 (1R,3S,4R)-3-[(tert-butoxycarbonyl)amino]-4-(methoxymethoxy)cyclopentane-1-carboxylic Acid A mixture of the compound (66.5 g) obtained in the above Step 8, 1N aqueous sodium hydroxide solution (400 mL), methanol (20 mL) and THF (580 mL) was stirred at room temperature for 2 hr. 1N Hydrochloric acid was added to the reaction solution at 0° C., and the mixture was extracted twice with ethyl acetate. The combined organic layers were washed with saturated brine, dried over anhydrous sodium sulfate, and concentrated under reduced pressure. The residue was purified by silica gel column chromatography (n-hexane/ethyl acetate) to give the title compound (53.6 g) as an oil.

¹H-NMR (CDCl₃) δ: 1.44 (9H, s), 1.86-1.99 (1H, m), 2.03-2.17 (1H, m), 2.17-2.26 (1H, m), 2.26-2.38 (1H, m), 2.81-2.93 (1H, m), 3.38 (3H, s), 3.91-4.08 (2H, m), 4.62 (1H, d, J=6.7 Hz), 4.70 (1H, d, J=6.7 Hz), 5.09 (1H, d, J=6.7 Hz).

MS (m/z): 288 (M−H)⁻.

Step 10 Benzyl Tert-butyl [(1R,3S,4R)-4-(methoxymethoxy)cyclopentane-1,3-diyl]biscarbamate

[Formula 92]

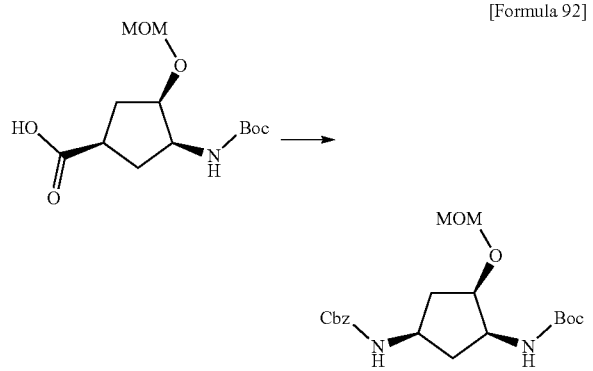

A mixture of the compound (53.6 g) obtained in the above Step 9, diphenylphosphoryl azide (DPPA) (CAS: 26386-88-9) (51.9 mL), TEA (CAS: 121-44-8) (33.4 mL) and toluene (730 mL) was stirred at 90° C. for 30 min. Benzyl alcohol (38.3 mL) was added to the reaction solution, and the mixture was stirred at 90° C. for 2.5 hr. The reaction solution was allowed to cool to room temperature, water was added thereto, and the mixture was extracted twice with ethyl acetate. The combined organic layers were washed with saturated brine, dried over anhydrous sodium sulfate, and concentrated under reduced pressure. The residue was purified by silica gel column chromatography (n-hexane/ethyl acetate) to give the title compound (63.2 g) as an oil.

¹H-NMR (CDCl₃) δ: 1.35-1.50 (10H, m), 1.70-1.78 (1H, m), 2.01-2.19 (1H, m), 2.47-2.63 (1H, m), 3.36 (3H, s), 3.80-4.06 (2H, m), 4.08-4.24 (1H, m), 4.62 (1H, d, J=6.7 Hz), 4.68 (1H, d, J=6.7 Hz), 4.97-5.19 (4H, m), 7.29-7.42 (5H, m).

MS (m/z): 295 (M−Boc+H)⁺.

Step 11 Benzyl [(1R,3S,4R)-3-amino-4-hydroxycyclopentyl]carbamate Hydrochloride

[Formula 93]

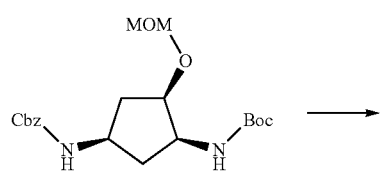

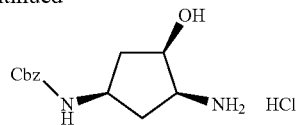

A mixture of the compound (120 g) obtained in the above Step 10, hydrogen chloride (4 mol/L, 1,4-dioxane solution, 420 mL) and methanol (420 mL) was stirred at room temperature for 30 min. The reaction solution was concentrated under reduced pressure to give the title compound (87.2 g) as a solid.

¹H-NMR (DMSO-D₆) δ: 1.51-1.70 (2H, m), 2.15-2.29 (2H, m), 3.20-3.35 (1H, m), 3.72-4.14 (3H, m), 5.01 (2H, s), 7.27-7.49 (5H, m), 8.00 (3H, s).

MS (m/z): 251 (M+H)⁻.

Step 12 Benzyl {(1R,3R,4S)-3-hydroxy-4-[(2-nitrobenzene-1-sulfonyl)amino]cyclopentyl}carbamate

[Formula 94]

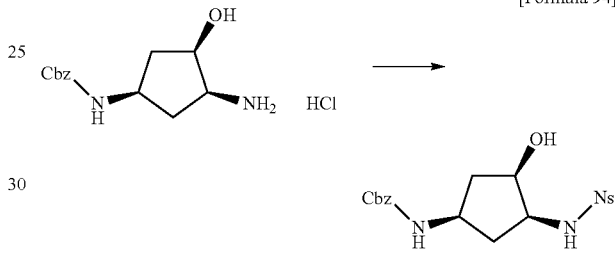

A mixture of the compound (87.2 g) obtained in the above Step 11, 2-nitrobenzenesulfonyl chloride (74.5 g), DIPEA (159 mL) and dichloromethane (1000 mL) was stirred at 0° C. for 1 hr. Water was added to the reaction solution, and the mixture was extracted with dichloromethane. The organic layer was washed with saturated brine, dried over anhydrous sodium sulfate, and concentrated under reduced pressure. Ethyl acetate was added to the residue, and the solid was collected by filtration to give the title compound (33.0 g) as a solid. The filtrate was concentrated, ethyl acetate was added to the residue, and the solid was collected by filtration to give the title compound (25.2 g) as a solid. The filtrate was concentrated, and the residue was purified by amino silica gel column chromatography (n-hexane/ethyl acetate) to give the title compound (40.9 g) as a solid. In total, the title compound (99.1 g) was obtained as a solid.

¹H-NMR (CDCl₃) δ: 1.38-1.88 (2H, m), 2.08-2.34 (2H, m), 3.42 (1H, br s), 3.59-3.73 (1H, m), 3.86-4.09 (2H, m), 5.05 (2H, s), 5.29 (1H, d, J=6.1 Hz), 6.00 (1H, br s), 7.29-7.51 (5H, m), 7.72-7.76 (2H, m), 7.86-7.89 (1H, m), 8.13-8.16 (1H, m).

Step 13 Benzyl {(1R,3R,4S)-3-hydroxy-4-[methyl(2-nitrobenzene-1-sulfonyl)amino]cyclopentyl}carbamate

[Formula 95]

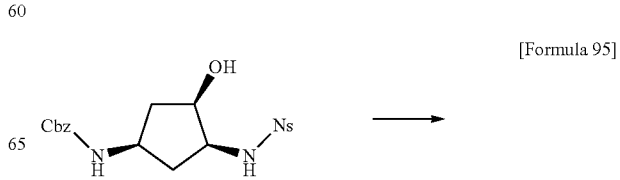

-continued

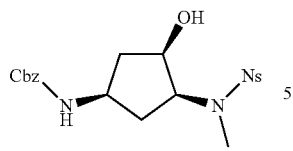

To a mixture of the compound (87.2 g) obtained in the above Step 12 and DMF (630 mL) were added cesium carbonate (74.2 g) and methyl iodide (21.3 mL) at 0° C., and the mixture was stirred at room temperature for 2 hr. Water was added to the reaction solution, and the mixture was extracted twice with ethyl acetate. The combined organic layers were washed three times with water and saturated brine, dried over anhydrous sodium sulfate, and concentrated under reduced pressure. Ethyl acetate/n-hexane was added to the residue, and the solid was collected by filtration to give the title compound (80.9 g) as a solid.

$^1$H-NMR (CDCl$_3$) δ: 1.60-1.69 (1H, m), 1.96-2.09 (1H, m), 2.16-2.33 (2H, m), 2.98-3.11 (4H, m), 3.89-4.06 (2H, m), 4.22-4.30 (1H, m), 5.08 (2H, s), 5.26 (1H, d, J=7.3 Hz), 7.29-7.41 (5H, m), 7.61-7.76 (3H, m), 8.02-8.05 (1H, m).

MS (m/z): 450 (M+H)$^-$.

Step 14 Benzyl [(1R,3R,4S)-3-hydroxy-4-(methylamino)cyclopentyl]carbamate

[Formula 96]

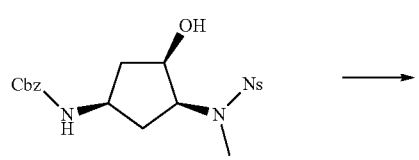

A mixture of the compound (40.4 g) obtained in the above Step 13, cesium carbonate (52.7 g), 4-isopropylbenzenethiol (16.8 mL), THF (140 mL) and methanol (140 mL) was stirred at room temperature for 3 hr. Amino silica gel was added to the reaction solution, and the mixture was concentrated under reduced pressure. The residue was purified by amino silica gel column chromatography (n-hexane/ethyl acetate, followed by ethyl acetate/methanol) to give an oil. Ethyl acetate/n-hexane was added thereto, and the solid was collected by filtration to give the title compound (22.0 g) as a solid.

$^1$H-NMR (CDCl$_3$) δ: 1.28-1.39 (1H, m), 1.78-1.89 (1H, m), 1.91-2.04 (1H, m), 2.33-2.48 (4H, m), 2.78-2.88 (1H, m), 3.95-4.03 (1H, m), 4.11-4.24 (1H, m), 5.07 (2H, s), 5.54 (1H, d, J=9.2 Hz), 7.28-7.40 (5H, m).

MS (m/z): 265 (M+H)$^+$.

Reference Example A-2

Tert-butyl [(1S,3R)-3-aminocyclohexyl]carbamate

Step 1 Benzyl Tert-butyl (1R,3S)-cyclohexane-1,3-diylbiscarbamate

[Formula 97]

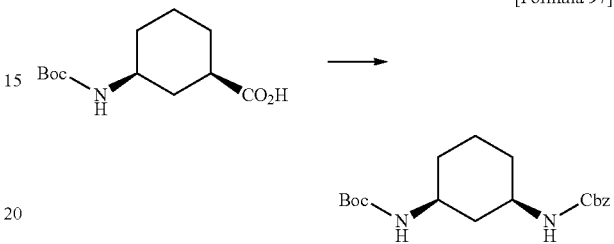

The title compound was obtained in the same manner as in Step 10 of Reference Example A-1, using (1R,3S)-3-(tert-butoxycarbonylamino)cyclohexanecarboxylic acid (CAS: 222530-34-9).

$^1$H-NMR (CDCl$_3$) δ: 0.90-1.07 (3H, m), 1.31-1.42 (1H, m), 1.44 (9H, s), 1.72-1.81 (1H, m), 1.93-2.03 (2H, m), 2.26-2.31 (1H, m), 3.42-3.60 (2H, m), 4.39 (1H, br s), 4.58-4.64 (1H, m), 5.08 (2H, s), 7.28-7.72 (5H, m).

MS (m/z): 249 (M-Boc+H)$^+$.

Step 2 Tert-butyl [(1S,3R)-3-aminocyclohexyl]carbamate

[Formula 98]

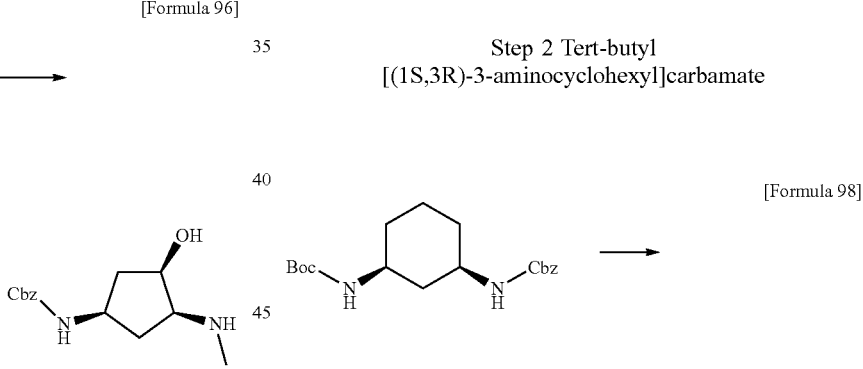

The compound (12.37 g) obtained in the above Step 1 was suspended in ethanol (120 mL), 10% palladium on carbon wet (4.0 g) was added thereto, and the mixture was stirred under hydrogen atmosphere at room temperature for 4 hr. The palladium catalyst was removed by filtration, and the filtrate was concentrated under reduced pressure to give the title compound (8.26 g) as a solid. This was directly used in the next step.

$^1$H-NMR (CDCl$_3$) δ: 0.88-1.03 (3H, m), 1.28-1.39 (1H, m), 1.44 (9H, s), 1.54 (2H, br s), 1.73-1.82 (2H, m), 1.88-1.95 (1H, m), 2.07-2.13 (1H, m), 2.73-2.81 (1H, m), 3.48 (1H, br s), 4.57 (1H, br s).

Reference Example A-3

N-[(1R,3S)-3-aminocyclopentyl]-N-methyl-2-nitrobenzene-1-sulfonamide

Step 1 Benzyl Tert-butyl (1R,3S)-cyclopentane-1,3-diylbiscarbamate

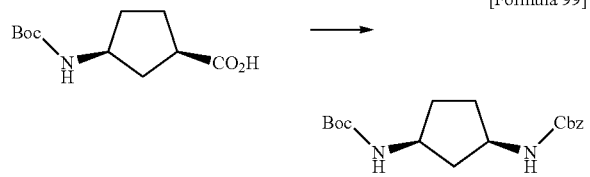

[Formula 99]

The title compound was obtained in the same manner as in Step 10 of Reference Example A-1, using (−)-(1R,3S)—N—BOC-3-aminocyclopentanecarboxylic acid (CAS: 161660-94-2).

$^1$H-NMR (DMSO-D$_6$) δ: 1.20-1.30 (1H, m), 1.37 (9H, s), 1.43-1.50 (2H, m), 1.72-1.79 (2H, m), 2.10-2.17 (1H, m), 3.69-3.81 (2H, m), 5.00 (2H, s), 6.85 (1H, d, J=7.3 Hz), 7.29-7.39 (5H, m).

Step 2 Tert-butyl {(1S,3R)-3-[(2-nitrobenzene-1-sulfonyl)amino]cyclopentyl}carbamate

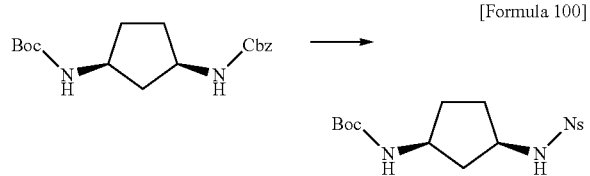

[Formula 100]

The compound (19.0 g) obtained in the above Step 1 was suspended in ethanol (280 mL), 10% palladium on carbon wet (2.5 g) was added thereto, and the mixture was stirred under hydrogen atmosphere at room temperature for 1.5 hr. The palladium was removed by filtration, and the filtrate was concentrated under reduced pressure. Dichloromethane (230 mL) and DIPEA (14.8 mL) were added thereto, and 2-nitrobenzenesulfonyl chloride (12.6 g) was added thereto under ice-cooling. After stirring at room temperature for 2 hr, dichloromethane and water were added to the reaction solution, and the mixture was subjected to liquid separation. The organic layer was dried over anhydrous sodium sulfate, and concentrated under reduced pressure. The obtained residue was purified by silica gel column chromatography (n-hexane/ethyl acetate) to give the title compound (12.77 g) as a solid.

$^1$H-NMR (CDCl$_3$) δ: 1.40-1.48 (1H, m), 1.42 (9H, s), 1.55-1.70 (2H, m), 1.81-1.99 (2H, m), 2.20-2.27 (1H, m), 3.74-3.82 (1H, m), 3.83-3.93 (1H, m), 4.60 (1H, br s), 5.61 (1H, br s), 7.73-7.78 (2H, m), 7.85-7.87 (1H, m), 8.15-8.17 (1H, m).

Step 3 Tert-butyl {(1S,3R)-3-[methyl(2-nitrobenzene-1-sulfonyl)amino]cyclopentyl}carbamate

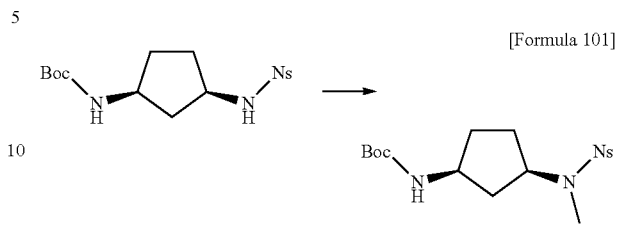

[Formula 101]

The title compound was obtained in the same manner as in Step 13 of Reference Example A-1, using the compound obtained in the above Step 2.

$^1$H-NMR (CDCl$_3$) δ: 1.38-1.51 (2H, m), 1.42 (9H, s), 1.56-2.02 (3H, m), 2.14-2.22 (1H, m), 2.85 (3H, s), 3.81-3.89 (1H, m), 4.26-4.34 (1H, m), 4.50 (1H, br s), 7.60-7.64 (1H, m), 7.66-7.72 (2H, m), 8.00-8.04 (1H, m).

Step 4 N—[(R,3S)-3-aminocyclopentyl]-N-methyl-2-nitrobenzene-1-sulfonamide

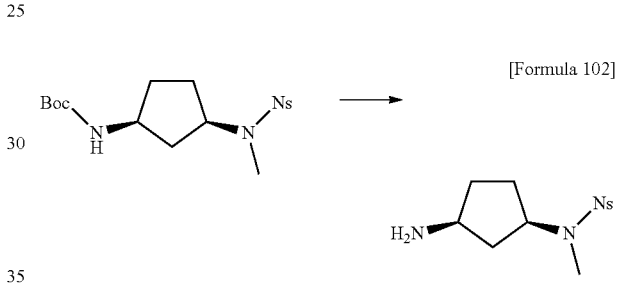

[Formula 102]

The compound (2.04 g) obtained in the above Step 3 was dissolved in dichloromethane (20 mL), hydrogen chloride (4 mol/L, 1,4-dioxane solution, 20 mL) was added thereto, and the mixture was stirred at room temperature for 1 hr. The solvent was evaporated under reduced pressure, dichloromethane and saturated aqueous sodium hydrogencarbonate solution were added to the residue, and the mixture was subjected to liquid separation. The aqueous layer was extracted with dichloromethane. The organic layers were combined, dried over anhydrous sodium sulfate, and concentrated under reduced pressure. The obtained residue was purified by amino silica gel column chromatography (ethyl acetate/methanol) to give the title compound (1.21 g) as an oil.

$^1$H-NMR (CDCl$_3$) δ: 1.17-1.40 (4H, m), 1.73-1.86 (3H, m), 2.02-2.09 (1H, m), 2.88 (3H, s), 3.29-3.36 (1H, m), 4.30-4.39 (1H, m), 7.60-7.62 (1H, m), 7.66-7.71 (2H, m), 8.00-8.04 (1H, m).

Reference Example A-4

Tert-butyl [(1S,3R)-3-(methylamino)cyclopentyl]carbamate

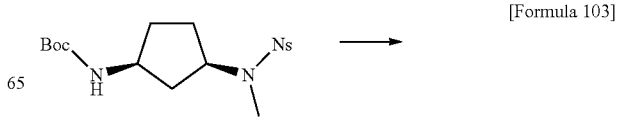

[Formula 103]

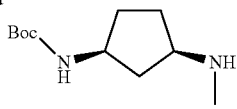

The title compound was obtained in the same manner as in Step 14 of Reference Example A-1, using the compound obtained in Step 3 of Reference Example A-3.

¹H-NMR (CDCl₃) δ: 1.33-1.72 (4H, m), 1.44 (9H, s), 1.77-2.11 (3H, m), 2.38 (3H, s), 3.03-3.09 (1H, m), 4.00-4.08 (1H, m), 5.30 (1H, br s).

Reference Example A-5

Tert-butyl [(1S,3R)-3-(ethylamino)cyclopentyl]carbamate

Step 1 Tert-butyl {(1S,3R)-3-[ethyl(2-nitrobenzene-1-sulfonyl)amino]cyclopentyl}carbamate

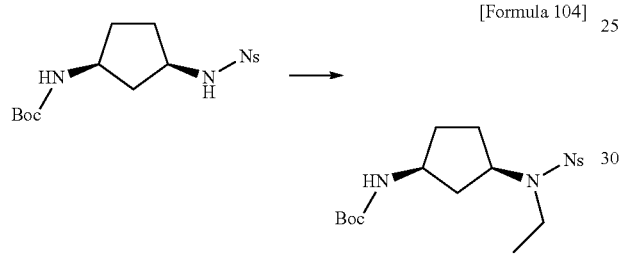

[Formula 104]

The title compound was obtained in the same manner as in Step 13 of Reference Example A-1 except that bromoethane (CAS: 74-96-4) was used instead of iodomethane, using the compound obtained in Step 2 of Reference Example A-3.

¹H-NMR (CDCl₃) δ: 1.24 (3H, t, J=7.4 Hz), 1.41-1.52 (2H, m), 1.43 (9H, s), 1.65-1.74 (1H, m), 1.83-2.01 (2H, m), 2.22-2.28 (1H, m), 3.31-3.37 (2H, m), 3.81-3.88 (1H, m), 4.07-4.17 (1H, m), 4.54 (1H, br s), 7.59-7.63 (1H, m), 7.65-7.72 (2H, m), 7.99-8.03 (1H, m).

MS (m/z): 314 (M-Boc+H)⁺.

Step 2 Tert-butyl [(1S,3R)-3-(ethylamino)cyclopentyl]carbamate

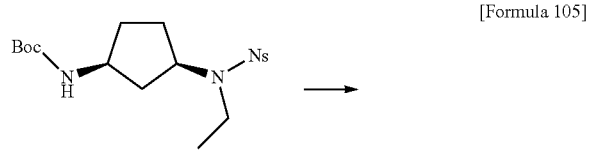

[Formula 105]

The title compound was obtained in the same manner as in Step 14 of Reference Example A-1, using the compound obtained in the above Step 1.

¹H-NMR (CDCl₃) δ: 0.88 (1H, br s), 1.09 (3H, t, J=7.3 Hz), 1.30-1.36 (1H, m), 1.44 (9H, s), 1.45-1.65 (2H, m), 1.80-2.09 (3H, m), 2.60 (2H, q, J=7.3 Hz), 3.13-3.19 (1H, m), 4.01 (1H, br s), 5.27 (1H, br s).

MS (m/z): 229 (M+H)⁻.

Reference Example A-6

Benzyl (1R,3S,5R)-3-amino-5-(methoxymethoxy)cyclohexane-1-carboxylate (Racemate)

Step 1 Methoxymethyl (1S,3R,5S)-3-{[(benzyloxy)carbonyl]amino}-5-hydroxycyclohexane-1-carboxylate (Racemate)

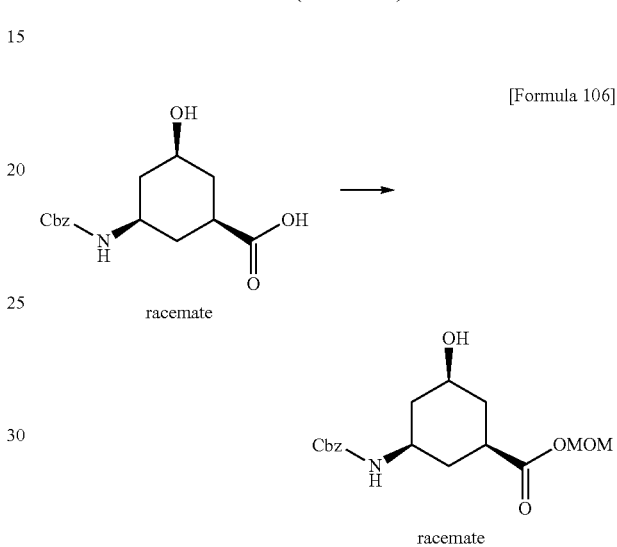

[Formula 106]

A mixture of (1S,3R,5S)-3-{[(benzyloxy)carbonyl]amino}-5-hydroxycyclohexane-1-carboxylic acid (racemate) (11.4 g) synthesized according to the method described in a literature (Bioorg. Med. Chem. 2006, 14, 2242-2252), DIPEA (20.4 mL) and dichloromethane (390 mL) was ice-cooled, chloromethyl methyl ether (3.08 mL) was added thereto, and the mixture was stirred at room temperature for 3 hr. Aqueous saturated ammonium chloride solution was added to the reaction solution, and the mixture was extracted with ethyl acetate. The organic layer was washed with saturated brine, dried over anhydrous sodium sulfate, and concentrated under reduced pressure to give the title compound (11.8 g) as an oil. The obtained compound was directly used in the next step without purification.

MS (m/z): 338 (M+H)⁺.

Step 2 Methoxymethyl (1S,3R,5S)-3-{[(benzyloxy)carbonyl]amino}-5-(methoxymethoxy)cyclohexane-1-carboxylate (Racemate)

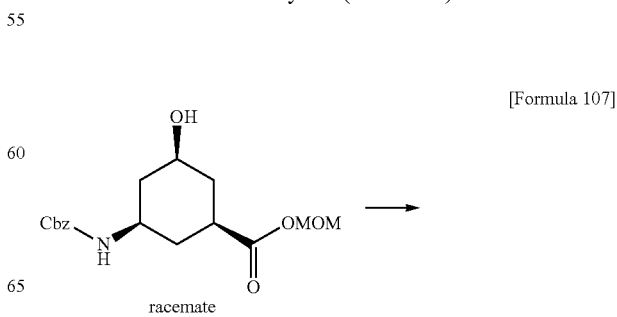

[Formula 107]

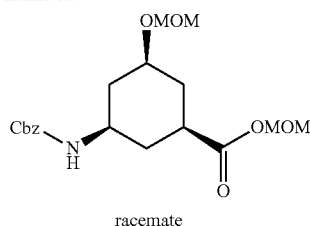

racemate

A mixture of the compound (11.8 g) obtained in the above Step 1, DIPEA (18.2 mL), chloromethyl methyl ether (3.4 mL) and dichloromethane (350 mL) was stirred at room temperature for 2 hr. The reaction solution was ice-cooled, chloromethyl methyl ether (10.5 mL) was added thereto, and the mixture was stirred at room temperature for additional 18 hr. Aqueous saturated ammonium chloride solution was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (7.88 g) as an oil.

$^1$H-NMR (CDCl$_3$) δ: 1.24-1.48 (3H, m), 2.29-2.32 (3H, m), 2.44-2.47 (1H, m), 3.36 (3H, s), 3.46 (3H, s), 3.60-3.63 (2H, m), 4.66-4.68 (3H, m), 5.11 (2H, s), 5.24 (2H, s), 7.32-7.35 (5H, m).

MS (m/z): 382 (M+H)$^+$.

Step 3 (1S,3R,5S)-3-{[(benzyloxy)carbonyl]amino}-5-(methoxymethoxy)cyclohexane-1-carboxylic Acid (Racemate)

[Formula 108]

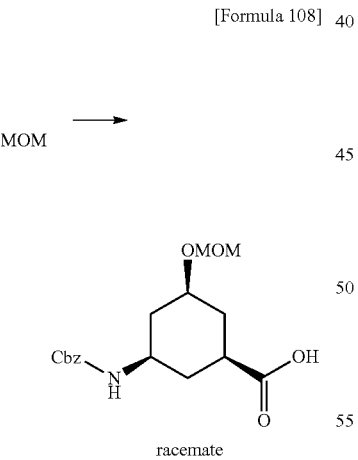

The title compound was obtained in the same manner as in Step 9 of Reference Example A-1, using the compound (7.88 g) obtained in the above Step 2.

$^1$H-NMR (DMSO-D$_6$) δ: 1.09-1.24 (3H, m), 1.94-2.11 (3H, m), 2.31-2.34 (1H, m), 3.25 (3H, s), 3.40-3.43 (1H, m), 3.50-3.58 (1H, m), 4.60 (2H, s), 5.02 (2H, s), 7.01 (1H, s), 7.27-7.37 (5H, m), 11.88 (1H, br s).

MS (m/z): 338 (M+H)$^+$.

Step 4 Benzyl Prop-2-en-1-yl [(1R,3S,5S)-5-(methoxymethoxy)cyclohexane-1,3-diyl]biscarbamate (Racemate)

[Formula 109]

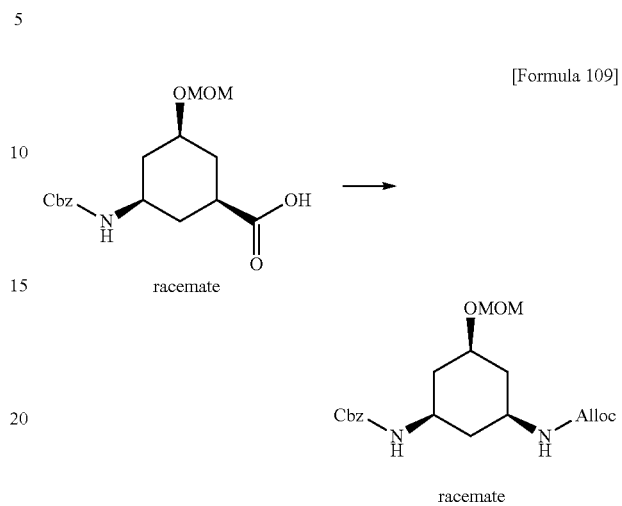

A mixture of the compound (6.65 g) obtained in the above Step 3, diphenylphosphoryl azide (5.52 mL), TEA (3.57 mL) and toluene (98.6 mL) was stirred at 90° C. for 30 min. Allyl alcohol (1.40 g) was added thereto, and the mixture was stirred at the same temperature for 5 hr, and concentrated under reduced pressure. The residue was purified by silica gel column chromatography (n-hexane/ethyl acetate) to give the title compound (6.2 g) as a solid.

$^1$H-NMR (CDCl$_3$) δ: 1.03-1.27 (3H, m), 2.18-2.28 (3H, m), 3.34 (3H, s), 3.62-3.66 (3H, m), 4.54 (2H, d, J=5.2 Hz), 4.67-4.75 (4H, m), 5.09 (2H, s), 5.20-5.28 (2H, m), 5.87-5.93 (1H, m), 7.30-7.33 (5H, m).

MS (m/z): 393 (M+H)$^+$.

Step 5 Benzyl (1R,3S,5R)-3-amino-5-(methoxymethoxy)cyclohexane-1-carboxylate (Racemate)

[Formula 110]

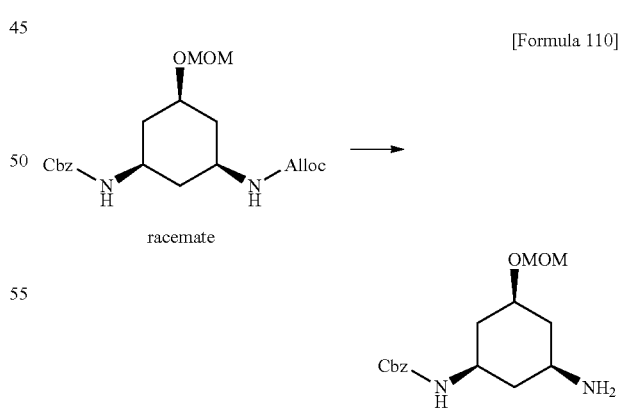

A mixture of the compound (335 mg) obtained in the above Step 4, dichloromethane (8 mL), pyrrolidine (0.177 mL) and tetrakis(triphenylphosphine)palladium(0) (20 mg) was stirred at room temperature for 30 min, and concentrated under reduced pressure. The residue was purified by silica gel column chromatography (ethyl acetate/methanol) to give the title compound (93 mg) as a solid.

$^1$H-NMR (CDCl$_3$) δ: 0.93-0.95 (1H, m), 1.07-1.13 (2H, m), 2.12-2.18 (2H, m), 2.29-2.32 (1H, m), 2.78-2.81 (1H, m), 3.35 (3H, s), 3.57-3.62 (2H, m), 4.61-4.65 (3H, m), 5.10 (2H, s), 7.28-7.32 (5H, m).

MS (m/z): 309 (M+H)$^+$.

Reference Example A-7

Benzyl [(1S,3R,5S)-3-amino-5-(dimethylcarbamoyl)cyclohexyl]carbamate (Racemate)

Step 1 Benzyl [(1S,3R,5R)-3-(dimethylcarbamoyl)-5-(methoxymethoxy)cyclohexyl]carbamate (Racemate)

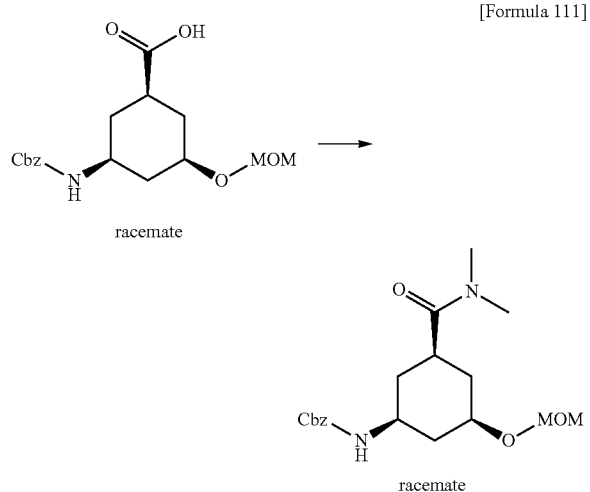

[Formula 111]

To a mixture of the compound (1.59 g) obtained in Step 3 of Reference Example A-6 and dichloromethane (15 mL) were added dimethylamine hydrochloride (CAS: 506-59-2) (0.48 g), anhydrous HOBt (CAS: 123333-53-9) (0.77 g), 1-(3-dimethylaminopropyl)-3-ethylcarbodiimide hydrochloride (CAS: 1892-57-5) (1.10 g) and TEA (1.31 mL) at room temperature. This reaction solution was warmed to room temperature, and stirred for 18 hr. Ethyl acetate (30 mL) was added to this reaction solution, and the mixture was washed successively with saturated aqueous ammonium chloride solution (10 mL), saturated aqueous sodium hydrogencarbonate solution (10 mL) and saturated brine (10 mL), and the organic layer was dried over anhydrous sodium sulfate, and concentrated under reduced pressure. The residue was purified by silica gel column chromatography (methanol/dichloromethane) to give the title compound (1.65 g) as an oil.

$^1$H-NMR (CDCl$_3$) δ: 1.21 (1H, q, J=11.7 Hz), 1.36 (1H, q, J=12.5 Hz), 1.51 (1H, q J=12.5 Hz), 2.02 (2H, t, J=14.0 Hz), 2.35-2.36 (1H, m), 2.64-2.70 (1H, m), 2.95 (3H, s), 3.08 (3H, s), 3.38 (3H, s), 3.64-3.67 (2H, m), 4.67-4.71 (2H, m), 4.74-4.76 (1H, m), 5.11 (2H, s), 7.33-7.41 (5H, m).

MS (m/z): 365 (M+H)$^+$.

Step 2 Benzyl [(1S,3R,5R)-3-(dimethylcarbamoyl)-5-hydroxycyclohexyl]carbamate (Racemate)

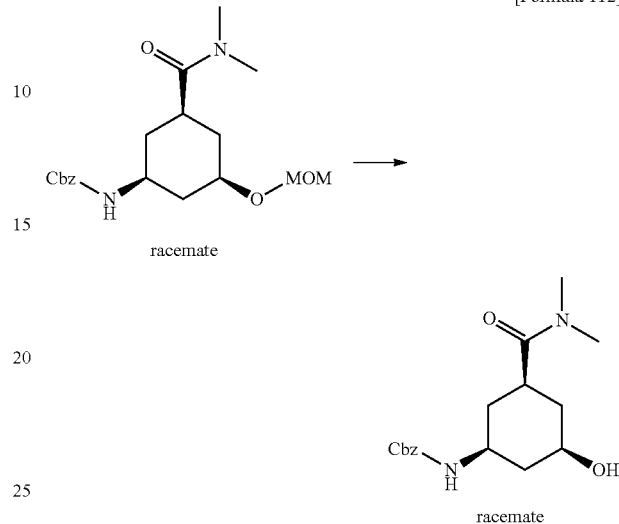

[Formula 112]

To a mixture of the compound (1.65 g) obtained in the above Step 1 and 1,4-dioxane (5 mL) was added hydrogen chloride (4 mol/L, 1,4-dioxane solution, 5.66 mL) at room temperature. This reaction solution was stirred at room temperature for 2 hr, and water (20 mL) and ethyl acetate (30 mL) were added thereto. This mixture was washed twice with water (10 mL), and washed successively with saturated aqueous sodium hydrogencarbonate solution (10 mL) and saturated brine (20 mL), and the organic layer was dried over anhydrous sodium sulfate, and concentrated under reduced pressure. The residue was purified by silica gel column chromatography (methanol/dichloromethane) to give the title compound (1.12 g) as an oil.

$^1$H-NMR (CDCl$_3$) δ: 1.25 (1H, q, J=11.5 Hz), 1.46 (1H, q, J=12.1 Hz), 1.52-1.61 (1H, m), 1.99-2.02 (2H, m), 2.29-2.30 (2H, m), 2.69-2.75 (1H, m), 2.95 (3H, s), 3.07 (3H, s), 3.69-3.72 (1H, m), 3.74-3.82 (1H, m), 5.01 (1H, d, J=7.9 Hz), 5.10 (2H, s), 7.34-7.39 (5H, m).

Step 3 (1S,3S,5R)-3-{[(benzyloxy)carbonyl]amino}-5-(dimethylcarbamoyl)cyclohexyl 4-nitrobenzoate (Racemate)

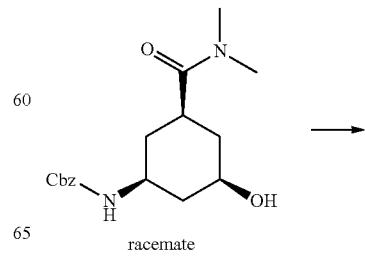

[Formula 113]

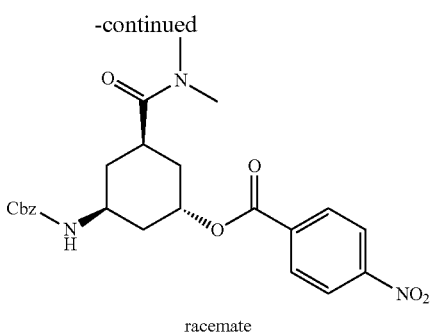

racemate

To a mixture of the compound (1.06 g) obtained in the above Step 2, 4-nitrobenzoic acid (CAS: 62-23-7) (0.66 g), triphenylphosphine (CAS: 14264-16-5) (purity 97%, 1.04 g) and THF (15 mL) was added diisopropyl azodicarboxylate (40% toluene solution) (CAS: 2446-83-5) (2.1 mL) under ice-cooling. This mixture was warmed to room temperature, and stirred at room temperature for 5.5 hr. Saturated aqueous sodium hydrogencarbonate solution (20 mL), ethyl acetate (20 mL) and saturated brine (20 mL) were added thereto, and the mixture was subjected to liquid separation. The organic layer was washed with saturated brine, dried over anhydrous sodium sulfate, and concentrated under reduced pressure. The residue was purified by silica gel column chromatography (methanol/dichloromethane) to give the title compound (1.55 g) as an oil.

$^1$H-NMR (CDCl$_3$) δ: 1.53-1.58 (2H, m), 1.90-1.95 (1H, m), 2.10-2.11 (1H, m), 2.20-2.23 (1H, m), 2.35-2.39 (1H, m), 2.97 (3H, s), 3.06 (3H, s), 3.09-3.17 (1H, m), 4.06-4.10 (1H, m), 4.87-4.89 (1H, m), 5.12 (2H, s), 5.60 (1H, s), 7.37-7.38 (5H, m), 8.23 (2H, d, J=8.8 Hz), 8.34 (2H, d, J=8.8 Hz).

MS (m/z): 470 (M+H)$^+$.

Step 4 Benzyl [(1S,3R,5S)-3-(dimethylcarbamoyl)-5-hydroxycyclohexyl]carbamate (Racemate)

[Formula 114]

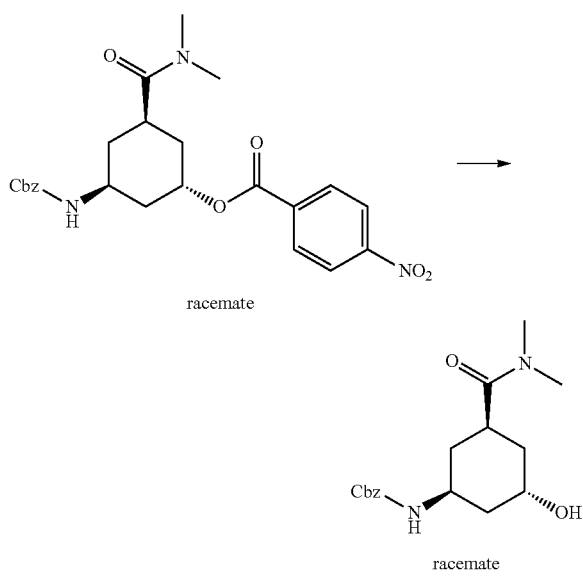

racemate

To a mixture of the compound (1.55 g) obtained in the above Step 3 and ethanol (22 mL) was added potassium carbonate (CAS: 584-08-7) (1.37 g) at room temperature, and the mixture was stirred for 2 hr. Saturated aqueous sodium hydrogencarbonate solution (20 mL), ethyl acetate (20 mL) and saturated brine (20 mL) were added thereto, and the mixture was subjected to liquid separation. The organic layer was washed with saturated brine, dried over anhydrous sodium sulfate, and concentrated under reduced pressure. The residue was purified by silica gel column chromatography (methanol/dichloromethane) to give the title compound (0.710 g) as a solid.

$^1$H-NMR (CDCl$_3$) δ: 1.36-1.44 (1H, m), 1.44-1.50 (1H, m), 1.64-1.71 (1H, m), 1.81-1.84 (1H, m), 2.06-2.10 (3H, m), 2.95 (3H, s), 3.09 (3H, s), 3.22-3.26 (1H, m), 4.03-4.11 (1H, m), 4.32 (1H, s), 4.92 (1H, d, J=8.5 Hz), 5.10 (2H, s), 7.34-7.37 (5H, m).

MS (m/z): 321 (M+H)$^+$.

Step 5 Benzyl [(1S,3R,5R)-3-azido-5-(dimethylcarbamoyl)cyclohexyl]carbamate (Racemate)

[Formula 115]

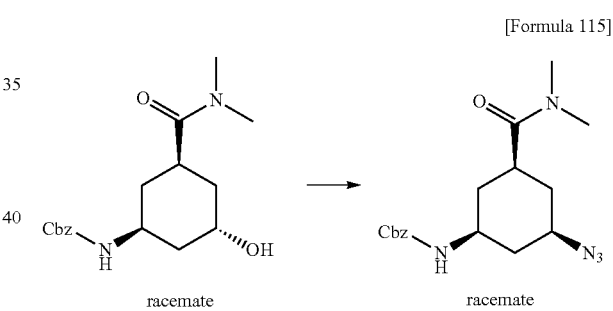

To a mixture of the compound (0.513 g) obtained in the above Step 4, triphenylphosphine (CAS: 14264-16-5) (0.752 g), diphenylphosphoryl azide (0.412 mL) and THF (15 mL) was added diisopropyl azodicarboxylate (40% toluene solution) (1.50 mL) under ice-cooling. This reaction solution was warmed to room temperature, and stirred for 3 hr. Ethyl acetate (30 mL) was added to this reaction solution, and the mixture was washed twice with saturated brine (10 mL). The organic layer was dried over anhydrous sodium sulfate, and concentrated under reduced pressure. The residue was purified by silica gel column chromatography (methanol/dichloromethane) to give the title compound (0.553 g) as an oil.

$^1$H-NMR (CDCl$_3$) δ: 1.17-1.27 (1H, m), 1.39 (1H, q, J=12.2 Hz), 1.57 (1H, q, J=12.5 Hz), 1.99-2.02 (2H, m), 2.33-2.35 (1H, m), 2.68-2.74 (1H, m), 2.94 (3H, s), 3.06 (3H, s), 3.38-3.44 (1H, m), 3.67-3.71 (1H, m), 5.10 (2H, s), 6.55 (1H, s), 7.33-7.38 (5H, m).

MS (m/z): 346 (M+H)$^+$.

111

Step 6 Benzyl [(1S,3R,5S)-3-amino-5-(dimethylcarbamoyl)cyclohexyl]carbamate (Racemate)

[Formula 116]

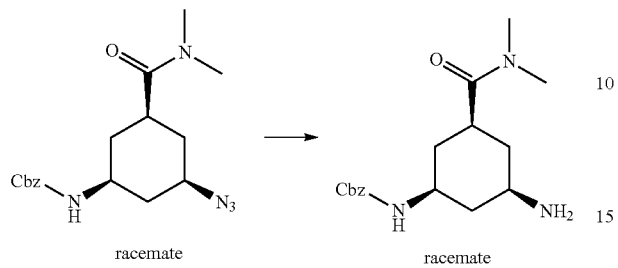

To a mixture of the compound (0.553 g) obtained in the above Step 5 and THF (15 mL) was added triphenylphosphine (CAS: 14264-16-5) (0.840 g) under ice-cooling. This reaction solution was warmed to room temperature, and stirred for 30 min. Water (10 mL) was added to this reaction solution, and the mixture was allowed to stand for 19 hr, heated to 85° C., and stirred for 2 hr. The reaction solution was concentrated under reduced pressure. Ethanol (20 mL) was added to the residue, and the mixture was concentrated under reduced pressure. These concentration operations were conducted three times to give the crude title compound (0.511 g) as an oil. The product was used in the next step without purification.

MS (m/z): 320 (M+H)$^+$.

Reference Example A-8

Benzyl [(1S,3R)-3-aminocyclohexyl]carbamate Hydrochloride

Step 1 Benzyl Tert-butyl (1R,3S)-cyclohexane-1,3-diylbiscarbamate

[Formula 117]

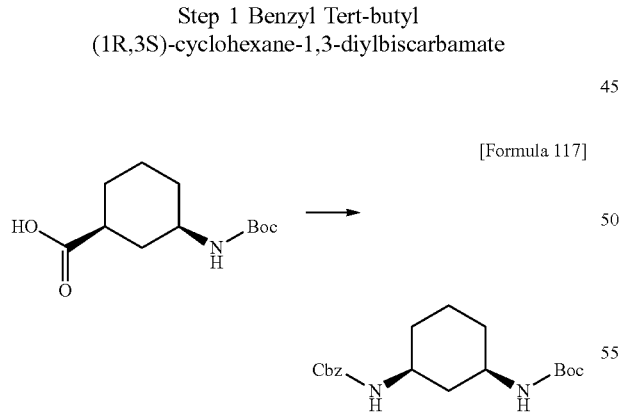

The title compound was obtained in the same manner as in Step 10 of Reference Example A-1, using (1S,3R)-3-[(tert-butoxycarbonyl)amino]cyclohexane-1-carboxylic acid (CAS: 222530-34-9).

$^1$H-NMR (CDCl$_3$) δ: 1.05-0.87 (3H, m), 1.47-1.33 (10H, m), 1.82-1.73 (1H, m), 2.04-1.91 (2H, m), 2.33-2.25 (1H, m), 3.66-3.38 (2H, m), 4.38 (1H, br s), 4.59 (1H, br s), 5.08 (2H, br s), 7.40-7.28 (5H, m).

112

Step 2 Benzyl [(1S,3R)-3-aminocyclohexyl]carbamate Hydrochloride

[Formula 118]

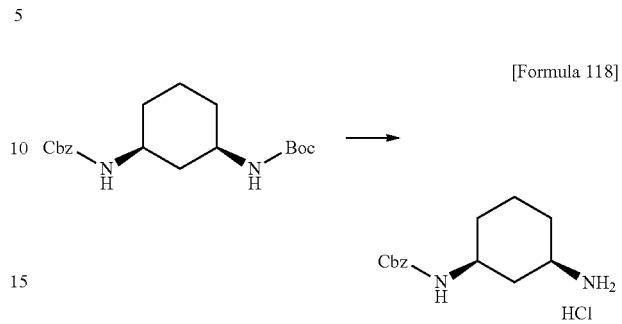

The compound (1.90 g) obtained in the above Step 1 was dissolved in hydrogen chloride (4 mol/L, 1,4-dioxane solution, 54.5 mL), and the solution was stirred at room temperature for 30 min. The reaction solution was concentrated under reduced pressure, and the residue was subjected to slurry washing with ethyl acetate to give the title compound (1.54 g) as a solid.

$^1$H-NMR (DMSO-D$_6$) δ: 0.97-1.37 (4H, m), 1.68-1.90 (3H, m), 2.09 (1H, d, J=11.5 Hz), 2.96-3.12 (1H, m), 3.32-3.42 (1H, m), 5.01 (2H, s), 7.29-7.42 (5H, m), 7.99 (3H, br s).

Reference Example A-9

Methyl (1S,3R,5S)-3-amino-5-{[(benzyloxy)carbonyl]amino}cyclohexane-1-carboxylate (Racemate)

Step 1 (1S,3S,5R)-3-{[(benzyloxy)carbonyl]amino}-5-(methoxycarbonyl)cyclohexyl 4-nitrobenzoate (Racemate)

[Formula 119]

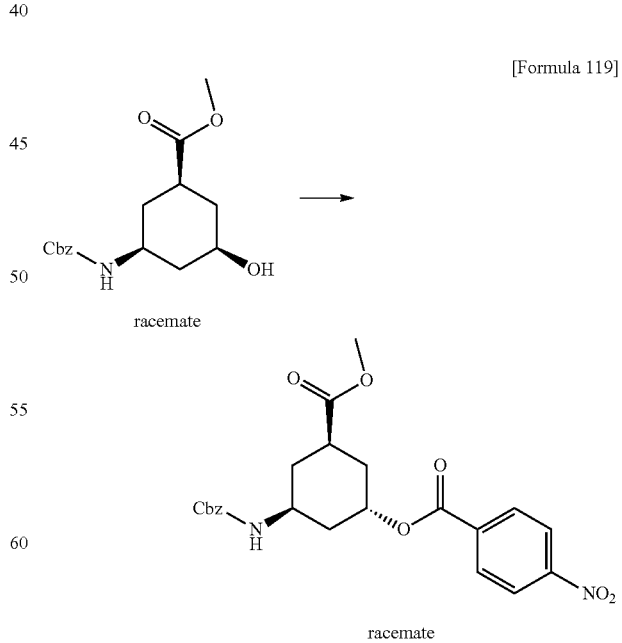

The title compound was obtained in the same manner as in Step 3 of Reference Example A-7, using methyl (1R,3S, 5R)-3-(benzyloxycarbonylamino)-5-hydroxy-cyclohexan-ecarboxylate (racemate) synthesized according to the method described in a literature (Bioorg. Med. Chem., 2006, 14, 2242-2252).

MS (m/z): 457 (M+H)⁺.

Step 2 Methyl (1R,3S,5S)-3-{[(benzyloxy)carbonyl] amino}-5-hydroxycyclohexane-1-carboxylate (Racemate)

[Formula 120]

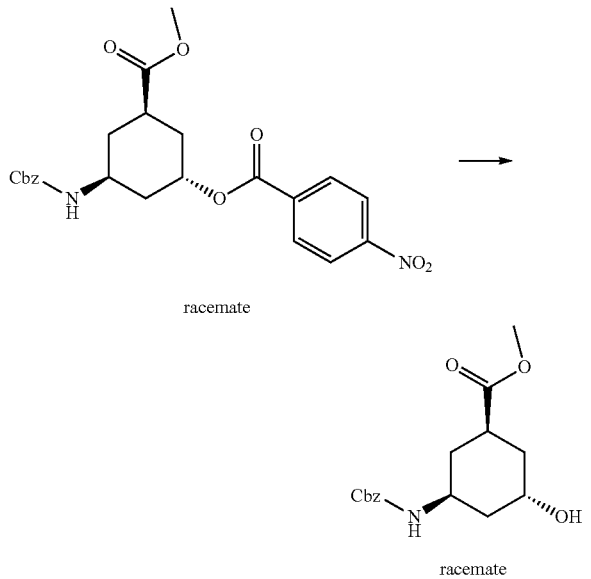

The title compound was obtained in the same manner as in Step 4 of Reference Example A-7, using the compound obtained in the above Step 1.

¹H-NMR (CDCl₃) δ: 1.24-1.39 (2H, m), 1.51-1.62 (2H, m), 1.97-2.12 (2H, m), 2.25-2.34 (1H, m), 2.86-3.02 (1H, m), 3.67 (3H, s), 3.94-4.08 (1H, m), 4.26-4.33 (1H, m), 4.60-4.74 (1H, m), 5.08 (2H, s), 7.28-7.39 (5H, m).

MS (m/z): 308 (M+H)⁺.

Step 3 Methyl (1R,3R,5S)-3-azido-5-{[(benzyloxy) carbonyl]amino}cyclohexane-1-carboxylate (Racemate)

[Formula 121]

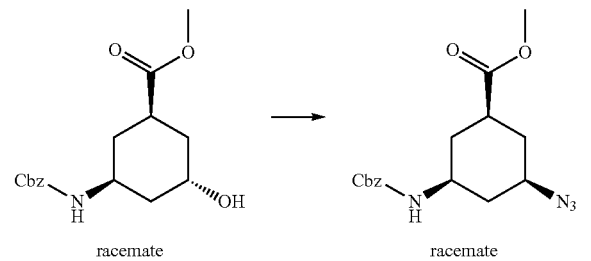

The title compound was obtained in the same manner as in Step 5 of Reference Example A-7, using the compound obtained in the above Step 2.

MS (m/z): 333 (M+H)⁺.

Step 4 Methyl (1S,3R,5S)-3-amino-5-{[(benzyloxy) carbonyl]amino}cyclohexane-1-carboxylate (Racemate)

[Formula 122]

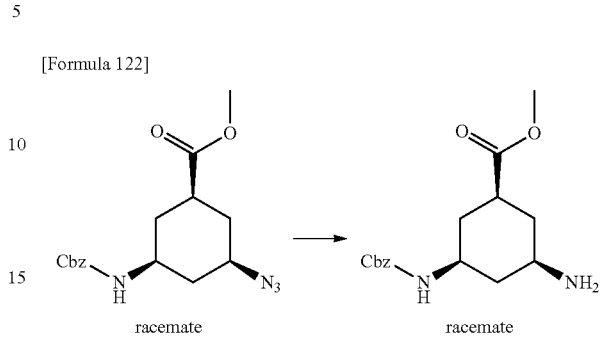

The title compound was obtained in the same manner as in Step 6 of Reference Example A-7, using the compound obtained in the above Step 3.

¹H-NMR (CDCl₃) δ: 0.90-1.79 (5H, m), 2.06-2.20 (2H, m), 2.22-2.30 (1H, m), 2.41-2.53 (1H, m), 2.77-2.90 (1H, m), 3.53-3.70 (1H, m), 3.68 (3H, s), 4.63-4.75 (1H, m), 5.09 (2H, s), 7.29-7.41 (5H, m).

MS (m/z): 307 (M+H)⁺.

Reference Example A-10

Tert-butyl [(1S,2S,5S)-5-amino-2-methoxycyclohexyl]carbamate

Step 1 Ethyl (1R,3S,4S)-3-[(tert-butoxycarbonyl) amino]-4-(methoxymethoxy)cyclohexane-1-carboxylate

[Formula 123]

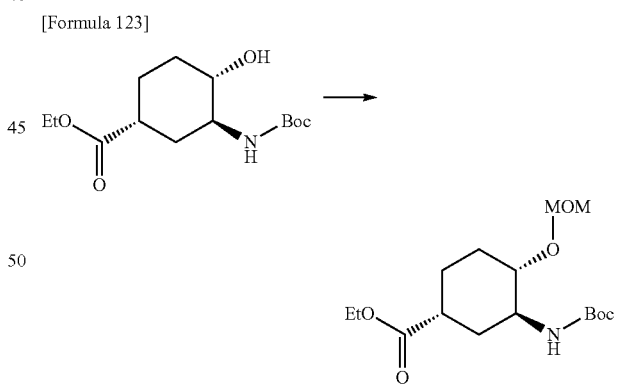

A mixture of ethyl(R,3S,4S)-3-[(tert-butoxycarbonyl) amino]-4-hydroxycyclohexane-1-carboxylate (13.84 g) synthesized according to the method described in a literature (Tetrahedron 2017, 73, 1381-1388), dimethoxyethane (155 mL), sodium iodide (CAS: 7681-82-5) (6.97 g), chloromethyl methyl ether (10.5 mL) and DIPEA (49 mL) was heated under reflux at 105° C. for 2 hr. Saturated brine and water were added to the reaction solution, the mixture was extracted with ethyl acetate, and the organic layer was dried over anhydrous sodium sulfate, and concentrated under reduced pressure. The residue was purified by silica gel column chromatography (dichloromethane/ethyl acetate) to give the title compound (14.43 g) as a solid.

¹H-NMR (CDCl₃) δ: 1.26 (3H, t, J=7.0 Hz), 1.45 (9H, s), 1.57-1.78 (4H, m), 1.89-2.00 (1H, m), 2.21-2.30 (1H, m), 2.43-2.52 (1H, m), 3.39 (3H, s), 3.51-3.59 (1H, m), 3.68-3.80 (1H, m), 4.15 (2H, q, J=7.0 Hz), 4.60 (1H, br s), 4.66 (1H, d, J=6.7 Hz), 4.69 (1H, d, J=6.7 Hz).

Step 2 (1S,3S,4S)-3-[(tert-butoxycarbonyl)amino]-4-(methoxymethoxy)cyclohexane-1-carboxylic Acid

[Formula 124]

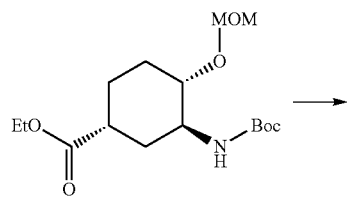

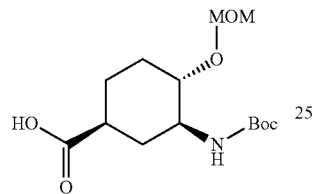

The compound (14.43 g) synthesized in the above Step 1 was dissolved in ethanol (150 mL), sodium ethoxide (CAS: 141-52-6) (concentration 20%, ethanol solution, 24 mL) was added thereto, and the mixture was stirred at 50° C. for 40 hr. 1N Hydrochloric acid ethanol solution (CAS: 7647-01-0) (61 mL) was added to the reaction solution, and the mixture was concentrated under reduced pressure. Water was added to the obtained residue, and the mixture was extracted with dichloromethane. The organic layer was dried over anhydrous sodium sulfate, and concentrated under reduced pressure. The residue was subjected to silica gel column chromatography (dichloromethane/ethyl acetate). The obtained residue was suspended in n-hexane/ethyl acetate, and the solid was collected by filtration to give a mixture (4.11 g) containing the title compound as a solid.

Step 3 Benzyl Tert-butyl [(1S,3S,4S)-4-(methoxymethoxy)cyclohexane-1,3-diyl]biscarbamate

[Formula 125]

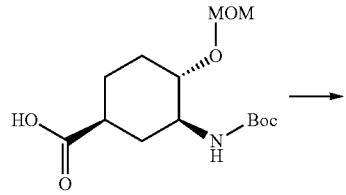

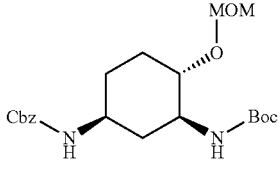

A mixture of the compound (4.11 g) obtained in the above Step 2, 1,4-dioxane (66 mL), diphenylphosphoryl azide (CAS: 26386-88-9) (3.5 mL) and TEA (2.5 mL) was stirred at 90° C. for 2 hr. Then, benzyl alcohol (CAS: 100-51-6) (2.2 mL) was added thereto, and the mixture was stirred at 90° C. for 5 hr. Saturated brine and water were added to the reaction solution, and the mixture was extracted with ethyl acetate. The organic layer was dried over anhydrous sodium sulfate, and concentrated under reduced pressure. The residue was purified by silica gel column chromatography (dichloromethane/ethyl acetate) to give the title compound (2.64 g) as a solid.

¹H-NMR (CDCl₃) δ: 1.08-1.25 (2H, m), 1.40-1.46 (1H, m), 1.43 (9H, s), 2.00-2.13 (2H, m), 2.37-2.46 (1H, m), 3.21-3.32 (1H, m), 3.39-3.51 (1H, m), 3.39 (3H, s), 3.53-3.66 (1H, m), 4.59 (1H, br s), 4.60 (1H, d, J=6.7 Hz), 4.70 (1H, d, J=6.7 Hz), 4.74 (1H, br s), 5.08 (2H, s), 7.29-7.40 (5H, m).

Step 4 Benzyl Tert-butyl [(1S,3S,4S)-4-hydroxycyclohexane-1,3-diyl]biscarbamate

[Formula 126]

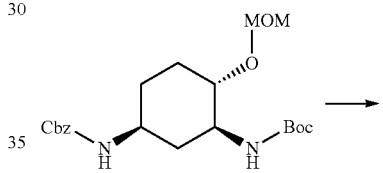

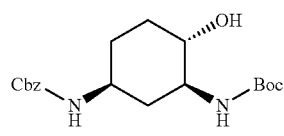

The compound (0.595 g) obtained in the above Step 3 was dissolved in 1,4-dioxane (18 mL), hydrogen chloride (4 mol/L, 1,4-dioxane solution, 36 mL) was added thereto, and the mixture was stirred at room temperature for 3 hr. Then, the solvent was evaporated under reduced pressure, and the residue was dried. A solution of THF (10 mL), TEA (0.57 mL) and di-tert-butyl dicarbonate (CAS: 24424-99-5) (0.418 g) in THF (6.0 mL) was added to the obtained residue, and the mixture was stirred at room temperature for 2.5 hr. Saturated aqueous sodium bicarbonate solution was added to the reaction solution, and the mixture was extracted with dichloromethane. The organic layer was dried over anhydrous sodium sulfate, and concentrated under reduced pressure. The residue was purified by silica gel column chromatography (n-hexane/ethyl acetate) to give the title compound (0.403 g) as a solid.

¹H-NMR (CDCl₃) δ: 1.06-1.24 (2H, m), 1.37-1.49 (1H, m), 1.45 (9H, s), 1.96-2.10 (2H, m), 2.24-2.32 (1H, m), 3.26-3.50 (3H, m), 3.53-3.68 (1H, m), 4.53 (1H, br s), 4.59 (1H, d, J=6.1 Hz), 5.08 (2H, s), 7.30-7.39 (5H, m).

Step 5 Benzyl Tert-butyl [(1S,3S,4S)-4-methoxycyclohexane-1,3-diyl]biscarbamate

[Formula 127]

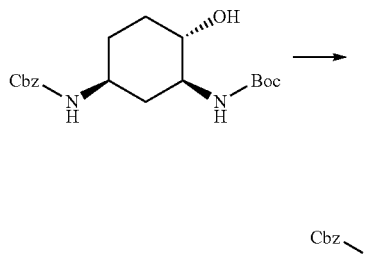

A mixture of the compound (0.350 g) obtained in the above Step 4, dichloromethane (14 mL), silver(I) oxide (CAS: 20667-12-3) (0.677 g), molecular sieves 3A (CAS: 308080-99-1) (0.460 g, used after dried under reduced pressure at 180° C. for 2 hr) and methyl iodide (CAS: 74-88-4) (1.2 mL) was stirred vigorously at 45° C. for 9 hr. The reaction solution was filtered through Celite, and the filtrate was concentrated under reduced pressure. The obtained residue was purified by silica gel column chromatography (n-hexane/ethyl acetate) to give the title compound (0.269 g) as a solid.

$^1$H-NMR (CDCl$_3$) δ: 1.08-1.38 (3H, m), 1.44 (9H, s), 2.03-2.20 (2H, m), 2.41-2.50 (1H, m), 2.94-3.07 (1H, m), 3.32-3.44 (1H, m), 3.36 (3H, s), 3.52-3.66 (1H, m), 4.50-4.67 (2H, m), 5.08 (2H, s), 7.29-7.39 (5H, m).

MS (m/z): 279 (M-Boc+H)$^+$.

Step 6 Tert-butyl [(1S,2S,5S)-5-amino-2-methoxycyclohexyl]carbamate

[Formula 128]

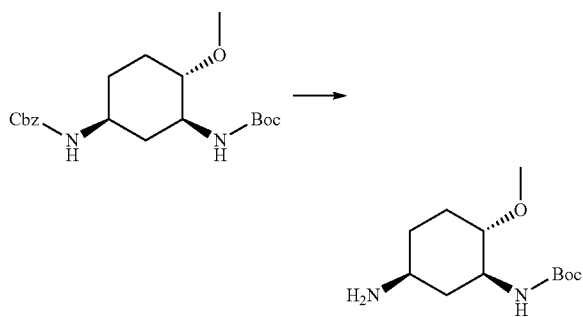

A mixture of the compound (0.267 g) obtained in the above Step 5, 5% palladium on carbon (PH) wet (CAS: 7440-05-3) (0.304 g) and ethanol (12 mL) was stirred under hydrogen atmosphere at room temperature for 3.5 hr. The reaction solution was filtered, and the filtrate was concentrated under reduced pressure. The obtained residue was purified by amino silica gel column chromatography (ethyl acetate/methanol) to give the title compound (0.161 g) as a solid.

$^1$H-NMR (CDCl$_3$) δ: 1.11-1.22 (2H, m), 1.27-1.40 (1H, m), 1.45 (9H, s), 1.83-1.92 (1H, m), 2.07-2.15 (1H, m), 2.17-2.27 (1H, m), 2.92-3.00 (1H, m), 3.04 (1H, td, J=8.7, 3.9 Hz), 3.37 (3H, s), 3.46-3.56 (1H, m), 5.25 (1H, br s).

Reference Example A-11

Benzyl [(1R,3S,5S)-3-amino-5-methoxycyclohexyl]carbamate (Racemate)

Step 1 Methyl (1S,3R,5S)-3-{[(benzyloxy)carbonyl]amino}-5-methoxycyclohexane-1-carboxylate (Racemate)

[Formula 129]

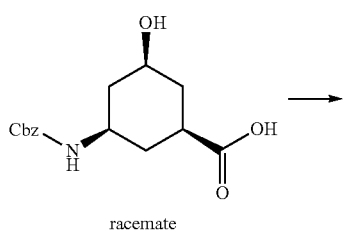

racemate

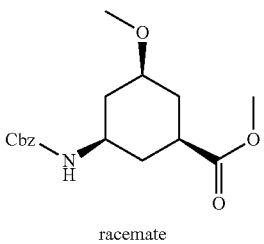

racemate

To a solution of (1S,3R,5S)-3-{[(benzyloxy)carbonyl]amino}-5-hydroxycyclohexane-1-carboxylic acid (racemate) (0.498 g) synthesized according to the method described in a literature (Bioorg. Med. Chem. 2006, 14, 2242-2252) and dichloromethane (17.0 mL) were added silver(I) oxide (1.57 g), molecular sieves 3A (0.249 g) and methyl iodide (2.11 mL), and the mixture was stirred at 40° C. for 3 hr. Additional methyl iodide (2.11 mL) was added thereto, and the mixture was stirred at 40° C. for 7.5 hr. The insoluble substance was removed by filtration through Celite, and washed with dichloromethane and methanol, and the filtrate was concentrated under reduced pressure. The obtained crude product was purified by column chromatography (methanol/dichloromethane) to give the title compound (0.480 g) as an oil.

$^1$H-NMR (CDCl$_3$) δ: 1.06 (1H, q, J=11.5 Hz), 1.19-1.32 (2H, br m), 2.20-2.41 (4H, br m), 3.17-3.26 (1H, m), 3.34 (3H, s), 3.55-3.62 (1H, m), 3.66 (3H, s), 5.05-5.14 (1H, m), 5.07 (2H, s), 7.32-7.34 (5H, br m).

MS (m/z): 322 (M+H)$^+$.

Step 2 (1S,3R,5S)-3-{[(benzyloxy)carbonyl]amino}-5-methoxycyclohexane-1-carboxylic Acid (Racemate)

[Formula 130]

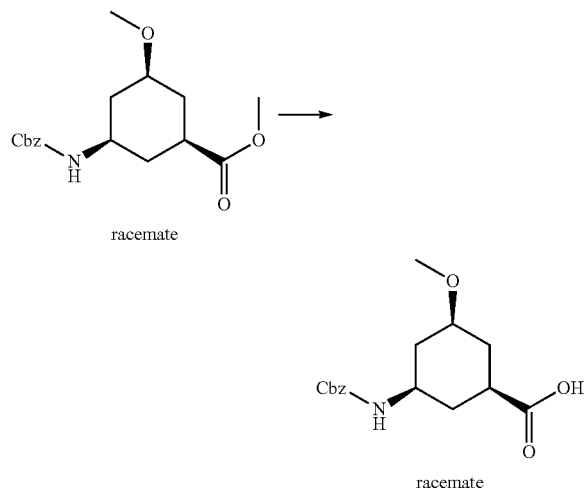

racemate

The title compound was obtained in the same manner as in Step 9 of Reference Example A-1, using the compound obtained in the above Step 1. The obtained crude product was directly used in the next step.

Step 3 Benzyl Prop-2-en-1-yl [(1R,3S,5S)-5-methoxycyclohexane-1,3-diyl]biscarbamate (Racemate)

[Formula 131]

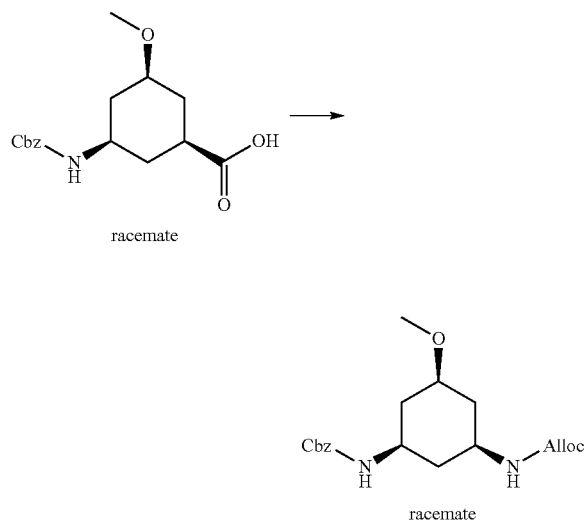

The title compound was obtained in the same manner as in Step 4 of Reference Example A-6, using the compound obtained in the above Step 2.

MS (m/z): 363 (M+H)⁺.

Step 4 Benzyl [(1R,3S,5S)-3-amino-5-methoxycyclohexyl]carbamate (Racemate)

[Formula 132]

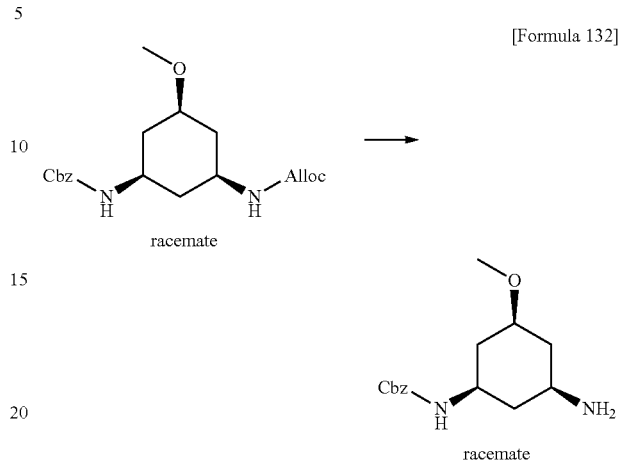

The title compound was obtained in the same manner as in Step 5 of Reference Example A-6, using the compound obtained in the above Step 3.

¹H-NMR (CDCl₃) δ: 0.90-1.03 (3H, m), 1.35 (2H, s), 2.12 (1H, d, J=11.6 Hz), 2.21 (1H, d, J=12.2 Hz), 2.36 (1H, d, J=11.6 Hz), 2.79 (1H, t, J=11.3 Hz), 3.24 (1H, t, J=10.7 Hz), 3.35 (3H, s), 3.58 (1H, d, J=7.9 Hz), 4.72 (1H, s), 5.09 (2H, s), 7.30-7.36 (5H, m).

MS (m/z): 279 (M+H)⁺.

Reference Example A-12

Tert-butyl [(1R,2R,4S)-2-(methoxymethoxy)-4-(methylamino)cyclopentyl]carbamate

Step 1 Methyl (1S,3R,4R)-3-[(tert-butoxycarbonyl)amino]-4-(methoxymethoxy)cyclopentane-1-carboxylate

[Formula 133]

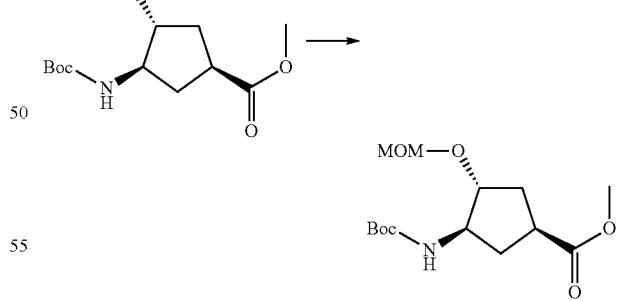

The title compound was obtained in the same manner as in Step 2 of Reference Example A-6, using methyl (1S,3R,4R)-3-[(tert-butoxycarbonyl)amino]-4-hydroxycyclopentane-1-carboxylate (CAS: 321744-16-5).

¹H-NMR (CDCl₃) δ: 1.44 (9H, s), 1.67-1.75 (1H, m), 2.05-2.13 (2H, m), 2.40 (1H, br s), 3.00-3.08 (1H, m), 3.37 (3H, s), 3.70 (3H, s), 3.97 (1H, br s), 4.00-4.04 (1H, m), 4.63 (1H, d, J=6.7 Hz), 4.72 (1H, d, J=6.7 Hz), 5.10 (1H, br s).

MS (m/z): 204 (M-Boc+H)⁺.

Step 2 (1S,3R,4R)-3-[(tert-butoxycarbonyl)amino]-4-(methoxymethoxy)cyclopentane-1-carboxylic Acid

[Formula 134]

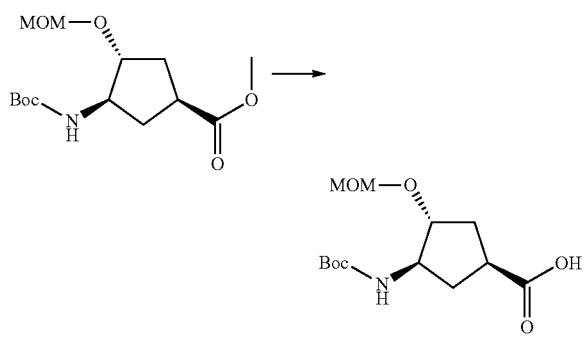

The title compound was obtained in the same manner as in Step 9 of Reference Example A-1, using the compound obtained in the above Step 1.

Step 3 Benzyl Tert-butyl [(1S,3R,4R)-4-(methoxymethoxy)cyclopentane-1,3-diyl]biscarbamate

[Formula 135]

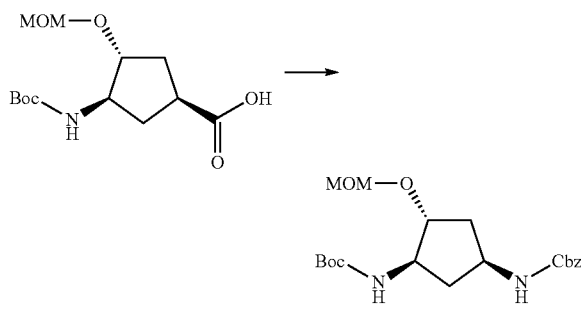

The title compound was obtained in the same manner as in Step 10 of Reference Example A-1, using the compound obtained in the above Step 2.

$^1$H-NMR (CDCl$_3$) δ: 1.37-1.62 (1H, m), 1.44 (9H, s), 1.93-2.09 (2H, m), 2.51-2.61 (1H, m), 3.35 (3H, s), 3.73-3.81 (1H, m), 4.01-4.17 (2H, m), 4.62 (1H, d, J=6.7 Hz), 4.69 (1H, d, J=6.7 Hz), 5.08-5.23 (4H, m), 7.30-7.40 (5H, m).

Step 4 Tert-butyl [(1R,2R,4S)-4-amino-2-(methoxymethoxy)cyclopentyl]carbamate

[Formula 136]

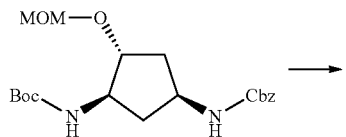

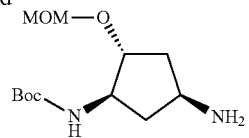

The title compound was obtained in the same manner as in Step 2 of Reference Example A-2, using the compound obtained in the above Step 3.

$^1$H-NMR (DMSO-D$_6$) δ: 1.10-1.20 (1H, m), 1.37 (9H, s), 1.53-1.61 (1H, m), 1.69-1.77 (1H, m), 2.03-2.11 (1H, m), 3.21 (3H, s), 3.24-3.32 (1H, m), 3.58-3.70 (1H, m), 3.81-3.91 (1H, m), 4.49-4.55 (1H, m), 4.57-4.62 (1H, m), 6.91-6.94 (1H, m).

Step 5 Tert-butyl {(1R,2R,4S)-2-(methoxymethoxy)-4-[(2-nitrobenzene-1-sulfonyl)amino]cyclopentyl}carbamate

[Formula 137]

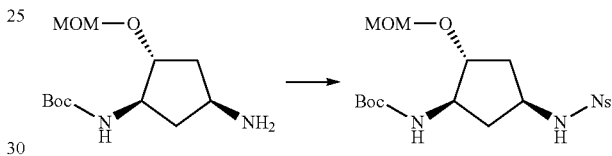

The title compound was obtained in the same manner as in Step 12 of Reference Example A-1, using the compound obtained in the above Step 4.

$^1$H-NMR (DMSO-D$_6$) δ: 1.24-1.34 (1H, m), 1.36 (9H, s), 1.66-1.79 (2H, m), 2.05-2.17 (1H, m), 3.17 (3H, s), 3.52-3.63 (1H, m), 3.65-3.75 (1H, m), 3.75-3.82 (1H, m), 4.47 (1H, d, J=6.7 Hz), 4.54 (1H, d, J=6.7 Hz), 6.96 (1H, d, J=7.9 Hz), 7.84-7.93 (2H, m), 7.95-8.01 (1H, m), 8.02-8.07 (1H, m), 8.09-8.15 (1H, m).

Step 6 Tert-butyl {(1R,2R,4S)-2-(methoxymethoxy)-4-[methyl(2-nitrobenzene-1-sulfonyl)amino]cyclopentyl}carbamate

[Formula 138]

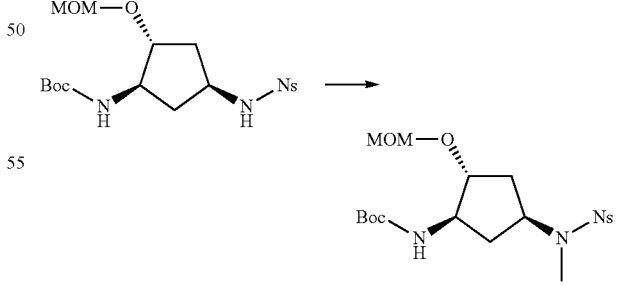

The title compound was obtained in the same manner as in Step 13 of Reference Example A-1, using the compound obtained in the above Step 5.

$^1$H-NMR (DMSO-D$_6$) δ: 1.36 (9H, s), 1.42-1.52 (1H, m), 1.59-1.67 (1H, m), 1.82-1.96 (2H, m), 2.79 (3H, s), 3.20 (3H, s), 3.60-3.68 (1H, m), 3.76-3.81 (1H, m), 4.31-4.40

(1H, m), 4.52 (1H, d, J=6.7 Hz), 4.59 (1H, d, J=6.7 Hz), 7.00 (1H, d, J=7.9 Hz), 7.83-7.92 (2H, m), 7.96-8.03 (2H, m).

Step 7 Tert-butyl [(1R,2R,4S)-2-(methoxymethoxy)-4-(methylamino)cyclopentyl]carbamate

[Formula 139]

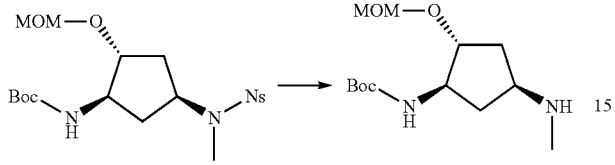

The title compound was obtained in the same manner as in Step 14 of Reference Example A-1, using the compound obtained in the above Step 6.

¹H-NMR (DMSO-D$_6$) δ: 1.16-1.26 (1H, m), 1.37 (9H, s), 1.59-1.68 (1H, m), 1.69-1.78 (1H, m), 2.03-2.12 (1H, m), 2.20 (3H, s), 2.94-3.01 (1H, m), 3.22 (3H, s), 3.63-3.70 (1H, m), 3.82-3.86 (1H, m), 4.52 (1H, d, J=6.1 Hz), 4.59 (1H, d, J=6.7 Hz), 6.82-6.87 (1H, m).

Reference Example A-13

Tert-butyl [(1R,2S,4S)-2-(methoxymethoxy)-4-(methylamino)cyclopentyl]carbamate

Step 1 Methyl (1S,3R,4S)-3-[(tert-butoxycarbonyl)amino]-4-(methoxymethoxy)cyclopentane-1-carboxylate

[Formula 140]

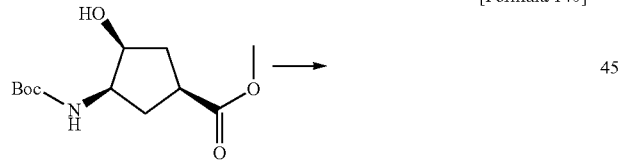

The title compound was obtained in the same manner as in Step 2 of Reference Example A-6, using methyl (1R,2S,4S)—N—BOC-1-amino-2-hydroxycyclopentane-4-carboxylate (CAS: 321744-14-3).

¹H-NMR (CDCl$_3$) δ: 1.44 (9H, s), 1.84-1.94 (1H, m), 2.05-2.33 (3H, m), 2.75-2.85 (1H, m), 3.37 (3H, s), 3.68 (3H, s), 3.90-3.99 (1H, m), 4.00-4.05 (1H, m), 4.61 (1H, d, J=6.7 Hz), 4.69 (1H, d, J=6.7 Hz), 5.04-5.12 (1H, m).

Step 2 (1S,3R,4S)-3-[(tert-butoxycarbonyl)amino]-4-(methoxymethoxy)cyclopentane-1-carboxylic Acid

[Formula 141]

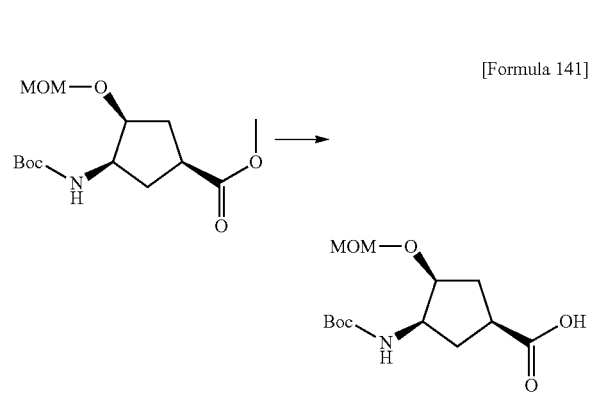

The title compound was obtained in the same manner as in Step 9 of Reference Example A-1, using the compound obtained in the above Step 1.

Step 3 Benzyl Tert-butyl [(1S,3R,4S)-4-(methoxymethoxy)cyclopentane-1,3-diyl]biscarbamate

[Formula 142]

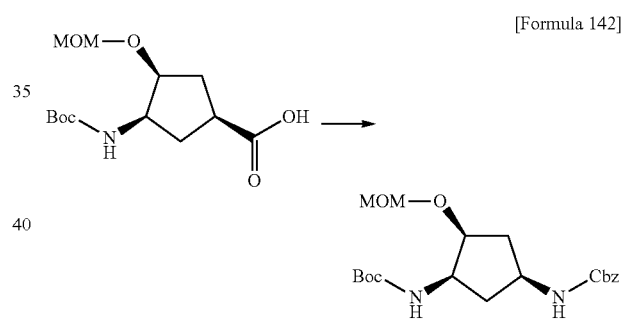

The title compound was obtained in the same manner as in Step 10 of Reference Example A-1, using the compound obtained in the above Step 2.

¹H-NMR (CDCl$_3$) δ: 1.39-1.48 (1H, m), 1.44 (9H, s), 1.73-1.80 (1H, m), 2.08-2.16 (1H, m), 2.52-2.60 (1H, m), 3.37 (3H, s), 3.85-3.97 (1H, m), 4.00-4.05 (1H, m), 4.12-4.22 (1H, m), 4.61-4.71 (2H, m), 5.01-5.13 (4H, m), 7.30-7.41 (5H, m).

Step 4 Tert-butyl [(1R,2S,4S)-4-amino-2-(methoxymethoxy)cyclopentyl]carbamate

[Formula 143]

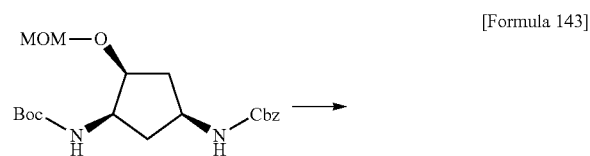

-continued

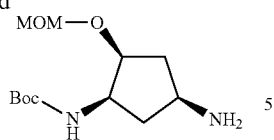

The title compound was obtained in the same manner as in Step 2 of Reference Example A-2, using the compound obtained in the above Step 3.

Step 5 Tert-butyl {(1R,2S,4S)-2-(methoxymethoxy)-4-[(2-nitrobenzene-1-sulfonyl)amino]cyclopentyl}carbamate

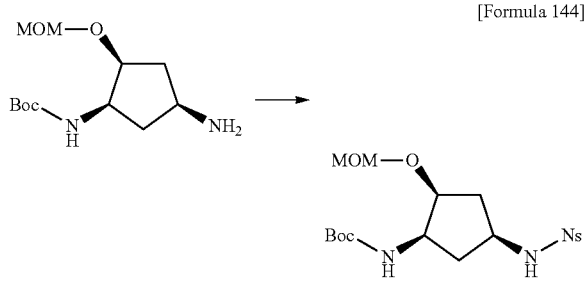

[Formula 144]

The title compound was obtained in the same manner as in Step 12 of Reference Example A-1, using the compound obtained in the above Step 4.

$^1$H-NMR (CDCl$_3$) δ: 1.35-1.44 (1H, m), 1.41 (9H, s), 1.77-1.82 (1H, m), 1.91-2.00 (1H, m), 2.32-2.40 (1H, m), 3.39 (3H, s), 3.82-3.90 (1H, m), 3.98-4.03 (2H, m), 4.65 (1H, d, J=6.7 Hz), 4.68 (1H, d, J=6.7 Hz), 4.97-5.06 (1H, m), 5.88 (1H, d, J=9.7 Hz), 7.72-7.78 (2H, m), 7.85-7.90 (1H, m), 8.11-8.16 (1H, m).

Step 6 Tert-butyl {(1R,2S,4S)-2-(methoxymethoxy)-4-[methyl(2-nitrobenzene-1-sulfonyl)amino]cyclopentyl}carbamate

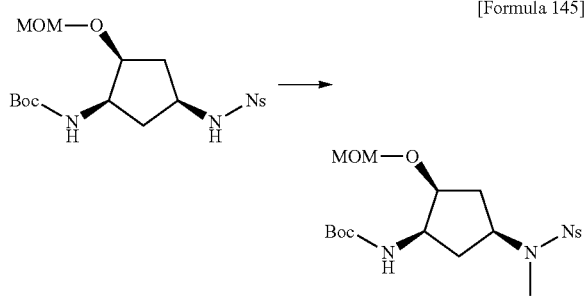

[Formula 145]

The title compound was obtained in the same manner as in Step 13 of Reference Example A-1, using the compound obtained in the above Step 5.

$^1$H-NMR (CDCl$_3$) δ: 1.43 (9H, s), 1.65-1.76 (2H, m), 2.06-2.12 (1H, m), 2.17-2.25 (1H, m), 2.86 (3H, s), 3.37 (3H, s), 3.77-3.87 (1H, m), 3.95-3.99 (1H, m), 4.35-4.45 (1H, m), 4.62 (1H, d, J=6.7 Hz), 4.69 (1H, d, J=6.7 Hz), 4.98-5.06 (1H, m), 7.60-7.65 (1H, m), 7.67-7.74 (2H, m), 8.01-8.04 (1H, m).

Step 7 Tert-butyl [(1R,2S,4S)-2-(methoxymethoxy)-4-(methylamino)cyclopentyl]carbamate

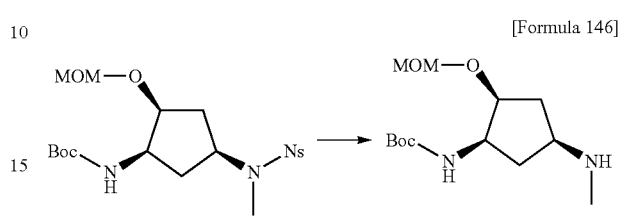

[Formula 146]

The title compound was obtained in the same manner as in Step 14 of Reference Example A-1, using the compound obtained in the above Step 6.

$^1$H-NMR (CDCl$_3$) δ: 1.44 (9H, s), 1.51-1.64 (2H, m), 2.04-2.15 (1H, m), 2.24-2.33 (1H, m), 2.37 (3H, s), 2.98-3.05 (1H, m), 3.38 (3H, s), 3.88-3.99 (1H, m), 4.00-4.06 (1H, m), 4.64 (1H, d, J=6.7 Hz), 4.68 (1H, d, J=6.7 Hz), 5.19-5.26 (1H, m).

Reference Example A-14

Benzyl [(1R,3S,4S)-3-hydroxy-4-(methylamino)cyclopentyl]carbamate

Step 1 Methyl (1R,3S,4S)-3-(acetyloxy)-4-[(tert-butoxycarbonyl)amino]cyclopentane-1-carboxylate

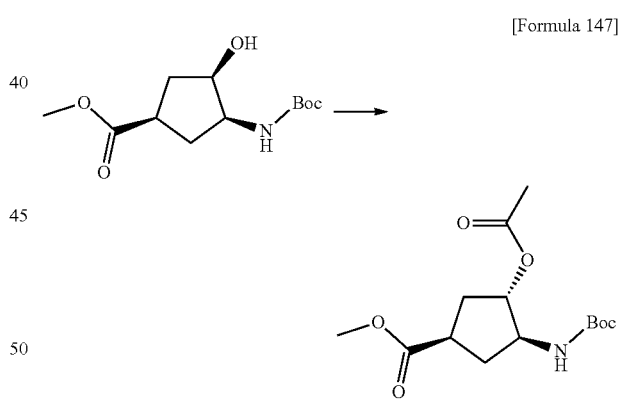

[Formula 147]

Methyl (1R,3S,4R)-3-[(tert-butoxycarbonyl)amino]-4-hydroxycyclopentane-1-carboxylate (CAS: 321744-23-4) (0.300 g) was dissolved in THF (2.3 mL), and diphenyl-2-pyridylphosphine (0.487 g), 1,1'-(azodicarbonyl)dipiperazine (0.394 g) and acetic acid (0.132 mL) were added thereto, and the mixture was stirred at room temperature for 2 hr. 2N Hydrochloric acid and ethyl acetate were added to the reaction solution, and the mixture was subjected to extraction operation. The organic layer was washed with saturated aqueous sodium bicarbonate solution and saturated brine, and dried over anhydrous sodium sulfate. The solvent was evaporated under reduced pressure, and the residue was washed with a mixed solvent of n-hexane/ethyl acetate=3/1, whereby the insoluble substance was removed by filtration.

The filtrate was concentrated under reduced pressure, and the residue was purified by silica gel chromatography (ethyl acetate/dichloromethane) to give the title compound (0.230 g) as a solid.

$^1$H-NMR (CDCl$_3$) δ: 1.44 (9H, s), 1.76 (1H, dt, J=14.0, 6.0 Hz), 1.98-2.08 (4H, m), 2.21-2.29 (1H, m), 2.38-2.52 (1H, m), 2.96-3.05 (1H, m), 3.71 (3H, s), 4.01 (1H, br s), 5.01-5.15 (2H, m).

Step 2 (1R,3S,4S)-3-[(tert-butoxycarbonyl)amino]-4-hydroxycyclopentane-1-carboxylic Acid

[Formula 148]

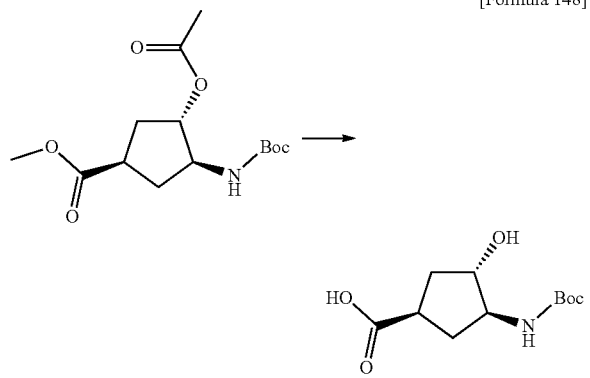

The compound (46.6 g) obtained in the above Step 1 was dissolved in THF (406 mL), and lithium hydroxide hydrate (51.9 g), water (309 mL) and methanol (77 mL) were added thereto, and the mixture was stirred at room temperature for 3 hr. Ice block was added to the reaction solution, and then 5N hydrochloric acid (263 mL) was added thereto. Sodium chloride and 10% methanol/dichloromethane solution were added thereto, and the mixture was subjected to extraction. 10% Methanol/dichloromethane solution was added to the aqueous layer, and the mixture was subjected to extraction. The combined organic layers were dried over anhydrous sodium sulfate, and the solvent was evaporated under reduced pressure to give the title compound (36.8 g) as a solid.

$^1$H-NMR (DMSO-D$_6$) δ: 1.38 (9H, s), 1.46-1.56 (1H, m), 1.60-1.69 (1H, m), 1.90-1.99 (1H, m), 2.08-2.20 (1H, m), 2.76-2.86 (1H, m), 3.48-3.58 (1H, m), 3.77-3.84 (1H, m), 4.80 (1H, d, J=4.5 Hz), 6.76 (1H, d, J=7.5 Hz), 12.10 (1H, br s).

Step 3 Methoxymethyl (1R,3S,4S)-3-[(tert-butoxycarbonyl)amino]-4-(methoxymethoxy)cyclopentane-1-carboxylate

[Formula 149]

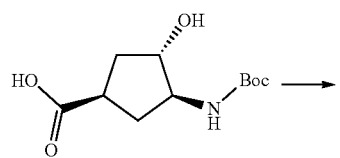

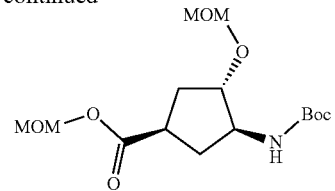

The title compound was obtained in the same manner as in Step 8 of Reference Example A-1, using the compound obtained in the above Step 2.

$^1$H-NMR (CDCl$_3$) δ: 1.44 (9H, s), 1.69-1.79 (1H, m), 2.06-2.17 (2H, m), 2.39-2.51 (1H, m), 3.02-3.12 (1H, m), 3.37 (3H, s), 3.48 (3H, s), 3.93-4.06 (2H, m), 4.64 (1H, d, J=7.0 Hz), 4.72 (1H, d, J=7.0 Hz), 5.05 (1H, br s), 5.25 (2H, s).

MS (m/z): 234 (M-Boc+H)$^+$.

Step 4 (1R,3S,4S)-3-[(tert-butoxycarbonyl)amino]-4-(methoxymethoxy)cyclopentane-1-carboxylic Acid

[Formula 150]

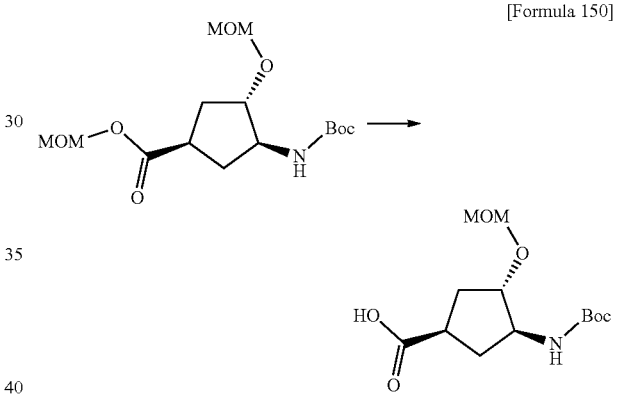

The title compound was obtained in the same manner as in Step 9 of Reference Example A-1, using the compound obtained in the above Step 3.

Step 5 Benzyl Tert-butyl [(1R,3S,4S)-4-(methoxymethoxy)cyclopentane-1,3-diyl]biscarbamate

[Formula 151]

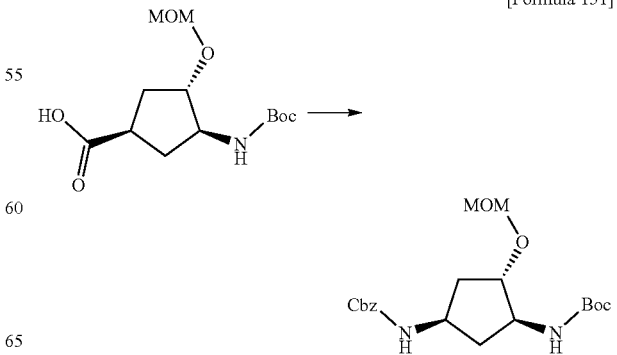

The title compound was obtained in the same manner as in Step 10 of Reference Example A-1, using the compound obtained in the above Step 4.

$^1$H-NMR (CDCl$_3$) δ: 1.36-1.51 (1H, m), 1.44 (9H, s), 1.91-2.04 (2H, m), 2.51-2.61 (1H, m), 3.35 (3H, s), 3.77 (1H, br s), 4.03-4.13 (2H, m), 4.62 (1H, d, J=6.7 Hz), 4.66-4.72 (1H, m), 5.15-5.22 (1H, m), 5.09 (2H, s), 7.32-7.36 (5H, m).

MS (m/z): 295 (M-Boc+H)$^+$.

Step 6 Benzyl [(1R,3S,4S)-3-amino-4-hydroxycyclopentyl]carbamate

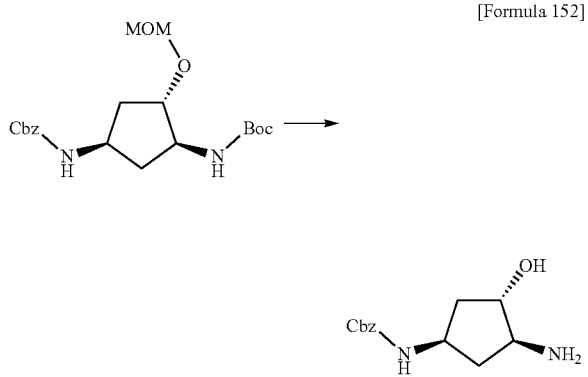

[Formula 152]

The title compound was obtained in the same manner as in Step 4 of Reference Example A-3, using the compound obtained in the above Step 5.

$^1$H-NMR (CDCl$_3$) δ: 1.25-1.33 (1H, m), 2.02 (2H, t, J=6.1 Hz), 2.34-2.42 (1H, m), 3.19-3.24 (1H, m), 3.95 (1H, dt, J=4.9, 4.9 Hz), 4.22-4.30 (1H, m), 5.08 (2H, s), 5.36 (1H, br s), 7.30-7.40 (5H, m).

MS (m/z): 251 (M+H)$^+$.

Step 7 Benzyl {(1R,3S,4S)-3-hydroxy-4-[(2-nitrobenzene-1-sulfonyl)amino]cyclopentyl}carbamate

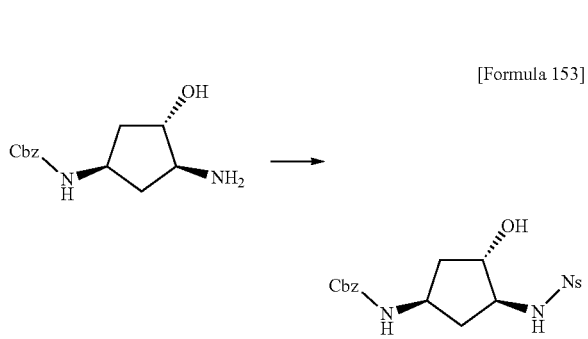

[Formula 153]

The title compound was obtained in the same manner as in Step 12 of Reference Example A-1, using the compound obtained in the above Step 6.

$^1$H-NMR (CDCl$_3$) δ: 1.45-1.53 (1H, m), 2.01 (2H, t, J=7.1 Hz), 2.35 (1H, br s), 2.41-2.51 (1H, m), 3.49 (1H, br s), 4.07 (1H, dd, J=15.0, 7.7 Hz), 4.26 (1H, br s), 4.86 (1H, br s), 5.08 (2H, s), 6.02 (1H, br s), 7.30-7.39 (5H, m), 7.74-7.78 (2H, m), 7.87 (1H, dd, J=6.1, 3.1 Hz), 8.15 (1H, dd, J=5.5, 3.1 Hz).

MS (m/z): 436 (M+H)$^+$.

Step 8 Benzyl {(1R,3S,4S)-3-hydroxy-4-[methyl(2-nitrobenzene-1-sulfonyl)amino]cyclopentyl}carbamate

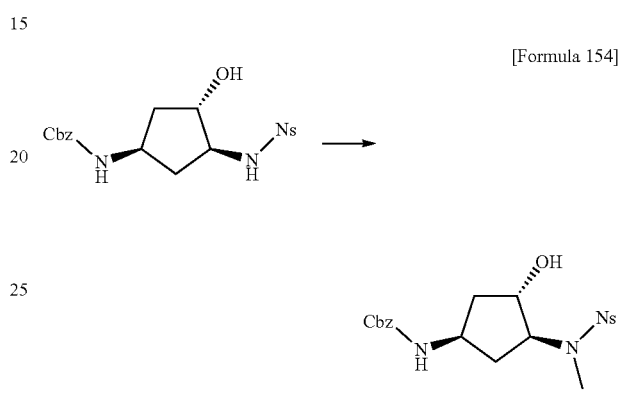

[Formula 154]

The title compound was obtained in the same manner as in Step 13 of Reference Example A-1, using the compound obtained in the above Step 7.

$^1$H-NMR (CDCl$_3$) δ: 1.83-1.92 (1H, m), 2.00-2.08 (1H, m), 2.22-2.30 (1H, m), 2.46 (1H, br s), 2.90 (3H, s), 3.94 (1H, dt, J=11.7, 7.4 Hz), 4.05-4.11 (1H, m), 4.27 (1H, br s), 4.76 (1H, br s), 5.07 (2H, s), 7.29-7.38 (5H, m), 7.63-7.67 (1H, m), 7.69-7.74 (2H, m), 8.07-8.10 (1H, m).

MS (m/z): 450 (M+H)$^+$.

Step 9 Benzyl [(1R,3S,4S)-3-hydroxy-4-(methylamino)cyclopentyl]carbamate

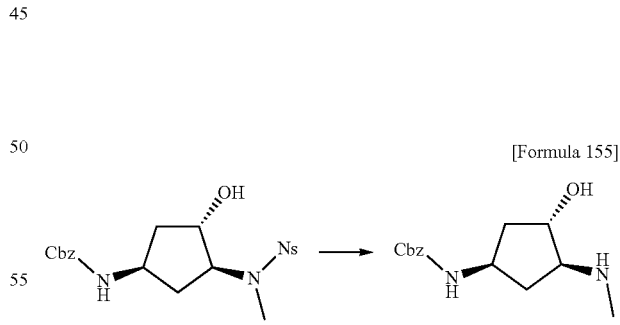

[Formula 155]

The title compound was obtained in the same manner as in Step 14 of Reference Example A-1, using the compound obtained in the above Step 8.

$^1$H-NMR (CDCl$_3$) δ: 1.34 (1H, dt, J=13.5, 5.5 Hz), 1.96-2.01 (2H, m), 2.32-2.39 (1H, m), 2.41 (3H, s), 2.85-2.90 (1H, m), 4.05-4.09 (1H, m), 4.27 (1H, br s), 5.08 (2H, s), 5.39 (1H, br s), 7.30-7.39 (5H, m).

MS (m/z): 265 (M+H)$^+$.

Reference Example A-15 tert-butyl [(1R,3R,4S)-3-hydroxy-4-(methylamino)cyclopentyl]carbamate

Step 1 Tert-butyl {(1R,3R,4S)-3-hydroxy-4-[methyl(2-nitrobenzene-1-sulfonyl)amino]cyclopentyl}carbamate

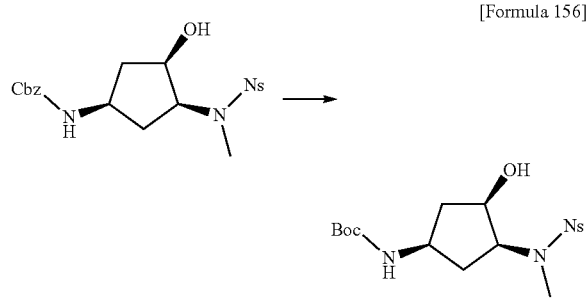

[Formula 156]

The compound (20.6 g) obtained in Step 13 of Reference Example A-1 was dissolved in acetonitrile (305 mL), and iodotrimethylsilane (18.8 mL) was added dropwise thereto under ice-cooling, and the mixture was stirred at the same temperature for 1 hr. 1N Hydrochloric acid ethanol solution (45.8 mL) was added to the reaction solution, and the mixture was stirred at the same temperature for 30 min, and concentrated under reduced pressure. The residue was dissolved in ethanol (15 mL), and THF (153 mL), sodium carbonate (24.3 g) and di-tert-butyl dicarbonate (15.0 g) were added thereto, and the mixture was stirred at room temperature for 3 hr. Ethyl acetate and saturated brine were added to the reaction solution, and the mixture was subjected to extraction operation. The organic layer was dried over anhydrous sodium sulfate, and the solvent was evaporated under reduced pressure. The residue was purified by silica gel chromatography (n-hexane/ethyl acetate) to give the title compound (17.1 g) as a solid.

$^1$H-NMR (CDCl$_3$) δ: 1.45 (9H, s), 1.57-1.65 (1H, m), 1.97-2.20 (2H, m), 2.23-2.32 (1H, m), 3.08 (3H, s), 3.28-3.32 (1H, m), 3.84-3.94 (2H, m), 4.20-4.26 (1H, m), 5.00 (1H, br s), 7.63-7.67 (1H, m), 7.67-7.75 (2H, m), 8.02-8.05 (1H, m).

Step 2 Tert-butyl [(1R,3R,4S)-3-hydroxy-4-(methylamino)cyclopentyl]carbamate

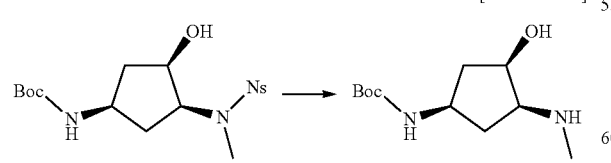

[Formula 157]

The title compound was obtained in the same manner as in Step 14 of Reference Example A-1, using the compound obtained in the above Step 1.

$^1$H-NMR (CDCl$_3$) δ: 1.32 (1H, ddd, J=13.0, 9.5, 5.5 Hz), 1.42 (9H, s), 1.80 (1H, d, J=14.5 Hz), 1.99 (1H, ddd, J=14.5, 8.5, 4.0 Hz), 2.34-2.44 (4H, m), 2.81 (1H. td, J=8.5, 4.0 Hz), 3.99 (1H, td, J=4.0, 2.0 Hz), 4.04-4.15 (1H, m), 5.19-5.31 (1H, m).

Reference Example A-16

Tert-butyl [(1S,2R,4R)-4-amino-2-methoxycyclopentyl]methylcarbamate

Step 1 Methyl (1R,3S,4R)-3-[(tert-butoxycarbonyl)amino]-4-methoxycyclopentane-1-carboxylate

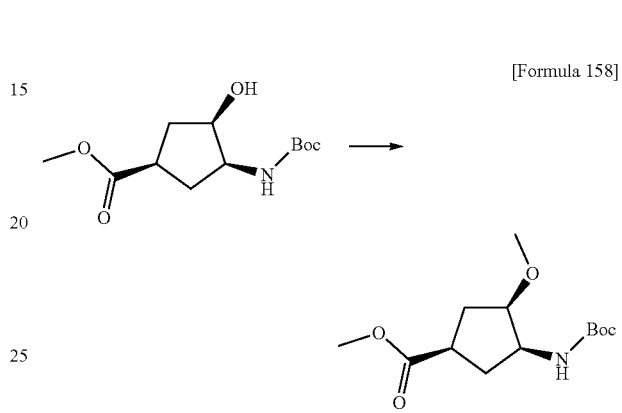

[Formula 158]

A mixture of methyl (1R,3S,4R)-3-(tert-butoxycarbonylamino)-4-hydroxy-cyclopentanecarboxylate (CAS: 321744-23-4) (3.55 g), dichloromethane (60 mL), silver(I) oxide (CAS: 20667-12-3) (9.18 g), molecular sieves 3A (CAS: 308080-99-1) (4.73 g, used after dried under reduced pressure at 180° C. for 2 hr) and methyl iodide (CAS: 74-88-4) (16.2 mL) was stirred vigorously at 55° C. for 42 hr. The reaction solution was filtered through Celite, and the filtrate was concentrated under reduced pressure. The obtained residue was purified by silica gel column chromatography (n-hexane/ethyl acetate) to give the title compound (3.25 g) as an oil.

$^1$H-NMR (CDCl$_3$) δ: 1.45 (9H, s), 1.85 (1H, dt, J=16.8, 6.4 Hz), 1.93-2.03 (1H, m), 2.15-2.23 (1H, m), 2.29 (1H, dt, J=14.9, 6.4 Hz), 2.75-2.84 (1H, m), 3.30 (3H, s), 3.59-3.66 (1H, m), 3.68 (3H, s), 3.88-3.98 (1H, m), 5.12 (1H, d, J=7.4 Hz).

Step 2 (1R,3S,4R)-3-[(tert-butoxycarbonyl)amino]-4-methoxycyclopentane-1-carboxylic Acid

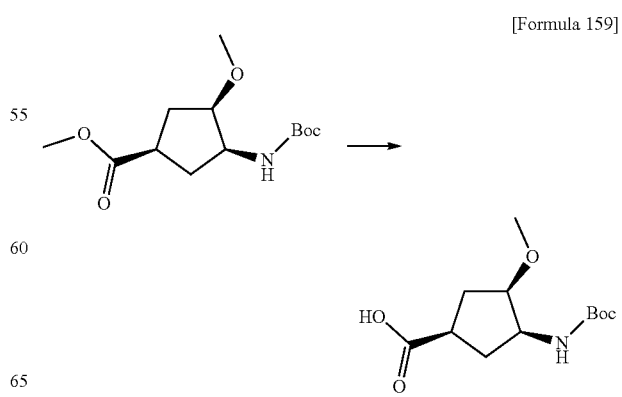

[Formula 159]

The title compound was obtained in the same manner as in Step 9 of Reference Example A-1, using the compound obtained in the above Step 1.

$^1$H-NMR (CDCl$_3$) δ: 1.45 (9H, s), 1.83-1.94 (1H, m), 1.94-2.03 (1H, m), 2.23 (1H, ddd, J=14.7, 5.0, 2.4 Hz), 2.28-2.39 (1H, m), 2.81-2.91 (1H, m), 3.32 (3H, s), 3.65 (1H, td, J=4.9, 2.4 Hz), 3.89-4.01 (1H, m), 5.12 (1H, d, J=6.1 Hz).

Step 3 Benzyl Tert-butyl [(1R,3S,4R)-4-methoxycyclopentane-1,3-diyl]biscarbamate

[Formula 160]

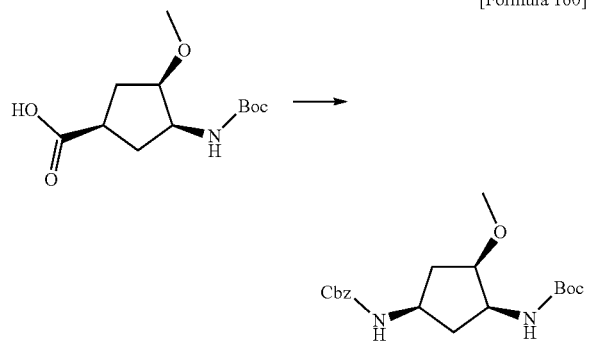

The title compound was obtained in the same manner as in Step 10 of Reference Example A-1, using the compound obtained in the above Step 2.

$^1$H-NMR (CDCl$_3$) δ: 1.34-1.43 (1H, m), 1.45 (9H, s), 1.73-1.83 (1H, m), 1.94-2.04 (1H, m), 2.48-2.60 (1H, m), 3.32 (3H, s), 3.60-3.65 (1H, m), 3.84-3.96 (1H, m), 4.12-4.20 (1H, m), 5.00-5.16 (4H, m), 7.30-7.38 (5H, m).

Step 4 Benzyl {(1R,3R,4S)-3-methoxy-4-[(2-nitrobenzene-1-sulfonyl)amino]cyclopentyl}carbamate

[Formula 161]

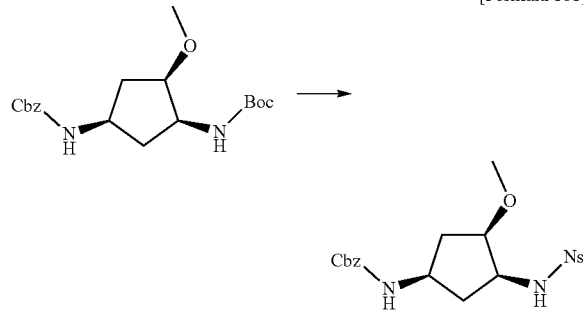

The title compound was obtained in the same manner as in Step 11 and Step 12 of Reference Example A-1, using the compound obtained in the above Step 3.

$^1$H-NMR (CDCl$_3$) δ: 1.43-1.52 (1H, m), 1.69-1.76 (1H, m), 1.94-2.03 (1H, m), 2.35 (1H, dt, J=15.3, 6.9 Hz), 3.14 (3H, s), 3.45-3.50 (1H, m), 3.73-3.81 (1H, m), 4.09-4.19 (1H, m), 5.01 (1H, d, J=8.6 Hz), 5.05 (2H, s), 6.04 (1H, d, J=8.6 Hz), 7.29-7.38 (5H, m), 7.71-7.78 (2H, m), 7.87-7.91 (1H, m), 8.13-8.18 (1H, m).

MS (m/z): 450 (M+H)$^+$.

Step 5 Benzyl {(1R,3R,4S)-3-methoxy-4-[methyl(2-nitrobenzene-1-sulfonyl)amino]cyclopentyl}carbamate

[Formula 162]

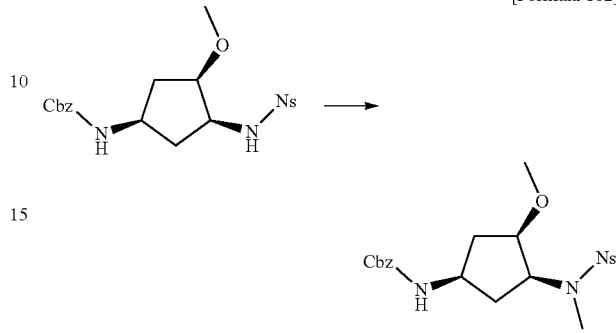

The title compound was obtained in the same manner as in Step 13 of Reference Example A-1, using the compound obtained in the above Step 4.

$^1$H-NMR (CDCl$_3$) δ: 1.66 (1H, dd, J=14.7, 2.5 Hz), 1.76 (1H, td, J=12.1, 6.3 Hz), 1.99-2.10 (1H, m), 2.22-2.34 (1H, m), 3.01 (3H, s), 3.29 (3H, s), 3.74-3.80 (1H, m), 4.02-4.24 (2H, m), 5.03-5.16 (3H, m), 7.29-7.40 (5H, m), 7.60-7.73 (3H, m), 7.96-8.03 (1H, m).

MS (m/z): 464 (M+H)$^+$.

Step 6 Benzyl [(1R,3R,4S)-3-methoxy-4-(methylamino)cyclopentyl]carbamate

[Formula 163]

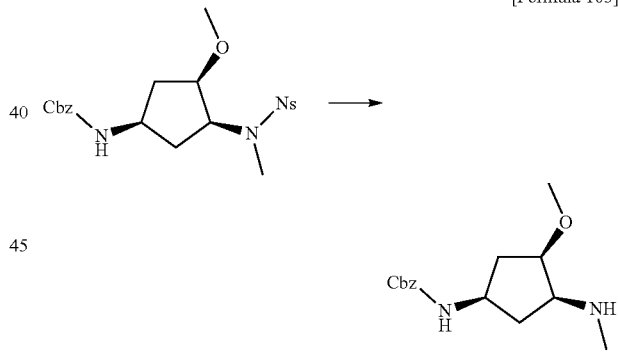

The title compound was obtained as a crude product in the same manner as in Step 14 of Reference Example A-1, using the compound obtained in the above Step 5.

Step 7 Benzyl {(1R,3S,4R)-3-[(tert-butoxycarbonyl)(methyl)amino]-4-methoxycyclopentyl}carbamate

[Formula 164]

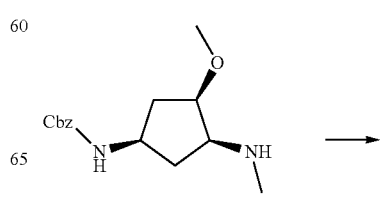

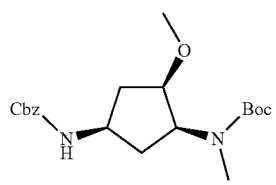

The compound (4.82 g) obtained in the above Step 6 was dissolved in THF (40 mL), and a solution of di-tert-butyl dicarbonate (CAS: 24424-99-5) (3.02 g) in THF (20 mL), and TEA (CAS: 121-44-8) (2.3 mL) were added thereto, and the mixture was stirred at room temperature for 16 hr. The solvent was evaporated under reduced pressure, and the obtained residue was purified by silica gel column chromatography (n-hexane/ethyl acetate) to give the title compound (3.15 g) as an oil.

$^1$H-NMR (CDCl$_3$) δ: 1.47 (9H, s), 1.59-1.66 (1H, m), 1.80 (1H, td, J=12.1, 7.0 Hz), 2.02-2.14 (1H, m), 2.25 (1H, dt, J=14.9, 6.4 Hz), 2.89 (3H, s), 3.27 (3H, s), 3.71-3.80 (1H, m), 4.01-4.32 (2H, m), 5.05-5.18 (3H, m), 7.30-7.38 (5H, m).

Step 8 Tert-butyl [(1S,2R,4R)-4-amino-2-methoxy-cyclopentyl]methylcarbamate

[Formula 165]

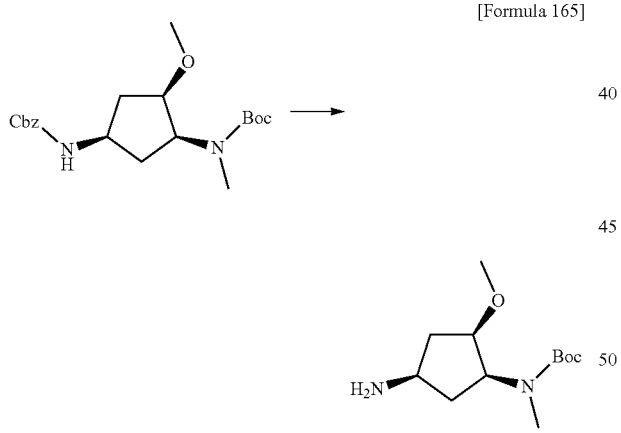

A mixture of the compound (3.15 g) obtained in the above Step 7, 5% palladium on carbon (PH) wet (CAS: 7440-05-3) (3.41 g) and ethanol (100 mL) was stirred under hydrogen atmosphere at room temperature for 3.5 hr. The reaction solution was filtered, and the filtrate was concentrated under reduced pressure. The obtained residue was purified by amino silica gel column chromatography (ethyl acetate/methanol) to give the title compound (1.78 g) as an oil.

$^1$H-NMR (CDCl$_3$) δ: 1.40-1.47 (1H, m), 1.47 (9H, s), 1.68-1.79 (1H, m), 2.07 (1H, dt, J=13.3, 6.1 Hz), 2.12-2.22 (1H, m), 2.92 (3H, s), 3.21-3.31 (1H, m), 3.28 (3H, s), 3.69-3.81 (1H, m), 3.95-4.34 (1H, m).

Reference Example A-17

Tert-butyl [(1S,2S,4R)-4-amino-2-methoxycyclo-pentyl]methylcarbamate

Step 1 Benzyl {(1R,3S,4S)-3-[(tert-butoxycarbonyl)(methyl)amino]-4-hydroxycyclopentyl}carbamate

[Formula 166]

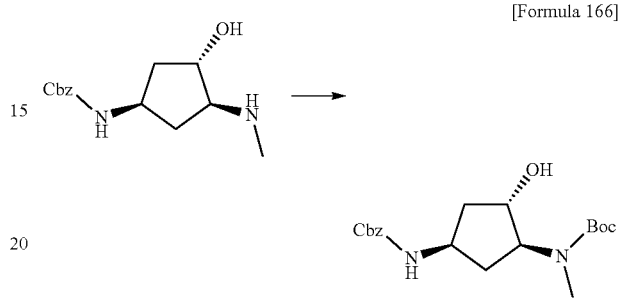

The title compound was obtained in the same manner as in Step 7 of Reference Example A-16, using the compound obtained in Step 9 of Reference Example A-14.

$^1$H-NMR (CDCl$_3$) δ: 1.47 (9H, s), 1.57-1.69 (1H, m), 1.82-1.94 (1H, m), 1.95-2.06 (1H, m), 2.27-2.40 (1H, m), 2.83 (3H, s), 3.89-4.01 (1H, m), 4.09-4.21 (1H, m), 4.22-4.33 (1H, m), 5.09 (3H, br s), 7.29-7.38 (5H, m).

Step 2 Benzyl {(1R,3S,4S)-3-[(tert-butoxycarbonyl)(methyl)amino]-4-methoxycyclopentyl}carbamate

[Formula 167]

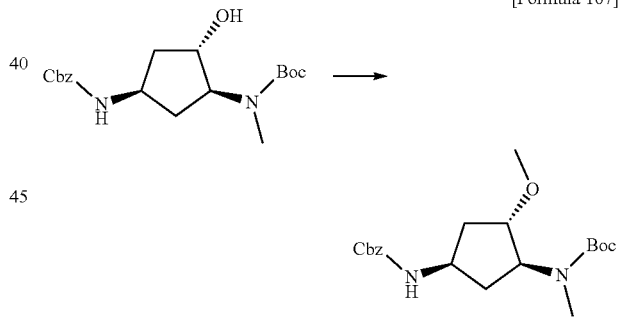

The compound (1.10 g) obtained in the above Step 1 was dissolved in THF (37 mL), and methyl iodide (0.31 mL) and sodium hydride (CAS: 7646-69-7) (purity 55%, 0.205 g) were added thereto, and the mixture was stirred at 0° C. for 1 hr. Then, additional methyl iodide (0.10 mL) and sodium hydride (purity 55%, 0.067 g) were added thereto, and the mixture was stirred at 0° C. for 1 hr. Water was added to the reaction solution, and the mixture was extracted with ethyl acetate. The organic layer was dried over anhydrous sodium sulfate, and concentrated under reduced pressure. The residue was purified by silica gel column chromatography (n-hexane/acetone) to give the title compound (0.827 g) as an oil.

$^1$H-NMR (CDCl$_3$) δ: 1.46 (9H, s), 1.55-1.71 (1H, m), 1.76-2.04 (2H, m), 2.25-2.39 (1H, m), 2.86 (3H, br s), 3.30 (3H, s), 3.71-4.15 (3H, m), 5.10 (2H, s), 7.29-7.38 (5H, m).

Step 3 Tert-butyl [(1S,2S,4R)-4-amino-2-methoxy-cyclopentyl]methylcarbamate

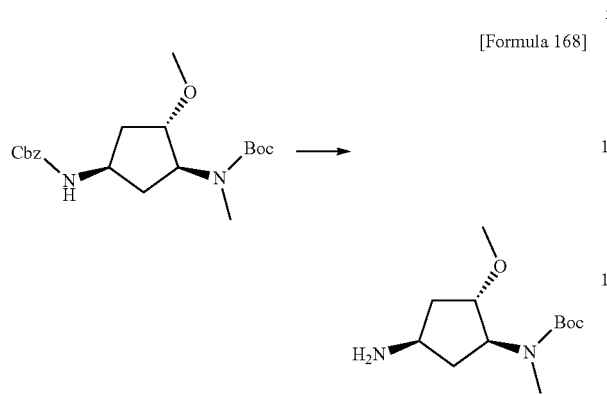

[Formula 168]

The title compound was obtained in the same manner as in Step 8 of Reference Example A-16, using the compound obtained in the above Step 2.

$^1$H-NMR (CDCl$_3$) δ: 1.34-1.45 (1H, m), 1.47 (9H, s), 1.64 (1H, dt, J=15.1, 6.7 Hz), 1.89-1.97 (1H, m), 2.10-2.19 (1H, m), 2.83 (3H, s), 3.30 (3H, s), 3.37-3.47 (1H, m), 3.87 (1H, dt, J=8.8, 4.0 Hz), 4.17-4.31 (1H, m).

Reference Example A-18

Tert-butyl [(1R,5S)-5-amino-3,3-difluorocyclohexyl]carbamate

Step 1 Benzyl Tert-butyl [(1R,3S)-5,5-difluorocyclohexane-1,3-diyl]biscarbamate

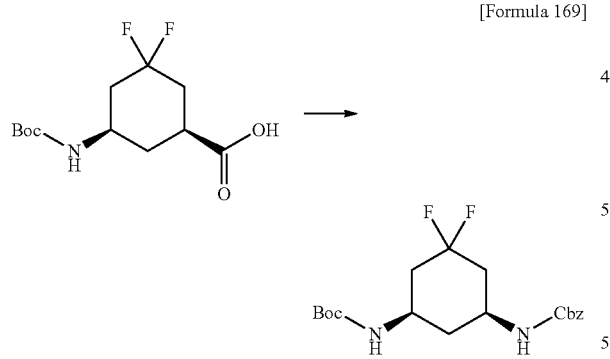

[Formula 169]

The title compound was obtained in the same manner as in Step 10 of Reference Example A-1, using (1S,5R)-5-[(tert-butoxycarbonyl)amino]-3,3-difluorocyclohexane-1-carboxylic acid (CAS: 2227198-19-6).

$^1$H-NMR (DMSO-D$_6$) δ: 1.16-1.28 (1H, m), 1.38 (9H, s), 1.58-1.69 (2H, m), 1.93-1.96 (1H, m), 2.19-2.20 (2H, m), 3.48-3.49 (2H, m), 5.02 (2H, s), 7.10-7.12 (1H, m), 7.20-7.22 (1H, m), 7.32-7.37 (4H, m), 7.48-7.50 (1H, m).

MS (m/z): 285 (M-Boc+H)$^+$.

Step 2 Tert-butyl [(1R,5S)-5-amino-3,3-difluorocyclohexyl]carbamate

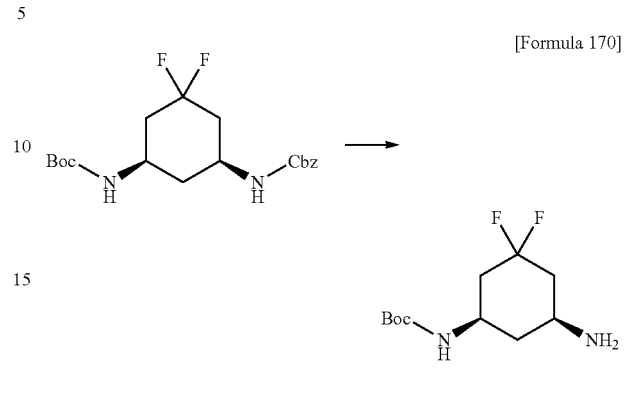

[Formula 170]

To a solution of the compound (596 mg) obtained in the above Step 1 in ethanol (20 mL) was added 10% palladium on carbon catalyst wet (400 mg), and the mixture was stirred under hydrogen atmosphere at room temperature for 4 hr. After nitrogen substitution, the mixture was filtered through Celite, and the filtrate was concentrated under reduced pressure to give the title compound (445 mg) as an oil. The obtained compound was directly used in the next step.

MS (m/z): 251 (M+H)$^+$.

Reference Example A-19

Tert-butyl {(1S,3R)-3-[(2-{[tert-butyl(dimethyl)silyl]oxy}ethyl)amino]cyclopentyl}carbamate

Step 1 Tert-butyl {(1S,3R)-3-[(2-{[tert-butyl(dimethyl)silyl]oxy}ethyl)(2-nitrobenzene-1-sulfonyl)amino]cyclopentyl}carbamate

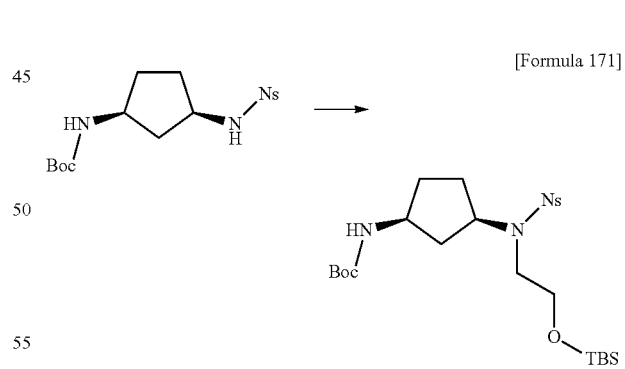

[Formula 171]

The title compound was obtained in the same manner as in Step 13 of Reference Example A-1 except that (2-bromoethoxy)-tert-butyldimethylsilane (CAS: 86864-60-0) was used instead of iodomethane, using the compound obtained in Step 2 of Reference Example A-3.

$^1$H-NMR (DMSO-D$_6$) δ: 0.05 (6H, s), 0.87 (9H, s), 1.35 (9H, s), 1.51-1.80 (6H, m), 3.31-3.33 (2H, m), 3.68-3.70 (3H, m), 4.03-4.06 (1H, m), 6.94 (1H, s), 7.82-8.08 (4H, m).

MS (m/z): 444 (M-Boc+H)$^+$.

Step 2 Tert-butyl {(1S,3R)-3-[(2-{[tert-butyl(dimethyl)silyl]oxy}ethyl)amino]cyclopentyl}carbamate

[Formula 172]

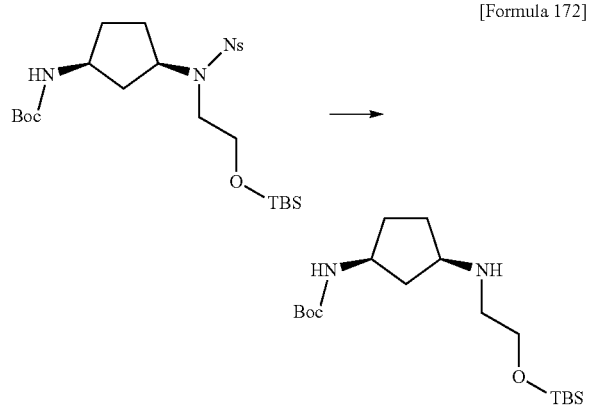

A mixture of the compound (585 mg) obtained in the above Step 1, 4-tert-butylbenzenethiol (0.362 mL), potassium carbonate (595 mg) and DMF (5.4 mL) was stirred at 40° C. 6 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (428 mg) as an oil.

$^1$H-NMR (DMSO-D$_6$) δ: 0.04 (6H, s), 0.87 (9H, s), 1.16-1.23 (1H, m), 1.37 (9H, s), 1.43-1.47 (2H, m), 1.72-1.73 (2H, m), 2.00-2.03 (1H, m), 2.60 (2H, t, J=5.8 Hz), 3.01-3.03 (1H, m), 3.62 (2H, t, J=5.8 Hz), 3.71-3.73 (1H, m), 6.79 (1H, d, J=7.7 Hz).

MS (m/z): 359 (M+H)$^+$.

Reference Example B-1

4-chloro-2-methyl-6-(2,2,2-trifluoroethyl)thieno[2,3-d]pyrimidine

Step 1 2-amino-5-(2,2,2-trifluoroethyl)thiophene-3-carboxamide

[Formula 173]

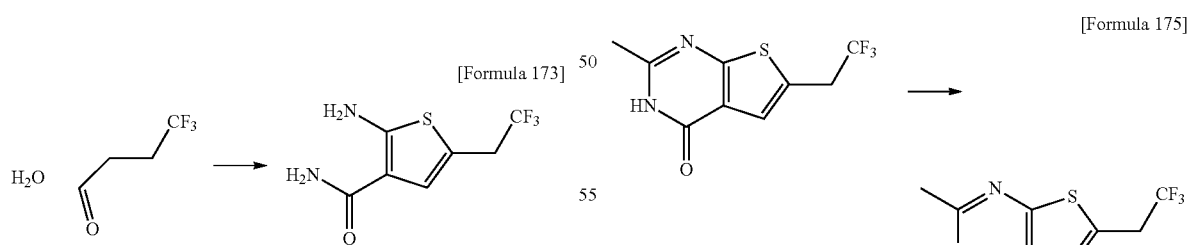

To 4,4,4-trifluorobutanal hydrate (2.00 g), 2-cyanoacetamide (CAS: 107-91-5) (1.75 g) and sulfur (668 mg) was added DMF (14 mL), and TEA (3.46 mL) was added dropwise thereto under ice-cooling. After the completion of dropwise addition, the mixture was allowed to warm to room temperature, stirred for 10 hr, and allowed to stand overnight. Ethyl acetate and saturated brine were added to the reaction solution, and the mixture was subjected to liquid separation. The organic layer was washed with saturated brine, dried over anhydrous sodium sulfate, and concentrated under reduced pressure. The obtained residue was purified by silica gel column chromatography (n-hexane/ethyl acetate) to give the title compound (3.00 g) as a solid.

$^1$H-NMR (DMSO-D$_6$) δ: 3.59 (2H, q, J=11.1 Hz), 6.75 (1H, br s), 7.00 (1H, s), 7.21 (1H, br s), 7.30 (2H, s).

MS (m/z): 225 (M+H)$^+$.

Step 2 2-methyl-6-(2,2,2-trifluoroethyl)thieno[2,3-d]pyrimidin-4(3H)-one

[Formula 174]

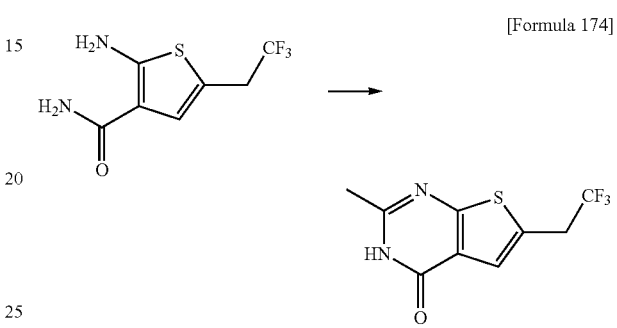

To the compound (2.95 g) obtained in the above Step 1 were added acetic acid (13 mL) and triethyl orthoacetate (CAS: 78-39-7) (10 mL), and the mixture was heated under reflux for 3 hr. Then, the mixture was heated in a microwave reactor (at 150° C. for 5.5 hr). Saturated aqueous sodium hydrogencarbonate solution and ethyl acetate were added to the reaction solution, and the mixture was subjected to liquid separation. The aqueous layer was extracted three times with ethyl acetate, and the organic layer was dried over anhydrous sodium sulfate, and concentrated under reduced pressure. The obtained residue was purified by silica gel column chromatography (n-hexane/ethyl acetate, dichloromethane/methanol) to give the title compound (0.86 g) as a solid.

$^1$H-NMR (CDCl$_3$) δ: 2.59 (3H, s), 3.62 (2H, q, J=10.1 Hz), 7.39 (1H, s), 12.35 (1H, br s).

Step 3 4-chloro-2-methyl-6-(2,2,2-trifluoroethyl)thieno[2,3-d]pyrimidine

[Formula 175]

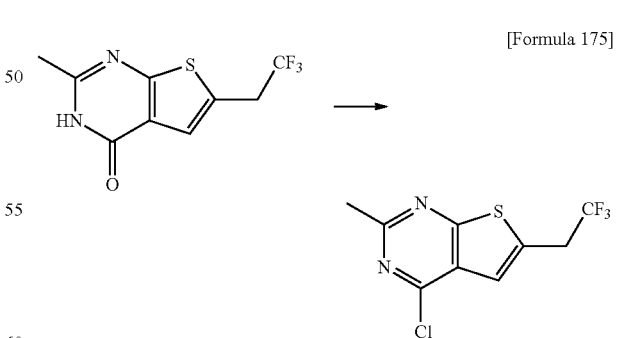

To 2-methyl-6-(2,2,2-trifluoroethyl)thieno[2,3-d]pyrimidin-4(3H)-one (0.86 g) were added phosphorus oxychloride (10.33 g) and DMF (0.03 mL), and the mixture was stirred at 110° C. for 3.5 hr. The reaction solution was added little by little to a mixture of dichloromethane and ice, and the mixture was stirred vigorously for 1 hr, and subjected to liquid separation. The organic layer was washed with water, dried over anhydrous sodium sulfate, and concentrated under reduced pressure. The obtained residue was purified by silica gel column chromatography (n-hexane/ethyl acetate) to give the title compound (0.89 g) as an oil.

$^1$H-NMR (CDCl$_3$) δ: 2.81 (3H, s), 3.71 (2H, q, J=10.0 Hz), 7.32 (1H, s).

Reference Example B-2

4-chloro-6-(cyclopropylmethyl)thieno[2,3-d]pyrimidine

Step 1 6-(cyclopropylmethyl)thieno[2,3-d]pyrimidin-4(3H)-one

[Formula 176]

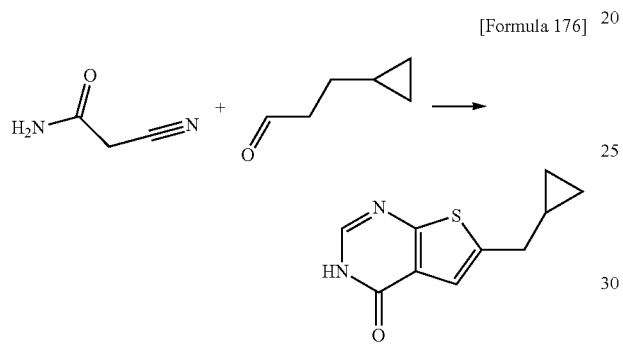

To 3-cyclopropylpropanal (CAS: 5618-02-0) (968 mg), 2-cyanoacetamide (829 mg) and sulfur (316 mg) was added DMF (10 mL), and the mixture was cooled well in an ice-salt bath. TEA (1.64 mL) was added dropwise thereto. After the completion of dropwise addition, and the mixture was allowed to warm to room temperature, and stirred for 10 hr. The solvent was evaporated under reduced pressure. Acetic acid (10 mL) and triethyl orthoformate (6.8 mL) were added to the residue, and the mixture was heated under reflux for 3.5 hr. The solvent was evaporated under reduced pressure, and a mixed solvent of n-hexane/ethyl acetate=1/1 was added to the residue. The solid was collected by filtration, and washed with a mixed solvent of n-hexane/ethyl acetate=1/1 to give the title compound (1.32 g) as a solid.

$^1$H-NMR (DMSO-D$_6$) δ: 0.24-0.29 (2H, m), 0.51-0.57 (2H, m), 0.99-1.08 (1H, m), 2.75 (2H, d, J=6.7 Hz), 7.16 (1H, s), 8.06 (1H, s), 12.43 (1H, br s).

MS (m/z): 207 (M+H)$^+$.

Step 2 4-chloro-6-(cyclopropylmethyl)thieno[2,3-d]pyrimidine

[Formula 177]

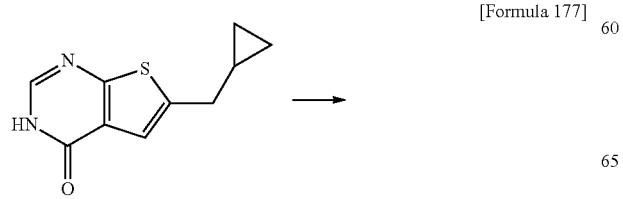

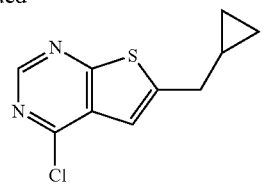

The title compound was obtained in the same manner as in Step 3 of Reference Example B-1, using the compound obtained in the above Step 1.

$^1$H-NMR (CDCl$_3$) δ: 0.32-0.36 (2H, m), 0.67-0.71 (2H, m), 1.08-1.18 (1H, m), 2.86 (2H, d, J=7.3 Hz), 7.18 (1H, s), 8.78 (1H, s).

MS (m/z): 225, 227 (M+H)$^+$.

Reference Example B-3

4-chloro-6-cyclopropylthieno[2,3-d]pyrimidine

[Formula 178]

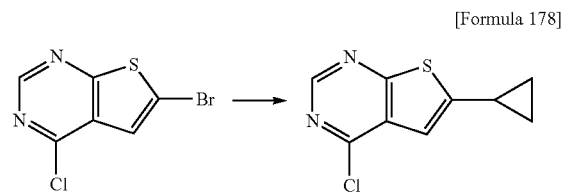 [SMILES: Clc1ncnc2sc(Br)cc12 ; Clc1ncnc2sc(C3CC3)cc12]

A mixture of 6-bromo-4-chlorothieno[2,3-d]pyrimidine (100 mg), cyclopropylboronic acid (79.0 mg), sodium carbonate (144 mg), toluene (1.5 mL), water (0.5 mL) and tetrakis(triphenylphosphine)palladium(0) (56.0 mg) was stirred under nitrogen atmosphere at 110° C. Water was added to the reaction solution, and the mixture was extracted with dichloromethane. The organic layer was washed with saturated brine, dried over anhydrous sodium sulfate, and concentrated under reduced pressure. The residue was purified by silica gel column chromatography (n-hexane/ethyl acetate) to give the title compound (36.8 mg) as a solid.

$^1$H-NMR (CDCl$_3$) δ: 0.92-0.96 (2H, m), 1.20-1.23 (2H, m), 2.19-2.26 (1H, m), 7.05 (1H, s), 8.75 (1H, s).

MS (m/z): 211, 213 (M+H)+.

Reference Example B-4

2,4-dichloro-6-(2,2,2-trifluoroethyl)thieno[2,3-d]pyrimidine

Step 1 6-(2,2,2-trifluoroethyl)thieno[2,3-d]pyrimidine-2,4(1H,3H)-dione

[Formula 179]

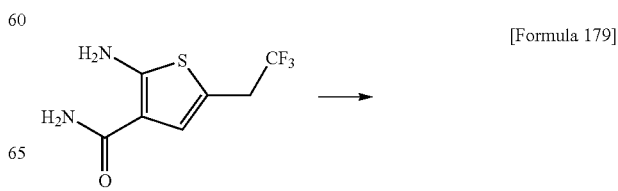

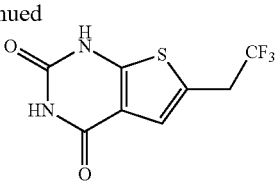

The compound (6.20 g) obtained in Step 1 of Reference Example B-1 was dissolved in 1,4-dioxane (100 mL), and triphosgene (3.55 g) was added thereto, and the mixture was heated under reflux for 6 hr. The reaction solution was allowed to cool to room temperature, and concentrated under reduced pressure. The residue was subjected to slurry washing with dichloromethane to give the title compound (2.41 g) as a solid.

$^1$H-NMR (DMSO-D$_6$) δ: 3.93 (2H, q, J=11.0 Hz), 7.14 (1H, s), 11.19 (1H, s), 11.92 (1H, s).

Step 2 2,4-dichloro-6-(2,2,2-trifluoroethyl)thieno[2,3-d]pyrimidine

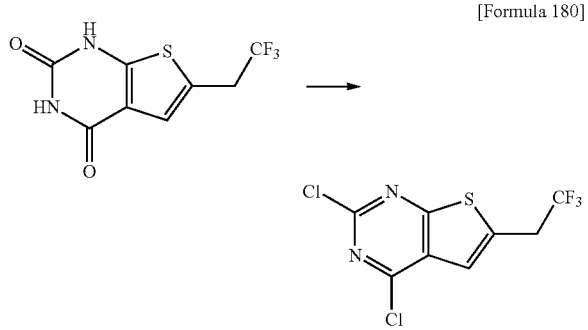

[Formula 180]

The compound (2.41 g) obtained in the above Step 1 was suspended in phosphorus oxychloride (11.5 mL), and DMF (0.030 mL) was added thereto, and the mixture was stirred with heating at 110° C. for 4 hr. The reaction solution was allowed to cool to room temperature, washed with dichloromethane, and poured into ice water, and the mixture was stirred vigorously at room temperature for 1 hr. The organic layer was dried over anhydrous sodium sulfate, and the solvent was evaporated under reduced pressure. The residue was purified by silica gel chromatography (dichloromethane/n-hexane) to give the title compound (1.42 g) as a solid.

$^1$H-NMR (CDCl$_3$) δ: 3.74 (2H, q, J=10.0 Hz), 7.37 (1H, s).

Reference Example B-5

4-chloro-2-methoxy-6-(2,2,2-trifluoroethyl)thieno[2,3-d]pyrimidine

Step 1 2-(methylsulfanyl)-6-(2,2,2-trifluoroethyl)thieno[2,3-d]pyrimidin-4(3H)-one

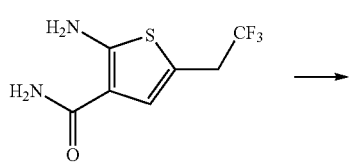

[Formula 181]

A mixture of the compound (40.0 g) obtained in Step 1 of Reference Example B-1, ethanol (500 mL) and potassium ethylxanthate (85.8 g) was heated under reflux under nitrogen atmosphere for 19 hr. The reaction solution was concentrated under reduced pressure, and the residue was subjected to slurry washing with dichloromethane (200 mL), and the solid (101 g) was collected by filtration. To a mixture of the obtained solid (101 g) and DMF (2.09 L) was added methyl iodide (13.0 mL) under ice-cooling, and the mixture was stirred at room temperature for 1 hr. Methyl iodide (8.5 mL) was added thereto, and the mixture was stirred for additional 30 min. Water was added to the reaction solution, and the precipitated solid was collected by filtration to give the title compound (14.5 g) as a solid. Ethyl acetate was added to the filtrate, and the mixture was subjected to extraction. The organic layer was washed with saturated brine, dried over anhydrous sodium sulfate, and concentrated under reduced pressure. Water was added thereto, and the precipitated solid was collected by filtration to give the title compound (3.85 g) as a solid. The filtrate was acidified with hydrochloric acid, and extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (17.1 g) as a solid.

$^1$H-NMR (CDCl$_3$) δ: 2.65 (3H, s), 3.59 (2H, q, J=10.0 Hz), 7.36 (1H, s), 11.35 (1H, s).

MS (m/z): 281 (M+H)$^+$.

Step 2 2-(methanesulfonyl)-6-(2,2,2-trifluoroethyl)thieno[2,3-d]pyrimidin-4(3H)-one

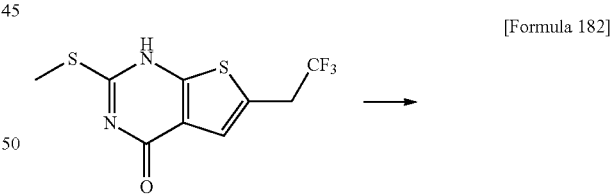

[Formula 182]

To a mixture of the compound (42.2 g) obtained in the above Step 1 and THF (600 mL) was added a mixture of Oxone (CAS: 10058-23-8) (278 g) and water (600 mL) under ice-cooling, and the mixture was stirred at room temperature for 4 hr. Water was added to the reaction solution, and the precipitated solid was collected by filtration to give the title compound (43.7 g) as a solid.

¹H-NMR (DMSO-D₆) δ: 3.44 (3H, s), 4.20 (2H, q, J=11.0 Hz), 7.56 (1H, s).

MS (m/z): 313 (M+H)⁺.

Step 3 2-methoxy-6-(2,2,2-trifluoroethyl)thieno[2,3-d]pyrimidin-4(1H)-one

[Formula 183]

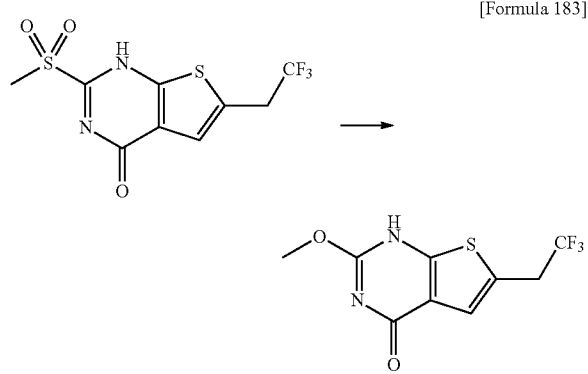

To the compound (14.3 g) obtained in the above Step 2 were added methanol (450 mL) and potassium carbonate (12.7 g), and the mixture was heated under reflux for 2 hr. Additional potassium carbonate (6.33 g) was added thereto, and the mixture was heated under reflux for 1 hr. The reaction solution was concentrated to about one-half to one-third volume, and acidified with 2N hydrochloric acid. Ethyl acetate was added thereto, and the mixture was subjected to liquid separation, and the aqueous layer was extracted with ethyl acetate. The organic layers were combined, washed with saturated brine, dried over anhydrous sodium sulfate, and concentrated under reduced pressure. Diethyl ether was added to the obtained residue, and the solid was collected by filtration to give the title compound (7.85 g) as a solid.

¹H-NMR (CDCl₃) δ: 3.57 (2H, q, J=10.3 Hz), 4.06 (3H, s), 7.33 (1H, s), 11.08 (1H, br s).

Step 4 4-chloro-2-methoxy-6-(2,2,2-trifluoroethyl)thieno[2,3-d]pyrimidine

[Formula 184]

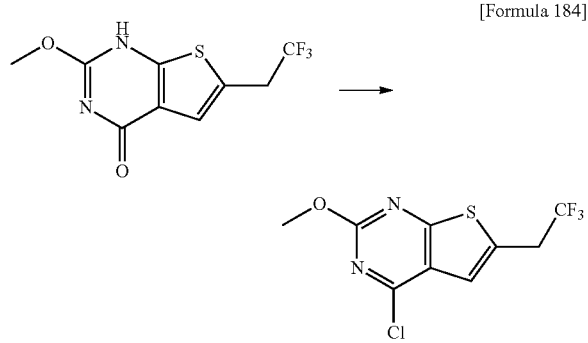

To a suspension of the compound (8.39 g) obtained in the above Step 3 in phosphorus oxychloride (36.9 mL) was added DMF (8 drops), and the mixture was stirred at room temperature for 2.5 hr, and then at 60° C. for 15 min. The reaction solution was allowed to cool, and added little by little to a mixture of sodium hydrogencarbonate and ice water, and the used container was washed with dichloromethane. The mixture was stirred for 10 min, dichloromethane was added thereto, and the mixture was subjected to liquid separation. The aqueous layer was adjusted to pH=ca. 9 with saturated aqueous sodium bicarbonate solution, and extracted with dichloromethane. The combined organic layers were washed with saturated aqueous sodium bicarbonate solution, dried over sodium sulfate, and concentrated under reduced pressure. The obtained residue was purified by silica gel column chromatography (ethyl acetate/n-hexane) to give the title compound (7.85 g) as a solid.

¹H-NMR (CDCl₃) δ: 3.66 (2H, q, J=10.1 Hz), 4.09 (3H, s), 7.24 (1H, s).

MS (m/z): 283, 285 (M+H)⁺.

Reference Example B-6

4-chloro-6-(2,2,2-trifluoroethyl)thieno[3,2-d]pyrimidine

Step 1 4-chloro-6-{2,2,2-trifluoro-1-[(trimethylsilyl)oxy]ethyl}thieno[3,2-d]pyrimidine

[Formula 185]

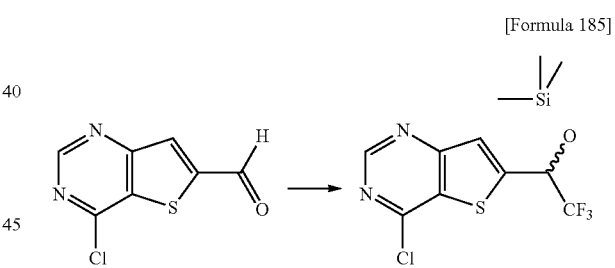

4-Chlorothieno[3,2-d]pyrimidine-6-carbaldehyde (CAS: 875340-14-0) (500 mg) was dissolved in THF (6 mL), and (trifluoromethyl)trimethylsilane (CAS: 81290-20-2) (0.558 mL) was added thereto, and then tetrabutylammonium fluoride (1.0 mol/L, THF solution) (0.126 mL) was added thereto under ice-cooling. The mixture was allowed to cool to room temperature, and stirred for 1 hr. Ethyl acetate and saturated brine were added to the reaction solution, and the mixture was subjected to liquid separation. The organic layer was washed with saturated brine, dried over anhydrous sodium sulfate, and concentrated under reduced pressure. The obtained residue was purified by silica gel column chromatography (n-hexane/ethyl acetate) to give the title compound (294 mg) as an oil.

¹H-NMR (CDCl₃) δ: 0.25 (9H, s), 5.37 (1H, q, J=6.0 Hz), 7.60 (1H, s), 9.00 (1H, s).

MS (m/z): 341, 343 (M+H)⁺.

Step 2 1-(4-chlorothieno[3,2-d]pyrimidin-6-yl)-2,2,2-trifluoroethan-1-ol

[Formula 186]

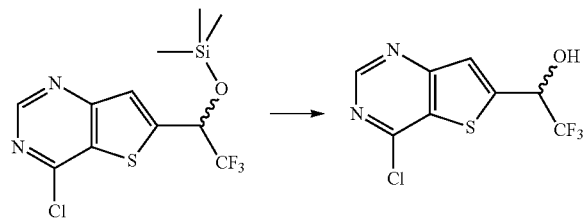

The compound (260 mg) obtained in the above Step 1 was dissolved in THF (15 mL), 1N hydrochloric acid (1.1 mL) was added thereto, and the mixture was stirred at room temperature for 15 min. Ethyl acetate and saturated aqueous sodium hydrogencarbonate solution were added to the reaction solution, and the mixture was subjected to liquid separation. The organic layer was washed with saturated brine, dried over anhydrous sodium sulfate, and concentrated under reduced pressure to give the title compound (206 mg) as a solid.

$^1$H-NMR (CDCl$_3$) δ: 3.43 (1H, s), 5.50-5.55 (1H, m), 7.68 (1H, s), 9.01 (1H, s).
MS (m/z): 269, 271 (M+H)$^+$.

Step 3 O-[1-(4-chlorothieno[3,2-d]pyrimidin-6-yl)-2,2,2-trifluoroethyl] O-phenyl carbonothioate

[Formula 187]

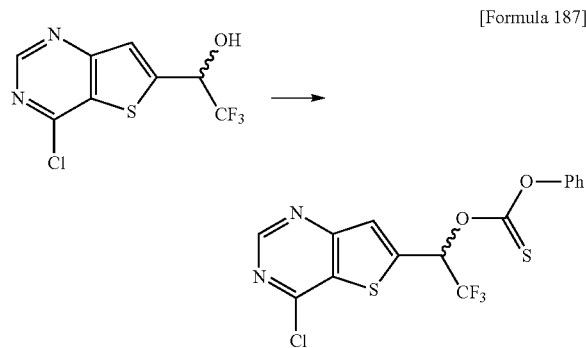

To a dichloromethane solution (1 mL) of phenyl chlorothionocarbonate (CAS: 1005-56-7) (77 mg) were added the compound (100 mg) obtained in the above Step 2 and TEA (0.067 mL), and the mixture was stirred at room temperature for 2 hr. Water and dichloromethane were added to the reaction solution, and the mixture was subjected to liquid separation. The organic layer was dried over anhydrous sodium sulfate, and concentrated under reduced pressure. The obtained residue was purified by silica gel column chromatography (n-hexane/ethyl acetate) to give the title compound (125 mg) as a solid.

$^1$H-NMR (CDCl$_3$) δ: 7.07-7.15 (3H, m), 7.33 (1H, t, J=7.6 Hz), 7.44 (2H, t, J=7.6 Hz), 7.84 (1H, s), 9.05 (1H, s).
MS (m/z): 405, 407 (M+H)$^+$.

Step 4 4-chloro-6-(2,2,2-trifluoroethyl)thieno[3,2-d]pyrimidine

[Formula 188]

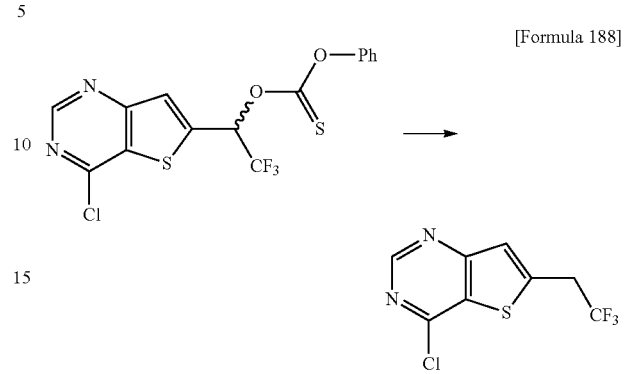

The compound (2.42 g) obtained in the above Step 3 was dissolved in toluene (120 mL), tributyltin hydride (CAS: 688-73-3) (3.45 mL) and 2,2'-azobis(isobutyronitrile) (CAS: 78-67-1) (393 mg) were added thereto, and the mixture was stirred at 80° C. for 2 hr. The solvent was evaporated under reduced pressure, and the residue was purified by silica gel column chromatography (n-hexane/ethyl acetate) to give the title compound (1.22 g) as a solid.

$^1$H-NMR (CDCl$_3$) δ: 3.81 (2H, q, J=10.1 Hz), 7.55 (1H, s), 9.00 (1H, s).
MS (m/z): 253, 255 (M+H)$^+$.

Reference Example B-7

6-(2,2,2-trifluoroethyl)quinazolin-4(3H)-one

Step 1 (4-methoxyquinazolin-6-yl)methanol

[Formula 189]

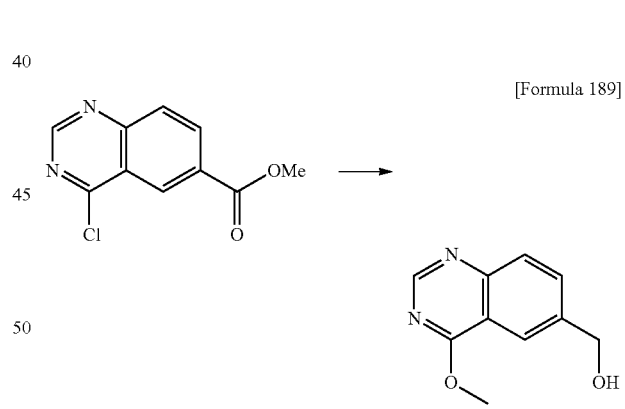

A mixture of methyl 4-chloroquinazoline-6-carboxylate (CAS: 152536-17-9) (3.00 g) and THF (30 mL) was cooled to −50° C., diisobutylaluminium hydride (CAS: 1191-15-7) (1.0 mol/L, toluene solution, 29.0 mL) was added slowly thereto, and the mixture was warmed to 0° C. over 1.5 hr. Then, the mixture was allowed to warm to room temperature, and stirred for 20 hr. Then, the reaction solution was cooled to 0° C., diisobutylaluminium hydride (1.0 mol/L, toluene solution, 15.0 mL) was added slowly thereto, and the mixture was stirred at the same temperature for 15 min, and then at room temperature for 2 hr. The reaction solution was cooled again to 0° C., aqueous potassium sodium tartrate solution (2 mol/L, 75 mL) was added thereto. The mixture was allowed to warm to room temperature, and stirred overnight. The reaction mixture was extracted with ethyl acetate and dichloromethane, and the organic layer was dried over anhydrous sodium sulfate, and concentrated under reduced pressure. The residue was subjected to silica gel column chromatography (n-hexane/ethyl acetate). The obtained residue was dissolved in methanol, and the solution was concentrated under reduced pressure to give the title compound (1.46 g, containing impurities (purity ca. 60%)) as a solid. This compound was used in the next reaction without further purification.

$^1$H-NMR (DMSO-D$_6$) δ: 4.20 (3H, s), 4.72 (2H, s), 7.96 (2H, s), 8.14 (1H, s), 8.96 (1H, s).

MS (m/z): 191 (M+H)$^+$.

Step 2 4-methoxyquinazoline-6-carbaldehyde

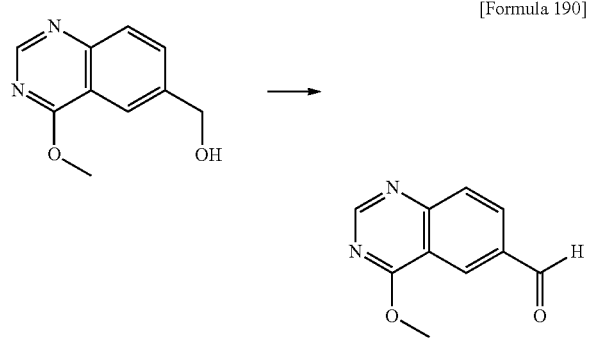

[Formula 190]

A mixture of the compound (1.45 g, containing impurities (purity ca. 60%)) obtained in the above Step 1, dichloromethane (60 mL) and Dess-Martin periodinane (CAS: 87413-09-0) (3.51 g) was stirred at room temperature for 3 hr. Saturated aqueous sodium bicarbonate solution was added to the reaction solution, and the mixture was extracted with dichloromethane. The organic layer was washed with saturated brine, dried over anhydrous sodium sulfate, and concentrated under reduced pressure, and the residue was subjected to silica gel column chromatography (n-hexane/ethyl acetate). The obtained solid was dissolved in ethyl acetate, and the solution was washed with saturated aqueous sodium bicarbonate solution, water and saturated brine, dried over anhydrous sodium sulfate, and concentrated under reduced pressure to give the title compound (0.893 g, containing impurities (purity ca. 60%)) as a solid. This compound was used in the next reaction without further purification.

$^1$H-NMR (CDCl$_3$) δ: 4.25 (3H, s), 8.05 (1H, d, J=8.5 Hz), 8.33 (1H, dd, J=8.5, 1.8 Hz), 8.70 (1H, d, J=1.8 Hz), 8.93 (1H, s), 10.18 (1H, s).

MS (m/z): 189 (M+H)$^+$.

Step 3 4-methoxy-6-{2,2,2-trifluoro-1-[(trimethylsilyl)oxy]ethyl}quinazoline

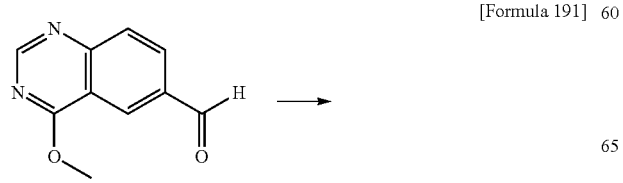

[Formula 191]

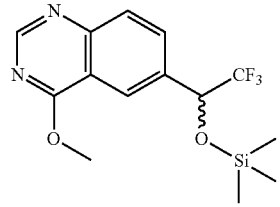

To a mixture of the compound (0.890 g, containing impurities (purity ca. 60%)) obtained in the above Step 2 and THF (23 mL) were added (trifluoromethyl)trimethylsilane (1.1 mL) and cesium fluoride (CAS: 13400-13-0) (0.0336 g) under ice-cooling. The mixture was stirred at the same temperature for 10 min, and then at room temperature for 5 hr. Then, additional cesium fluoride (0.240 g) was added thereto, and the mixture was stirred at room temperature for 3.5 hr. Then, additional cesium fluoride (0.240 g) was added thereto, and the mixture was stirred at room temperature for 14 hr. Then, additional (trifluoromethyl)trimethylsilane (0.37 mL) and cesium fluoride (0.250 g) were added thereto, and the mixture was stirred at room temperature for 5 hr. Saturated brine was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (0.633 g) as a solid.

$^1$H-NMR (CDCl$_3$) δ: 0.15 (9H, s), 4.21 (3H, s), 5.09 (1H, q, J=6.5 Hz), 7.93-7.99 (2H, m), 8.23 (1H, s), 8.84 (1H, s).

Step 4 2,2,2-trifluoro-1-(4-methoxyquinazolin-6-yl)ethan-1-ol

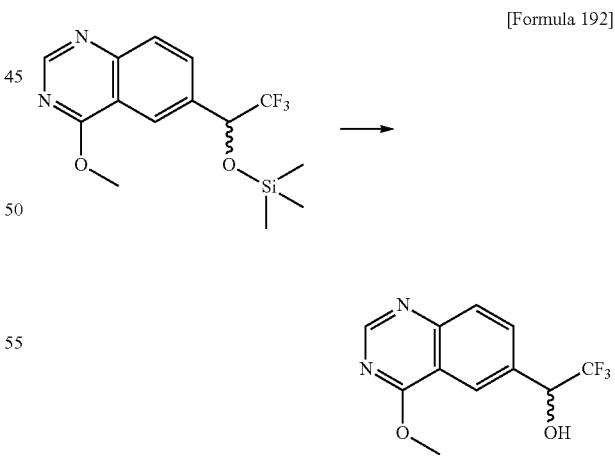

[Formula 192]

The title compound was obtained in the same manner as in Step 2 of Reference Example B-6, using the compound obtained in the above Step 3.

$^1$H-NMR (DMSO-D$_6$) δ: 4.16 (3H, s), 5.46-5.56 (1H, m), 7.16 (1H, d, J=6.1 Hz), 7.97 (1H, d, J=8.5 Hz), 8.05 (1H, dd, J=8.5, 1.2 Hz), 8.32 (1H, d, J=1.2 Hz), 8.85 (1H, s).

Step 5 O-phenyl O-[2,2,2-trifluoro-1-(4-methoxyquinazolin-6-yl)ethyl] carbonothioate

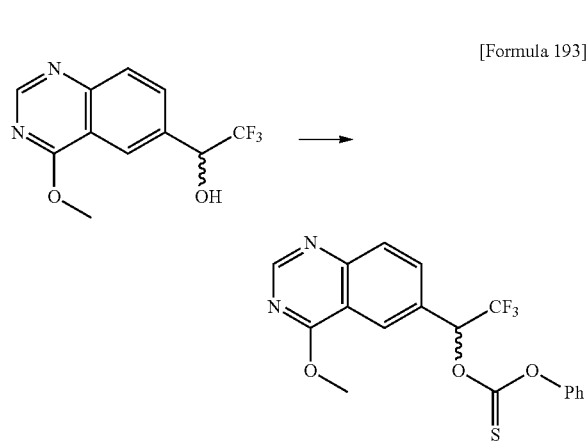

[Formula 193]

The title compound was obtained in the same manner as in Step 3 of Reference Example B-6, using the compound obtained in the above Step 4.

$^1$H-NMR (CDCl$_3$) δ: 4.23 (3H, s), 6.77 (1H, q, J=6.7 Hz), 7.09-7.13 (2H, m), 7.29-7.34 (1H, m), 7.39-7.46 (2H, m), 7.98 (1H, dd, J=8.5, 1.8 Hz), 8.04 (1H, d, J=8.5 Hz), 8.37 (1H, d, J=1.8 Hz), 8.87 (1H, s).

MS (m/z): 395 (M+H)$^+$.

Step 6
4-methoxy-6-(2,2,2-trifluoroethyl)quinazoline

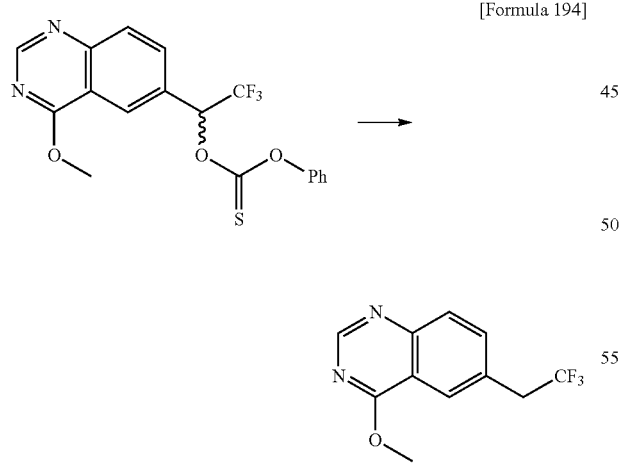

[Formula 194]

The title compound was obtained in the same manner as in Step 4 of Reference Example B-6, using the compound obtained in the above Step 5.

$^1$H-NMR (CDCl$_3$) δ: 3.56 (2H, q, J=10.7 Hz), 4.20 (3H, s), 7.77 (1H, dd, J=8.5, 1.8 Hz), 7.95 (1H, d, J=8.5 Hz), 8.12 (1H, d, J=1.8 Hz), 8.83 (1H, s).

Step 7 6-(2,2,2-trifluoroethyl)quinazolin-4(3H)-one

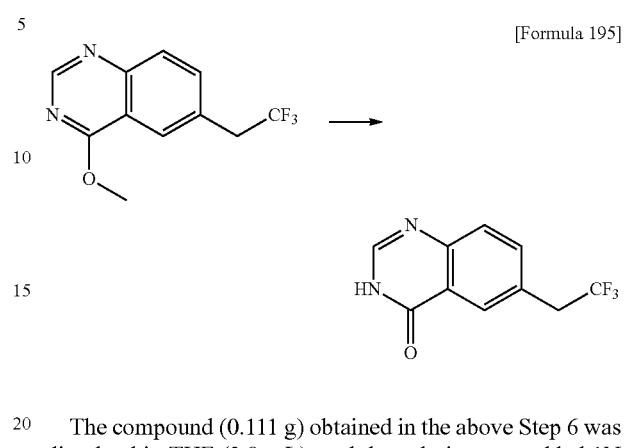

[Formula 195]

The compound (0.111 g) obtained in the above Step 6 was dissolved in THF (2.8 mL), and the solution was added 1N hydrochloric acid (1.4 mL) under ice-cooling. The reaction solution was warmed to room temperature over 5.5 hr, and saturated aqueous sodium bicarbonate solution was added thereto. The reaction mixture was extracted with dichloromethane. The obtained aqueous layer was acidified with 1N hydrochloric acid, and extracted with dichloromethane. All of the organic layers were combined, dried over anhydrous sodium sulfate, and concentrated under reduced pressure to give the title compound (0.101 g) as a solid.

$^1$H-NMR (DMSO-D$_6$) δ: 3.86 (2H, q, J=11.5 Hz), 7.69 (1H, d, J=8.5 Hz), 7.79 (1H, dd, J=8.5, 1.8 Hz), 8.12 (1H, s), 8.14 (1H, d, J=1.8 Hz), 12.32 (1H, s).

MS: m/z 229 (M+H)$^+$.

Reference Example B-8

6-(methoxymethyl)thieno[2,3-d]pyrimidin-4(3H)-one

[Formula 196]

The title compound was obtained in the same manner as in Step 1 of Reference Example B-2 except that 3-methoxypropanal (1.00 g) (CAS2806-84-0) was used instead of 3-cyclopropylpropanal.

$^1$H-NMR (DMSO-D$_6$) δ: 3.30 (3H, s), 4.63 (2H, s), 7.33 (1H, s), 8.12 (1H, s), 11.42 (1H, br s).

MS (m/z): 197 (M+H)$^+$.

Reference Example B-9

6-(oxetan-3-yl)thieno[2,3-d]pyrimidin-4(3H)-one

[Formula 197]

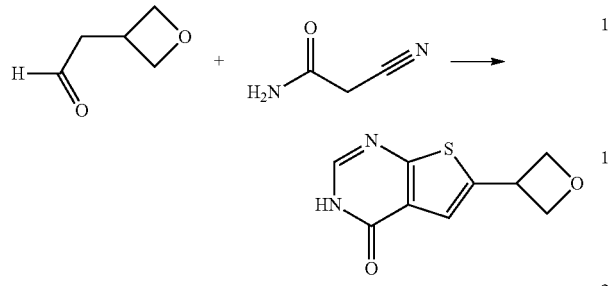

The title compound was obtained in the same manner as in Step 1 of Reference Example B-2 except that (oxetan-3-yl)acetaldehyde synthesized according to the method described in a literature (WO 2014/049133 A1) was used instead of 3-cyclopropylpropanal.

$^1$H-NMR (DMSO-D$_6$) δ: 4.56-4.58 (1H, m), 4.63-4.65 (2H, m), 4.94-4.96 (2H, m), 7.33 (1H, s), 8.11 (1H, s), 12.54 (1H, br s).

MS (m/z): 209 (M+H)$^+$.

Reference Example B-10

6-[(4-chloropyrimidin-5-yl)oxy]-2,3-difluoro-N,N-di(propan-2-yl)benzamide

Step 1 2,3-difluoro-6-methoxy-N,N-di(propan-2-yl)benzamide

[Formula 198]

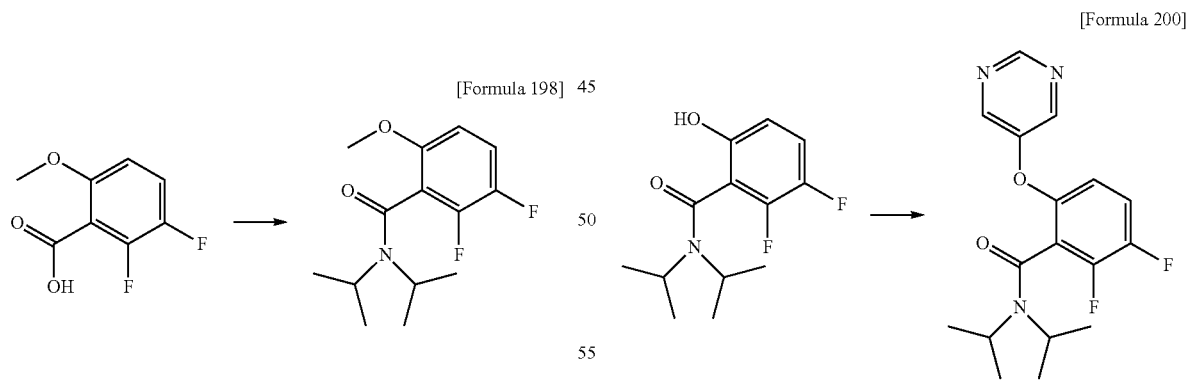

To a mixture of 2,3-difluoro-6-methoxybenzoic acid (CAS: 773873-26-0) (2.0 g), diisopropylamine (3.00 mL) and dichloromethane (28 mL) was added HATU (4.85 g) under ice-cooling, and the mixture was stirred at room temperature for 5 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (2.41 g) as a solid.

$^1$H-NMR (CDCl$_3$) δ: 1.14 (6H, d, J=6.7 Hz), 1.55 (6H, d, J=6.7 Hz), 3.49-3.56 (1H, m), 3.65-3.72 (1H, m), 3.80 (3H, s), 6.57-6.59 (1H, m), 7.05-7.07 (1H, m).

MS (m/z): 272 (M+H)$^+$.

Step 2 2,3-difluoro-6-hydroxy-N,N-di(propan-2-yl)benzamide

[Formula 199]

A mixture of the compound (2.41 g) obtained in the above Step 1 and dichloromethane (17.8 mL) was cooled to −78° C., and boron tribromide (ca. 1 mol/L, dichloromethane solution) (17.8 mL) was added dropwise thereto over 30 min. After the completion of dropwise addition, the mixture was stirred at 0° C. for 30 min. After cooled to −78° C., methanol (5 mL) was added dropwise thereto. After allowed to warm, water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (2.41 g) as a solid.

$^1$H-NMR (CDCl$_3$) δ: 1.37-1.40 (12H, m), 1.62-1.65 (2H, m), 6.61-6.63 (1H, m), 6.97-6.99 (1H, m), 8.01 (1H, s).

MS (m/z): 258 (M+H)$^+$.

Step 3 2,3-difluoro-N,N-di(propan-2-yl)-6-[(pyrimidin-5-yl)oxy]benzamide

[Formula 200]

A mixture of the compound (2.41 g) obtained in the above Step 2, 5-bromopyrimidine (CAS: 4595-59-9) (4.24 g), DMF (44.5 mL) and cesium carbonate (8.70 g) was stirred at 120° C. for 12 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (812 mg) as a solid.

$^1$H-NMR (CDCl$_3$) δ: 1.17 (3H, d, J=6.4 Hz), 1.22 (3H, d, J=6.4 Hz), 1.38 (3H, d, J=6.7 Hz), 1.52 (3H, d, J=6.7 Hz), 3.48-3.55 (1H, m), 3.74-3.81 (1H, m), 6.75-6.78 (1H, m), 7.17-7.19 (1H, m), 8.48 (2H, s), 8.98 (1H, s).

MS (m/z): 336 (M+H)$^+$.

Step 4 2,3-difluoro-6-[(1-oxo-1λ$^5$-pyrimidin-5-yl)oxy]-N,N-di(propan-2-yl)benzamide

[Formula 201]

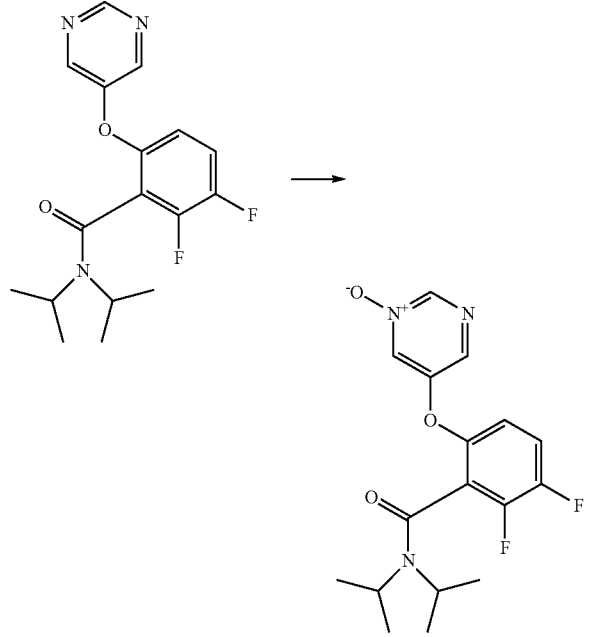

The compound (810 mg) obtained in the above Step 3 was dissolved in dichloromethane (24.2 mL), 3-chloroperbenzoic acid (containing 30% water) (1.79 g) was added thereto under ice-cooling, and the mixture was stirred at 0° C. for 1 hr, and then at room temperature for 20 hr. The reaction solution was ice-cooled, and saturated aqueous sodium thiosulfate solution was added thereto. The organic layer was washed twice with saturated aqueous sodium hydrogencarbonate solution, dried over anhydrous sodium sulfate, and concentrated under reduced pressure to give the title compound as an oil (849 mg). The obtained compound was directly used in the next reaction.

MS (m/z): 352 (M+H)$^+$.

Step 5 6-[(4-chloropyrimidin-5-yl)oxy]-2,3-difluoro-N,N-di(propan-2-yl)benzamide

[Formula 201]

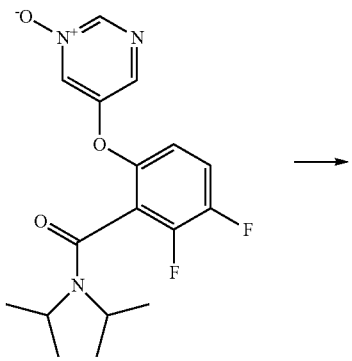

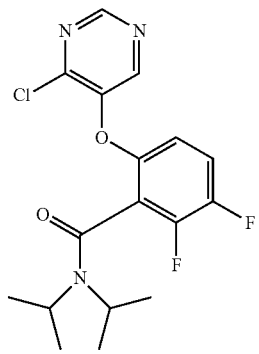

To a mixture of TEA (0.502 mL) and chloroform (1.3 mL) was added phosphorus oxychloride (0.92 g) under ice-cooling. A solution of the compound (849 mg) obtained in the above Step 4 in chloroform (12 mL) was added dropwise thereto. The mixture was heated to 65° C., and stirred for 4.5 hr. After allowed to cool, the reaction solution was added little by little to ice-cooled saturated aqueous sodium hydrogencarbonate solution, and the mixture was stirred vigorously for 30 min. The mixture was adjusted to pH 7 to 8 with saturated sodium hydrogencarbonate, and subjected to liquid separation. The aqueous layer was extracted with dichloromethane, and the organic layers were combined, dried over anhydrous sodium sulfate, and concentrated under reduced pressure. The obtained residue was purified by silica gel column chromatography (n-hexane/ethyl acetate) to give the title compound (236 mg) as a solid.

$^1$H-NMR (CDCl$_3$) δ: 1.22 (3H, d, J=6.4 Hz), 1.25 (3H, d, J=6.4 Hz), 1.39 (3H, d, J=7.0 Hz), 1.52 (3H, d, J=7.0 Hz), 3.50-3.57 (1H, m), 3.78-3.80 (1H, m), 6.74-6.77 (1H, m), 7.18-7.21 (1H, m), 8.29 (1H, s), 8.75 (1H, s).

MS (m/z): 370, 372 (M+H)$^+$.

Reference Example C-1

(1R,3S)—N$^1$-[6-(2,2,2-trifluoroethyl)thieno[2,3-d]pyrimidin-4-yl]cyclohexane-1,3-diamine Step 1 Benzyl [(1S,3R)-3-{[6-(2,2,2-trifluoroethyl)thieno[2,3-d]pyrimidin-4-yl]amino}cyclohexyl]carbamate

[Formula 203]

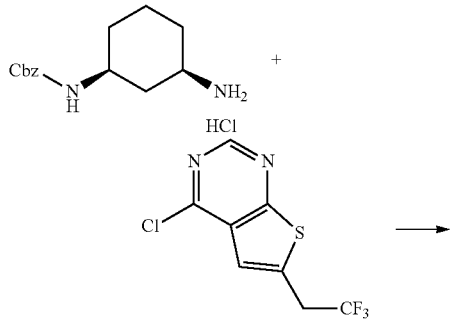

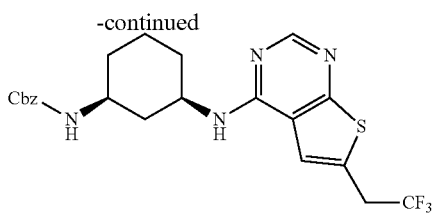

The compound (11.6 g) obtained in Step 2 of Reference Example A-8 was dissolved in 2-propanol (407 mL), and 4-chloro-6-(2,2,2-trifluoroethyl)thieno[2,3-d]pyrimidine (CAS: 1628317-85-0) (10.3 g) synthesized according to the method described in a literature (cancer cell 2015, 27, 589-602.) and DIPEA (21.6 mL) were added thereto, and the reaction solution was heated under reflux for 3 days. The reaction solution was allowed to cool to room temperature, and concentrated under reduced pressure. The residue was purified by silica gel chromatography (dichloromethane/ethyl acetate) to give the title compound (13.2 g) as a solid.

$^1$H-NMR (CDCl$_3$) δ: 1.05-1.22 (3H, m), 1.51-1.57 (1H, m), 1.88 (1H, d, J=13.0 Hz), 2.08 (1H, d, J=13.0 Hz), 2.16 (1H, d, J=11.0 Hz), 2.52 (1H, d, J=11.0 Hz), 3.63 (2H, q, J=10.3 Hz), 3.67-3.76 (1H, m), 4.22-4.34 (1H, m), 4.59-4.70 (1H, m), 4.91 (1H, d, J=8.0 Hz), 5.10 (2H, s), 7.02 (1H, s), 7.38-7.26 (5H, m), 8.47 (1H, s).

MS (m/z): 465 (M+H)$^+$.

Step 2 (1R,3S)—N$^1$-[6-(2,2,2-trifluoroethyl)thieno[2,3-d]pyrimidin-4-yl]cyclohexane-1,3-diamine

[Formula 204]

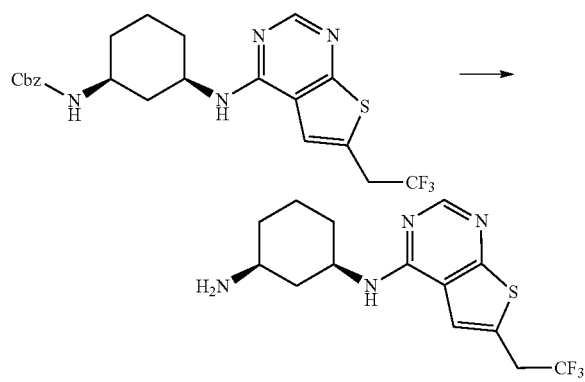

The compound (12.9 g) obtained in the above Step 1 was dissolved in dichloromethane (92.6 mL). Iodotrimethylsilane (5.33 mL) was added dropwise thereto under ice-cooling. The reaction solution was warmed to room temperature, and stirred for 2 hr. Methanol (0.500 mL) was added to the reaction solution, and the mixture was concentrated under reduced pressure. The residue was purified by amino silica gel chromatography (dichloromethane/methanol) to give the title compound (4.00 g) as an oil.

$^1$H-NMR (CDCl$_3$) δ: 1.22-1.50 (4H, m), 1.78-1.96 (3H, m), 2.13 (1H, d, J=13.5 Hz), 3.11-3.21 (1H, m), 3.64 (2H, q, J=10.3 Hz), 4.31-4.42 (1H, m), 6.44 (1H, br s), 7.03 (1H, s), 8.46 (1H, s).

MS (m/z): 331 (M+H)$^+$.

Reference Example C-2

(1R,3S)—N$^1$-[6-(2,2,2-trifluoroethyl)thieno[2,3-d]pyrimidin-4-yl]cyclohexane-1,3-diamine Hydrochloride Step 1 Tert-butyl [(1S,3R)-3-{[6-(2,2,2-trifluoroethyl)thieno[2,3-d]pyrimidin-4-yl]amino}cyclohexyl]carbamate

[Formula 205]

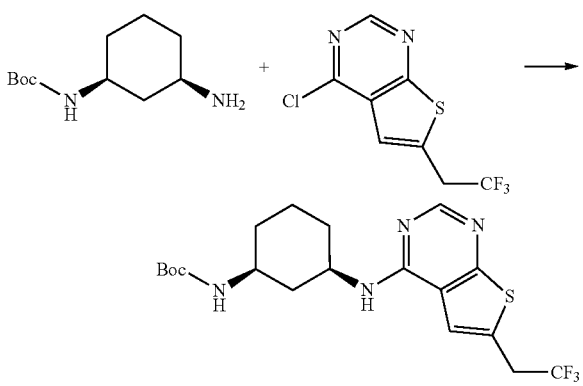

The compound (6.20 g) obtained in Step 2 of Reference Example A-2 and 4-chloro-6-(2,2,2-trifluoroethyl)thieno[2,3-d]pyrimidine (6.72 g) were dissolved in 2-propanol (90 mL), and DIPEA (9.27 mL) was added thereto, the mixture was heated under reflux for 7 hr. Ethyl acetate and saturated brine were added to the reaction solution, and the mixture was subjected to liquid separation, and the aqueous layer was extracted with ethyl acetate. The organic layers were combined, washed with saturated brine, dried over anhydrous sodium sulfate, and concentrated under reduced pressure. The obtained residue was purified by silica gel column chromatography (n-hexane/ethyl acetate) to give the title compound (7.50 g) as a solid.

$^1$H-NMR (CDCl$_3$) δ: 1.04-1.20 (3H, m), 1.44 (9H, s), 1.47-1.56 (1H, m), 1.84-1.89 (1H, m), 2.02-2.07 (1H, m), 2.13-2.18 (1H, m), 2.47-2.50 (1H, m), 3.55-3.68 (1H, m), 3.63 (2H, q, J=10.1 Hz), 4.21-4.31 (1H, m), 4.43 (1H, br s), 4.97 (1H, d, J=7.3 Hz), 7.03 (1H, s), 8.47 (1H, s).

Step 2 (1R,3S)—N$^1$-[6-(2,2,2-trifluoroethyl)thieno[2,3-d]pyrimidin-4-yl]cyclohexane-1,3-diamine Hydrochloride

[Formula 206]

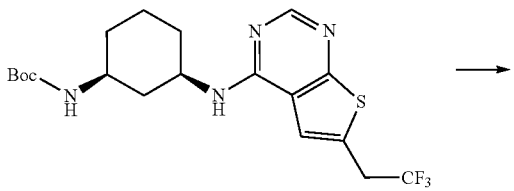

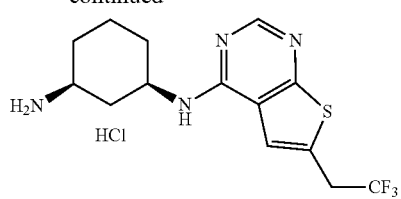

The title compound was obtained in the same manner as in Step 11 of Reference Example A-1, using the compound obtained in the above Step 1.

$^1$H-NMR (DMSO-D$_6$) δ: 1.29-1.44 (3H, m), 1.69-2.02 (4H, m), 2.23-2.29 (1H, m), 3.14 (1H, br s), 4.16 (2H, q, J=10.9 Hz), 4.31 (1H, br s), 8.13 (1H, s), 8.48 (3H, br s), 8.68 (1H, s), 10.01 (1H, d, J=7.9 Hz).

Reference Example C-3

(1R,3R)—N$^1$-[6-(2,2,2-trifluoroethyl)thieno[2,3-d]pyrimidin-4-yl]cyclopentane-1,3-diamine Hydrochloride Step 1 Tert-butyl [(1R,3R)-3-{[6-(2,2,2-trifluoroethyl)thieno[2,3-d]pyrimidin-4-yl]amino}cyclopentyl]carbamate

[Formula 207]

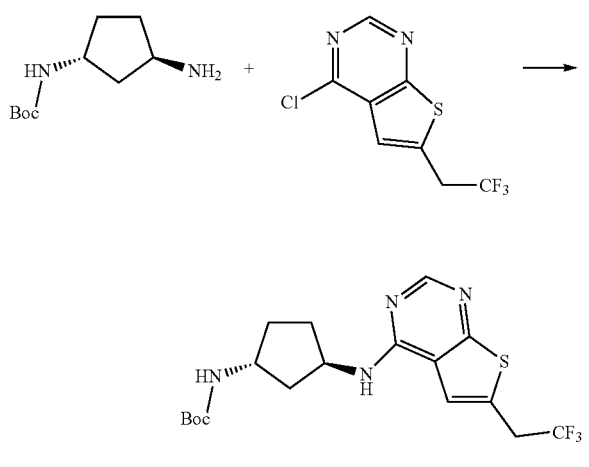

The title compound was obtained in the same manner as in Step 1 of Reference Example C-2, using tert-butyl [(1R,3R)-3-aminocyclopentyl]carbamate (CAS: 1009075-44-8) and 4-chloro-6-(2,2,2-trifluoroethyl)thieno[2,3-d]pyrimidine.

$^1$H-NMR (CDCl$_3$) δ: 1.45 (9H, s), 1.46-1.63 (2H, m), 1.91-2.05 (2H, m), 2.18-2.25 (1H, m), 2.30-2.39 (1H, m), 3.62 (2H, q, J=10.4 Hz), 4.13-4.20 (1H, m), 4.63-4.71 (2H, m), 5.54 (1H, d, J=4.9 Hz), 7.11 (1H, s), 8.45 (1H, s).

MS (m/z): 417 (M+H)$^+$.

Step 2 (1R,3R)—N$^1$-[6-(2,2,2-trifluoroethyl)thieno[2,3-d]pyrimidin-4-yl]cyclopentane-1,3-diamine Hydrochloride

[Formula 208]

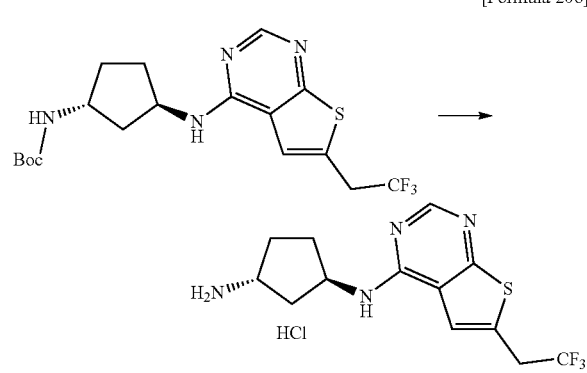

The title compound was obtained in the same manner as in Step 11 of Reference Example A-1, using the compound obtained in the above Step 1.

$^1$H-NMR (DMSO-D$_6$) δ: 1.61-1.79 (2H, m), 2.11 (2H, t, J=7.3 Hz), 2.14-2.27 (2H, m), 3.70-3.78 (1H, m), 4.14 (2H, q, J=10.9 Hz), 4.72-4.80 (1H, m), 7.95 (1H, s), 8.19 (3H, br s), 8.58 (1H, s), 9.11 (1H, br s).

MS (m/z): 317 (M+H)$^+$.

Reference Example C-4

(1R,3S)—N$^1$-methyl-N$^1$-[6-(2,2,2-trifluoroethyl)thieno[2,3-d]pyrimidin-4-yl]cyclopentane-1,3-diamine Hydrochloride Step 1 Tert-butyl [(1S,3R)-3-{methyl[6-(2,2,2-trifluoroethyl)thieno[2,3-d]pyrimidin-4-yl]amino}cyclopentyl]carbamate

[Formula 209]

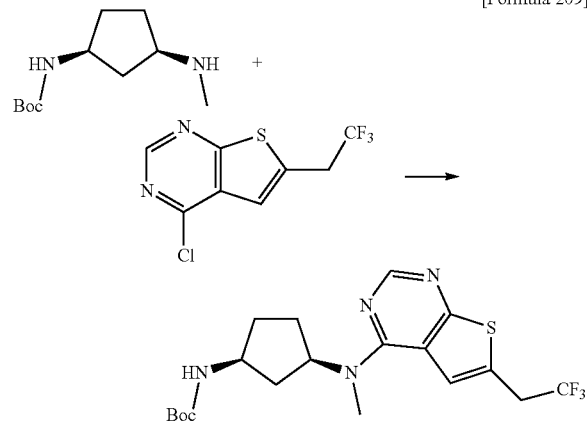

The title compound was obtained in the same manner as in Step 1 of Reference Example C-2, using the compound obtained in Reference Example A-4 and 4-chloro-6-(2,2,2-trifluoroethyl)thieno[2,3-d]pyrimidine $^1$H-NMR (CDCl$_3$) δ: 1.46 (9H, s), 1.57-1.68 (2H, m), 1.87-2.11 (3H, m), 2.36-2.43 (1H, m), 3.27 (3H, s), 3.64 (2H, q, J=10.5 Hz), 4.00 (1H, br s), 4.95 (1H, br s), 5.10 (1H, br s), 7.32 (1H, s), 8.43 (1H, s).
MS (m/z): 431 (M+H)$^+$.

Step 2 (1R,3S)—N$^1$-methyl-N$^1$-[6-(2,2,2-trifluoroethyl)thieno[2,3-d]pyrimidin-4-yl]cyclopentane-1,3-diamine Hydrochloride

[Formula 210]

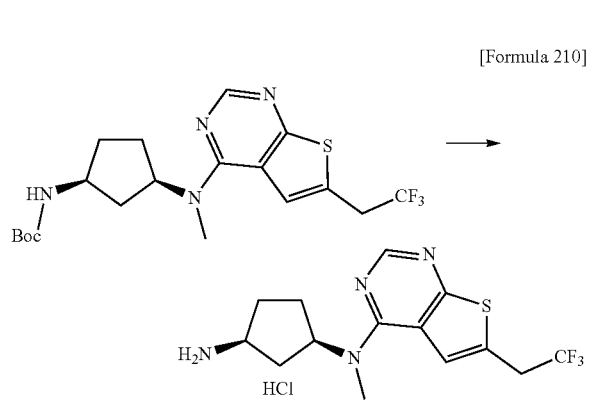

The title compound was obtained in the same manner as in Step 11 of Reference Example A-1, using the compound obtained in the above Step 1.
$^1$H-NMR (DMSO-D$_6$) δ: 1.82-2.14 (5H, m), 2.28-2.35 (1H, m), 3.38 (3H, s), 3.53-3.62 (1H, m), 4.17 (2H, q, J=10.9 Hz), 5.24-5.35 (1H, m), 7.88 (1H, s), 8.50 (3H, br s), 8.64 (1H, s).

Reference Example C-5

(1R,3S)—N$^1$-ethyl-N$^1$-[6-(2,2,2-trifluoroethyl)thieno[2,3-d]pyrimidin-4-yl]cyclopentane-1,3-diamine Hydrochloride Step 1 Tert-butyl [(1S,3R)-3-{ethyl[6-(2,2,2-trifluoroethyl)thieno[2,3-d]pyrimidin-4-yl]amino}cyclopentyl]carbamate

[Formula 211]

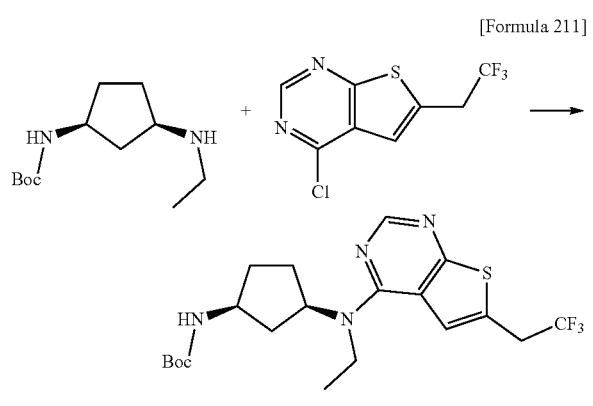

The title compound was obtained in the same manner as in Step 1 of Reference Example C-2, using the compound obtained in Step 2 of Reference Example A-5 and 4-chloro-6-(2,2,2-trifluoroethyl)thieno[2,3-d]pyrimidine.
$^1$H-NMR (CDCl$_3$) δ: 1.38 (3H, t, J=7.3 Hz), 1.47 (9H, s), 1.71-1.82 (2H, m), 1.88-1.97 (2H, m), 2.06-2.19 (1H, m), 2.33-2.40 (1H, m), 3.64 (2H, q, J=10.3 Hz), 3.65-3.75 (2H, m), 4.07 (1H, br s), 4.55 (1H, br s), 5.83 (1H, s), 7.20 (1H, s), 8.43 (1H, s).
MS (m/z): 445 (M+H)$^+$.

Step 2 (1R,3S)—N$^1$-ethyl-N$^1$-[6-(2,2,2-trifluoroethyl)thieno[2,3-d]pyrimidin-4-yl]cyclopentane-1,3-diamine Hydrochloride

[Formula 212]

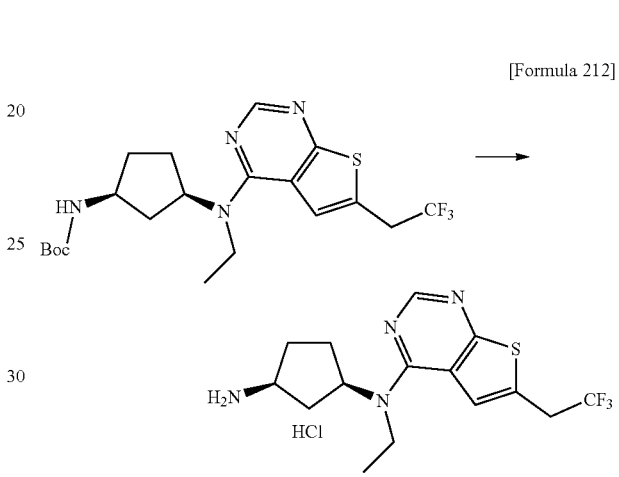

The title compound was obtained in the same manner as in Step 11 of Reference Example A-1, using the compound obtained in the above Step 1.
$^1$H-NMR (DMSO-D$_6$) δ: 1.28 (3H, t, J=6.7 Hz), 1.79-2.11 (5H, m), 2.29-2.37 (1H, m), 3.57-3.66 (1H, m), 3.71-3.85 (2H, m), 4.16 (2H, q, J=10.7 Hz), 5.05-5.14 (1H, m), 7.63 (1H, s), 8.26 (3H, br s), 8.49 (1H, s).

Reference Example C-6

(1R,3S)—N$^1$-methyl-N$^1$-[6-(2,2,2-trifluoroethyl)quinazolin-4-yl]cyclopentane-1,3-diamine Hydrochloride Step 1 Tert-butyl [(1S,3R)-3-{methyl[6-(2,2,2-trifluoroethyl)quinazolin-4-yl]amino}cyclopentyl]carbamate

[Formula 213]

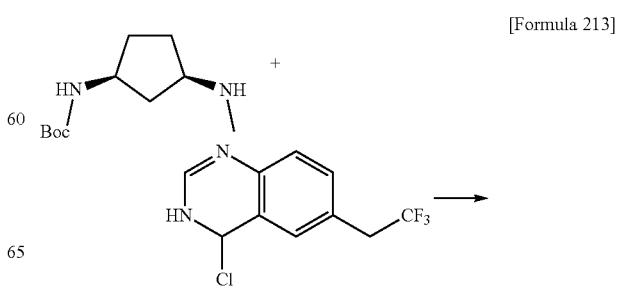

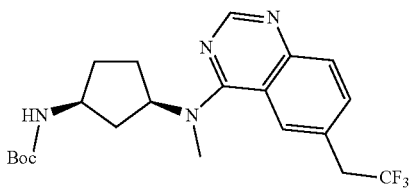

A mixture of the compound (0.0974 g) obtained in Step 7 of Reference Example B-7, BOP (CAS: 56602-33-6) (0.250 g), acetonitrile (8.5 mL) and DBU (CAS: 6674-22-2) (0.145 mL) was stirred at room temperature for 7 min. Then, a solution of the compound (0.218 g) obtained in Reference Example A-4 in acetonitrile (8.5 mL) was added thereto, and the mixture was stirred at 60° C. for 1 hr. The reaction solution was concentrated under reduced pressure, and the obtained residue was purified by silica gel column chromatography (n-hexane/ethyl acetate) to give the title compound (0.178 g) as an oil.

$^1$H-NMR (DMSO-D$_6$) δ: 1.39 (9H, s), 1.53-1.63 (1H, m), 1.65-1.76 (1H, m), 1.80-1.95 (3H, m), 2.24-2.34 (1H, m), 3.19 (3H, s), 3.76-3.87 (1H, m), 3.89 (2H, q, J=11.5 Hz), 4.75-4.86 (1H, m), 7.05 (1H, d, J=7.3 Hz), 7.75 (2H, s), 8.05 (1H, br s), 8.53 (1H, s).

MS (m/z): 425 (M+H)$^+$.

Step 2 (1R,3S)—N$^1$-methyl-N$^1$-[6-(2,2,2-trifluoroethyl)quinazolin-4-yl]cyclopentane-1,3-diamine Hydrochloride

[Formula 214]

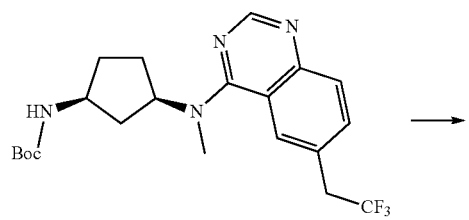

The title compound was obtained in the same manner as in Step 11 of Reference Example A-1, using the compound obtained in the above Step 1.

$^1$H-NMR (DMSO-D$_6$) δ: 1.83-2.22 (5H, m), 2.38-2.49 (1H, m), 3.51 (3H, s), 3.97 (2H, q, J=11.3 Hz), 5.21-5.35 (1H, m), 7.92 (1H, d, J=8.5 Hz), 7.99 (1H, d, J=8.5 Hz), 8.31 (1H, br s), 8.35 (3H, br s), 8.80-8.84 (1H, m).

MS (m/z): 325 (M+H)$^+$.

Reference Example C-7

N$^4$-[(1R,3S)-3-aminocyclopentyl]-N$^2$,N$^4$-dimethyl-6-(2,2,2-trifluoroethyl)thieno[2,3-d]pyrimidine-2,4-diamine hydrochloride Step 1 Tert-butyl [(1S,3R)-3-{[2-chloro-6-(2,2,2-trifluoroethyl)thieno[2,3-d]pyrimidin-4-yl](methyl)amino}cyclopentyl]carbamate

[Formula 215]

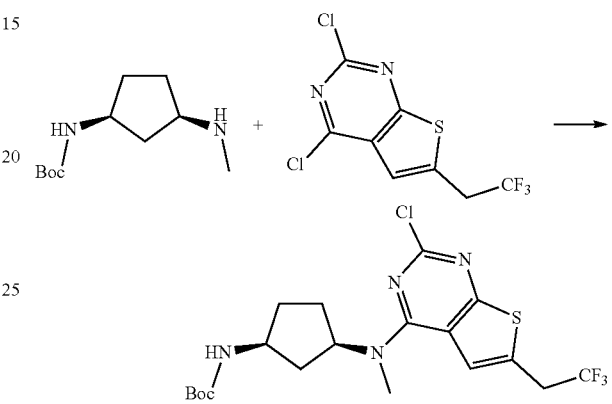

The title compound was obtained in the same manner as in Step 1 of Reference Example C-2, using the compound obtained in Reference Example A-4 and the compound obtained in Step 2 of Reference Example B-4.

$^1$H-NMR (CDCl$_3$) δ: 7.29 (1H, s), 5.09 (1H, br s), 4.72 (1H, br s), 4.06-3.93 (1H, m), 3.64 (1H, d, J=10.5 Hz), 3.59 (1H, d, J=10.5 Hz), 3.28 (3H, s), 2.46-2.37 (1H, m), 2.13-1.95 (2H, m), 1.94-1.81 (1H, m), 1.71-1.59 (2H, m), 1.46 (9H, s).

MS (m/z): 465, 467 (M+H)$^+$.

Step 2 Tert-butyl [(1S,3R)-3-{methyl[2-(methylamino)-6-(2,2,2-trifluoroethyl)thieno[2,3-d]pyrimidin-4-yl]amino}cyclopentyl]carbamate

[Formula 216]

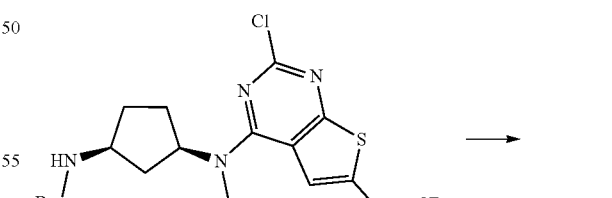

The compound (800 mg) obtained in the above Step 1 was suspended in butyronitrile (6 mL), and 40% aqueous methylamine solution (0.741 mL) was added thereto, and the mixture was stirred with heating in a microwave reactor at 150° C. for 1 hr and 45 min. Ethyl acetate and saturated brine were added to the reaction solution, and the mixture was subjected to liquid separation. The organic layer was washed with saturated brine, dried over anhydrous sodium sulfate, and concentrated under reduced pressure. A mixed solvent of dichloromethane/n-hexane=1/3 was added to the obtained residue, and the solid was collected by filtration to give the title compound (650 mg) as a solid.

$^1$H-NMR (DMSO-D$_6$) δ: 1.39 (9H, s), 1.52-1.61 (2H, m), 1.71-1.88 (3H, m), 2.09-2.16 (1H, m), 2.76 (3H, d, J=4.9 Hz), 3.10 (3H, s), 3.76-3.85 (1H, m), 3.88 (2H, q, J=11.0 Hz), 5.00-5.09 (1H, m), 6.60 (1H, q, J=4.9 Hz), 7.03 (1H, d, J=7.9 Hz), 7.38 (1H, s).

MS (m/z): 460 (M+H)$^+$.

Step 3 N$^4$-[(1R,3S)-3-aminocyclopentyl]-N$^2$,N$^4$-dimethyl-6-(2,2,2-trifluoroethyl)thieno[2,3-d]pyrimidine-2,4-diamine Hydrochloride

[Formula 217]

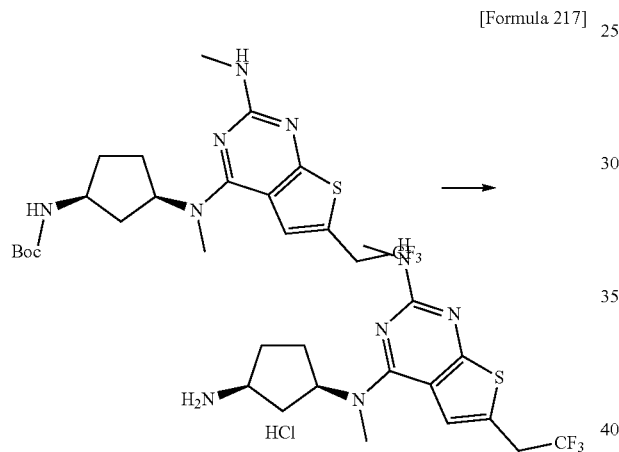

The title compound was obtained in the same manner as in Step 11 of Reference Example A-1, using the compound obtained in the above Step 2.

$^1$H-NMR (DMSO-D$_6$) δ: 1.84-1.94 (3H, m), 2.01-2.08 (2H, m), 2.31-2.37 (1H, m), 2.94 (3H, s), 3.34 (3H, s), 3.52-3.60 (1H, m), 4.05 (2H, q, J=11.0 Hz), 5.18 (1H, br s), 7.66 (1H, s), 8.02 (1H, br s), 8.47 (3H, s).

MS (m/z): 360 (M+H)$^+$.

Reference Example C-8

(1R,3S)—N$^1$-[6-(methoxymethyl)thieno[2,3-d]pyrimidin-4-yl]-N$^1$-methylcyclopentane-1,3-diamine Hydrochloride Step 1 Tert-butyl [(1S,3R)-3-{[6-(methoxymethyl)thieno[2,3-d]pyrimidin-4-yl](methyl)amino}cyclopentyl]carbamate

[Formula 218]

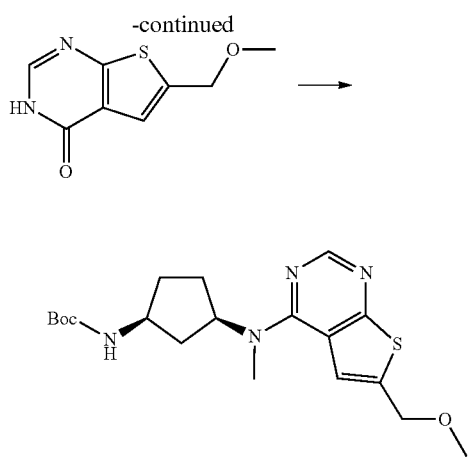

The title compound was obtained in the same manner as in Step 1 of Reference Example C-6, using the compound obtained in Reference Example A-4 and the compound obtained in Reference Example B-8.

$^1$H-NMR (CDCl$_3$) δ: 1.28-1.29 (1H, m), 1.49 (9H, s), 1.93-2.14 (4H, m), 2.41-2.43 (1H, m), 3.29 (3H, s), 3.46 (3H, s), 4.01-4.04 (1H, m), 4.68 (2H, s), 5.09-5.11 (1H, m), 7.29 (1H, s), 7.31 (1H, s), 8.44 (1H, s).

MS (m/z): 393 (M+H)$^+$.

Step 2 (1R,3S)—N$^1$-[6-(methoxymethyl)thieno[2,3-d]pyrimidin-4-yl]-N$^1$-methylcyclopentane-1,3-diamine Hydrochloride

[Formula 219]

The title compound was obtained in the same manner as in Step 11 of Reference Example A-1, using the compound (140 mg) obtained in the above Step 1.

MS (m/z): 293 (M+H)$^+$.

Reference Example C-9

2-{[(1R,3S)-3-aminocyclopentyl][6-(2,2,2-trifluoro-ethyl)thieno[2,3-d]pyrimidin-4-yl]amino}ethan-1-ol Hydrochloride Step 1 Tert-butyl [(1S,3R)-3-{(2-{[tert-butyl(dimethyl)silyl]oxy}ethyl)[6-(2,2,2-trifluoroethyl)thieno[2,3-d]pyrimidin-4-yl]amino}cyclopentyl]carbamate

[Formula 220]

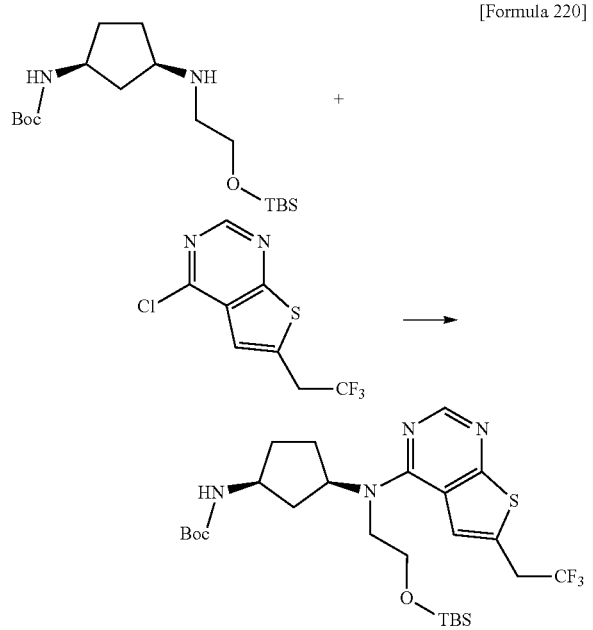

The title compound was obtained in the same manner as in Step 1 of Reference Example C-2, using the compound obtained in Step 2 of Reference Example A-19 and 4-chloro-6-(2,2,2-trifluoroethyl)thieno[2,3-d]pyrimidine.

$^1$H-NMR (DMSO-D$_6$) δ: −0.03 (6H, s), 0.81 (9H, s), 1.17-1.22 (1H, m), 1.39 (9H, s), 1.57-1.59 (1H, m), 1.66-1.72 (1H, m), 1.85-1.88 (2H, m), 2.20-2.22 (1H, m), 3.71-3.86 (5H, m), 4.02-4.13 (2H, m), 4.81-4.83 (1H, m), 7.08 (1H, d, J=7.4 Hz), 7.55 (1H, s), 8.36 (1H, s).

MS (m/z): 575 (M+H)$^+$.

Step 2 2-{[(1R,3S)-3-aminocyclopentyl][6-(2,2,2-trifluoroethyl)thieno[2,3-d]pyrimidin-4-yl]amino}ethan-1-ol Hydrochloride

[Formula 221]

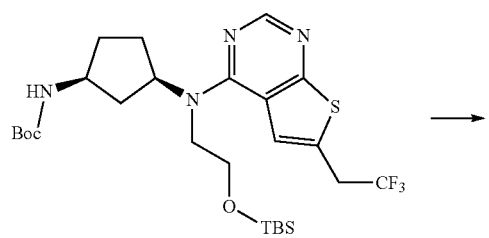

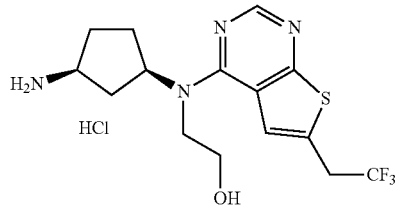

The title compound was obtained in the same manner as in Step 11 of Reference Example A-1, using the compound obtained in the above Step 1. The obtained compound was directly used in the next step without purification.

MS (m/z): 361 (M+H)$^+$.

Reference Example C-10

(1R,3S)—N$^1$-methyl-N$^1$-[2-methyl-6-(2,2,2-trifluoroethyl)thieno[2,3-d]pyrimidin-4-yl]cyclopentane-1,3-diamine Hydrochloride Step 1 Tert-butyl [(1S,3R)-3-{methyl[2-methyl-6-(2,2,2-trifluoroethyl)thieno[2,3-d]pyrimidin-4-yl]amino}cyclopentyl]carbamate

[Formula 222]

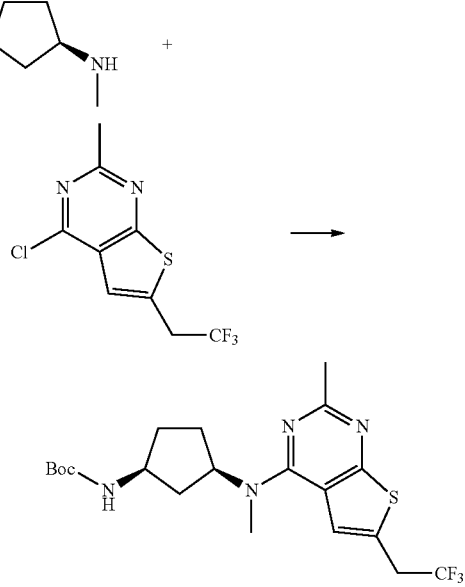

The title compound was obtained in the same manner as in Step 1 of Reference Example C-2, using the compound obtained in Reference Example A-4 and the compound obtained in Step 3 of Reference Example B-1.

$^1$H-NMR (CDCl$_3$) δ: 1.48 (9H, s), 1.59-1.62 (2H, m), 1.92-2.02 (3H, m), 2.36-2.43 (1H, m), 2.57 (3H, s), 3.24 (3H, s), 3.60 (2H, q, J=10.1 Hz), 4.00 (1H, br s), 4.74 (1H, br s), 5.15-5.17 (1H, br m), 7.26 (1H, s).

MS (m/z): 445 (M+H)$^+$.

Step 2 (1R,3S)—N¹-methyl-N¹-[2-methyl-6-(2,2,2-trifluoroethyl)thieno[2,3-d]pyrimidin-4-yl]cyclopentane-1,3-diamine Hydrochloride

[Formula 223]

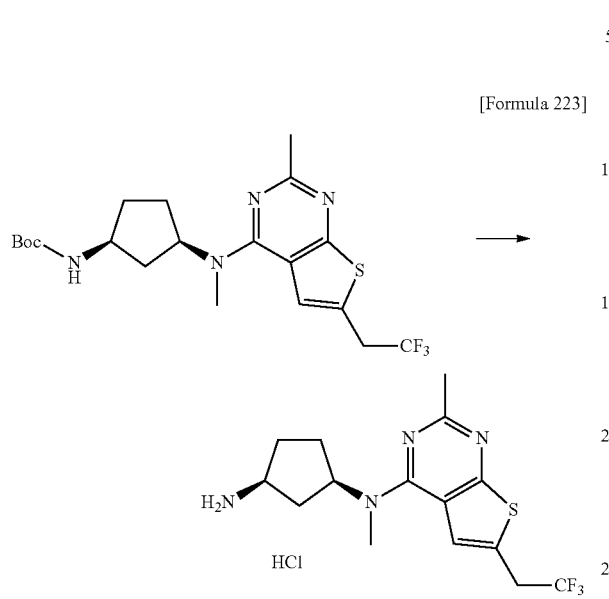

The title compound was obtained in the same manner as in Step 11 of Reference Example A-1, using the compound obtained in the above Step 1.

¹H-NMR (DMSO-D₆) δ: 1.76-1.96 (3H, m), 1.96-2.11 (2H, m), 2.24-2.35 (1H, m), 2.52 (3H, s), 3.33 (3H, s), 3.58-3.64 (1H, m), 4.11 (2H, q, J=11.1 Hz), 5.31-5.33 (1H, br m), 7.76 (1H, s), 8.23 (3H, br s).

MS (m/z): 345 (M+H)⁺.

Reference Example C-11

(1R,3S)—N¹-methyl-N¹-[6-(oxetan-3-yl)thieno[2,3-d]pyrimidin-4-yl]cyclopentane-1,3-diamine Hydrochloride Step 1 Tert-butyl [(1S,3R)-3-{methyl[6-(oxetan-3-yl)thieno[2,3-d]pyrimidin-4-yl]amino}cyclopentyl]carbamate

[Formula 224]

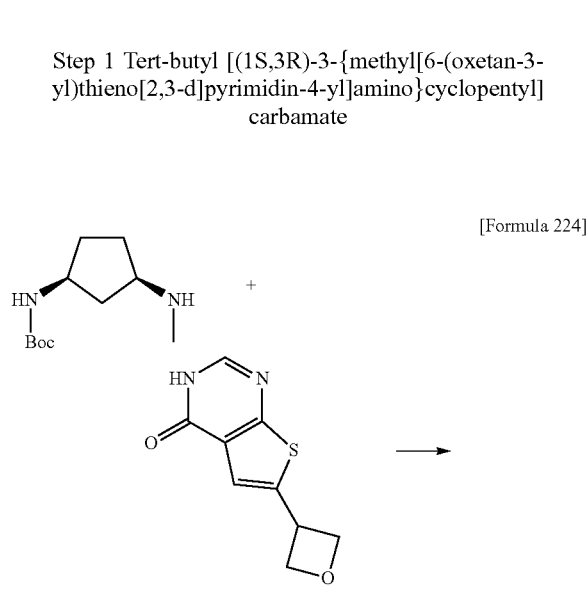

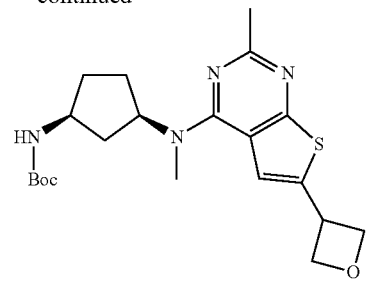

The title compound was obtained in the same manner as in Step 1 of Reference Example C-6, using the compound obtained in Step 1 of Reference Example A-4 and the compound obtained in Reference Example B-9.

¹H-NMR (DMSO-D₆) δ: 1.39 (9H, s), 1.56-1.64 (2H, m), 1.78-1.90 (3H, m), 2.11-2.17 (1H, m), 3.20 (3H, s), 3.82-3.84 (1H, m), 4.60-4.69 (3H, m), 4.96-4.98 (2H, m), 5.14-5.16 (1H, m), 7.04 (1H, d, J=7.4 Hz), 7.50 (1H, s), 8.32 (1H, s).

MS (m/z): 405 (M+H)⁺.

Step 2 (1R,3S)—N¹-methyl-N¹-[6-(oxetan-3-yl)thieno[2,3-d]pyrimidin-4-yl]cyclopentane-1,3-diamine Hydrochloride

[Formula 225]

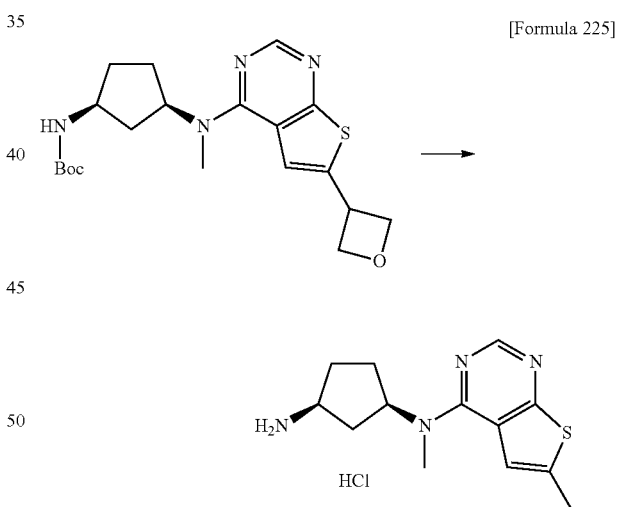

The title compound was obtained in the same manner as in Step 11 of Reference Example A-1, using the compound obtained in the above Step 1. The obtained compound was directly used in the next step without purification.

¹H-NMR (DMSO-D₆) δ: 1.80-2.33 (7H, m), 3.35 (3H, s), 3.67-3.71 (2H, m), 3.78-3.85 (1H, m), 3.88-3.95 (1H, m), 4.01-4.04 (1H, m), 5.27-5.30 (1H, m), 7.65 (1H, s), 8.26 (3H, s), 8.54 (1H, s).

MS (m/z): 305 (M+H)⁺.

Reference Example C-12

(1R,3S)—N¹-(6-cyclopropylthieno[2,3-d]pyrimidin-4-yl)-N¹-methylcyclopentane-1,3-diamine Hydrochloride Step 1 Tert-butyl {(1S,3R)-3-[(6-cyclopropylthieno[2,3-d]pyrimidin-4-yl)(methyl)amino]cyclopentyl}carbamate

[Formula 226]

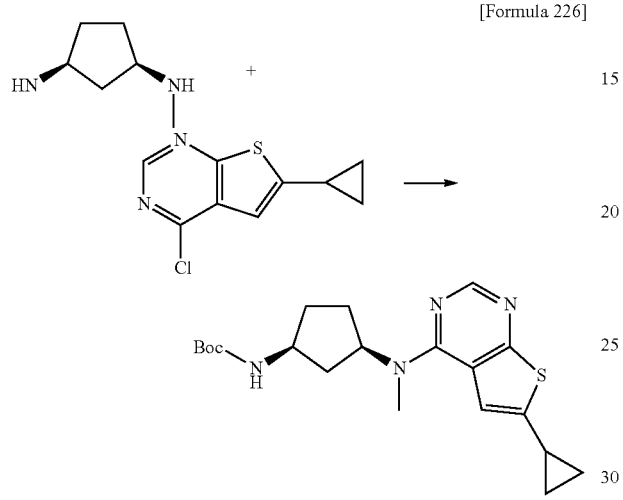

The title compound was obtained in the same manner as in Step 1 of Reference Example C-2, using the compound obtained in Reference Example A-4 and the compound obtained in Reference Example B-3.
¹H-NMR (DMSO-D₆) δ: 0.79-0.80 (2H, m), 1.04-1.07 (2H, m), 1.40 (9H, s), 1.52-1.68 (2H, m), 1.78-1.94 (3H, m), 2.16-2.23 (2H, m), 3.18 (3H, s), 3.78-3.86 (1H, m), 5.04-5.12 (1H, m), 6.68 (1H, s), 7.24 (1H, s), 8.25 (1H, s).
MS (m/z): 389 (M+H)⁺.

Step 2 (1R,3S)—N¹-(6-cyclopropylthieno[2,3-d]pyrimidin-4-yl)-N¹-methylcyclopentane-1,3-diamine Hydrochloride

[Formula 227]

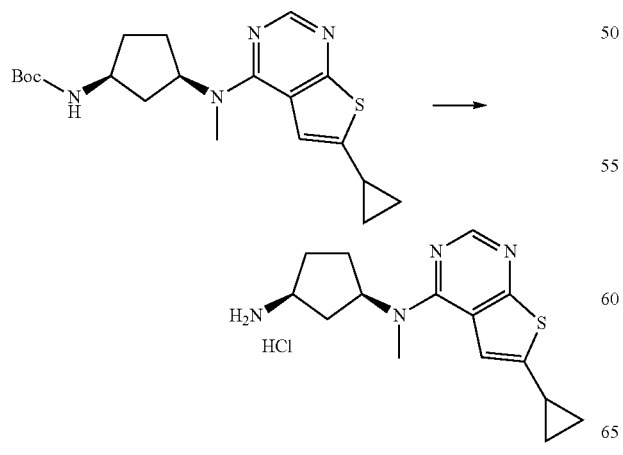

The title compound was obtained in the same manner as in Step 11 of Reference Example A-1, using the compound obtained in the above Step 1. The obtained compound was directly used in the next step without purification.
MS (m/z): 289 (M+H)⁺.

Reference Example C-13

(1S,3R)-5,5-difluoro-N¹-[6-(2,2,2-trifluoroethyl)thieno[2,3-d]pyrimidin-4-yl]cyclohexane-1,3-diamine Hydrochloride Step 1 Tert-butyl [(1R,5S)-3,3-difluoro-5-{[6-(2,2,2-trifluoroethyl)thieno[2,3-d]pyrimidin-4-yl]amino}cyclohexyl]carbamate

[Formula 228]

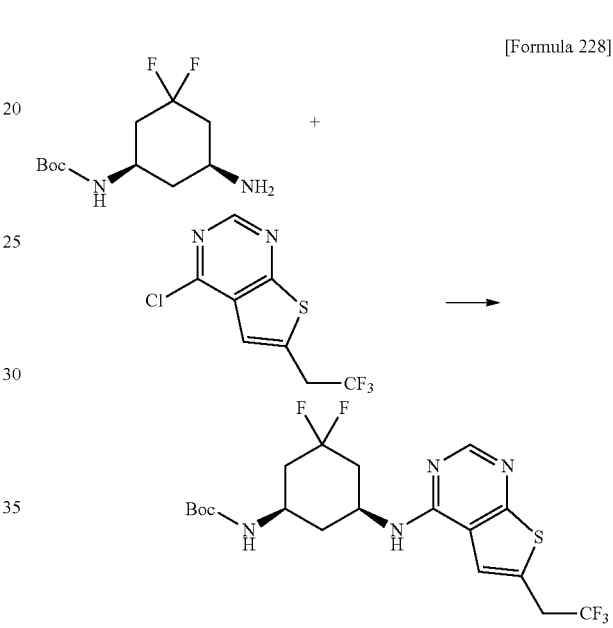

The title compound was obtained in the same manner as in Step 1 of Reference Example C-2, using the compound obtained in Step 2 of Reference Example A-18 and 4-chloro-6-(2,2,2-trifluoroethyl)thieno[2,3-d]pyrimidine.
¹H-NMR (CDCl₃) δ: 1.43-1.45 (11H, m), 1.66-1.78 (2H, m), 2.51-2.58 (2H, m), 3.59-3.62 (2H, m), 3.85-3.87 (1H, m), 4.66-4.68 (2H, m), 5.66-5.68 (1H, m), 7.11 (1H, s), 8.48 (1H, s).
MS (m/z): 467 (M+H)⁺.

Step 2 (1S,3R)-5,5-difluoro-N¹-[6-(2,2,2-trifluoroethyl)thieno[2,3-d]pyrimidin-4-yl]cyclohexane-1,3-diamine Hydrochloride

[Formula 229]

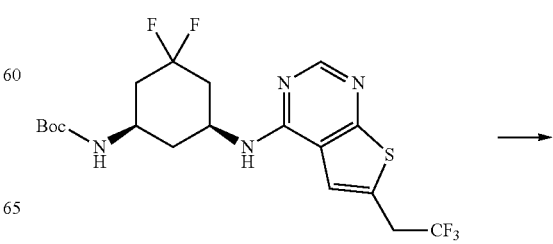

-continued

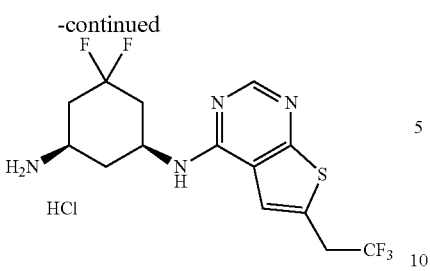

The title compound was obtained in the same manner as in Step 11 of Reference Example A-1, using the compound obtained in the above Step 1.

¹H-NMR (CD₃OD) δ: 1.84-2.23 (3H, m), 2.50-2.53 (3H, m), 3.52-3.58 (1H, m), 4.04 (2H, q, J=10.4 Hz), 4.72-4.75 (1H, m), 7.86 (1H, s), 8.76 (1H, s).
MS (m/z): 367 (M+H)⁺.

Reference Example C-14

(1R,2S,4R)-4-amino-2-{methyl[6-(2,2,2-trifluoro-ethyl)thieno[2,3-d]pyrimidin-4-yl]amino}cyclopentan-1-ol Hydrochloride Step 1 Benzyl [(1R,3R,4S)-3-hydroxy-4-{methyl[6-(2,2,2-trifluoroethyl)thieno[2,3-d]pyrimidin-4-yl]amino}cyclopentyl]carbamate

[Formula 230]

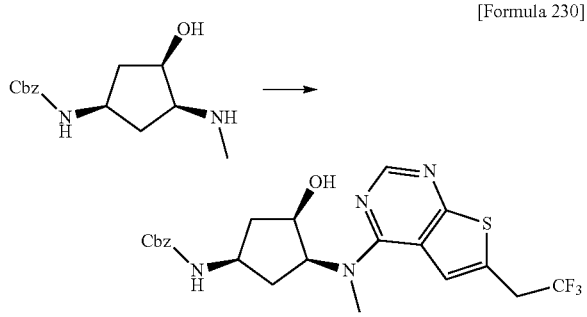

A mixture of the compound (43.3 g) obtained in Step 14 of Reference Example A-1, 4-chloro-6-(2,2,2-trifluoroethyl)thieno[2,3-d]pyrimidine (CAS: 1628317-85-0) (43.5 g), DIPEA (57.1 mL) and 2-propanol (820 mL) was stirred at 90° C. for 5 hr. The reaction solution was concentrated under reduced pressure, water was added thereto, and the mixture was extracted with ethyl acetate/dichloromethane/methanol. The organic layer was dried over anhydrous sodium sulfate, and concentrated under reduced pressure. Ethyl acetate/n-hexane was added to the residue, and the solid was collected by filtration to give the title compound (64.2 g) as a solid. The filtrate was concentrated, and ethyl acetate/n-hexane was added to the residue, and the solid was collected by filtration to give the title compound (26.5 g) as a solid. The filtrate was concentrated, and the residue was purified by silica gel column chromatography (dichloromethane/ethyl acetate). Ethyl acetate was added to the obtained solid, and the solid was collected by filtration to give the title compound (3.67 g) as a solid.

¹H-NMR (CDCl₃) δ: 1.72-1.84 (1H, m), 2.22-2.44 (3H, m), 3.49 (3H, s), 3.62 (2H, q, J=10.2 Hz), 3.90-3.98 (1H, m), 4.08-4.19 (1H, m), 4.54-4.62 (1H, m), 4.65-4.73 (1H, m), 5.12 (2H, s), 5.46 (1H, d, J=7.9 Hz), 7.31-7.42 (6H, m), 8.35 (1H, s).
MS (m/z): 481 (M+H)⁺.

Step 2 (1R,2S,4R)-4-amino-2-{methyl[6-(2,2,2-trifluoroethyl)thieno[2,3-d]pyrimidin-4-yl]amino}cyclopentan-1-ol

[Formula 231]

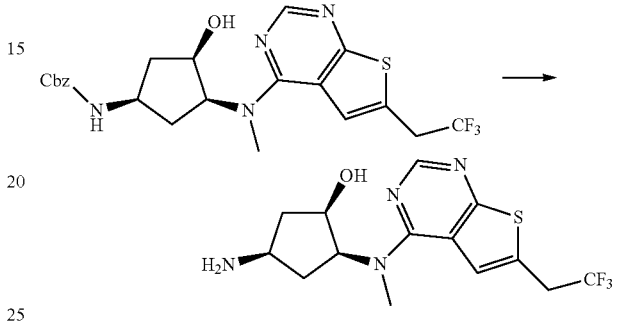

To a mixture of the compound (8.98 g) obtained in the above Step 1 and acetonitrile (90 mL) was added iodotrimethylsilane (8.1 mL) at 0° C., and the mixture was stirred at 0° C. for 30 min. 1N Hydrochloric acid and water were added to the reaction solution, and the mixture was washed with ethyl acetate. The organic layer was extracted with 1N hydrochloric acid, 2N aqueous sodium hydroxide solution was added to the combined aqueous layers, and the mixture was extracted nine times with dichloromethane/methanol. The combined organic layers were dried over anhydrous sodium sulfate, and concentrated under reduced pressure to give the title compound (6.53 g) as a solid.

¹H-NMR (CDCl₃) δ: 1.65-1.73 (1H, m), 1.80-1.91 (1H, m), 2.03-2.12 (1H, m), 2.25-2.36 (1H, m), 3.56 (3H, s), 3.58-3.73 (3H, m), 4.46-4.52 (1H, m), 5.06-5.16 (1H, m), 7.41 (1H, s), 8.39 (1H, s).
MS (m/z): 347 (M+H)⁺.

Step 3 (1R,2S,4R)-4-amino-2-{methyl[6-(2,2,2-trifluoroethyl)thieno[2,3-d]pyrimidin-4-yl]amino}cyclopentan-1-ol Hydrochloride

[Formula 232]

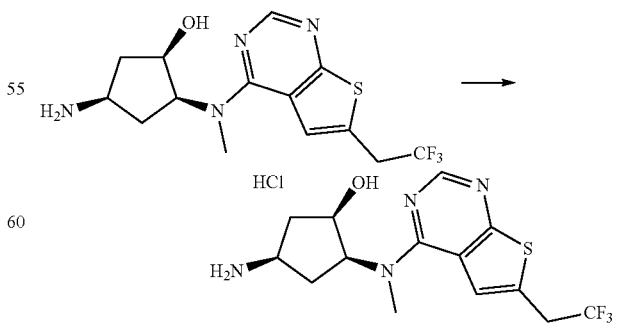

A mixture of the compound (6.53 g) obtained in the above Step 2, 1N hydrochloric acid (21 mL) and acetonitrile (60 mL) was stirred at room temperature for 10 min. The reaction solution was concentrated under reduced pressure, acetonitrile was added thereto, and the solid was collected by filtration to give the title compound (5.83 g) as a solid. The filtrate was concentrated, acetonitrile was added thereto, and the solid was collected by filtration to give the title compound (1.13 g) as a solid.

$^1$H-NMR (DMSO-D$_6$) δ: 1.59-1.69 (1H, m), 2.18-2.27 (2H, m), 2.32-2.43 (1H, m), 3.43 (3H, s), 3.50-3.63 (1H, m), 4.10 (2H, q, J=11.1 Hz), 4.31-4.39 (1H, m), 4.89-5.00 (1H, m), 5.19 (1H, br s), 7.75 (1H, s), 8.08 (3H, br s), 8.38 (1H, s).

MS (m/z): 347 (M+H)$^+$.

Reference Example C-15

(1R,2S,4R)-4-amino-2-{[2-methoxy-6-(2,2,2-trifluoroethyl)thieno[2,3-d]pyrimidin-4-yl](methyl)amino}cyclopentan-1-ol Hydrochloride Step 1 Tert-butyl [(1R,3R,4S)-3-hydroxy-4-{[2-methoxy-6-(2,2,2-trifluoroethyl)thieno[2,3-d]pyrimidin-4-yl](methyl)amino}cyclopentyl]carbamate

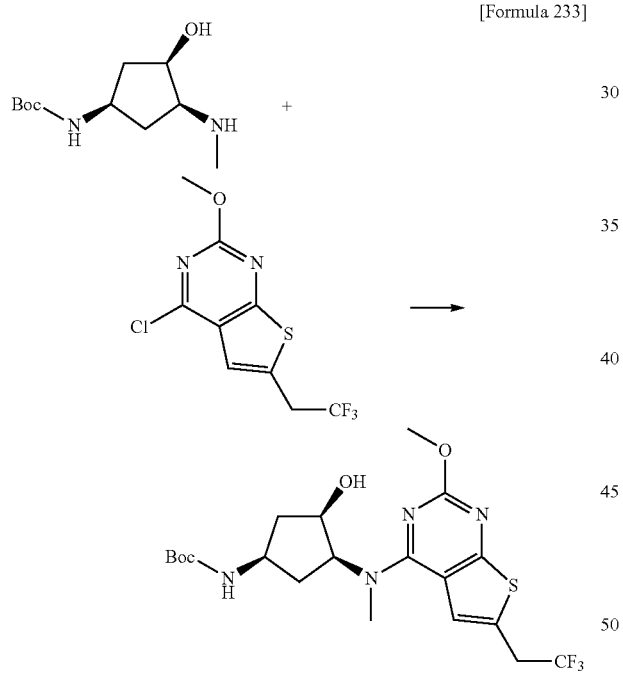

[Formula 233]

To the compound (3.33 g) obtained in Step 2 of Reference Example A-15 and the compound (4.09 g) obtained in Step 4 of Reference Example B-5 were added 2-propanol (49 mL) and DIPEA (7.56 mL), and the mixture was heated under reflux for 3 hr, and allowed to stand overnight at room temperature. Ethyl acetate and saturated brine were added to the reaction solution, and the mixture was subjected to liquid separation. The organic layer was washed with saturated brine, dried over anhydrous sodium sulfate, and concentrated under reduced pressure. The obtained residue was purified by silica gel column chromatography (n-hexane/ ethyl acetate) to give the title compound (5.05 g) as a solid.

$^1$H-NMR (CDCl$_3$) δ: 1.46 (9H, s), 1.73 (1H, d, J=13.4 Hz), 2.23-2.30 (2H, m), 2.35-2.42 (1H, m), 3.48 (3H, s), 3.56 (2H, q, J=10.1 Hz), 3.67 (1H, br s), 3.93 (3H, s), 3.95-4.03 (1H, m), 4.54-4.58 (1H, m), 4.72 (1H, td, J=9.7, 4.9 Hz), 5.13-5.18 (1H, m), 7.27 (1H, s).

MS (m/z): 477 (M+H)$^+$.

Step 2 (1R,2S,4R)-4-amino-2-{[2-methoxy-6-(2,2,2-trifluoroethyl)thieno[2,3-d]pyrimidin-4-yl](methyl)amino}cyclopentan-1-ol Hydrochloride

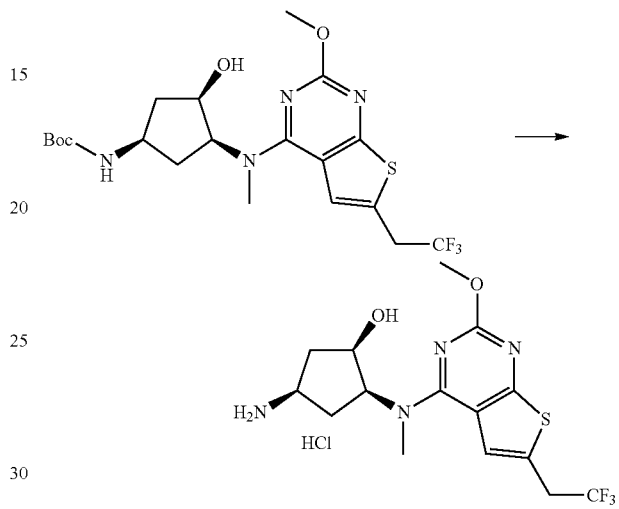

[Formula 234]

A mixture of the compound (810 mg) obtained in the above Step 1, dichloromethane (7 mL) and hydrogen chloride (4 mol/L, 1,4-dioxane solution, 7 mL) was stirred at room temperature. A small amount of methanol was added thereto to make a solution, and the solution was further stirred, and concentrated under reduced pressure. The residue was suspended in n-hexane/ethanol, and the solid was collected by filtration to give the title compound (724 mg) as a solid.

$^1$H-NMR (DMSO-D$_6$) δ: 1.64-1.68 (1H, m), 2.23-2.26 (2H, m), 2.34-2.42 (1H, m), 3.40 (3H, s), 3.54-3.58 (1H, m), 3.65-3.68 (1H, m), 3.86 (3H, s), 3.97-4.09 (2H, m), 4.34-4.36 (1H, m), 4.83-4.85 (1H, m), 7.64 (1H, s), 8.20-8.23 (3H, m).

MS (m/z): 377 (M+H)$^+$.

Reference Example C-16

(1S,2S,4R)-4-amino-2-{methyl[6-(2,2,2-trifluoroethyl)thieno[2,3-d]pyrimidin-4-yl]amino}cyclopentan-1-ol Step 1 Benzyl [(1R,3S,4S)-3-hydroxy-4-{methyl[6-(2,2,2-trifluoroethyl)thieno[2,3-d]pyrimidin-4-yl]amino}cyclopentyl]carbamate

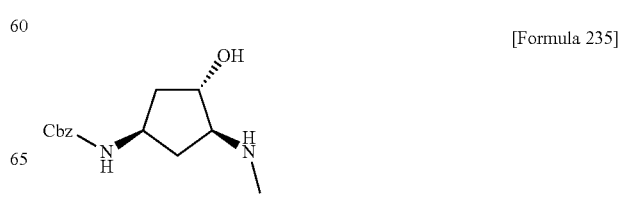

[Formula 235]

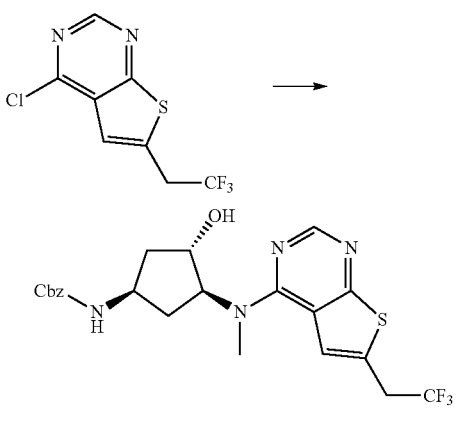

The title compound was obtained in the same manner as in Step 1 of Reference Example C-2, using the compound obtained in Step 9 of Reference Example A-14 and 4-chloro-6-(2,2,2-trifluoroethyl)thieno[2,3-d]pyrimidine.

$^1$H-NMR (CDCl$_3$) δ: 1.85-1.99 (2H, m), 2.16-2.23 (1H, m), 2.47 (1H, br s), 3.32 (3H, s), 3.66 (2H, q, J=10.2 Hz), 4.23-4.35 (2H, m), 4.65 (1H, dt, J=10.4, 7.4 Hz), 4.95 (1H, br s), 5.12 (3H, br s), 7.32-7.42 (5H, m), 8.43 (1H, s), 7.37 (1H, s).

MS (m/z): 481 (M+H)$^+$.

Step 2 (1S,2S,4R)-4-amino-2-{methyl[6-(2,2,2-trifluoroethyl)thieno[2,3-d]pyrimidin-4-yl]amino}cyclopentan-1-ol

[Formula 236]

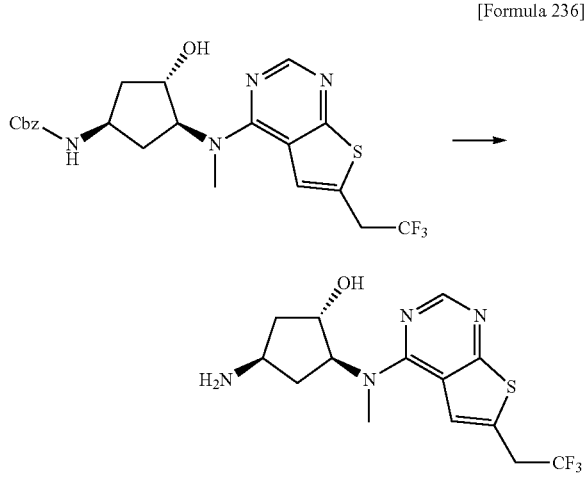

The title compound was obtained in the same manner as in Step 2 of Reference Example C-1, using the compound obtained in the above Step 1.

$^1$H-NMR (DMSO-D$_6$) δ: 1.28-1.39 (1H, m), 1.59-1.73 (4H, m), 2.15-2.24 (1H, m), 3.24 (3H, s), 3.29-3.42 (2H, m), 4.06 (1H, d, J=11.0 Hz), 4.12 (1H, d, J=11.0 Hz), 4.33-4.42 (1H, m), 4.80-4.93 (2H, m), 7.73 (1H, s), 8.33 (1H, s).

MS (m/z): 347 (M+H)$^+$.

Reference Example C-17

(1R,3S,5R)-3-amino-N,N-dimethyl-5-{[6-(2,2,2-trifluoroethyl)thieno[2,3-d]pyrimidin-4-yl]amino}cyclohexane-1-carboxamide (Racemate)

Step 1 Benzyl [(1S,3S,5R)-3-(dimethylcarbamoyl)-5-{[6-(2,2,2-trifluoroethyl)thieno[2,3-d]pyrimidin-4-yl]amino}cyclohexyl]carbamate (Racemate)

[Formula 237]

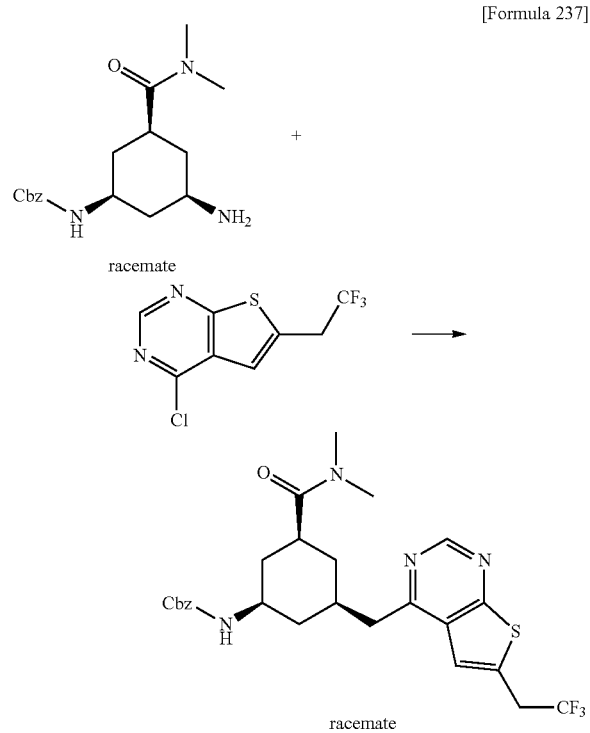

The title compound was obtained in the same manner as in Step 1 of Reference Example C-2, using the compound obtained in Step 6 of Reference Example A-7 and 4-chloro-6-(2,2,2-trifluoroethyl)thieno[2,3-d]pyrimidine.

$^1$H-NMR (CDCl$_3$) δ: 1.37 (1H, q, J=11.5 Hz), 1.57-1.71 (2H, m), 1.91 (1H, s), 2.09-2.13 (2H, m), 2.42-2.45 (1H, m), 2.89-2.91 (1H, m), 2.94 (3H, s), 3.12 (3H, s), 3.60 (2H, q, J=10.3 Hz), 3.75-3.78 (1H, m), 4.45-4.48 (1H, m), 5.06 (2H, s), 5.28-5.30 (1H, m), 6.34 (1H, d, J=7.9 Hz), 7.29-7.32 (5H, m), 8.46 (1H, s).

MS (m/z): 536 (M+H)$^+$.

Step 2 (1R,3S,5R)-3-amino-N,N-dimethyl-5-{[6-(2,2,2-trifluoroethyl)thieno[2,3-d]pyrimidin-4-yl]amino}cyclohexane-1-carboxamide (Racemate)

[Formula 238]

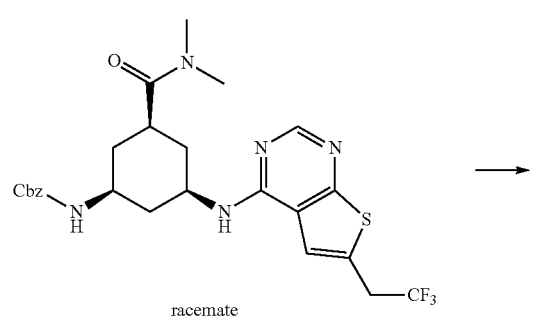

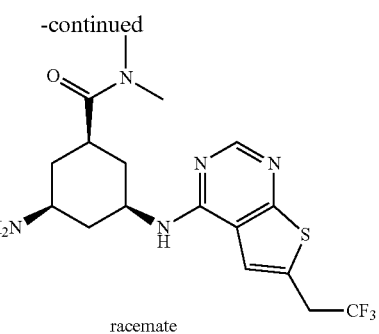
racemate

The title compound was obtained in the same manner as in Step 2 of Reference Example C-1, using the compound obtained in the above Step 1.

$^1$H-NMR (CDCl$_3$) δ: 1.21 (1H, q, J=11.5 Hz), 1.42 (1H, q, J=12.4 Hz), 1.62 (1H, q, J=12.1 Hz), 1.95 (1H, d, J=13.4 Hz), 2.16 (1H, d, J=12.8 Hz), 2.31 (1H, d, J=11.5 Hz), 2.86-2.89 (1H, m), 2.98 (3H, s), 3.00-3.02 (1H, m), 3.13 (3H, s), 3.64 (2H, q, J=10 Hz), 4.41-4.44 (1H, m), 5.96 (1H, d, J=8.5 Hz), 7.24 (1H, s), 8.47 (1H, s).
MS (m/z): 402 (M+H)$^+$.

Reference Example C-18

(1S,3R,5R)-5-methoxy-N$^1$-[6-(2,2,2-trifluoroethyl)thieno[2,3-d]pyrimidin-4-yl]cyclohexane-1,3-diamine (Racemate)

Step 1 Benzyl [(1R,3S,5S)-3-methoxy-5-{[6-(2,2,2-trifluoroethyl)thieno[2,3-d]pyrimidin-4-yl]amino}cyclohexyl]carbamate (Racemate)

[Formula 239]

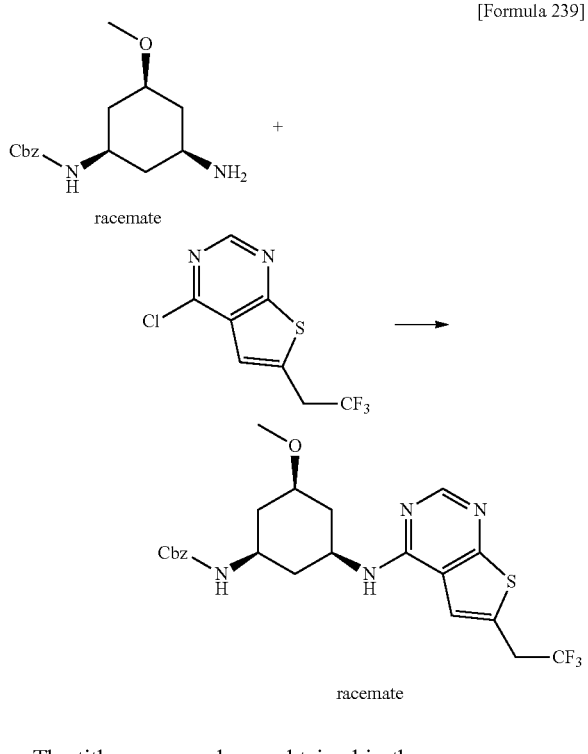

The title compound was obtained in the same manner as in Step 1 of Reference Example C-2, using the compound obtained in Step 4 of Reference Example A-11 and 4-chloro-6-(2,2,2-trifluoroethyl)thieno[2,3-d]pyrimidine.
MS (m/z): 495 (M+H)$^+$.

Step 2 (1S,3R,5R)-5-methoxy-N$^1$-[6-(2,2,2-trifluoroethyl)thieno[2,3-d]pyrimidin-4-yl]cyclohexane-1,3-diamine (Racemate)

[Formula 240]

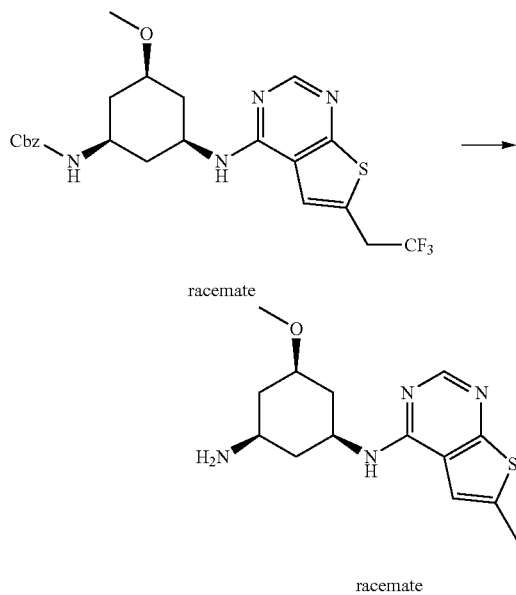

The title compound was obtained in the same manner as in Step 2 of Reference Example C-14, using the compound obtained in the above Step 1.

$^1$H-NMR (CD$_3$OD) δ: 1.06 (1H, q, J=11.6 Hz), 1.17-1.29 (2H, m), 2.20 (1H, d, J=11.6 Hz), 2.30 (1H, d, J=12.2 Hz), 2.42 (1H, d, J=11.0 Hz), 2.80-2.88 (1H, m), 3.37-3.44 (4H, m), 3.85 (2H, q, J=10.4 Hz), 4.21-4.29 (1H, m), 7.51 (1H, s), 8.31 (1H, s).
MS (m/z): 361 (M+H)$^+$.

Reference Example C-19

(1R,3R,5S)-3-amino-5-{[6-(2,2,2-trifluoroethyl)thieno[2,3-d]pyrimidin-4-yl]amino}cyclohexan-1-ol (Racemate)

Step 1 Benzyl [(1R,3S,5S)-3-(methoxymethoxy)-5-{[6-(2,2,2-trifluoroethyl)thieno[2,3-d]pyrimidin-4-yl]amino}cyclohexyl]carbamate (Racemate)

[Formula 241]

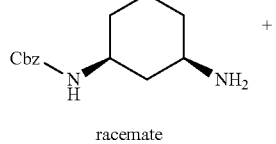
racemate

-continued

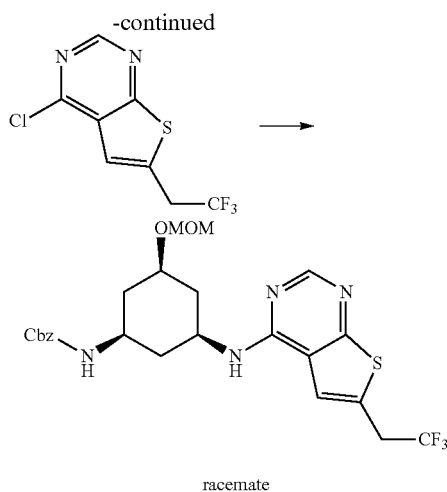
racemate

The title compound was obtained in the same manner as in Step 1 of Reference Example C-2, using the compound obtained in Step 5 of Reference Example A-6 and 4-chloro-6-(2,2,2-trifluoroethyl)thieno[2,3-d]pyrimidine.

¹H-NMR (CDCl₃) δ: 1.31-1.47 (3H, m), 2.34-2.43 (3H, m), 3.38 (3H, s), 3.60-3.62 (2H, m), 3.80-3.85 (2H, m), 4.40-4.41 (1H, m), 4.72-4.79 (3H, m), 5.10-5.18 (3H, m), 7.01 (1H, s), 7.31-7.36 (5H, m), 8.48 (1H, s).
MS (m/z): 525 (M+H)⁺.

Step 2 (1R,3R,5S)-3-amino-5-{[6-(2,2,2-trifluoroethyl)thieno[2,3-d]pyrimidin-4-yl]amino}cyclohexan-1-ol (Racemate)

[Formula 242]

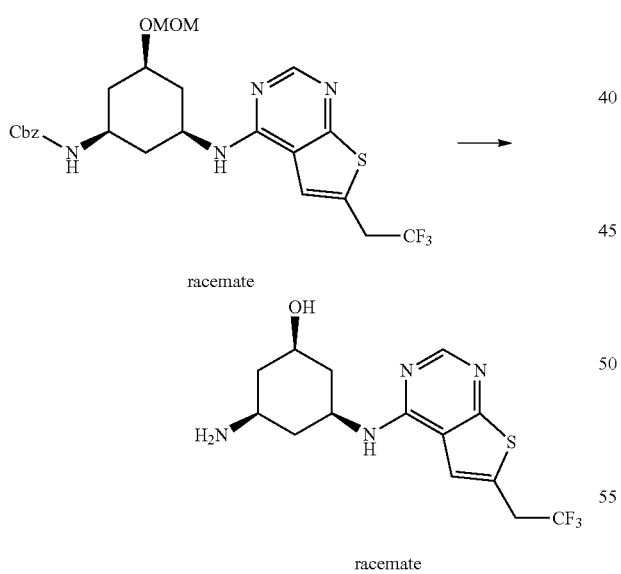
racemate

The title compound was obtained in the same manner as in Step 2 of Reference Example C-1, using the compound obtained in the above Step 1.

¹H-NMR (CD₃OD) δ: 1.15-1.19 (2H, m), 1.33-1.36 (1H, m), 2.16-2.19 (2H, m), 2.25-2.28 (1H, m), 2.83-2.86 (1H, m), 3.72-3.75 (1H, m), 3.84-3.87 (2H, m), 4.25-4.27 (1H, m), 7.52 (1H, s), 8.30 (1H, s).
MS (m/z): 347 (M+H)⁺.

Reference Example C-20

(1R,2S,4R)-4-amino-2-{methyl[2-(methylamino)-6-(2,2,2-trifluoroethyl)thieno[2,3-d]pyrimidin-4-yl]amino}cyclopentan-1-ol Step 1 Benzyl [(1R,3S,4R)-3-{[2-chloro-6-(2,2,2-trifluoroethyl)thieno[2,3-d]pyrimidin-4-yl](methyl)amino}-4-hydroxycyclopentyl]carbamate

[Formula 243]

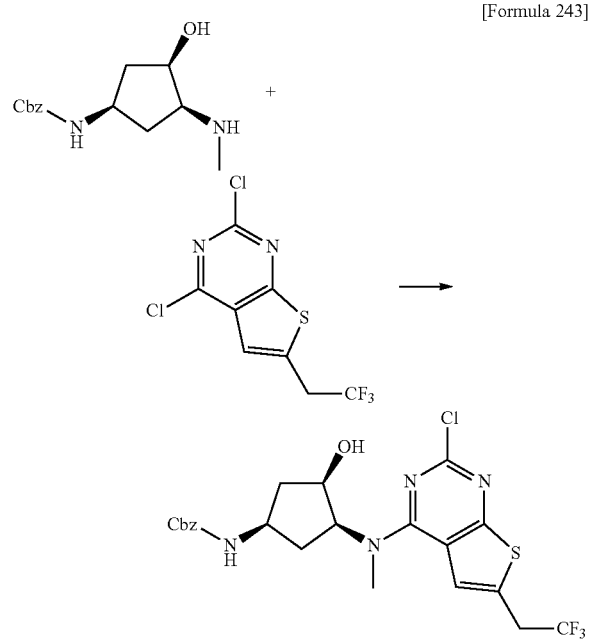

The title compound was obtained in the same manner as in Step 1 of Reference Example C-2, using the compound obtained in Step 14 of Reference Example A-1 and the compound obtained in Step 2 of Reference Example B-4.

¹H-NMR (CDCl₃) δ: 1.76-1.80 (1H, m), 2.29-2.33 (2H, m), 2.39-2.46 (1H, m), 3.14 (1H, d, J=5.5 Hz), 3.50 (3H, s), 3.61 (2H, q, J=10.2 Hz), 4.06-4.11 (1H, m), 4.55-4.58 (1H, m), 4.80 (1H, td, J=10.0, 4.7 Hz), 5.13 (2H, s), 5.39 (1H, d, J=6.7 Hz), 7.33-7.38 (6H, m).

Step 2 Benzyl [(1R,3R,4S)-3-hydroxy-4-{methyl[2-(methylamino)-6-(2,2,2-trifluoroethyl)thieno[2,3-d]pyrimidin-4-yl]amino}cyclopentyl]carbamate

[Formula 244]

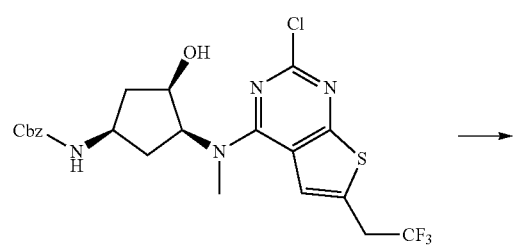

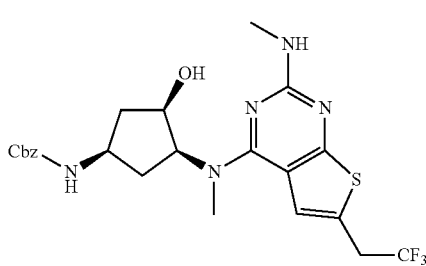

The title compound was obtained in the same manner as in Step 2 of Reference Example C-7, using the compound obtained in the above Step 1.

$^1$H-NMR (CDCl$_3$) δ: 1.71-1.76 (1H, m), 2.24-2.32 (3H, m), 2.92 (3H, d, J=5.5 Hz), 3.40 (3H, s), 3.51 (2H, q, J=10.4 Hz), 4.12 (2H, q, J=7.2 Hz), 4.43-4.47 (1H, m), 4.54-4.56 (1H, m), 4.74-4.77 (1H, m), 5.11 (2H, s), 5.38-5.42 (1H, m), 7.13 (1H, s), 7.30-7.41 (5H, m).

MS (m/z): 510 (M+H)$^+$.

Step 3 (1R,2S,4R)-4-amino-2-{methyl[2-(methylamino)-6-(2,2,2-trifluoroethyl)thieno[2,3-d]pyrimidin-4-yl]amino}cyclopentan-1-ol

[Formula 245]

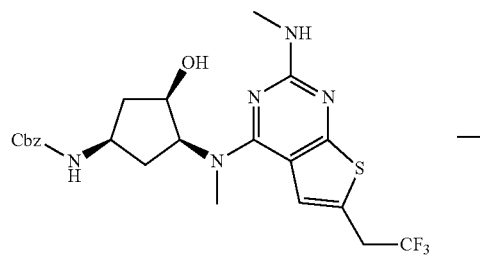

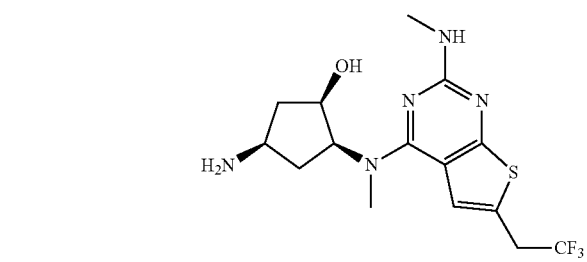

The title compound was obtained in the same manner as in Step 2 of Reference Example C-14, using the compound obtained in the above Step 2.

$^1$H-NMR (CDCl$_3$) δ: 1.62-1.66 (1H, m), 1.85-1.92 (1H, m), 2.07-2.12 (1H, m), 2.21-2.28 (1H, m), 2.96 (3H, d, J=5.5 Hz), 3.46 (3H, s), 3.52 (2H, q, J=10.4 Hz), 3.58-3.62 (1H, m), 4.47-4.50 (1H, m), 4.71-4.74 (1H, m), 4.84 (1H, td, J=9.7, 5.1 Hz), 7.19 (1H, s).

Reference Example C-21

(1R,2S,4R)-4-amino-2-{[2-chloro-6-(2,2,2-trifluoroethyl)thieno[2,3-d]pyrimidin-4-yl](methyl)amino}cyclopentan-1-ol Hydrochloride Step 1 Tert-butyl [(1R,3S,4R)-3-{[2-chloro-6-(2,2,2-trifluoroethyl)thieno[2,3-d]pyrimidin-4-yl](methyl)amino}-4-hydroxycyclopentyl]carbamate

[Formula 246]

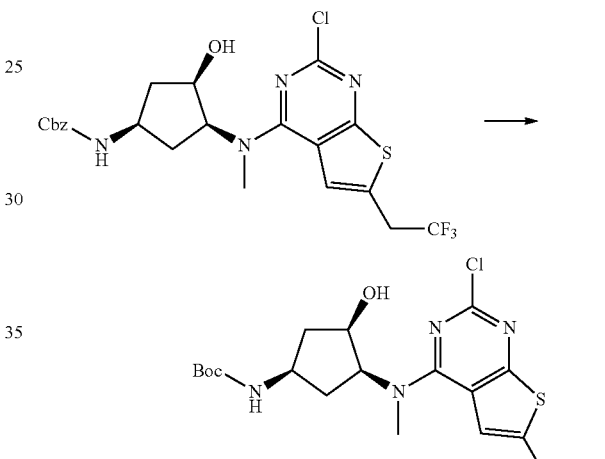

A mixture of the compound (8.41 g) obtained in Step 1 of Reference Example C-20, acetonitrile (100 mL) and iodotrimethylsilane (6.71 mL) was stirred under ice-cooling for 1 hr. Methanol (10 mL) was added thereto, the mixture was stirred for 20 min, and the solvent was evaporated under reduced pressure. THF (100 mL), water (100 mL), sodium carbonate (6.93 g) and di-tert-butyl dicarbonate (5.70 g) were added to the obtained oil, and the mixture was stirred at room temperature for 1 hr. Water and ethyl acetate were added to the reaction solution, and the mixture was subjected to liquid separation. The organic layer was washed with saturated brine, dried over anhydrous sodium sulfate, and concentrated under reduced pressure. Dichloromethane/n-hexane was added to the obtained residue, and the solid was collected by filtration to give the title compound (6.51 g) as a solid. The filtrate was concentrated, and the residue was purified by silica gel column chromatography (n-hexane/ethyl acetate) to give the title compound (0.903 g) as a solid.

$^1$H-NMR (CDCl$_3$) δ: 1.47 (9H, s), 1.74-1.77 (1H, m), 2.17-2.31 (2H, m), 2.39-2.46 (1H, m), 3.52 (3H, s), 3.57-3.69 (3H, m), 3.94-3.99 (1H, m), 4.53-4.55 (1H, m), 4.76-4.79 (1H, m), 5.13-5.15 (1H, m), 7.36 (1H, s).

MS (m/z): 481 (M+H)+.

Step 2 (1R,2S,4R)-4-amino-2-{[2-chloro-6-(2,2,2-trifluoroethyl)thieno[2,3-d]pyrimidin-4-yl](methyl)amino}cyclopentan-1-ol Hydrochloride

[Formula 247]

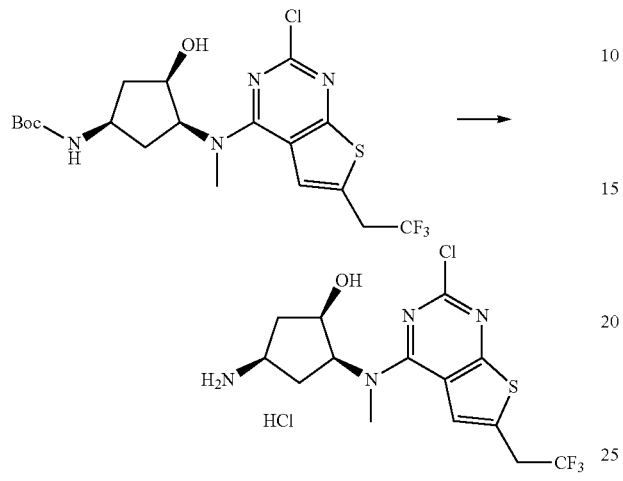

The title compound was obtained in the same manner as in Step 11 of Reference Example A-1, using the compound obtained in the above Step 1.

$^1$H-NMR (DMSO-D$_6$) δ: 1.67-1.70 (1H, m), 2.23-2.44 (3H, m), 3.41 (3H, s), 3.54-3.60 (1H, m), 4.08-4.16 (2H, m), 4.33-4.34 (1H, m), 4.79-4.81 (1H, m), 7.77 (1H, s), 8.29 (3H, s).

MS (m/z): 381 (M+H)+.

Reference Example C-22

(1S,2S,4R)-4-amino-2-{methyl[2-(methylamino)-6-(2,2,2-trifluoroethyl)thieno[2,3-d]pyrimidin-4-yl]amino}cyclopentan-1-ol Step 1 Benzyl [(1R,3S,4S)-3-{[2-chloro-6-(2,2,2-trifluoroethyl)thieno[2,3-d]pyrimidin-4-yl](methyl)amino}-4-hydroxycyclopentyl]carbamate

[Formula 248]

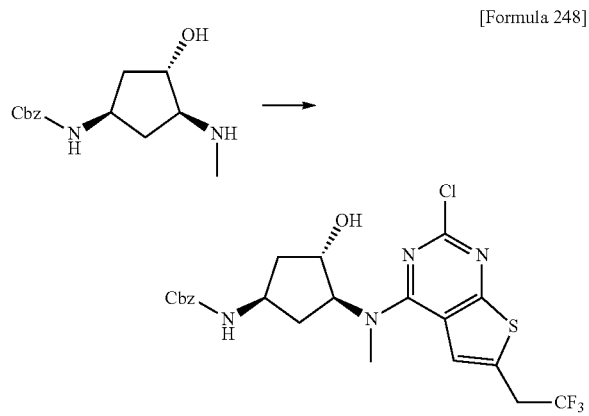 [SMILES: CN[C@H]1C[C@@H](NC(=O)OCc2ccccc2)C[C@@H]1O ; CN(c1nc(Cl)nc2sc(CC(F)(F)F)cc12)[C@H]1C[C@@H](NC(=O)OCc2ccccc2)C[C@@H]1O]

The title compound was obtained in the same manner as in Step 1 of Reference Example C-2, using the compound obtained in Step 9 of Reference Example A-14 and the compound obtained in Step 2 of Reference Example B-4.

$^1$H-NMR (CDCl$_3$) δ: 1.90-2.03 (2H, m), 2.14-2.21 (1H, m), 2.44-2.52 (1H, m), 3.35 (3H, s), 3.63 (2H, q, J=10.0 Hz), 3.96-4.05 (1H, m), 4.21-4.32 (1H, m), 4.34-4.43 (1H, m), 4.54-4.61 (1H, m), 4.92-4.99 (1H, m), 5.12 (2H, s), 7.31-7.40 (6H, m).

Step 2 Benzyl [(1R,3S,4S)-3-hydroxy-4-{methyl[2-(methylamino)-6-(2,2,2-trifluoroethyl)thieno[2,3-d]pyrimidin-4-yl]amino}cyclopentyl]carbamate

[Formula 249]

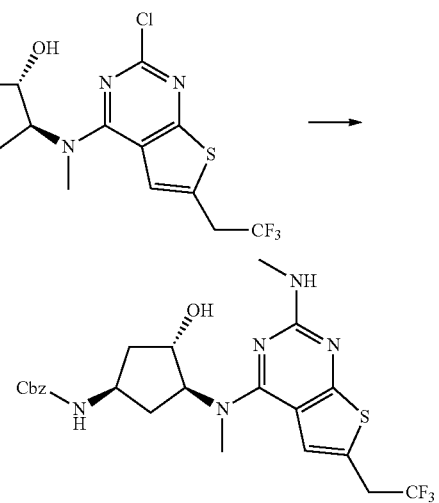

The title compound was obtained in the same manner as in Step 2 of Reference Example C-7, using the compound obtained in the above Step 1.

$^1$H-NMR (DMSO-D$_6$) δ: 1.58-1.66 (1H, m), 1.80-1.85 (2H, m), 2.23-2.31 (1H, m), 2.80 (3H, d, J=4.9 Hz), 3.07 (3H, s), 3.82 (2H, q, J=11.2 Hz), 3.98-4.06 (1H, m), 4.25-4.33 (1H, m), 4.62-4.69 (1H, m), 4.73-4.76 (1H, m), 5.03 (2H, s), 6.27-6.33 (1H, m), 7.11-7.20 (1H, m), 7.27-7.35 (5H, m), 7.38 (1H, s).

Step 3 (1S,2S,4R)-4-amino-2-{methyl[2-(methylamino)-6-(2,2,2-trifluoroethyl)thieno[2,3-d]pyrimidin-4-yl]amino}cyclopentan-1-ol

[Formula 250]

-continued

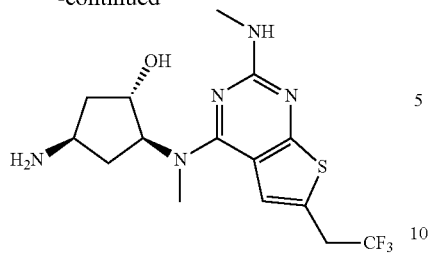

The title compound was obtained in the same manner as in Step 2 of Reference Example C-14, using the compound obtained in the above Step 2.

¹H-NMR (DMSO-D₆) δ: 1.26-1.34 (1H, m), 1.60-1.70 (2H, m), 2.13-2.23 (1H, m), 2.77 (3H, d, J=4.9 Hz), 3.14 (3H, s), 3.30-3.37 (1H, m), 3.89 (2H, q, J=11.4 Hz), 4.30-4.38 (1H, m), 4.67-4.75 (1H, m), 4.84 (1H, d, J=4.9 Hz), 6.56-6.59 (1H, m), 7.41 (1H, s).

Reference Example C-23

(1R,2S,4R)-4-amino-2-{[2-{[(4-methoxyphenyl)methyl]amino}-6-(2,2,2-trifluoroethyl)thieno[2,3-d]pyrimidin-4-yl](methyl)amino}cyclopentan-1-ol Step 1 Benzyl [(1R,3R,4S)-3-hydroxy-4-{[2-{[(4-methoxyphenyl)methyl]amino}-6-(2,2,2-trifluoroethyl)thieno[2,3-d]pyrimidin-4-yl](methyl)amino}cyclopentyl]carbamate

[Formula 251]

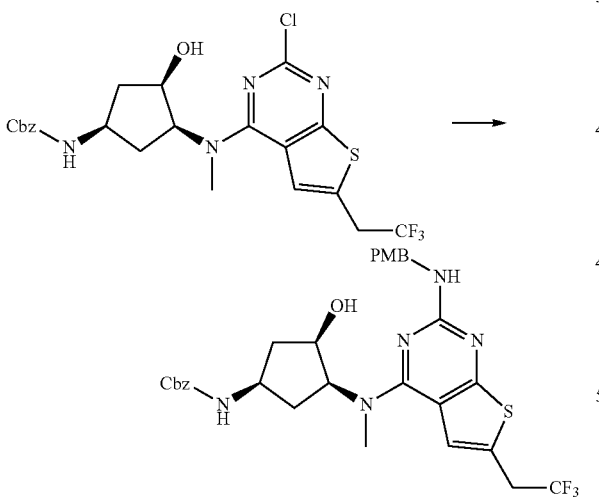

A mixture of the compound (1.57 g) obtained in Step 1 of Reference Example C-20, 4-methoxybenzylamine (1.97 mL), DIPEA (2.66 mL) and butyronitrile (9.0 mL) was stirred with heating in a microwave reactor at 150° C. for 1.5 hr. The insoluble substance in the reaction solution was filtered off, water was added to the filtrate, and the mixture was extracted with ethyl acetate. The organic layer was washed with saturated brine, dried over anhydrous sodium sulfate, and concentrated under reduced pressure, and the residue was subjected to silica gel column chromatography (chloroform/methanol) to give the title compound (1.62 g) as a solid.

¹H-NMR (CDCl₃) δ: 1.55-1.68 (2H, m), 2.12-2.29 (2H, m), 3.37 (3H, d, J=3.7 Hz), 3.51 (2H, qd, J=10.4, 3.7 Hz), 3.77 (3H, d, J=1.2 Hz), 4.00-4.10 (1H, m), 4.38 (1H, br s), 4.42-4.56 (3H, m), 5.09 (2H, br s), 5.11-5.20 (1H, m), 5.31 (1H, br s), 6.83 (2H, dd, J=8.6, 2.5 Hz), 7.14 (1H, d, J=6.1 Hz), 7.19-7.23 (2H, m), 7.28-7.38 (5H, m).

MS (m/z): 616 (M+H)⁺.

Step 2 (1R,2S,4R)-4-amino-2-{[2-{[(4-methoxyphenyl)methyl]amino}-6-(2,2,2-trifluoroethyl)thieno[2,3-d]pyrimidin-4-yl](methyl)amino}cyclopentan-1-ol

[Formula 252]

The title compound was obtained in the same manner as in Step 2 of Reference Example C-14, using the compound obtained in the above Step 1.

¹H-NMR (CDCl₃) δ: 1.54-1.60 (1H, m), 1.80 (1H, ddd, J=14.1, 9.2, 4.9 Hz), 2.00 (1H, dt, J=14.1, 5.5 Hz), 2.17 (1H, ddd, J=13.5, 9.2, 6.1 Hz), 3.44 (3H, s), 3.51 (2H, q, J=10.0 Hz), 3.53-3.57 (1H, m), 3.79 (3H, s), 4.32 (1H, s), 4.52 (2H, d, J=5.5 Hz), 4.81 (1H, td, J=9.7, 5.1 Hz), 5.09 (1H, br s), 6.84 (2H, d, J=8.6 Hz), 7.19 (1H, s), 7.24 (2H, d, J=8.6 Hz).

MS (m/z): 482 (M+H)⁺.

Reference Example C-24

2-[(4-{[(1S,2R,4R)-4-amino-2-hydroxycyclopentyl](methyl)amino}pyrimidin-5-yl)oxy]-5-fluoro-N,N-di(propan-2-yl)benzamide Step 1 Benzyl {(1R,3S,4R)-3-[(5-{2-[di(propan-2-yl)carbamoyl]-4-fluorophenoxy}pyrimidin-4-yl)(methyl)amino]-4-hydroxycyclopentyl}carbamate

[Formula 253]

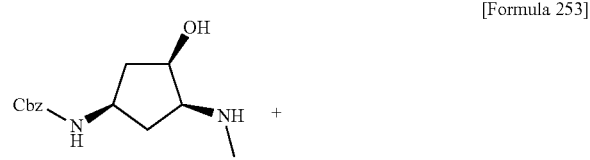

-continued

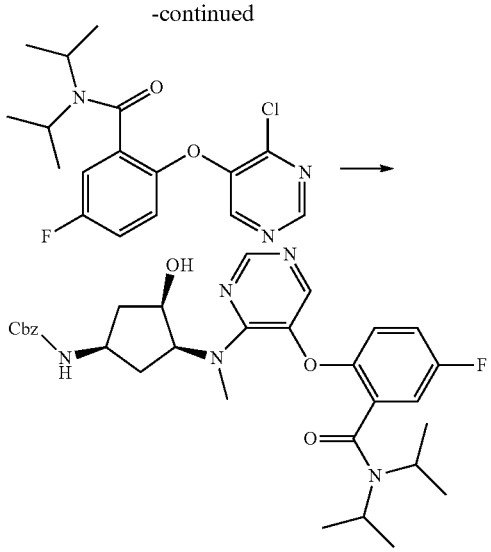

A mixture of the compound (0.233 g) obtained in Step 14 of Reference Example A-1, 2-[(4-chloropyrimidin-5-yl)oxy]-5-fluoro-N,N-di(propan-2-yl)benzamide (0.308 g) produced according to the method described in a literature (WO 2017/214367), 2-propanol (3.50 mL) and DIPEA (0.305 mL) was stirred in a microwave reactor at 110° C. for 30 min, and then stirred under the same condition for 2 hr. The compound (0.0463 g) obtained in Step 14 of Reference Example A-1 was added thereto, and the mixture was stirred at 110° C. for 2 hr in a microwave reactor, and allowed to stand at room temperature for 16 hr. The compound (0.0463 g) obtained in Step 14 of Reference Example A-1 was added thereto, and the mixture was stirred at 110° C. for 2 hr in a microwave reactor. The reaction solution was concentrated under reduced pressure, diluted with water, and extracted with ethyl acetate. The organic layer was washed with saturated brine, and dried over anhydrous sodium sulfate. The solvent was evaporated under reduced pressure, and the obtained residue was subjected to silica gel column chromatography (n-hexane/ethyl acetate, followed by ethyl acetate/methanol) to give the title compound (0.475 g) as a solid.

$^1$H-NMR (CDCl$_3$) δ: 0.97-1.77 (14H, m), 2.06-2.39 (3H, m), 3.16-3.26 (3H, m), 3.37-3.54 (1H, m), 3.68-3.88 (1H, m), 3.96-4.12 (1H, m), 4.17-4.55 (2H, m), 5.09 (2H, s), 5.29-5.43 (1H, m), 6.62-7.07 (3H, m), 7.28-7.41 (5H, m), 7.79-7.91 (1H, m), 8.37-8.44 (1H, m).

MS (m/z): 580 (M+H)$^+$.

Step 2 2-[(4-{[(1S,2R,4R)-4-amino-2-hydroxycyclopentyl](methyl)amino}pyrimidin-5-yl)oxy]-5-fluoro-N,N-di(propan-2-yl)benzamide

[Formula 254]

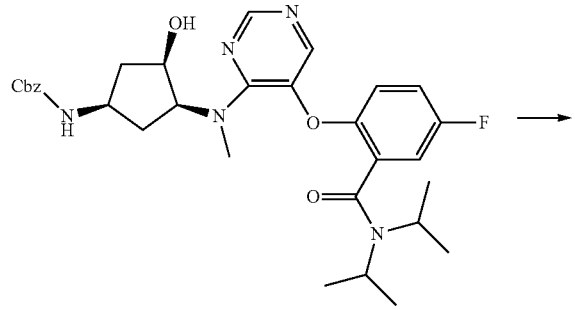

-continued

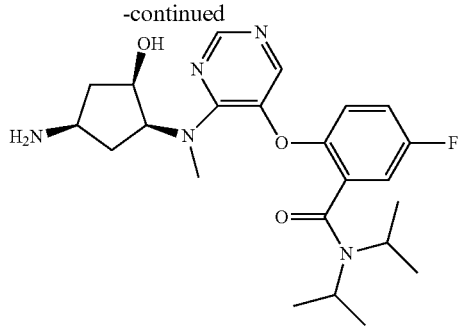

The title compound was obtained in the same manner as in Step 2 of Reference Example A-2, using the compound obtained in the above Step 1.

$^1$H-NMR (CDCl$_3$) δ: 1.01-1.22 (7H, m), 1.31-1.59 (8H, m), 1.89-1.99 (1H, m), 2.11-2.34 (3H, m), 3.17-3.23 (3H, m), 3.40-3.55 (1H, m), 3.66-3.87 (2H, m), 4.31-4.37 (1H, m), 4.55-4.71 (1H, m), 6.51-6.70 (1H, m), 6.85-7.01 (2H, m), 7.85-7.88 (1H, m), 8.44 (1H, s).

MS (m/z): 446 (M+H)$^+$.

Reference Example C-25

(1R,2S,4R)-4-amino-2-[(5-{4-fluoro-2-[4-(propan-2-yl)pyrimidin-5-yl]phenoxy}pyrimidin-4-yl)(methyl)amino]cyclopentan-1-ol Step 1 Benzyl [(1R,3S,4R)-3-{[5-(2-bromo-4-fluorophenoxy)pyrimidin-4-yl](methyl)amino}-4-hydroxycyclopentyl]carbamate

[Formula 255]

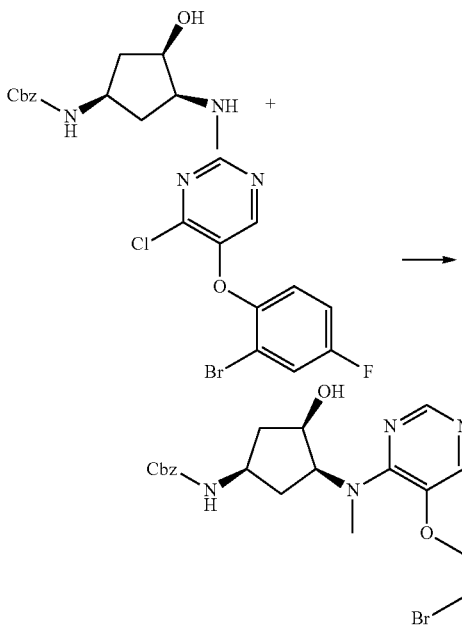

The title compound was obtained in the same manner as in Step 1 of Reference Example C-2, using the compound obtained in Step 14 of Reference Example A-1 and 5-(2-bromo-4-fluorophenoxy)-4-chloropyrimidine produced according to the method described in a literature (WO 2017/214367).

$^1$H-NMR (CDCl$_3$) δ: 1.65-1.69 (1H, m), 2.19-2.27 (3H, m), 3.14-3.20 (1H, m), 3.25 (3H, s), 4.08-4.12 (1H, m), 4.39-4.41 (2H, m), 5.10 (2H, s), 5.23-5.26 (1H, m), 6.68-6.72 (1H, m), 6.96-6.99 (1H, m), 7.34-7.40 (5H, m), 7.83 (1H, s), 8.42 (1H, s).

MS (m/z): 531, 533 (M+H)⁺.

Step 2 Benzyl {(1R,3S,4R)-3-[(5-{4-fluoro-2-[4-(propan-2-yl)pyrimidin-5-yl]phenoxy}pyrimidin-4-yl)(methyl)amino]-4-hydroxycyclopentyl}carbamate

[Formula 256]

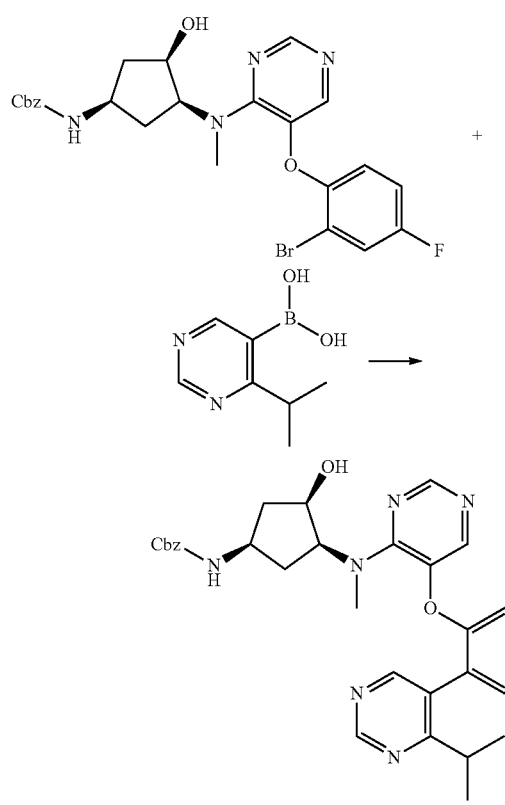

A mixture of the compound (140 mg) obtained in the above Step 1, 4-isopropylpyrimidine-5-boronic acid (CAS: 913835-27-5) (52.5 mg), tetrakis(triphenylphosphine)palladium(0) (30.4 mg), sodium carbonate (112 mg), water (1.1 mL) and 1,4-dioxane (3.3 mL) was stirred at 90° C. for 1.5 hr. Water was added to the reaction solution, and the mixture was extracted with ethyl acetate. The organic layer was washed with saturated brine, dried over anhydrous sodium sulfate, and concentrated under reduced pressure. The residue was subjected to silica gel column chromatography (n-hexane/ethyl acetate). n-Hexane/ethyl acetate was added to the obtained residue, and the resulting solid was collected by filtration to give the title compound (92.5 mg) as a solid.

¹H-NMR (CDCl₃) δ: 1.22-1.26 (6H, m), 1.66-1.69 (1H, m), 2.12-2.23 (3H, m), 3.01-3.07 (4H, m), 3.49-3.50 (1H, m), 3.99-4.06 (1H, m), 4.34-4.37 (1H, m), 5.10 (2H, s), 5.30 (1H, s), 6.81 (1H, s), 7.01-7.03 (1H, m), 7.09-7.14 (1H, m), 7.30-7.39 (5H, m), 7.79-7.82 (1H, m), 8.33-8.35 (1H, m), 8.47 (1H, s), 9.15 (1H, s).

MS (m/z): 573 (M+H)⁺.

Step 3 (1R,2S,4R)-4-amino-2-[(5-{4-fluoro-2-[4-(propan-2-yl)pyrimidin-5-yl]phenoxy}pyrimidin-4-yl)(methyl)amino]cyclopentan-1-ol

[Formula 257]

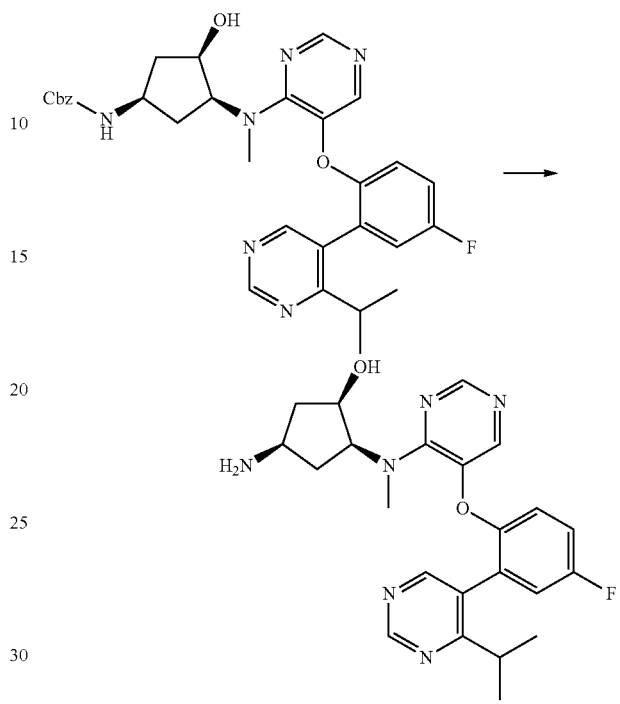

The title compound was obtained in the same manner as in Step 2 of Reference Example C-14, using the compound obtained in the above Step 2.

¹H-NMR (DMSO-D₆) δ: 1.15-1.21 (7H, m), 1.71-1.76 (3H, m), 1.98-2.01 (1H, m), 2.32-2.34 (1H, m), 2.99-3.01 (5H, m), 4.01-4.08 (1H, m), 4.33-4.35 (1H, m), 6.89-6.91 (1H, m), 7.30-7.32 (1H, m), 7.39-7.41 (1H, m), 7.90-7.94 (1H, m), 8.33 (1H, s), 8.64-8.67 (1H, m), 9.17 (1H, s).

MS (m/z): 439 (M+H)⁺.

Reference Example C-26

(1R,2S,4R)-4-amino-2-[(5-{[5-fluoro-2'-(propan-2-yl)[1,1'-biphenyl]-2-yl]oxy}pyrimidin-4-yl)(methyl)amino]cyclopentan-1-ol Step 1 Benzyl {(1R,3S,4R)-3-[(5-{[5-fluoro-2'-(propan-2-yl)[1,1'-biphenyl]-2-yl]oxy}pyrimidin-4-yl)(methyl)amino]-4-hydroxycyclopentyl}carbamate

[Formula 258]

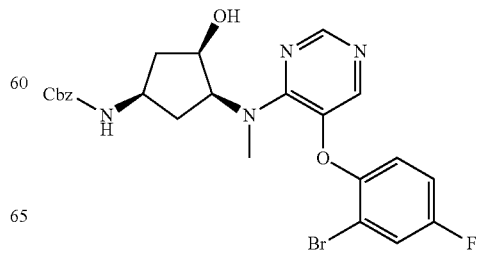

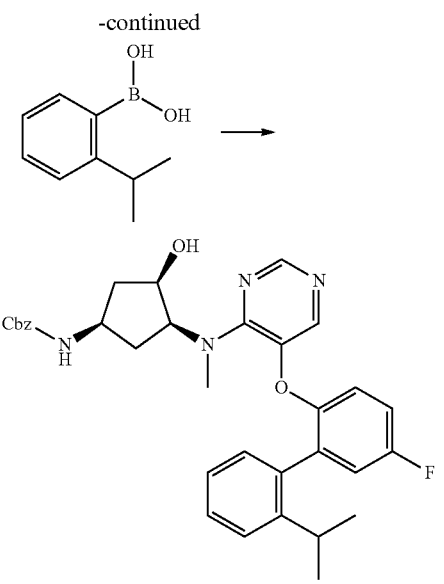

The title compound was obtained in the same manner as in Step 2 of Reference Example C-25, using the compound obtained in Step 1 of Reference Example C-25 and 2-isopropylphenylboronic acid (CAS: 89787-12-2).

MS (m/z): 571 (M+H)⁺.

Step 2 (1R,2S,4R)-4-amino-2-[(5-{[5-fluoro-2'-(propan-2-yl)[1,1'-biphenyl]-2-yl]oxy}pyrimidin-4-yl)(methyl)amino]cyclopentan-1-ol

[Formula 259]

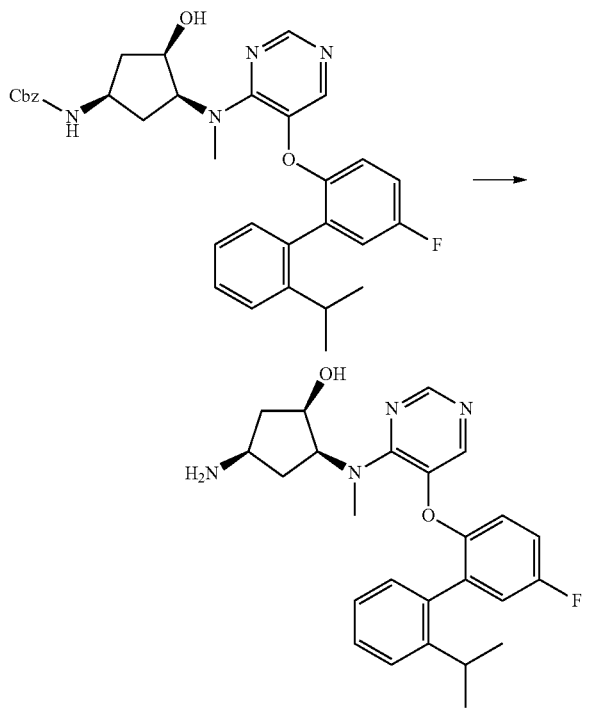

The title compound was obtained in the same manner as in Step 2 of Reference Example C-14, using the compound obtained in the above Step 1.

MS (m/z): 437 (M+H)⁺.

Reference Example C-27

(1R,2S,4R)-4-amino-2-[(5-{4-fluoro-2-[1-(propan-2-yl)-1H-pyrazol-5-yl]phenoxy}pyrimidin-4-yl)(methyl)amino]cyclopentan-1-ol Step 1 Benzyl {(1R,3S,4R)-3-[(5-{4-fluoro-2-[1-(propan-2-yl)-1H-pyrazol-5-yl]phenoxy}pyrimidin-4-yl)(methyl)amino]-4-hydroxycyclopentyl}carbamate

[Formula 260]

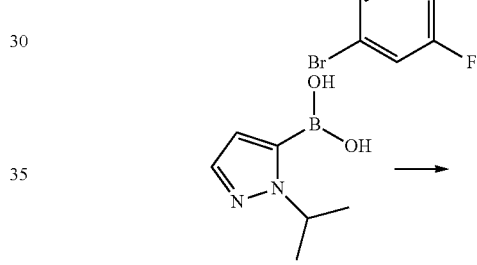

+

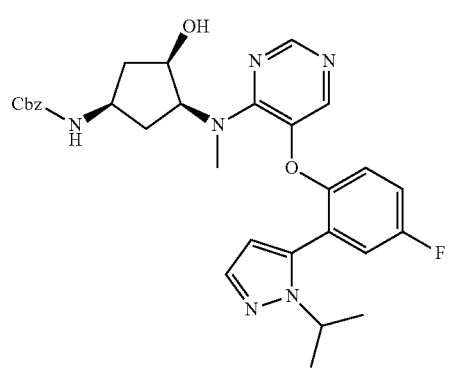

The title compound was obtained in the same manner as in Step 2 of Reference Example C-25, using the compound obtained in Step 1 of Reference Example C-25 and 1-isopropylpyrazole-5-boronic acid (CAS: 839714-33-9).

¹H-NMR (CDCl₃) δ: 1.41-1.45 (6H, m), 1.63-1.66 (1H, m), 2.10-2.25 (3H, m), 3.06 (3H, s), 3.26-3.29 (1H, m), 4.00-4.03 (1H, m), 4.20-4.25 (1H, m), 4.32-4.38 (2H, m), 5.09 (2H, s), 5.29-5.31 (1H, m), 6.16-6.16 (1H, m), 6.74-6.77 (1H, m), 7.06-7.12 (2H, m), 7.33-7.36 (4H, m), 7.57 (1H, s), 7.85 (1H, s), 8.39 (1H, s).

MS (m/z): 561 (M+H)⁺.

195

Step 2 (1R,2S,4R)-4-amino-2-[(5-{4-fluoro-2-[1-(propan-2-yl)-1H-pyrazol-5-yl]phenoxy}pyrimidin-4-yl)(methyl)amino]cyclopentan-1-ol

[Formula 261]

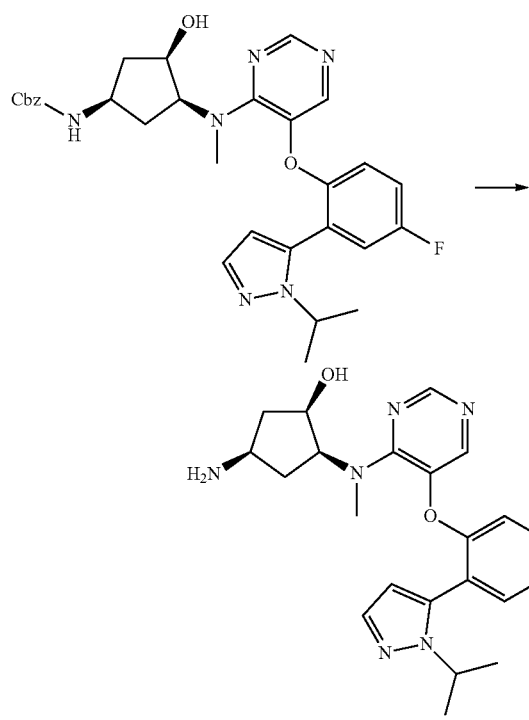

The title compound was obtained in the same manner as in Step 2 of Reference Example C-14, using the compound obtained in the above Step 1.

$^1$H-NMR (CDCl$_3$) δ: 1.41-1.59 (9H, m), 1.68-1.75 (2H, m), 1.86-1.93 (1H, m), 2.09-2.11 (1H, m), 3.12-3.14 (3H, m), 3.53-3.58 (1H, m), 4.26-4.27 (1H, m), 4.35-4.38 (1H, m), 4.56-4.59 (1H, m), 6.18 (1H, d, J=1.8 Hz), 6.76-6.78 (1H, m), 7.02-7.11 (2H, m), 7.58 (1H, d, J=1.8 Hz), 7.83 (1H, s), 8.40 (1H, s).

MS (m/z): 427 (M+H)$^+$.

Reference Example C-28

6-[(4-{[(1S,2R,4R)-4-amino-2-hydroxycyclopentyl](methyl)amino}pyrimidin-5-yl)oxy]-2,3-difluoro-N,N-di(propan-2-yl)benzamide Step 1 Benzyl {(1R,3S,4R)-3-[(5-{2-[di(propan-2-yl)carbamoyl]-3,4-difluorophenoxy}pyrimidin-4-yl)(methyl)amino]-4-hydroxycyclopentyl}carbamate

[Formula 262]

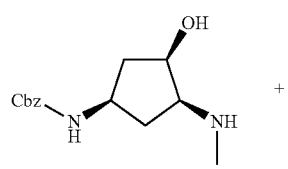 +

196

-continued

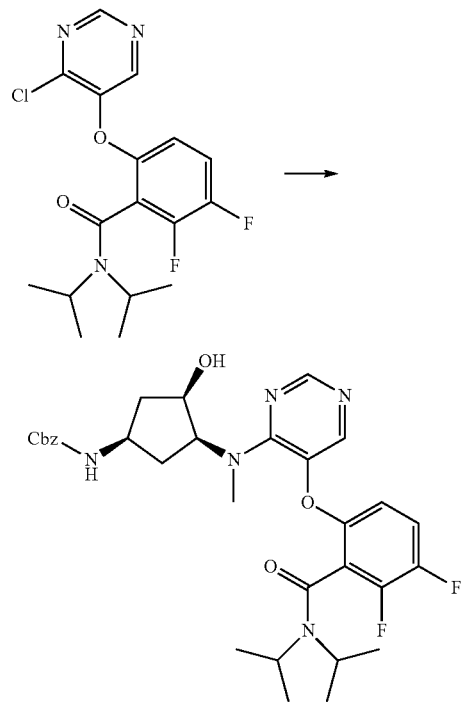

The title compound was obtained in the same manner as in Step 1 of Reference Example C-2, using the compound obtained in Step 14 of Reference Example A-1 and the compound obtained in Step 5 of Reference Example B-10.

$^1$H-NMR (CDCl$_3$) δ: 1.09-1.10 (1H, m), 1.20-1.25 (5H, m), 1.43-1.46 (3H, m), 1.53-1.55 (3H, m), 1.64-1.73 (1H, m), 2.08-2.25 (2H, m), 2.32-2.41 (1H, m), 3.20-3.22 (3H, m), 3.49-3.54 (1H, m), 3.78-3.84 (1H, m), 4.01-4.08 (1H, m), 4.23-4.47 (2H, m), 5.09 (2H, s), 5.30-5.32 (1H, m), 6.38-6.42 (1H, m), 7.03-7.08 (1H, m), 7.30-7.38 (5H, m), 7.89 (1H, d, J=14.1 Hz), 8.44 (1H, d, J=3.7 Hz).

MS (m/z): 598 (M+H)$^+$.

Step 2 6-[(4-{[(1S,2R,4R)-4-amino-2-hydroxycyclopentyl](methyl)amino}pyrimidin-5-yl)oxy]-2,3-difluoro-N,N-di(propan-2-yl)benzamide

[Formula 263]

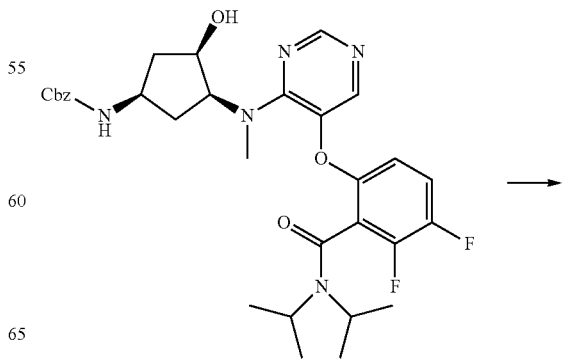

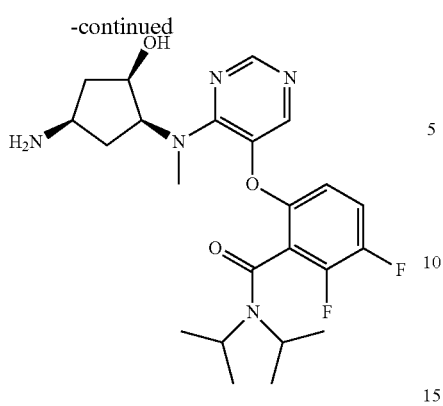

The title compound was obtained in the same manner as in Step 2 of Reference Example C-14, using the compound obtained in the above Step 1.
MS (m/z): 464 (M+H)⁺.

Reference Example C-29

Tert-butyl [(1S,3R)-3-{[6-(cyclopropylmethyl)thieno[2,3-d]pyrimidin-4-yl](methyl)amino}cyclopentyl]carbamate

[Formula 264]

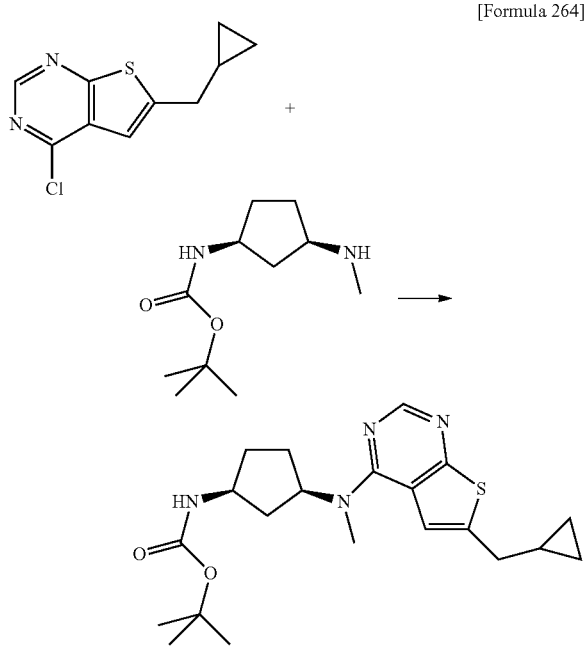

To tert-butyl [(1S,3R)-3-(methylamino)cyclopentyl]carbamate (200 mg) and the compound (210 mg) obtained in Step 2 of Reference Example B-2 were added 2-propanol (5 mL) and DIPEA (0.325 mL), and the mixture was heated under reflux for 6 hr. Ethyl acetate and saturated brine were added to the reaction solution, and the mixture was subjected to liquid separation. The organic layer was washed with saturated brine, dried over anhydrous sodium sulfate, and concentrated under reduced pressure. The obtained residue was purified by silica gel column chromatography (n-hexane/ethyl acetate) to give the title compound (205 mg) as an oil.

¹H-NMR (CDCl₃) δ: 0.27-0.31 (2H, m), 0.60-0.64 (2H, m), 1.02-1.12 (1H, m), 1.46 (9H, s), 1.58-1.71 (2H, m), 1.84-2.13 (3H, m), 2.35-2.42 (1H, m), 2.76 (2H, d, J=7.3 Hz), 3.25 (3H, s), 3.97-4.04 (1H, m), 4.97-5.08 (1H, m), 5.11-5.20 (1H, m), 7.12 (1H, s), 8.39 (1H, s).
MS (m/z): 403 (M+H)⁺.

Reference Example C-30

(1R,2R,4S)-2-amino-4-{methyl[6-(2,2,2-trifluoroethyl)thieno[2,3-d]pyrimidin-4-yl]amino}cyclopentan-1-ol Hydrochloride Step 1 Tert-butyl [(1R,2R,4S)-2-(methoxymethoxy)-4-{methyl[6-(2,2,2-trifluoroethyl)thieno[2,3-d]pyrimidin-4-yl]amino}cyclopentyl]carbamate

[Formula 265]

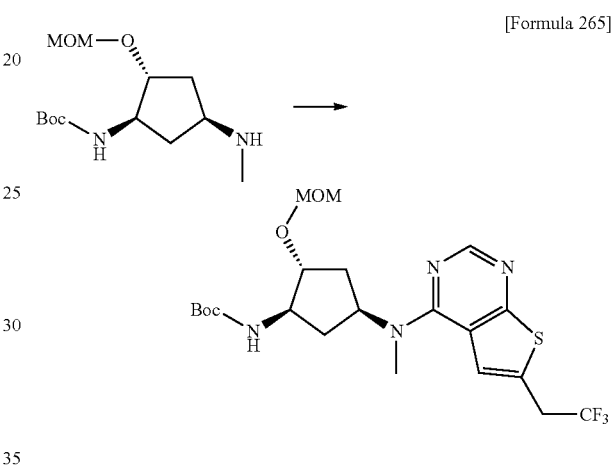

A mixture of the compound (0.370 g) obtained in Step 7 of Reference Example A-12, 4-chloro-6-(2,2,2-trifluoroethyl)thieno[2,3-d]pyrimidine (0.358 g), DIPEA (0.469 mL) and 2-propanol (15.0 mL) was stirred at 100° C. for 10 hr. The mixture was concentrated under reduced pressure, and the obtained residue was subjected to silica gel column chromatography (n-hexane/ethyl acetate) to give the title compound (0.592 g) as a solid.

¹H-NMR (DMSO-D₆, 80° C.) δ: 1.40 (9H, s), 1.65-1.73 (1H, m), 1.85-1.92 (1H, m), 2.04-2.11 (1H, m), 2.21-2.28 (1H, m), 3.21 (3H, s), 3.28 (3H, s), 3.75-3.83 (1H, m), 3.95-4.06 (3H, m), 4.60 (1H, d, J=6.7 Hz), 4.67 (1H, d, J=6.7 Hz), 5.24-5.34 (1H, m), 6.73-6.82 (1H, m), 7.61 (1H, s), 8.34 (1H, s).

Step 2 (1R,2R,4S)-2-amino-4-{methyl[6-(2,2,2-trifluoroethyl)thieno[2,3-d]pyrimidin-4-yl]amino}cyclopentan-1-ol Hydrochloride

[Formula 266]

-continued

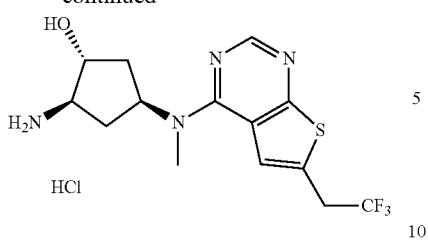

A mixture of the compound (0.162 g) obtained in the above Step 1, hydrogen chloride (4 mol/L, 1,4-dioxane solution, 5 mL) and methanol (5 mL) was stirred at room temperature for 1 hr. The mixture was concentrated, and the residue was dried to give the title compound (0.138 g) as a solid. This was directly used in the next step.

Reference Example C-31

(1S,2R,4S)-2-amino-4-{methyl[6-(2,2,2-trifluoroethyl)thieno[2,3-d]pyrimidin-4-yl]amino}cyclopentan-1-ol Step 1 Tert-butyl [(1R,2S,4S)-2-(methoxymethoxy)-4-{methyl[6-(2,2,2-trifluoroethyl)thieno[2,3-d]pyrimidin-4-yl]amino}cyclopentyl]carbamate

[Formula 267]

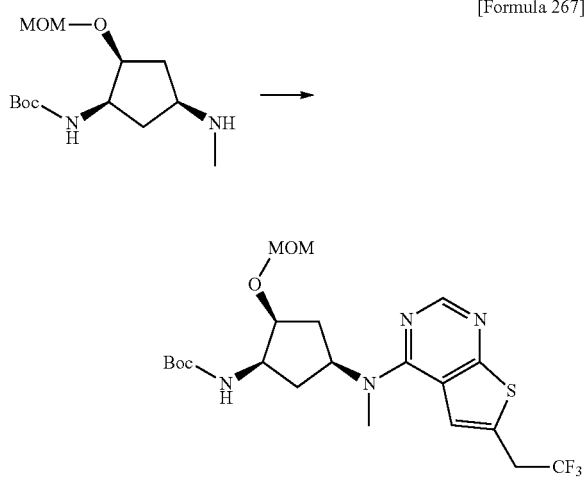

A mixture of tert-butyl [(1R,2S,4S)-2-(methoxymethoxy)-4-(methylamino)cyclopentyl]carbamate (0.414 g), 4-chloro-6-(2,2,2-trifluoroethyl)thieno[2,3-d]pyrimidine (0.400 g), 2-propanol (15.0 mL) and DIPEA (0.525 mL) was stirred at 100° C. for 4 hr. The mixture was concentrated under reduced pressure, and the obtained residue was subjected to silica gel column chromatography (n-hexane/ethyl acetate) to give the title compound (0.662 g) as a solid.

$^1$H-NMR (CDCl$_3$) δ: 1.46 (9H, s), 1.75-1.90 (2H, m), 2.24-2.42 (2H, m), 3.30 (3H, s), 3.42 (3H, s), 3.63 (2H, q, J=10.1 Hz), 3.93-4.03 (1H, m), 4.07-4.14 (1H, m), 4.70 (1H, d, J=6.7 Hz), 4.76 (1H, d, J=6.7 Hz), 5.11-5.19 (1H, m), 5.37-5.50 (1H, m), 7.33 (1H, s), 8.42 (1H, s).

Step 2 (1S,2R,4S)-2-amino-4-{methyl[6-(2,2,2-trifluoroethyl)thieno[2,3-d]pyrimidin-4-yl]amino}cyclopentan-1-ol

[Formula 268]

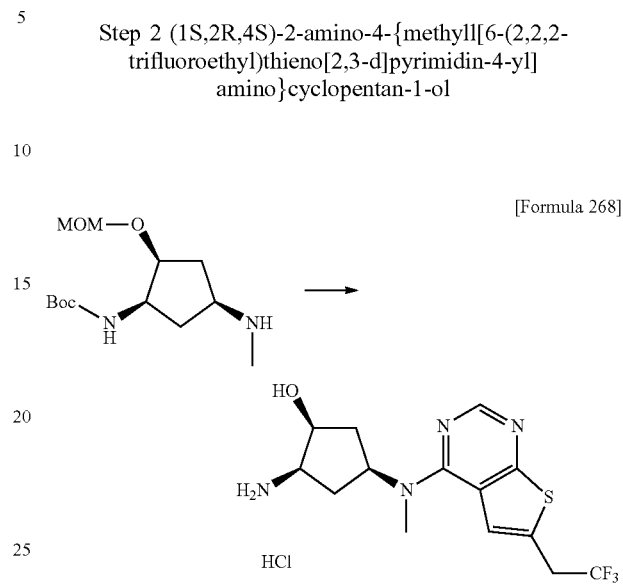

The title compound was obtained in the same manner as in Step 11 of Reference Example A-1, using the compound obtained in the above Step 1. This compound was directly used in the next reaction.

Reference Example C-32

(1R,3S,5R)-5-(1,3-oxazol-2-yl)-N$^1$-[6-(2,2,2-trifluoroethyl)thieno[2,3-d]pyrimidin-4-yl]cyclohexane-1,3-diamine (Racemate)

Step 1 Methyl (1S,3S,5R)-3-{[(benzyloxy)carbonyl]amino}-5-{[6-(2,2,2-trifluoroethyl)thieno[2,3-d]pyrimidin-4-yl]amino}cyclohexane-1-carboxylate (Racemate)

[Formula 269]

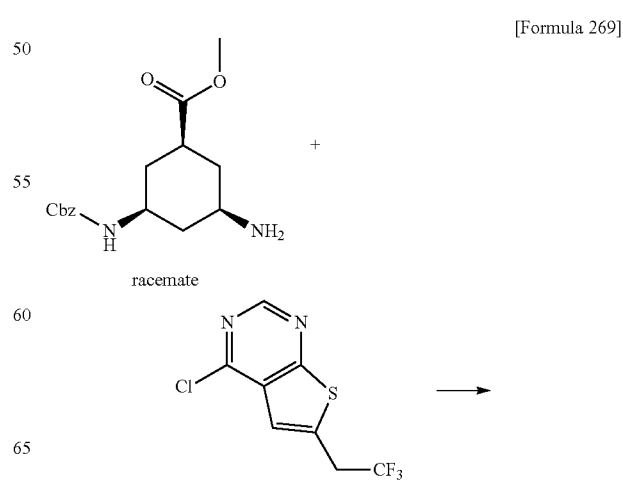

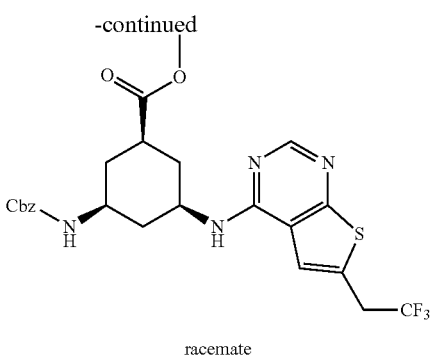

racemate

The title compound was obtained in the same manner as in Step 1 of Reference Example C-2, using the compound obtained in Step 4 of Reference Example A-9 and chloro-6-(2,2,2-trifluoroethyl)thieno[2,3-d]pyrimidine produced according to the method described in a literature (cancer cell 2015, 27, 589-602.).

$^{1}$H-NMR (CDCl$_3$) δ: 1.12-1.47 (3H, m), 2.31-2.53 (3H, m), 2.60-2.72 (1H, m), 3.53-3.87 (6H, m), 4.31-4.44 (1H, m), 4.73-4.83 (1H, m), 5.00-5.20 (3H, m), 7.03 (1H, s), 7.29-7.40 (5H, m), 8.47 (1H, s).

MS (m/z): 523 (M+H)$^+$.

Step 2 (1S,3S,5R)-3-{[(benzyloxy)carbonyl]amino}-5-{[6-(2,2,2-trifluoroethyl)thieno[2,3-d]pyrimidin-4-yl]amino}cyclohexane-1-carboxylic Acid (Racemate)

[Formula 270]

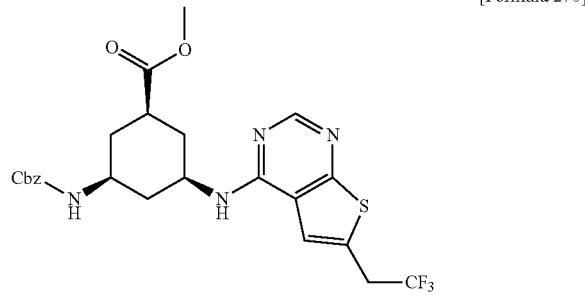

racemate

A mixture of the compound (1.00 g) obtained in the above Step 1, THF (15.0 mL) and lithium hydroxide monohydrate (210 mg) was stirred at room temperature for 2 hr. The reaction mixture was concentrated under reduced pressure, the residue was acidified (pH3-4) to with 2N hydrochloric acid (2.00 mL) at 0° C., and the mixture was extracted with ethyl acetate. The organic layer was washed with saturated brine, and dried over anhydrous sodium sulfate. The solvent was evaporated under reduced pressure to give the title compound (0.949 g) as a solid.

$^{1}$H-NMR (DMSO-D$_6$) δ: 1.15-1.41 (3H, m), 1.96-2.17 (3H, m), 2.38-2.52 (1H, m), 3.43-3.59 (1H, m), 4.01-4.13 (2H, m), 4.14-4.27 (1H, m), 5.01 (2H, s), 7.27-7.44 (6H, m), 7.64 (1H, s), 7.86-7.92 (1H, m), 8.34 (1H, s).

MS (m/z): 509 (M+H)$^+$.

Step 3 Benzyl [(1S,3S,5R)-3-[(2,2-dimethoxyethyl)carbamoyl]-5-{[6-(2,2,2-trifluoroethyl)thieno[2,3-d]pyrimidin-4-yl]amino}cyclohexyl]carbamate (Racemate)

[Formula 271]

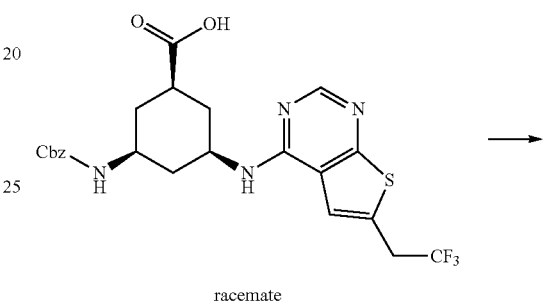

racemate

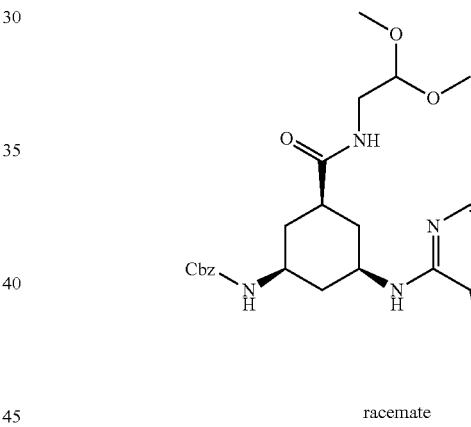

racemate

To a solution of the compound (0.455 g) obtained in the above Step 2 in DMF (4.50 mL) were successively added COMU (CAS: 1075198-30-9) (0.471 g), DIPEA (0.234 mL) and aminoacetaldehyde dimethylacetal (CAS: 22483-09-6) (0.118 mL) at 0° C., and the mixture was stirred at room temperature for 16 hr. The reaction mixture was poured into water, and extracted with a mixed solvent of ethyl acetate/diethyl ether. The organic layer was washed successively with water (three times) and saturated brine, and dried over anhydrous sodium sulfate. The solvent was evaporated under reduced pressure, and the obtained residue was subjected to silica gel column chromatography (n-hexane/ethyl acetate, followed by ethyl acetate/methanol) to give the title compound (0.491 g) as a solid.

$^{1}$H-NMR (CDCl$_3$) δ: 1.21-1.37 (1H, m), 1.45-1.64 (2H, m), 2.13-2.29 (2H, m), 2.38-2.50 (2H, m), 3.33-3.43 (8H, m), 3.56-3.68 (2H, m), 3.70-3.83 (1H, m), 4.31-4.47 (2H, m), 4.94-5.10 (3H, m), 5.43-5.60 (1H, m), 5.77-5.87 (1H, m), 7.10 (1H, br s), 7.28-7.38 (5H, m), 8.46 (1H, s).

MS (m/z): 596 (M+H)$^+$.

203

Step 4 Benzyl [(1S,3S,5R)-3-[(2-oxoethyl)carbamoyl]-5-{[6-(2,2,2-trifluoroethyl)thieno[2,3-d]pyrimidin-4-yl]amino}cyclohexyl]carbamate (Racemate)

[Formula 272]

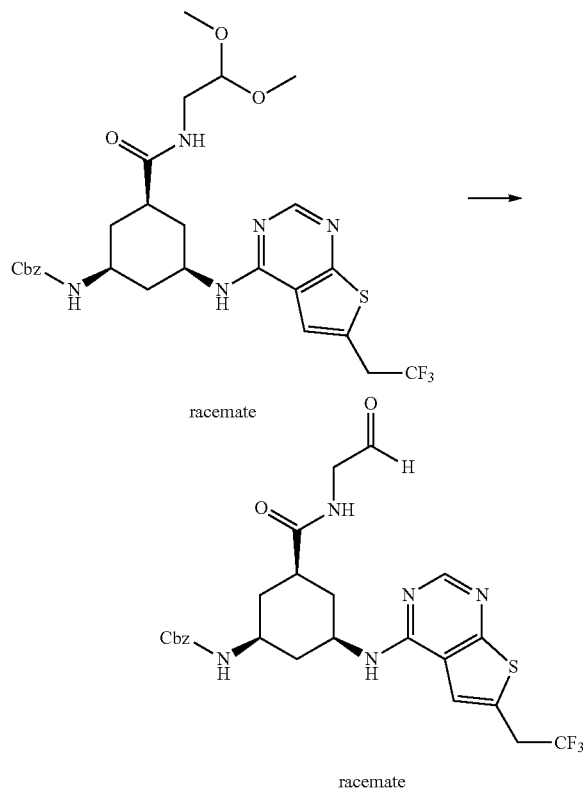

racemate

To a solution of the compound (0.491 g) obtained in the above Step 3 in dichloromethane (80.0 mL) was added trifluoroacetic acid (24.0 mL) at room temperature, and the mixture was stirred at the same temperature for 16 hr. The mixture was stirred with heating under reflux for additional 2 hr. The solvent was evaporated under reduced pressure, ethyl acetate and saturated aqueous sodium hydrogencarbonate solution were added to the obtained residue, and the mixture was extracted with ethyl acetate. The organic layer was washed with saturated brine, and dried over anhydrous sodium sulfate. The solvent was evaporated under reduced pressure, and the residue was dried to give the title compound as a solid. This was directly used in the next step.
MS (m/z): 550 (M+H)+.

Step 5 Benzyl [(1S,3S,5R)-3-(1,3-oxazol-2-yl)-5-{[6-(2,2,2-trifluoroethyl)thieno[2,3-d]pyrimidin-4-yl]amino}cyclohexyl]carbamate (Racemate)

[Formula 273]

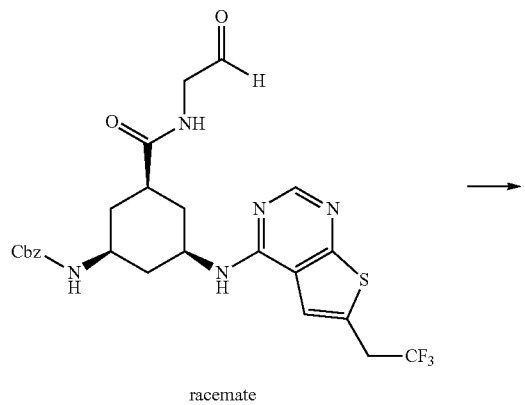

racemate

204

-continued

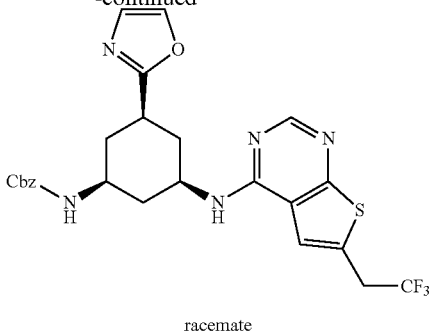

racemate

To a solution of the compound (0.382 g) obtained in the above Step 4 in dichloromethane (7.00 mL) were added triphenylphosphine (0.273 g), hexachloroethane (CAS: 67-72-1) (0.247 g) and TEA (0.193 mL) at room temperature, and the mixture was stirred for 3 days. The reaction mixture was concentrated under reduced pressure, and the residue was subjected to silica gel column chromatography (ethyl acetate/methanol) to give a mixture containing the objective product as an oil. This compound was used in the next step without further purification.

Step 6 (1R,3S,5R)-5-(1,3-oxazol-2-yl)-$N^1$-[6-(2,2,2-trifluoroethyl)thieno[2,3-d]pyrimidin-4-yl]cyclohexane-1,3-diamine (Racemate)

[Formula 274]

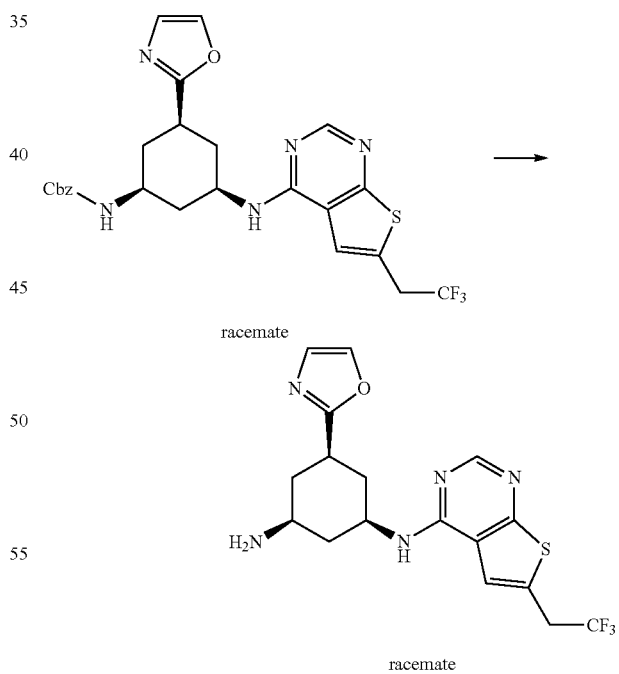

To a solution of the compound obtained in the above Step 5 in acetonitrile (15.0 mL) was added iodotrimethylsilane (0.239 mL) at 0° C., and the mixture was stirred at room temperature for 2 hr. Additional iodotrimethylsilane (0.239 mL) was added thereto, and the mixture was stirred for 0.5 hr. The solvent was evaporated under reduced pressure, and the obtained residue was subjected to amino silica gel column chromatography (n-hexane/ethyl acetate, followed by ethyl acetate/methanol) to give the title compound (0.0472 g) as an oil.

$^1$H-NMR (CDCl$_3$) δ: 1.13-1.72 (5H, m), 2.29-2.44 (2H, m), 2.54-2.63 (1H, m), 3.05-3.18 (2H, m), 3.57-3.70 (2H, m), 4.37-4.50 (1H, m), 5.11-5.25 (1H, m), 6.97-7.07 (2H, m), 7.57 (1H, s), 8.48 (1H, s).

MS (m/z): 398 (M+H)$^+$.

Reference Example C-33

Tert-butyl [(1R,2R,3S,4S)-2,3-dihydroxy-4-{methyl [6-(2,2,2-trifluoroethyl)thieno[2,3-d]pyrimidin-4-yl] amino}cyclopentyl]carbamate (Isomer A)

Tert-butyl [(1R,2S,3R,4S)-2,3-dihydroxy-4-{methyl [6-(2,2,2-trifluoroethyl)thieno[2,3-d]pyrimidin-4-yl] amino}cyclopentyl]carbamate (Isomer B)

Step 1 Tert-butyl prop-2-en-1-yl (1R,3S)-cyclopent-4-ene-1,3-diylbiscarbamate

[Formula 275]

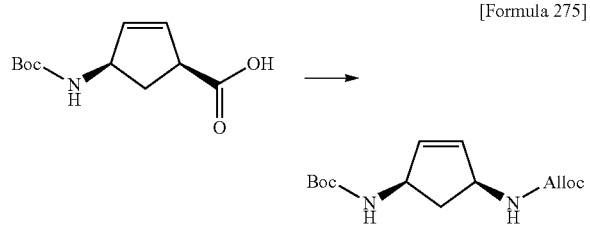

The title compound was obtained in the same manner as in Step 4 of Reference Example A-6, using (1S,4R)-4-[(tert-butoxycarbonyl)amino]cyclopent-2-ene-1-carboxylic acid (1.00 g) synthesized according to the method described in a literature (Eur. J. Org. Chem. 2013, 17, 3477-3493).

$^1$H-NMR (CDCl$_3$) δ: 1.45-1.46 (11H, m), 2.81-2.90 (1H, m), 4.60-4.91 (5H, m), 5.21-5.23 (1H, m), 5.30-5.32 (1H, m), 5.79-5.96 (3H, m).

MS (m/z): 183 (M+H-Boc)$^+$.

Step 2 Tert-butyl [(1R,4S)-4-aminocyclopent-2-en-1-yl]carbamate

[Formula 276]

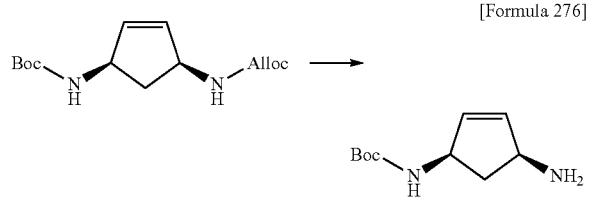

A mixture of the compound (2.87 g) obtained in the above Step 2, dichloromethane (15 mL), pyrrolidine (0.366 mL) and tetrakis(triphenylphosphine)palladium(0) (41 mg) was stirred at room temperature for 1 hr. The mixture was concentrated under reduced pressure, and the residue was purified by silica gel column chromatography (ethyl acetate/methanol) to give the title compound (1.35 g, containing a small amount of a stereoisomer) as an oil.

$^1$H-NMR (CDCl$_3$) δ: 1.11-1.18 (1H, m), 1.45 (9H, s), 2.76-2.83 (1H, m), 3.85-3.88 (1H, m), 4.61-4.67 (2H, m), 5.77-5.85 (2H, m).

MS (m/z): 199 (M+H)$^+$.

Step 3 Tert-butyl {(1R,4S)-4-[(2-nitrobenzene-1-sulfonyl)amino]cyclopent-2-en-1-yl}carbamate

[Formula 277]

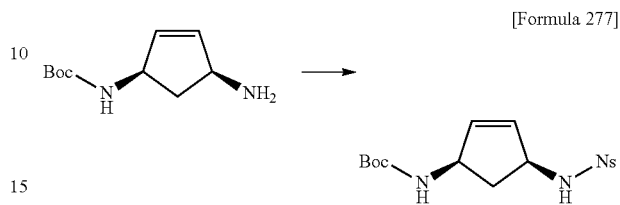

The title compound (containing a small amount of a stereoisomer) was obtained in the same manner as in Step 12 of Reference Example A-1, using the compound obtained in the above Step 2.

$^1$H-NMR (CDCl$_3$) δ: 1.37-1.40 (10H, m), 2.63-2.67 (1H, m), 4.46-4.49 (2H, m), 4.71-4.75 (1H, m), 5.76-5.83 (3H, m), 7.73-7.78 (2H, m), 7.85-7.89 (1H, m), 8.17-8.18 (1H, m).

Step 4 Tert-butyl {(1R,4S)-4-[methyl(2-nitrobenzene-1-sulfonyl)amino]cyclopent-2-en-1-yl}carbamate

[Formula 278]

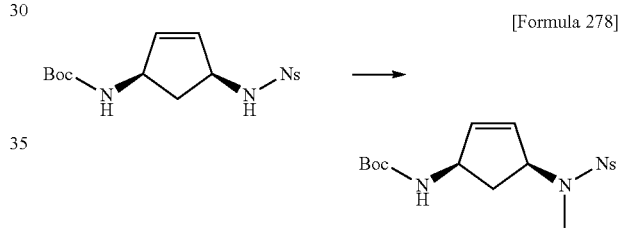

The title compound (containing a small amount of a stereoisomer) was obtained in the same manner as in Step 13 of Reference Example A-1, using the compound obtained in the above Step 3.

$^1$H-NMR (CDCl$_3$) δ: 1.37-1.41 (10H, m), 2.71-2.74 (4H, m), 4.58-4.60 (2H, m), 4.97-4.99 (1H, m), 5.69-5.70 (1H, m), 5.89-5.90 (1H, m), 7.63-7.65 (1H, m), 7.67-7.74 (2H, m), 8.02-8.07 (1H, m).

MS (m/z): 298 (M+H)$^+$.

Step 5 Tert-butyl [(1R,4S)-4-(methylamino)cyclopent-2-en-1-yl]carbamate

[Formula 279]

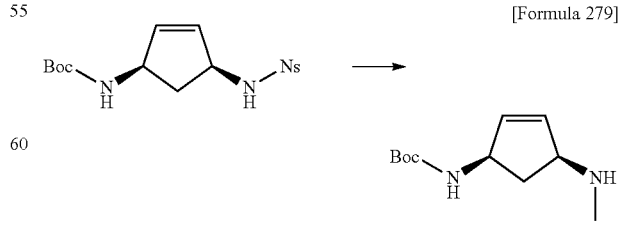

A mixture of the compound (887 mg) obtained in the above Step 4, 4-tert-butylbenzenethiol (0.751 mL), potassium carbonate (1.23 g) and DMF (11.2 mL) was stirred at 40° C. for 2.5 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (ethyl acetate/methanol) to give the title compound (498 mg, containing a small amount of a stereoisomer) as an oil.

$^1$H-NMR (CDCl$_3$) δ: 1.23-1.31 (1H, m), 1.45 (9H, s), 2.41-2.44 (3H, m), 2.66-2.74 (1H, m), 3.61-3.64 (1H, m), 4.64-4.75 (2H, m), 5.82-5.92 (2H, m).

MS (m/z): 213 (M+H)$^+$.

Step 6 Tert-butyl [(1R,4S)-4-{methyl[6-(2,2,2-trifluoroethyl)thieno[2,3-d]pyrimidin-4-yl]amino}cyclopent-2-en-1-yl]carbamate

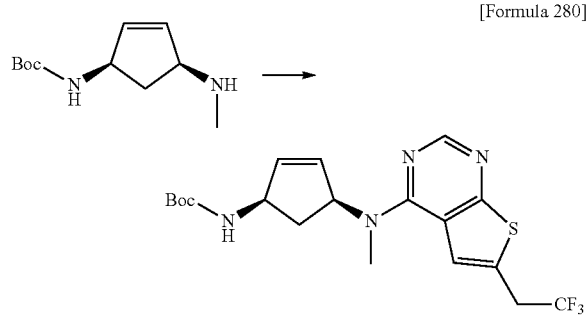

[Formula 280]

To a mixture of the compound (622 mg) obtained in the above Step 5 and 2-propanol (23.4 mL) was added DIPEA (0.816 mL), and the mixture was stirred overnight at 90° C. The mixture was concentrated under reduced pressure, and the residue was purified by silica gel column chromatography (n-hexane/ethyl acetate) to give a solid (800 mg). 750 mg of the obtained solid was purified by chiral column (DAICEL, CHIRALPAK (registered trademark, Daicel Corporation) IA, n-hexane/2-propanol) to give the title compound (541 mg) as a solid.

$^1$H-NMR (CDCl$_3$) δ: 1.45-1.48 (10H, m), 2.96-2.99 (1H, m), 3.19 (3H, s), 3.64 (2H, q, J=10.0 Hz), 4.70-4.72 (2H, m), 5.85-5.86 (1H, m), 5.93-5.98 (2H, m), 7.36 (1H, s), 8.44 (1H, s).

MS (m/z): 429 (M+H)$^+$.

Step 7 Tert-butyl [(1R,2R,3S,4S)-2,3-dihydroxy-4-{methyl[6-(2,2,2-trifluoroethyl)thieno[2,3-d]pyrimidin-4-yl]amino}cyclopentyl]carbamate (Isomer A)

Tert-butyl [(1R,2S,3R,4S)-2,3-dihydroxy-4-{methyl[6-(2,2,2-trifluoroethyl)thieno[2,3-d]pyrimidin-4-yl]amino}cyclopentyl]carbamate (Isomer B)

[Formula 281]

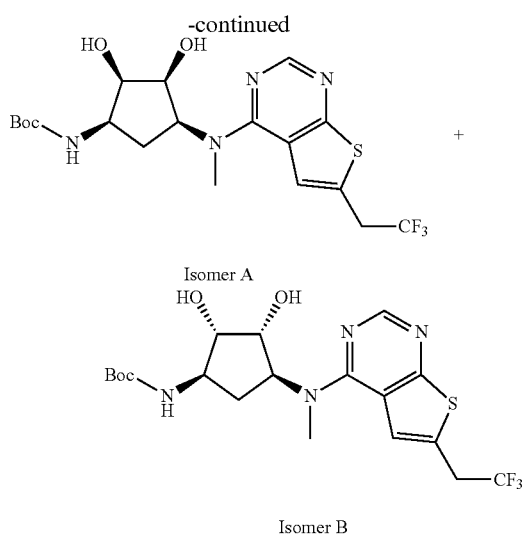

Isomer A

Isomer B

A mixture of the compound (172 mg) obtained in the above Step 6, osmium tetraoxide (4% aqueous solution) (0.051 mL), 4-methylmorpholine N-oxide (70.5 mg), acetone (3.6 mL) and water (0.40 mL) was stirred at room temperature for 4 hr. Additional 4-methylmorpholine N-oxide (70.5 mg) and osmium tetraoxide (4% aqueous solution) (0.13 mL) were added to the reaction solution, and the mixture was stirred for additional 3 hr. Aqueous sodium thiosulfate solution was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (isomer A, an earlier eluted component) (44.9 mg), and the title compound (isomer B, a later eluted component) (56.4 mg), respectively as a solid.

the isomer A (earlier eluted component)

$^1$H-NMR (CD$_3$OD) δ: 1.46 (9H, s), 2.16-2.18 (2H, m), 3.47 (3H, s), 3.86-3.89 (3H, m), 4.04-4.05 (1H, m), 4.36-4.38 (1H, m), 5.23-5.27 (1H, m), 7.65 (1H, s), 8.30 (1H, s).

MS (m/z): 463 (M+H)$^+$.

the isomer B (later eluted component)

$^1$H-NMR (CD$_3$OD) δ: 1.46 (9H, s), 1.60-1.67 (1H, m), 2.42 (1H, dt, J=15.5, 6.7 Hz), 3.33 (3H, s), 3.80 (1H, td, J=7.7, 3.7 Hz), 3.85-3.93 (3H, m), 4.30 (1H, dd, J=8.6, 5.5 Hz), 5.04 (1H, q, J=9.6 Hz), 7.67 (1H, s), 8.32 (1H, s).

MS (m/z): 463 (M+H)$^+$.

Reference Example D-1

5-formyl-1H-indole-2-carbonitrile

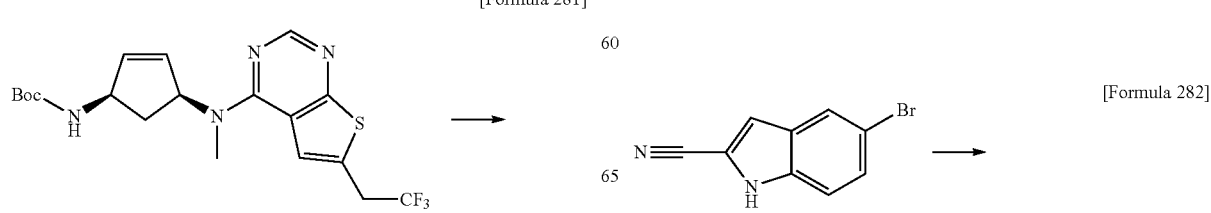

[Formula 282]

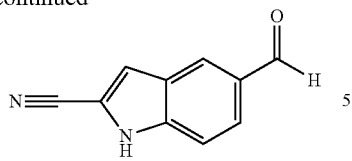

Sodium hydride (purity 55%, 628 mg) was placed in a reaction container, the container was subjected to nitrogen substitution, and THF (30 mL) was added thereto while ice-cooling. A THF solution (42 mL) of 5-bromo-1H-indole-2-carbonitrile (1.59 g) synthesized according to the method described in a literature (WO 2014/164749) was added dropwise thereto, and the mixture was stirred at room temperature for 15 min. The reaction solution was cooled to −78° C., tert-butyllithium (1.65 mol/L, n-pentane solution, 10.9 mL) was added dropwise thereto over 20 min, and the mixture was stirred at the same temperature for 45 min. DMF (2.8 mL) was added dropwise thereto over 5 min, and the mixture was stirred at −78° C. for 45 min. Acetic acid (4.1 mL) was added dropwise thereto, and the mixture was allowed to warm to room temperature. Ethyl acetate and 0.5N aqueous hydrochloric acid solution were added to the reaction solution. The insoluble substance was removed by filtration, and the filtrate was subjected to liquid separation. The aqueous layer was extracted with ethyl acetate, and the organic layers were combined, washed with saturated brine, dried over anhydrous sodium sulfate, and concentrated under reduced pressure. The residue was purified by silica gel column chromatography (n-hexane/ethyl acetate) to give the title compound (946 mg) as a solid.

$^1$H-NMR (DMSO-D$_6$) δ: 7.61-7.65 (2H, m), 7.84 (1H, d, J=9.1 Hz), 8.35 (1H, s), 10.02 (1H, s), 12.90 (1H, s).

Reference Example D-2

5-formyl-4-methyl-1-{[1-(triphenylmethyl)-1H-pyrazol-4-yl]methyl}-1H-indole-2-carbonitrile Step 1 5-formyl-4-methyl-1H-indole-2-carbonitrile

[Formula 283]

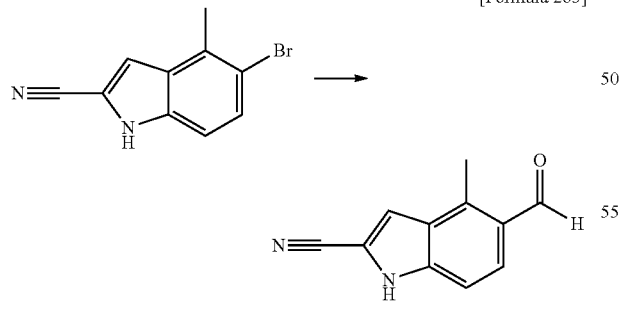

The title compound was obtained in the same manner as in Reference Example D-1, using 5-bromo-4-methyl-1H-indole-2-carbonitrile (1.22 g) synthesized according to the method described in a literature (cancer cell 2015, 27, 589-602.).

$^1$H-NMR (CD$_3$CN) δ: 2.85 (3H, s), 7.42 (1H, d, J=8.5 Hz), 7.50 (1H, s), 7.81 (1H, d, J=8.5 Hz), 10.37 (1H, s).

Step 2 5-formyl-4-methyl-1-{[1-(triphenylmethyl)-1H-pyrazol-4-yl]methyl}-1H-indole-2-carbonitrile

[Formula 284]

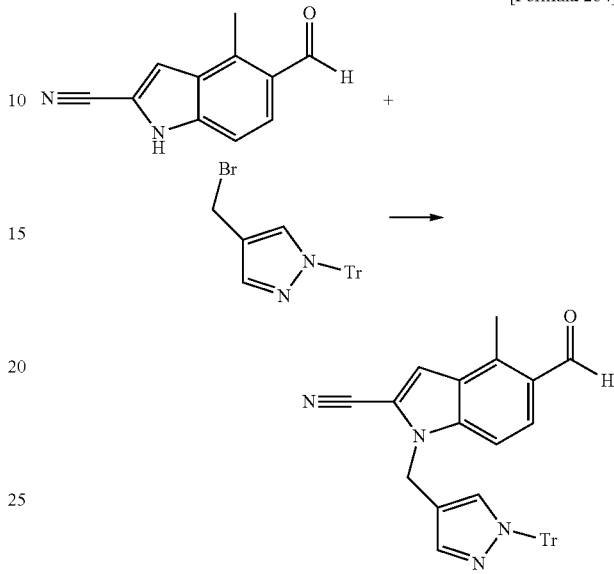

Under argon atmosphere, to a mixture of the compound (0.250 g) obtained in the above Step 1, cesium carbonate (0.619 g) and DMF (50 mL) was added a mixture of 4-(bromomethyl)-1-(triphenylmethyl)-1H-pyrazole (0.821 g) synthesized according to the method described in a literature (J. Med. Chem. 2016, 59(3), 892-913.) and DMF (90 mL) at 0° C., and the mixture was stirred at room temperature for 1 hr. Water was added to the reaction solution, and the mixture was extracted with ethyl acetate/ diethyl ether. The solid of the organic layer was collected by filtration to give the title compound (0.369 g) as a solid. The filtrate was concentrated, diethyl ether was added to the residue, and the solid was collected by filtration to give the title compound (0.193 g) as a solid.

$^1$H-NMR (CDCl$_3$) δ: 2.88 (3H, s), 5.32 (2H, s), 7.07-7.09 (6H, m), 7.26-7.31 (10H, m), 7.37 (1H, s), 7.44 (1H, s), 7.52 (1H, s), 7.88 (1H, d, J=9.1 Hz), 10.42 (1H, s).

Reference Example D-3

4-bromo-1-(methanesulfonyl)-1H-pyrrolo[2,3-c]pyridine

[Formula 285]

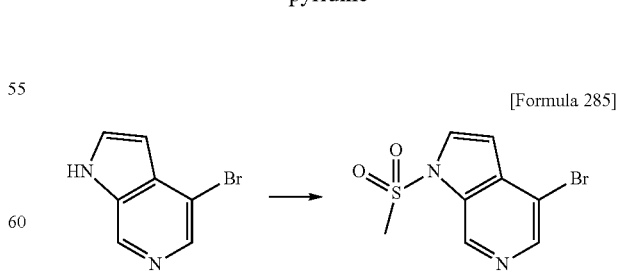

To a mixture of 4-bromo-1H-pyrrolo[2,3-c]pyridine (CAS: 69872-17-9) (401 mg), DIPEA (1.05 mL) and dichloromethane (15 mL) was added dropwise methanesulfonyl chloride (0.281 mL) under ice-cooling. The mixture was stirred at room temperature for 10 min, saturated aqueous sodium hydrogencarbonate solution was added to the reaction solution under ice-cooling, and the mixture was extracted with ethyl acetate. The organic layer was washed with saturated brine, dried over anhydrous sodium sulfate, and concentrated under reduced pressure, and the residue was subjected to silica gel column chromatography (n-hexane/ethyl acetate) to give the title compound (394 mg) as a solid.

1H-NMR (CDCl3) δ: 3.24 (3H, s), 6.82 (1H, d, J=3.7 Hz), 7.66 (1H, d, J=3.7 Hz), 8.59 (1H, s), 9.17 (1H, s).

MS (m/z): 275, 277 (M+H)+.

Reference Example D-4

4-bromo-1-methyl-1H-pyrazolo[3,4-c]pyridine

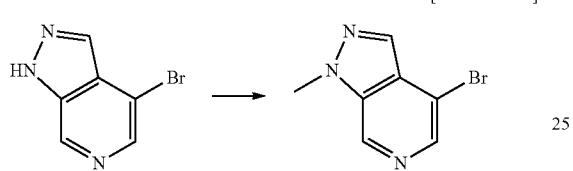

[Formula 286]

To a mixture of 4-bromo-1H-pyrazolo[3,4-c]pyridine (CAS: 1032943-43-3) (262 mg), cesium carbonate (863 mg) and DMF (6.5 mL) was added dropwise methyl iodide (CAS: 74-88-4) (0.107 mL) under ice-cooling. The mixture was stirred at room temperature for 20 hr, water was added to the reaction solution under ice-cooling, and the mixture was extracted with ethyl acetate. The organic layer was washed with saturated brine, dried over anhydrous sodium sulfate, and concentrated under reduced pressure, and the residue was subjected to silica gel column chromatography (chloroform/methanol) to give the title compound (160 mg) as an oil.

1H-NMR (CDCl3) δ: 4.21 (3H, s), 8.06 (1H, s), 8.40 (1H, s), 8.89 (1H, s).

MS (m/z): 212, 214 (M+H)+.

Reference Example D-5

4-bromo-1-(methanesulfonyl)-1H-indazole

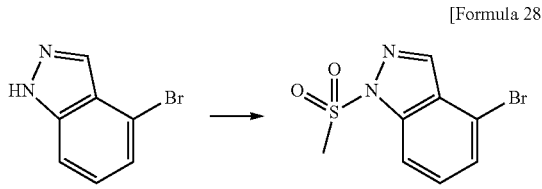

[Formula 287]

To a suspension of sodium hydride (CAS: 7646-69-7) (purity 55%, 734 mg) and DMF (100 mL) was added 4-bromoindazole (3.00 g) little by little under ice-cooling, the mixture was stirred at room temperature for 15 min, and methanesulfonyl chloride (2.27 g) was added dropwise thereto under ice-cooling. The mixture was stirred at room temperature for 3 hr, and the reaction solution was weakly acidified with 1N hydrochloric acid under ice-cooling, and extracted with ethyl acetate. The organic layer was washed with saturated brine, dried over anhydrous sodium sulfate, and concentrated under reduced pressure, and the residue was subjected to silica gel column chromatography (n-hexane/ethyl acetate) to give the title compound (2.93 g) as a solid.

1H-NMR (CDCl3) δ: 3.30 (3H, s), 7.43 (1H, dd, J=8.6, 7.4 Hz), 7.53 (1H, d, J=8.6 Hz), 8.04 (1H, d, J=7.4 Hz), 8.32 (1H, s).

MS (m/z): 275, 277 (M+H)+.

Reference Example D-6

4-bromo-6-fluoro-1-(methanesulfonyl)-1H-indazole

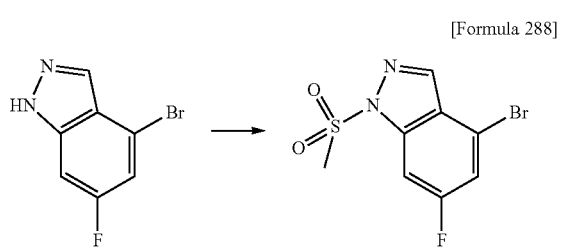

[Formula 288]

The title compound was obtained in the same manner as in Reference Example D-5, using 4-bromo-6-fluoro-1H-indazole (CAS: 885520-35-4).

1H-NMR (CDCl3) δ: 3.32 (3H, s), 7.35 (1H, dd, J=8.6, 1.8 Hz), 7.76 (1H, dd, J=8.3, 1.8 Hz), 8.27 (1H, d, J=1.2 Hz).

Reference Example D-7

N-(3-bromophenyl)-N-methylmethanesulfonamide

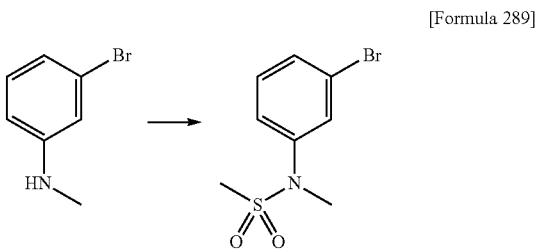

[Formula 289]

The title compound was obtained in the same manner as in Reference Example D-3, using 3-bromo-N-methyl-aniline.

1H-NMR (DMSO-D6) δ: 2.98 (3H, s), 3.24 (3H, s), 7.33-7.46 (2H, m), 7.49-7.54 (1H, m), 7.61-7.65 (1H, m).

MS (m/z): 264, 266 (M+H)+.

Reference Example D-8

1-bromo-2,4-difluoro-3-methoxybenzene

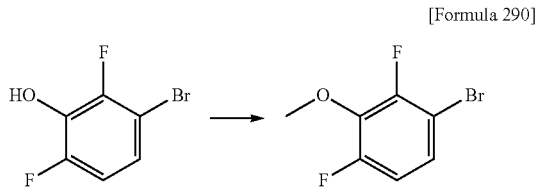

[Formula 290]

The title compound was obtained in the same manner as in Reference Example D-4, using 3-bromo-2,6-difluorophenol.

¹H-NMR (CDCl₃) δ: 4.01 (3H, s), 6.82-6.85 (1H, m), 7.19-7.20 (1H, m).

Reference Example D-9

(5-bromo-3-methoxypyridin-2-yl)methanol

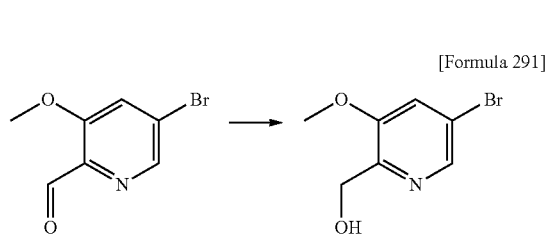

[Formula 291]

A mixture of 5-bromo-3-methoxypyridine-2-carbaldehyde (1.22 g), sodium borohydride (0.214 g) and ethanol (20.0 mL) was stirred for 1 hr under ice-cooling. 1N Hydrochloric acid was added thereto, and the mixture was extracted with ethyl acetate. The organic layers were combined, washed with saturated brine, dried over anhydrous magnesium sulfate, and concentrated under reduced pressure. The obtained residue was subjected to silica gel column chromatography (n-hexane/ethyl acetate) to give the title compound (0.819 g) as a solid.

¹H-NMR (CDCl₃) δ: 3.87 (3H, s), 3.94 (1H, t, J=4.9 Hz), 4.69 (2H, d, J=4.9 Hz), 7.28 (1H, d, J=1.5 Hz), 8.23 (1H, d, J=1.5 Hz).

Reference Example D-10

5-bromo-3-methoxy-N-methylpyridin-2-amine

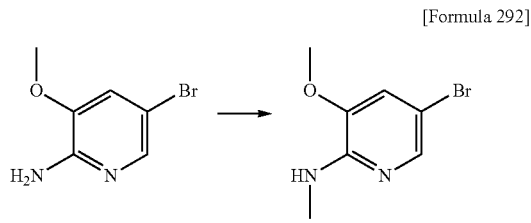

[Formula 292]

To a mixture of 5-bromo-3-methoxy-pyridin-2-amine (1.00 g) and THF (25.0 mL) was sodium hydride (purity 55%, 0.431 g) at 0° C., and the mixture was stirred for 10 min. Methyl iodide (0.370 mL) was added thereto, and the mixture was stirred at the same temperature for 1 hr. Ice was added to the reaction solution, and the reaction mixture was extracted with diethyl ether. The organic layer was washed successively with water and saturated brine, dried over anhydrous sodium sulfate, filtered, and concentrated under reduced pressure. The obtained residue was subjected to silica gel column chromatography (n-hexane/ethyl acetate) to give the title compound (0.960 g) as a solid.

¹H-NMR (CDCl₃) δ: 2.96-3.01 (3H, m), 3.82 (3H, s), 4.85-4.98 (1H, m), 6.89 (1H, d, J=1.8 Hz), 7.78 (1H, d, J=1.8 Hz).

MS (m/z): 217, 219 (M+H)⁺.

Reference Example D-11

4-[6-(dimethylamino)-5-methoxypyridin-3-yl]benzaldehyde Step 1 5-bromo-3-methoxy-N,N-dimethylpyridin-2-amine

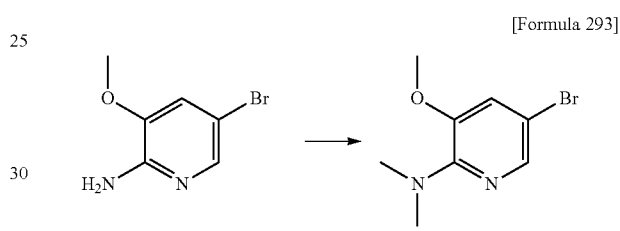

[Formula 293]

To a mixture of 5-bromo-3-methoxypyridin-2-amine (3.00 g) and THF (75 mL) was added sodium hydride (purity 55%, 2.58 g) under ice-cooling. After 10 min, methyl iodide (2.77 mL) was added thereto, and the mixture was stirred at same temperature for 1 hr, and then at room temperature for 16 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (3.41 g) as an oil.

¹H-NMR (CDCl₃) δ: 2.97 (6H, s), 3.83 (3H, s), 7.07 (1H, s), 7.86 (1H, s).

MS (m/z): 231, 233 (M+H)⁺.

Step 2 4-[6-(dimethylamino)-5-methoxypyridin-3-yl]benzaldehyde

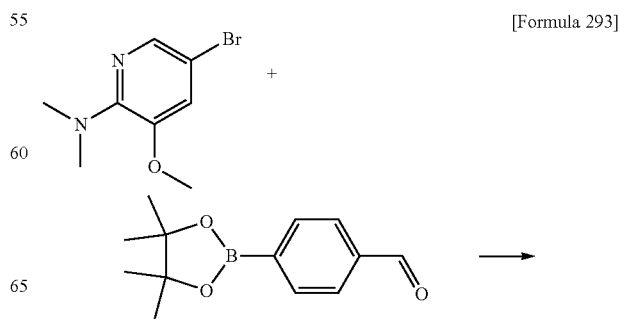

[Formula 293]

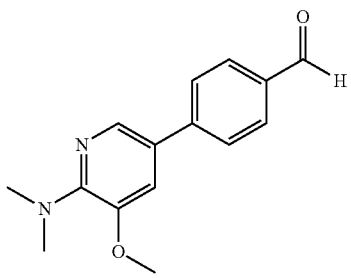

A mixture of 5-bromo-3-methoxy-N,N-dimethylpyridin-2-amine (3.41 g), 4-(4,4,5,5-tetramethyl-1,3,2-dioxaborolan-2-yl)benzaldehyde (3.49 g), tetrakis(triphenylphosphine)palladium(0) (1.71 g), sodium carbonate (6.26 g), water (62 mL) and 1,4-dioxane (184 mL) was stirred under nitrogen atmosphere at 100° C. for 3 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate). The obtained residue was suspended in n-hexane/ethyl acetate, and the solid was collected by filtration to give the title compound (2.37 g) as a solid.

$^1$H-NMR (CDCl$_3$) δ: 3.08 (6H, s), 3.94 (3H, s), 7.23 (1H, d, J=1.8 Hz), 7.71 (2H, d, J=8.6 Hz), 7.94 (2H, d, J=8.6 Hz), 8.16 (1H, d, J=1.8 Hz), 10.04 (1H, s).

MS (m/z): 257 (M+H)$^+$.

Reference Example D-12

5-bromo-3-methoxy-N,N-bis[($^2$H$_3$)methyl]pyridin-2-amine

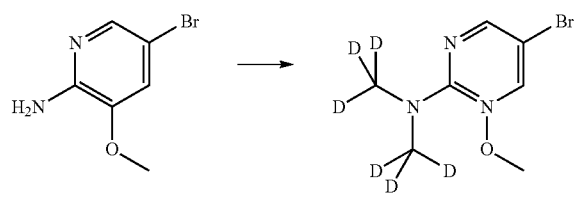

[Formula 295]

The title compound was obtained in the same manner as in Step 1 of Reference Example D-11 except that methyl iodide-D3 (CAS: 865-50-9) was used instead of iodomethane.

$^1$H-NMR (CDCl$_3$) δ: 3.84 (3H, s), 7.08 (1H, d, J=1.8 Hz), 7.87 (1H, d, J=1.8 Hz).

MS (m/z): 237, 239 (M+H)$^+$.

Reference Example D-13

6-chloro-4-methoxy-N,N-dimethylpyridazin-3-amine

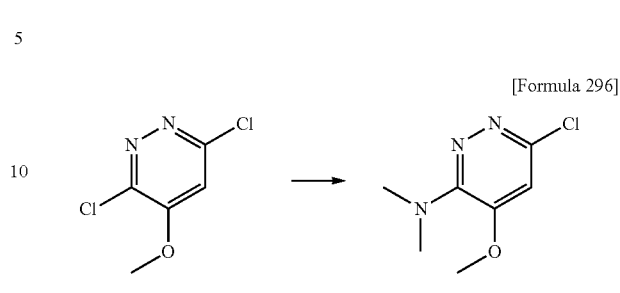

[Formula 296]

A mixture of 3,6-dichloro-4-methoxypyridazine (CAS: 70952-62-4) (0.506 g) synthesized according to the method described in a literature (J. Org. Chem. 2014, 79, 10311-10322), THF (2.1 mL) and dimethylamine (CAS: 124-40-3) (concentration 2.0 mol/L, THF solution, 2.1 mL) was stirred at room temperature for 21 hr. Then, additional dimethylamine (CAS: 124-40-3) (concentration 2.0 mol/L, THF solution, 6.4 mL) was added thereto, and the mixture was stirred at room temperature for 21 hr. Then, additional dimethylamine (CAS: 124-40-3) (concentration 2.0 mol/L, THF solution, 8.4 mL) was added thereto, and the mixture was stirred at room temperature for 24 hr. The reaction mixture was concentrated under reduced pressure, and the residue was purified by silica gel column chromatography (n-hexane/ethyl acetate) to give the title compound (0.110 g) as a solid.

$^1$H-NMR (CDCl$_3$) δ: 3.08 (6H, s), 3.92 (3H, s), 6.65 (1H, s).

Reference Example D-14

6-chloro-4-methoxy-3-(2-methoxyethoxy)pyridazine

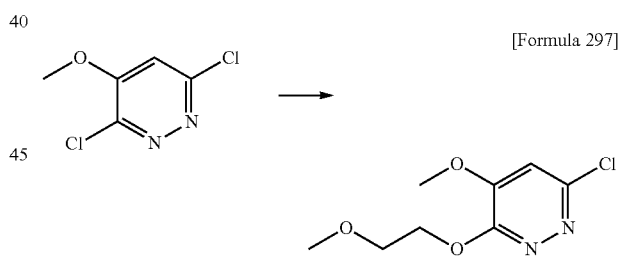

[Formula 297]

To a suspension of sodium hydride (purity 55%, 203 mg) and toluene (40 mL) was added 2-methoxyethanol (0.330 mL) little by little under ice-cooling, and the mixture was stirred at room temperature for 15 min, and 3,6-dichloro-4-methoxy-pyridazine (750 mg) was added thereto little by little under ice-cooling. The mixture was stirred at room temperature for 4 hr, and the reaction solution was weakly acidified with 1N hydrochloric acid under ice-cooling, and extracted with ethyl acetate. The organic layer was washed with saturated brine, dried over anhydrous sodium sulfate, and concentrated under reduced pressure, and the residue was subjected to silica gel column chromatography (n-hexane/ethyl acetate) to give the title compound (295 mg) as a solid.

$^1$H-NMR (CDCl$_3$) δ: 3.44 (3H, s), 3.82 (2H, t, J=4.9 Hz), 3.93 (3H, s), 4.68 (2H, t, J=4.9 Hz), 6.76 (1H, s).

MS (m/z): 219 (M+H)$^+$.

Reference Example D-15

6-chloro-3-{[1-(methanesulfonyl)piperidin-4-yl]oxy}-4-methoxypyridazine

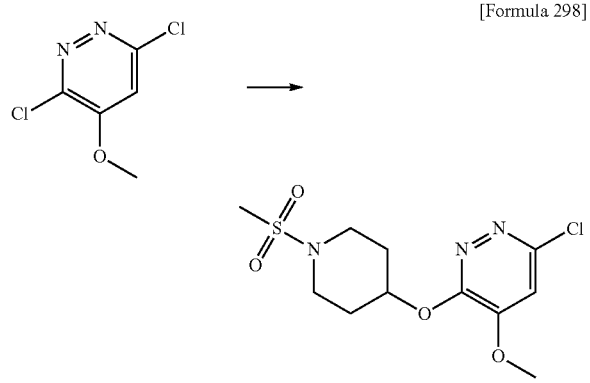

[Formula 298]

To a solution of sodium hydride (purity 55%, 156 mg) in toluene (10 mL) was added 1-(methylsulfonyl)piperidin-4-ol (561 mg) under ice-cooling, and the mixture was stirred for 15 min. 3,6-Dichloro-4-methoxy-pyridazine (400 mg) was added thereto at the same temperature, and the mixture was stirred at 80° C. for 2.5 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (288 mg) as a solid.

$^1$H-NMR (CDCl$_3$) δ: 2.01-2.04 (2H, m), 2.18-2.22 (2H, m), 2.83 (3H, s), 3.18-3.24 (2H, m), 3.54-3.58 (2H, m), 3.94 (3H, s), 5.43-5.47 (1H, m), 6.78 (1H, s).

MS (m/z): 322, 324 (M+H)$^+$.

Reference Example D-16

4-{5-methoxy-6-[(pyridin-3-yl)oxy]pyridazin-3-yl}benzaldehyde Step 1 6-chloro-4-methoxy-3-[(pyridin-3-yl)oxy]pyridazine, 3-chloro-4-methoxy-6-[(pyridin-3-yl)oxy]pyridazine

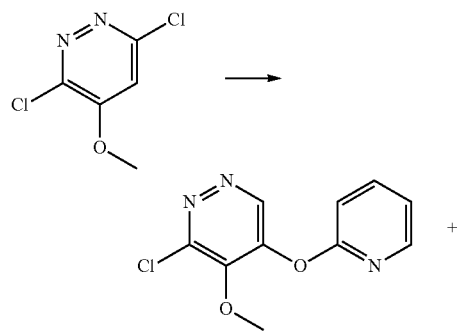

[Formula 299]

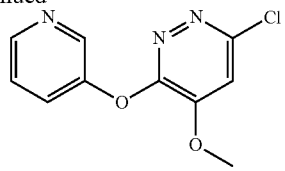

A mixture of 3,6-dichloro-4-methoxypyridazine (300 mg), 3-hydroxypyridine (159 mg), DMF (11.2 mL) and potassium carbonate (463 mg) was stirred at 120° C. for 2 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give a mixture (88.6 mg) of the title two isomers as a solid. This was directly used in the next step.

Step 2 4-{5-methoxy-6-[(pyridin-3-yl)oxy]pyridazin-3-yl}benzaldehyde

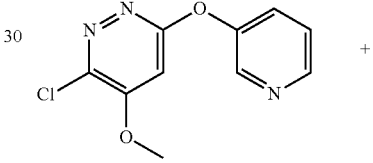

[Formula 300]

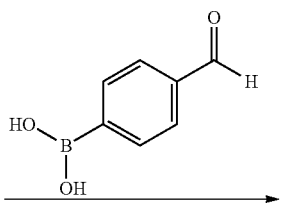

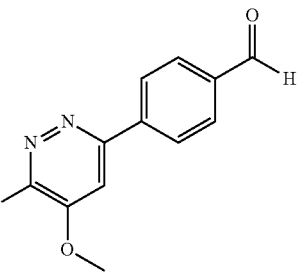

The title compound was obtained in the same manner as in Step 2 of Reference Example D-11, using the compound obtained in the above Step 1.

MS (m/z): 308 (M+H)$^+$.

Reference Example D-17

6-chloro-4-methoxy-3-[(oxan-3-yl)oxy]pyridazine (Racemate)

[Formula 301]

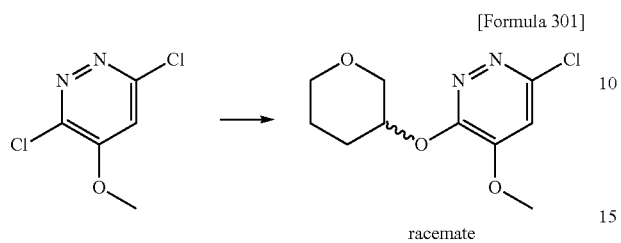

racemate

The title compound was obtained in the same manner as in Reference Example D-15 except that 3-hydroxytetrahydropyran was used instead of 1-(methylsulfonyl)piperidin-4-ol.

$^1$H-NMR (CDCl$_3$) δ: 1.90-1.98 (3H, m), 2.13-2.17 (1H, m), 3.62-3.90 (4H, m), 3.92 (3H, s), 5.31-5.36 (1H, m), 6.76 (1H, s).
MS (m/z): 245, 247 (M+H)$^+$.

Reference Example D-18

3-(azetidin-1-yl)-6-chloro-4-methoxypyridazine

[Formula 302]

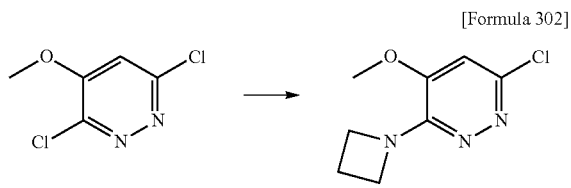

A mixture of 3,6-dichloro-4-methoxy-pyridazine (4.00 g), azetidine (4.98 g), THF (40 mL) and DIPEA (2.43 mL) was stirred at 0° C. for 1 hr, and then at room temperature for 16 hr. Water was added to the reaction solution, and the mixture was extracted with ethyl acetate. The organic layers were combined, washed with saturated brine, dried over anhydrous magnesium sulfate, and concentrated under reduced pressure. The obtained residue was subjected to silica gel column chromatography to give the title compound (0.498 g) as a solid.

$^1$H-NMR (CDCl$_3$) δ: 2.38 (2H, quint., J=7.4 Hz), 3.83 (3H, s), 4.24 (4H, t, J=7.4 Hz), 6.53 (1H, s).

Reference Example D-19

6-chloro-4-methoxypyridazin-3-ol

[Formula 303]

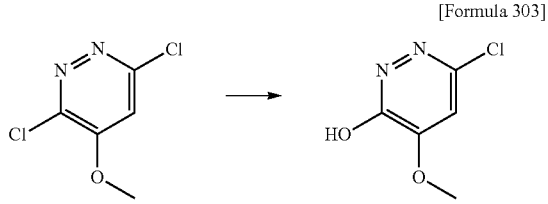

A mixture of 3,6-dichloro-4-methoxypyridazine (2.00 g) and acetic acid (40 mL) was stirred at 110° C. for 3.5 hr. The reaction solution was concentrated under reduced pressure, the residue was suspended in dichloromethane, and the insoluble substance was removed by filtration. The filtrate was concentrated, and the residue was subjected to silica gel column chromatography (dichloromethane/methanol) to give the title compound (0.572 g) as a solid.

$^1$H-NMR (DMSO-D$_6$) δ: 3.85 (3H, s), 6.91 (1H, s), 13.04 (1H, br s).
MS (m/z): 161, 163 (M+H)$^+$.

Reference Example D-20

6-chloro-5-methoxypyridazin-3-ol

[Formula 304]

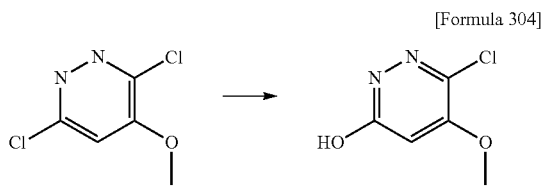

To a mixture of 3,6-dichloro-4-methoxy-pyridazine (2.00 g) and potassium acetate (1.21 g) were added acetic acid (29 mL)/water (5.8 mL), and the mixture was stirred with heating in a microwave reactor at 140° C. for 1 hr. After the completion of the reaction, water was added to the reaction solution, and the insoluble solid was collected by filtration to give the title compound (739 mg) as a solid.

$^1$H-NMR (DMSO-D$_6$) δ: 3.87 (3H, s), 6.38 (1H, s), 12.83 (1H, s).
MS (m/z): 161, 163 (M+H)$^+$.

Reference Example D-21

6-chloro-3-(difluoromethoxy)-4-methoxypyridazine

[Formula 305]

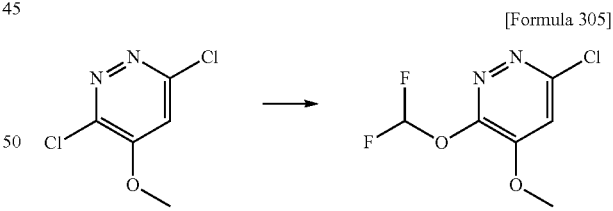

To a mixture of the compound (0.570 g) obtained in Reference Example D-19, 50% aqueous potassium hydroxide solution (3.5 mL), water (3.5 mL) and acetonitrile (7.0 mL) was added difluoromethyl trifluoromethanesulfonate (CAS: 1885-46-7) (1.35 mL) at 0° C., and the mixture was stirred at room temperature for 4 hr. Difluoromethyl trifluoromethanesulfonate (1.35 mL) was added thereto at 0° C., and the mixture was stirred at room temperature for 1 hr, and then at 60° C. for 1 hr. Water was added to the reaction solution, and the mixture was extracted with ethyl acetate. The organic layer was washed with saturated brine, dried over anhydrous sodium sulfate, and concentrated under reduced pressure. The residue was subjected to silica gel column chromatography (n-hexane/ethyl acetate) to give the title compound (0.130 g) as a solid.

$^1$H-NMR (CDCl$_3$) δ: 3.99 (3H, s), 6.94 (1H, s), 7.60 (1H, t, J=71.7 Hz).

MS (m/z): 211, 213 (M+H)$^+$.

Reference Example D-22

3-chloro-6-(difluoromethoxy)-4-methoxypyridazine (Isomer A)

6-chloro-2-(difluoromethyl)-5-methoxypyridazin-3 (2H)-one (Isomer B)

[Formula 306]

To a mixture of the compound (200 mg) obtained in Reference Example D-20 and acetonitrile (2.5 mL) were added 50% aqueous potassium hydroxide solution (1.25 mL) and water (1.25 mL). Difluoromethyl trifluoromethanesulfonate (0.475 mL) was added thereto under ice-cooling, and the mixture was stirred at room temperature for 1 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (isomer A, an earlier eluted component, 139 mg), and the title compound (isomer B, a later eluted component, 46.5 mg), respectively as a solid.

the isomer A $^1$H-NMR (CDCl$_3$) δ: 4.01 (3H, s), 6.52 (1H, s), 7.62 (1H, t, J=71.8 Hz).

MS (m/z): 211, 213 (M+H)$^+$.

the isomer B $^1$H-NMR (CDCl$_3$) δ: 3.94 (3H, s), 6.12 (1H, s), 7.59 (1H, t, J=58.3 Hz).

MS (m/z): 211, 213 (M+H)$^+$.

The structural formulas of the isomer A and isomer B are estimated structures, and the structural formula of the isomer A and the structural formula of the isomer B may be interchanged. The same applies to the subsequent steps (Reference Example D-59 and Reference Example D-60, and Examples 110 and 111).

Reference Example D-23

6-chloro-3,4-dimethoxypyridazine

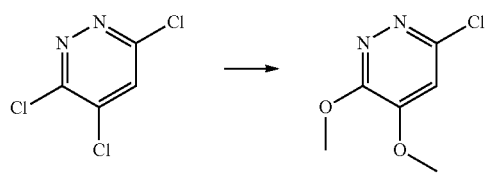

[Formula 307]

3,4,6-Trichloropyridazine (CAS: 6082-66-2) (2.57 g) was dissolved in methanol (50 mL), and sodium methoxide (CAS: 124-41-4) (1.56 g) was added thereto. The mixture was stirred at 0° C. for 10 min, allowed to warm to room temperature, and stirred for 20 hr. The reaction solution was concentrated under reduced pressure, ethyl acetate and saturated aqueous ammonium chloride solution were added thereto, and the mixture was subjected to liquid separation operation. The organic layer was washed with saturated brine, dried over anhydrous sodium sulfate, filtered, and concentrated under reduced pressure. The residue was subjected to silica gel column chromatography (dichloromethane/ethyl acetate), and the obtained solid was suspended in n-hexane/ethyl acetate. The insoluble substance was collected by filtration, and dried to give the title compound (1.10 g) as a solid.

$^1$H-NMR (CDCl$_3$) δ: 3.95 (3H, s), 4.16 (3H, s), 6.77 (1H, s).

MS: m/z 175, 177 (M+H)$^+$.

Reference Example D-24

6-chloro-3,4-bis[($^2$H$_3$)methyloxy]pyridazine

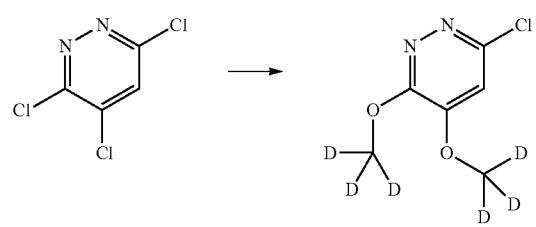

[Formula 308]

The title compound was obtained in the same manner as in Reference Example D-23 except that methanol-D3 was used instead of methanol.

$^1$H-NMR (CDCl$_3$) δ: 6.77 (1H, s).

MS (m/z): 181, 183 (M+H)$^+$.

Reference Example D-25

5-(4-formylphenyl)-3-methoxypyridine-2-carbonitrile

Step 1
3-fluoro-5-(4-formylphenyl)pyridine-2-carbonitrile

[Formula 309]

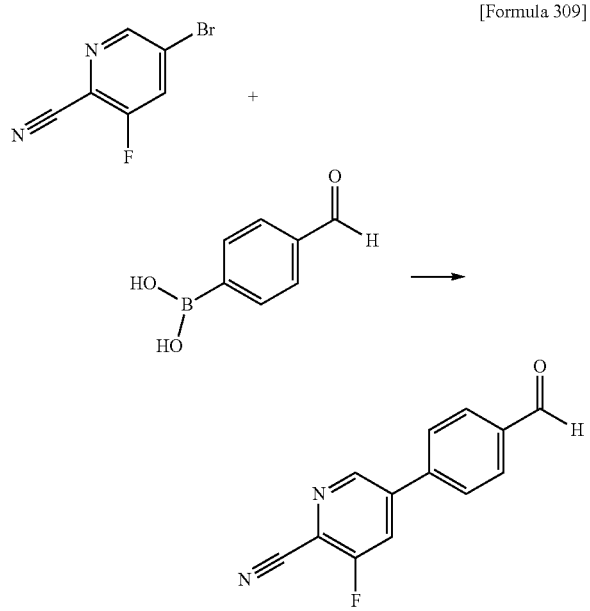

A mixture of 5-bromo-3-fluoro-pyridine-2-carbonitrile (CAS: 886373-28-0) (2.00 g), (4-formylphenyl)boronic acid (1.49 g), tetrakis(triphenylphosphine)palladium(0) (1.15 g), sodium carbonate (3.16 g), water (8.0 mL) and 1,4-dioxane (24 mL) was stirred at 100° C. for 4 hr. The reaction solution was diluted with ethyl acetate, washed successively with water and saturated brine, dried over anhydrous magnesium sulfate, and concentrated under reduced pressure. The obtained residue was subjected to silica gel column chromatography (n-hexane/ethyl acetate). The fraction was concentrated, and the obtained solid was subjected to slurry washing with n-hexane to give the title compound (1.28 g) as a solid.

$^1$H-NMR (CDCl$_3$) δ: 7.79 (2H, d, J=8.6 Hz), 7.83 (1H, dd, J=9.2, 1.8 Hz), 8.07 (2H, d, J=8.6 Hz), 8.82-8.83 (1H, m), 10.12 (1H, s).

Step 2 5-(4-formylphenyl)-3-methoxypyridine-2-carbonitrile

[Formula 310]

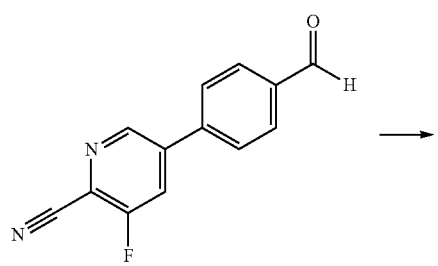

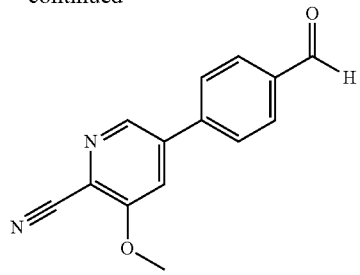

A mixture of the compound (0.250 g) obtained in the above Step 1, potassium carbonate (0.458 g) and methanol (10.0 mL) was stirred at 70° C. for 10 min. The reaction solution was diluted with ethyl acetate, washed with water and saturated brine, dried over anhydrous magnesium sulfate, and concentrated under reduced pressure. The obtained residue was subjected to silica gel column chromatography (dichloromethane/ethyl acetate) to give the title compound (0.163 g) as a solid.

$^1$H-NMR (CDCl$_3$) δ: 4.07 (3H, s), 7.51 (1H, d, J=1.8 Hz), 7.78 (2H, d, J=8.6 Hz), 8.05 (2H, d, J=8.6 Hz), 8.55 (1H, d, J=1.8 Hz), 10.11 (1H, s).

Reference Example D-26

4-(5,6-dimethoxypyridazin-3-yl)benzaldehyde

[Formula 311]

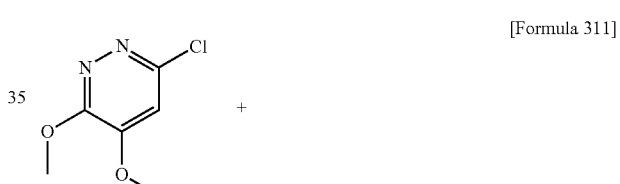

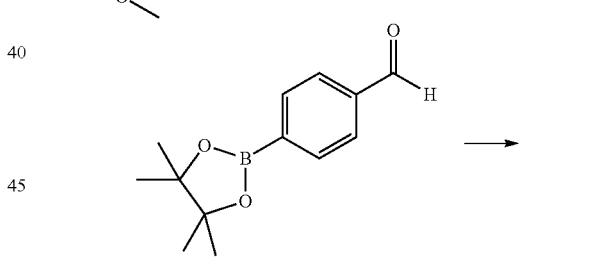

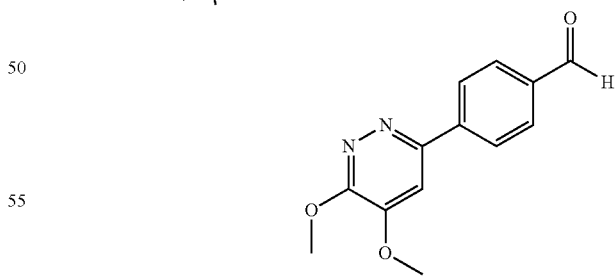

A mixture of the compound (1.10 g) obtained in Reference Example D-23, 4-(4,4,5,5-tetramethyl-1,3,2-dioxaborolan-2-yl)benzaldehyde (CAS: 128376-64-7) (2.17 g), tetrakis(triphenylphosphine)palladium(0) (CAS: 14221-01-3) (0.720 g), sodium carbonate (1.70 g), 1,2-dimethoxyethane (30 mL) and water (10 mL) was stirred at 100° C. for 5 hr. The reaction solution was allowed to cool to room temperature, saturated brine was added thereto, and the mixture was extracted with ethyl acetate. The organic layer was dried over anhydrous sodium sulfate, filtered, and concentrated under reduced pressure. The residue was subjected to silica gel column chromatography (n-hexane/ethyl acetate, followed by ethyl acetate/methanol), and the obtained solid was suspended in n-hexane/ethyl acetate. The resulting solid was collected by filtration, and dried to give the title compound (1.21 g) as a solid.

$^1$H-NMR (CDCl$_3$) δ: 4.05 (3H, s), 4.26 (3H, s), 7.20 (1H, s), 7.99-8.04 (2H, m), 8.15-8.20 (2H, m), 10.10 (1H, s).

Reference Example D-27 tert-butyl 4-(4-formylphenyl)-1H-pyrazole-1-carboxylate

[Formula 312]

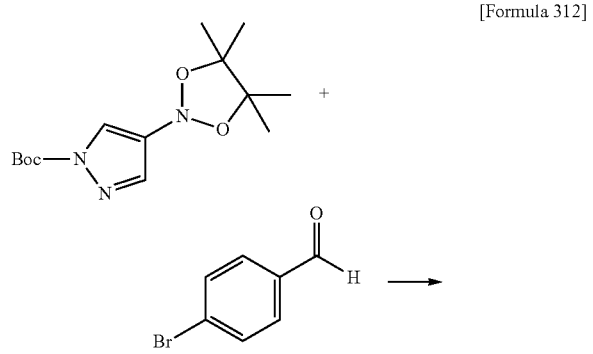

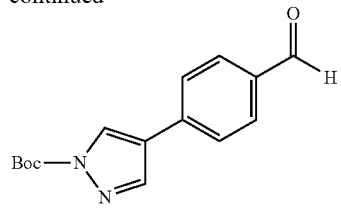

A mixture of 1-boc-4-(4,4,5,5-tetramethyl-1,3,2-dioxaborolan-2-yl)pyrazole (1.43 g), 4-bromobenzaldehyde (150 mg), cesium carbonate (3.17 g), [1,1'-bis(diphenylphosphino)ferrocene]palladium(II) dichloride dichloromethane adduct (397 mg), 1,4-dioxane (25.6 mL) and water (2.56 mL) was stirred at 70° C. for 4 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (842 mg) as a solid.

$^1$H-NMR (CDCl$_3$) δ: 1.69 (9H, s), 7.70 (2H, d, J=5.5 Hz), 7.92 (2H, d, J=5.5 Hz), 8.07 (1H, s), 8.43 (1H, s), 10.02 (1H, s).

MS (m/z): 173 (M-Boc+H)$^+$.

The products described in the following Table 1-1 to Table 1-12 were produced from Raw Material 1 and Raw Material 2 described in the tables, in the same manner as in Reference Example D-26 or D-27.

TABLE 1-1

| Ref. Ex. No. | Product Compound Name, NMR, MS | Raw Material 1 | Raw Material 2 |
|---|---|---|---|
| D-28 | ![structure] 4-(6-chloro-5-methoxypyridazin-3-yl)benzaldehyde<br>$^1$H-NMR (CDCl$_3$) δ: 4.11 (3H, s), 7.29 (1H, s), 8.01-8.07 (2H, m), 8.17-8.24 (2H, m), 10.12 (1H, s).<br>MS (m/z): 249, 251 (M + H)$^+$. | ![structure] CAS: 70952-62-4 | ![structure] CAS: 128376-64-7 |
| D-29 | ![structure] 4-[6-(dimethylamino)-5-methoxypyridazin-3-yl]benzaldehyde<br>$^1$H-NMR (CDCl$_3$) δ: 3.20 (6H, s), 4.01 (3H, s), 7.09 (1H, s), 7.99 (2H, d, J = 8.6 Hz), 8.20 (2H, d, J = 8.6 Hz), 10.08 (1H, s). MS (m/z): 258 (M + H)$^+$. | Reference Example D-13 | ![structure] CAS: 128376-64-7 |

TABLE 1-1-continued

| Ref. Ex. No. | Product Compound Name, NMR, MS | Raw Material 1 | Raw Material 2 |
| --- | --- | --- | --- |
| D-30 | 4-(6-{bis[($^2$H$_3$)methyl]amino}-5-methoxypyridin-3-yl)benzaldehyde<br>$^1$H-NMR (CDCl$_3$) δ: 3.93 (3H, s), 7.23 (1H, d, J = 2.6 Hz), 7.70 (2H, d, J = 8.6 Hz), 7.94 (2H, d, J = 8.6 Hz), 8.16 (1H, d, J = 2.5 Hz), 10.04 (1H, s). MS (m/z): 263 (M + H)$^+$. | Reference Example D-12 | CAS: 128376-64-7 |
| D-31 | 4-{5,6-bis[($^2$H$_3$)methyloxy]pyridazin-3-yl}benzaldehyde<br>$^1$H-NMR (CDCl$_3$) δ: 7.20 (1H, s), 8.01 (2H, d, J = 8.5 Hz), 8.18 (2H, d, J = 8.5 Hz), 10.10 (1H, s). MS (m/z): 251 (M + H)$^+$. | Reference Example D-24 | CAS: 87199-17-5 |

TABLE 1-2

| D-32 | 4-(1,3-oxazol-2-yl)benzaldehyde<br>$^1$H-NMR (DMSO-D$_6$) δ: 7.50 (1H, s), 8.07 (2H, d, J = 8.2 Hz), 8.20 (2H, d, J = 8.2 Hz), 8.35 (1H, s), 10.08 (1H, s). MS (m/z): 174 (M + H)$^+$. | CAS: 125533-82-6 | CAS: 87199-17-5 |
| --- | --- | --- | --- |
| D-33 | 2',4'-difluoro-3'-methoxy[1,1'-biphenyl]-4-carbaldehyde<br>$^1$H-NMR (CDCl$_3$) δ: 4.05 (3H, s), 6.98-7.03 (1H, m), 7.09-7.11 (1H, m), 7.66-7.68 (2H, m), 7.96-7.97 (2H, m), 10.07 (1H, s). MS (m/z): 249 (M + H)$^+$. | CAS: 221221-00-7 | CAS: 87199-17-5 |

TABLE 1-2-continued

D-34

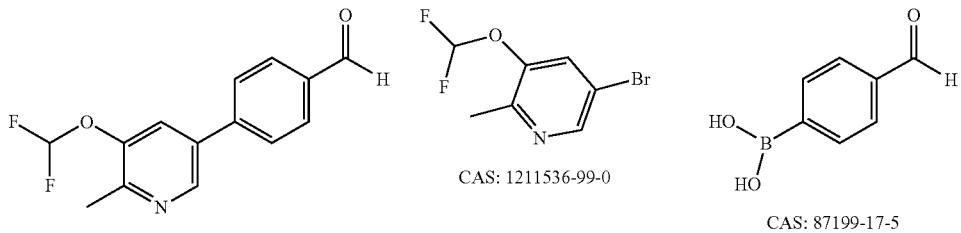

4-[5-(difluoromethoxy)-6-methylpyridin-3-yl]benzaldehyde $^{1}$H-NMR (CDCl$_{3}$) δ: 2.60 (3H, s), 6.63 (1H, t, J = 72.6 Hz), 7.67 (1H, s), 7.73 (2H, d, J = 7.9 Hz), 7.99 (2H, d, J = 8.5 Hz), 8.64 (1H, s), 10.07 (1H, s). MS (m/z): 264 (M + H)$^{+}$.

D-35

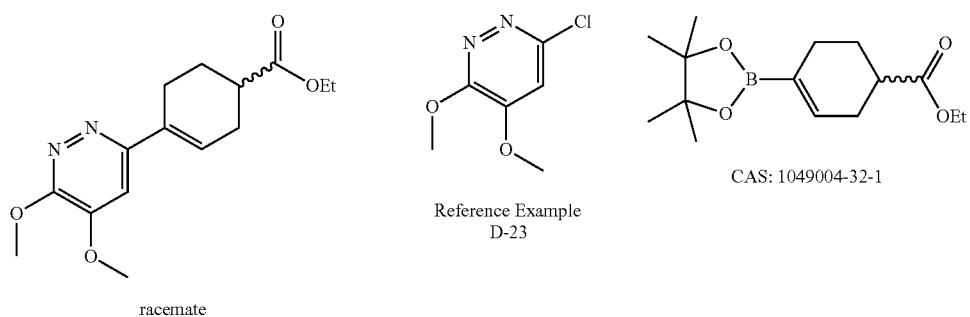

Reference Example D-23 racemate ethyl 4-(5,6-dimethoxypyridazin-3-yl)cyclohex-3-ene-1-carboxylate (racemate)

$^{1}$H-NMR (CDCl$_{3}$) δ: 1.37 (3H, t, J = 7.0 Hz), 1.79-1.90 (1H, m), 2.18-2.26 (1H, m), 6.90 (1H, s), 2.51-2.56 (2H, m), 2.58-2.69 (2H, m), 2.85-2.94 (1H, m), 3.95 (3H, s), 4.16-4.22 (5H, m), 6.43-6.47 (1H, m). MS (m/z): 293 (M + H)$^{+}$.

TABLE 1-3

D-36

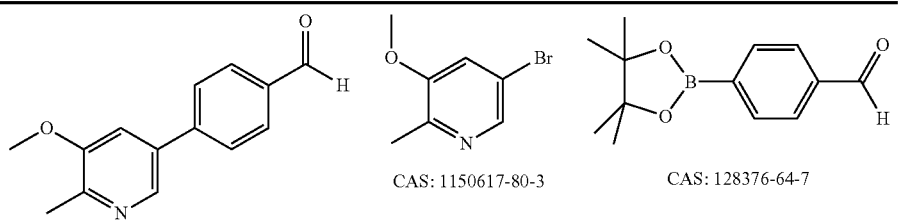

4-(5-methoxy-6-methylpyridin-3-yl)benzaldehyde $^{1}$H-NMR (CDCl$_{3}$) δ: 2.53 (3H, s), 3.93 (3H, s), 7.28 (1H, d, J = 1.8 Hz), 7.73-7.78 (2H, m), 7.96-8.01 (2H, m), 8.35 (1H, d, J = 1.8 Hz), 10.08 (1H, s).

D-37

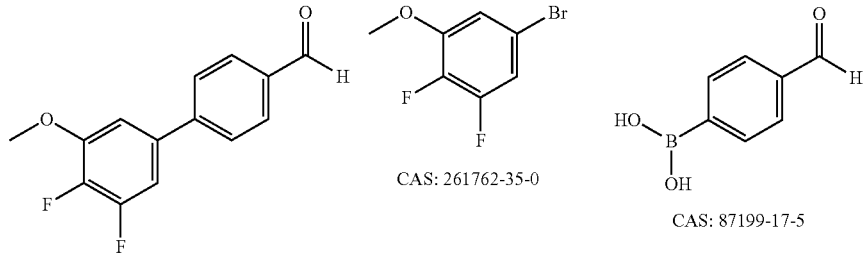

3',4'-difluoro-5'-methoxy[1,1'-biphenyl]-4-carbaldehyde $^{1}$H-NMR (CDCl$_{3}$) δ: 3.99 (3H, s), 6.97-7.07 (2H, m), 7.69 (2H, d, J = 8.3 Hz), 7.96 (2H, d, J = 8.3 Hz), 10.07 (1H, s). MS (m/z): 249 (M + H)$^{+}$.

TABLE 1-3-continued

D-38

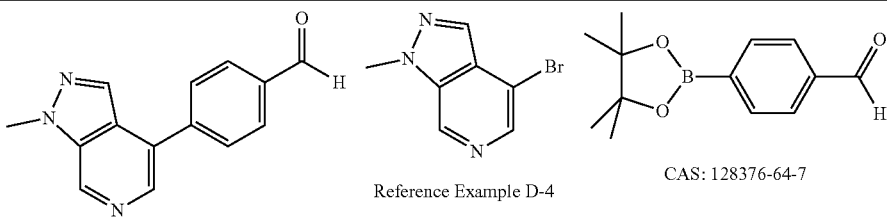

Reference Example D-4    CAS: 128376-64-7

4-(1-methyl-1H-pyrazolo[3,4-c]pyridin-4-yl)benzaldehyde
$^1$H-NMR (CDCl$_3$) δ: 4.27 (3H, s), 7.90 (2H, d, J = 8.6 Hz), 8.07 (2H, d, J = 8.6 Hz), 8.19 (1H, s),
8.48 (1H, s), 9.02 (1H, s), 10.13 (1H, s). MS (m/z): 238 (M + H )$^+$.

D-39

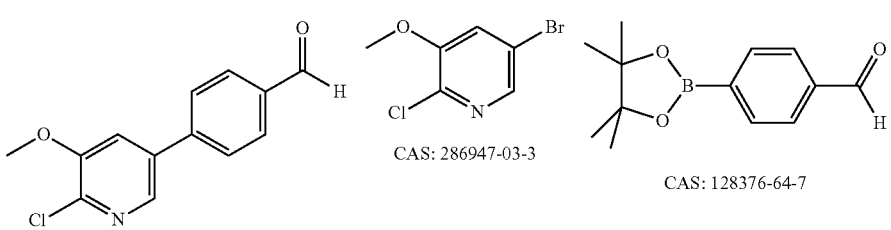

CAS: 286947-03-3    CAS: 128376-64-7

4-(6-chloro-5-methoxypyridin-3-yl)benzaldehyde
$^1$H-NMR (DMSO-D$_6$) δ: 4.02 (3H, s), 7.39 (1H, d, J = 1.8 Hz), 7.74 (2H, d, J = 8.0 Hz), 8.01 (2H,
d, J = 8.0 Hz), 8.26 (1H, d, J = 1.8 Hz), 10.09 (1H, s). MS (m/z): 248, 250 (M + H)$^+$.

TABLE 1-4

D-40

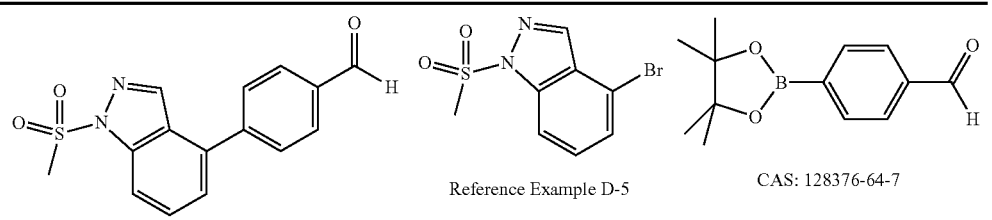

Reference Example D-5    CAS: 128376-64-7

4-[1-(methanesulfonyl)-1H-indazol-4-yl]benzaldehyde
$^1$H-NMR (CDCl$_3$) δ: 3.32 (3H, s), 7.49 (1H, d, J = 6.7 Hz), 7.68 (1H, dd, J = 8.0, 6.7 Hz), 7.80
(2H, d, J = 8.6 Hz), 8.07 (2H, d, J = 8.6 Hz), 8.16 (1H, d, J = 8.0 Hz), 8.39 (1H, s), 10.13 (1H, s).
MS (m/z): 301 (M + H)$^+$.

D-41

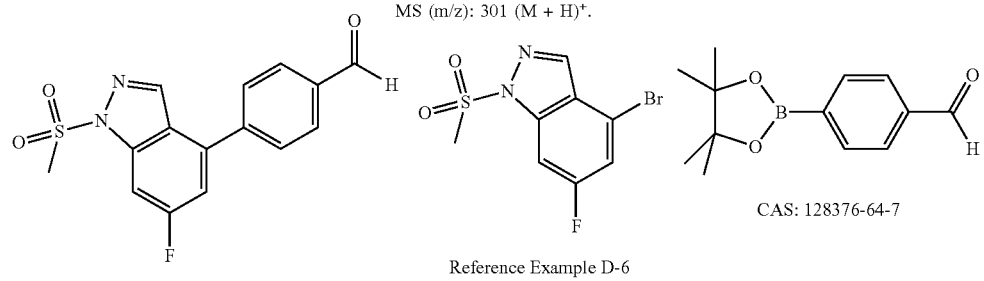

CAS: 128376-64-7

Reference Example D-6

4-[6-fluoro-1-(methanesulfonyl)-1H-indazol-4-yl]benzaldehyde
$^1$H-NMR (CDCl$_3$) δ: 3.34 (3H, s), 7.26 (1H, dd, J = 9.2, 1.8 Hz), 7.78 (2H, d, J = 8.6 Hz), 7.84-
7.87 (1H, m), 8.08 (2H, d, J = 8.6 Hz), 8.33 (1H, d, J = 1.2 Hz), 10.13 (1H, s). MS (m/z): 319
(M + H)$^+$.

D-42

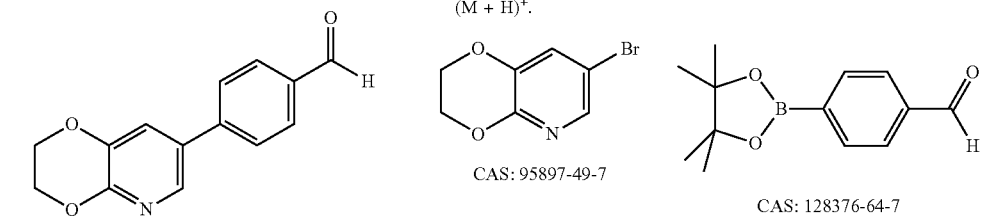

CAS: 95897-49-7    CAS: 128376-64-7

4-(2,3-dihydro[1,4]dioxino[2,3-b]pyridin-7-yl)benzaldehyde
$^1$H-NMR (CDCl$_3$) δ: 4.30-4.33 (2H, m), 4.46-4.48 (2H, m), 7.74 (1H, d, J = 1.8 Hz), 7.93 (2H,
d, J = 8.0 Hz), 7.98 (2H, d, J = 8.0 Hz), 8.20 (1H, d, J = 1.8 Hz), 10.04 (1H, s). MS (m/z): 242
(M + H)$^+$.

TABLE 1-4-continued

D-43

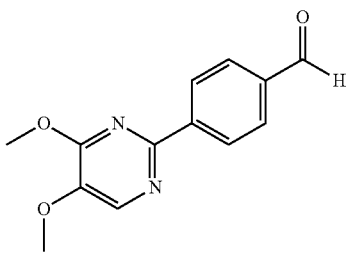 [SMILES: COc1cnc(-c2ccc(C=O)cc2)nc1OC] 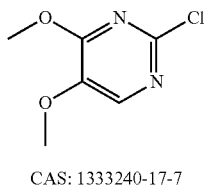 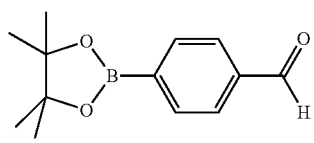

CAS: 1333240-17-7   CAS: 128376-64-7

4-(4,5-dimethoxypyrimidin-2-yl)benzaldehyde
¹H-NMR (CDCl₃) δ: 4.00 (3H, s), 4.19 (3H, s), 7.97 (2H, d, J = 8.6 Hz), 8.17 (1H, s), 8.53 (2H,
d, J = 8.6 Hz), 10.09 (1H, s). MS (m/z): 245 (M + H)⁺.

TABLE 1-5

D-44

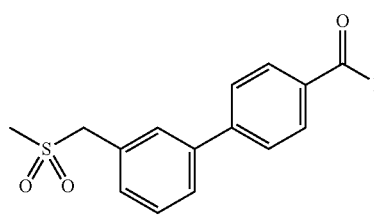 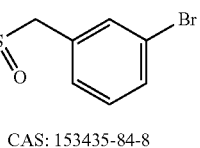 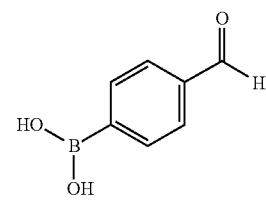

CAS: 153435-84-8   CAS: 87199-17-5

3'-[(methanesulfonyl)methyl][1,1'-biphenyl]-4-carbaldehyde
¹H-NMR (CDCl₃) δ: 2.81 (3H, s), 4.31 (2H, s), 7.44-7.55 (2H, m), 7.66-7.68 (2H, m), 7.75 (2H,
d, J = 8.3 Hz), 7.96 (2H, d, J = 8.3 Hz), 10.07 (1H, s). MS (m/z): 275 (M + H)⁺.

D-45

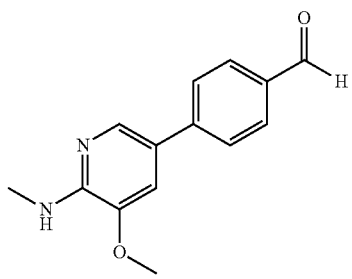 [SMILES: CNc1ncc(-c2ccc(C=O)cc2)cc1OC] 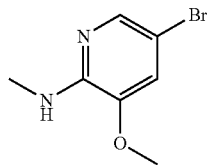 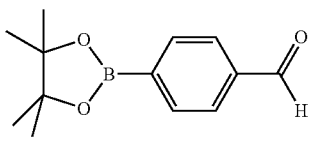

Reference Example D-10   CAS: 128376-64-7

4-[5-methoxy-6-(methylamino)pyridin-3-yl]benzaldehyde
¹H-NMR (CDCl₃) δ: 3.09 (3H, d, J = 4.9 Hz), 3.93 (3H, s), 5.12 (1H, d, J = 4.9 Hz), 7.08 (1H, d,
J = 1.8 Hz), 7.66-7.71 (2H, m), 7.90-7.94 (2H, m), 8.09 (1H, d, J = 1.8 Hz), 10.02 (1H, s). MS
(m/z): 243 (M + H)⁺.

D-46

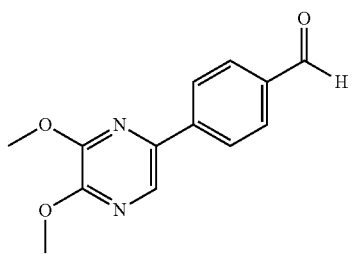 [SMILES: COc1ncc(-c2ccc(C=O)cc2)nc1OC] 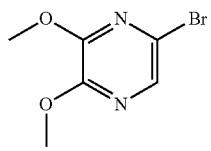 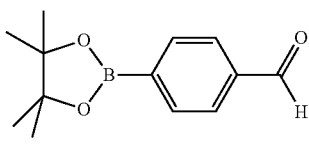

CAS: 89466-19-3   CAS: 128376-64-7

4-(5,6-dimethoxypyrazin-2-yl)benzaldehyde
¹H-NMR (CDCl₃) δ: 4.10 (3H, s), 4.15 (3H, s), 7.96 (2H, d, J = 8.5 Hz), 8.12 (2H, d, J = 7.9
Hz), 8.20 (1H, s), 10.06 (1H, s). MS (m/z): 245 (M + H)⁺.

TABLE 1-5-continued

D-47

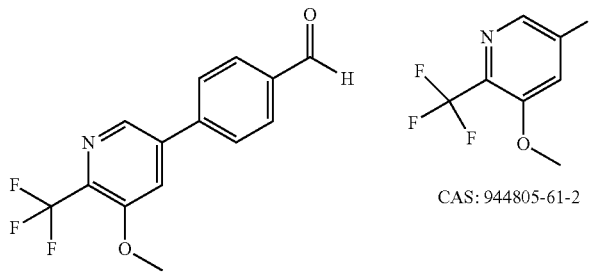 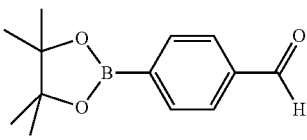

CAS: 944805-61-2

CAS: 128376-64-7

4-[5-methoxy-6-(trifluoromethyl)pyridin-3-yl]benzaldehyde $^1$H-NMR (CDCl$_3$) δ: 4.11 (3H, s), 7.67-7.76 (2H, m), 7.96-8.04 (2H, m), 8.08-8.14 (1H, m), 8.55-
8.63 (1H, m), 10.08 (1H, s). MS (m/z): 282 (M + H)$^+$.

TABLE 1-6

D-48

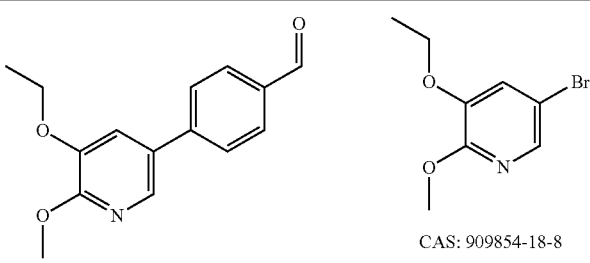 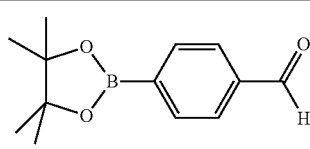

CAS: 909854-18-8

CAS: 128376-64-7

4-(5-ethoxy-6-methoxypyridin-3-yl)benzaldehyde $^1$H-NMR (CDCl$_3$) δ: 1.53 (3H, t, J = 7.0 Hz), 4.08 (3H, s), 4.19 (2H, q, J = 7.0 Hz), 7.28 (1H, d,
J = 1.8 Hz), 7.68-7.72 (2H, m), 7.94-7.98 (2H, m), 8.01 (1H, d, J = 1.8 HZ), 10.06 (1H, s).
(m/z): 258 (M + H)$^+$.

D-49

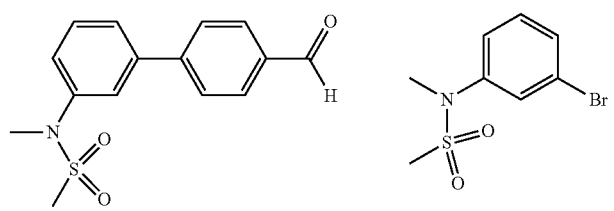 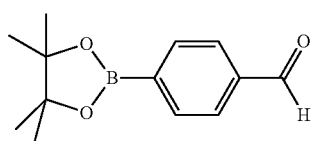 [SMILES: CC1(C)OB(c2ccc(C=O)cc2)OC1(C)C]

Reference Example D-7

CAS: 128376-64-7

N-(4'-formyl[1,1'-biphenyl]-3-yl)-N-methylmethanesulfonamide $^1$H-NMR (CDCl$_3$) δ: 2.90 (3H, s), 3.40 (3H, s), 7.40 7.44 (1H, m), 7.49-7.54 (1H, m). 7.56-7.59
(1H, m), 7.66-7.68 (1H, m), 7.73-7.77 (2H, m), 7.95-7.99 (2H, m). 10.07 (1H, s). MS (m/z): 290 (M + H)$^+$.

D-50

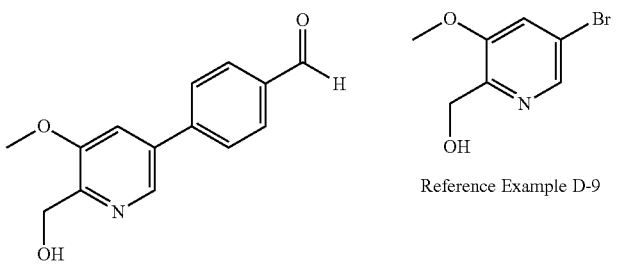 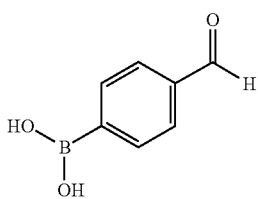

Reference Example D-9

CAS: 87199-17-5

4-[6-(hydroxymethyl)-5'-methoxypyridin-3-yl]benzaldehyde $^1$H-NMR (CDCl$_3$) δ: 3.95 (3H, s), 4.18 (1H, t, J = 4.9 Hz), 4.81 (2H, d, J = 4.9 Hz), 7.33 (1H, s),
7.76 (2H, d, J = 8.6 Hz), 8.01 (2H, d, J = 8.6 Hz), 8.43 (1H, s), 10.09 (1H, s). 13H TABLE 1-6-continued

D-51

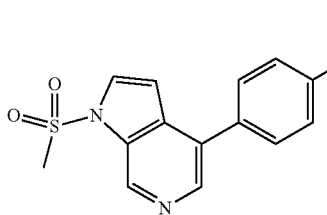 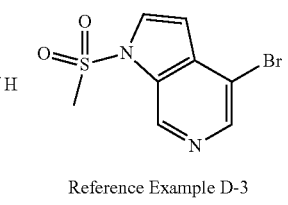 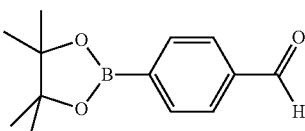

Reference Example D-3  CAS: 128376-64-7

4-[1-(methanesulfonyl)-1H-pyrrolol[2,3-c]pyridin-4-yl]benzaldehyde
¹H-NMR (CDCl₃) δ: 3.28 (3H, s), 6.90 (1H, d, J = 3.7 Hz), 7.70 (1H, d, J = 3.7 Hz), 7.80 (2H, d, J = 8.6 Hz), 8.06 (2H, d, J = 8.6 Hz), 8.61 (1H, s), 9.30 (1H, s), 10.12 (1H, s).

TABLE 1-7

D-52

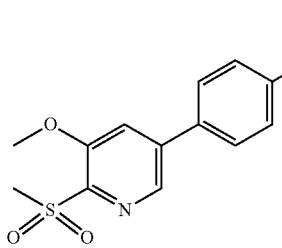 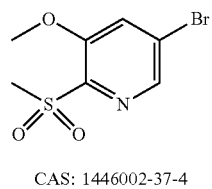 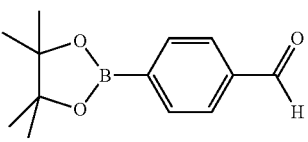 [SMILES: CC1(C)OB(c2ccc(C=O)cc2)OC1(C)C]

CAS: 1446002-37-4  CAS: 128376-64-7

4-[6-(methanesulfonyl)-5-methoxypyridin-3-yl]benzaldehyde
¹H-NMR (DMSO-D₆) δ: 3.35 (3H, s), 4.10 (3H, s), 8.08 (2H, d, J = 8.6 Hz), 8.13 (2H, d, J = 8.6 Hz), 8.12 (1H, d, J = 1.8 Hz), 8.65 (1H, d, J = 1.8 Hz), 10.11 (1H, s). MS (m/z): 292 (M + H)⁺.

D-53

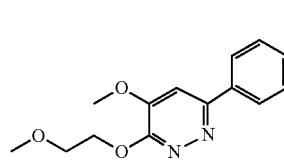 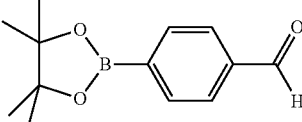

Reference Example D-14  CAS: 128376-64-7

4-[5-methoxy-6-(2-methoxyethoxy)pyridazin-3-yl]benzaldehyde
¹H-NMR (CDCl₃) δ: 3.47 (3H, s), 3.88 (2H, dd, J = 5.2, 4.0 Hz), 4.03 (3H, s), 4.78-4.81 (2H, m), 7.19 (1H, s), 8.01 (2H, d, J = 8.6 Hz), 8.17 (2H, d, J = 8.6 Hz), 10.10 (1H, s). MS (m/z): 289 (M + H)⁺.

D-54

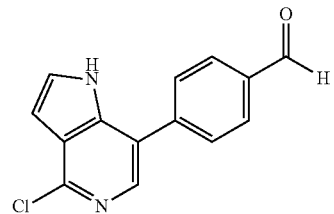 [SMILES: O=Cc1ccc(-c2cnc(Cl)c3cc[nH]c23)cc1] 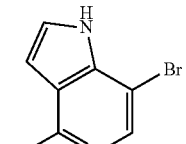 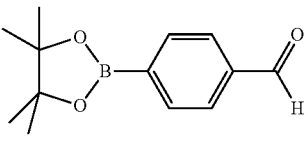 [SMILES: CC1(C)OB(c2ccc(C=O)cc2)OC1(C)C]

CAS: 1000342-04-0  CAS: 128376-64-7

4-(4-chloro-1H-pyrrolo[3,2-c]pyridin-7-yl)benzaldehyde
¹H-NMR (DMSO-D₆) δ: 6.69 (1H, dd, J = 3.1, 1.8 Hz), 7.61 (1H, dd, J = 3.1, 2.5 Hz), 7.93 (2H, d, J = 8.0 Hz), 8.09 (2H, d, J = 8.0 Hz), 8.11 (1H, s), 10.13 (1H, s), 12.08 (1H, br s). MS (m/z): 257 (M + H)⁺.

D-55

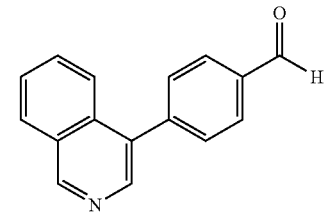 [SMILES: O=Cc1ccc(-c2cncc3ccccc23)cc1] 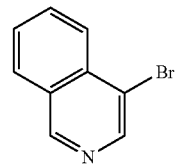 [SMILES: Brc1cncc2ccccc12] 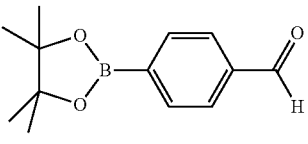 [SMILES: CC1(C)OB(c2ccc(C=O)cc2)OC1(C)C]

CAS: 1532-97-4  CAS: 128376-64-7

4-(isoquinolin-4-yl)benzaldehyde
¹H-NMR (CDCl₃) δ: 7.65-7.75 (4H, m), 7.87 (1H, 8.09 d, J = 8.0 Hz), 8.06 (2H, d, J = 8.0 Hz), 8.09 (1H, d, J = 7.4 Hz), 8.51 (1H, s), 9.31 (1H, s), 10.14 (1H, s). MS (m/z): 234 (M + H)⁺.

TABLE 1-8

D-56 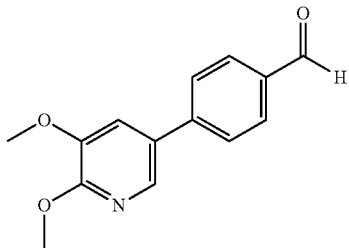 [SMILES: COc1cc(-c2ccc(C=O)cc2)cnc1OC] 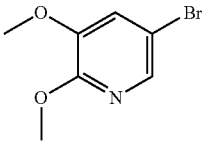 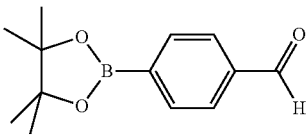

CAS: 52605-98-8    CAS: 128376-64-7

4-(5,6-dimethoxypyridin-3-yl)benzaldehyde

¹H-NMR (CDCl₃) δ: 3.97 (3H, s), 4.09 (3H, s), 7.28 (1H, d, J = 1.8 Hz), 7.71 (2H, d, J = 8.6 Hz), 7.97 (2H, d, J = 8.6 Hz), 8.02 (1H, d, J = 1.8 Hz), 10.06 (1H, s). MS (m/z): 244 (M + H)⁺.

D-57 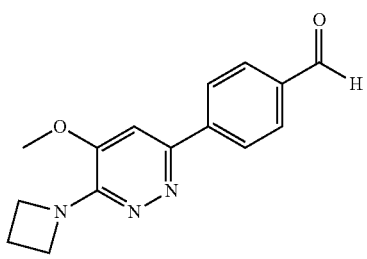 [SMILES: COc1cc(-c2ccc(C=O)cc2)nnc1N1CCC1] 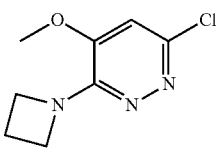 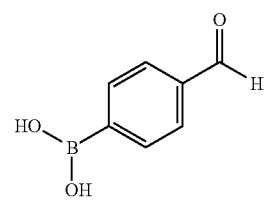 [SMILES: O=Cc1ccc(B(O)O)cc1]

Reference Example D-18    CAS: 87199-17-5

4-[6-(azetidin-1-yl)-5-methoxypyridazin-3-yl]benzaldehyde

¹H-NMR (CDCl₃) δ: 2.43 (2H, quint, J = 7.4 Hz), 3.93 (3H, s), 4.35 (4H, t, J = 7.4 Hz), 6.98 (1H, s), 7.97 (2H, d, J = 8.6 Hz), 8.16 (2H, d, J = 8.6 Hz), 10.07 (1H, s).

D-58 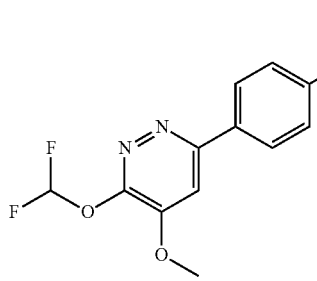 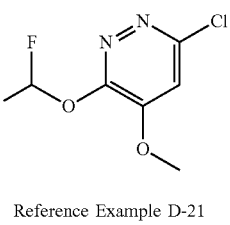 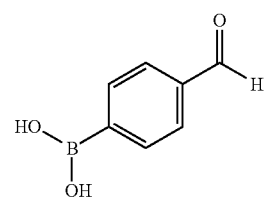 [SMILES: O=Cc1ccc(B(O)O)cc1]

Reference Example D-21    CAS: 87199-17-5

4-[6-(difluoromethoxy)-5-methoxypyridazin-3-yl]benzaldehyde

¹H-NMR (CDCl₃) δ: 4.09 (3H, s), 7.33 (1H, s), 7.73 (1H, t, J = 71.7 Hz), 8.04 (2H, d, J = 7.9 Hz), 8.17 (2H, d, J = 7.9 Hz), 10.12 (1H, s). MS (m/z) : 281 (M + H)⁺.

D-59 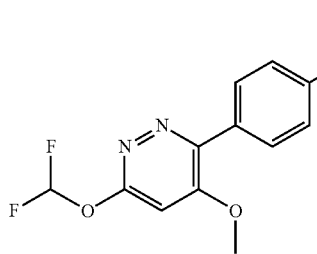 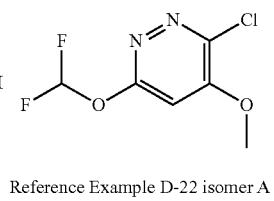 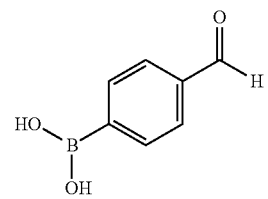 [SMILES: O=Cc1ccc(B(O)O)cc1]

Reference Example D-22 isomer A    CAS: 87199-17-5

4-[6-(difluoromethoxy)-4-methoxypyridazin-3-yl]benzaldehyde

¹H-NMR (CDCl₃) δ: 4.00 (3H, s), 6.65 (1H, s), 7.75 (1H, t, J = 72.0 Hz), 7.98-8.01 (2H, m), 8.05-8.08 (2H, m), 10.10 (1H, s). MS (m/z): 281 (M + H)⁺.

TABLE 1-9

D-60

Reference Example D-22 (isomer B)

CAS: 87199-17-5

4-[1-(difluoromethyl)-4-methoxy-6-oxo-1,6-dihydropyridazin-3-yl]benzaldehyde $^1$H-NMR (CDCl$_3$) δ: 3.93 (3H, s), 6.23 (1H, s), 7.74 (1H, t, J = 58.9 Hz), 7.90 (2H, d, J = 8.2 Hz), 7.97 (2H, d, J = 8.2 Hz), 10.09 (1H, s) MS (m/z): 281 (M + H)$^+$.

D-61

CAS: 1227502-46-6

CAS: 87199-17-5

4-(4,5-dimethoxypyridin-2-yl)benzaldehyde $^1$H-NMR (CDCl$_3$) δ: 4.02 (3H, s), 4.03 (3H, s), 7.30 (1H, s), 7.97 (2H, d, J = 8.0 Hz), 8.10 (2H, d, J = 8.0 Hz), 8.26 (1H, s), 10.07 (1H, s). MS (m/z): 244 (M + H)$^+$.

D-62

Reference Example D-15

CAS: 87199-17-5

4-(6-{[1-(methanesulfonyl)piperidin-4-yl]oxy}-5-methoxypyridazin-3-yl)benzaldehyde MS (m/z): 392 (M + H)$^+$.

D-63

CAS: 808770-39-0

CAS: 87199-17-5

4-(6-amino-5-methoxypyridazin-3-yl)benzaldehyde $^1$H-NMR (DMSO-D$_6$) δ: 3.99 (3H, s), 6.49 (2H, br s), 7.49 (1H, s), 8.00 (2H, d, J = 8.5 Hz), 8.29 (2H, d, J = 8.5 Hz), 10.06 (1H, s).

TABLE 1-10

D-64

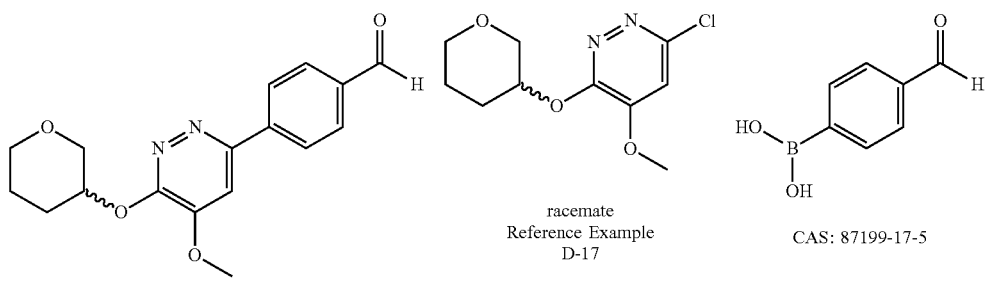

racemate                racemate
                        Reference Example
                        D-17

CAS: 87199-17-5

4-{5-methoxy-6-[(oxan-3-yl)oxy]pyridazin-3-yl}benzaldehyde

¹H-NMR (CDCl₃) δ: 1.70-1.72 (1H, m), 1.97-2.00 (2H, m), 2.23-2.25 (1H, m), 3.71-3.73 (2H, m), 3.84-3.87 (1H, m), 4.02-4.03 (4H, m), 5.47-5.48 (1H, m), 7.19 (1H, s), 8.01 (2H, d, J = 8.3 Hz), 8.17 (2H, d, J = 8.3 Hz), 10.10 (1H, s). MS (m/z): 315 (M + H)⁺.

D-65

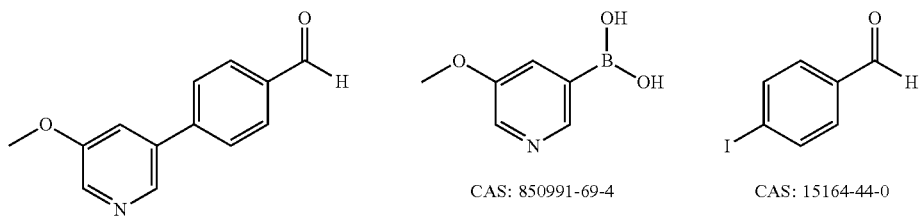

CAS: 850991-69-4    CAS: 15164-44-0

4-(5-methoxypyridin-3-yl)benzaldehyde

¹H-NMR (CDCl₃) δ: 3.95 (3H, s), 7.40-7.42 (1H, m),
7.73-7.78 (2H, m), 7.98-8.02 (2H, m), 8.37 (1H,
d, J = 3.0 Hz), 8.50 (1H, d, J = 1.8 Hz), 10.09 (1H, s).

D-66

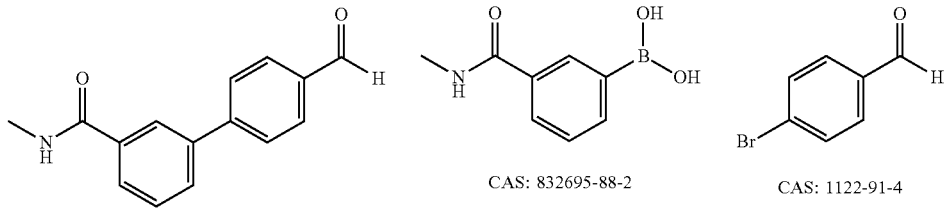

CAS: 832695-88-2    CAS: 1122-91-4

4'-formyl-N-methyl[1,1'-biphenyl]-3-carboxamide

¹H-NMR (DMSO-D₆) δ: 3.06 (3H, s), 6.24 (1H, s),
7.54-7.56 (1H, m), 7.76-7.78 (4H, m), 7.97-
7.98 (2H, m), 8.07-8.07 (1H, m), 10.07 (1H, s).
MS (m/z): 240 (M + H)⁺.

D-67

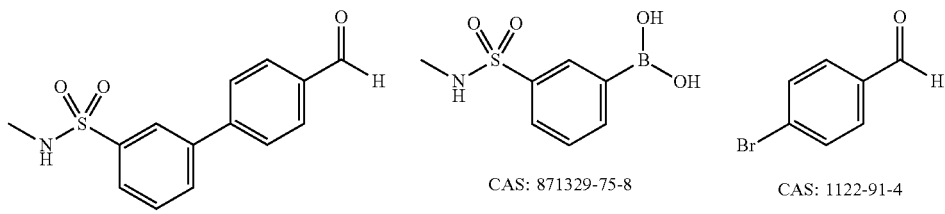

CAS: 871329-75-8    CAS: 1122-91-4

4'-formyl-N-methyl[1,1'-biphenyl]-3-sulfonamide

¹H-NMR (CDCl₃) δ: 2.73 (3H, d, J = 5.5 Hz), 4.49-4.50
(1H, m), 7.65-7.67 (1H, m), 7.78 (2H, d, J = 8.3 Hz),
7.85-7.87 (1H, m), 7.91-7.93 (1H, m), 8.00 (2H, d,
J = 8.3 Hz), 8.14-8.14 (1H, m), 10.09 (1H, s).
MS (m/z): 276 (M + H)⁺.

TABLE 1-11

D-68

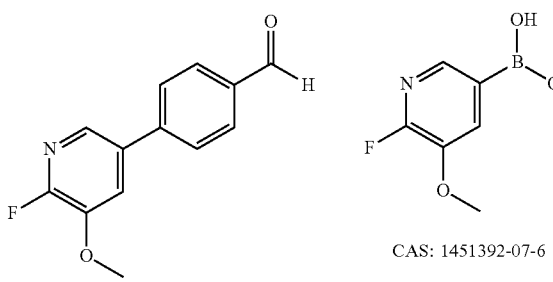 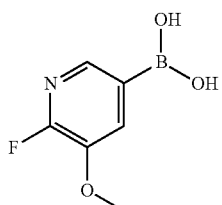 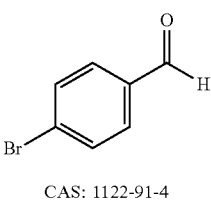

CAS: 1451392-07-6

CAS: 1122-91-4

4-(6-fluoro-5-methoxypyridin-3-yl)benzaldehyde
$^1$H-NMR (CDCl$_3$) δ: 4.00 (3H, s), 7.44-7.51 (1H, m), 7.69-7.75 (2H, m), 7.95-8.03 (3H, m), 10.09 (1H, s). MS (m/z): 232 (M + H)$^+$.

D-69

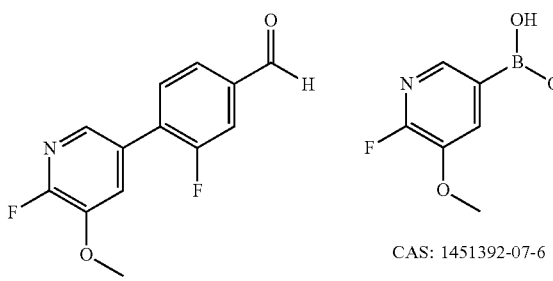 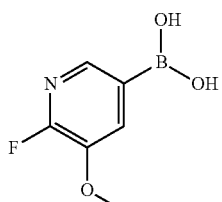 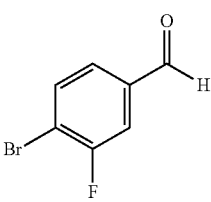

CAS: 1451392-07-6

CAS: 133059-43-5

3-fluoro-4-(6-fluoro-5-methoxypyridin-3-yl)benzaldehyde
$^1$H-NMR (CDCl$_3$) δ: 3.98 (3H, s), 7.49-7.53 (1H, m), 7.61-7.66 (1H, m), 7.70-7.73 (1H, m), 7.78-7.80 (1H, m), 7.93-7.95 (1H, m), 10.05 (1H, d, J = 1.8 Hz).

D-70

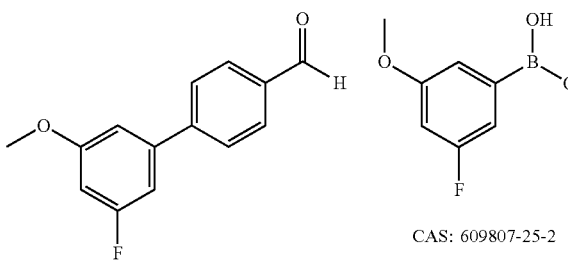 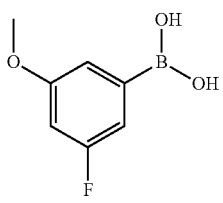 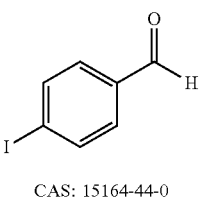

CAS: 609807-25-2

CAS: 15164-44-0

3'-fluoro-5'-methoxy[1,1'-biphenyl]-4-carbaldehyde
$^1$H-NMR (CDCl$_3$) δ: 3.87 (3H, s), 6.68 (1H, dt, J = 10.3, 2.1 Hz), 6.92-6.95 (2H, m), 7.72 (2H, d, J = 8.5 Hz), 7.96 (2H, d, J = 8.5 Hz), 10.07 (1H, s).

D-71

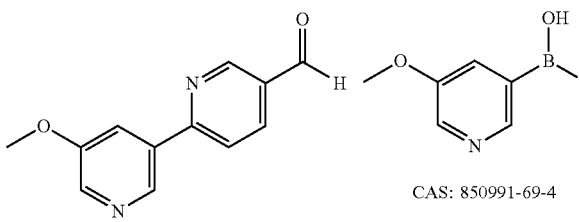 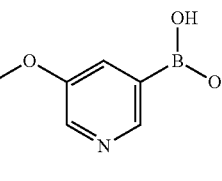 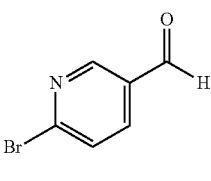

CAS: 850991-69-4

CAS: 149806-06-4

5'-methoxy[2,3'-bipyridine]-5-carbaldehyde
$^1$H-NMR (CDCl$_3$) δ: 3.97 (3H, s), 7.96 (1H, d, J = 8.0 Hz), 7.99 (1H, dd, J = 3.1, 1.8 Hz), 8.27 (1H, dd, J = 8.0, 1.8 Hz), 8.43 (1H, d, J = 3.1 Hz), 8.85 (1H, d, J = 1.8 Hz), 9.16 (1H, d, J = 1.8 Hz), 10.17 (1H, s). MS (m/z): 215 (M + H)$^+$.

TABLE 1-12

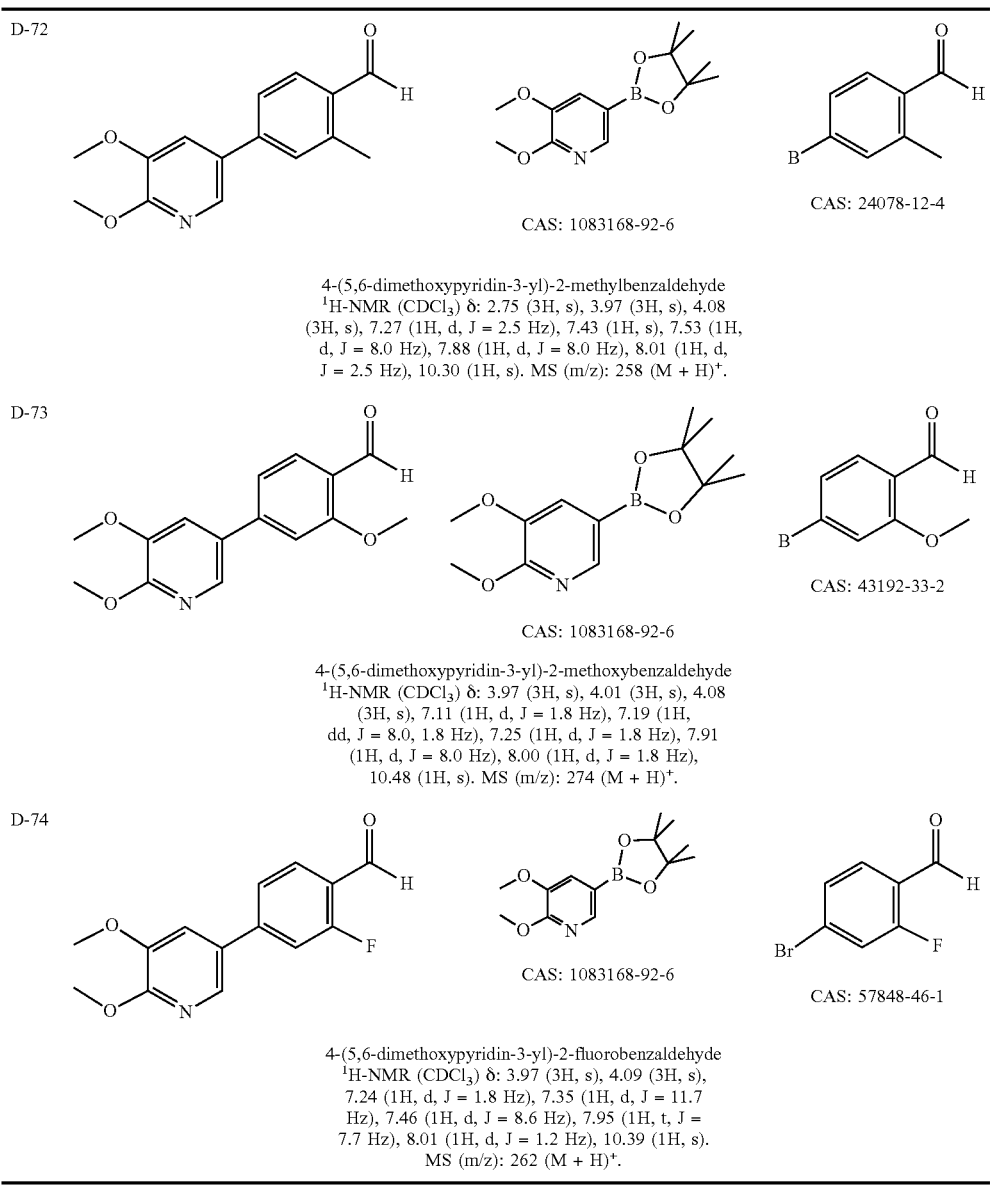

D-72: 4-(5,6-dimethoxypyridin-3-yl)-2-methylbenzaldehyde
$^1$H-NMR (CDCl$_3$) δ: 2.75 (3H, s), 3.97 (3H, s), 4.08 (3H, s), 7.27 (1H, d, J = 2.5 Hz), 7.43 (1H, s), 7.53 (1H, d, J = 8.0 Hz), 7.88 (1H, d, J = 8.0 Hz), 8.01 (1H, d, J = 2.5 Hz), 10.30 (1H, s). MS (m/z): 258 (M + H)$^+$.

D-73: 4-(5,6-dimethoxypyridin-3-yl)-2-methoxybenzaldehyde
$^1$H-NMR (CDCl$_3$) δ: 3.97 (3H, s), 4.01 (3H, s), 4.08 (3H, s), 7.11 (1H, d, J = 1.8 Hz), 7.19 (1H, dd, J = 8.0, 1.8 Hz), 7.25 (1H, d, J = 1.8 Hz), 7.91 (1H, d, J = 8.0 Hz), 8.00 (1H, d, J = 1.8 Hz), 10.48 (1H, s). MS (m/z): 274 (M + H)$^+$.

D-74: 4-(5,6-dimethoxypyridin-3-yl)-2-fluorobenzaldehyde
$^1$H-NMR (CDCl$_3$) δ: 3.97 (3H, s), 4.09 (3H, s), 7.24 (1H, d, J = 1.8 Hz), 7.35 (1H, d, J = 11.7 Hz), 7.46 (1H, d, J = 8.6 Hz), 7.95 (1H, t, J = 7.7 Hz), 8.01 (1H, d, J = 1.2 Hz), 10.39 (1H, s). MS (m/z): 262 (M + H)$^+$.

Reference Example D-75

4-[1-(methanesulfonyl)-1H-pyrazol-4-yl]benzaldehyde

Step 1  4-(1H-pyrazol-4-yl)benzaldehyde Hydrochloride

[Formula 313]

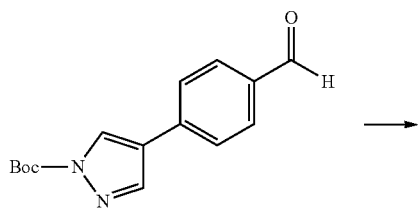

→

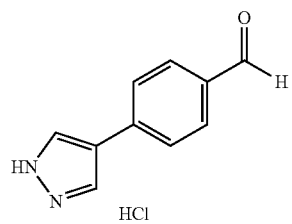

The title compound was obtained in the same manner as in Step 11 of Reference Example A-1, using the compound obtained in Reference Example D-27.

$^1$H-NMR (DMSO-D$_6$) δ: 7.86-7.90 (4H, m), 8.29 (2H, s), 9.96 (1H, s), 11.97 (2H, s).

MS (m/z): 173 (M+H)$^+$.

Step 2 4-[1-(methanesulfonyl)-1H-pyrazol-4-yl]benzaldehyde

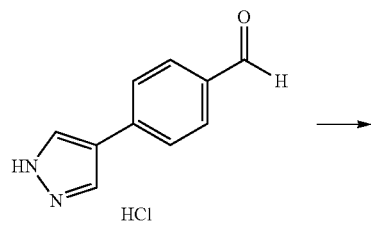

[Formula 314]

The title compound was obtained in the same manner as in Reference Example D-3, using the compound obtained in the above Step 1.

$^1$H-NMR (CDCl$_3$) δ: 3.42 (3H, s), 7.70 (2H, d, J=8.3 Hz), 7.95 (2H, d, J=8.3 Hz), 8.17 (1H, s), 8.38 (1H, s), 10.03 (1H, s).

Reference Example D-76

4-(5-methoxy-6-phenoxypyridazin-3-yl)benzaldehyde

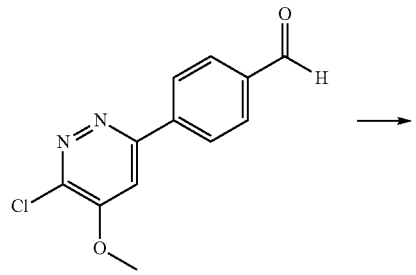

[Formula 315]

The title compound was obtained in the same manner as in Step 1 of Reference Example D-16, using the compound obtained in Reference Example D-28 and phenol.

$^1$H-NMR (CDCl$_3$) δ: 4.12 (3H, s), 7.27-7.28 (2H, m), 7.33 (1H, s), 7.41-7.44 (2H, m), 8.00-8.01 (2H, m), 8.04-8.05 (1H, m), 8.18-8.20 (2H, m), 10.09 (1H, s).
MS (m/z): 307 (M+H)$^+$.

Reference Example D-77

4'-formyl-N,N-dimethyl[1,1'-biphenyl]-3-sulfonamide

[Formula 316]

The title compound was obtained in the same manner as in Step 13 of Reference Example A-1, using the compound obtained in Reference Example D-67

$^1$H-NMR (CDCl$_3$) δ: 2.77 (6H, s), 7.71-7.84 (5H, m), 8.00-8.03 (3H, m), 10.09 (1H, s).
MS (m/z): 290 (M+H)$^+$.

Reference Example D-78

4-(5,6-dimethoxypyridazin-3-yl)cyclohexane-1-carbaldehyde (Cis-Trans Mixture)

Step 1 4-(5,6-dimethoxypyridazin-3-yl)cyclohex-3-ene-1-carbaldehyde (Racemate)

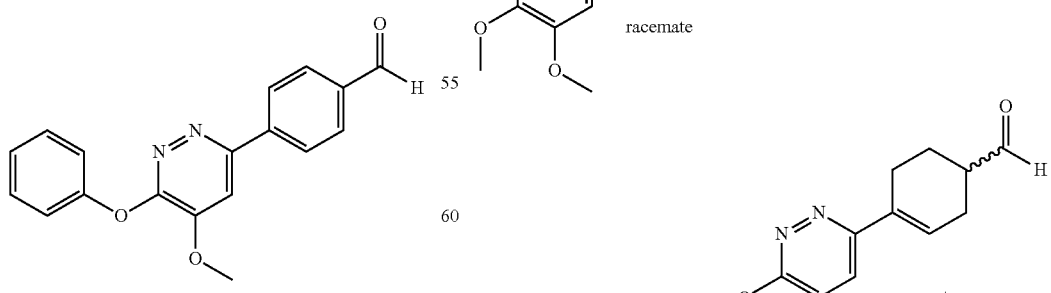

[Formula 317]

The compound (0.400 g) obtained in Reference Example D-35 was dissolved in dichloromethane (11 mL), and diisobutylaluminium hydride (1.22 mol/L, dichloromethane solution, 2.24 mL) was added dropwise thereto at −78° C. The reaction solution was stirred at the same temperature for 2 hr. Methanol (0.400 mL) was added to the reaction solution, and then saturated aqueous potassium sodium tartrate solution was added thereto, and the mixture was allowed to warmed to room temperature. The mixture was extracted with ethyl acetate, the organic layer was dried over anhydrous sodium sulfate, and the solvent was evaporated under reduced pressure. The residue was purified by silica gel chromatography (n-hexane/ethyl acetate) to give the title compound (0.178 g) as a solid.

$^1$H-NMR (CDCl$_3$) δ: 1.79-1.89 (1H, m), 2.19-2.27 (1H, m), 2.43-2.77 (4H, m), 2.81-2.90 (1H, m), 3.95 (3H, s), 4.18 (3H, s), 6.44-6.49 (1H, m), 6.90 (1H, s), 9.78 (1H, s).

MS (m/z): 249 (M+H)$^+$.

Step 2 4-(5,6-dimethoxypyridazin-3-yl)cyclo-hexane-1-carbaldehyde (Cis-Trans Mixture)

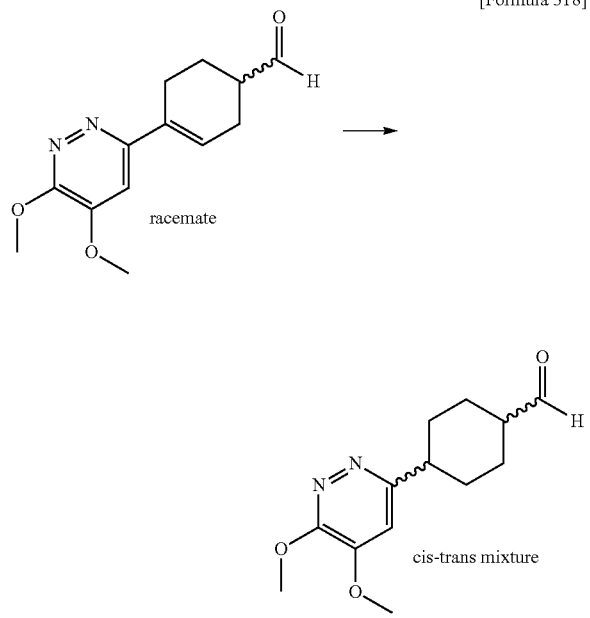

[Formula 318]

The compound (0.175 g) obtained in the above Step 1 was dissolved in ethyl acetate (7 mL), 10% palladium on carbon wet (0.300 g) was added thereto, and the mixture was stirred under hydrogen atmosphere at room temperature for 5 hr. The reaction solution was filtered, and the filtrate was concentrated under reduced pressure to give the title compound (0.179 g) as an oil.

$^1$H-NMR (CDCl$_3$) δ: 1.39-2.94 (10H, m), 3.91-3.94 (3H, m), 4.14-4.16 (3H, m), 6.54-6.60 (1H, m), 9.69-9.78 (1H, m).

Reference Example D-79

N-[6-(4-formylphenyl)-4-methoxypyridazin-3-yl]-N-methylprop-2-enamide

Step 1 4-[5-methoxy-6-(methylamino)pyridazin-3-yl]benzaldehyde

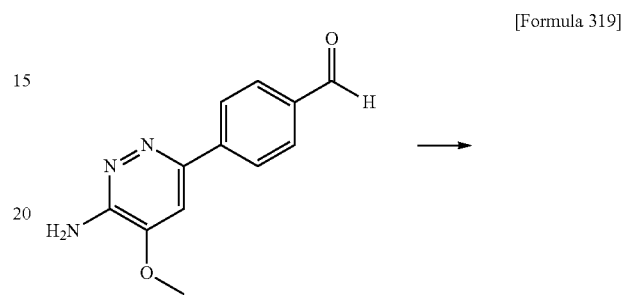

[Formula 319]

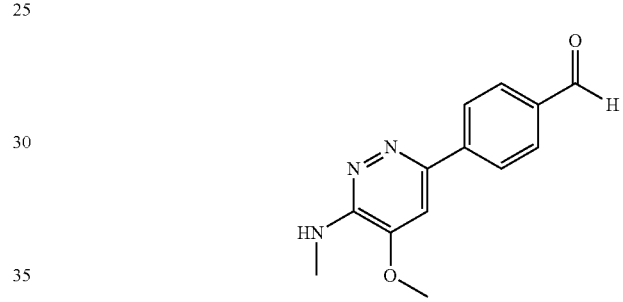

A mixture of the compound (100 mg) obtained in Reference Example D-63, methyl iodide (0.032 mL), potassium carbonate (121 mg) and DMF (2.2 mL) was stirred at 70° C. for 1.5 hr. Water was added to the reaction solution, and the precipitated solid was collected by filtration to give the title compound (62.3 mg) as a solid.

$^1$H-NMR (DMSO-D$_6$) δ: 3.73 (3H, s), 4.00 (3H, s), 7.03 (1H, s), 7.99 (2H, d, J=8.3 Hz), 8.13 (2H, d, J=8.3 Hz), 10.05 (1H, s).

MS (m/z): 244 (M+H)$^+$.

Step 2 N-[6-(4-formylphenyl)-4-methoxypyridazin-3-yl]-N-methylprop-2-enamide

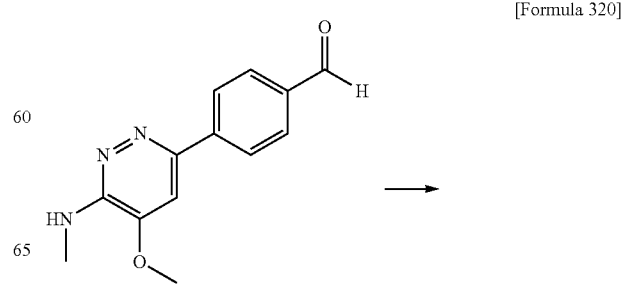

[Formula 320]

253 -continued

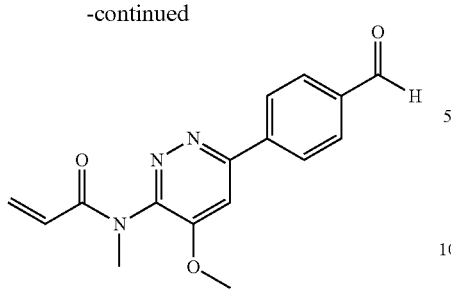

To a mixture of the compound (62.3 mg) obtained in the above Step 1, DIPEA (0.134 mL) and dichloromethane (2.56 mL) was added acryloyl chloride (0.0228 mL) under ice-cooling, and the mixture was stirred at room temperature for 1 hr. Water was added to the reaction solution, and the mixture was extracted with dichloromethane. The organic layer was washed with saturated brine, dried over anhydrous sodium sulfate, and concentrated under reduced pressure. The residue was purified by silica gel column chromatography (ethyl acetate/methanol) to give the title compound (43.4 mg) as a solid.

$^1$H-NMR (DMSO-D$_6$) δ: 3.86 (3H, s), 3.94 (3H, s), 5.63 (1H, dd, J=10.0, 2.1 Hz), 6.00 (1H, dd, J=17.3, 2.1 Hz), 6.26 (1H, dd, J=17.3, 10.0 Hz), 7.46 (1H, s), 8.04 (2H, d, J=8.2 Hz), 8.22 (2H, d, J=8.2 Hz), 10.09 (1H, s).

MS (m/z): 298 (M+H)$^+$.

Reference Example D-80

4-[(pyridin-3-yl)amino]benzaldehyde

[Formula 321]

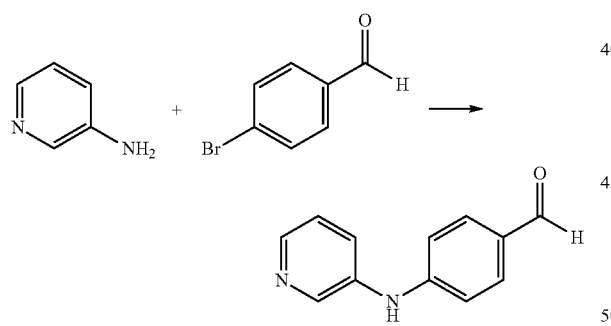

A mixture of 4-bromobenzaldehyde (150 mg), pyridin-3-amine (91.6 mg), tris(dibenzylideneacetone)dipalladium(0) (37.1 mg), 4,5-bis(diphenylphosphino)-9,9-dimethylxanthene (51.6 mg), cesium carbonate (370 mg) and 1,4-dioxane (1.62 mL) was stirred overnight under nitrogen atmosphere at 100° C. The reaction solution was cooled, and filtered through Celite, and the filtrate was concentrated under reduced pressure. The residue was purified by silica gel column chromatography (ethyl acetate/methanol) to give the title compound (146 mg) as a solid.

$^1$H-NMR (DMSO-D$_6$) δ: 7.15 (2H, d, J=8.6 Hz), 7.36-7.38 (1H, m), 7.65-7.67 (1H, m), 7.77 (2H, d, J=8.6 Hz), 8.22-8.25 (1H, m), 8.47-8.48 (1H, m), 9.13 (1H, s), 9.75 (1H, s).

MS (m/z): 199 (M+H)$^+$.

254

Reference Example D-81

3-[(pyridin-3-yl)amino]benzaldehyde

[Formula 322]

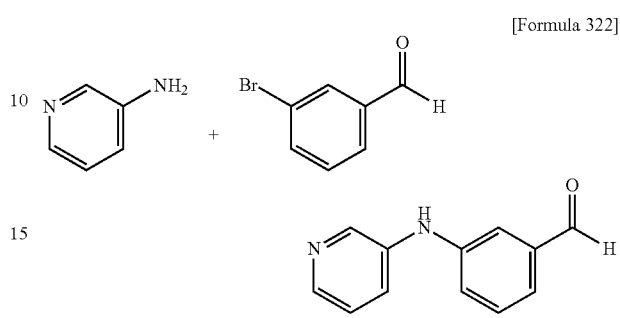

The title compound was obtained in the same manner as in Reference Example D-80 except that 3-bromobenzaldehyde was used instead of 4-bromobenzaldehyde.

$^1$H-NMR (CDCl$_3$) δ: 6.04 (1H, s), 7.22-7.33 (2H, m), 7.44-7.48 (3H, m), 7.55-7.56 (1H, m), 8.25 (1H, dd, J=4.6, 1.5 Hz), 8.44 (1H, d, J=2.4 Hz), 9.96 (1H, s).

MS (m/z): 199 (M+H)$^+$.

Reference Example D-82

4-(2,3-dihydro-1H-indol-1-yl)benzaldehyde

Step 1 1-[4-(1,3-dioxolan-2-yl)phenyl]-2,3-dihydro-1H-indole

[Formula 323]

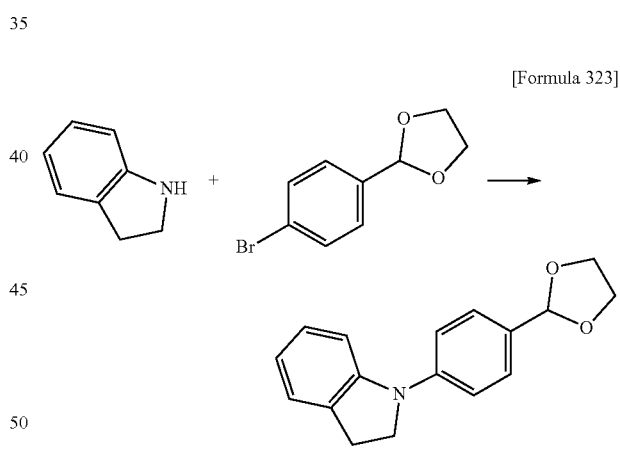

A mixture of indoline (0.280 mL), 2-(4-bromophenyl)-1,3-dioxolane (CAS: 10602-01-4) (1.15 g), TEA (1.15 mL), (±)-2,2'-bis(diphenylphosphino)-1,1'-binaphthyl (54.9 mg), tris(dibenzylideneacetone)dipalladium(0) (69.2 mg), cesium carbonate (2.46 g) and toluene (20 mL) was stirred under nitrogen atmosphere at 110° C. for 5 hr. Saturated aqueous sodium hydrogencarbonate solution was added to the reaction solution, and the mixture was extracted with ethyl acetate. The organic layer was washed with saturated brine, dried over anhydrous sodium sulfate, and concentrated under reduced pressure, and the residue was subjected to silica gel column chromatography (n-hexane/ethyl acetate) to give the title compound (342 mg) as a solid.

$^1$H-NMR (CDCl$_3$) δ: 3.13 (2H, t, J=8.3 Hz), 3.96 (2H, t, J=8.3 Hz), 4.02-4.06 (2H, m), 4.14-4.18 (2H, m), 5.78 (1H, s), 6.76 (1H, td, J=7.4, 1.2 Hz), 7.07 (1H, t, J=7.4 Hz), 7.14-7.18 (2H, m), 7.22 (2H, d, J=8.6 Hz), 7.45 (2H, d, J=8.6 Hz).

Step 2 4-(2,3-dihydro-1H-indol-1-yl)benzaldehyde

[Formula 324]

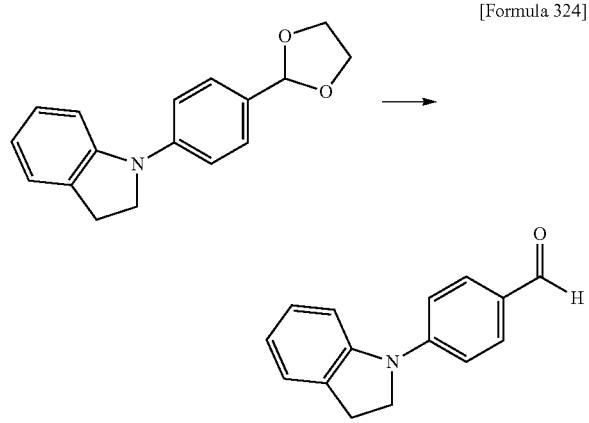

To a solution of the compound (155 mg) obtained in the above Step 1 in THF (2.3 mL) was added 1N hydrochloric acid (2.32 mL) at room temperature, and the mixture was stirred at the same temperature for 16 hr. Saturated aqueous sodium hydrogencarbonate solution was added to the reaction solution, and the mixture was extracted with chloroform. The organic layer was washed with saturated brine, dried over anhydrous sodium sulfate, and concentrated under reduced pressure, and the residue was subjected to silica gel column chromatography (n-hexane/ethyl acetate) to give the title compound (115 mg) as a solid.

$^1$H-NMR (CDCl$_3$) δ: 3.19 (2H, t, J=8.3 Hz), 4.06 (2H, t, J=8.3 Hz), 6.89 (1H, t, J=8.0 Hz), 7.16 (1H, t, J=8.0 Hz), 7.24 (1H, d, J=8.0 Hz), 7.28 (2H, d, J=9.2 Hz), 7.35 (1H, d, J=8.0 Hz), 7.84 (2H, d, J=9.2 Hz), 9.84 (1H, s).

MS (m/z): 224 (M+H)$^+$.

Reference Example D-83

N-[3-(4-formylanilino)phenyl]prop-2-enamide

Step 1 N-[4-(1,3-dioxolan-2-yl)phenyl]-3-nitroaniline

[Formula 325]

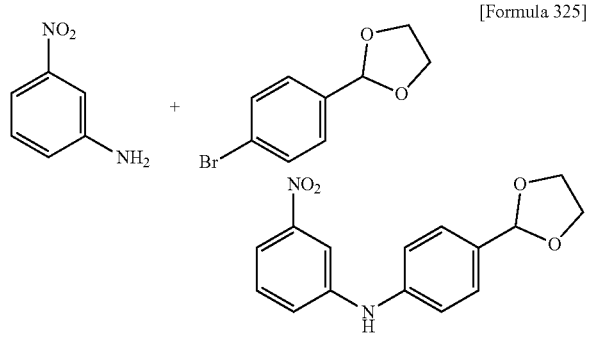

A mixture of 3-nitroaniline (CAS: 99-09-2) (4.13 g), 2-(4-bromophenyl)-1,3-dioxolane (5.71 g), sodium tert-butoxide (CAS: 865-48-5) (4.31 g), tris(dibenzylideneacetone)dipalladium(0) (1.14 g), tri-tert-butylphosphine (10% n-hexane solution) (CAS: 13716-12-6) (7.42 mL) and toluene (50 mL) was stirred at room temperature for 1 hr, and then at 80° C. for 1 hr. Ethyl acetate and water were added to the reaction solution, and the mixture was filtered through Celite. The filtrate was subjected to liquid separation, and the aqueous layer was extracted with ethyl acetate. The organic layers were combined, washed with saturated brine, dried over anhydrous sodium sulfate, and concentrated under reduced pressure. The obtained residue was purified by amino silica gel column chromatography (n-hexane/ethyl acetate). The solvent was evaporated under reduced pressure, a mixed solvent of n-hexane/diethyl ether=1/1 was added to the residue, and the solid was collected by filtration to give the title compound (4.08 g) as a solid.

$^1$H-NMR (CDCl$_3$) δ: 4.03-4.10 (2H, m), 4.11-4.18 (2H, m), 5.78 (1H, s), 6.02 (1H, br s), 7.12-7.15 (2H, m), 7.30 (1H, dd, J=7.9, 2.4 Hz), 7.38 (1H, t, J=7.9 Hz), 7.44-7.48 (2H, m), 7.70-7.73 (1H, m), 7.87 (1H, t, J=2.4 Hz).

Step 2 N$^1$-[4-(1,3-dioxolan-2-yl)phenyl]benzene-1,3-diamine

[Formula 326]

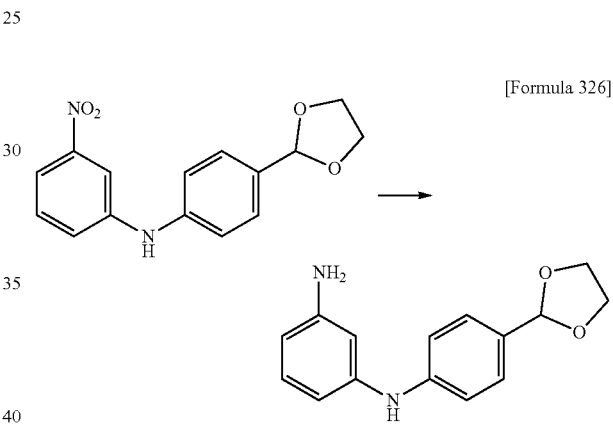

To the compound (1.50 g) obtained in the above Step 1 and 10% palladium on carbon wet (0.300 g) was added ethanol (20 mL), and the mixture was stirred under hydrogen atmosphere at room temperature for 2 hr. The palladium was removed by filtration, and the filtrate was concentrated under reduced pressure to give the title compound (1.29 g) as a solid. This was used in the next reaction without further purification.

$^1$H-NMR (CDCl$_3$) δ: 3.62 (2H, br s), 3.99-4.07 (2H, m), 4.10-4.19 (2H, m), 5.69 (1H, br s), 5.74 (1H, s), 6.29 (1H, dd, J=7.9, 1.8 Hz), 6.44 (1H, t, J=1.8 Hz), 6.47 (1H, dd, J=7.9, 1.8 Hz), 7.03-7.07 (3H, m), 7.34-7.38 (2H, m).

Step 3 N-{3-[4-(1,3-dioxolan-2-yl)anilino]phenyl}prop-2-enamide

[Formula 327]

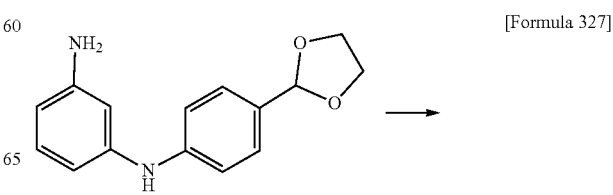

-continued

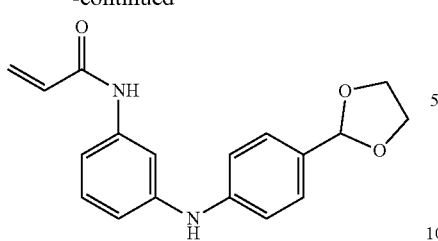

The compound (590 mg) obtained in the above Step 2 was dissolved in dichloromethane (15 mL), and DIPEA (1.2 mL) and acryloyl chloride (CAS: 814-68-6) (0.205 mL) were added thereto, and the mixture was stirred at room temperature for 1 hr. Dichloromethane and water was added thereto, and the mixture was subjected to liquid separation. The organic layer was dried over anhydrous sodium sulfate, and concentrated under reduced pressure. The obtained residue was purified by silica gel column chromatography (n-hexane/ethyl acetate) to give the title compound (709 mg) as a solid.

$^1$H-NMR (CDCl$_3$) δ: 3.99-4.08 (2H, m), 4.10-4.19 (2H, m), 5.73-5.77 (2H, m), 5.83 (1H, br s), 6.22 (1H, dd, J=17.0, 10.3 Hz), 6.42 (1H, dd, J=17.0, 1.2 Hz), 6.84 (1H, dd, J=8.5, 1.8 Hz), 7.04-7.09 (3H, m), 7.20 (1H, t, J=8.5 Hz), 7.35-7.42 (4H, m).

Step 4 N-[3-(4-formylanilino)phenyl]prop-2-enamide

[Formula 328]

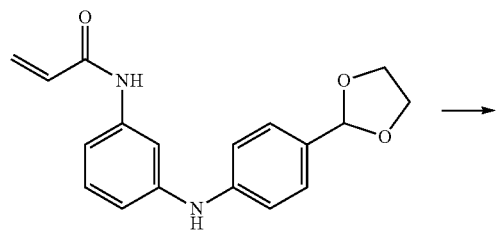

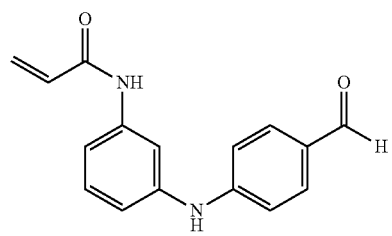

The title compound was obtained in the same manner as in Step 2 of Reference Example D-82, using the compound obtained in the above Step 3.

$^1$H-NMR (DMSO-D$_6$) δ: 5.77 (1H, dd, J=10.3, 1.5 Hz), 6.26 (1H, dd, J=17.0, 1.5 Hz), 6.44 (1H, dd, J=17.0, 10.3 Hz), 6.91 (1H, d, J=7.9 Hz), 7.15 (2H, d, J=8.5 Hz), 7.24-7.31 (2H, m), 7.72-7.76 (3H, m), 9.05 (1H, s), 9.73 (1H, s), 10.17 (1H, s).

Reference Example D-84

4-formyl-N-[(1-methyl-1H-pyrazol-4-yl)methyl]benzamide

[Formula 329]

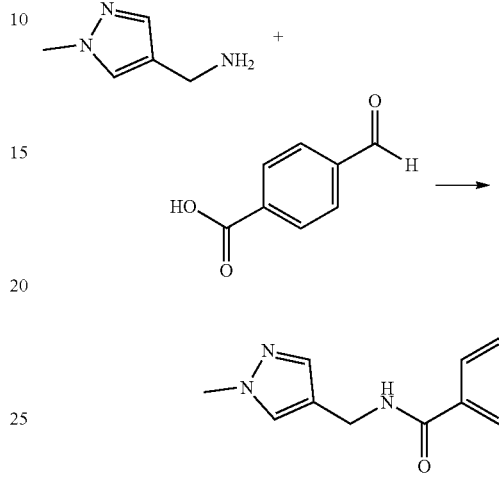

A mixture of 4-formylbenzoic acid (CAS: 619-66-9) (150 mg), (1-methyl-1H-pyrazol-4-yl)methanamine (122 mg), HOBt (162 mg), 1-ethyl-3-(3-dimethylaminopropyl)carbodiimide hydrochloride (WSCD) (230 mg) and DMF (8.0 mL) was stirred at room temperature for 15 hr. Water was added to the reaction solution, and the mixture was extracted with ethyl acetate. The organic layer was washed with saturated brine, dried over anhydrous sodium sulfate, and concentrated under reduced pressure, and the residue was subjected to silica gel column chromatography (chloroform/methanol) to give the title compound (200 mg) as a solid.

$^1$H-NMR (CDCl$_3$) δ: 3.83 (3H, s), 4.48 (2H, d, J=6.1 Hz), 6.12 (1H, br s), 7.38-7.47 (2H, m), 7.69-7.82 (1H, m), 7.88-7.93 (3H, m), 10.03 (1H, s).

MS (m/z): 244 (M+H)$^+$.

Reference Example D-85

N-{3-[(ethenesulfonyl)amino]propyl}-4-formylbenzamide

Step 1 Tert-butyl [3-(4-formylbenzamido)propyl]carbamate

[Formula 330]

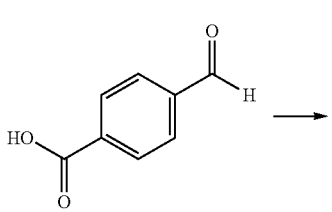

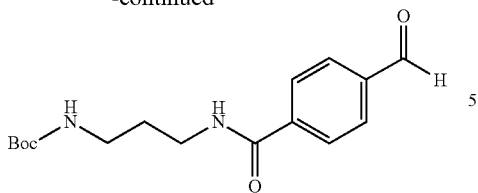

The title compound was obtained in the same manner as in Reference Example D-84 except that tert-butyl N-(3-aminopropyl)carbamate (CAS: 75178-96-0) was used instead of (1-methyl-1H-pyrazol-4-yl)methanamine.

$^1$H-NMR (CDCl$_3$) δ: 1.46 (9H, s), 1.71-1.77 (2H, m), 3.25-3.29 (2H, m), 3.51-3.55 (2H, m), 5.01 (1H, br s), 7.75 (1H, br s), 7.96 (2H, d, J=7.9 Hz), 8.04 (2H, d, J=7.9 Hz), 10.09 (1H, s).

MS (m/z): 207 (M-Boc+H)$^+$.

Step 2 N-{3-[(ethenesulfonyl)amino]propyl}-4-formylbenzamide

[Formula 331]

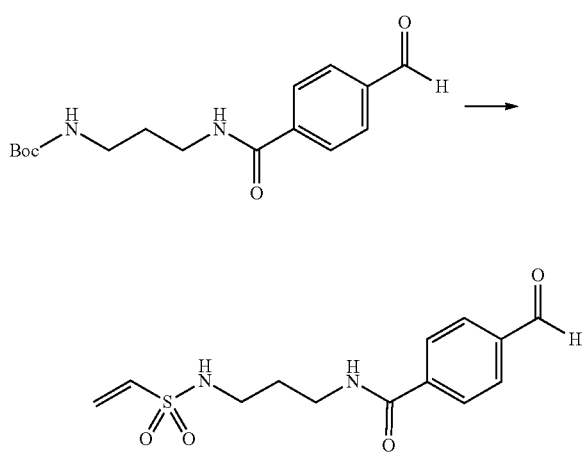

The compound (449 mg) obtained in the above Step 1 was dissolved in dichloromethane (3 mL), and hydrogen chloride (4 mol/L, 1,4-dioxane solution, 3 mL) was added thereto. The mixture was stirred at room temperature for 2 hr, and the solvent was evaporated under reduced pressure. Dichloromethane (11 mL), DIPEA (1.92 mL) and 2-chloroethanesulfonyl chloride (CAS: 1622-32-8) (0.174 mL) were added to the residue, and the mixture was stirred at room temperature for 3 hr. The solvent was evaporated under reduced pressure. The residue was purified by silica gel column chromatography (ethyl acetate) to give the title compound (110 mg) as a solid.

$^1$H-NMR (CDCl$_3$) δ: 1.85 (2H, quint. J=6.1 Hz), 3.12 (2H, q, J=6.1 Hz), 3.62 (2H, q, J=6.1 Hz), 5.57 (1H, t, J=6.1 Hz), 5.94 (1H, d, J=9.7 Hz), 6.22 (1H, d, J=17.0 Hz), 6.55 (1H, dd, J=17.0, 9.7 Hz), 7.16 (1H, t, J=6.1 Hz), 7.91-7.96 (4H, m), 10.06 (1H, s).

MS (m/z): 297 (M+H)+.

Reference Example D-86

4-[(2-oxopyrrolidin-1-yl)methyl]benzaldehyde

Step 1 Methyl 4-[(2-oxopyrrolidin-1-yl)methyl]benzoate

[Formula 332]

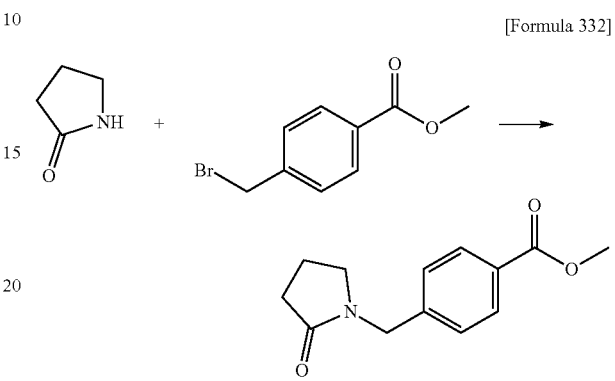

To a suspension of sodium hydride (purity 55%, 238 mg) and DMF (15 mL) was added 2-pyrrolidinone (CAS: 616-45-5) (557 mg) under ice-cooling, and after 30 min, a solution of methyl 4-(bromomethyl)benzoate (CAS: 2417-72-3) (1.00 g) in DMF (15 mL) was added dropwise thereto at the same temperature. The mixture was stirred at room temperature for 16 hr, water was added to the reaction solution, and the mixture was extracted with ethyl acetate. The organic layer was washed with saturated brine, dried over anhydrous sodium sulfate, and concentrated under reduced pressure, and the residue was subjected to silica gel column chromatography (n-hexane/ethyl acetate) to give the title compound (576 mg) as a solid.

$^1$H-NMR (CDCl$_3$) δ: 1.99-2.06 (2H, m), 2.47 (2H, t, J=7.9 Hz), 3.27 (2H, t, J=7.3 Hz), 3.92 (3H, s), 4.51 (2H, s), 7.31 (2H, d, J=8.5 Hz), 8.01 (2H, d, J=8.5 Hz).

MS (m/z): 234 (M+H)$^+$.

Step 2 1-{[4-(hydroxymethyl)phenyl]methyl}pyrrolidin-2-one

[Formula 333]

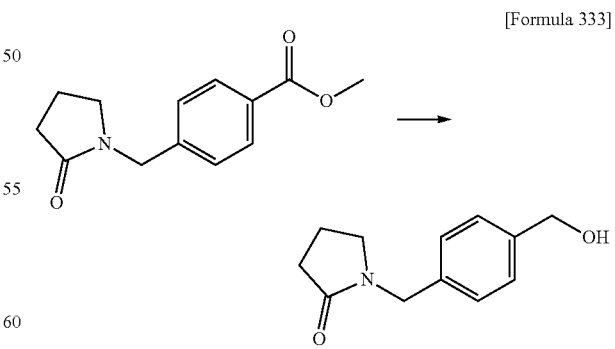

To a solution of the compound (576 mg) obtained in the above Step 1 in THF (20 mL) was added lithium borohydride (CAS: 16949-15-8) (108 mg) little by little under ice-cooling, and methanol (0.2 mL) was added thereto at the same temperature. The mixture was stirred at room temperature for 18 hr, and then at 50° C. for 4 hr. Lithium borohydride (108 mg) was again added little by little under ice-cooling to the reaction solution, and the mixture was stirred at 60° C. for 9 hr. The reaction solution was weakly acidified with 1N hydrochloric acid by addition little by little under ice-cooling, and extracted with chloroform. The organic layer was washed with saturated brine, dried over anhydrous sodium sulfate, and concentrated under reduced pressure, and the residue was subjected to silica gel column chromatography (chloroform/methanol) to give the title compound (338 mg) as a solid.

$^1$H-NMR (CDCl$_3$) δ: 1.95-2.03 (2H, m), 2.44 (2H, t, J=7.9 Hz), 3.25 (2H, t, J=7.3 Hz), 4.44 (2H, s), 4.69 (2H, s), 7.23 (2H, d, J=7.9 Hz), 7.34 (2H, d, J=7.9 Hz).

MS (m/z): 206 (M+H)$^+$.

Step 3 4-[(2-oxopyrrolidin-1-yl)methyl]benzaldehyde

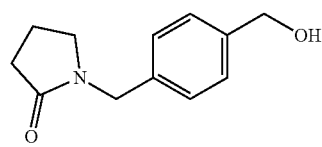

[Formula 334]

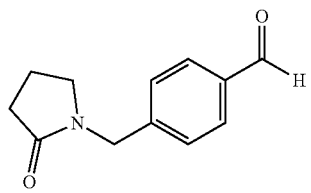

To a solution of the compound (336 mg) obtained in the above Step 2 in dichloromethane (15 mL) was added Dess-Martin periodinane (CAS: 87413-09-0) (764 mg) under ice-cooling. The mixture was stirred at room temperature for 1.5 hr, water was added to the reaction solution, and the mixture was extracted with ethyl acetate. The organic layer was washed with saturated brine, dried over anhydrous sodium sulfate, and concentrated under reduced pressure, and the residue was subjected to silica gel column chromatography (chloroform/methanol) to give the title compound (343 mg) as an oil.

$^1$H-NMR (CDCl$_3$) δ: 2.01-2.08 (2H, m), 2.48 (2H, t, J=8.6 Hz), 3.30 (2H, t, J=7.4 Hz), 4.54 (2H, s), 7.41 (2H, d, J=8.0 Hz), 7.86 (2H, d, J=8.0 Hz), 10.01 (1H, s).

MS (m/z): 204 (M+H)$^+$.

Reference Example D-87

4-(5-oxopyrrolidin-2-yl)benzaldehyde (Racemate)

Step 1 methyl 4-(5-oxopyrrolidin-2-yl)benzoate (Racemate)

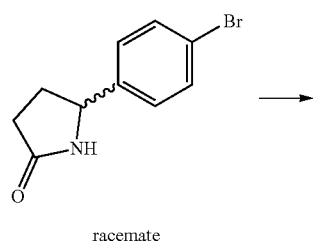

racemate

[Formula 335]

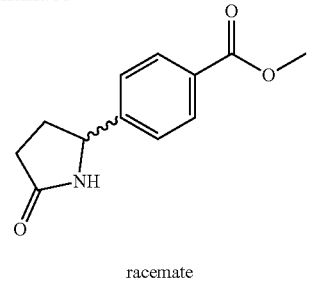

racemate

A mixture of 5-(4-bromophenyl)pyrrolidin-2-one (CAS: 207989-90-0) (1.00 g), TEA (1.15 mL), methanol (15 mL), [1,1'-bis(diphenylphosphino)ferrocene]palladium(II) dichloride dichloromethane adduct (170 mg) and DMF (30 mL) was stirred under carbon monoxide atmosphere at 90° C. for 2 hr. Aqueous saturated ammonium chloride solution was added to the reaction solution, and the mixture was extracted with ethyl acetate. The organic layer was washed with saturated brine, dried over anhydrous sodium sulfate, and concentrated under reduced pressure, and the residue was subjected to silica gel column chromatography (chloroform/methanol) to give the title compound (342 mg) as a solid.

$^1$H-NMR (CDCl$_3$) δ: 1.91-2.02 (1H, m), 2.41-2.50 (2H, m), 2.56-2.67 (1H, m), 3.93 (3H, s), 4.82 (1H, t, J=7.4 Hz), 5.96-6.18 (1H, m), 7.38 (2H, d, J=8.0 Hz), 8.05 (2H, d, J=8.0 Hz).

MS (m/z): 220 (M+H)$^+$.

Step 2 5-[4-(hydroxymethyl)phenyl]pyrrolidin-2-one (Racemate)

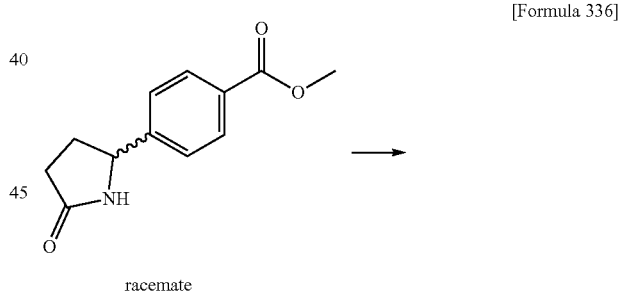

racemate

[Formula 336]

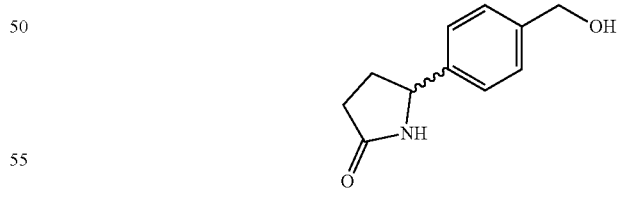

racemate

The title compound was obtained in the same manner as in Step 2 of Reference Example D-86, using the compound obtained in the above Step 1.

$^1$H-NMR (DMSO-D$_6$) δ: 1.67-1.77 (1H, m), 2.22 (2H, t, J=8.0 Hz), 2.39-2.47 (1H, m), 4.47 (2H, d, J=5.5 Hz), 4.64 (1H, t, J=7.1 Hz), 5.15 (1H, t, J=5.8 Hz), 7.24 (2H, d, J=8.0 Hz), 7.29 (2H, d, J=8.0 Hz), 8.07 (1H, br s).

MS (m/z): 192 (M+H)$^+$.

Step 3 4-(5-oxopyrrolidin-2-yl)benzaldehyde (Racemate)

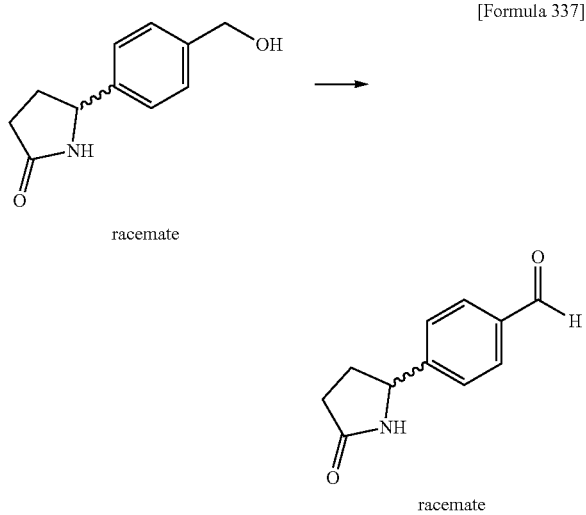

racemate

The compound (110 mg) obtained in the above Step 2 was dissolved in chloroform (5 mL), manganese dioxide (498 mg) was added thereto, and the mixture was stirred at room temperature for 1.5 hr. Ethyl acetate and water were added thereto, the insoluble substance was removed by filtration, and the filtrate was subjected to liquid separation. The aqueous layer was extracted with ethyl acetate, and the organic layers were combined, washed with saturated brine, dried over anhydrous sodium sulfate, and concentrated under reduced pressure. The obtained residue was purified by silica gel column chromatography (chloroform/methanol) to give the title compound (56 mg) as an oil.

$^1$H-NMR (CDCl$_3$) δ: 1.93-2.03 (1H, m), 2.44-2.52 (2H, m), 2.60-2.71 (1H, m), 4.85 (1H, t, J=7.4 Hz), 6.04 (1H, br s), 7.48 (2H, d, J=8.0 Hz), 7.91 (2H, d, J=8.0 Hz), 10.02 (1H, s).

MS (m/z): 190 (M+H)$^+$.

Reference Example D-88

4-(cyclohexylamino)benzaldehyde

Step 1 methyl 4-(cyclohexylamino)benzoate

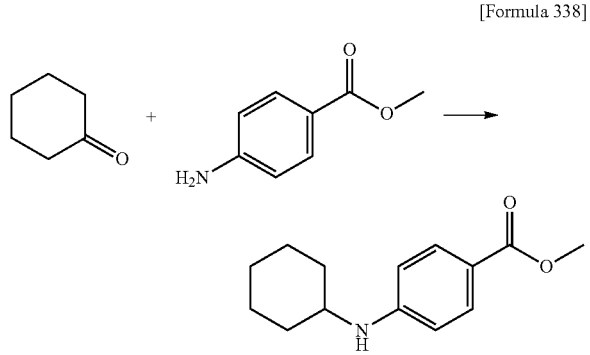

A mixture of methyl 4-aminobenzoate (CAS: 619-45-4) (1.13 g), magnesium sulfate (1.81 g), cyclohexanone (3.01 g), acetic acid (7.58 mL), sodium triacetoxyborohydride (14.3 g), methanol (30 mL) and dichloromethane (10 mL) was stirred at room temperature for 36 hr, and then at 60° C. for 9 hr. Saturated aqueous sodium hydrogencarbonate solution was added to the reaction mixture, and the mixture was extracted with chloroform. The organic layer was washed with saturated brine, dried over anhydrous sodium sulfate, filtered, and concentrated under reduced pressure. The obtained residue was subjected to silica gel column chromatography (n-hexane/ethyl acetate) to give the title compound (1.16 g) as a solid.

$^1$H-NMR (CDCl$_3$) δ: 1.12-1.28 (3H, m), 1.32-1.44 (2H, m), 1.61-1.70 (1H, m), 1.77 (2H, dt, J=13.5, 3.7 Hz), 2.05 (2H, dd, J=12.9, 3.1 Hz), 3.31 (1H, br s), 3.84 (3H, s), 4.03 (1H, br s), 6.50-6.54 (2H, m), 7.81-7.85 (2H, m).

MS (m/z): 234 (M+H)$^+$.

Step 2 [4-(cyclohexylamino)phenyl]methanol

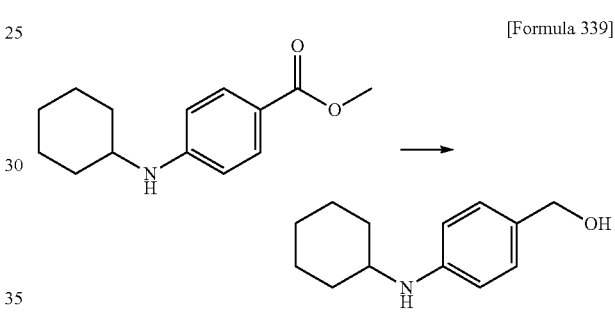

The title compound was obtained in the same manner as in Step 2 of Reference Example D-86, using the compound obtained in the above Step 1.

Step 3 4-(cyclohexylamino)benzaldehyde

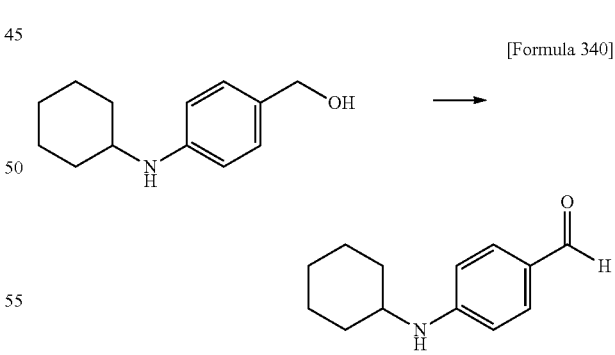

The title compound was obtained in the same manner as in Step 3 of Reference Example D-87, using the compound obtained in the above Step 2.

$^1$H-NMR (CDCl$_3$) δ: 1.15-1.29 (3H, m), 1.34-1.45 (2H, m), 1.68 (1H, dt, J=12.9, 3.7 Hz), 1.79 (2H, dt, J=13.5, 3.7 Hz), 2.03-2.10 (2H, m), 3.32-3.41 (1H, m), 4.25 (1H, d, J=8.0 Hz), 6.58 (2H, d, J=8.6 Hz), 7.67 (2H, d, J=8.6 Hz), 9.70 (1H, s).

MS (m/z): 204 (M+H)$^+$.

Reference Example D-89

Tert-butyl Benzyl (4-formylphenyl)carbamate

Step 1 Methyl 4-[benzyl (tert-butoxycarbonyl)amino]benzoate

[Formula 341]

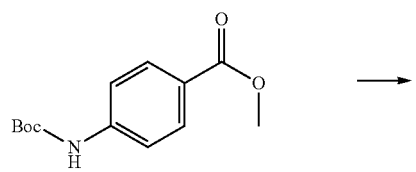

To a suspension of sodium hydride (purity 55%, 131 mg) and THF (10 mL) was added a solution of methyl 4-[(tert-butoxycarbonyl)amino]benzoate (503 mg) synthesized according to the method described in a literature (J. Med. Chem. 2016, 59(18), 8233-8262) in THF (5 mL) under ice-cooling. The mixture was stirred at room temperature for 30 min, and benzyl bromide (CAS: 100-39-0) (0.310 mL) was added dropwise thereto under ice-cooling. The mixture was stirred at room temperature for 15 hr, water was added to the reaction solution, and the mixture was extracted with ethyl acetate. The organic layer was washed with saturated brine, dried over anhydrous sodium sulfate, and concentrated under reduced pressure, and the residue was subjected to silica gel column chromatography (n-hexane/ethyl acetate) to give the title compound (408 mg) as a solid.

$^1$H-NMR (CDCl$_3$) δ: 1.42 (9H, s), 3.89 (3H, s), 4.88 (2H, s), 7.19-7.32 (7H, m), 7.94 (2H, d, J=8.6 Hz).

MS (m/z): 242 (M-Boc+H)$^+$.

Step 2 Tert-butyl Benzyl [4-(hydroxymethyl)phenyl]carbamate

[Formula 342]

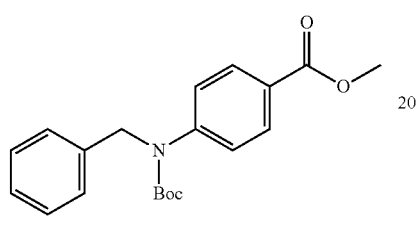

To a solution of the compound (405 mg) obtained in the above Step 1 in THF (10 mL) was added lithium borohydride (CAS: 16949-15-8) (78.9 mg) little by little under ice-cooling. The mixture was stirred at room temperature for 1 hr, and the mixture was stirred at 50° C. for 4 hr. The reaction solution was weakly acidified with 1N hydrochloric acid by addition little by little under ice-cooling, and extracted with chloroform. The organic layer was washed with saturated brine, and dried over anhydrous sodium sulfate to give a crude product (369 mg) of the title compound as an oil.

MS (m/z): 258 (M+H-tBu)$^+$.

Step 3 Tert-butyl Benzyl (4-formylphenyl)carbamate

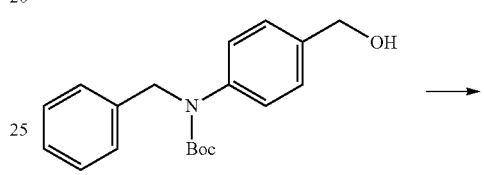

[Formula 343]

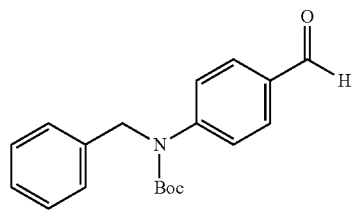

The title compound was obtained in the same manner as in Step 3 of Reference Example D-87, using the compound obtained in the above Step 2.

$^1$H-NMR (CDCl$_3$) δ: 1.43 (9H, s), 4.92 (2H, s), 7.22 (2H, d, J=6.7 Hz), 7.27-7.35 (3H, m), 7.39 (2H, d, J=8.6 Hz), 7.79 (2H, d, J=8.6 Hz), 9.93 (1H, s).

MS (m/z): 212 (M-Boc+H)$^+$.

Reference Example D-90

1-(5,6-dimethoxypyridazin-3-yl)piperidine-4-carbaldehyde

Step 1 [1-(5,6-dimethoxypyridazin-3-yl)piperidin-4-yl]methanol

[Formula 344]

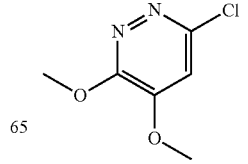

-continued

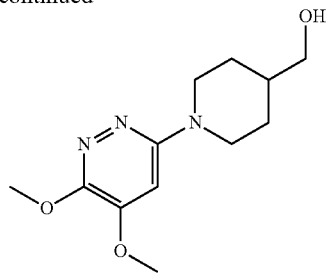

A mixture of 6-chloro-3,4-dimethoxypyridazine (364 mg), 4-piperidine methanol (CAS: 586-95-8, 200 mg), (+/−)-2,2'-bis(diphenylphosphino)-1,1'-binaphthyl (216 mg), sodium tert-butoxide (200 mg), toluene (4 mL) and tris(dibenzylideneacetone)dipalladium(0) (159 mg) was stirred under nitrogen atmosphere at 100° C. for 4 hr. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (ethyl acetate/methanol) to give the title compound (208 mg) as a solid.

$^1$H-NMR (CDCl$_3$) δ: 1.35-1.38 (2H, m), 1.75-1.78 (1H, m), 1.83-1.86 (2H, m), 2.89-2.93 (2H, m), 3.54-3.55 (2H, m), 3.90 (3H, s), 4.08 (3H, s), 4.18-4.19 (1H, m), 4.20-4.23 (1H, m), 5.30 (1H, s), 6.35 (1H, s).

MS (m/z): 254 (M+H)$^+$.

Step 2 1-(5,6-dimethoxypyridazin-3-yl)piperidine-4-carbaldehyde

[Formula 345]

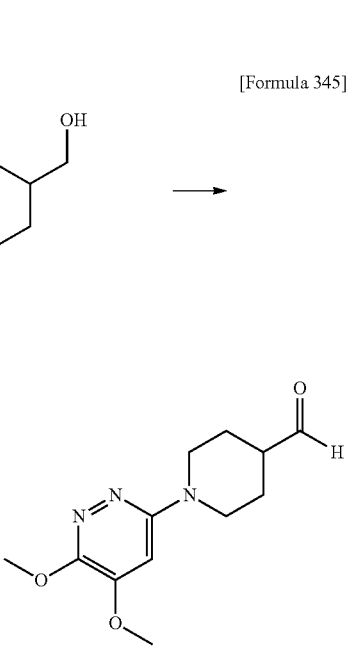

The title compound was obtained in the same manner as in Step 3 of Reference Example D-86, using the compound obtained in the above Step 1.

$^1$H-NMR (CDCl$_3$) δ: 1.70-1.79 (2H, m), 2.02-2.04 (2H, m), 2.50-2.53 (1H, m), 3.08-3.15 (2H, m), 3.90 (3H, s), 4.06-4.07 (5H, m), 6.35 (1H, s), 9.70 (1H, s).

MS (m/z): 252 (M+H)$^+$.

Reference Example D-91

4-(1H-1,2,4-triazol-5-yl)benzaldehyde

Step 1 [4-(1H-1,2,4-triazol-5-yl)phenyl]methanol

[Formula 346]

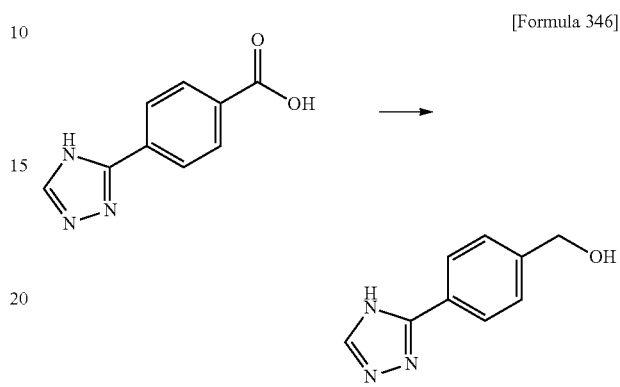

The title compound was obtained in the same manner as in Step 2 of Reference Example D-86, using 4-(1H-1,2,4-triazol-5-yl)benzoic acid (CAS: 876715-40-1). The obtained compound was directly used in the next step without purification.

MS (m/z): 176 (M+H)$^+$.

Step 2 4-(1H-1,2,4-triazol-5-yl)benzaldehyde

[Formula 347]

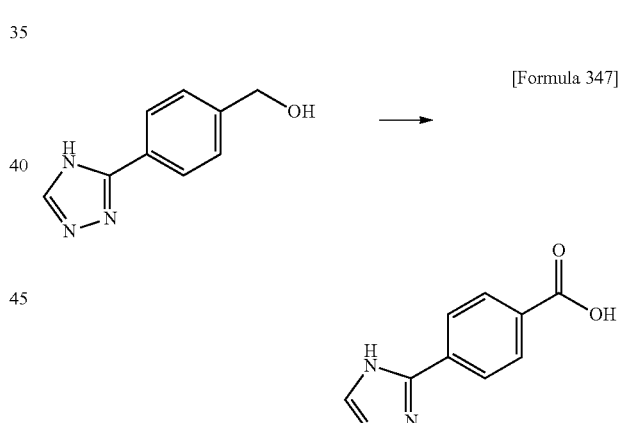

A mixture of the compound (155 mg) obtained in the above Step 1, pyridinium chlorochromate (381 mg), DMSO (3 mL) and dichloromethane (8 mL) was stirred overnight at room temperature. Saturated aqueous sodium hydrogencarbonate solution was added to the reaction solution, and the mixture was extracted with ethyl acetate. The organic layer was washed with saturated brine, dried over anhydrous sodium sulfate, and concentrated under reduced pressure. The residue was purified by silica gel column chromatography (ethyl acetate) to give the title compound (118 mg) as a solid.

$^1$H-NMR (DMSO-D$_6$) δ: 8.03 (2H, d, J=8.0 Hz), 8.25 (2H, d, J=8.0 Hz), 8.71 (1H, br s), 10.06 (1H, s), 14.37 (1H, br s).

MS (m/z): 174 (M+H)$^+$.

Reference Example D-92

4-(3-hydroxypiperidine-1-sulfonyl)benzaldehyde (Racemate)

[Formula 348]

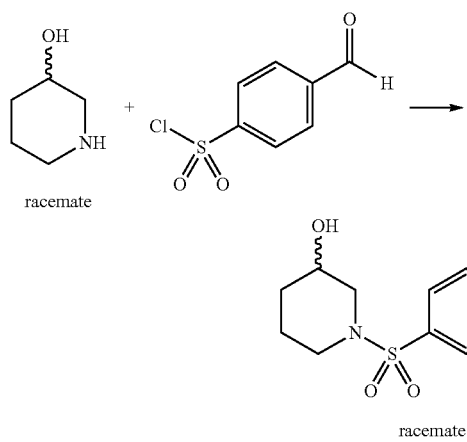

To a solution of 3-hydroxypiperidine (51.4 mg) in dichloromethane (1 mL) was added a solution of 4-formylbenzene-1-sulfonyl chloride (80 mg) in dichloromethane (1 mL), and the mixture was stirred at room temperature for 1 hr. Water was added to the reaction solution, and the mixture was extracted with dichloromethane. The organic layer was washed with saturated brine, dried over anhydrous sodium sulfate, and concentrated under reduced pressure. The residue was purified by silica gel column chromatography (n-hexane/ethyl acetate) to give the title compound (102 mg) as a solid.

$^1$H-NMR (CDCl$_3$) δ: 1.40-1.44 (1H, m), 1.63-1.67 (1H, m), 1.76-1.95 (3H, m), 2.73-2.87 (2H, m), 3.18-3.23 (1H, m), 3.40 (1H, m), 3.87-3.89 (1H, m), 7.94 (2H, m), 8.05-8.07 (2H, m), 10.12 (1H, s).

MS (m/z): 270 (M+H)$^+$.

Reference Example D-93

4-(azepane-1-sulfonyl)benzaldehyde

[Formula 349]

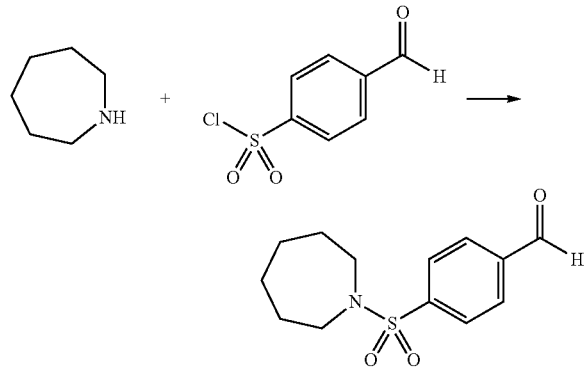

The title compound was obtained in the same manner as in Reference Example D-92 except that azepane was used instead of 3-hydroxypiperidine.

$^1$H-NMR (CDCl$_3$) δ: 1.58-1.61 (4H, m), 1.72-1.75 (4H, m), 3.30-3.31 (4H, m), 7.96-8.02 (4H, m), 10.10 (1H, s).

MS (m/z): 268 (M+H)$^+$.

Reference Example D-94

6-(4-formylphenyl)-4-methoxypyridazine-3-carbonitrile

[Formula 350]

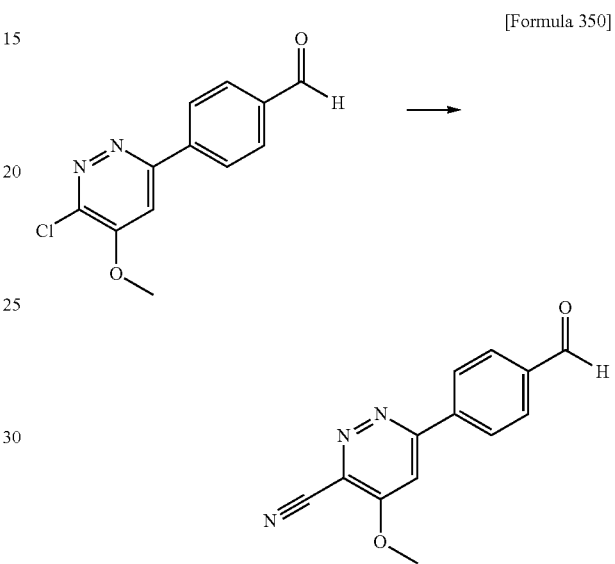

A mixture of the compound (0.200 g) obtained in Reference Example D-28, zinc cyanide (0.0965 g), tetrakis(triphenylphosphine)palladium(0) (0.0930 g) and N,N-dimethylacetamide (3.00 mL) was stirred under nitrogen atmosphere at 100° C. for 1 hr. The reaction solution was diluted with ethyl acetate, washed successively with water and saturated brine, dried over anhydrous magnesium sulfate, and concentrated under reduced pressure. The obtained residue was subjected to silica gel column chromatography (dichloromethane/ethyl acetate). The fraction was concentrated under reduced pressure, and the obtained solid was subjected to slurry washing with dichloromethane, and dried to give the title compound (0.0826 g) as a solid.

$^1$H-NMR (DMSO-D$_6$) δ: 4.20 (3H, s), 8.14 (2H, d, J=8.5 Hz), 8.21 (1H, s), 8.51 (2H, d, J=8.5 Hz), 10.15 (1H, s).

MS (m/z): 240 (M+H)$^+$.

Reference Example D-95

{4-[(5-methoxypyridin-3-yl)amino]phenyl}methanol

Step 1 N-[4-({[tert-butyl(dimethyl)silyl]oxy}methyl)phenyl]-5-methoxypyridin-3-amine

[Formula 351]

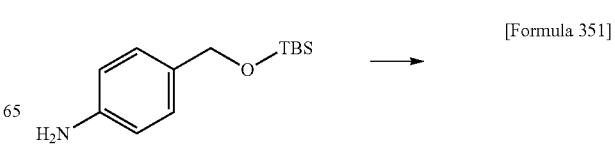

-continued

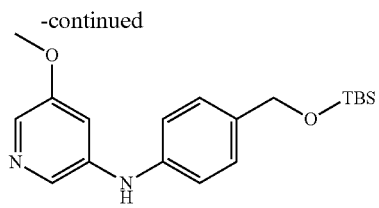

To 4-({[tert-butyl(dimethyl)silyl]oxy}methyl)aniline (0.404 g) synthesized according to the method described in a literature (Tetrahedron 2015, 71(49), 9240-9244), 3-bromo-5-methoxypyridine (CAS: 50720-12-2) (0.320 g), tris(dibenzylideneacetone)dipalladium(0) (0.156 g), 4,5-bis (diphenylphosphino)-9,9-dimethylxanthene (CAS: 161265-03-8) (0.197 g) and cesium carbonate (1.67 g) was added 1,4-dioxane (2.43 mL), and the mixture was stirred under nitrogen atmosphere at 70° C. for 2 hr. The reaction mixture was concentrated under reduced pressure, and the residue was purified by silica gel column chromatography (n-hexane/ethyl acetate) to give the title compound (0.252 g) as a solid.

$^1$H-NMR (CDCl$_3$) δ: 0.11 (6H, s), 0.94 (9H, s), 3.81 (3H, s), 4.70 (2H, s), 5.91 (1H, br s), 6.92 (1H, t, J=2.4 Hz), 7.08 (2H, d, J=8.5 Hz), 7.26 (2H, d, J=8.5 Hz), 7.84 (1H, d, J=2.4 Hz), 7.97 (1H, d, J=2.4 Hz).

MS (m/z): 345 (M+H)$^+$.

Step 2 {4-[(5-methoxypyridin-3-yl)amino] phenyl}methanol

[Formula 352]

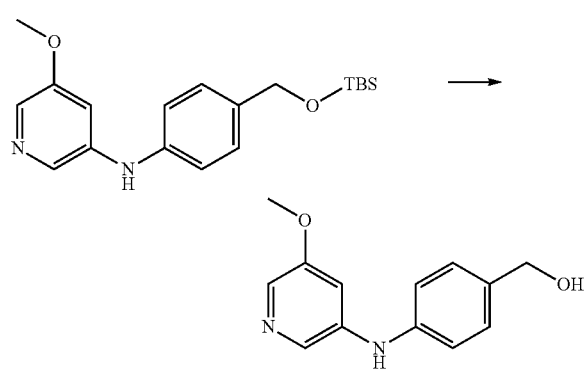

To a solution of the compound (0.252 g) obtained in the above Step 1 in THF (7.31 mL) was added 1N tetrabutylammonium fluoride THF solution (1.46 mL), and the mixture was stirred overnight at room temperature. The reaction mixture was concentrated under reduced pressure, brine was added to the residue, and the mixture was extracted three times with dichloromethane. The organic layer was dried over anhydrous sodium sulfate, and concentrated under reduced pressure. The residue was purified by silica gel column chromatography (dichloromethane/ethyl acetate) to give the title compound (0.117 g) as a solid.

$^1$H-NMR (CD$_3$OD) δ: 3.80 (3H, s), 4.54 (2H, s), 7.03 (1H, t, J=2.4 Hz), 7.12 (2H, d, J=8.5 Hz), 7.29 (2H, d, J=8.5 Hz), 7.66 (1H, d, J=2.4 Hz), 7.86 (1H, br s).

MS (m/z): 231 (M+H)$^+$.

Reference Example D-96

4-(5-methoxy-6-phenoxypyridazin-3-yl)benzaldehyde

[Formula 353]

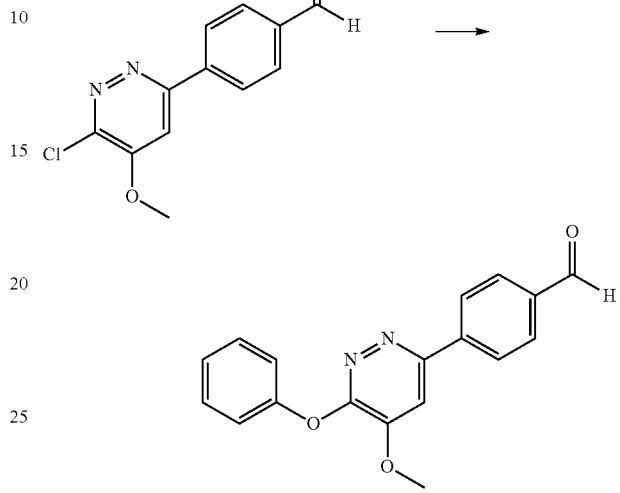

A mixture of the compound (100 mg) obtained in Reference Example D-28, phenol (37.8 mg), DMF (2.68 mL) and potassium carbonate (111 mg) was stirred at 100° C. for 15 hr. The reaction solution was allowed to cool to room temperature. Water was added to the reaction solution, and the mixture was extracted with ethyl acetate. The organic layer was washed with saturated brine, dried over anhydrous sodium sulfate, and concentrated under reduced pressure. The residue was purified by silica gel column chromatography (n-hexane/ethyl acetate) to give the title compound (63.9 mg) as a solid.

$^1$H-NMR (CDCl$_3$) δ: 4.12 (3H, s), 7.27-7.28 (2H, m), 7.33 (1H, s), 7.41-7.44 (2H, m), 8.00-8.01 (2H, m), 8.04-8.05 (1H, m), 8.18-8.20 (2H, m), 10.09 (1H, s).

MS (m/z): 307 (M+H)$^+$.

Reference Example E-1

5-({[(1S,3R)-3-(methylamino)cyclopentyl] amino}methyl)-1H-indole-2-carbonitrile

Step 1 Tert-butyl 2-cyano-5-[({(1S,3R)-3-[methyl (2-nitrobenzene-1-sulfonyl)amino] cyclopentyl}amino)methyl]-1H-indole-1-carboxylate

[Formula 354]

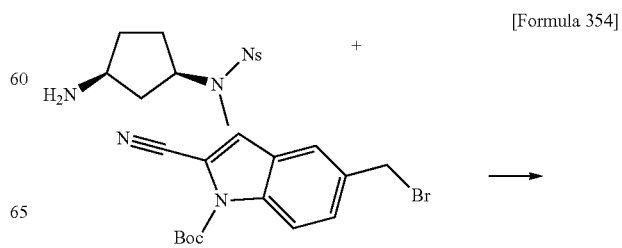

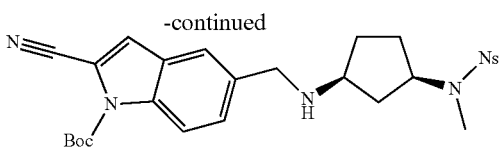

To the compound (1.11 g) obtained in Step 4 of Reference Example A-3, tert-butyl 5-(bromomethyl)-2-cyano-indole-1-carboxylate (1.24 g) produced according to the method described in a literature (cancer cell 2015, 27, 589-602) and potassium carbonate (1.02 g) was added DMF (12 mL), and the mixture was stirred at room temperature for 2 hr, and allowed to stand overnight. Ethyl acetate and saturated brine were added to the reaction solution, and the mixture was subjected to liquid separation. The organic layer was washed with saturated brine, dried over anhydrous sodium sulfate, and concentrated under reduced pressure. The obtained residue was purified by silica gel column chromatography (n-hexane/ethyl acetate, dichloromethane/methanol) to give the title compound (916 mg) as a solid.

$^1$H-NMR (CDCl$_3$) δ: 1.37-1.60 (3H, m), 1.70-1.88 (2H, m), 1.73 (9H, s), 2.04-2.12 (1H, m), 2.89 (3H, s), 3.08-3.14 (1H, m), 3.82 (2H, s), 4.30-4.39 (1H, m), 7.30 (1H, s), 7.44 (1H, d, J=9.1 Hz), 7.55 (1H, s), 7.59-7.63 (1H, m), 7.66-7.73 (2H, m), 7.98-8.02 (1H, m), 8.15 (1H, d, J=9.1 Hz).

MS (m/z): 554 (M+H)$^+$.

Step 2 5-({[(1S,3R)-3-(methylamino)cyclopentyl]amino}methyl)-1H-indole-2-carbonitrile

[Formula 355]

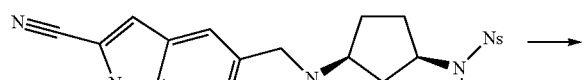

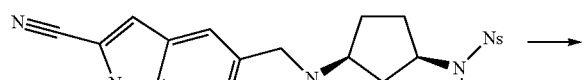

The compound (916 mg) obtained in the above Step 1 was dissolved in a mixed solvent of THF (10 mL) and methanol (10 mL), and 4-isopropylbenzenethiol (0.504 mL) and cesium carbonate (1.08 g) were added thereto, and the mixture was stirred at room temperature for 1 hr, and allowed to stand overnight. Ethyl acetate and saturated brine were added to the reaction solution, and the mixture was subjected to liquid separation. The organic layer was washed with saturated brine, and the aqueous layer was extracted five times with ethyl acetate. The organic layers were combined, dried over anhydrous sodium sulfate, and concentrated under reduced pressure. The obtained residue was purified by amino silica gel column chromatography (n-hexane/ethyl acetate, followed by dichloromethane/methanol) to give the title compound (0.281 g).

$^1$H-NMR (CDCl$_3$) δ: 1.38-1.44 (1H, m), 1.59-1.71 (2H, m), 1.86-1.93 (2H, m), 2.15-2.22 (1H, m), 2.46 (3H, s), 3.07-3.14 (1H, m), 3.22-3.28 (1H, m), 3.78-3.86 (2H, m), 7.05 (1H, s), 7.17 (2H, s), 7.51 (1H, s).

Reference Example E-2

(1R,3S,4S)—N$^1$-{[4-(5,6-dimethoxypyridin-3-yl)phenyl]methyl}-4-methoxy-N$^3$-methylcyclopentane-1,3-diamine Hydrochloride Step 1 Tert-butyl [(1S,2S,4R)-4-({[4-(5,6-dimethoxypyridin-3-yl)phenyl]methyl}amino)-2-methoxycyclopentyl]methylcarbamate

[Formula 356]

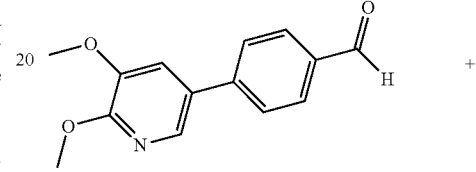

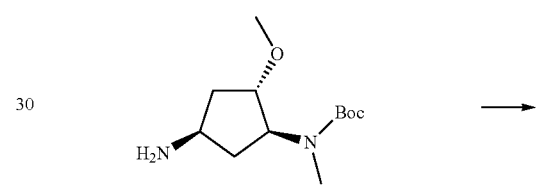

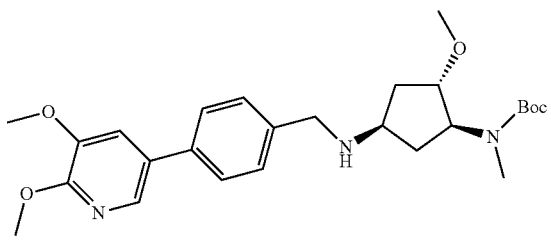

To a suspension of the compound (0.460 g) obtained in Step 3 of Reference Example A-17 and the compound (0.525 g) obtained in Reference Example D-56 in dichloromethane (16 mL) were added successively sodium triacetoxyborohydride (1.35 g) and acetic acid (0.320 mL), and the mixture was stirred at room temperature for 17 hr. Water (25 mL) was added to the reaction mixture, and the mixture was extracted twice (80 mL, 50 mL) with a mixed solvent of dichloromethane/methanol (9/1). The organic layers were combined, and dried over anhydrous sodium sulfate. The solvent was evaporated under reduced pressure, and the obtained residue was purified by silica gel column chromatography (dichloromethane/methanol) to give the title compound (0.733 g) as a solid.

$^1$H-NMR (CDCl$_3$) δ: 1.47 (9H, s), 1.53-1.65 (1H, m), 1.83-1.99 (2H, m), 2.17-2.27 (1H, m), 2.84 (3H, s), 3.25-3.36 (1H, m), 3.31 (3H, s), 3.85 (2H, s), 3.87-3.94 (1H, m), 3.95 (3H, s), 4.07 (3H, s), 4.20-4.29 (1H, m), 7.24 (1H, d, J=1.8 Hz), 7.38-7.43 (2H, m), 7.48-7.53 (2H, m), 7.94 (1H, d, J=1.8 Hz).

MS (m/z): 472 (M+H)$^+$.

Step 2 (1R,3S,4S)—N$^1$-{[4-(5,6-dimethoxypyridin-3-yl)phenyl]methyl}-4-methoxy-N$^3$-methylcyclopentane-1,3-diamine Hydrochloride

[Formula 357]

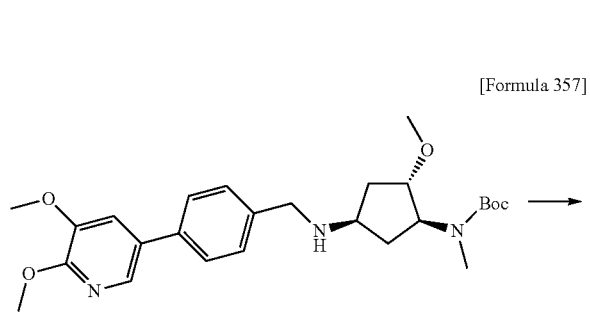

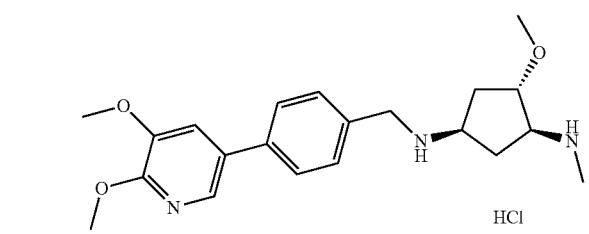

The title compound was obtained in the same manner as in Step 11 of Reference Example A-1, using the compound obtained in the above Step 1.

MS (m/z): 372 (M+H)$^+$.

Reference Example E-3

(1S,3S,4S)—N$^1$-{[4-(5,6-dimethoxypyridazin-3-yl)phenyl]methyl}-4-methoxycyclohexane-1,3-diamine Step 1 Tert-butyl [(1S,2S,5S)-5-({[4-(5,6-dimethoxypyridazin-3-yl)phenyl]methyl}amino)-2-methoxycyclohexyl]carbamate

[Formula 358]

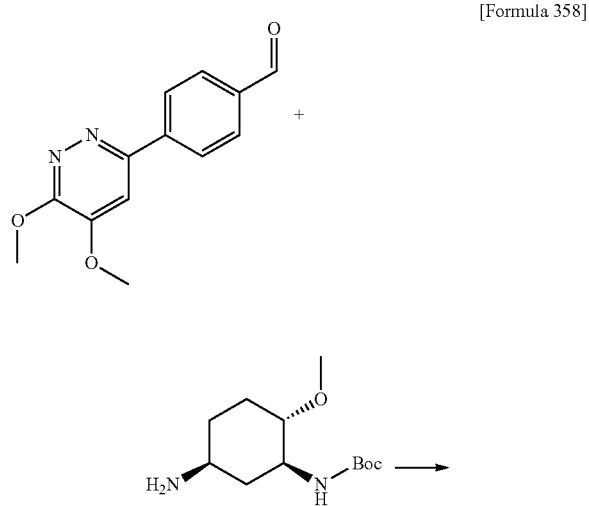

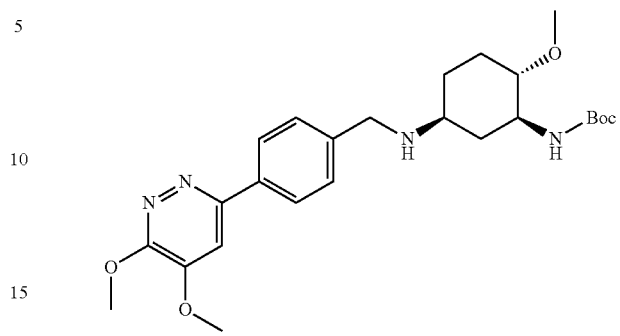

To a mixture of the compound (0.143 g) obtained in Step 6 of Reference Example A-10, the compound (0.175 g) obtained in Reference Example D-26 and chloroform (15 mL) was added tetraisopropyl orthotitanate (0.520 mL) at room temperature, and the mixture was stirred for 1.5 hr. Sodium triacetoxyborohydride (0.692 g) was added thereto, and the mixture was stirred for 16 hr. Saturated aqueous sodium hydrogencarbonate solution (5.00 mL) and aqueous Rochelle salt solution (5.00 mL) were added thereto, and the mixture was stirred for 2 hr, and the reaction mixture was extracted with dichloromethane. The organic layer was dried over anhydrous sodium sulfate, the solvent was evaporated under reduced pressure, and the obtained residue was subjected to silica gel column chromatography (ethyl acetate/methanol) using amino silica gel column as a charge column to give the title compound (0.179 g) as a solid.

$^1$H-NMR (CDCl$_3$) δ: 1.22-1.66 (4H, m), 1.47 (9H, s), 1.92-2.24 (3H, m), 2.81-2.90 (1H, m), 3.13-3.22 (1H, m), 3.38 (3H, s), 3.62-3.70 (1H, m), 3.75-3.80 (1H, m), 3.88-3.94 (1H, m), 4.02 (3H, s), 4.23 (3H, s), 5.96-6.22 (1H, m), 7.13 (1H, s), 7.43-7.48 (2H, m), 7.92-7.97 (2H, m).

MS (m/z): 473 (M+H)$^+$.

Step 2 (1S,3S,4S)—N$^1$-{[4-(5,6-dimethoxypyridazin-3-yl)phenyl]methyl}-4-methoxycyclohexane-1,3-diamine

[Formula 359]

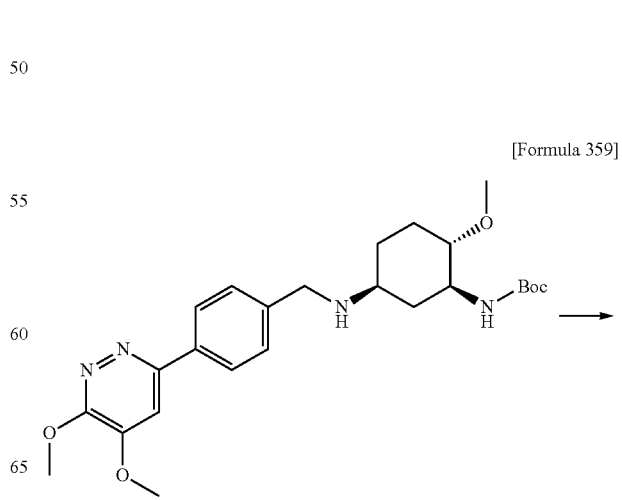

277
-continued

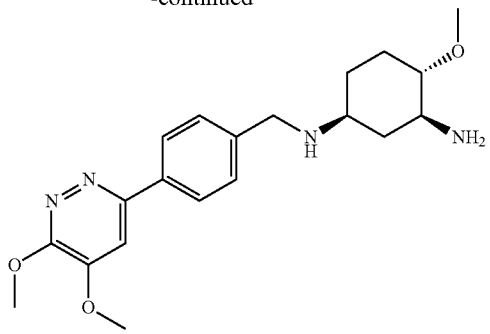

The title compound was obtained in the same manner as in Step 4 of A-3, using the above Step 1.
¹H-NMR (CDCl₃) δ: 1.02-1.70 (6H, m), 1.98-2.06 (1H, m), 2.10-2.19 (2H, m), 2.58-2.70 (2H, m), 2.75-2.85 (1H, m), 3.40 (3H, s), 3.88 (2H, s), 4.02 (3H, s), 4.23 (3H, s), 7.13 (1H, s), 7.41-7.47 (2H, m), 7.92-7.98 (2H, m).
MS (m/z): 373 (M+H)⁺.

Reference Example E-4

Tert-butyl [(1S,2R,4R)-4-({[4-(5,6-dimethoxy-pyridazin-3-yl)phenyl]methyl}amino)-2-methoxycyclopentyl]methylcarbamate

[Formula 360]

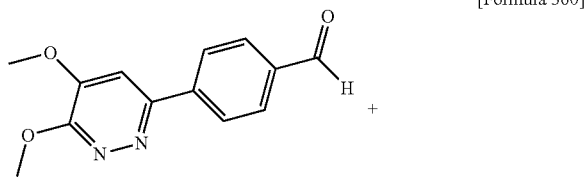

278
-continued

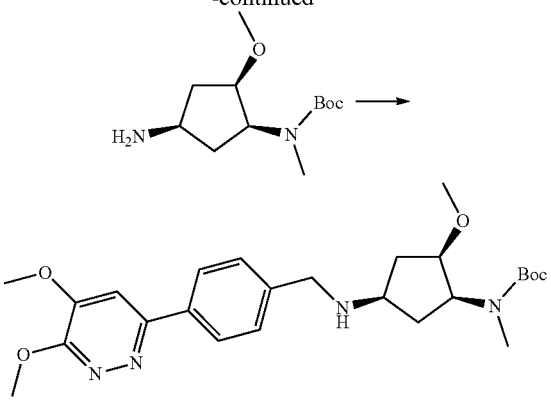

The title compound was obtained in the same manner as in Step 1 of Reference Example E-2, using the compound obtained in Step 8 of Reference Example A-16 and the compound obtained in Reference Example D-26.
¹H-NMR (CDCl₃) δ: 1.47 (9H, s), 1.58-1.62 (1H, m), 1.79-1.88 (1H, m), 2.08-2.18 (2H, m), 2.93 (3H, s), 3.10-3.17 (1H, m), 3.28 (3H, s), 3.73-3.79 (1H, m), 3.82-3.90 (2H, m), 4.01-4.02 (1H, m), 4.02 (3H, s), 4.23 (3H, s), 7.13 (1H, s), 7.46 (2H, d, J=8.0 Hz), 7.95 (2H, d, J=8.0 Hz).

Example 1

5-({[(1R,3R)-3-{[6-(2,2,2-trifluoroethyl)thieno[2,3-d]pyrimidin-4-yl]amino}cyclopentyl]amino}methyl)-1H-indole-2-carbonitrile Hydrochloride Step 1 Tert-butyl 2-cyano-5-({[(1R,3R)-3-{[6-(2,2,2-trifluoroethyl)thieno[2,3-d]pyrimidin-4-yl]amino}cyclopentyl]amino}methyl)-1H-indole-1-carboxylate

[Formula 361]

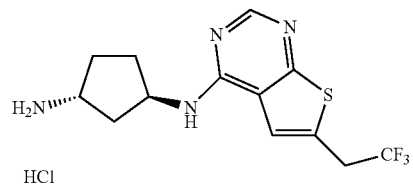

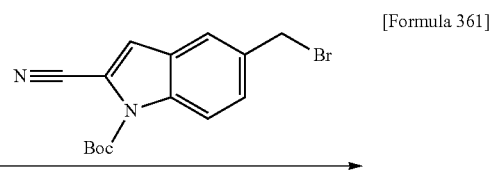

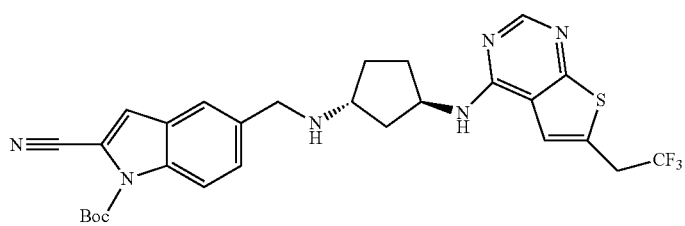

The compound (160 mg) obtained in Step 2 of Reference Example C-3 and tert-butyl 5-(bromomethyl)-2-cyano-indole-1-carboxylate (117 mg) produced according to the method described in a literature (cancer cell 2015, 27, 589-602.) were dissolved in DMF (2 mL), and potassium carbonate (121 mg) was added thereto, and the mixture was stirred overnight at room temperature. Ethyl acetate and saturated brine were added to the reaction solution, and the mixture was subjected to liquid separation. The organic layer was washed with saturated brine, dried over anhydrous sodium sulfate, and concentrated under reduced pressure. The obtained residue was purified by silica gel column chromatography (dichloromethane/methanol) to give the title compound (133 mg) as a solid.

$^1$H-NMR (CDCl$_3$) δ: 1.52-1.66 (2H, m), 1.71 (9H, s), 1.88-1.95 (1H, m), 2.11-2.18 (2H, m), 2.34-2.43 (1H, m), 3.38-3.45 (1H, m), 3.62 (2H, q, J=10.3 Hz), 3.91 (2H, s), 4.70-4.78 (1H, m), 5.39 (1H, d, J=6.7 Hz), 7.11 (1H, s), 7.28 (1H, s), 7.50 (1H, dd, J=8.8, 1.5 Hz), 7.62 (1H, s), 8.17 (1H, d, J=8.8 Hz), 8.45 (1H, s).

MS (m/z): 571 (M+H)$^+$.

Step 2 5-({[(1R,3R)-3-{[6-(2,2,2-trifluoroethyl) thieno[2,3-d]pyrimidin-4-yl]amino}cyclopentyl] amino}methyl)-1H-indole-2-carbonitrile

[Formula 362]

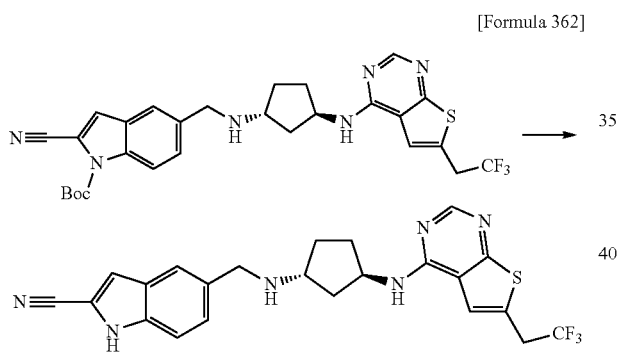

The compound (133 mg) obtained in the above Step 1 was dissolved in acetonitrile (5 mL), and tin(IV) chloride (ca. 1.0 mol/L, dichloromethane solution) (2.3 mL) was added thereto, and the mixture was stirred at room temperature for 1 hr. Ethyl acetate and saturated aqueous sodium hydrogencarbonate solution were added to the reaction solution, and the insoluble substance was removed by filtration through Celite, and the filtrate was subjected to liquid separation. The aqueous layer was extracted with ethyl acetate, and the organic layers were combined, washed with saturated brine, dried over anhydrous sodium sulfate, and concentrated under reduced pressure. The obtained residue was purified by silica gel column chromatography (dichloromethane/methanol) to give the title compound (76 mg) as a solid.

$^1$H-NMR (CD$_3$OD) δ: 1.53-1.62 (1H, m), 1.63-1.73 (1H, m), 1.97-2.09 (2H, m), 2.16-2.23 (1H, m), 2.25-2.33 (1H, m), 3.39-3.46 (1H, m), 3.83 (2H, q, J=10.7 Hz), 3.91 (2H, s), 4.68-4.75 (1H, m), 7.15 (1H, s), 7.38 (1H, dd, J=8.8, 1.5 Hz), 7.43 (1H, d, J=8.8 Hz), 7.50 (1H, s), 7.64 (1H, s), 8.31 (1H, s).

MS (m/z): 471 (M+H)$^+$.

Step 3 5-({[(1R,3R)-3-{[6-(2,2,2-trifluoroethyl) thieno[2,3-d]pyrimidin-4-yl]amino}cyclopentyl] amino}methyl)-1H-indole-2-carbonitrile Hydrochloride

[Formula 363]

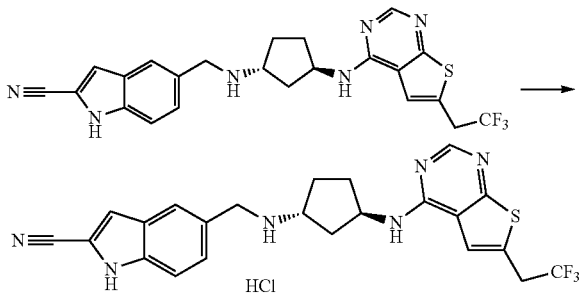

The compound (76 mg) obtained in the above Step 2 was dissolved in ethanol (3 mL), and 1N hydrochloric acid (0.178 mL) was added thereto, and the solvent was evaporated under reduced pressure. Diethyl ether was added to the residue, and the solid was collected by filtration to give the title compound (62 mg) as a solid.

$^1$H-NMR (DMSO-D$_6$) δ: 1.65-1.74 (1H, m), 1.77-1.87 (1H, m), 2.06-2.13 (1H, m), 2.17-2.30 (3H, m), 3.67-3.74 (1H, m), 4.10 (2H, q, J=11.2 Hz), 4.23 (2H, t, J=5.5 Hz), 4.69-4.77 (1H, m), 7.45 (1H, d, J=1.8 Hz), 7.55 (2H, s), 7.74 (1H, s), 7.89 (1H, s), 8.37 (1H, br s), 8.45 (1H, s), 9.27 (2H, br s), 12.62 (1H, s).

MS (m/z): 471 (M+H)$^+$.

Example 2

4-methyl-5-({[(1S,3R)-3-{methyl[6-(2,2,2-trifluoroethyl)thieno[2,3-d]pyrimidin-4-yl] amino}cyclopentyl]amino}methyl)-1-[(1H-pyrazol-4-yl)methyl]-1H-indole-2-carbonitrile Hydrochloride Step 1 4-methyl-5-({[(1S,3R)-3-{methyl[6-(2,2,2-trifluoroethyl)thieno[2,3-d]pyrimidin-4-yl] amino}cyclopentyl]amino}methyl)-1-{[1-(triphenylmethyl)-1H-pyrazol-4-yl]methyl}-1H-indole-2-carbonitrile

[Formula 364]

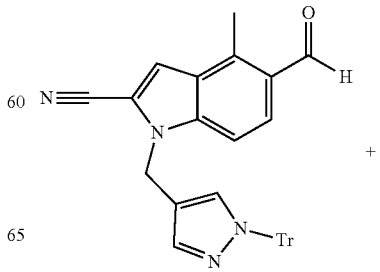

+

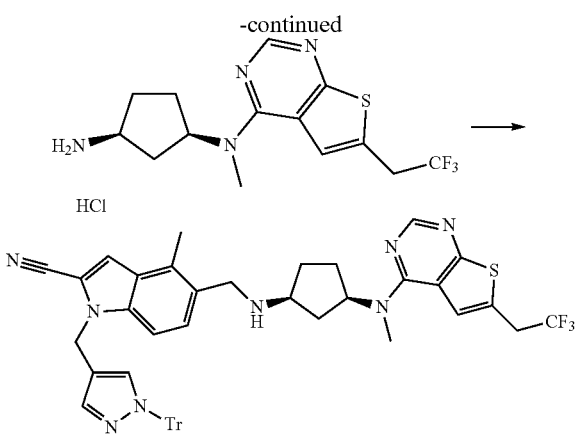

A mixture of the compound (0.362 g) obtained in Step 2 of Reference Example D-2, the compound (0.320 g) obtained in Step 2 of Reference Example C-4, DIPEA (0.373 mL), acetic acid (0.245 mL) and dichloromethane (15 mL) was stirred under argon atmosphere at room temperature for 30 min. Sodium triacetoxyborohydride (0.468 g) was added to the reaction solution, and the mixture was stirred overnight at room temperature. Saturated aqueous sodium hydrogencarbonate solution was added to the reaction solution, and the mixture was extracted with dichloromethane. The organic layer was dried over anhydrous sodium sulfate, and concentrated under reduced pressure. The residue was subjected to amino silica gel column chromatography (dichloromethane/methanol, n-hexane/ethyl acetate) to give the title compound (0.238 g) as an oil.

$^1$H-NMR (CDCl$_3$) δ: 1.52-1.56 (3H, m), 1.89-1.94 (3H, m), 2.29-2.36 (1H, m), 2.55 (3H, s), 3.24-3.28 (4H, m), 3.62 (2H, q, J=10.1 Hz), 3.87 (2H, s), 5.28 (2H, s), 5.37 (1H, t, J=8.5 Hz), 7.09-7.12 (6H, m), 7.19 (2H, t, J=3.9 Hz), 7.28-7.32 (11H, m), 7.45 (1H, s), 7.50 (1H, s), 8.42 (1H, s).

Step 2 4-methyl-5-({[(1S,3R)-3-{methyl[6-(2,2,2-trifluoroethyl)thieno[2,3-d]pyrimidin-4-yl]amino}cyclopentyl]amino}methyl)-1-[(1H-pyrazol-4-yl)methyl]-1H-indole-2-carbonitrile

[Formula 365]

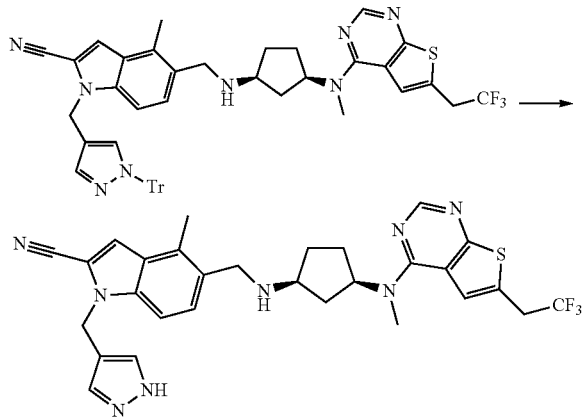

A mixture of the compound (0.228 g) obtained in the above Step 1, hydrogen chloride (4 mol/L, 1,4-dioxane solution, 0.75 mL), methanol (2.5 mL) and dichloromethane (15 mL) was stirred under argon atmosphere at room temperature for 30 min. The reaction solution was concentrated under reduced pressure, and the residue was subjected to amino silica gel column chromatography (dichloromethane/methanol) to give the title compound (0.139 g) as a solid.

$^1$H-NMR (CDCl$_3$) δ: 1.56-1.69 (3H, m), 1.94-1.96 (3H, m), 2.28-2.35 (1H, m), 2.55 (3H, s), 3.21-3.30 (4H, m), 3.63 (2H, q, J=10.1 Hz), 3.87 (2H, s), 5.36-5.38 (3H, m), 7.22 (1H, s), 7.25-7.28 (1H, m), 7.35-7.37 (2H, m), 7.56 (2H, s), 8.42 (1H, s).

MS (m/z): 579 (M+H)$^+$.

Step 3 4-methyl-5-({[(1S,3R)-3-{methyl[6-(2,2,2-trifluoroethyl)thieno[2,3-d]pyrimidin-4-yl]amino}cyclopentyl]amino}methyl)-1-[(1H-pyrazol-4-yl)methyl]-1H-indole-2-carbonitrile Hydrochloride

[Formula 366]

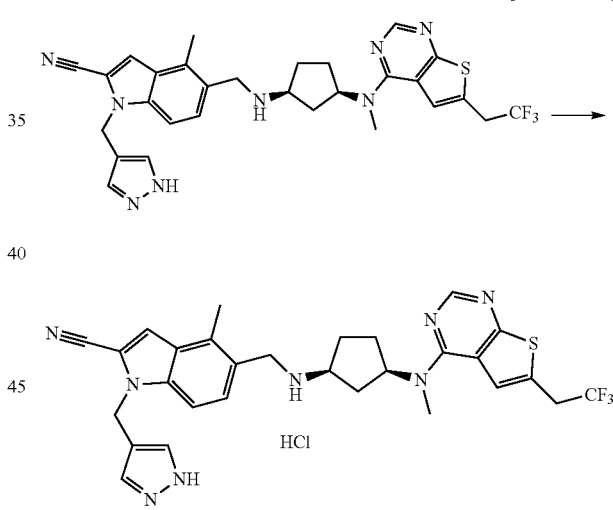

A mixture of the compound (0.129 g) obtained in the above Step 2, 1N hydrochloric acid (0.210 mL) and ethanol (4.0 mL) was stirred at room temperature for 30 min. The reaction solution was concentrated under reduced pressure, and the residue was suspended in diethyl ether, and collected by filtration to give the title compound (0.133 g) as a solid.

$^1$H-NMR (DMSO-D$_6$) δ: 1.90-1.98 (3H, m), 2.13-2.15 (1H, m), 2.35-2.41 (1H, m), 2.50-2.51 (1H, m), 2.59 (3H, s), 3.27 (3H, s), 3.73-3.75 (1H, m), 4.09 (2H, q, J=11.3 Hz), 4.26 (2H, s), 5.28-5.31 (1H, m), 5.44 (2H, s), 7.55 (1H, d, J=8.5 Hz), 7.67 (1H, s), 7.74-7.76 (2H, m), 8.38 (1H, s), 8.96 (1H, br s), 9.07 (1H, br s).

MS (m/z): 579 (M+H)$^+$.

Example 3

5-({[(1S,3R)-3-{methyl[2-(2,2,2-trifluoroethyl)[1,3]thiazolo[5,4-d]pyrimidin-7-yl]amino}cyclopentyl]amino}methyl)-1H-indole-2-carbonitrile Hydrochloride Step 1 5-({[(1S,3R)-3-{methyl[2-(2,2,2-trifluoroethyl)[1,3]thiazolo[5,4-d]pyrimidin-7-yl]amino}cyclopentyl]amino}methyl)-1H-indole-2-carbonitrile

[Formula 367]

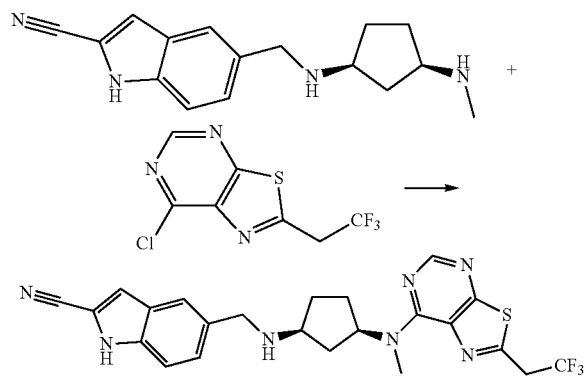

A mixture of the compound (0.0790 g) obtained in Step 2 of Reference Example E-1, 7-chloro-2-(2,2,2-trifluoroethyl)[1,3]thiazolo[5,4-d]pyrimidine (75.0 mg) produced according to the method described in a literature (WO 2016/195776), potassium carbonate (0.0610 g) and DMF (2 mL) was stirred under argon atmosphere at room temperature for 1 hr. Water was added to the reaction solution, and the mixture was extracted with ethyl acetate/diethyl ether. The organic layer was dried over anhydrous sodium sulfate, and concentrated under reduced pressure. The residue was subjected to diol-modified silica gel column chromatography (dichloromethane/methanol) to give the title compound (0.0184 g) as a solid. $^1$H-NMR (CDCl$_3$) δ: 1.53-1.71 (3H, m), 1.90-2.04 (3H, m), 2.27-2.33 (1H, m), 3.27 (1H, t, J=6.7 Hz), 3.42 (3H, s), 3.78-3.95 (4H, m), 5.88 (1H, br s), 7.17 (1H, s), 7.39 (2H, s), 7.63 (1H, s), 8.41 (1H, s), 8.59 (1H, br s).

MS (m/z): 486 (M+H)$^+$.

Step 2 5-({[(1S,3R)-3-{methyl[2-(2,2,2-trifluoroethyl)[1,3]thiazolo[5,4-d]pyrimidin-7-yl]amino}cyclopentyl]amino}methyl)-1H-indole-2-carbonitrile Hydrochloride

[Formula 368]

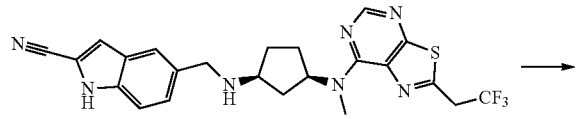

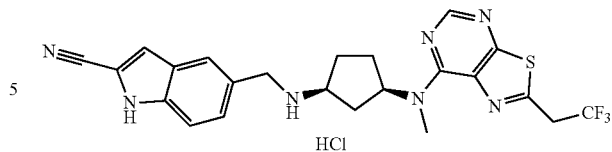

The title compound was obtained in the same manner as in Step 3 of Example 2, using the compound obtained in the above Step 1.

$^1$H-NMR (DMSO-D$_6$) δ: 1.01-1.35 (2H, m), 1.81-2.23 (4H, m), 3.25-3.78 (4H, m), 4.19-4.52 (4H, m), 5.61-5.89 (1H, m), 7.44-7.67 (3H, m), 7.85-7.92 (1H, m), 8.41-8.48 (1H, m), 9.14 (1H, br s), 9.23 (1H, br s), 12.59 (1H, s).

MS (m/z): 486 (M+H)$^+$.

Example 4

5-({[(1S,3R)-3-{methyl[6-(2,2,2-trifluoroethyl)thieno[3,2-d]pyrimidin-4-yl]amino}cyclopentyl]amino}methyl)-1H-indole-2-carbonitrile

[Formula 369]

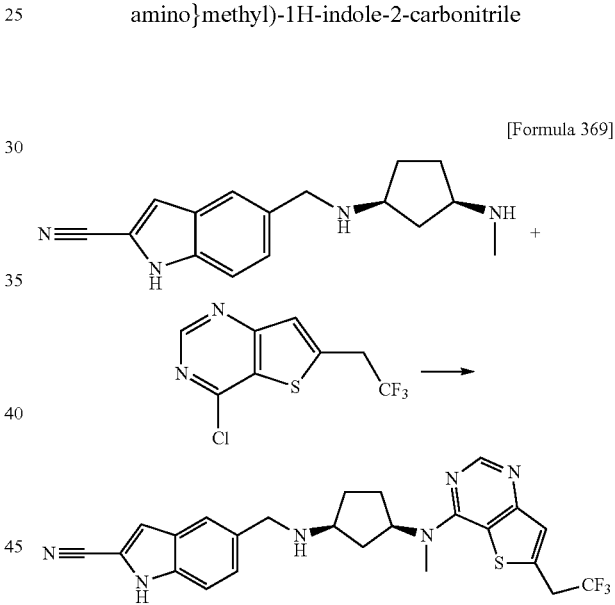

The compound (83 mg) obtained in Step 2 of Reference Example E-1 and the compound (78 mg) obtained in Step 4 of Reference Example B-6 were dissolved in 2-propanol (5 mL), and DIPEA (0.108 mL) was added thereto, and the mixture was stirred at 70° C. for 5 hr, and allowed to stand overnight at room temperature. The reaction mixture was subjected to silica gel column chromatography (diol silica gel, dichloromethane/methanol), and then purified by ChiralFlash (registered trademark, Daicel Corporation) IA (n-hexane/IPA) to give the title compound.

$^1$H-NMR (CDCl$_3$) δ: 1.55-1.72 (2H, m), 1.90-2.02 (3H, m), 2.25-2.33 (1H, m), 3.26-3.33 (1H, m), 3.36 (3H, s), 3.68 (2H, q, J=10.1 Hz), 3.90 (2H, s), 5.27-5.35 (1H, m), 7.15 (1H, s), 7.32-7.37 (3H, m), 7.61 (1H, s), 8.52 (1H, s), 10.19 (1H, br s).

MS (m/z): 485 (M+H)$^+$.

Example 5

4-({[(1S,3R)-3-{methyl[6-(2,2,2-trifluoroethyl)quinazolin-4-yl]amino}cyclopentyl]amino}methyl)phenol Hydrochloride

Step 1 (1R,3S)—N³-[(4-methoxyphenyl)methyl]-N¹-methyl-N¹-[6-(2,2,2-trifluoroethyl)quinazolin-4-yl]cyclopentane-1,3-diamine

[Formula 370]

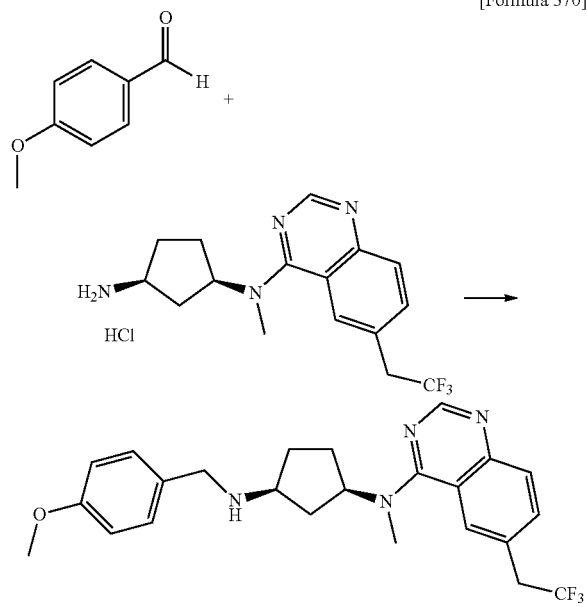

The title compound (containing impurities, purity ca. 80%) was obtained in the same manner as in Step 1 of Example 2, using the compound obtained in Step 2 of Reference Example C-6 and 4-anisaldehyde (CAS: 1122-91-4).

$^1$H-NMR (CDCl$_3$) δ: 1.61-1.70 (2H, m), 1.88-1.98 (1H, m), 1.99-2.08 (2H, m), 2.30-2.39 (1H, m), 3.16-3.25 (1H, m), 3.27 (3H, s), 3.51 (2H, q, J=10.5 Hz), 3.73 (2H, s), 3.81 (3H, s), 4.84-4.94 (1H, m), 6.88 (2H, d, J=8.5 Hz), 7.25 (2H, d, J=8.5 Hz), 7.61 (1H, dd, J=8.5, 1.2 Hz), 7.84 (1H, d, J=8.5 Hz), 7.89 (1H, s), 8.64 (1H, s).

MS (m/z): 445 (M+H)$^+$.

Step 2 4-({[(1S,3R)-3-{methyl[6-(2,2,2-trifluoroethyl)quinazolin-4-yl]amino}cyclopentyl]amino}methyl)phenol

[Formula 371]

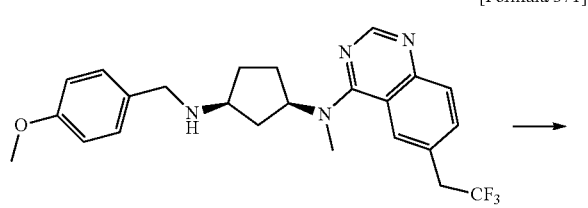

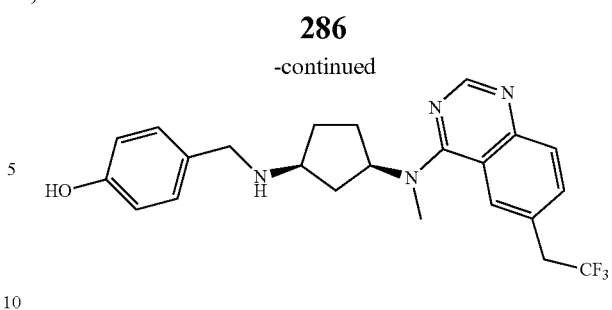

The compound (0.0920 g, containing impurities, purity ca. 80%) obtained in the above Step 1 was dissolved in dichloromethane (4.2 mL), and boron tribromide (CAS: 10294-33-4) (1N dichloromethane solution, 2.6 mL) was added thereto, and the mixture was stirred at room temperature for 50 min. The reaction solution was cooled to 0° C., and saturated aqueous sodium bicarbonate solution was added slowly thereto. The reaction mixture was stirred vigorously at 0° C. for 5 min, and extracted with dichloromethane/methanol (9/1), and the organic layer was dried over anhydrous sodium sulfate, and concentrated under reduced pressure. The residue was purified by silica gel column chromatography (dichloromethane/methanol) to give the title compound (0.0653 g) as a solid.

$^1$H-NMR (CDCl$_3$) δ: 1.93-2.29 (5H, m), 2.40-2.51 (1H, m), 3.34 (3H, s), 3.38-3.46 (1H, m), 3.51 (2H, q, J=10.5 Hz), 3.81 (1H, d, J=12.8 Hz), 3.87 (1H, d, J=12.8 Hz), 4.69-4.81 (1H, m), 6.81 (2H, d, J=8.5 Hz), 7.27 (2H, d, J=8.5 Hz), 7.63 (1H, d, J=8.5 Hz), 7.84 (1H, d, J=8.5 Hz), 7.89 (1H, s), 8.28 (1H, br s).

MS (m/z): 431 (M+H)$^+$.

Step 3 4-({[(1S,3R)-3-{methyl[6-(2,2,2-trifluoroethyl)quinazolin-4-yl]amino}cyclopentyl]amino}methyl)phenol Hydrochloride

[Formula 372]

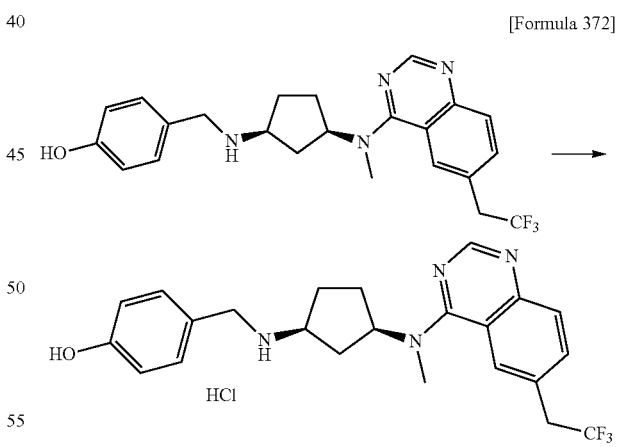

The title compound was obtained in the same manner as in Step 3 of Example 2, using the compound obtained in the above Step 2.

$^1$H-NMR (DMSO-D$_6$) δ: 1.96-2.25 (5H, m), 2.42-2.51 (1H, m), 3.51-3.62 (1H, m), 3.54 (3H, s), 3.90-4.09 (4H, m), 5.21-5.42 (1H, m), 6.81 (2H, d, J=8.5 Hz), 7.39 (2H, d, J=8.5 Hz), 7.91 (1H, d, J=8.5 Hz), 8.01 (1H, d, J=8.5 Hz), 8.32 (1H, br s), 8.84 (1H, s), 9.34-9.46 (1H, m), 9.57-9.70 (1H, m), 9.74 (1H, br s).

MS (m/z): 431 (M+H)$^+$.

Example 6

4-({[(1S,3R)-3-{methyl[6-(2,2,2-trifluoroethyl) thieno[2,3-d]pyrimidin-4-yl]amino}cyclopentyl] amino}methyl)-N-{3-[(prop-2-enoyl)amino] propyl}benzamide Hydrochloride Step 1 Tert-butyl {3-[4-({[(1S,3R)-3-{methyl[6-(2, 2,2-trifluoroethyl)thieno[2,3-d]pyrimidin-4-yl] amino}cyclopentyl]amino}methyl)benzamide] propyl}carbamate

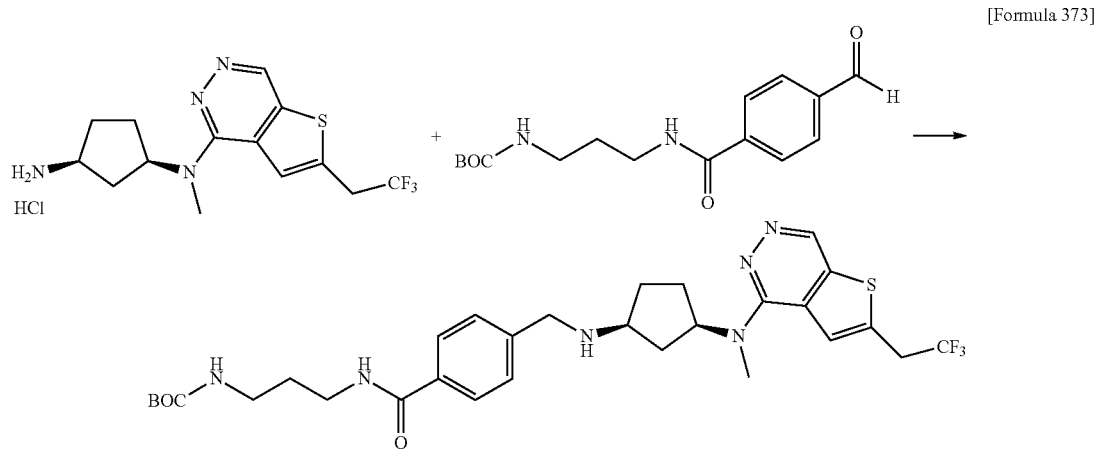

[Formula 373]

The title compound was obtained in the same manner as in Step 1 of Example 2, using the compound obtained in Step 2 of Reference Example C-4 and the compound obtained in Step 1 of Reference Example D-85.

$^1$H-NMR (CDCl$_3$) δ: 1.46 (9H, s), 1.50-1.73 (5H, m), 1.85-1.99 (3H, m), 2.24-2.30 (1H, m), 3.20-3.28 (3H, m), 3.31 (3H, s), 3.49-3.54 (2H, m), 3.63 (2H, q, J=10.3 Hz), 3.84 (2H, t, J=14.0 Hz), 4.90-4.95 (1H, m), 5.30-5.38 (1H, m), 7.28 (1H, br s), 7.34 (1H, s), 7.41 (2H, d, J=8.5 Hz), 7.83 (2H, d, J=8.5 Hz), 8.41 (1H, s).

MS (m/z): 621 (M+H)$^+$.

Step 2 N-(3-aminopropyl)-4-({[(1S,3R)-3-{methyl [6-(2,2,2-trifluoroethyl)thieno[2,3-d]pyrimidin-4-yl] amino}cyclopentyl]amino}methyl)benzamide Hydrochloride

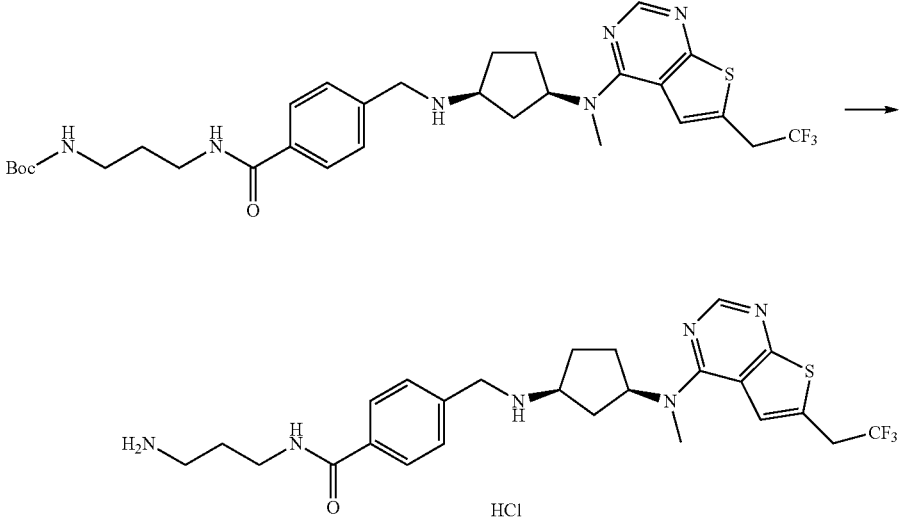

[Formula 374]

The title compound (608 mg) was obtained in the same manner as in Step 11 of Reference Example A-1, using the compound obtained in the above Step 1.

$^1$H-NMR (DMSO-D$_6$) δ: 1.81-1.93 (3H, m), 2.04-2.23 (4H, m), 2.34-2.41 (1H, m), 2.79-2.86 (2H, m), 3.32-3.38 (2H, m), 3.43 (3H, s), 4.13-4.22 (4H, m), 5.28-5.37 (1H, m), 7.74 (2H, d, J=7.9 Hz), 7.89 (1H, s), 7.95 (2H, d, J=7.9 Hz), 8.11 (3H, br s), 8.65 (1H, s), 8.90 (1H, t, J=5.8 Hz), 9.89-9.98 (1H, m), 10.09-10.19 (1H, m).

MS (m/z): 521 (M+H)$^+$.

Step 3 4-({[(1S,3R)-3-{methyl[6-(2,2,2-trifluoroethyl)thieno[2,3-d]pyrimidin-4-yl]amino}cyclopentyl]amino}methyl)-N-{3-[(prop-2-enoyl)amino]propyl}benzamide Hydrochloride

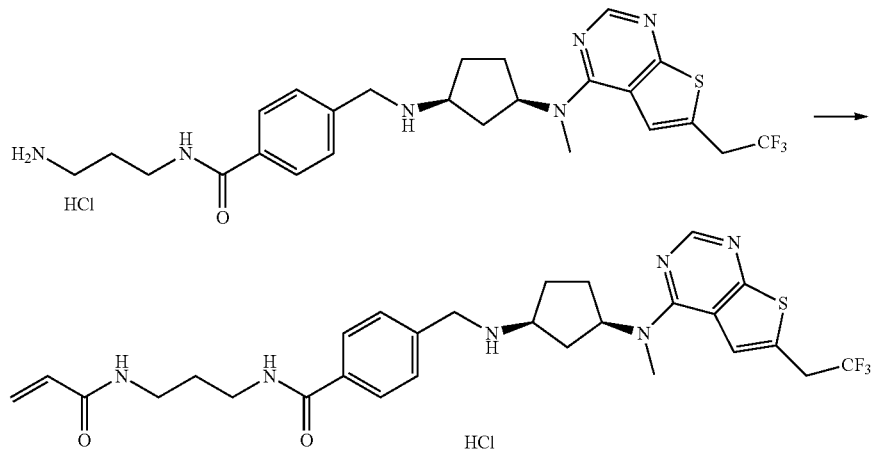

[Formula 375]

To the compound (250 mg) obtained in the above Step 2 were added dichloromethane (5 mL) and DIPEA (0.435 mL). Acryloyl chloride (0.022 mL) was added thereto under ice-cooling, and the mixture was stirred at 0° C. for 1 hr. Water and dichloromethane were added to the reaction solution, and the mixture was subjected to liquid separation. The organic layer was dried over anhydrous sodium sulfate, and concentrated under reduced pressure. The obtained residue was purified by silica gel column chromatography (dichloromethane/methanol) to give a free form (37 mg) of the title compound as a solid. This was dissolved in ethanol (3 mL), and 1N hydrochloric acid (0.064 mL) was added thereto, and the solvent was evaporated under reduced pressure. Ether was added to the residue, and the solid was collected by filtration to give the title compound (39 mg) as a solid.

$^1$H-NMR (DMSO-D$_6$) δ: 1.66-1.73 (2H, m), 1.87-2.10 (5H, m), 2.31-2.38 (1H, m), 3.17-3.22 (2H, m), 3.27-3.31 (5H, m), 3.59-3.65 (1H, m), 4.09 (2H, q, J=11.1 Hz), 4.23 (2H, t, J=6.1 Hz), 5.23-5.31 (1H, m), 5.58 (1H, dd, J=10.3, 2.1 Hz), 6.07 (1H, dd, J=17.0, 2.1 Hz), 6.22 (1H, dd, J=17.0, 10.3 Hz), 7.66 (2H, d, J=7.9 Hz), 7.72 (1H, s), 7.92 (2H, d, J=7.9 Hz), 8.20 (1H, t, J=5.5 Hz), 8.38 (1H, s), 8.59 (1H, t, J=5.8 Hz), 9.30-9.38 (1H, m), 9.43-9.51 (1H, m).

MS (m/z): 575 (M+H)$^+$.

Example 7

(1R,3S)—N$^3$-{[4-(benzylamino)phenyl]methyl}-N$^1$-methyl-N$^1$-[6-(2,2,2-trifluoroethyl)thieno[2,3-d]pyrimidin-4-yl]cyclopentane-1,3-diamine Hydrochloride Step 1 Tert-butyl Benzyl [4-({[(1S,3R)-3-{methyl[6-(2,2,2-trifluoroethyl)thieno[2,3-d]pyrimidin-4-yl]amino}cyclopentyl]amino}methyl)phenyl]carbamate

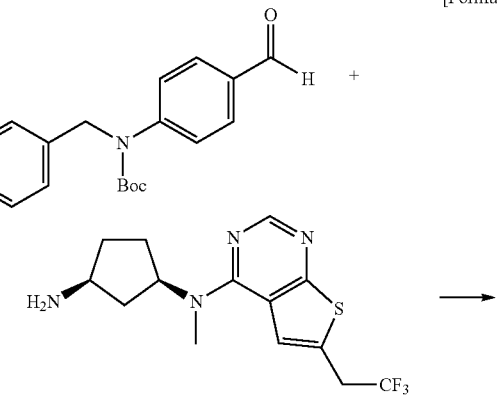

[Formula 376]

291

-continued

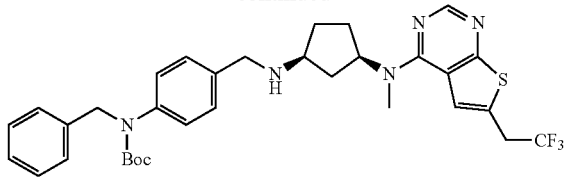

The title compound was obtained in the same manner as in Step 1 of Example 2, using the compound obtained in Step 2 of Reference Example C-4 and the compound obtained in Step 3 of Reference Example D-89.

292

$^1$H-NMR (CDCl$_3$) δ: 1.42 (9H, s), 1.55-1.68 (2H, m), 1.85-1.96 (3H, m), 2.21-2.28 (1H, m), 3.18-3.25 (1H, m), 3.30 (3H, s), 3.63 (2H, q, J=10.2 Hz), 3.74 (2H, s), 4.82 (2H, s), 5.28-5.35 (1H, m), 7.08-7.16 (2H, m), 7.20-7.26 (5H, m), 7.27-7.35 (3H, m), 8.41 (1H, s).

MS (m/z): 626 (M+H)$^+$.

Step 2 (1R,3S)—N$^3$-{[4-(benzylamino)phenyl]methyl}-N$^1$-methyl-N$^1$-[6-(2,2,2-trifluoroethyl)thieno[2,3-d]pyrimidin-4-yl]cyclopentane-1,3-diamine

[Formula 377]

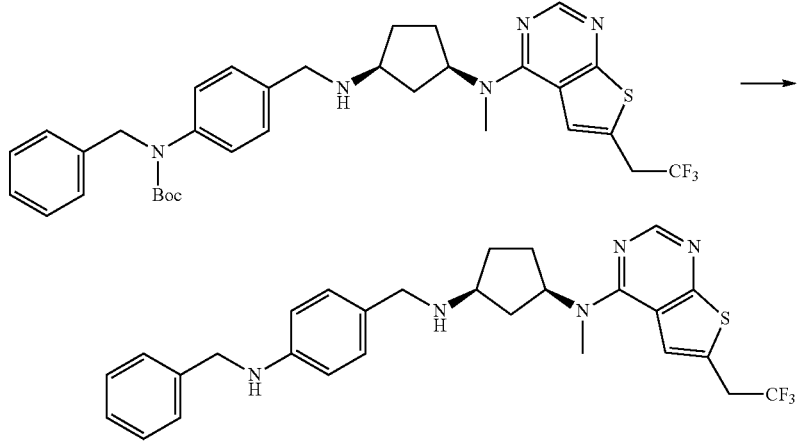

To a solution of the compound (397 mg) obtained in the above Step 1 in dichloromethane (1.5 mL) was added trifluoroacetic acid (CAS: 76-05-1) (1.5 mL) at room temperature. The mixture was stirred at room temperature for 15 hr, and the reaction solution was basified with saturated aqueous sodium hydrogencarbonate solution, and extracted with chloroform. The organic layer was washed with saturated brine, dried over anhydrous sodium sulfate, and concentrated under reduced pressure, and the residue was subjected to reversed phase high-performance liquid chromatography (water/acetonitrile/0.1% formic acid) to give the title compound (301 mg) as a solid.

$^1$H-NMR (CDCl$_3$) δ: 1.46-1.62 (3H, m), 1.85-1.98 (3H, m), 2.21-2.29 (1H, m), 3.19-3.27 (1H, m), 3.30 (3H, s), 3.62 (2H, q, J=10.1 Hz), 3.67 (2H, s), 4.04 (1H, br s), 4.32 (2H, s), 5.27-5.36 (1H, m), 6.61 (2H, d, J=8.6 Hz), 7.12 (2H, d, J=8.6 Hz), 7.27-7.30 (1H, m), 7.32-7.39 (5H, m), 8.41 (1H, s).

Step 3 (1R,3S)—N$^3$-{[4-(benzylamino)phenyl]methyl}-N$^1$-methyl-N$^1$-[6-(2,2,2-trifluoroethyl)thieno[2,3-d]pyrimidin-4-yl]cyclopentane-1,3-diamine Hydrochloride

[Formula 378]

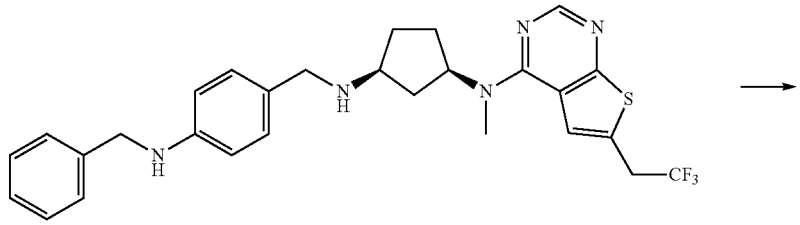

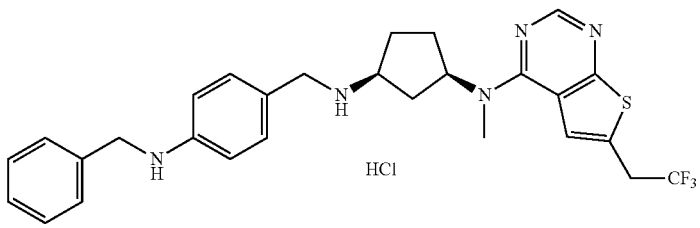

The title compound was obtained in the same manner as in Step 3 of Example 2, using the compound obtained in the above Step 2.

$^1$H-NMR (DMSO-D$_6$) δ: 1.81-2.10 (5H, m), 2.28-2.35 (1H, m), 3.25 (3H, s), 3.55 (1H, br s), 3.94 (2H, s), 4.08 (2H, q, J=11.0 Hz), 4.30 (2H, s), 5.19-5.28 (1H, m), 6.56 (1H, br s), 6.60 (2H, d, J=8.6 Hz), 7.17-7.24 (3H, m), 7.29-7.36 (4H, m), 7.70 (1H, s), 8.36 (1H, s), 8.79-9.04 (2H, m).

MS (m/z): 526 (M+H)$^+$.

Example 8

(1R,3S)—N$^3$-({4-[(5-methoxypyridin-3-yl)amino]phenyl}methyl)-N$^1$-methyl-N$^1$-[6-(2,2,2-trifluoroethyl)thieno[2,3-d]pyrimidin-4-yl]cyclopentane-1,3-diamine Hydrochloride Step 1 4-[(5-methoxypyridin-3-yl)amino]benzaldehyde To a solution of the compound (0.117 g) obtained in Step 2 of Reference Example D-94 in THF (5.07 mL) was added manganese dioxide (0.441 g), and the mixture was stirred at room temperature for 5 hr, and allowed to stand overnight. Additional manganese dioxide (0.441 g) was added thereto, and the mixture was stirred at 45° C. for 2 hr. The reaction mixture was allowed to cool to room temperature, and filtered through Celite, and the filtrate was concentrated under reduced pressure. The obtained crude product of the title compound was directly used in the next step.

Step 2 (1R,3S)—N$^3$-({4-[(5-methoxypyridin-3-yl)amino]phenyl}methyl)-N$^1$-methyl-N$^1$-[6-(2,2,2-trifluoroethyl)thieno[2,3-d]pyrimidin-4-yl]cyclopentane-1,3-diamine Hydrochloride

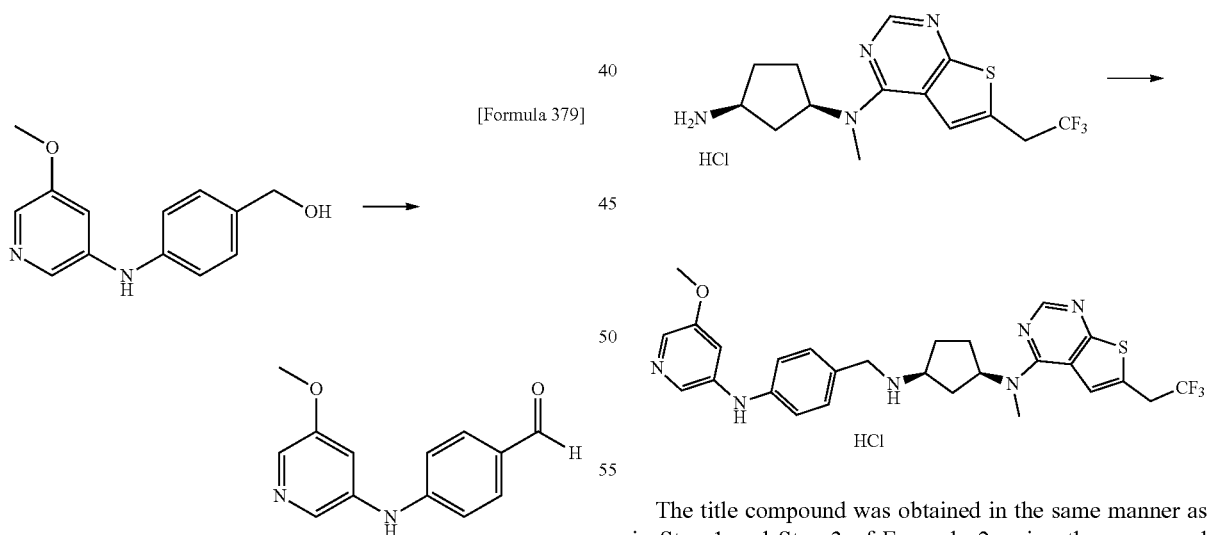

The title compound was obtained in the same manner as in Step 1 and Step 3 of Example 2, using the compound obtained in the above Step 1 and the compound obtained in Step 2 of Reference Example C-4.

$^1$H-NMR (DMSO-D$_6$) δ: 1.86-1.89 (1H, br m), 2.00-2.08 (4H, m), 2.33-2.38 (1H, m), 3.30 (3H, s), 3.61 (1H, br s), 3.91 (3H, s), 4.06-4.12 (4H, m), 5.28 (1H, br s), 7.31 (2H, d, J=8.5 Hz), 7.46 (1H, s), 7.58 (2H, d, J=8.5 Hz), 7.75 (1H, s), 8.05-8.07 (2H, m), 8.40 (1H, s), 9.37-9.52 (3H, br m).

MS (m/z): 543 (M+H)$^+$.

Example 9

(1R,3S)—N$^1$-[6-(cyclopropylmethyl)thieno[2,3-d]pyrimidin-4-yl]-N$^3$-{[4-(5-methoxypyridin-3-yl)phenyl]methyl}-N$^1$-methylcyclopentane-1,3-diamine Hydrochloride

[Formula 381]

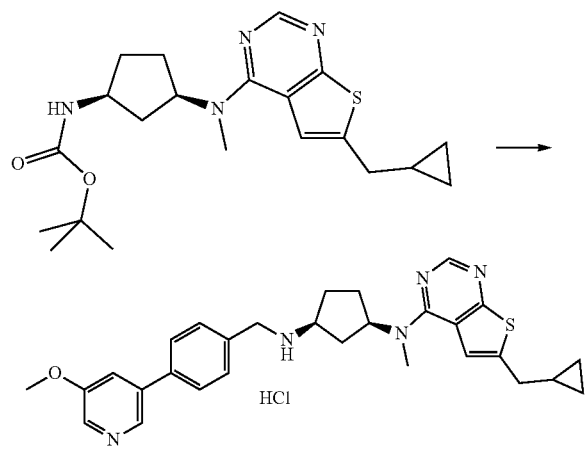

The compound (205 mg) obtained in Reference Example C-29 was dissolved in dichloromethane (5 mL), and hydrogen chloride (4 mol/L, 1,4-dioxane solution, 5 mL) was added thereto, and the mixture was stirred at room temperature for 1 hr. The solvent was evaporated under reduced pressure. Dichloromethane (5 mL) and DIPEA (0.266 mL) were added to the obtained residue. The compound (119 mg) obtained in Reference Example D-65, sodium triacetoxyborohydride (324 mg) and acetic acid (0.132 mL) were added thereto, and the mixture was stirred at room temperature for 1 hr. Dichloromethane and saturated aqueous sodium hydrogencarbonate solution were added thereto, and the mixture was subjected to liquid separation, and the aqueous layer was extracted with dichloromethane. The organic layers were combined, washed with saturated aqueous sodium hydrogencarbonate solution, dried over anhydrous sodium sulfate, and concentrated under reduced pressure. The obtained residue was purified by silica gel column chromatography (dichloromethane/methanol, followed by ethyl acetate/methanol) to give a free form (40 mg) of the title compound. This was dissolved in ethanol (3 mL), and 1N hydrochloric acid (0.240 mL) was added thereto, and the solvent was evaporated under reduced pressure. Diethyl ether was added to the residue, and the solid was collected by filtration to give the title compound (23 mg) as a solid.

$^1$H-NMR (DMSO-D$_6$) δ: 0.29-0.32 (2H, m), 0.54-0.59 (2H, m), 1.02-1.09 (1H, m), 1.86-1.91 (1H, m), 2.06-2.17 (4H, m), 2.34-2.41 (1H, m), 2.82 (2H, d, J=7.3 Hz), 3.36 (3H, s), 3.59-3.65 (1H, m), 4.01 (3H, s), 4.24 (2H, br s), 5.23-5.32 (1H, m), 7.51 (1H, s), 7.80 (2H, d, J=7.9 Hz), 7.96 (2H, d, J=7.9 Hz), 8.14 (1H, s), 8.48 (1H, s), 8.54 (1H, s), 8.76 (1H, s), 9.74 (1H, br s), 9.94 (1H, br s).

MS (m/z): 500 (M+H)$^+$.

Example 10

N-(oxetan-3-yl)-4-({[(1S,3R)-3-{[6-(2,2,2-trifluoroethyl)thieno[2,3-d]pyrimidin-4-yl]amino}cyclohexyl]amino}methyl)benzamide Hydrochloride Step 1 Methyl 4-({[(1S,3R)-3-{[6-(2,2,2-trifluoroethyl)thieno[2,3-d]pyrimidin-4-yl]amino}cyclohexyl]amino}methyl)benzoate

[Formula 382]

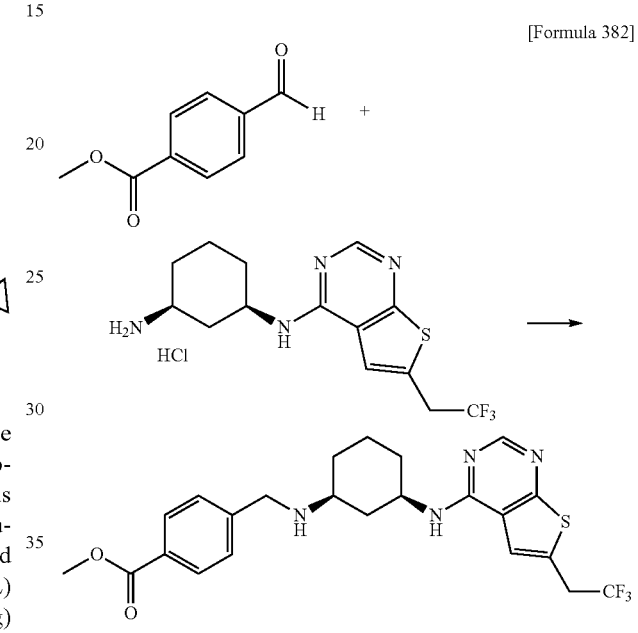

The title compound was obtained in the same manner as in Step 1 of Example 2, using the compound obtained in Step 2 of Reference Example C-2 and methyl 4-formylbenzoate (CAS: 1571-08-0).

$^1$H-NMR (CDCl$_3$) δ: 1.19-1.43 (2H, m), 1.49-1.72 (2H, m), 1.79-2.00 (3H, m), 2.28 (1H, br s), 2.99 (1H, br s), 3.56 (2H, q, J=10.0 Hz), 3.88 (3H, s), 3.91-4.06 (2H, m), 4.26 (1H, br s), 6.60-6.79 (1H, m), 7.06 (1H, br s), 7.50 (2H, d, J=8.0 Hz), 7.98 (2H, d, J=8.0 Hz), 8.42 (1H, s).

MS (m/z): 479 (M+H)$^+$.

Step 2 Methyl 4-({{(tert-butoxycarbonyl)[(1S,3R)-3-{[6-(2,2,2-trifluoroethyl)thieno[2,3-d]pyrimidin-4-yl]amino}cyclohexyl]amino}methyl)benzoate

[Formula 383]

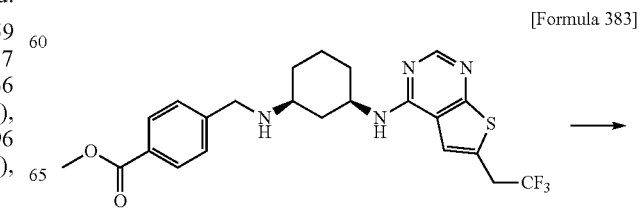

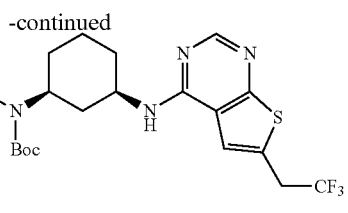

The title compound was obtained in the same manner as in Step 7 of Reference Example A-16, using the compound obtained in the above Step 1.

¹H-NMR (CDCl₃) δ: 1.02-1.12 (1H, m), 1.26-1.56 (12H, m), 1.72-1.86 (2H, m), 2.11 (1H, d, J=11.7 Hz), 2.22 (1H, d, J=11.0 Hz), 3.62 (2H, q, J=10.2 Hz), 3.91 (3H, s), 4.04-4.15 (1H, m), 4.25 (1H, br s), 4.42 (2H, br s), 4.88 (1H, d, J=7.4 Hz), 7.00 (1H, s), 7.30 (2H, d, J=8.0 Hz), 7.98 (2H, d, J=8.0 Hz), 8.46 (1H, s).

MS (m/z): 579 (M+H)⁺.

Step 3 4-({(tert-butoxycarbonyl)[(1S,3R)-3-{[6-(2,2,2-trifluoroethyl)thieno[2,3-d]pyrimidin-4-yl]amino}cyclohexyl]amino}methyl)benzoic Acid

[Formula 384]

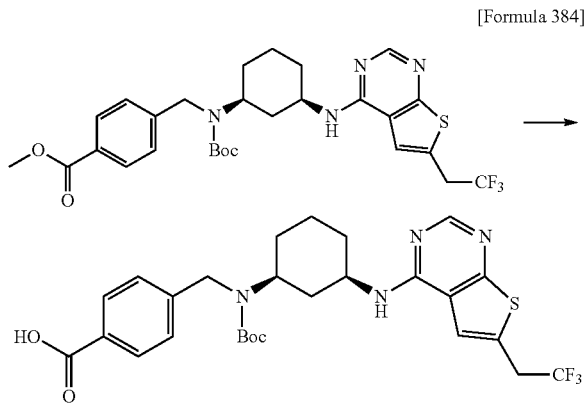

The title compound was obtained in the same manner as in Step 9 of Reference Example A-1, using the compound obtained in the above Step 2.

¹H-NMR (DMSO-D₆) δ: 1.09-1.36 (9H, m), 1.35-1.55 (5H, m), 1.76 (1H, d, J=11.7 Hz), 1.86 (1H, d, J=11.7 Hz), 1.96 (1H, d, J=10.0 Hz), 4.04 (2H, q, J=11.7 Hz), 4.05-4.22 (2H, m), 4.42 (2H, br s), 7.34 (2H, d, J=8.0 Hz), 7.61 (1H, s), 7.83 (1H, d, J=7.4 Hz), 7.89 (2H, d, J=8.0 Hz), 8.32 (1H, s), 12.84 (1H, s).

MS (m/z): 565 (M+H)⁺.

Step 4 Tert-butyl ({4-[(oxetan-3-yl)carbamoyl]phenyl}methyl)[(1S,3R)-3-{[6-(2,2,2-trifluoroethyl)thieno[2,3-d]pyrimidin-4-yl]amino}cyclohexyl]carbamate

[Formula 385]

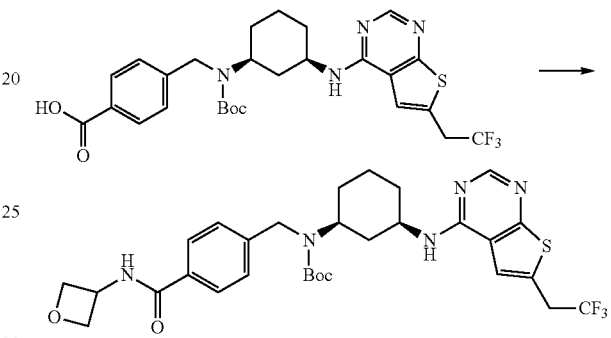

The title compound was obtained in the same manner as in Step 3 of Reference Example C-32, using the compound obtained in the above Step 3 and 3-oxetanamine.

¹H-NMR (CDCl₃) δ: 1.02-1.13 (1H, m), 1.24-1.58 (13H, m), 1.76 (1H, d, J=11.7 Hz), 1.84 (1H, d, J=9.8 Hz), 2.10 (1H, d, J=10.4 Hz), 2.20 (1H, d, J=11.0 Hz), 3.56-3.66 (2H, m), 4.24 (1H, br s), 4.41 (2H, br s), 4.60 (2H, td, J=6.7, 2.5 Hz), 4.94-5.01 (1H, m), 5.01 (2H, t, J=7.1 Hz), 5.23 (1H, dt, J=6.7, 6.1 Hz), 6.69 (1H, d, J=6.1 Hz), 7.02 (1H, s), 7.30 (2H, d, J=8.0 Hz), 7.72 (2H, br s), 8.45 (1H, s).

MS (m/z): 620 (M+H)⁺.

Step 5 N-(oxetan-3-yl)-4-({[(1S,3R)-3-{[6-(2,2,2-trifluoroethyl)thieno[2,3-d]pyrimidin-4-yl]amino}cyclohexyl]amino}methyl)benzamide

[Formula 386]

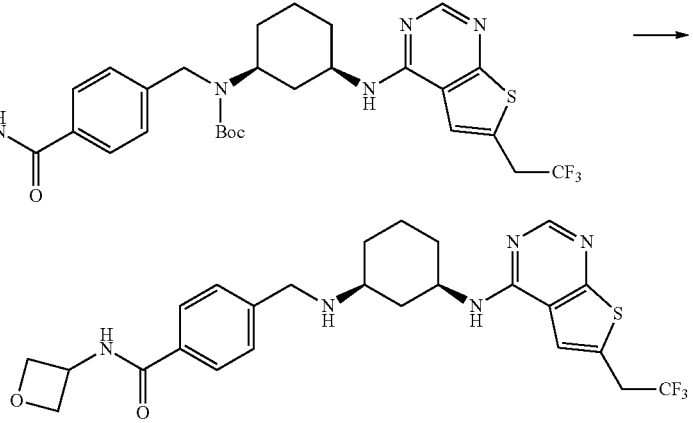

To a solution of the compound (47.9 mg) obtained in the above Step 4 in dichloromethane (0.4 mL) was added trifluoroacetic acid (CAS: 76-05-1) (0.2 mL) at room temperature. The mixture was stirred at room temperature for 15 hr, and the reaction solution was basified with saturated aqueous sodium hydrogencarbonate solution, and extracted with chloroform. The organic layer was washed with saturated brine, dried over anhydrous sodium sulfate, and concentrated under reduced pressure, and the residue was subjected to reversed phase high-performance liquid chromatography (water/acetonitrile/0.1% formic acid) to give the title compound (34.1 mg) as a solid.

$^1$H-NMR (CD$_3$OD) δ: 1.39-1.63 (4H, m), 2.00-2.10 (2H, m), 2.22-2.28 (1H, m), 2.58-2.65 (1H, m), 3.35 (1H, s), 3.67 (1H, br s), 3.76-3.91 (4H, m), 4.25 (1H, br s), 4.33 (2H, s), 4.48-4.61 (2H, m), 7.53 (1H, s), 7.66 (2H, d, J=8.0 Hz), 8.17 (2H, d, J=8.0 Hz), 8.33 (1H, s), 8.48 (2H, br s).

Step 6 N-(oxetan-3-yl)-4-({[(1S,3R)-3-{[6-(2,2,2-trifluoroethyl)thieno[2,3-d]pyrimidin-4-yl]amino}cyclohexyl]amino}methyl)benzamide Hydrochloride

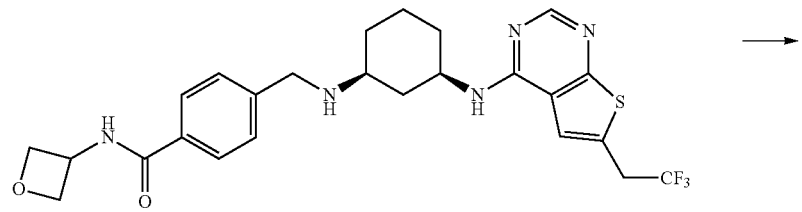

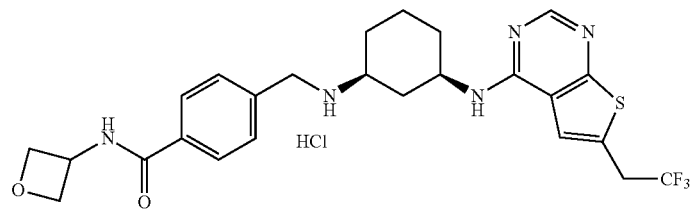

The title compound was obtained in the same manner as in Step 3 of Example 2, using the compound obtained in the above Step 5.

$^1$H-NMR (DMSO-D$_6$) δ: 1.21-1.50 (4H, m), 1.79-1.93 (2H, m), 2.08 (1H, br s), 2.32-2.39 (1H, m), 2.54 (1H, s), 2.88 (1H, br s), 3.47-3.53 (1H, m), 3.63-3.73 (2H, m), 4.03-4.16 (4H, m), 4.35-4.47 (2H, m), 7.63-7.70 (3H, m), 8.00 (1H, br s), 8.11 (2H, d, J=8.0 Hz), 8.18 (1H, s), 8.32 (1H, s).

Example 11

5-[4-({[(1S,3R)-3-{methyl[6-(2,2,2-trifluoroethyl)thieno[2,3-d]pyrimidin-4-yl]amino}cyclopentyl]amino}methyl)phenyl]pyridin-2(1H)-one Hydrochloride Step 1 (1R,3S)—N$^3$-[(4-iodophenyl)methyl]-N$^1$-methyl-N$^1$-[6-(2,2,2-trifluoroethyl)thieno[2,3-d]pyrimidin-4-yl]cyclopentane-1,3-diamine

[Formula 388]

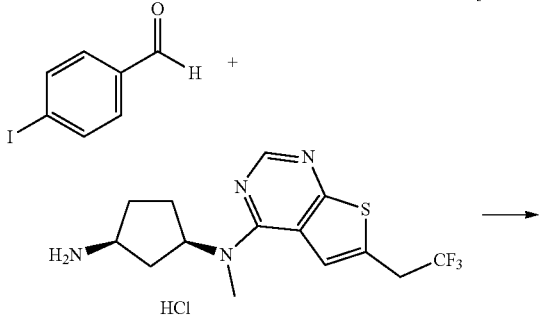

[Formula 387]

-continued

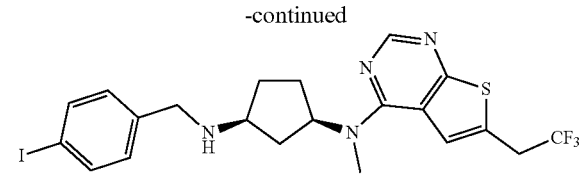

The title compound was obtained in the same manner as in Step 1 of Example 2, using the compound obtained in Step 2 of Reference Example C-4 and 4-iodobenzaldehyde (CAS: 15164-44-0).

¹H-NMR (CDCl₃) δ: 1.58-1.73 (2H, m), 1.88-1.97 (3H, m), 2.23-2.30 (1H, m), 3.22-3.28 (1H, m), 3.30 (3H, s), 3.63 (2H, q, J=10.4 Hz), 3.73-3.80 (2H, m), 5.04 (1H, br s), 5.27-5.35 (1H, m), 7.10 (2H, d, J=8.0 Hz), 7.33 (1H, s), 7.66 (2H, d, J=8.0 Hz), 8.40 (1H, s).

Step 2 5-[4-({[(1S,3R)-3-{methyl[6-(2,2,2-trifluoroethyl)thieno[2,3-d]pyrimidin-4-yl]amino}cyclopentyl]amino}methyl)phenyl]pyridin-2(1H)-one

[Formula 389]

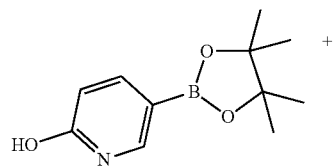

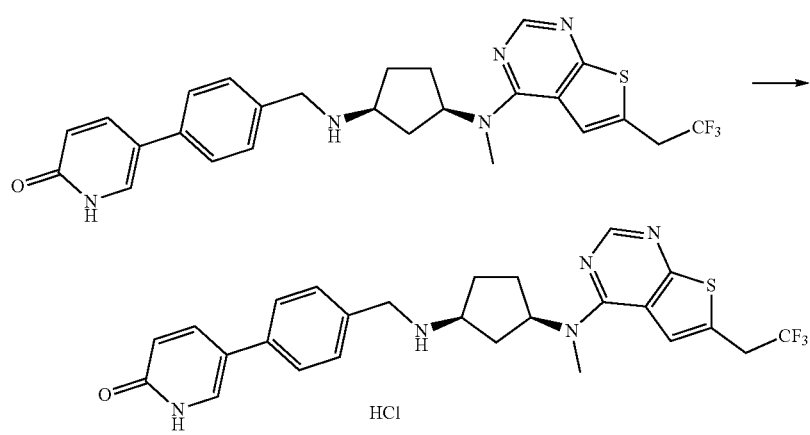

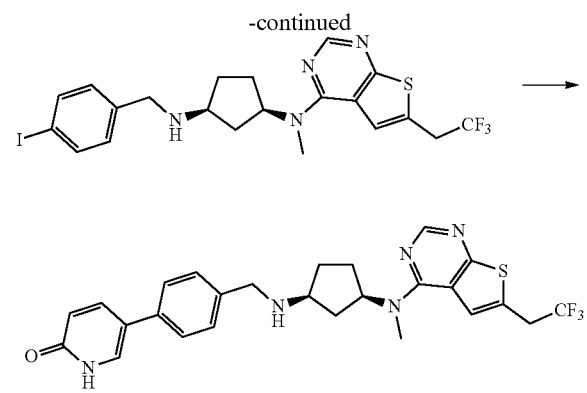

The compound (0.110 g) obtained in the above Step 1 was dissolved in 1,4-dioxane (2.00 mL), and 2-hydroxy-5-(4,4,5,5-tetramethyl-1,3,2-dioxaborolan-2-yl)pyridine (CAS: 1054483-78-1) (0.0600 g), [1,1'-bis(diphenylphosphino)ferrocene]palladium(II) dichloride dichloromethane adduct (0.0295 g) and saturated aqueous sodium bicarbonate solution (1.00 mL) were added thereto, and the mixture was stirred with heating in a microwave reactor at 110° C. for 10 min. The reaction mixture was allowed to cool to room temperature, water was added thereto, and the mixture was extracted twice with dichloromethane. The organic layer was concentrated under reduced pressure, and the residue was purified by amino silica gel chromatography (dichloromethane/ethyl acetate/methanol) to give the title compound (0.0828 g) as a solid.

¹H-NMR (CDCl₃) δ: 1.22 (1H, dd, J=13.5, 6.7 Hz), 1.52-1.55 (1H, br m), 1.65-1.66 (1H, br m), 1.96 (3H, d, J=8.6 Hz), 2.26-2.33 (1H, m), 3.23-3.30 (4H, m), 3.63 (2H, q, J=10.0 Hz), 3.83 (2H, s), 5.30-5.35 (1H, br m), 6.70 (1H, d, J=9.2 Hz), 7.35-7.39 (5H, br m), 7.61 (1H, s), 7.78 (1H, d, J=9.2 Hz), 8.41-8.42 (1H, br m).

MS (m/z): 514 (M+H)⁺.

Step 3 5-[4-({[(1S,3R)-3-{methyl[6-(2,2,2-trifluoroethyl)thieno[2,3-d]pyrimidin-4-yl]amino}cyclopentyl]amino}methyl)phenyl]pyridin-2(1H)-one Hydrochloride

[Formula 390]

The compound (0.0828 g) obtained in the above Step 2 was dissolved in ethanol (3.00 mL), and 1N hydrochloric acid (0.161 mL) was added thereto, and the solvent was evaporated under reduced pressure. Diethyl ether was added to the residue, and the solid was collected by filtration to give the title compound (0.0505 g) as a solid.

¹H-NMR (DMSO-D₆) δ: 1.87-2.11 (5H, m), 2.33-2.39 (1H, m), 3.28 (3H, s), 3.62 (1H, s), 4.09 (2H, q, J=11.2 Hz), 4.18 (2H, t, J=5.5 Hz), 5.27 (1H, t, J=7.9 Hz), 6.46 (1H, d, J=9.8 Hz), 7.59 (2H, d, J=7.9 Hz), 7.66-7.68 (2H, m), 7.72 (1H, s), 7.79 (1H, d, J=2.7 Hz), 7.89 (1H, dd, J=9.8, 2.7 Hz), 8.37 (1H, s), 9.22 (1H, br s), 9.33 (1H, br s).

Example 12

(1R,3S)—N¹-methyl-N³-({4-[(1-methyl-1H-pyrazol-4-yl)amino]phenyl}methyl)-N¹-[6-(2,2,2-trifluoroethyl)thieno[2,3-d]pyrimidin-4-yl]cyclopentane-1,3-diamine

[Formula 391]

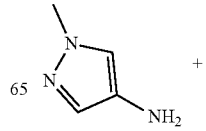

-continued

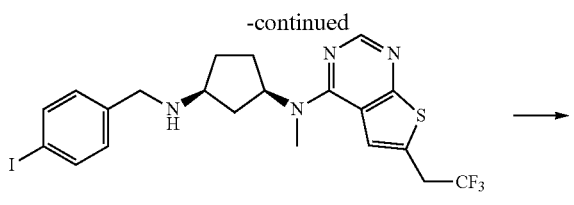

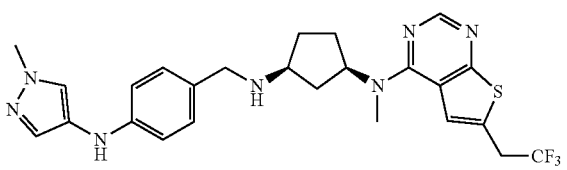

A mixture of the compound (50.0 mg) obtained in Step 1 of Example 11, 1-methyl-1H-pyrazol-4-amine (CAS: 69843-13-6) (16.2 mg), cesium carbonate (89.5 mg), 4,5-bis(diphenylphosphino)-9,9-dimethylxanthene (15.9 mg), palladium(II) acetate (4.8 mg) and 1,4-dioxane (1.0 mL) was stirred with heating under nitrogen atmosphere in a microwave reactor at 110° C. for 1 hr. Water was added to the reaction solution, and the mixture was extracted with chloroform. The organic layer was washed with saturated brine, dried over anhydrous sodium sulfate, and concentrated under reduced pressure, and the residue was subjected to reversed phase high-performance liquid chromatography (water/acetonitrile/0.1% formic acid) to give the title compound (9.86 mg) as a solid.

$^1$H-NMR (CD$_3$OD) δ: 1.92-2.13 (4H, m), 2.19-2.29 (1H, m), 2.47-2.55 (1H, m), 2.65 (1H, s), 3.37 (3H, s), 3.65-3.74 (1H, m), 3.87 (3H, s), 3.90 (2H, q, J=10.7 Hz), 4.11 (2H, s), 5.24-5.33 (1H, m), 6.85 (2H, d, J=8.6 Hz), 7.27 (2H, d, J=8.6 Hz), 7.37 (1H, s), 7.56 (1H, s), 7.63 (1H, s), 8.26 (1H, s), 8.48 (1H, br s).

MS (m/z): 516 (M+H)$^+$.

Example 13

(1R,3S)—N$^3$-{[4-(6'-chloro[2,3'-bipyridine]-5-yl)phenyl]methyl}-N$^1$-methyl-N$^1$-[6-(2,2,2-trifluoroethyl)thieno[2,3-d]pyrimidin-4-yl]cyclopentane-1,3-diamine

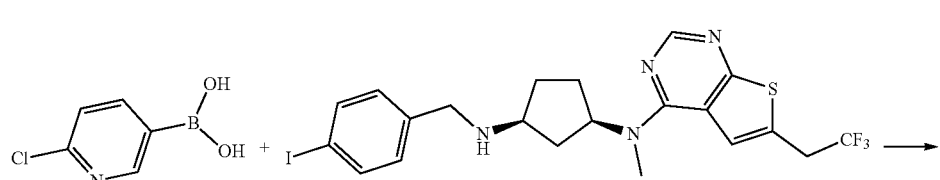

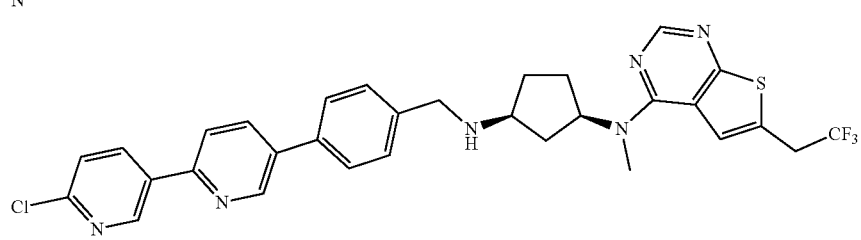

The compound (0.269 g) obtained in Step 1 of Example 11 was dissolved in ethylene glycol dimethyl ether (2.28 mL), and 6-chloro-3-pyridinylboronic acid (CAS: 444120-91-6) (0.143 g), bis(triphenylphosphine)palladium(II) dichloride dichloromethane adduct (0.0320 g), potassium carbonate (0.189 g) and water (0.228 mL) were added thereto, and the mixture was stirred under nitrogen atmosphere at 60° C. for 4 hr. Water was added to the reaction solution, and the mixture was extracted twice with dichloromethane. The organic layer was concentrated under reduced pressure, and the residue was purified by silica gel chromatography (dichloromethane/methanol) to give the title compound (0.0101 g) as a solid.

$^1$H-NMR (CDCl$_3$) δ: 1.52-1.67 (3H, br m), 1.94-1.97 (2H, br m), 2.26-2.33 (1H, m), 3.24-3.29 (1H, m), 3.31 (3H, s), 3.62 (2H, q, J=10.2 Hz), 3.85 (2H, s), 5.35 (1H, q, J=8.3 Hz), 7.34 (1H, s), 7.39 (1H, d, J=8.5 Hz), 7.44-7.48 (3H, m), 7.51-7.56 (3H, m), 7.64-7.69 (1H, m), 7.83 (1H, dd, J=8.5, 2.7 Hz), 8.41 (1H, s), 8.60 (1H, s).

MS (m/z): 610 (M+H)$^+$.

Example 14

(1R,3S)—N$^3$-{[4-(furo[3,2-b]pyridin-6-yl)phenyl]methyl}-N$^1$-methyl-N$^1$-[6-(2,2,2-trifluoroethyl)thieno[2,3-d]pyrimidin-4-yl]cyclopentane-1,3-diamine Hydrochloride

[Formula 393]

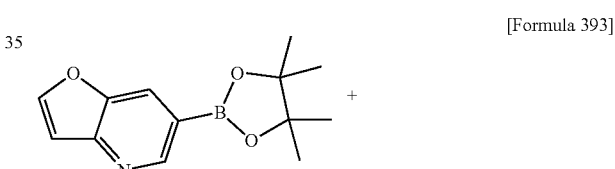

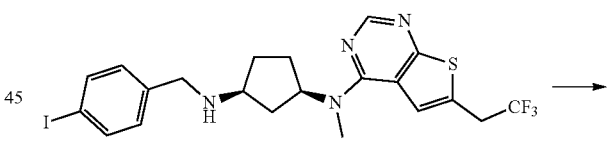

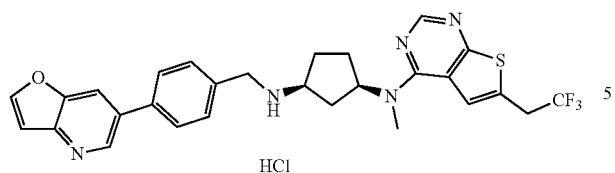

HCl

The title compound was obtained in the same manner as in Step 2 and Step 3 of Example 11, using the compound obtained in Step 1 of Example 11 and 6-(4,4,5,5-tetramethyl-1,3,2-dioxaborolan-2-yl)furo[3,2-b]pyridine (CAS: 1188539-34-5).

$^1$H-NMR (DMSO-D$_6$) δ: 1.88-2.13 (4H, m), 2.33-2.42 (2H, m), 3.29 (3H, s), 3.65 (1H, br s), 4.09 (2H, q, J=11.0 Hz), 4.25 (2H, t, J=6.4 Hz), 5.24-5.33 (1H, m), 7.21 (1H, dd, J=2.4, 1.2 Hz), 7.71 (2H, d, J=7.9 Hz), 7.73 (1H, s), 7.93 (2H, d, J=7.9 Hz), 8.38 (1H, s), 8.39 (1H, d, J=1.8 Hz), 8.42 (1H, dd, J=1.8, 1.2 Hz), 8.92 (1H, d, J=1.8 Hz), 9.26 (1H, br s), 9.38 (1H, br s).

MS (m/z): 538 (M+H)$^+$.

Example 15

(1R,3R,5S)-3-({[4-(5-methoxypyridin-3-yl)phenyl]methyl}amino)-5-{[6-(2,2,2-trifluoroethyl)thieno[2,3-d]pyrimidin-4-yl]amino}cyclohexan-1-ol Hydrochloride (15A)

(1S,3S,5R)-3-({[4-(5-methoxypyridin-3-yl)phenyl]methyl}amino)-5-{[6-(2,2,2-trifluoroethyl)thieno[2,3-d]pyrimidin-4-yl]amino}cyclohexan-1-ol Hydrochloride (15B)

Step 1 (1R,3R,5S)-3-({[4-(5-methoxypyridin-3-yl)phenyl]methyl}amino)-5-{[6-(2,2,2-trifluoroethyl)thieno[2,3-d]pyrimidin-4-yl]amino}cyclohexan-1-ol (Racemate)

[Formula 394]

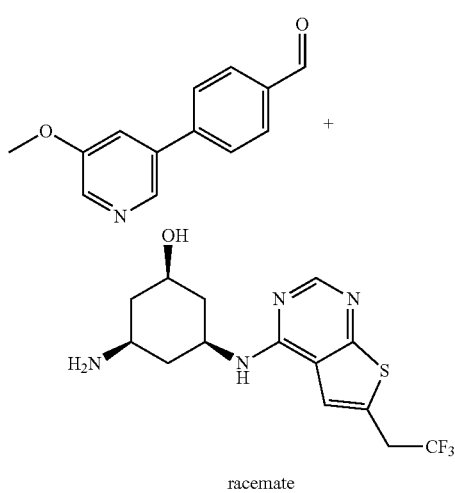

racemate

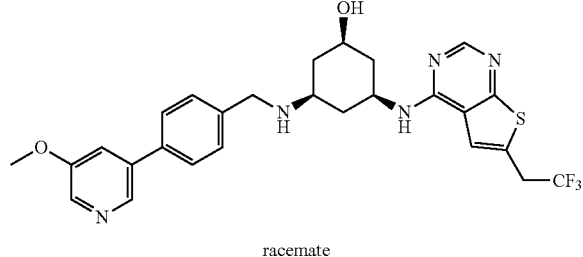

racemate

The title compound (390 mg) was obtained in the same manner as in Step 1 of Example 2, using the compound obtained in Step 2 of Reference Example C-18 and the compound obtained in Reference Example D-65.

$^1$H-NMR (DMSO-D$_6$) δ: 0.95-1.11 (2H, m), 1.25-1.28 (1H, m), 2.10-2.16 (3H, m), 2.52-2.55 (1H, m), 3.48-3.50 (1H, m), 3.79 (2H, s), 3.91 (3H, s), 4.00-4.10 (3H, m), 4.71 (1H, d, J=4.9 Hz), 7.47 (2H, d, J=8.3 Hz), 7.61-7.61 (1H, m), 7.65 (1H, s), 7.70 (2H, d, J=8.3 Hz), 7.85-7.87 (1H, m), 8.27-8.27 (1H, m), 8.31 (1H, s), 8.48 (1H, s).

MS (m/z): 544 (M+H)$^+$.

Step 2 (1R,3R,5S)-3-({[4-(5-methoxypyridin-3-yl)phenyl]methyl}amino)-5-{[6-(2,2,2-trifluoroethyl)thieno[2,3-d]pyrimidin-4-yl]amino}cyclohexan-1-ol (a Free Form of 15A)

(1S,3S,5R)-3-({[4-(5-methoxypyridin-3-yl)phenyl]methyl}amino)-5-{[6-(2,2,2-trifluoroethyl)thieno[2,3-d]pyrimidin-4-yl]amino}cyclohexan-1-ol (a Free Form of 15B)

[Formula 395]

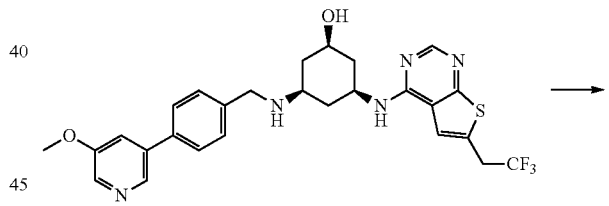

racemate

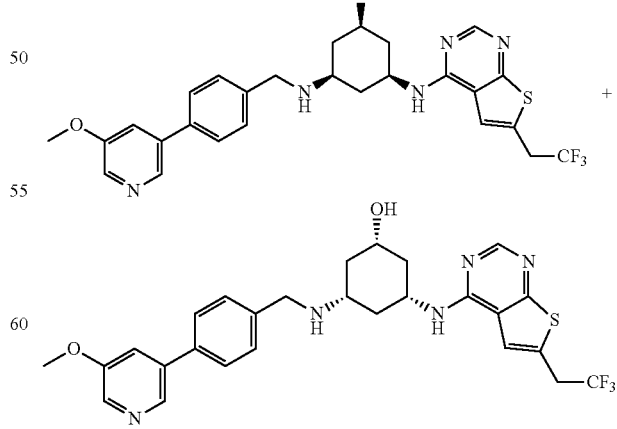

The compound (390 mg) obtained in the above Step 1 was subjected to optical resolution with chiral high-performance liquid chromatography (CHIRALPAK (registered trademark, Daicel Corporation) IA, mobile phase: n-hexane/2-propanol) to give a free form (an earlier eluted component, 150 mg) of 15A, and a free form (a later eluted component, 185 mg) of 15B, respectively as a solid.

the free form of 15A (earlier eluted component)
$^1$H-NMR (DMSO-D$_6$) δ: 0.95-1.29 (3H, m), 2.04-2.19 (4H, m), 2.47-2.57 (1H, m), 3.47-3.51 (1H, m), 3.78-3.79 (2H, m), 3.91 (3H, s), 3.99-4.10 (3H, m), 4.71-4.73 (1H, m), 7.47 (2H, d, J=8.3 Hz), 7.61-7.61 (1H, m), 7.66 (1H, s), 7.70 (2H, d, J=8.3 Hz), 7.87 (1H, d, J=8.0 Hz), 8.27-8.28 (1H, m), 8.31 (1H, s), 8.48 (1H, s).
MS (m/z): 544 (M+H)$^+$.

the free form of 15B (later eluted component)
$^1$H-NMR (DMSO-D$_6$) δ: 1.05-1.25 (3H, m), 2.12-2.19 (4H, m), 2.54-2.57 (1H, m), 3.51-3.54 (1H, m), 3.80 (2H, s), 3.92 (3H, s), 4.03-4.14 (3H, m), 4.76-4.78 (1H, m), 7.48 (2H, d, J=8.0 Hz), 7.62-7.62 (1H, m), 7.69 (1H, s), 7.71 (2H, d, J=8.0 Hz), 7.91 (1H, d, J=7.4 Hz), 8.29 (1H, s), 8.33 (1H, s), 8.49 (1H, s). separation condition (analysis) CHIRALPAK (registered trademark, Daicel Corporation) IA, size 0.46 cm×15 cm, flow rate 1.0 mL/min, mobile phase: n-hexane/2-propanol=20/80 to 0/100, temperature 26° C.

the free form of 15A retention time 3.0 min, the free form of 15B retention time 3.6 min separation condition (preparative) CHIRALPAK (registered trademark, Daicel Corporation) IA, size 2.5 cm×25 cm, flow rate 20 mL/min, mobile phase n-hexane/2-propanol=50/50, temperature 40° C.

the free form of 15A retention time 5.7 min, the free form of 15B retention time 7.2 min Step 3 (1R,3R,5S)-3-({[4-(5-methoxypyridin-3-yl)phenyl]methyl}amino)-5-{[6-(2,2,2-trifluoroethyl)thieno[2,3-d]pyrimidin-4-yl]amino}cyclohexan-1-ol Hydrochloride (15A)

[Formula 396]

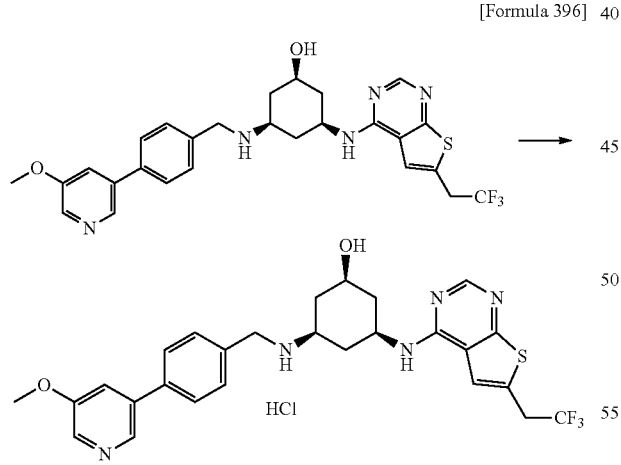

A mixture of the free form of 15A (lower polar isomer, 149 mg) obtained in the above Step 2, hydrochloric acid (1 mol/L, ethanol solution, 0.274 mL) and ethanol (2 mL) was stirred, and concentrated under reduced pressure. Ethanol/diethyl ether solution was added to the residue, and the resulting solid was collected by filtration to give the title compound (142 mg) as a solid.

$^1$H-NMR (DMSO-D$_6$) δ: 1.29-1.49 (3H, m), 2.10-2.13 (1H, m), 2.34-2.41 (2H, m), 3.24-3.31 (1H, m), 3.58-3.61 (2H, m), 3.91 (3H, s), 4.05-4.08 (2H, m), 4.19-4.24 (3H, m), 7.66-7.69 (4H, m), 7.84-7.86 (2H, m), 8.06-8.08 (1H, m), 8.33-8.34 (2H, m), 8.54 (1H, s), 9.18-9.21 (2H, m).
MS (m/z): 544 (M+H)$^+$.

Step 4 (1S,3S,5R)-3-({[4-(5-methoxypyridin-3-yl)phenyl]methyl}amino)-5-{[6-(2,2,2-trifluoroethyl)thieno[2,3-d]pyrimidin-4-yl]amino}cyclohexan-1-ol Hydrochloride (15B)

[Formula 397]

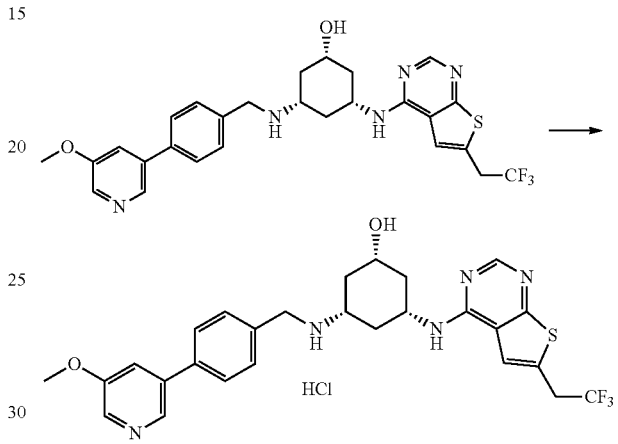

A mixture of the free form of 15B (125 mg) obtained in the above Step 9, hydrochloric acid (1 mol/L, ethanol solution, 0.23 mL) and ethanol (2 mL) was stirred, and concentrated under reduced pressure. Ethanol/diethyl ether solution was added to the residue, and the resulting solid was collected by filtration to give the title compound (116 mg) as a solid.

$^1$H-NMR (DMSO-D$_6$) δ: 1.40-1.52 (3H, m), 2.11-2.13 (1H, m), 2.45-2.48 (2H, m), 3.28-3.31 (1H, m), 3.60-3.64 (2H, m), 3.95 (3H, s), 4.08-4.11 (2H, m), 4.25-4.27 (3H, m), 7.70 (1H, s), 7.73 (2H, d, J=8.5 Hz), 7.80 (1H, s), 7.89 (2H, d, J=8.5 Hz), 8.17-8.19 (1H, m), 8.38-8.39 (2H, m), 8.60 (1H, s), 9.37-9.40 (2H, m).
MS (m/z): 544 (M+H)$^+$.

Example 16

(1R,3S,5R)-3-[{[4-(5-methoxypyridin-3-yl)phenyl]methyl}(methyl)amino]-5-{[6-(2,2,2-trifluoroethyl)thieno[2,3-d]pyrimidin-4-yl]amino}cyclohexan-1-ol

[Formula 398]

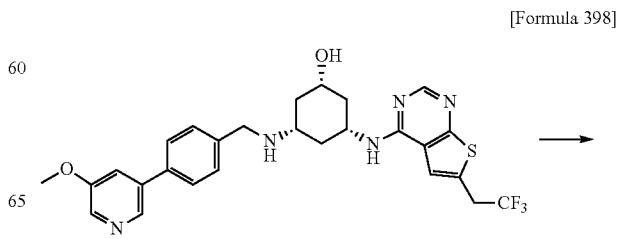

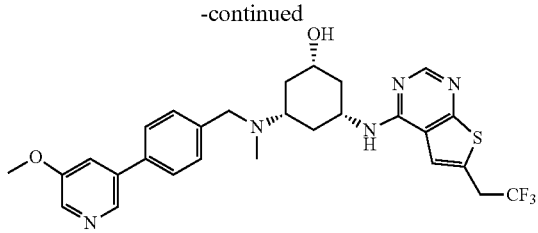

A mixture of the compound (the free form of 15B) (0.0353 g) obtained in Step 2 of Example 15, dichloromethane (0.649 mL) and pyridine (0.0157 mL) was ice-cooled, and methyl trifluoromethanesulfonate (0.0147 mL) was added thereto. The mixture was stirred at the same temperature for 2 hr, gradually warmed to room temperature, and stirred for 1 hr. The reaction mixture was ice-cooled, and additional pyridine (0.0261 mL) and methyl trifluoromethanesulfonate (0.0294 mL) were added thereto, and the mixture was stirred at same temperature for 1 hr, and then at room temperature overnight. Saturated aqueous sodium bicarbonate solution was added to the reaction mixture, and the mixture was extracted three times with ethyl acetate. The organic layer was dried over anhydrous sodium sulfate, and concentrated under reduced pressure. The residue was purified by preparative TLC (dichloromethane/methanol) and amino silica gel preparative TLC (dichloromethane/ethyl acetate) to give the title compound (0.0028 g).

$^1$H-NMR (CD$_3$OD) δ: 0.88-0.91 (2H, m), 1.38-1.51 (3H, m), 1.59 (1H, s), 2.23-2.32 (3H, m), 2.34 (3H, s), 2.85 (1H, t, J=11.6 Hz), 3.79 (2H, s), 3.86 (2H, q, J=10.6 Hz), 3.95 (3H, s), 4.63 (1H, br s), 7.50 (1H, s), 7.52 (2H, d, J=1.2 Hz), 7.63 (1H, s), 7.67 (2H, d, J=8.5 Hz), 8.22 (1H, s), 8.32 (1H, s), 8.39 (1H, s).

MS (m/z): 558 (M+H)$^+$.

Example 17

(1S,3R,5S)-3-({[4-(5-methoxypyridin-3-yl)phenyl]methyl}amino)-N,N-dimethyl-5-{[6-(2,2,2-trifluoroethyl)thieno[2,3-d]pyrimidin-4-yl]amino}cyclohexane-1-carboxamide Hydrochloride (17A)

(1R,3S,5R)-3-({[4-(5-methoxypyridin-3-yl)phenyl]methyl}amino)-N,N-dimethyl-5-{[6-(2,2,2-trifluoroethyl)thieno[2,3-d]pyrimidin-4-yl]amino}cyclohexane-1-carboxamide Hydrochloride (17B)

Step 1 (1R,3S,5R)-3-({[4-(5-methoxypyridin-3-yl)phenyl]methyl}amino)-N,N-dimethyl-5-{[6-(2,2,2-trifluoroethyl)thieno[2,3-d]pyrimidin-4-yl]amino}cyclohexane-1-carboxamide Hydrochloride (Racemate)

[Formula 399]

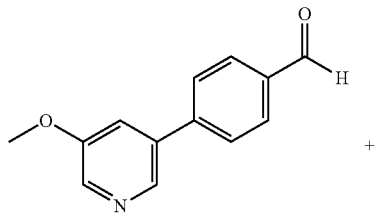
+

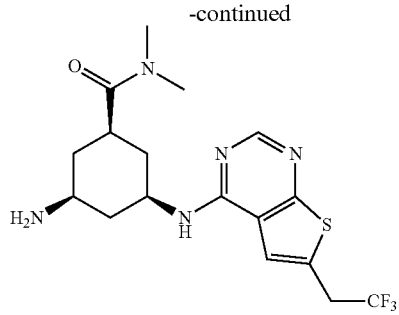

racemate

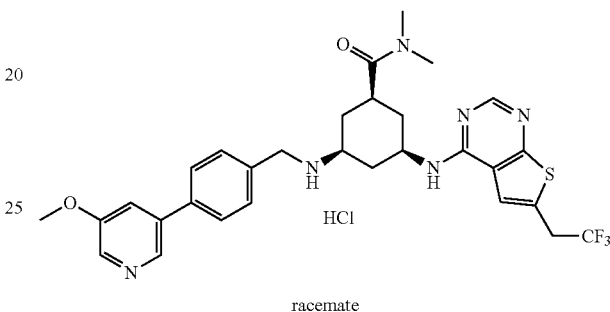

racemate

To a mixture of the compound (0.0375 g) obtained in Step 2 of Reference Example C-17, the compound (0.0240 g) obtained in Reference Example D-65 and chloroform (2.0 mL) was added tetraisopropyl orthotitanate (CAS: 546-68-9) (0.083 mL) at room temperature. This reaction solution was stirred at room temperature for 1.5 hr, sodium triacetoxyborohydride (purity 97%, 0.109 g) was added thereto, and the mixture was stirred at room temperature for 6 hr, and allowed to stand for 16 hr. Saturated aqueous sodium hydrogencarbonate solution (10 mL) and saturated aqueous potassium sodium tartrate solution (10 mL) were added to this reaction solution, and the mixture was extracted three times with dichloromethane (10 mL). The organic layer was dried over anhydrous sodium sulfate, and concentrated under reduced pressure. The residue was purified by amino silica gel column chromatography (methanol/ethyl acetate) to give an oil (0.0457 g). To a mixture of the obtained oil (0.0457 g) and ethanol (3.0 mL) was added 1N hydrogen chloride ethanol solution (0.076 mL) at room temperature. This reaction solution was stirred at room temperature for 2.5 hr, and concentrated under reduced pressure. A suspension of the residue in ethanol (0.05 mL) and diethyl ether (6.0 mL) was filtered, and the obtained solid was dried under reduced pressure at 40° C. for 2 hr to give the title compound (0.0419 g) as a solid.

$^1$H-NMR (DMSO-D$_6$) δ: 1.46-1.64 (3H, m), 1.91 (1H, d, J=12.2 Hz), 2.21 (1H, d, J=12.2 Hz), 2.53-2.55 (1H, m), 2.84 (3H, s), 3.01-3.04 (1H, m), 3.06 (3H, s), 3.93 (3H, s), 4.09 (2H, q, J=11.0 Hz), 4.26-4.28 (2H, m), 4.34-4.36 (1H, m), 7.67 (1H, s), 7.69 (1H, dd, J=2.4, 1.8 Hz), 7.72 (2H, d, J=7.9 Hz), 7.87 (2H, d, J=7.9 Hz), 8.10 (1H, d, J=7.9 Hz), 8.33 (1H, d, J=2.4 Hz), 8.37 (1H, s), 8.55 (1H, d, J=1.8 Hz), 9.26 (1H, br s), 9.34 (1H, br s).

Step 2 (1S,3R,5S)-3-({[4-(5-methoxypyridin-3-yl)phenyl]methyl}amino)-N,N-dimethyl-5-{[6-(2,2,2-trifluoroethyl)thieno[2,3-d]pyrimidin-4-yl]amino}cyclohexane-1-carboxamide (a Free Form of 17A)

(1R,3S,5R)-3-({[4-(5-methoxypyridin-3-yl)phenyl]methyl}amino)-N,N-dimethyl-5-{[6-(2,2,2-trifluoroethyl)thieno[2,3-d]pyrimidin-4-yl]amino}cyclohexane-1-carboxamide (a Free Form of 17B)

[Formula 400]

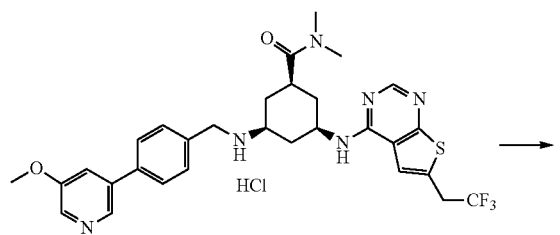

racemate

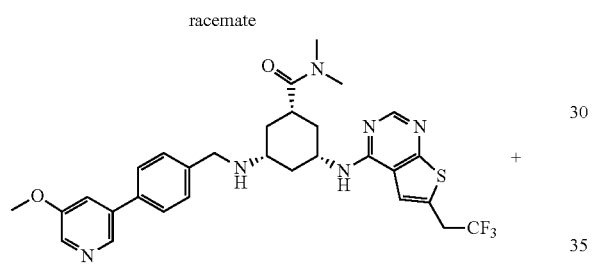

To a mixture of the compound (0.0339 g) obtained in the above Step 1 and dichloromethane (5.0 mL) was added saturated aqueous sodium hydrogencarbonate solution (5.0 mL) at room temperature. This mixture was stirred vigorously at room temperature for 1 hr, and extracted three times with dichloromethane (10 mL), and the organic layer was dried over anhydrous sodium sulfate, and concentrated under reduced pressure. The residue was purified by chiral high-performance liquid chromatography (CHIRALPAK (registered trademark, Daicel Corporation) IA, mobile phase: 2-propanol/n-hexane) to give a free form of 17A (an earlier eluted component, 0.0137 g) and a free form of 17B (a later eluted component, 0.0145 g), respectively as an oil.

the free form of 17A (earlier eluted component)

$^1$H-NMR (CDCl$_3$) δ: 1.31 (1H, q, J=11.5 Hz), 1.51 (1H, q, J=12.1 Hz), 1.65 (1H, q, J=12.1 Hz), 1.92 (1H, br s), 2.12-2.18 (2H, m), 2.48-2.51 (1H, m), 2.85-2.89 (2H, m), 2.97 (3H, s), 3.11 (3H, s), 3.61 (2H, q, J=10.3 Hz), 3.91-3.93 (2H, m), 3.93 (3H, s), 4.39-4.46 (1H, m), 5.92 (1H, d, J=8.5 Hz), 7.25 (1H, s), 7.35 (1H, dd, J=3.0, 1.8 Hz), 7.43 (2H, d, J=8.5 Hz), 7.54 (2H, d, J=8.5 Hz), 8.30 (1H, d, J=3.0 Hz), 8.45 (1H, d, J=1.8 Hz), 8.47 (1H, s).

the free form of 17B (later eluted component)

$^1$H-NMR (CDCl$_3$) δ: 1.31 (1H, q, J=11.5 Hz), 1.51 (1H, q, J=12.1 Hz), 1.65 (1H, q, J=12.1 Hz), 1.90 (1H, br s), 2.12-2.18 (2H, m), 2.48-2.50 (1H, m), 2.84-2.89 (2H, m), 2.98 (3H, s), 3.11 (3H, s), 3.61 (2H, q, J=10.3 Hz), 3.91-3.93 (2H, m), 3.93 (3H, s), 4.40-4.44 (1H, m), 5.91 (1H, d, J=8.5 Hz), 7.25 (1H, s), 7.36 (1H, dd, J=3.0, 1.8 Hz), 7.43 (2H, d, J=7.9 Hz), 7.54 (2H, d, J=7.9 Hz), 8.30 (1H, d, J=3.0 Hz), 8.45 (1H, d, J=1.8 Hz), 8.47 (1H, s).

separation condition (analysis) CHIRALPAK (registered trademark, Daicel Corporation) IA, size 0.46 cm×15 cm, flow rate 1.0 mL/min, mobile phase n-hexane/2-propanol=50/50 to 0/100, temperature 40° C.

the free form of 17A retention time 5.2 min, the free form of 17B retention time 7.3 min separation condition (preparative) CHIRALPAK (registered trademark, Daicel Corporation) IA, size 2.0 cm×25 cm, flow rate 10 mL/min, mobile phase n-hexane/2-propanol=25/75, temperature 20° C.

the free form of 17A retention time 14.0 min, the free form of 17B retention time 19.8 min

Step 3 (1S,3R,5S)-3-({[4-(5-methoxypyridin-3-yl)phenyl]methyl}amino)-N,N-dimethyl-5-{[6-(2,2,2-trifluoroethyl)thieno[2,3-d]pyrimidin-4-yl]amino}cyclohexane-1-carboxamide Hydrochloride (17A)

[Formula 401]

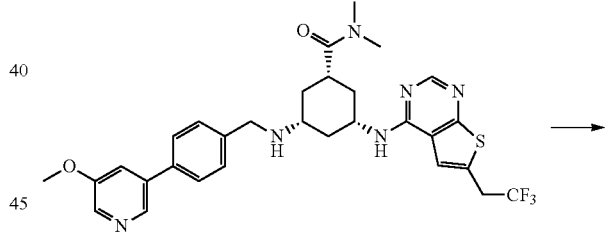

To a mixture of the free form of 17A (0.0137 g) obtained in the above Step 2 and ethanol (5.0 mL) was added 1N hydrogen chloride ethanol solution (0.030 mL) at room temperature. This reaction solution was stirred at room temperature for 2.5 hr, and concentrated under reduced pressure. A suspension of the residue in ethanol (0.05 mL) and diethyl ether (6.0 mL) was filtered, and the obtained solid was dried under reduced pressure at 40° C. for 2 hr to give the title compound (0.0120 g) as a solid.

$^1$H-NMR (DMSO-D$_6$) δ: 1.46-1.56 (3H, m), 1.91 (1H, d, J=13.4 Hz), 2.20 (1H, d, J=13.4 Hz), 2.54 (1H, s), 2.84 (3H, s), 3.01-3.03 (1H, m), 3.06 (3H, s), 3.93 (3H, s), 4.10 (2H, q, J=11.5 Hz), 4.29-4.31 (2H, m), 4.33-4.36 (1H, m), 7.65 (1H, s), 7.69 (2H, d, J=7.6 Hz), 7.71-7.73 (1H, m), 7.88 (2H, d, J=7.6 Hz), 8.09 (1H, m), 8.35 (1H, d, J=2.4 Hz), 8.38 (1H, s), 8.57 (1H, s), 9.09 (1H, br s), 9.16 (1H, br s).

MS (m/z): 599 (M+H)$^+$.

Step 4 (1R,3S,5R)-3-({[4-(5-methoxypyridin-3-yl)phenyl]methyl}amino)-N,N-dimethyl-5-{[6-(2,2,2-trifluoroethyl)thieno[2,3-d]pyrimidin-4-yl]amino}cyclohexane-1-carboxamide Hydrochloride (17B)

Example 18

(1R,3S,5R)-5-methoxy-N$^1$-{[4-(5-methoxypyridin-3-yl)phenyl]methyl}-N$^3$-[6-(2,2,2-trifluoroethyl)thieno[2,3-d]pyrimidin-4-yl]cyclohexane-1,3-diamine Hydrochloride (1S,3R,5S)-5-methoxy-N$^1$-{[4-(5-methoxypyridin-3-yl)phenyl]methyl}-N$^3$-[6-(2,2,2-trifluoroethyl)thieno[2,3-d]pyrimidin-4-yl]cyclohexane-1,3-diamine Hydrochloride Step 1 (1R,3S,5R)-5-methoxy-N$^1$-{[4-(5-methoxypyridin-3-yl)phenyl]methyl}-N$^3$-[6-(2,2,2-trifluoroethyl)thieno[2,3-d]pyrimidin-4-yl]cyclohexane-1,3-diamine (Racemate)

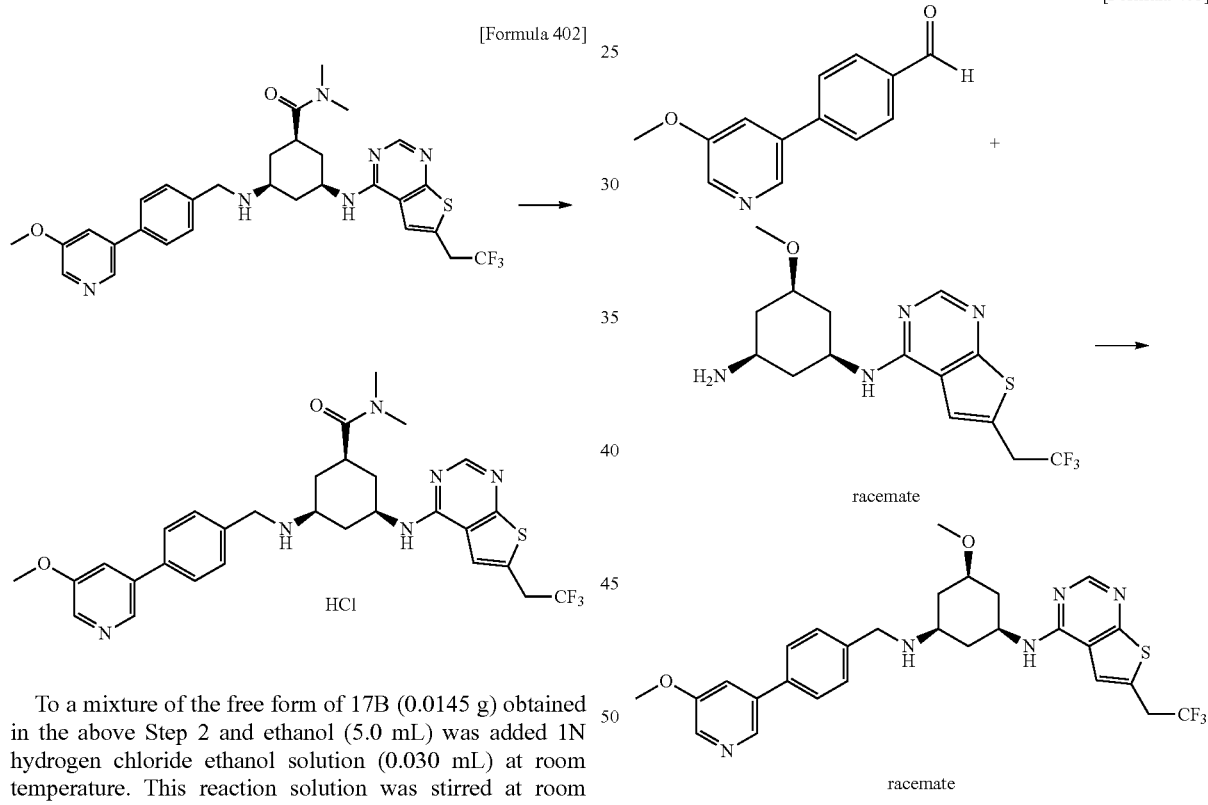

[Formula 402]

[Formula 403]

To a mixture of the free form of 17B (0.0145 g) obtained in the above Step 2 and ethanol (5.0 mL) was added 1N hydrogen chloride ethanol solution (0.030 mL) at room temperature. This reaction solution was stirred at room temperature for 2.5 hr, and concentrated under reduced pressure. A suspension of the residue in ethanol (0.05 mL) and diethyl ether (6.0 mL) was filtered, and the obtained solid was dried under reduced pressure at 40° C. for 2 hr to give the title compound (0.0145 g) as a solid.

$^1$H-NMR (DMSO-D$_6$) δ: 1.52-1.61 (3H, m), 1.90 (1H, d, J=12.1 Hz), 2.21 (1H, d, J=12.1 Hz), 2.53-2.54 (1H, m), 2.84 (3H, s), 2.99-3.02 (1H, m), 3.06 (3H, s), 3.94 (3H, s), 4.10 (2H, q, J=10.9 Hz), 4.27-4.29 (2H, m), 4.35-4.36 (1H, m), 7.66-7.68 (1H, m), 7.73 (2H, d, J=8.2 Hz), 7.82 (1H, s), 7.90 (2H, d, J=8.2 Hz), 8.20 (1H, s), 8.38-8.39 (2H, m), 8.61 (1H, s), 9.33 (1H, br s), 9.41 (1H, br s).

MS (m/z): 599 (M+H)$^+$.

The title compound was obtained in the same manner as in Step 1 of Reference Example E-3, using the compound obtained in Step 2 of Reference Example C-18 and the compound obtained in Reference Example D-65.

$^1$H-NMR (CDCl$_3$) δ: 1.25-1.39 (3H, m), 2.34-2.44 (3H, m), 2.83-2.88 (1H, m), 3.35 (3H, s), 3.39-3.44 (1H, m), 3.56-3.64 (2H, m), 3.89 (2H, s), 3.92 (3H, s), 4.36 (1H, d, J=7.3 Hz), 5.64 (1H, br s), 7.03 (1H, s), 7.36 (1H, s), 7.42 (2H, d, J=7.9 Hz), 7.55 (2H, d, J=7.9 Hz), 8.30 (1H, t, J=2.7 Hz), 8.45 (1H, t, J=2.1 Hz), 8.47 (1H, s).

MS (m/z): 558 (M+H)$^+$.

Step 2 (1R,3S,5R)-5-methoxy-N¹-{[4-(5-methoxy-pyridin-3-yl)phenyl]methyl}-N³-[6-(2,2,2-trifluoro-ethyl)thieno[2,3-d]pyrimidin-4-yl]cyclohexane-1,3-diamine Hydrochloride (1S,3R,5S)-5-methoxy-N¹-{[4-(5-methoxypyridin-3-yl)phenyl]methyl}-N³-[6-(2,2,2-trifluoroethyl)thieno[2,3-d]pyrimidin-4-yl]cyclohexane-1,3-diamine Hydrochloride

[Formula 404]

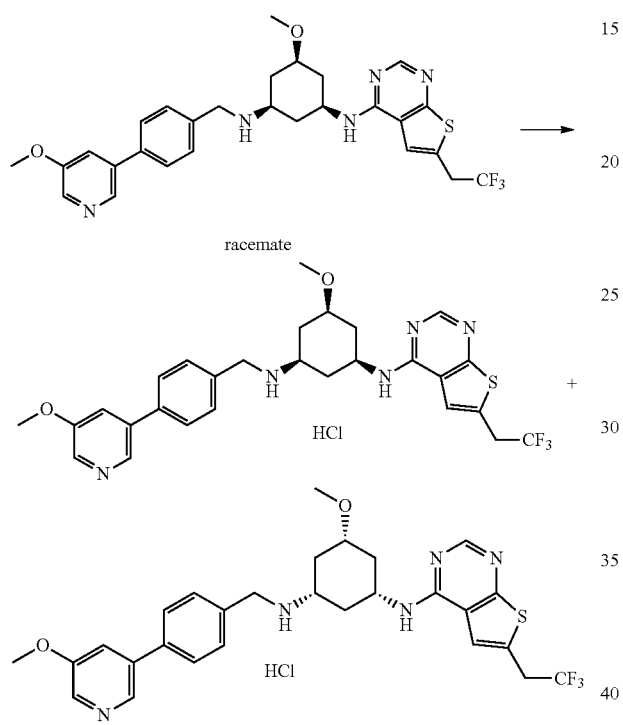

The compound (0.24 g) obtained in the above Step 1 was subjected to optical resolution with chiral high-performance liquid chromatography (CHRALPAK (registered trademark, Daicel Corporation) IA, mobile phase: n-hexane/2-propanol/ethyl acetate/diethylamine) to give a free form of 18A (an earlier eluted component, 69 mg) and a free form of 18B (a later eluted component, 51 mg).

The free form of 18A (0.069 g) was dissolved in methanol (3.00 mL), 1N hydrochloric acid (0.124 mL) was added thereto, and the solvent was evaporated under reduced pressure. Diethyl ether was added to the residue, and the solid was collected by filtration to give one compound (18A) (0.069 g) of the title compounds, as a solid.

¹H-NMR (CD₃OD) δ: 1.37-1.59 (3H, m), 2.48-2.54 (1H, m), 2.64-2.70 (2H, m), 3.40-3.53 (2H, m), 3.44 (3H, s), 3.87 (2H, q, J=10.5 Hz), 3.98 (3H, s), 4.31-4.41 (3H, m), 7.54 (1H, s), 7.67 (2H, d, J=8.5 Hz), 7.73-7.75 (1H, m), 7.82 (2H, d, J=8.5 Hz), 8.31 (1H, d, J=2.0 Hz), 8.37 (1H, s), 8.46 (1H, br s).

MS (m/z): 558 (M+H)⁺.

The free form of 18B (0.051 g) was dissolved in methanol (3.00 mL), 1N hydrochloric acid (0.092 mL) was added thereto, and the solvent was evaporated under reduced pressure. Diethyl ether was added to the residue, and the solid was collected by filtration to give the other compound (18B) (0.054 g) of the title compounds, as a solid.

¹H-NMR (CD₃OD) δ: 1.34-1.53 (3H, m), 2.48-2.53 (1H, m), 2.64-2.70 (2H, m), 3.41-3.49 (2H, m), 3.44 (3H, s), 3.88 (2H, q, J=10.5 Hz), 3.97 (3H, s), 4.32-4.39 (3H, m), 7.52 (1H, s), 7.66 (2H, d, J=8.2 Hz), 7.73 (1H, br s), 7.83 (2H, d, J=8.2 Hz), 8.30 (1H, d, J=1.8 Hz), 8.37 (1H, s), 8.45 (1H, br s).

MS (m/z): 558 (M+H)⁺.

separation condition (analysis) CHRALPAK (registered trademark, Daicel Corporation) IA, size 0.46 cm×25 cm, flow rate 1.0 mL/min, mobile phase n-hexane/2-propanol/ethyl acetate/diethylamine=50/30/20/0.1, temperature 40° C. the free form of 18A retention time 7.2 min, the free form of 18B retention time 9.8 min separation condition (preparative) CHRALPAK (registered trademark, Daicel Corporation) IA, size 2.0 cm×25 cm, flow rate 5.7 mL/min, mobile phase n-hexane/2-propanol/ethyl acetate/diethylamine=50/30/20/0.1, temperature 40° C. the free form of 18A retention time 21 min, the free form of 18B retention time 27 min Example 19

(1S,3R,5R)—N¹-{[4-(5-methoxypyridin-3-yl)phenyl]methyl}-5-(1,3-oxazol-2-yl)-N³-[6-(2,2,2-trifluoroethyl)thieno[2,3-d]pyrimidin-4-yl]cyclohexane-1,3-diamine Hydrochloride (1R,3S,5S)—N¹-{[4-(5-methoxypyridin-3-yl)phenyl]methyl}-5-(1,3-oxazol-2-yl)-N³-[6-(2,2,2-trifluoroethyl)thieno[2,3-d]pyrimidin-4-yl]cyclohexane-1,3-diamine Hydrochloride Step 1 (1S,3R,5R)—N¹-{[4-(5-methoxypyridin-3-yl)phenyl]methyl}-5-(1,3-oxazol-2-yl)-N³-[6-(2,2,2-trifluoroethyl)thieno[2,3-d]pyrimidin-4-yl]cyclohexane-1,3-diamine (Racemate)

[Formula 405]

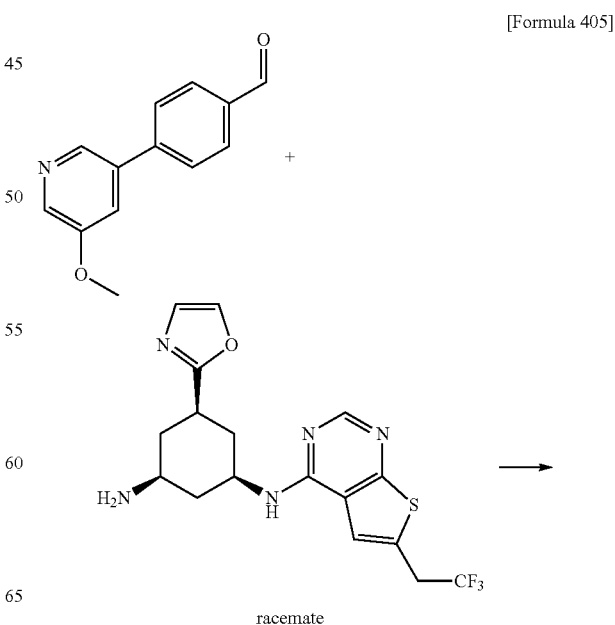

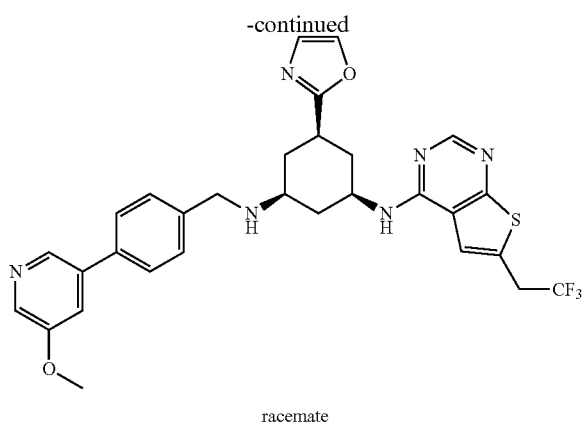

racemate

The title compound was obtained in the same manner as in Step 1 of Reference Example E-3, using the compound obtained in Step 6 of Reference Example C-32 and the compound obtained in Reference Example D-65.

$^1$H-NMR (CDCl$_3$) δ: 1.12-1.75 (4H, m), 2.42-2.63 (3H, m), 2.89-3.02 (1H, m), 3.05-3.19 (1H, m), 3.55-3.67 (2H, m), 3.88-3.98 (5H, m), 4.42-4.49 (1H, m), 5.35 (1H, s), 6.96-7.00 (1H, m), 7.02 (1H, s), 7.35-7.38 (1H, m), 7.41-7.46 (2H, m), 7.52-7.58 (3H, m), 8.29-8.31 (1H, m), 8.45-8.47 (1H, m), 8.48 (1H, s).

MS (m/z): 595 (M+H)$^+$.

Step 2 (1S,3R,5R)—N$^1$-{[4-(5-methoxypyridin-3-yl)phenyl]methyl}-5-(1,3-oxazol-2-yl)-N$^3$-[6-(2,2,2-trifluoroethyl)thieno[2,3-d]pyrimidin-4-yl]cyclohexane-1,3-diamine Hydrochloride (1R,3S,5S)—N$^1$-{[4-(5-methoxypyridin-3-yl)phenyl]methyl}-5-(1,3-oxazol-2-yl)-N$^3$-[6-(2,2,2-trifluoroethyl)thieno[2,3-d]pyrimidin-4-yl]cyclohexane-1,3-diamine Hydrochloride

[Formula 406]

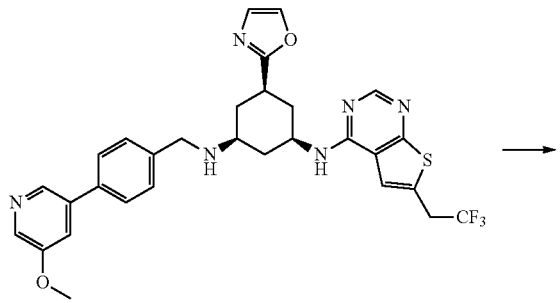

racemate

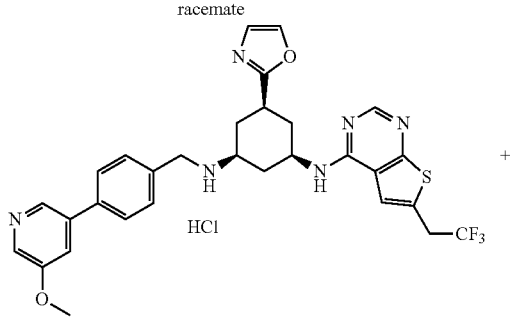

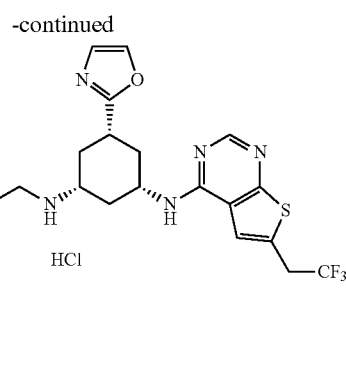

The compound obtained in the above Step 1 (68 mg) was subjected to optical resolution with chiral high-performance liquid chromatography (CHRALPAK (registered trademark, Daicel Corporation) IA, mobile phase: n-hexane/2-propanol) to give a free form of 19A (an earlier eluted component, 22 mg) and a free form of 19B (a later eluted component, 23 mg).

To a solution of the free form of 19A (22 mg) in ethanol (0.500 mL) was added 2N hydrochloric acid (0.0185 mL) at room temperature, and the mixture was concentrated under reduced pressure. Ethanol (1.00 mL) was added thereto, and the mixture was azeotropically concentrated, and the residue was solidified with diethyl ether to give one compound (19A) (23 mg) of the title compounds, as a solid.

$^1$H-NMR (DMSO-D$_6$) δ: 1.53-1.77 (3H, m), 2.28-2.35 (1H, m), 2.57-2.63 (2H, m), 3.22-3.31 (1H, m), 3.92-3.94 (3H, m), 4.10 (2H, q, J=11.0 Hz), 4.27-4.45 (3H, m), 7.18 (1H, s), 7.65-7.76 (4H, m), 7.89 (2H, d, J=8.6 Hz), 8.09 (1H, s), 8.14 (1H, br s), 8.33-8.37 (1H, m), 8.40 (1H, s), 8.55-8.59 (1H, m).

MS (m/z): 595 (M+H)$^+$.

To a solution of the free form of 19B (23 mg) in ethanol (0.500 mL) was added 2N hydrochloric acid (0.0196 mL) at room temperature, and the mixture was concentrated under reduced pressure. Ethanol (1.00 mL) was added thereto, and the mixture was azeotropically concentrated, and the residue was solidified with diethyl ether to give the other compound (19B) (23 mg) of the title compounds, as a solid.

$^1$H-NMR (DMSO-D$_6$) δ: 1.54-1.77 (3H, m), 2.29-2.36 (1H, m), 2.54-2.67 (2H, m), 3.22-3.31 (1H, m), 3.93-3.93 (3H, m), 4.10 (2H, q, J=11.0 Hz), 4.27-4.45 (3H, m), 7.18 (1H, s), 7.65-7.74 (4H, m), 7.89 (2H, d, J=8.0 Hz), 8.09 (1H, s), 8.11-8.19 (1H, m), 8.35 (1H, br s), 8.40 (1H, s), 8.54-8.58 (1H, m), 9.34 (2H, br s).

MS (m/z): 595 (M+H)$^+$.

separation condition (analysis) CHIRALPAK (registered trademark, Daicel Corporation) IA, size 0.46 cm×15 cm, flow rate 1.0 mL/min, mobile phase 2-propanol 100%, temperature 40° C. the free form of 19A retention time 5.4 min, the free form of 19B retention time 7.7 min separation condition (preparative) CHIRALPAK (registered trademark, Daicel Corporation) IA, size 2 cm×25 cm, flow rate 10 mL/min, mobile phase n-hexane/2-propanol=20/80, temperature ca. 20° C.

the free form of 19A retention time 19.9 min, the free form of 19B retention time 32.9 min

Example 20

(1S,2R,3R,5S)-3-({[4-(5-methoxypyridin-3-yl)phenyl]methyl}amino)-5-{methyl[6-(2,2,2-trifluoroethyl)thieno[2,3-d]pyrimidin-4-yl]amino}cyclopentane-1,2-diol Hydrochloride (20A)

(1R,2S,3R,5S)-3-({[4-(5-methoxypyridin-3-yl)phenyl]methyl}amino)-5-{methyl[6-(2,2,2-trifluoroethyl)thieno[2,3-d]pyrimidin-4-yl]amino}cyclopentane-1,2-diol Hydrochloride (20B)

Step 1 (1S,2R,3R,5S)-3-({[4-(5-methoxypyridin-3-yl)phenyl]methyl}amino)-5-{methyl[6-(2,2,2-trifluoroethyl)thieno[2,3-d]pyrimidin-4-yl]amino}cyclopentane-1,2-diol

[Formula 407]

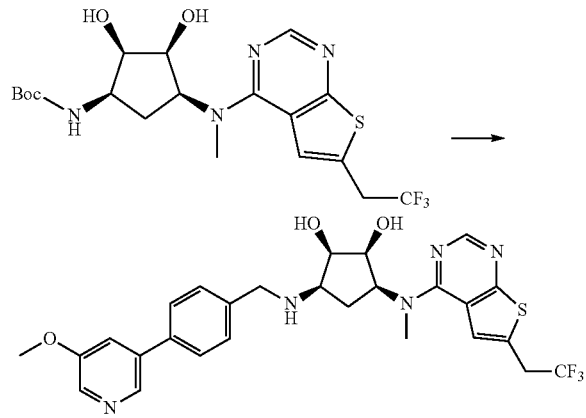

A mixture of the isomer A (193 mg) obtained in Step 7 of Reference Example C-33, dichloromethane (5 mL) and TFA (5 mL) was stirred at room temperature for 2 hr. The reaction solution was concentrated under reduced pressure to give an oil (283 mg). This was directly used in the next step. A mixture of the above oil (283 mg), the compound (75.6 mg) obtained in Reference Example D-65, DIPEA (0.218 mL), dichloromethane (4.2 mL), sodium triacetoxyborohydride (265 mg) and acetic acid (0.143 mL) was stirred at room temperature for 2.5 hr. The compound (25.0 mg) obtained in Reference Example D-65 was added again thereto, and the mixture was stirred for additional 1.5 hr. Saturated aqueous sodium hydrogencarbonate solution was added to the reaction solution, and the mixture was extracted with ethyl acetate. The organic layer was washed with saturated brine, dried over anhydrous sodium sulfate, and concentrated under reduced pressure. The residue was purified by silica gel column chromatography (ethyl acetate/methanol), followed by preparative TLC (ethyl acetate/methanol) to give the title compound (30.3 mg) as a solid.

$^1$H-NMR (DMSO-D$_6$) δ: 1.94-2.07 (2H, m), 2.93-2.95 (1H, m), 3.37 (3H, s), 3.82-3.87 (2H, m), 3.90 (3H, s), 3.95-3.97 (1H, m), 4.07-4.12 (3H, m), 4.67-4.70 (1H, m), 4.97-4.99 (1H, m), 5.18-5.21 (1H, m), 7.50 (2H, d, J=8.0 Hz), 7.61-7.62 (1H, m), 7.72 (3H, d, J=8.0 Hz), 8.28 (1H, s), 8.31 (1H, s), 8.49 (1H, s).

MS (m/z): 560 (M+H)$^+$.

Step 2 (1S,2R,3R,5S)-3-({[4-(5-methoxypyridin-3-yl)phenyl]methyl}amino)-5-{methyl[6-(2,2,2-trifluoroethyl)thieno[2,3-d]pyrimidin-4-yl]amino}cyclopentane-1,2-diol Hydrochloride (20A)

[Formula 408]

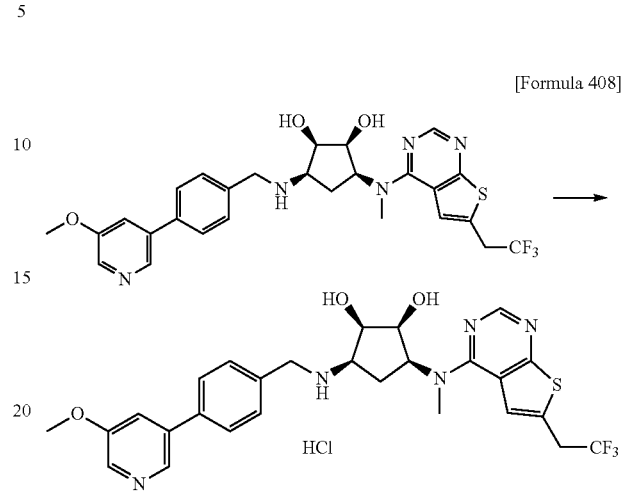

A mixture of the compound (28.3 mg) obtained in the above Step 1, hydrogen chloride (1 mol/L, ethanol solution, 0.0506 mL) and ethanol (1 mL) was stirred at room temperature. The mixture was concentrated under reduced pressure. Ethanol/diethyl ether was added to the residue, and the resulting solid was collected by filtration, and dried to give the title compound (25.0 mg) as a solid.

$^1$H-NMR (DMSO-D$_6$) δ: 2.22-2.33 (2H, m), 3.45 (3H, s), 3.94 (3H, s), 4.08 (2H, q, J=11.0 Hz), 4.18-4.21 (1H, m), 4.24-4.27 (3H, m), 5.23-5.40 (2H, m), 5.92-5.95 (1H, m), 7.69 (2H, d, J=8.0 Hz), 7.74-7.75 (2H, m), 7.88 (2H, d, J=8.0 Hz), 8.34-8.37 (2H, m), 8.57 (1H, s), 8.97 (1H, s), 9.16 (1H, s).

MS (m/z): 560 (M+H)$^+$.

Step 3 (1R,2S,3R,5S)-3-({[4-(5-methoxypyridin-3-yl)phenyl]methyl}amino)-5-{methyl[6-(2,2,2-trifluoroethyl)thieno[2,3-d]pyrimidin-4-yl]amino}cyclopentane-1,2-diol Hydrochloride (20B)

[Formula 409]

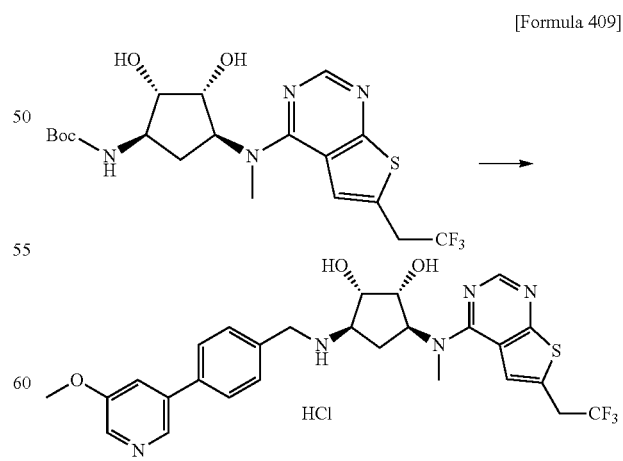

The title compound was obtained in the same manner as in the above Step 1 and Step 2, using the isomer B obtained in Step 7 of Reference Example C-33.

<sup>1</sup>H-NMR (DMSO-D<sub>6</sub>) δ: 1.85-1.91 (1H, m), 2.31-2.38 (1H, m), 3.30 (3H, s), 3.92 (3H, s), 4.07-4.13 (3H, m), 4.31-4.35 (3H, m), 5.09 (1H, s), 5.26 (2H, s), 7.67-7.75 (4H, m), 7.87 (2H, d, J=8.0 Hz), 8.32 (1H, d, J=3.1 Hz), 8.38 (1H, s), 8.54 (1H, d, J=1.8 Hz), 9.53-9.60 (2H, m).

MS (m/z): 560 (M+H)+.

Example 21

(1R,2S,4R)-2-{[2-amino-6-(2,2,2-trifluoroethyl)thieno[2,3-d]pyrimidin-4-yl](methyl)amino}-4-({[4-(1H-imidazol-1-yl)phenyl]methyl}amino)cyclopentan-1-ol Hydrochloride Step 1 (1R,2S,4R)-4-({[4-(1H-imidazol-1-yl)phenyl]methyl}amino)-2-{[2-{[(4-methoxyphenyl)methyl]amino}-6-(2,2,2-trifluoroethyl)thieno[2,3-d]pyrimidin-4-yl](methyl)amino}cyclopentan-1-ol

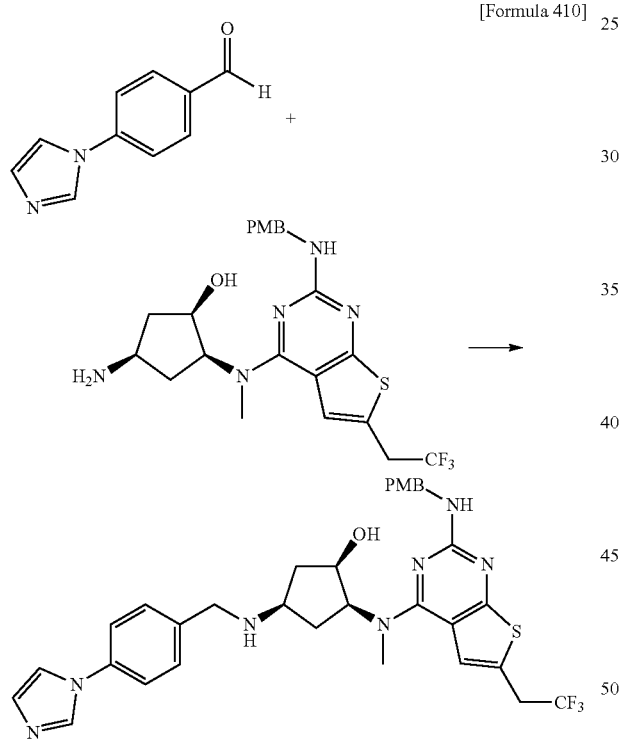

[Formula 410]

The title compound was obtained in the same manner as in Step 1 of Example 2, using the compound obtained in Step 2 of Reference Example C-23 and 4-(H-imidazol-1-yl)benzaldehyde (CAS: 10040-98-9).

<sup>1</sup>H-NMR (CDCl<sub>3</sub>) δ: 1.75 (1H, dt, J=14.1, 2.5 Hz), 1.88-2.04 (2H, m), 2.23 (1H, ddd, J=14.1, 8.6, 6.7 Hz), 3.28-3.34 (1H, m), 3.44 (3H, s), 3.52 (2H, q, J=10.2 Hz), 3.78 (3H, s), 3.86 (2H, d, J=1.8 Hz), 4.34 (1H, br s), 4.52 (2H, d, J=4.9 Hz), 4.79 (1H, td, J=9.7, 4.7 Hz), 5.09 (1H, br s), 6.84 (2H, d, J 30=8.6 Hz), 7.20 (2H, d, J=8.6 Hz), 7.24 (2H, d, J=8.6 Hz), 7.27-7.28 (1H, m), 7.36 (2H, d, J=8.6 Hz), 7.43 (2H, d, J=8.6 Hz), 7.84 (1H, s).

MS (m/z): 638 (M+H)<sup>+</sup>.

Step 2 (1R,2S,4R)-2-{[2-amino-6-(2,2,2-trifluoroethyl)thieno[2,3-d]pyrimidin-4-yl](methyl)amino}-4-({[4-(1H-imidazol-1-yl)phenyl]methyl}amino)cyclopentan-1-ol

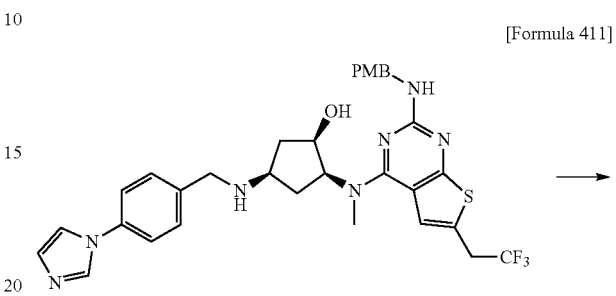

[Formula 411]

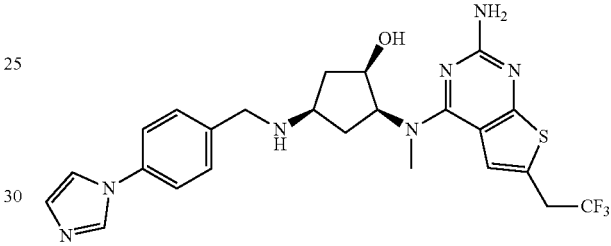

To a solution of the compound (137 mg) obtained in the above Step 1 in dichloromethane (0.55 mL) was added trifluoroacetic acid (CAS: 76-05-1) (1.64 mL) at room temperature. The mixture was stirred 60° C. for 1.5 hr, and the reaction solution was concentrated under reduced pressure. The obtained residue was subjected to silica gel column chromatography (ethyl acetate/methanol) to give the title compound (60.1 mg) as a solid.

<sup>1</sup>H-NMR (CD<sub>3</sub>OD) δ: 1.59 (1H, ddd, J=14.1, 6.7, 3.1 Hz), 2.10 (1H, td, J=12.3, 8.6 Hz), 2.18-2.25 (1H, m), 2.37-2.45 (1H, m), 3.09-3.21 (1H, m), 3.45 (3H, s), 3.71 (2H, q, J=10.6 Hz), 3.88 (2H, d, J=3.1 Hz), 4.47-4.51 (1H, m), 4.81-4.88 (1H, m), 7.15 (1H, s), 7.40 (1H, s), 7.55 (4H, s), 7.57-7.58 (1H, m), 8.14 (1H, s).

Step 3 (1R,2S,4R)-2-{[2-amino-6-(2,2,2-trifluoroethyl)thieno[2,3-d]pyrimidin-4-yl](methyl)amino}-4-({[4-(1H-imidazol-1-yl)phenyl]methyl}amino)cyclopentan-1-ol Hydrochloride

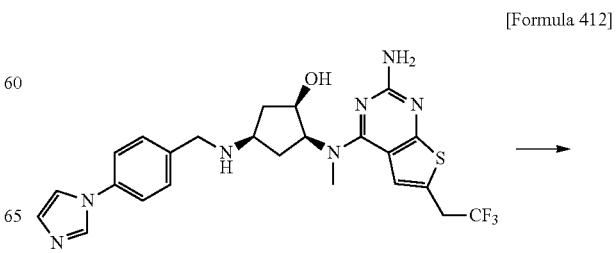

[Formula 412]

-continued

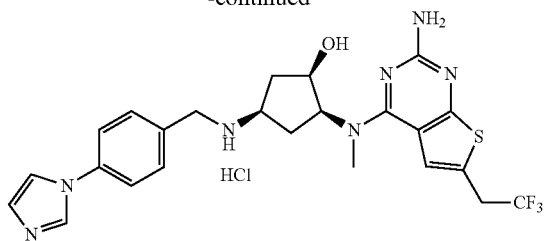

The compound (0.601 g) obtained in the above Step 2 was dissolved in ethanol (1.5 mL), and 1N hydrochloric acid (0.116 mL) was added thereto. The solvent was evaporated under reduced pressure, and the residue was dried. The obtained residue was suspended in diethyl ether (3 mL), and the resulting solid was collected by filtration, and dried to give the title compound (0.0605 g) as a solid.

$^1$H-NMR (DMSO-D$_6$) δ: 1.78-1.85 (1H, m), 2.21-2.29 (1H, m), 2.36-2.46 (2H, m), 3.33 (3H, s), 3.51 (1H, br s), 3.89 (2H, q, J=11.0 Hz), 4.24 (2H, br s), 4.35 (1H, br s), 4.74-4.81 (1H, m), 5.17 (1H, d, J=4.3 Hz), 6.16 (2H, s), 7.15 (1H, s), 7.43 (1H, s), 7.73 (2H, d, J=8.8 Hz), 7.77 (2H, d, J=8.8 Hz), 7.83 (1H, t, J=1.5 Hz), 8.37 (1H, s), 9.36-9.48 (2H, m).

MS (m/z): 518 (M+H)$^+$.

Example 22

5-[4-({[(1R,3R,4S)-3-hydroxy-4-{methyl[6-(2,2,2-trifluoroethyl)thieno[2,3-d]pyrimidin-4-yl]amino}cyclopentyl]amino}methyl)phenyl]-3-methoxypyridine-2-carbonitrile Hydrochloride Step 1 5-[4-({[(1R,3R,4S)-3-hydroxy-4-{methyl[6-(2,2,2-trifluoroethyl)thieno[2,3-d]pyrimidin-4-yl]amino}cyclopentyl]amino}methyl)phenyl]-3-methoxypyridine-2-carbonitrile

[Formula 413]

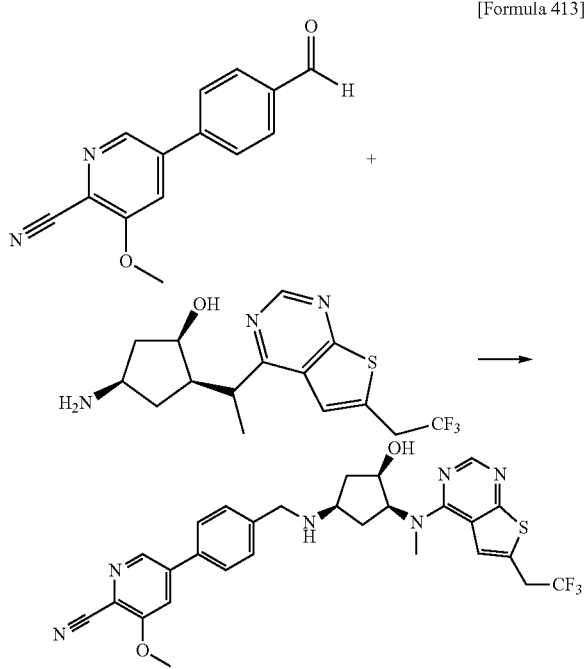

A mixture of the compound (0.0756 g) obtained in Step 2 of Reference Example D-25, the compound (0.110 g) obtained in Step 2 of Reference Example C-14, sodium triacetoxyborohydride (0.208 g), acetic acid (0.092 mL) and dichloromethane (5 mL) was stirred at room temperature for 15 hr. The reaction solution was diluted with dichloromethane, washed successively with saturated aqueous sodium bicarbonate solution and saturated brine, dried over anhydrous magnesium sulfate, and concentrated under reduced pressure. The obtained residue was subjected to silica gel column chromatography (ethyl acetate/methanol) to give the title compound (0.0707 g) as a solid.

$^1$H-NMR (CDCl$_3$) δ: 1.84-1.90 (1H, m), 1.95-2.03 (1H, m), 2.06-2.13 (1H, m), 2.32-2.40 (1H, m), 3.41-3.46 (1H, m), 3.55 (3H, s), 3.63 (2H, q, J=10.2 Hz), 3.89-3.96 (2H, m), 4.05 (3H, s), 4.49-4.53 (1H, m), 5.07 (1H, td, J=9.7, 4.5 Hz), 7.40 (1H, s), 7.46 (1H, d, J=1.8 Hz), 7.49 (2H, d, J=8.0 Hz), 7.59 (2H, d, J=8.0 Hz), 8.40 (1H, s), 8.50 (1H, d, J=1.8 Hz).

Step 2 5-[4-({[(1R,3R,4S)-3-hydroxy-4-{methyl[6-(2,2,2-trifluoroethyl)thieno[2,3-d]pyrimidin-4-yl]amino}cyclopentyl]amino}methyl)phenyl]-3-methoxypyridine-2-carbonitrile Hydrochloride

[Formula 414]

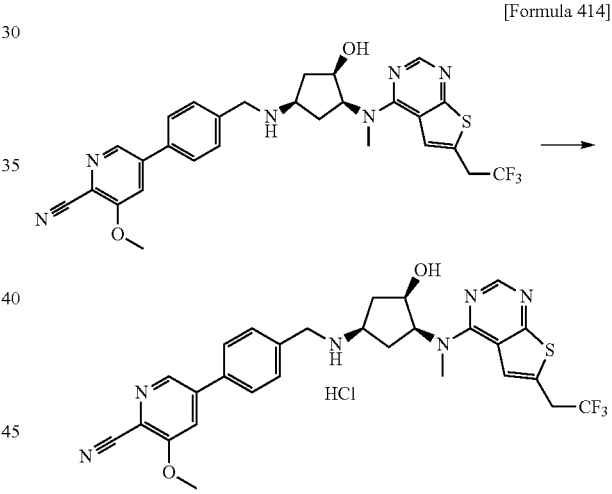

A mixture of the compound (0.0707 g) obtained in the above Step 1, 1N hydrochloric acid (0.120 mL) and ethanol (5.00 mL) was stirred at room temperature for 10 min, and concentrated under reduced pressure. The obtained residue was suspended in acetonitrile (10 mL), and the resulting solid was collected by filtration, and dried to give the title compound (0.0683 g) as a solid.

$^1$H-NMR (DMSO-D$_6$, 80° C.) δ: 1.82-1.90 (1H, m), 2.26-2.34 (1H, m), 2.40-2.51 (2H, m), 3.45 (3H, s), 3.58-3.65 (1H, m), 4.03 (2H, q, J=11.0 Hz), 4.09 (3H, s), 4.24-4.31 (2H, m), 4.36-4.40 (1H, m), 4.91-4.98 (1H, m), 5.01-5.09 (1H, m), 7.68 (1H, s), 7.74 (2H, d, J=8.0 Hz), 7.95 (2H, d, J=8.0 Hz), 7.98 (1H, s), 8.34 (1H, s), 8.65-8.66 (1H, m), 9.22-9.38 (1H, m).

MS (m/z): 569 (M+H)$^+$.

$[α]_D^{20}$ −22.9 (c 1.00, DMSO)

Example 23

(1R,2S,4R)-4-[({4-[1-(methanesulfonyl)-1H-indazol-4-yl]phenyl}methyl)amino]-2-{methyl[6-(2,2,2-trifluoroethyl)thieno[2,3-d]pyrimidin-4-yl]amino}cyclopentan-1-ol Hydrochloride Step 1 (1R,2S,4R)-4-[({4-[1-(methanesulfonyl)-1H-indazol-4-yl]phenyl}methyl)amino]-2-{methyl[6-(2,2,2-trifluoroethyl)thieno[2,3-d]pyrimidin-4-yl]amino}cyclopentan-1-ol

[Formula 415]

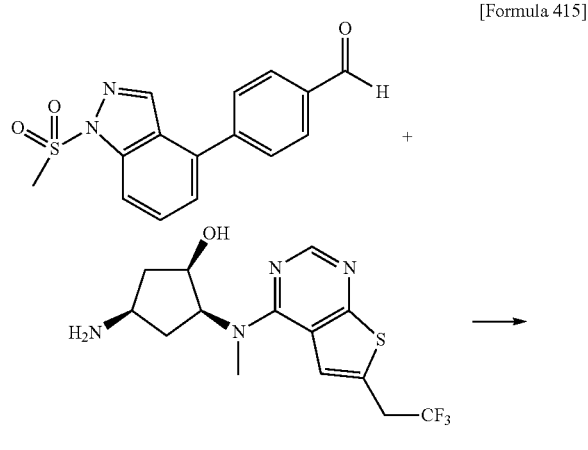

A mixture of the compound (0.0817 g) obtained in Step 2 of Reference Example C-14, the compound (0.0708 g) obtained in Reference Example D-40, dichloromethane (2.5 mL), DIPEA (0.0411 mL), acetic acid (0.0810 mL) and sodium triacetoxyborohydride (0.150 g) was stirred at room temperature for 2 hr. Saturated aqueous sodium hydrogencarbonate solution was added to the reaction mixture, and the mixture was extracted with chloroform. The organic layer was washed with saturated brine, dried over anhydrous sodium sulfate, filtered, and concentrated under reduced pressure. The obtained residue was subjected to silica gel column chromatography (ethyl acetate/methanol) using amino silica gel column as a charge column to give the title compound (0.105 g) as a solid.

$^1$H-NMR (CDCl$_3$) δ: 1.90 (1H, d, J=13.5 Hz), 1.95-2.04 (1H, m), 2.10 (1H, ddd, J=13.5, 6.1, 4.3 Hz), 2.38 (1H, ddd, J=12.9, 9.8, 6.7 Hz), 3.29 (3H, s), 3.46-3.54 (1H, m), 3.56 (3H, s), 3.64 (2H, q, J=10.0 Hz), 3.90-3.98 (2H, m), 4.49-4.53 (1H, m), 5.12 (1H, td, J=9.8, 4.3 Hz), 7.41 (1H, s), 7.43 (1H, d, J=7.4 Hz), 7.50 (2H, d, J=8.0 Hz), 7.61 (2H, d, J=8.0 Hz), 7.64 (1H, dd, J=8.6, 7.4 Hz), 8.09 (1H, d, J=8.6 Hz), 8.40 (1H, s), 8.40 (1H, s).

Step 2 (1R,2S,4R)-4-[({4-[1-(methanesulfonyl)-1H-indazol-4-yl]phenyl}methyl)amino]-2-{methyl[6-(2,2,2-trifluoroethyl)thieno[2,3-d]pyrimidin-4-yl]amino}cyclopentan-1-ol Hydrochloride

[Formula 416]

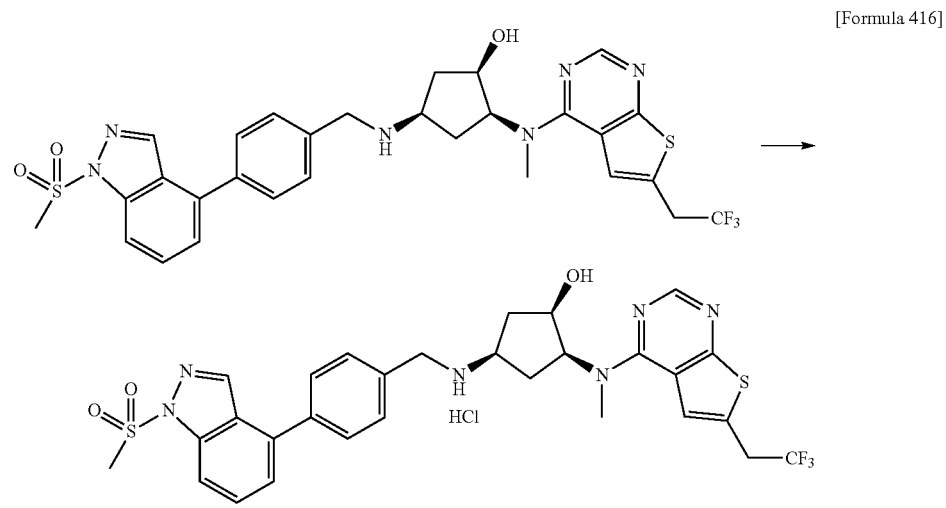

-continued

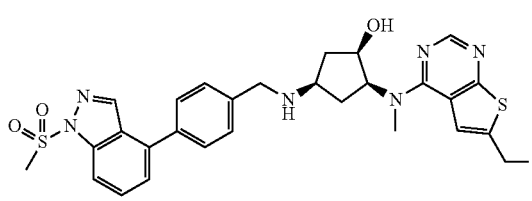

The compound (0.105 g) obtained in the above Step 1 was dissolved in ethanol (1.5 mL), and 1N hydrochloric acid (0.166 mL) was added thereto. The solvent was evaporated under reduced pressure, and the residue was dried. The obtained residue was suspended in diethyl ether (3 mL), and the resulting solid was collected by filtration, and dried to give the title compound (0.0966 g) as a solid.

$^1$H-NMR (DMSO-D$_6$) δ: 1.81-1.89 (1H, m), 2.28-2.47 (3H, m), 3.45 (3H, s), 3.53 (3H, s), 3.63 (1H, br s), 4.10 (2H, q, J=10.4 Hz), 4.27-4.33 (2H, m), 4.35-4.38 (1H, br m), 4.92-5.02 (1H, m), 5.20 (1H, br s), 7.58 (1H, d, J=6.7 Hz), 7.73-7.86 (6H, m), 8.03 (1H, d, J=8.6 Hz), 8.37 (1H, s), 8.64 (1H, s), 9.45-9.57 (2H, m).

MS (m/z): 631 (M+H)+.

$[\alpha]_D^{20}$ −20.4 (c 1.00, MeOH)

Example 24

$N^4$-[(1S,2S,4R)-4-({[4-(5,6-dimethoxypyridin-3-yl)phenyl]methyl}amino)-2-methoxycyclopentyl]-$N^2$,$N^4$-dimethyl-6-(2,2,2-trifluoroethyl)thieno[2,3-d]pyrimidine-2,4-diamine Hydrochloride Step 1 (1R,3S,4S)—$N^3$-[2-chloro-6-(2,2,2-trifluoroethyl)thieno[2,3-d]pyrimidin-4-yl]-$N^1$-{[4-(5,6-dimethoxypyridin-3-yl)phenyl]methyl}-4-methoxy-$N^3$-methylcyclopentane-1,3-diamine

[Formula 417]

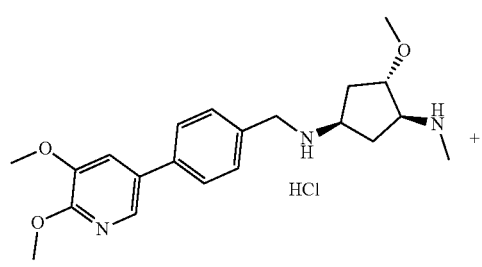

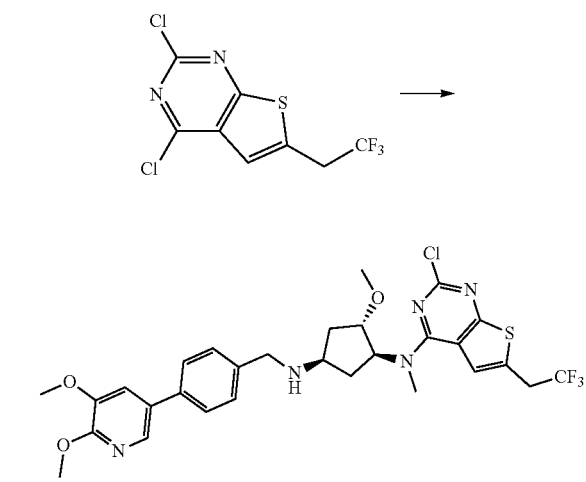

A mixture of the compound (0.440 g) obtained in Step 2 of Reference Example E-2, the compound (0.318 g) obtained in Step 2 of Reference Example B-4, 2-propanol (22 mL) and DIPEA (CAS: 7087-68-5) (3.2 mL) was stirred at 100° C. for 3 hr. Saturated brine/water (3:1) was added to the reaction solution, and the mixture was extracted with ethyl acetate. The organic layer was dried over anhydrous sodium sulfate, and concentrated under reduced pressure. The residue was purified by silica gel column chromatography (ethyl acetate/methanol) to give the title compound (0.508 g) as a solid.

1H-NMR (CDCl3) δ: 1.56-1.65 (1H, m), 1.90-2.05 (2H, m), 2.34-2.45 (1H, m), 3.32 (3H, s), 3.35-3.44 (1H, m), 3.36 (3H, s), 3.61 (2H, q, J=10.2 Hz), 3.83 (2H, s), 3.95 (3H, s), 4.07 (3H, s), 4.11-4.19 (1H, m), 5.01-5.13 (1H, m), 7.25 (1H, d, J=1.8 Hz), 7.38-7.44 (2H, m), 7.47 (1H, s), 7.49-7.55 (2H, m), 7.95 (1H, d, J=1.8 Hz).

MS (m/z): 622, 624 (M+H)+.

Step 2 $N^4$-[(1S,2S,4R)-4-({[4-(5,6-dimethoxypyridin-3-yl)phenyl]methyl}amino)-2-methoxycyclopentyl]-$N^2$,$N^4$-dimethyl-6-(2,2,2-trifluoroethyl)thieno[2,3-d]pyrimidine-2,4-diamine

[Formula 418]

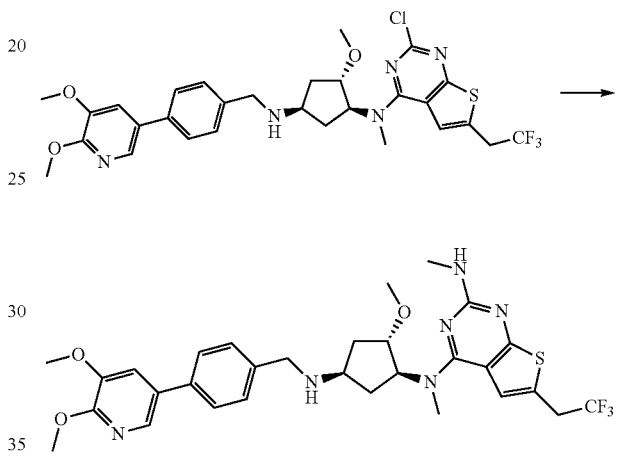

The compound (0.253 g) obtained in the above Step 1 was dissolved in butyronitrile (2.5 mL), and methylamine hydrochloride (CAS: 593-51-1) (0.109 g) and DIPEA (CAS: 7087-68-5) (0.42 mL) were added thereto, and the mixture was subjected to microwave irradiation at 150° C. for 1 hr. Then, additional methylamine hydrochloride (CAS: 593-51-1) (0.106 g) and DIPEA (CAS: 7087-68-5) (0.40 mL) were added thereto, and the mixture was subjected to microwave irradiation at 160° C. for 3 hr. Water was added to the reaction solution, and the mixture was extracted with ethyl acetate. The organic layer was washed with saturated brine, dried over anhydrous sodium sulfate, and concentrated under reduced pressure, and the residue was subjected to silica gel column chromatography (dichloromethane/methanol), reverse-phase HPLC (GILSON, water (0.10% formic acid)/acetonitrile (0.10% formic acid)) and amino silica gel column chromatography (ethyl acetate/methanol). The obtained oil was dissolved in diethyl ether, and the solution was washed with water and saturated brine, dried over anhydrous sodium sulfate, and concentrated under reduced pressure to give the title compound (0.0773 g) as a solid.

1H-NMR (CDCl3) δ: 1.53-1.58 (1H, m), 1.83-1.93 (1H, m), 1.97-2.06 (1H, m), 2.30-2.39 (1H, m), 2.99 (3H, d, J=4.9 Hz), 3.26 (3H, s), 3.30-3.40 (1H, m), 3.31 (3H, s), 3.52 (2H, q, J=10.2 Hz), 3.81 (1H, d, J=13.2 Hz), 3.85 (1H, d, J=13.2 Hz), 3.95 (3H, s), 4.06-4.14 (1H, m), 4.07 (3H, s), 4.75 (1H, q, J=4.9 Hz), 5.11-5.21 (1H, m), 7.24 (1H, d, J=2.5 Hz), 7.26 (1H, s), 7.40 (2H, d, J=8.6 Hz), 7.51 (2H, d, J=8.6 Hz), 7.95 (1H, d, J=2.5 Hz).

MS (m/z): 617 (M+H)+.

Step 3 N⁴-[(1S,2S,4R)-4-({[4-(5,6-dimethoxypyridin-3-yl)phenyl]methyl}amino)-2-methoxycyclopentyl]-N²,N⁴-dimethyl-6-(2,2,2-trifluoroethyl)thieno[2,3-d]pyrimidine-2,4-diamine Hydrochloride

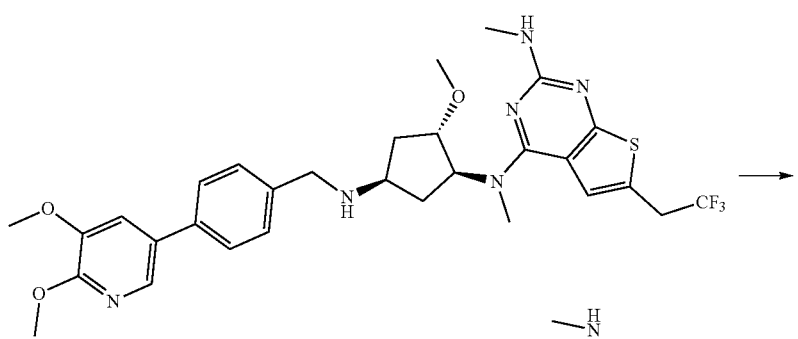

[Formula 419]

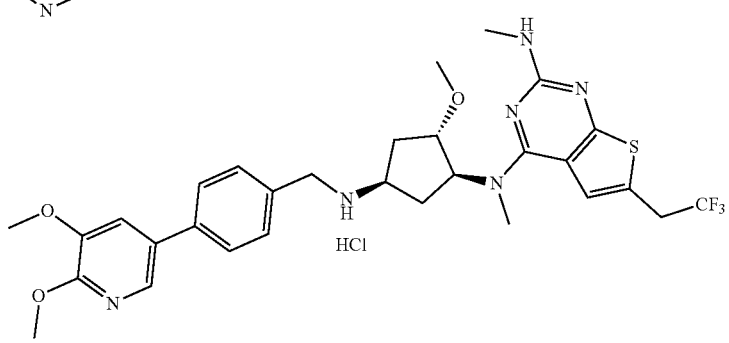

The title compound was obtained in the same manner as in Step 3 of Example 2, using the compound obtained in the above Step 2.

¹H-NMR (DMSO-D₆) δ: 1.99-2.13 (2H, m), 2.26-2.45 (2H, m), 2.78 (3H, d, J=4.9 Hz), 3.22 (6H, s), 3.58-3.71 (1H, m), 3.82-3.96 (2H, m), 3.90 (3H, s), 3.91 (3H, s), 4.12-4.29 (3H, m), 4.93-5.15 (1H, m), 6.71 (1H, q, J=4.9 Hz), 7.46 (1H, s), 7.58 (1H, d, J=1.8 Hz), 7.67 (2H, d, J=8.0 Hz), 7.81 (2H, d, J=8.0 Hz), 8.06 (1H, d, J=1.8 Hz), 9.50 (1H, br s), 9.56 (1H, br s).

MS (m/z): 617 (M+H)⁺.

Example 25

(1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol Hydrochloride Step 1 (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol

[Formula 420]

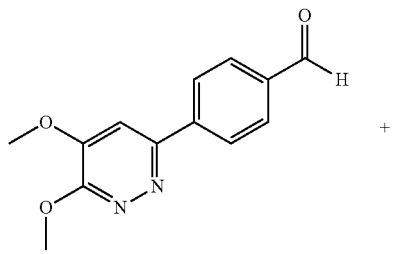

+

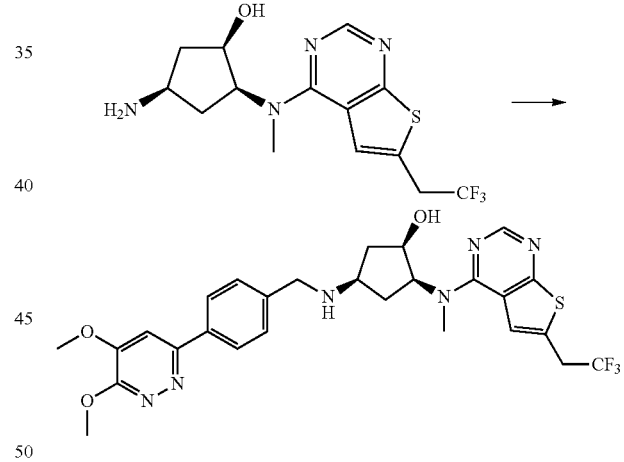

A mixture of the compound (0.102 g) obtained in Step 2 of Reference Example C-14, the compound (0.0844 g) obtained in Reference Example D-26, dichloromethane (3.2 mL), sodium triacetoxyborohydride (CAS: 56553-60-7) (0.215 g) and acetic acid (0.0500 mL) was stirred at room temperature for 17 hr. Water/saturated aqueous sodium bicarbonate solution (2/1) was added to the reaction solution, and the mixture was extracted with dichloromethane/methanol (9/1). The organic layer was dried over anhydrous sodium sulfate, filtered, and concentrated under reduced pressure, and the residue was purified by silica gel column chromatography (dichloromethane/methanol) to give the title compound (0.115 g) as an oil.

¹H-NMR (CDCl₃) δ: 1.80-1.86 (1H, m), 1.94-2.03 (1H, m), 2.10 (1H, dt, J=13.9, 5.7 Hz), 2.28-2.38 (1H, m), 3.38-3.45 (1H, m), 3.53 (3H, s), 3.61 (2H, q, J=10.2 Hz), 3.89 (1H, d, J=13.2 Hz), 3.93 (1H, d, J=13.2 Hz), 4.00 (3H, s), 4.23 (3H, s), 4.46-4.51 (1H, m), 5.04 (1H, td, J=9.7, 4.7 Hz), 7.11 (1H, s), 7.38 (1H, s), 7.44 (2H, d, J=8.0 Hz), 7.96 (2H, d, J=8.0 Hz), 8.40 (1H, s).
MS (m/z): 575 (M+H)⁺.

Step 2 (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol Hydrochloride

[Formula 421]

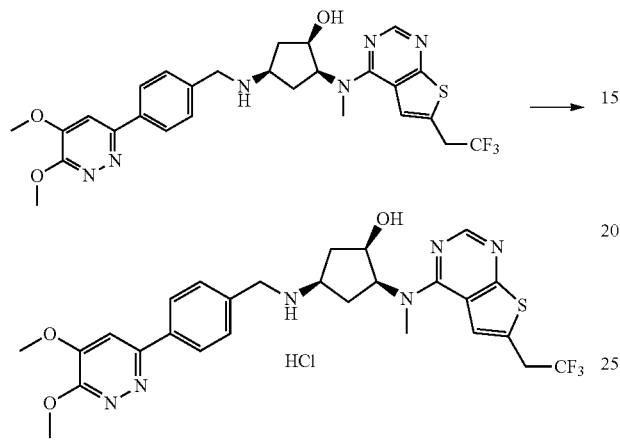

The compound (0.112 g) obtained in the above Step 1 was dissolved in ethanol (3.6 mL), 1N hydrochloric acid (0.173 mL) was added thereto, and the solvent was evaporated under reduced pressure. The obtained solid was suspended in diethyl ether, and the resulting solid was collected by filtration, and dried to give the title compound (0.104 g) as a solid.
¹H-NMR (DMSO-D₆) δ: 1.80-1.89 (1H, m), 2.26-2.36 (1H, m), 2.43-2.54 (2H, m), 3.44 (3H, s), 3.55-3.66 (1H, m), 4.01 (3H, s), 4.03-4.16 (5H, m), 4.22-4.40 (3H, m), 4.90-5.00 (1H, m), 5.20 (1H, d, J=4.3 Hz), 7.67 (1H, s), 7.71-7.79 (3H, m), 8.19 (2H, d, J=8.0 Hz), 8.36 (1H, s), 9.47 (1H, br s), 9.53 (1H, br s).
MS (m/z): 575 (M+H)⁺.
[α]$_D^{20}$ −23.5 (c 1.00, MeOH)

Example 26

(1R,2S,4R)-4-[({4-[6-(dimethylamino)-5-methoxypyridin-3-yl]phenyl}methyl)amino]-2-{methyl[6-(2,2,2-trifluoroethyl)thieno[2,3-d]pyrimidin-4-yl]amino}cyclopentan-1-ol Hydrochloride Step 1 (1R,2S,4R)-4-[({4-[6-(dimethylamino)-5-methoxypyridin-3-yl]phenyl}methyl)amino]-2-{methyl[6-(2,2,2-trifluoroethyl)thieno[2,3-d]pyrimidin-4-yl]amino}cyclopentan-1-ol

[Formula 422]

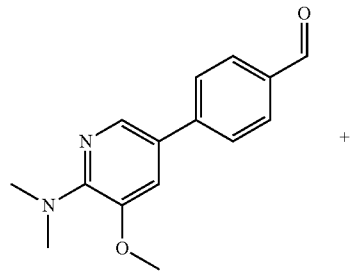

+

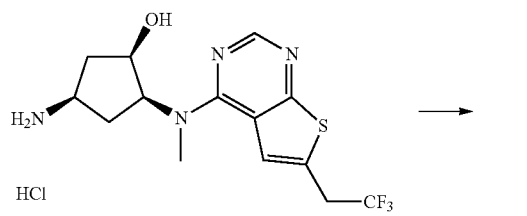

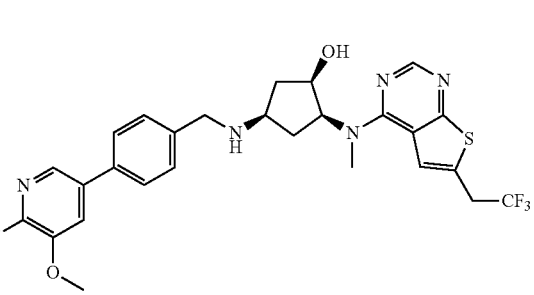

A mixture of the compound (0.112 g) obtained in Step 3 of Reference Example C-14, dichloromethane (3.0 mL), the compound (0.080 g) obtained in Step 2 of Reference Example D-11, DIPEA (0.153 mL), acetic acid (0.084 mL) and sodium triacetoxyborohydride (0.190 g) was stirred at room temperature for 16 hr. Saturated aqueous sodium hydrogencarbonate solution was added to the reaction mixture, and the mixture was extracted with ethyl acetate. The organic layer was washed with saturated brine, dried over anhydrous sodium sulfate, filtered, and concentrated under reduced pressure. The obtained residue was subjected to silica gel column chromatography (ethyl acetate-methanol) using amino silica gel column as a charge column to give the title compound (0.125 g) as a solid.
¹H-NMR (CDCl₃) δ: 1.46-1.82 (2H, m), 1.86-2.09 (3H, m), 2.30-2.40 (1H, m), 3.03 (6H, s), 3.43-3.50 (1H, m), 3.55 (3H, s), 3.59-3.68 (2H, m), 3.83-3.92 (2H, m), 3.93 (3H, s), 4.46-4.51 (1H, m), 5.09-5.18 (1H, m), 7.20 (1H, d, J=1.8 Hz), 7.37-7.42 (3H, m), 7.50-7.55 (2H, m), 8.10 (1H, d, J=1.8 Hz), 8.40 (1H, s).
MS (m/z): 587 (M+H)⁺.

Step 2 (1R,2S,4R)-4-[({4-[6-(dimethylamino)-5-methoxypyridin-3-yl]phenyl}methyl)amino]-2-{methyl[6-(2,2,2-trifluoroethyl)thieno[2,3-d]pyrimidin-4-yl]amino}cyclopentan-1-ol Hydrochloride

[Formula 423]

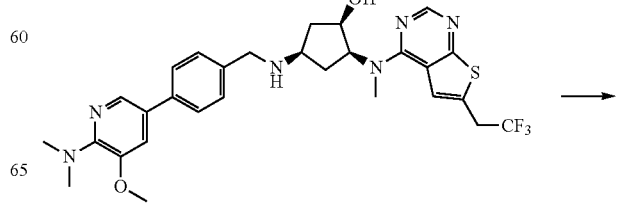

333

-continued

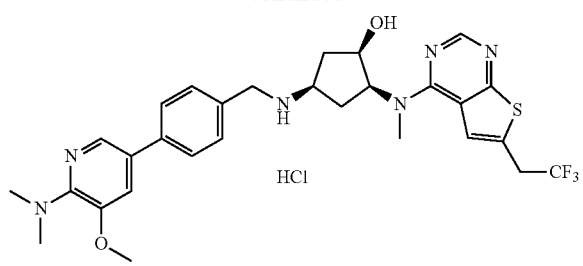

The compound (0.122 g) obtained in the above Step 1 was dissolved in ethanol (2 mL), and 5N aqueous hydrochloric acid solution (0.042 mL) was added thereto. The solvent was evaporated under reduced pressure, and the residue was dried. The obtained residue was suspended in acetonitrile (2 mL), and the resulting solid was collected by filtration, and dried to give the title compound (0.117 g) as a solid.

$^1$H-NMR (DMSO-D$_6$) δ: 1.79-1.88 (1H, m), 2.25-2.35 (1H, m), 2.38-2.55 (2H, m), 2.97 (6H, s), 3.44 (3H, s), 3.53-3.65 (1H, m), 3.91 (3H, s), 4.03-4.16 (2H, m), 4.17-4.30 (2H, m), 4.31-4.39 (1H, m), 4.88-5.01 (1H, m), 5.11-5.30 (1H, m), 7.47-7.51 (1H, m), 7.63-7.69 (2H, m), 7.73-7.81 (3H, m), 8.10-8.14 (1H, m), 8.36 (1H, s), 9.31-9.53 (2H, m).

MS (m/z): 587 (M+H)$^+$.

$[α]_D^{20}$ −24.1 (c 1.00, MeOH)

Example 27

(1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol Hydrochloride Step 1 (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol

[Formula 424]

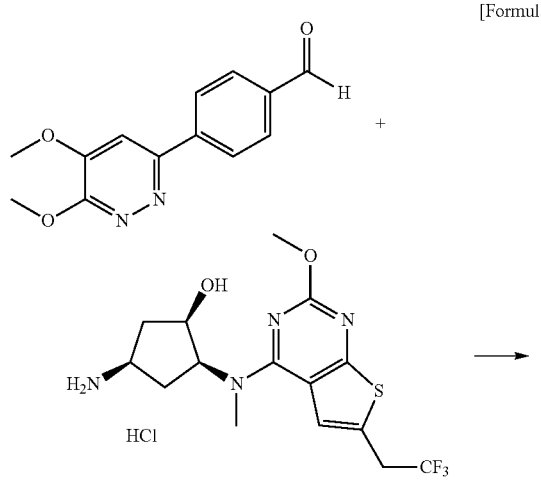

334

-continued

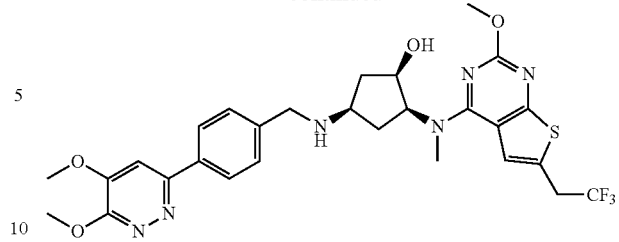

A mixture of the compound (90.0 mg) obtained in Step 2 of Reference Example C-15, the compound (55.9 mg) obtained in Reference Example D-26, DIPEA (0.114 mL), dichloromethane (2.18 mL), sodium triacetoxyborohydride (139 mg) and acetic acid (0.0624 mL) was stirred at room temperature for 1.5 hr. Saturated aqueous sodium hydrogencarbonate solution and dichloromethane were added to the reaction solution, and the mixture was subjected to liquid separation. The organic layer was dried over anhydrous sodium sulfate, and concentrated under reduced pressure. The obtained residue was purified by silica gel column chromatography (ethyl acetate/methanol) to give the title compound (94.0 mg) as a solid.

$^1$H-NMR (DMSO-D$_6$) δ: 1.49-1.51 (1H, m), 2.01-2.18 (3H, m), 3.07-3.10 (1H, m), 3.38 (3H, s), 3.81-3.83 (5H, m), 3.94-3.97 (5H, m), 4.06 (3H, s), 4.29-4.31 (1H, m), 4.72-4.74 (2H, m), 7.46-7.52 (4H, m), 8.00-8.02 (2H, m).

MS (m/z): 605 (M+H)$^+$.

Step 2 (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol Hydrochloride

[Formula 425]

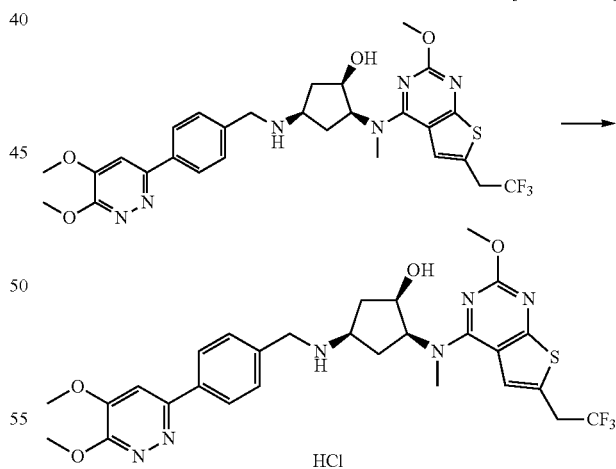

A mixture of the compound (90.0 mg) obtained in the above Step 1, ethanol (1 mL) and 1N hydrochloric acid ethanol solution (0.149 mL) was stirred at room temperature, and concentrated under reduced pressure. Ethanol/diethyl ether was added to the residue, and the resulting solid was collected by filtration, and dried to give the title compound (84.1 mg) as a solid.

$^1$H-NMR (DMSO-D$_6$) δ: 1.85-1.89 (1H, m), 2.29-2.35 (1H, m), 2.42-2.51 (2H, m), 3.42 (3H, s), 3.61-3.66 (1H, m), 3.85 (3H, s), 3.93-4.01 (5H, m), 4.08 (3H, s), 4.26-4.28 (2H, m), 4.36-4.39 (1H, m), 4.82-4.88 (1H, m), 7.59 (1H, s), 7.62 (1H, s), 7.73 (2H, d, J=8.3 Hz), 8.17 (2H, d, J=8.3 Hz), 9.40-9.46 (2H, m).

MS (m/z): 605 (M+H)$^+$.

$[\alpha]_D^{20}$ −35.6 (c 1.00, MeOH)

Each product in the following Table 2-1 to Table 2-54 was produced in the same manner as in Step 1 of Example 27, using Raw Material 1 and Raw Material 2 described in the tables. When the final form is hydrochloride, it was produced in the same manner as in Step 2 of Example 27 using the free product as a raw material. In Table 2-1 to Table 2-54, when the final form is shown by two items, the compound of Example is the salt compound shown in the lower item (for example, the compound of Example 54 in Table 2-14 is (1S,2S,4R)-2-{methyl[2-(methylamino)-6-(2,2,2-trifluoroethyl)thieno[2,3-d]pyrimidin-4-yl]amino}-4-[({4-[(pyridin-3-yl)amino]phenyl}methyl)amino]cyclopentan-1-ol hydrochloride, which is shown in the lower item). In Experimental Example, the above salt compound was used as the compound of Example.

TABLE 2-1

| Ex. | Product | Raw Material 1 | Raw Material 2 |
|---|---|---|---|
| Ex. 28 | (structure)<br>(1R,3S)-N³-(cyclohexylmethyl)-N¹-methyl-N¹-[6-(2,2,2-trifluoroethyl)thieno[2,3-d]pyrimidin-4-yl]cyclopentane-1,3-diamine hydrochloride<br>(structure with HCl)<br>¹H-NMR (DMSO-D₆) δ: 0.92-1.27 (5H, m), 1.60-2.10 (11H, m), 2.24-2.34 (1H, m), 2.74-2.79 (2H, m), 3.27 (3H, s), 3.54-3.61 (1H, m), 4.06 (1H, d, J = 12.0 Hz), 4.12 (1H, d, J = 12.0 Hz), 5.21-5.31 (1H, m), 7.72 (1H, s), 8.38 (1H, s), 8.76 (1H, br s), 8.88 (1H, br s). MS (m/z): 427 (M + H)$^+$. | (structure)<br>CAS: 2043-61-0 | (structure)<br>Reference Example C-4 Step 2 |
| Ex. 29 | (structure)<br>N-[4-({[(1S,3R)-3-{[6-(2,2,2-trifluoroethyl)thieno[2,3-d]pyrimidin-4-yl]amino}cyclohexyl]amino}methyl)phenyl]acetamide hydrochloride<br>(structure with HCl)<br>¹H-NMR (DMSO-D₆) δ: 1.31-1.44 (3H, m), 1.57 (1H, q, J = 11.9 Hz), 1.85-1.95 (2H, m), 2.05 (3H, s), 2.14-2.19 (1H, m), 2.42-2.48 (1H, m), 3.13-3.22 (1H, m), 4.06-4.22 (5H, m), 7.48 (2H, d, J = 8.5 Hz), 7.63 (2H, d, J = 8.5 Hz), 7.75 (1H, s), 8.44 (1H, s), 8.45 (1H, br s), 9.18 (2H, br s), 10.13 (1H, s). MS (m/z): 478 (M + H)$^+$. | (structure)<br>CAS: 122-85-0 | (structure)<br>Reference Example C-1 Step 2 |

TABLE 2-2

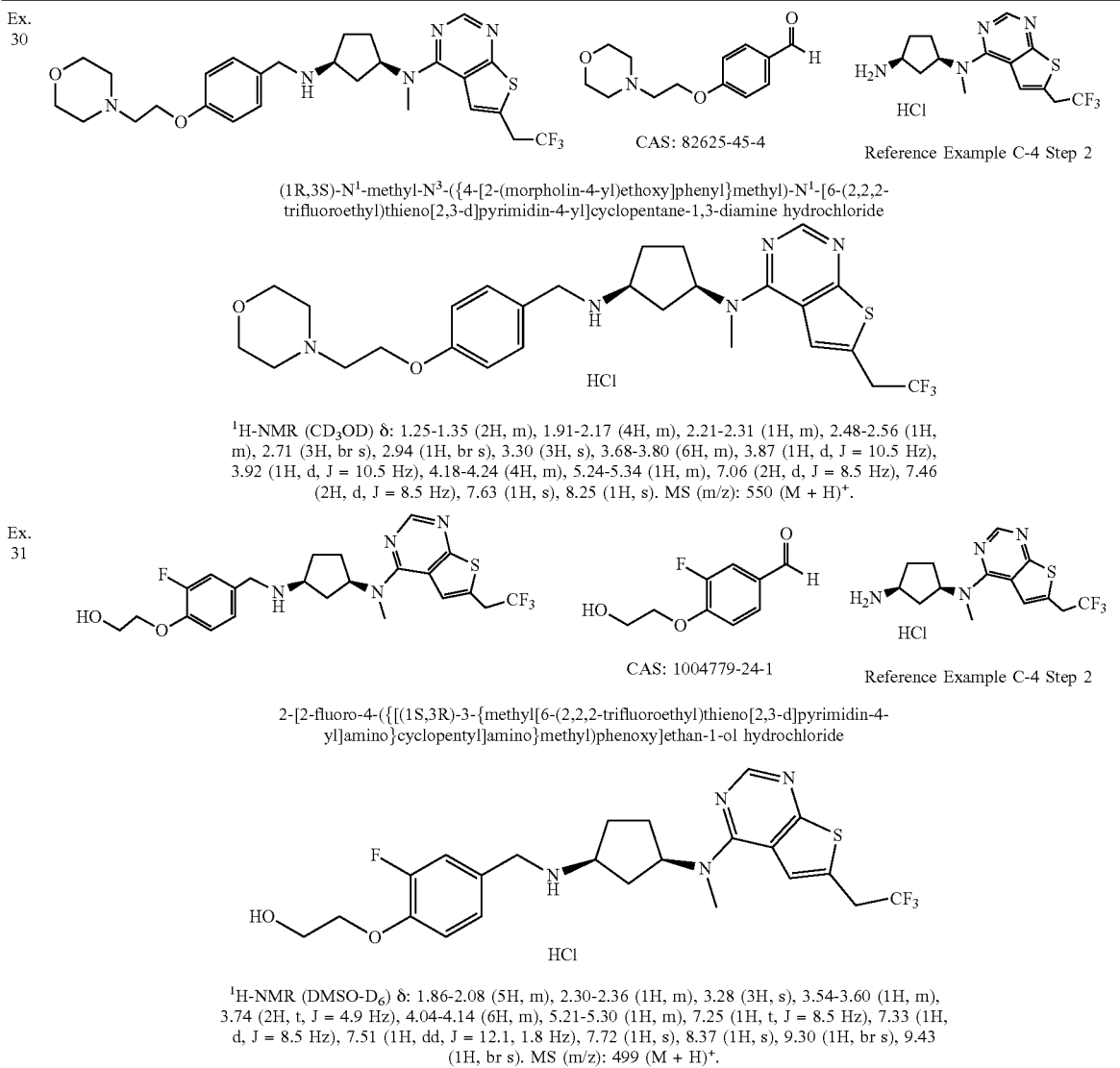

Ex. 30

(1R,3S)-N¹-methyl-N³-({4-[2-(morpholin-4-yl)ethoxy]phenyl}methyl)-N¹-[6-(2,2,2-trifluoroethyl)thieno[2,3-d]pyrimidin-4-yl]cyclopentane-1,3-diamine hydrochloride $^1$H-NMR (CD$_3$OD) δ: 1.25-1.35 (2H, m), 1.91-2.17 (4H, m), 2.21-2.31 (1H, m), 2.48-2.56 (1H, m), 2.71 (3H, br s), 2.94 (1H, br s), 3.30 (3H, s), 3.68-3.80 (6H, m), 3.87 (1H, d, J = 10.5 Hz), 3.92 (1H, d, J = 10.5 Hz), 4.18-4.24 (4H, m), 5.24-5.34 (1H, m), 7.06 (2H, d, J = 8.5 Hz), 7.46 (2H, d, J = 8.5 Hz), 7.63 (1H, s), 8.25 (1H, s). MS (m/z): 550 (M + H)$^+$.

Ex. 31

2-[2-fluoro-4-({[(1S,3R)-3-{methyl[6-(2,2,2-trifluoroethyl)thieno[2,3-d]pyrimidin-4-yl]amino}cyclopentyl]amino}methyl)phenoxy]ethan-1-ol hydrochloride $^1$H-NMR (DMSO-D$_6$) δ: 1.86-2.08 (5H, m), 2.30-2.36 (1H, m), 3.28 (3H, s), 3.54-3.60 (1H, m), 3.74 (2H, t, J = 4.9 Hz), 4.04-4.14 (6H, m), 5.21-5.30 (1H, m), 7.25 (1H, t, J = 8.5 Hz), 7.33 (1H, d, J = 8.5 Hz), 7.51 (1H, dd, J = 12.1, 1.8 Hz), 7.72 (1H, s), 8.37 (1H, s), 9.30 (1H, br s), 9.43 (1H, br s). MS (m/z): 499 (M + H)$^+$.

TABLE 2-3

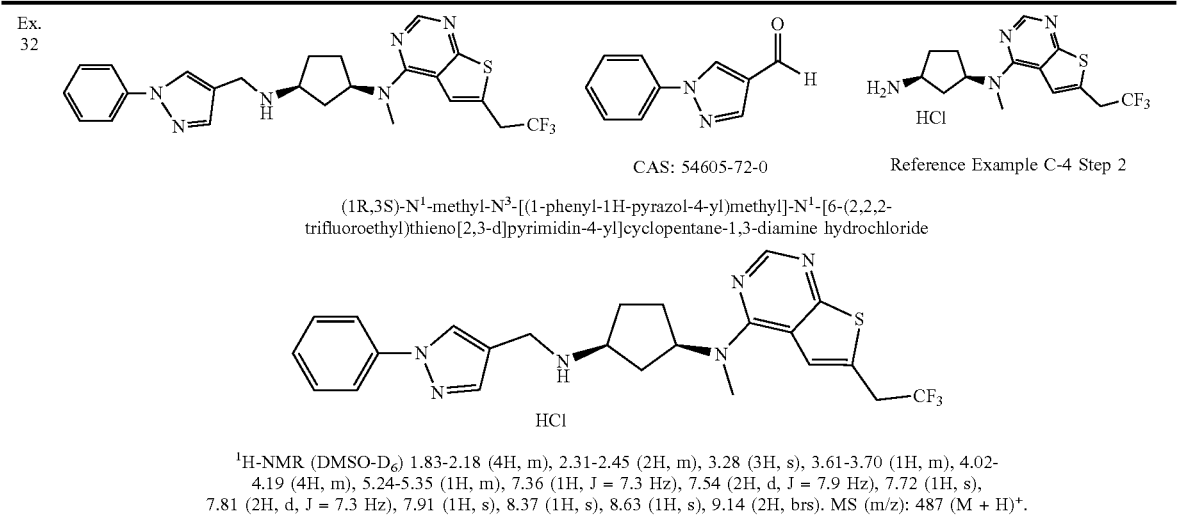

Ex. 32

(1R,3S)-N¹-methyl-N³-[(1-phenyl-1H-pyrazol-4-yl)methyl]-N¹-[6-(2,2,2-trifluoroethyl)thieno[2,3-d]pyrimidin-4-yl]cyclopentane-1,3-diamine hydrochloride $^1$H-NMR (DMSO-D$_6$) 1.83-2.18 (4H, m), 2.31-2.45 (2H, m), 3.28 (3H, s), 3.61-3.70 (1H, m), 4.02-4.19 (4H, m), 5.24-5.35 (1H, m), 7.36 (1H, J = 7.3 Hz), 7.54 (2H, d, J = 7.9 Hz), 7.72 (1H, s), 7.81 (2H, d, J = 7.3 Hz), 7.91 (1H, s), 8.37 (1H, s), 8.63 (1H, s), 9.14 (2H, brs). MS (m/z): 487 (M + H)$^+$.

TABLE 2-3-continued

| Ex. 33 | | | |
|---|---|---|---|
| 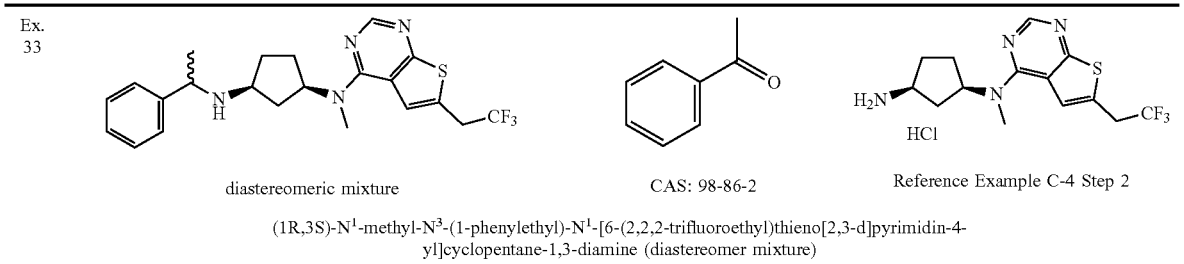 | | 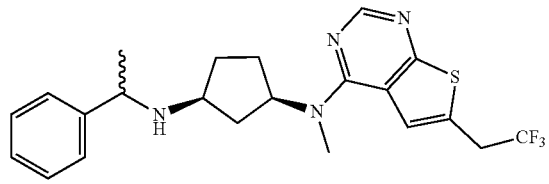 [SMILES: CC(N[C@H]1CC[C@@H](N(C)c2ncnc3sc(CC(F)(F)F)cc23)C1)c1ccccc1] | 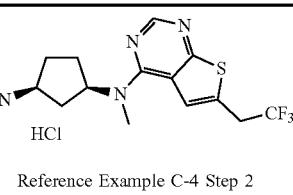 |
| diastereomeric mixture | | CAS: 98-86-2 | Reference Example C-4 Step 2 |

(1R,3S)-N[1]-methyl-N[3]-(1-phenylethyl)-N[1]-[6-(2,2,2-trifluoroethyl)thieno[2,3-d]pyrimidin-4-yl]cyclopentane-1,3-diamine (diastereomer mixture)

diastereomeric mixture $^1$H-NMR (CDCl$_3$) δ: 1.38 (1.5H, d, J = 1.8 Hz), 1.39 (1.5H, d, J = 1.8 Hz), 1.41-1.64 (2.0H, m), 1.77-2.26 (4.0H, m), 2.96-3.06 (1.0H, m), 3.24 (1.5H, s), 3.29 (1.5H, s), 3.61 (2.0H, q, J = 10.3 Hz), 3.80-3.87 (1.0H, m), 5.13-5.23 (1.0H, m), 7.23-7.37 (6.0H, m), 8.37 (0.5H, s), 8.39 (0.5H, s). MS (m/z): 435 (M + H)$^+$.

TABLE 2-4

| Ex. 34 | | | |
|---|---|---|---|
| 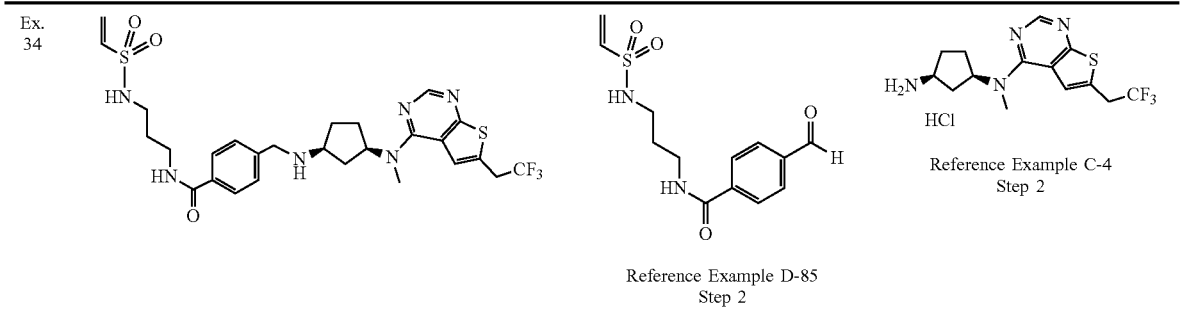 | | Reference Example D-85 Step 2 | Reference Example C-4 Step 2 |

N-{-3-[(ethenesulfonyl)amino]propyl}-4-({[[(1S,3R)-3-{methyl[6-(2,2,2-trifluoroethyl)thieno[2,3-d]pyrimidin-4-yl]amino}cyclopentyl]amino}methyl)benzamide hydrochloride

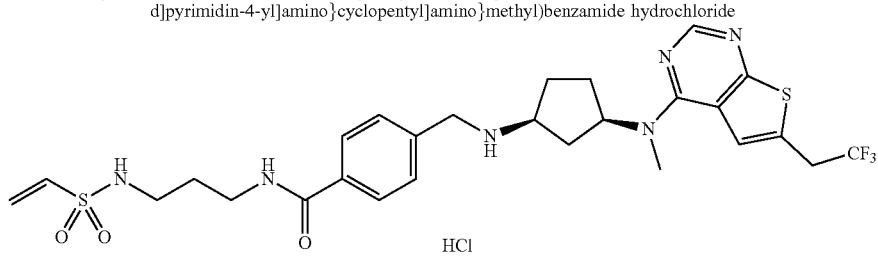

$^1$H-NMR (DMSO-D$_6$) δ: 1.72 (2H, quint, J = 7.1 Hz), 1.84-1.92 (1H, m), 1.99-2.12 (4H, m), 2.31-2.38 (1H, m), 2.86-2.91 (2H, m), 3.27-3.32 (2H, m), 3.29 (3H, s), 3.57-3.65 (1H, m), 4.09 (2H, q, J = 10.9 Hz), 4.19-4.24 (2H, m), 5.22-5.31 (1H, m), 5.97 (1H, d, J = 10.0 Hz), 6.02 (1H, d, J = 16.4 Hz), 6.70 (1H, dd, J = 16.4, 10.0 Hz), 7.33 (1H, t, J = 6.1 Hz), 7.69 (2H, d, J = 8.5 Hz), 7.73 (1H, s), 7.91 (2H, d, J = 8.5 Hz), 8.37 (1H, s), 8.59 (1H, t, J = 5.8 Hz), 9.53 (1H, br s), 9.68 (1H, br s). MS (m/z): 611 (M + H)$^+$.

| Ex. 35 | | | |
|---|---|---|---|
| 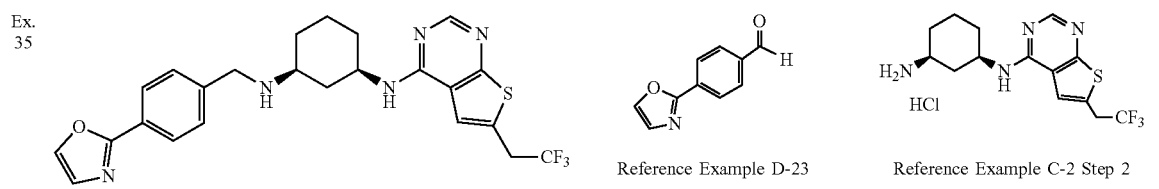 | | Reference Example D-23 | 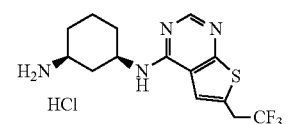 Reference Example C-2 Step 2 |

(1S,3R)-N[1]-{[4-(1,3-oxazol-2-yl)phenyl]methyl}-N[3]-[6-(2,2,2-trifluoroethyl)thieno[2,3-d]pyrimidin-4-yl]cyclohexane-1,3-diamine hydrochloride

TABLE 2-4-continued

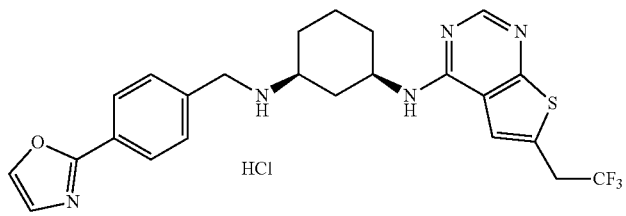 [SMILES: FC(F)(F)Cc1cc2c(N[C@@H]3CCC[C@H](NCc4ccc(-c5ncco5)cc4)C3)ncnc2s1 ; Cl]

$^1$H-NMR (DMSO-D$_6$) δ: 1.34-1.45 (3H, m), 1.61-1.64 (1H, m), 1.89-1.92 (2H, m), 2.18-2.21 (1H, m), 2.45-2.48 (1H, m), 3.22-3.24 (1H, m), 4.05-4.25 (5H, m), 7.42 (1H, s), 7.72 (1H, s), 7.77 (2H, d, J = 8.2 Hz), 8.05 (2H, d, J = 8.2 Hz), 8.21-8.27 (2H, m), 8.38 (1H, s), 9.47-9.53 (2H, m).
MS (m/z): 488 (M + H)$^+$.

TABLE 2-5

Ex. 36

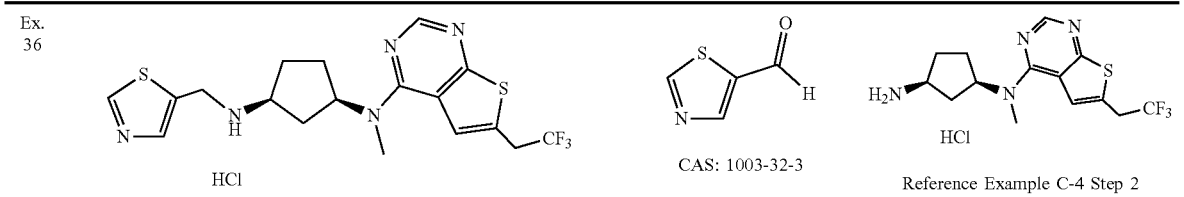

(1R,3S)-N$^1$-methyl-N$^3$-[(1,3-thiazol-5-yl)methyl]-N$^1$-[6-(2,2,2-trifluoroethyl)thieno[2,3-d]pyrimidin-4-yl]cyclopentane-1,3-diamine hydrochloride

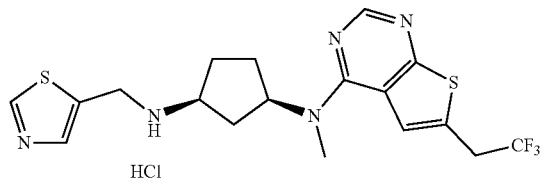 [SMILES: CN(c1ncnc2sc(CC(F)(F)F)cc12)[C@@H]1CC[C@H](NCc2cncs2)C1 ; Cl]

$^1$H-NMR (DMSO-D$_6$) δ: 1.81-2.12 (5H, m), 2.30-2.37 (1H, m), 3.28 (3H, s), 3.59-3.66 (1H, m), 4.09 (2H, q, J = 11.1 Hz), 4.51 (2H, t, J = 5.5 Hz), 5.22-5.31 (1H, m), 7.73 (1H, s), 8.11 (1H, s), 8.38 (1H, s), 9.19 (1H, s), 9.50-9.58 (1H, m), 9.66-9.73 (1H, m).
MS (m/z): 428 (M + H)$^+$.

Ex. 37

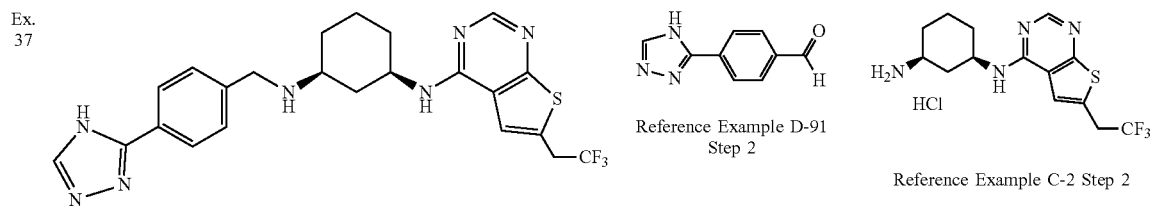

(1S,3R)-N$^1$-{[4-(4H-1,2,4-triazol-3-yl)phenyl]methyl}-N$^3$-[6-(2,2,2-trifluoroethyl)thieno[2,3-d]pyrimidin-4-yl]cyclohexane-1,3-diamine hydrochloride

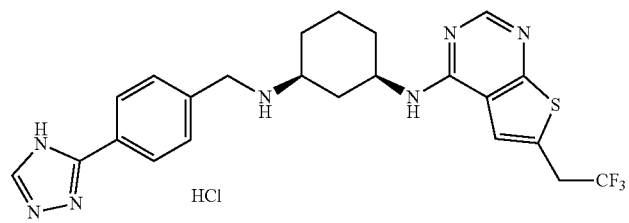 [SMILES: FC(F)(F)Cc1cc2c(N[C@@H]3CCC[C@H](NCc4ccc(-c5nnc[nH]5)cc4)C3)ncnc2s1 ; Cl]

$^1$H-NMR (DMSO-D$_6$) δ: 1.40-1.42 (3H, m), 1.67-1.70 (1H, m), 1.90-1.92 (2H, m), 2.18-2.20 (1H, m), 2.47-2.50 (1H, m), 3.22-3.25 (1H, m), 4.10-4.23 (5H, m), 7.72 (2H, d, J = 8.3 Hz), 7.84 (1H, s), 8.08 (2H, d, J = 8.3 Hz), 8.53-8.55 (2H, m), 8.86 (1H, s), 9.49-9.51 (2H, m).
MS (m/z): 488 (M + H)$^+$.

TABLE 2-6

Ex. 38

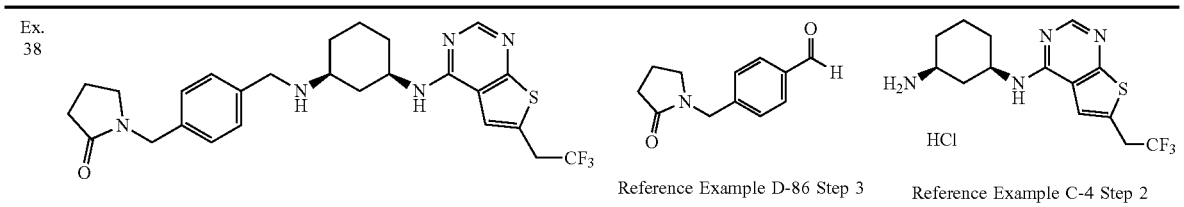

Reference Example D-86 Step 3   Reference Example C-4 Step 2

1-{[4-({[(1S,3R)-3-{[6-(2,2,2-trifluoroethyl)thieno[2,3-d]pyrimidin-4-yl[amino}cyclohexy]amino}methyl)phenyl]methyl}pyrrolidin-2-one hydrochloride

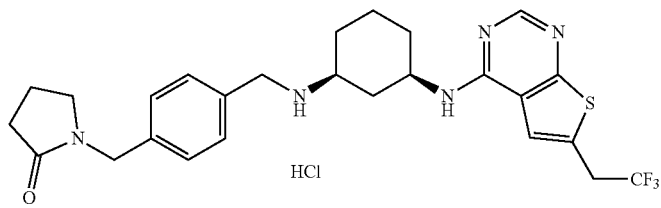 [SMILES: O=C1CCCN1Cc1ccc(CN[C@H]2CCC[C@@H](Nc3ncnc4sc(CC(F)(F)F)cc34)C2)cc1 ; Cl]

¹H-NMR (DMSO-D₆) δ: 1.24-1.58 (4H, m), 1.88-1.96 (4H, m), 2.14-2.19 (1H, m), 2.29 (2H, t, J = 8.3 Hz), 2.41-2.49 (1H, m), 3.16-3.25 (3H, m), 4.08 (2H, q, J = 11.2 Hz), 4.13-4.21 (3H, m), 4.38 (2H, s), 7.28 (2H, d, J = 8.0 Hz), 7.56 (2H, d, J = 8.0 Hz), 7.69 (1H, d, J = 3.7 Hz), 8.10 (1H, br s), 9.23 (2H, br s). MS (m/z): 518 (M + H)⁺.

Ex. 39

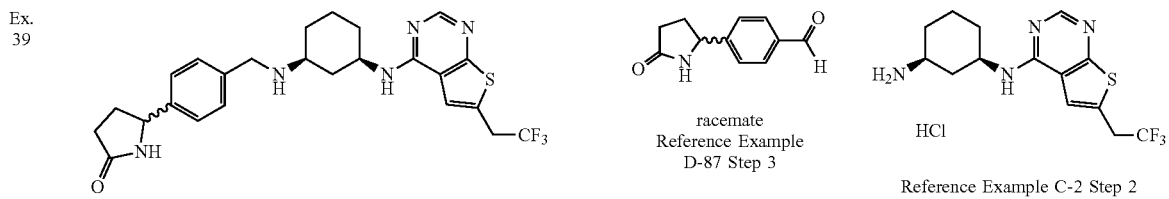

racemate
Reference Example
D-87 Step 3    Reference Example C-2 Step 2 diastereomeric mixture

5-[4-({[(1S,3R)-3-{[6-(2,2,2-trifluoroethyl)thieno[2,3-d]pyrimidin-4-yl[amino}cyclohexyl]amino}methyl)phenyl]pyrrolidin-2-one hydrochloride (diastereomer mixture)

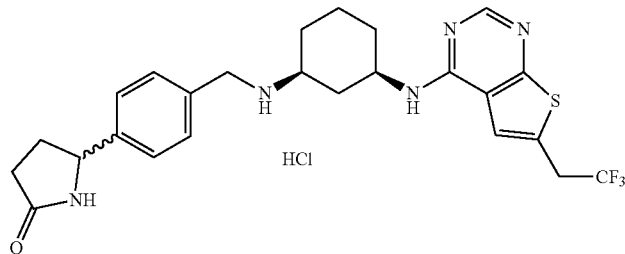 [SMILES: O=C1CCC(c2ccc(CN[C@H]3CCC[C@@H](Nc4ncnc5sc(CC(F)(F)F)cc45)C3)cc2)N1 ; Cl]

diastereomeric mixture

¹H-NMR (DMSO-D₆) δ: 1.25-1.62 (4H, m), 1.66-1.76 (1H, m), 1.85-1.95 (2H, m), 2.14-2.20 (1H, m), 2.23 (2H, t, J = 8.0 Hz), 2.42-2.48 (2H, m), 3.20 (1H, br s), 4.08 (2H, q, J = 11.2 Hz), 4.10-4.26 (3H, m), 4.69 (1H, t, J = 7.1 Hz), 7.36 (2H, d, J = 8.0 Hz), 7.53-7.57 (2H, m), 7.68-7.70 (1H, m), 8.01-8.22 (2H, m), 8.32-8.38 (1H, m), 9.00-9.32 (2H, m). MS (m/z): 504 (M + H)⁺.

TABLE 2-7

Ex. 40

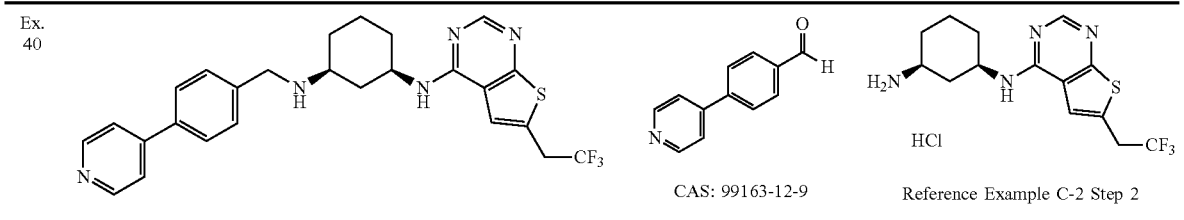

CAS: 99163-12-9    Reference Example C-2 Step 2

(1S,3R)-N¹-{[4-(pyridin-4-yl)phenyl]methyl}-N³-[6-(2,2,2-trifluoroethyl)thieno[2,3-d]pyrimidin-4-yl]cyclohexane-1,3-diamine hydrochloride TABLE 2-7-continued

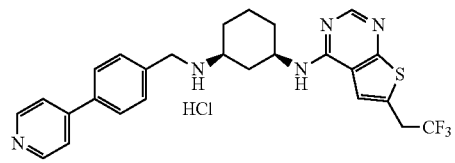 [SMILES: FC(F)(F)Cc1cc2c(N[C@@H]3CCC[C@H](NCc4ccc(-c5ccncc5)cc4)C3)ncnc2s1 ; Cl]

¹H-NMR (DMSO-D₆, 50° C.) δ: 1.34-1.45 (3H, m), 1.58 (1H, br s), 1.89-1.96 (2H, br m), 2.04-2.08 (1H, m), 2.18-2.21 (1H, br m), 3.25 (1H, br s), 4.03 (2H, q, J = 10.9 Hz), 4.21 (1H, br s), 4.26 (2H, br s), 7.68 (1H, s), 7.76 (2H, d, J = 6.1 Hz), 7.89 (2H, s), 7.93 (2H, d, J = 7.9 Hz), 7.97 (1H, br s), 8.35 (1H, s), 8.73 (2H, d, J = 4.9 Hz), 9.28 (2H, br s). MS (m/z): 498 (M + H)⁺.

Ex. 41

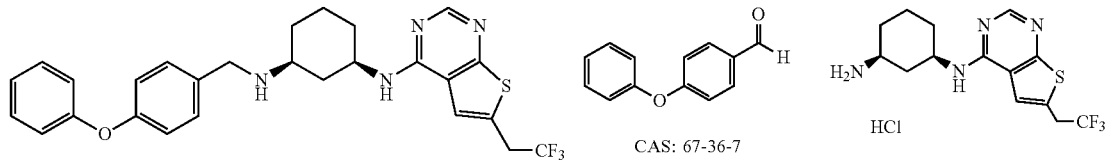

Reference Example C-2 Step 2

(1S,3R)-N¹-[(4-phenoxyphenyl)methyl]-N³-[6-(2,2,2-trifluoroethyl)thieno[2,3-d]pyrimidin-4-yl]cyclohexane-1,3-diamine hydrochloride

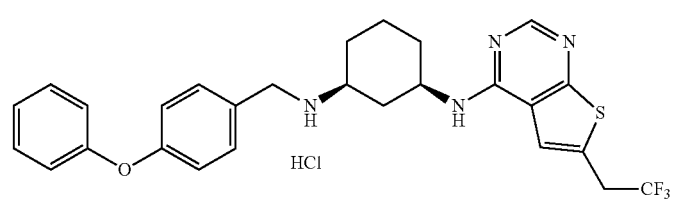 [SMILES: FC(F)(F)Cc1cc2c(N[C@@H]3CCC[C@H](NCc4ccc(Oc5ccccc5)cc4)C3)ncnc2s1 ; Cl]

¹H-NMR (DMSO-D₆) δ: 1.29-1.66 (4H, m), 1.85-1.97 (3H, m), 2.17 (1H, br s), 3.22 (1H, br s), 4.02-4.25 (5H, m), 7.02 (2H, d, J = 8.0 Hz), 7.06 (2H, d, J = 9.2 Hz), 7.18 (1H, t, J = 7.4 Hz), 7.42 (2H, t, J = 8.0 Hz), 7.56-7.63 (2H, m), 7.72 (1H, d, J = 15.3 Hz), 8.40 (1H, d, J = 11.7 Hz), 9.05-9.37 (2H, m). MS (m/z): 513 (M + H)⁺.

TABLE 2-8

Ex. 42

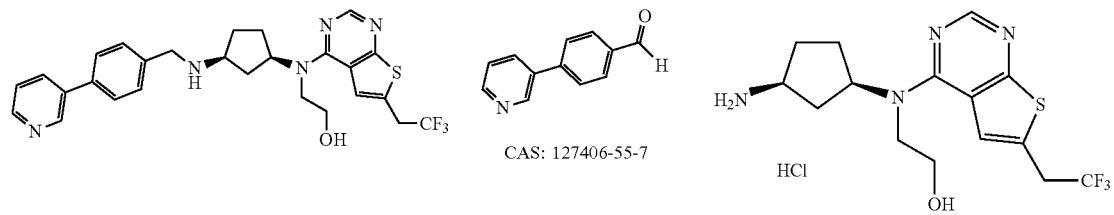

Reference Example C-9 Step 2

2-{[(1R,3S)-3-({[4-(pyridin-3-yl)phenyl]methyl}amino)cyclopentyl][6-(2,2,2-trifluoroethyl)thieno[2,3-d]pyrimidin-4-yl[amino}ethan-1-ol hydrochloride

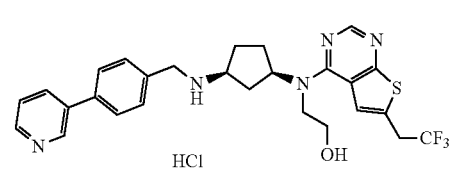 [SMILES: OCCN(c1ncnc2sc(CC(F)(F)F)cc12)[C@@H]1CC[C@H](NCc2ccc(-c3cccnc3)cc2)C1 ; Cl]

¹H-NMR (DMSO-D₆) δ: 1.92-1.94 (1H, m), 2.07-2.09 (4H, m), 2.39-2.40 (1H, m), 3.69-3.74 (6H, m), 4.11-4.14 (2H, m), 4.23-4.25 (2H, m), 5.03-5.05 (1H, m), 7.64 (1H, s), 7.70-7.71 (1H, m), 7.76 (2H, d, J = 8.2 Hz), 7.89 (2H, d, J = 8.2 Hz), 8.36-8.38 (2H, m), 8.69-8.71 (1H, m), 9.06 (1H, s), 9.54-9.60 (2H, m). MS (m/z): 528 (M + H)⁺.

TABLE 2-8-continued

Ex. 43

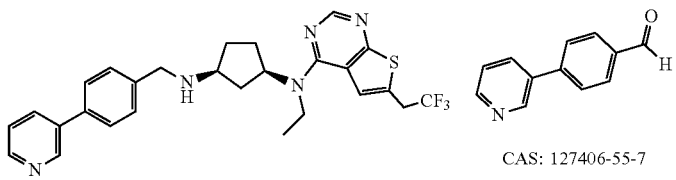 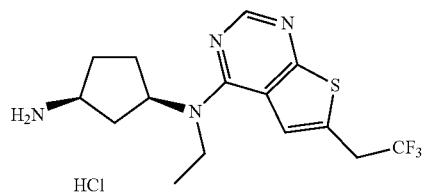 [SMILES: CCN(c1ncnc2sc(CC(F)(F)F)cc12)[C@@H]1CC[C@H](N)C1 ; Cl]

CAS: 127406-55-7

Reference Example C-5 Step 2

(1R,3S)-N$^1$-ethyl-N$^3$-{[4-(pyridin-3-yl)phenyl]methyl}-N$^1$-[6-(2,2,2 trifluoroethyl)thieno[2,3-d]pyrimidin-4-yl]cyclopentane-1,3-diamine hydrochloride

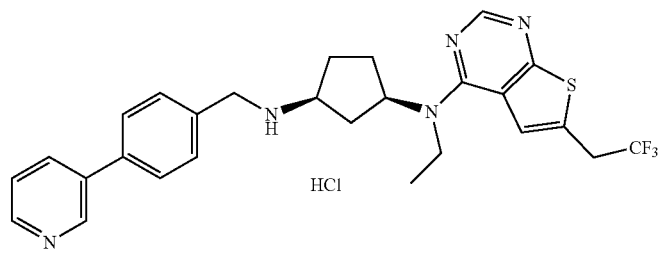 [SMILES: CCN(c1ncnc2sc(CC(F)(F)F)cc12)[C@@H]1CC[C@H](NCc2ccc(-c3cccnc3)cc2)C1 ; Cl]

$^1$H-NMR (DMSO-D$_6$) δ: 1.29 (3H, t, J = 6.7 Hz), 1.91-2.07 (5H, m), 2.36-2.43 (1H, m), 3.61-3.70 (1H, m), 3.71-3.82 (2H, m), 4.12 (2H, q, J = 10.9 Hz), 4.24 (2H, br s), 5.07-5.16 (1H, m), 7.53-7.58 (2H, m), 7.74 (2H, d, J = 7.9 Hz), 7.85 (2H, d, J = 7.9 Hz), 8.16 (1H, d, J = 7.9 Hz), 8.37 (1H, s), 8.62 (1H, d, J = 3.0 Hz), 8.96 (1H, s), 9.47 (1H, br s), 9.62 (1H, br s).
MS (m/z): 512 (M + H)$^+$.

TABLE 2-9

Ex. 44

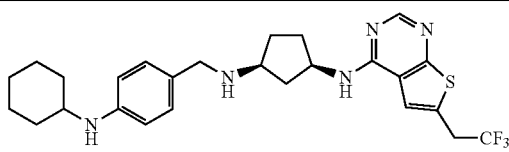 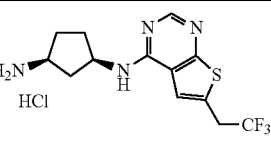

Reference Example D-88 Step 3    Reference Example C-2 Step 2

(1S,3R)-N$^1$-{[4-(cyclohexylamino)phenyl]methyl}-N$^3$-[6-(2,2,2-trifluoroethyl)thieno[2,3-d]pyrimidin-4-yl]cyclohexane-1,3-diamine hydrochloride

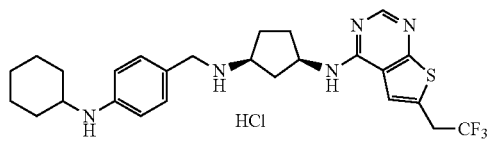

$^1$H-NMR (DMSO-D$_6$) δ: 1.13-1.21 (2H, m), 1.24-1.52 (6H, m), 1.55-1.63 (1H, m), 1.66-1.76 (3H, m), 1.82-1.96 (5H, m), 2.11-2.18 (1H, m), 2.32-2.44 (1H, m), 3.20 (1H, br s), 3.99 (2H, br s), 4.08 (2H, q, J = 11.0 Hz), 4.14-4.22 (1H, m), 5.60-5.72 (1H, m), 6.55-6.68 (2H, m), 7.15-7.22 (2H, m), 7.66 (1H, d, J = 4.9 Hz), 7.96-8.08 (1H, m), 8.35 (1H, s), 8.53-8.73 (2H, m). MS (m/z): 518 (M + H)$^+$.

Ex. 45

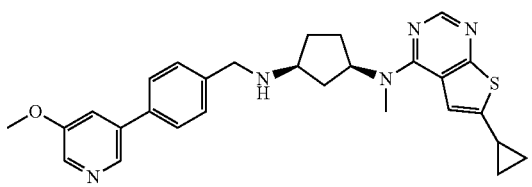 [SMILES: COc1cncc(-c2ccc(CN[C@H]3CC[C@@H](N(C)c4ncnc5sc(C6CC6)cc45)C3)cc2)c1] 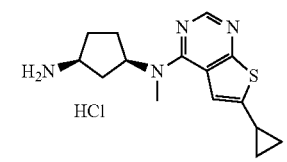 [SMILES: CN(c1ncnc2sc(C3CC3)cc12)[C@@H]1CC[C@H](N)C1 ; Cl]

Reference Example D-65    Reference Example C-12 Step 2

(1R,3S)-N$^1$-(6-cyclopropylthieno[2,3-d]pyrimidin-4-yl)-N$^3$-{[4-(5-methoxypyridin-3-yl)phenyl]methyl}-N$^1$-methylcyclopentane-1,3-diamine hydrochloride TABLE 2-9-continued

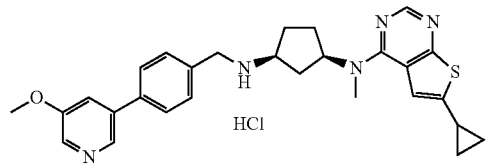 [SMILES: COc1cncc(-c2ccc(CN[C@H]3CC[C@@H](N(C)c4ncnc5sc(C6CC6)cc45)C3)cc2)c1 ; Cl]

¹H-NMR (DMSO-D₆) δ: 0.79-0.81 (2H, m), 1.06-1.09 (2H, m), 1.88-2.45 (7H, m), 3.26 (3H, s), 3.64-3.67 (1H, m), 3.92 (3H, s), 4.21-4.24 (2H, m), 5.16-5.19 (1H, m), 7.27 (1H, s), 7.62-7.62 (1H, m), 7.69 (2H, d, J = 8.3 Hz), 7.82 (2H, d, J = 8.3 Hz), 8.28 (1H, s), 8.31-8.31 (1H, m), 8.51-8.51 (1H, m), 9.25-9.35 (2H, m). MS (m/z): 486 (M + H)⁺.

TABLE 2-10

Ex. 46

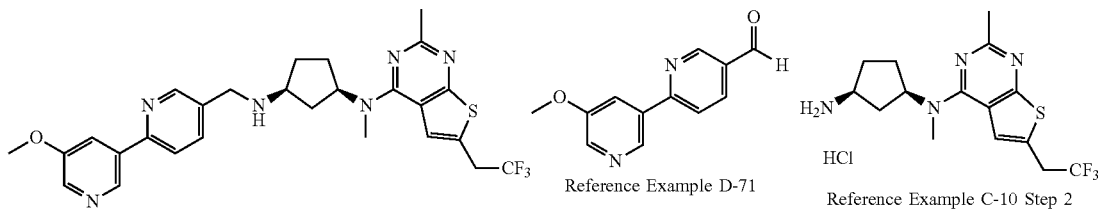

(1R,3S)-N³-[(5'-methoxy[2,3'-bipyridine]-5-yl)methyl]-N¹-methyl-
N¹-[2-methyl-6-(2,2,2-trifluoroethyl)thieno[2,3-d]pyrimidin-
4-yl]cyclopentane-1,3-diamine hydrochloride

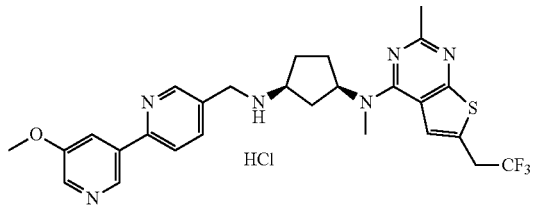 [SMILES: COc1cncc(-c2ccc(CN[C@H]3CC[C@@H](N(C)c4nc(C)nc5sc(CC(F)(F)F)cc45)C3)cn2)c1 ; Cl]

¹H-NMR (DMSO-D₆) δ: 1.86-2.16 (5H, m), 2.31-2.42 (1H, m), 2.46 (3H, s), 3.27 (3H, s), 3.68 (1H, br s), 3.94 (3H, s), 4.05 (2H, q, J = 11.2 Hz), 4.30 (2H, br s), 5.24-5.35 (1H, m), 7.66 (1H, s), 8.03-8.06 (1H, m), 8.16 (1H, dd, J = 8.0, 2.5 Hz), 8.23 (1H, d, J = 8.0 Hz), 8.41 (1H, d, J = 2.5 Hz), 8.88 (1H, s), 8.93 (1H, d, J = 1.8 Hz), 9.36-9.53 (2H, m). MS (m/z): 543 (M + H)⁺.

Ex. 47

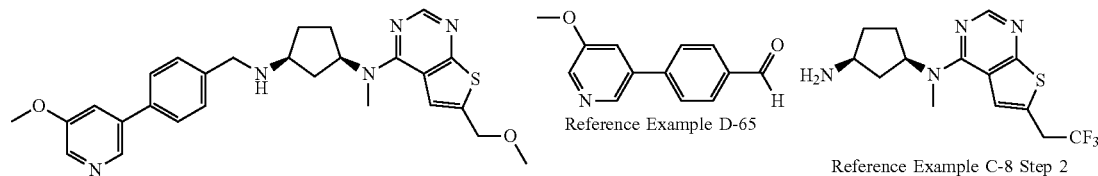

(1R,3S)-N¹-[6-(methoxymethyl)thieno[2,3-d]pyrimidin-4-yl]-
N³-{[4-(5-methoxypyridin-3-yl)phenyl]methyl}-
N¹-methylcyclopentane-1,3-diamine hydrochloride

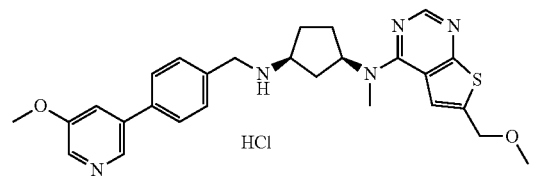

¹H-NMR (DMSO-D₆) δ: 1.91-1.93 (1H, m), 2.03-2.10 (4H, m), 2.35-2.42 (1H, m) 3.29 (3H, s), 3.34 (3H, s), 3.63-3.65 (1H, m), 3.92 (3H, s), 4.21 (2H, s), 4.67 (2H, s), 5.22-5.24 (1H, m), 7.57-7.70 (6H, m), 8.31-8.32 (2H, m), 8.51 (1H, s), 9.49-9.61 (2H, m). MS (m/z): 490 (M + H)⁺.

TABLE 2-11

Ex. 48

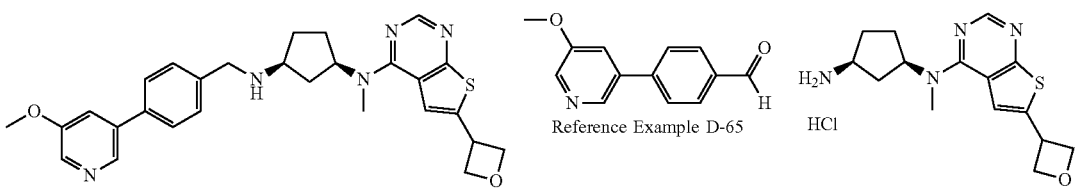

Reference Example D-65

Reference Example C-11 Step 2

(1R,3S)-N³-{[4-(5-methoxypyridin-3-yl)phenyl]methyl}-N¹-methyl-
N¹-[6-(oxetan-3-yl)thieno[2,3-d]pyrixnidin-4-yl]cyclopentane-
1,3-diamine hydrochloride ¹H-NMR (DMSO-D$_6$)δ: 1.56-1.62 (2H, m), 1.78-1.92 (3H, m), 2.14-2.20 (2H, m), 3.13-3.17 (2H, m), 3.42-3.48 (1H, m), 3.70-3.82 (5H, m), 3.89-3.93 (4H, m), 3.98-4.01 (1H, m), 4.88-4.91 (1H, m), 5.15-5.24 (1H, m), 7.45 (1H, s), 7.47 (2H, d, J = 8.2 Hz), 7.56-7.56 (1H, m), 7.66 (2H, d, J = 8.2 Hz), 8.27-8.28 (2H, m), 8.46 (1H, s).

Ex. 49

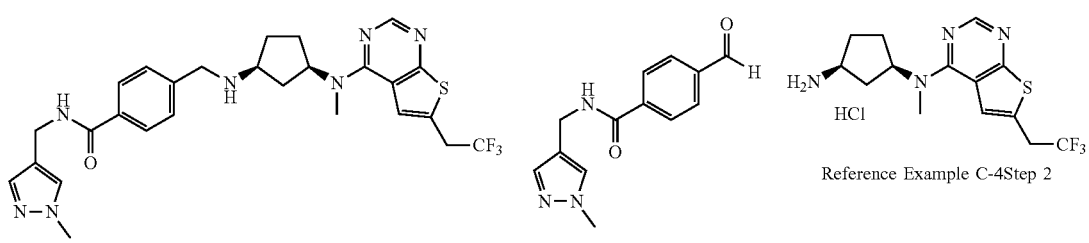

Reference Example D-84

Reference Example C-4Step 2

N-[(1-methyl-1H-pyrazol-4-yl)methyl]-4-({[(1S,3R)-3-{methyl[6-
(2,2,2-trifluoroethyl)thieno[2,3-d]pyrimidin-4-yl]amino}cyclopentyl]
amino}methyl)benzamide hydrochloride ¹H-NMR (DMSO-D$_6$) δ: 1.84-2.15 (5H, m), 2.31-2.39 (1H, m), 3.27 (3H, s), 3.63 (1H, br s), 3.78 (3H, s), 4.09 (2H, q, J = 11.0 Hz), 4.23 (2H, t, J = 6.1 Hz), 4.30 (2H, d, J = 5.5 Hz), 5.27 (1H, br s), 7.36 (1H, s), 7.61 (1H, s), 7.63 (2H, d, J = 8.0 Hz), 7.72 (1H, s), 7.93 (2H, d, J = 8.0 Hz), 8.37 (1H, s), 8.90 (1H, t, J = 5.5 Hz), 9.41-9.55 (2H, m). MS (m/z): 558 (M + H)⁺.

TABLE 2-12

Ex. 50

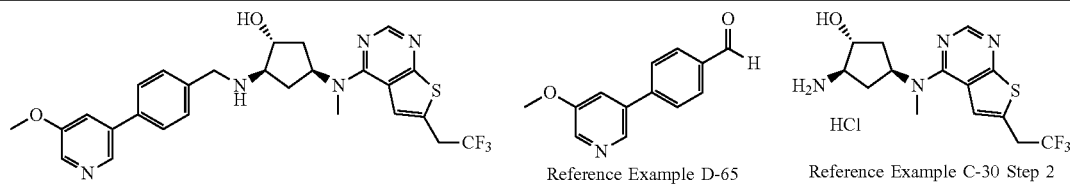

Reference Example D-65

Reference Example C-30 Step 2

(1R,2R,4S)-2-({[4-(5-methoxypyridin-3-yl)phenyl]methyl}amino)-4-
{methyl[6-(2,2,2-trifluoroethyl)thieno[2,3-d]pyrimidin-4-yl]
amino}cyclopentan-1-ol hydrochloride TABLE 2-12-continued

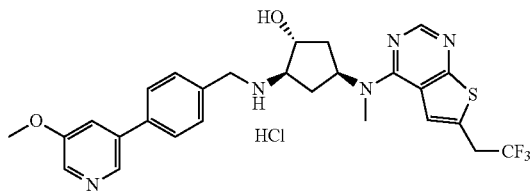 [SMILES: COc1cncc(-c2ccc(CN[C@@H]3C[C@H](N(C)c4ncnc5sc(CC(F)(F)F)cc45)C[C@H]3O)cc2)c1 ; Cl]

$^1$H-NMR (DMSO-D$_6$) δ: 1.80-1.91 (1H, m), 1.95-2.08 (1H, m), 2.25-2.35 (1H, m), 2.37-2.46 (1H, m), 3.27 (3H, s), 3.35-3.40 (1H, m), 3.94 (3H, s), 4.09 (2H, q, J = 10.7 Hz), 4.24-4.36 (2H, m), 4.44-4.54 (1H, m), 5.44-5.56 (2H, m), 7.69-7.80 (4H, m), 7.85-7.91 (2H, m), 8.31-8.41 (2H, m), 8.53-8.60 (1H, m), 9.52-9.79 (2H, m). MS (m/z): 544 (M + H)$^+$.

Ex. 51

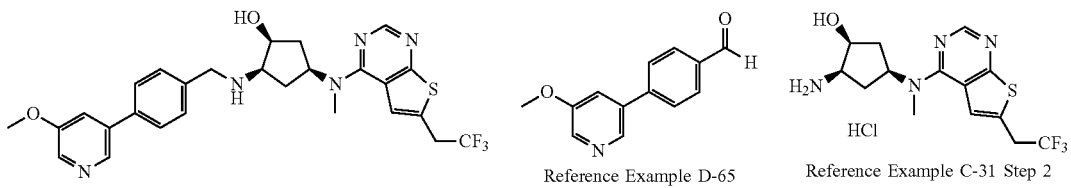

Reference Example D-65

Reference Example C-31 Step 2

(1S,2R,4S)-2-({[4(5methoxypyridin-3-yl)phenyl]methyl}amino)-4-{methyl[6-(2,2,2-trilluoroethyl)thieno[2,3-d]pyrimidin-4-yl]amino}cyclopentan-1-ol hydrochloride

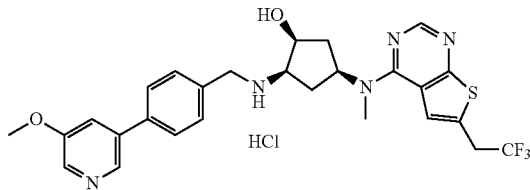 [SMILES: COc1cncc(-c2ccc(CN[C@@H]3C[C@H](N(C)c4ncnc5sc(CC(F)(F)F)cc45)C[C@@H]3O)cc2)c1 ; Cl]

$^1$H-NMR (CD$_3$OD, 50° C. δ: 1.96-2.03 (1H, m), 2.21-2.31 (1H, m), 2.42-2.55 (2H, m), 3.46 (3H, s), 3.56-3.64 (1H, m), 3.87 (2H, q, J = 10.5 Hz), 3.97 (3H, s), 4.32 (1H, d, J = 12.8 Hz), 4.39 (1H, d, J = 12.8 Hz), 4.46-4.49 (1H, m), 5.43-5.52 (1H, m), 7.61 (1H, s), 7.65 (1H, s), 7.67 (2H, d, J = 8.5 Hz), 7.80 (2H, d, J = 8.5 Hz), 8.28 (1H, d, J = 2.4 Hz), 8.32 (1H, s), 8.42 (1H, d, J = 2.4 Hz).

TABLE 2-13

Ex. 52

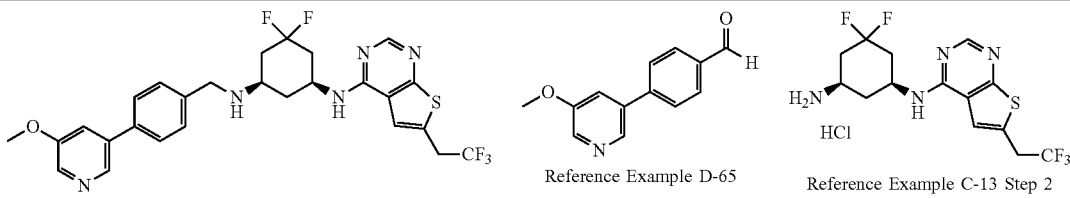

Reference Example D-65

Reference Example C-13 Step 2

(1R,3S)-5,5-difluoro-N$^1$-{[4-(5-methoxypyridin-3-yl)phenyl]methyl}-N$^3$-[6-(2,2,2-trifluoroethyl)thieno[2,3-d]pyrimidin-4-yl]cyclohexane-1,3-diamine hydrochloride

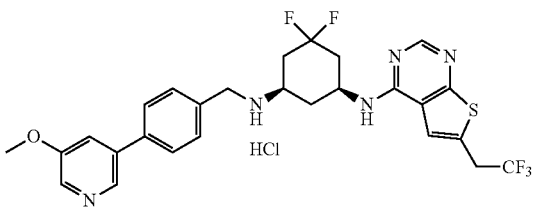 [SMILES: COc1cncc(-c2ccc(CN[C@@H]3C[C@H](Nc4ncnc5sc(CC(F)(F)F)cc45)CC(F)(F)C3)cc2)c1 ; Cl]

$^1$H-NMR (DMSO-D$_6$) δ: 1.81-1.84 (1H, m), 1.91-2.08 (1H, m), 2.17-2.34 (1H, m), 2.57-2.66 (3H, m), 2.78-2.81 (1H, m), 3.94 (3H, s), 4.11 (2H, q, J = 11.0 Hz), 4.33 (2H, s), 4.41-4.43 (1H, m), 7.64 (1H, s), 7.72 (2H, d, J = 8.3 Hz), 7.79 (1H, s), 7.89 (2H, d, J = 8.3 Hz), 8.26-8.28 (1H, m), 8.38 (1H, s), 8.42 (1H, s), 8.59 (1H, s), 9.66-9.73 (2H, m), MS (m/z): 564 (M + H)$^+$.

TABLE 2-13-continued

Ex. 53

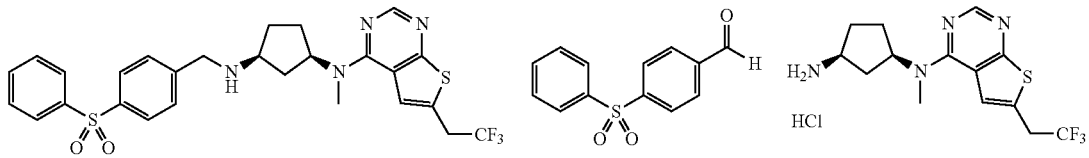

CAS:66-39-7

(1R,3S)N³-{[4-(benzenesulfonyl)phenyl]methyl}N¹-methyl-N¹-
[6-(2,2,2-trifluoroethyl)thieno[2,3-d]pyrimidin-4-yl]
cyclopentane-1,3-diamine hydrochloride Reference Example C-4 Step 2

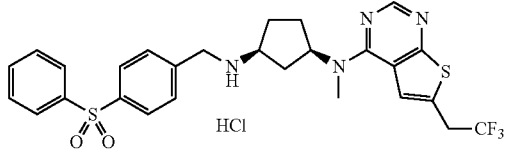 [SMILES: CN(c1ncnc2sc(CC(F)(F)F)cc12)[C@@H]1CC[C@H](NCc2ccc(S(=O)(=O)c3ccccc3)cc2)C1 ; Cl]

¹H-NMR (DMSO-D₆) δ: 1.89-1.98 (5H, m), 2.33-2.33 (1H, m), 3.25 (3H, s), 3.61-3.63 (1H, m),
4.07-4.10 (2H, m), 4.23-4.25 (2H, m), 5.23-5.25 (1H, m), 7.62-7.66 (2H, m), 7.70-7.71 (2H, m),
7.80 (2H, d, J = 8.0 Hz), 7.97-8.00 (2H, m), 8.07 (2H, d, J = 8.0 Hz), 8.36 (1H, s), 9.26-9.39 (2H,
m). MS (m/z): 561 (M + H)⁺.

TABLE 2-14

Ex. 54

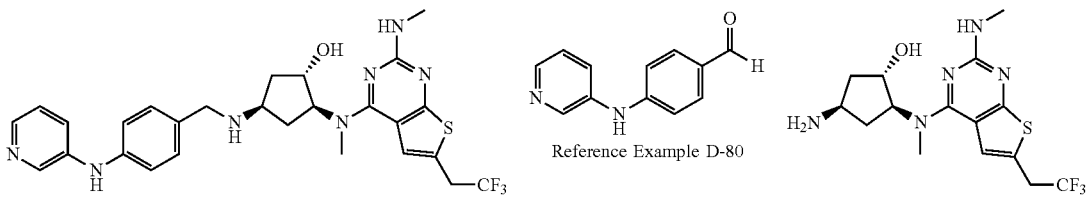

Reference Example D-80

(1S,2S,4R)-2-{methyl[2-(methylamino)-6-(2,2,2-trifluoroethyl)
thieno[2,3-d]pyrimidin-4-yl]amino}-4-[({4-[(pyridin-3yl)amino]
phenyl}methyl)amino]cyclopentan-1-ol Reference Example C-22 Step 3

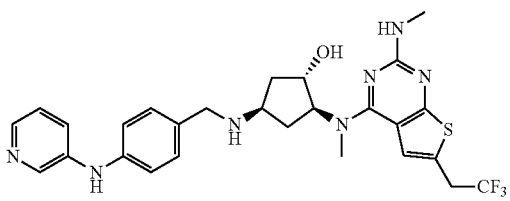 [SMILES: CNc1nc(N(C)[C@H]2C[C@@H](NCc3ccc(Nc4cccnc4)cc3)C[C@@H]2O)c2cc(CC(F)(F)F)sc2n1]

¹H-NMR (DMSO-D₆) δ: 1.44-1.48 (1H, m), 1.61-1.68 (1H, m), 1.81-1.84 (1H, m), 2.18-2.25 (1H,
m), 2.77 (3H, d, J = 4.9 Hz), 3.05-3.15 (4H, m), 3.60 (2H, s), 3.89 (2H, q, J = 11.2 Hz), 4.32-4.35
(1H, m), 4.71-4.74 (1H, m), 4.88-4.89 (1H, m), 6.57-6.58 (1H, m), 7.04-7.06 (2H, m), 7.20 7.24
(3H, m), 7.41-7.42 (2H, m), 7.98-8.00 (1H, m), 8.30-8.31 (2H, m). MS (m/z): 558 (M + H)⁺,

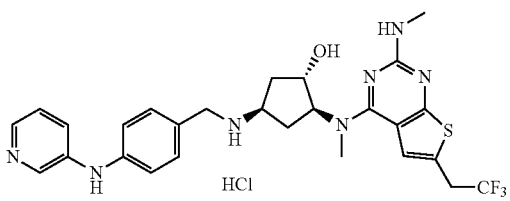 [SMILES: CNc1nc(N(C)[C@H]2C[C@@H](NCc3ccc(Nc4cccnc4)cc3)C[C@@H]2O)c2cc(CC(F)(F)F)sc2n1 ; Cl]

¹H-NMR (DMSO-D₆) δ: 1.85-1.96 (2H, m), 2.19-2.36 (2H, m), 2.79 (3H, d, J = 4.9 Hz), 3.19 (3H
s), 3.62-3.65 (1H, m), 3.90 (2H, q, J = 11.2 Hz), 4.05 (2H, s), 4.48-4.50 (1H, m), 4.72-4.75 (1H,
m), 5.20-5.22 (1H, m), 6.71 (1H, d, J = 4.3 Hz), 7.15 (2H, d, J = 8.6 Hz), 7.31-7.33 (1H, m), 7.46-
7.48 (3H, m), 7.53-7.56 (1H, m), 8.09-8.10 (1H, m), 8.38-8.39 (1H, m), 8.69 (1H, s), 9.28-9.43
(2H, m). MS (m/z): 558 (M + H)⁺.

TABLE 2-15

Ex. 55

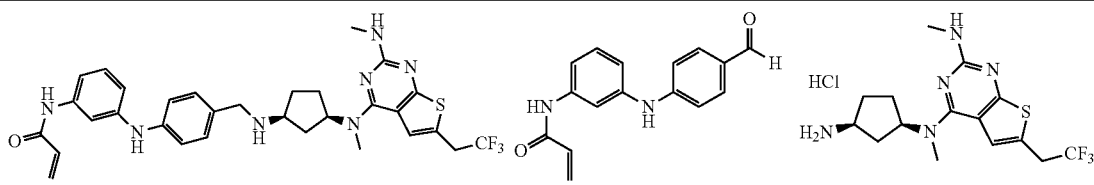

Reference Example D-83 Step 4
N-{3-[4-({[(1S,3R)-3{methyl[2-(methylamino)-6-(2,2,2-trifluoroethyl)thieno[2,3-d]pyrimidin-4-yl]amino}cyclopentyl]amino}methyl)anilino]phenyl}prop-2-enamide hydrochloride Reference Example C-7 Step 2

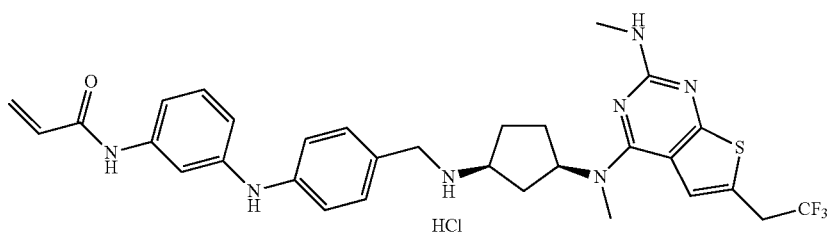 [SMILES: C=CC(=O)Nc1cccc(Nc2ccc(CN[C@H]3CC[C@@H](N(C)c4nc(NC)nc5sc(CC(F)(F)F)cc45)C3)cc2)c1 ; Cl]

$^1$H-NMR (DMSO-D$_6$) δ: 1.84-2.09 (5H, m), 2.31-2.39 (1H, m), 2.80 (3H, s), 3.19 (3H, s), 3.40-3.48 (1H, m), 3.51-3.59 (1H, m), 3.91 (2H, q, J = 11.1 Hz), 4.04-4.09 (2H, m), 5.09-5.17 (1H, m) ,5.73-5.77 (1H, m), 6.23 (1H, d, J = 17.0 Hz), 6.42-6.49 (1H, m), 6.76-6.79 (1H, m), 7.02-7.05 (1H, m), 7.11-7.21 (3H, m), 7.38-7.45 (3H, m), 7.74 (1H, s), 8.44 (1H, s), 9.16 (2H, br s), 10.13-10.15 (1H, m). MS (m/z): 610 (M + H)$^+$.

Ex. 56

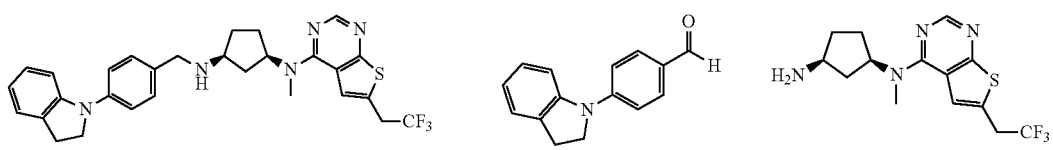

Reference Example D-81 Step 2
(1R,3S)-N$^3$-{[4-(2)-3-dihydro-1H-indol-1-yl)phenyl]methyl}-N$^1$-methyl-N$^1$-[6-(2,2,2-trifluoroethyl)thieno[2,3-d]pyrimidin-4-yl]cyclopentane-1,3-diamine hydrochloride Reference Example C-4 Step 2

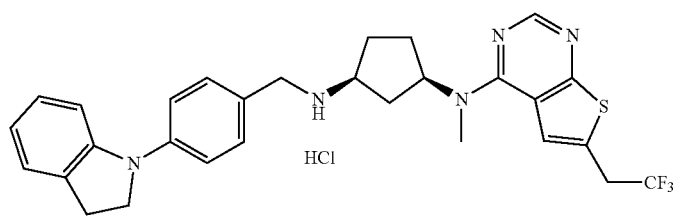 [SMILES: CN(c1ncnc2sc(CC(F)(F)F)cc12)[C@@H]1CC[C@H](NCc2ccc(N3CCc4ccccc43)cc2)C1 ; Cl]

$^1$H-NMR (DMSO-D$_6$) δ: 1.81-1.93 (1H, m), 1.95-2.12 (4H, m), 2.30-2.38 (1H, m), 3.11 (2H, t, J = 8.3 Hz), 3.29 (3H, s), 3.61 (1H, br s), 3.95 (2H, t, J = 8.3 Hz), 4.03-4.14 (4H, m), 5.27 (1H, br s), 6.76 (1H, t, J = 7.4 Hz), 7.07 (1H, t, J = 7.4 Hz), 7.15 (1H, d, J = 8.0 Hz), 7.20 (1H, d, J = 7.4 Hz), 7.29 (2H, d, J = 8.6 Hz), 7.55 (2H, d, J = 8.6 Hz), 7.73 (1H, s), 8.38 (1H, s), 9.23-9 48 (2H m). MS (m/z): 538 (M + H)$^+$.

TABLE 2-16

Ex. 57

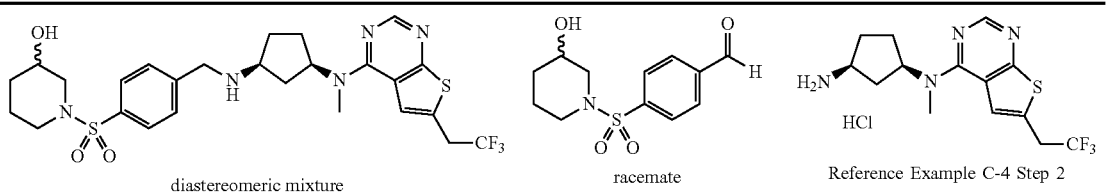

diastereomeric mixture     racemate     Reference Example C-4 Step 2

Reference ExampleD-92
1-[4-({[(1S,3R)-3-{methyl[6-(2,2,2trifluoroethyl)thieno[2,3-d]pyrimidin-4-yl]amino}cyclopentyl]amino}methyl)benzene-1-sulfonyl]piperidin-3-ol hydrochloride
(diastereomer mixture)

TABLE 2-16-continued

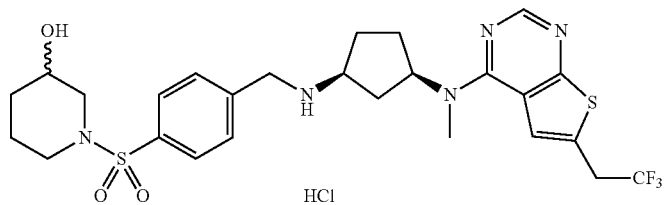 [SMILES: CN(c1ncnc2sc(CC(F)(F)F)cc12)[C@@H]1CC[C@H](NCc2ccc(S(=O)(=O)N3CCCC(O)C3)cc2)C1 ; Cl]

$^1$H-NMR (DMSO-D$_6$) δ: 1.05-1.11 (1H, m), 1.44-1.49 (1H, m), 1.70-2.15 (8H, m), 2.31-2.36 (2H, m), 3.25-3.39 (4H, m), 3.42-3.44 (1H, m), 3.52-3.56 (2H, m), 3.64-3.67 (1H, m), 4.08-4.11 (2H, m), 4.28-4.30 (2H, m), 5.26-5.28 (1H, m), 7.73 (1H, s), 7.83-7.85 (4H, m), 8.37 (1H, s), 9.54-9.61 (2H, m). MS (m/z): 584 (M + H)$^+$.

Ex. 58

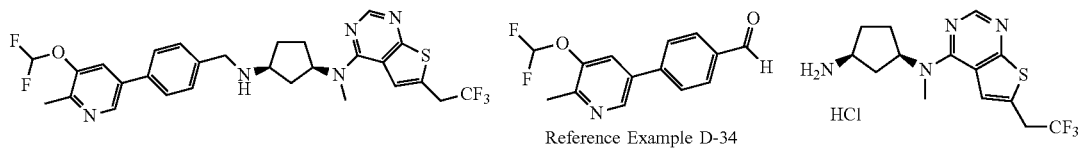

Reference Example D-34    Reference Example C-4 Step 2

(1R,3S)-N$^3$-({4-[5-(difluoromethoxy)-6-methylpyridin-3-yl]phenyl}methyl)-N$^1$-methyl-N$^1$-[6-(2,2,2-trifluoroethyl)thieno[2,3-d]pyrimidin-4-yl]cyclopentane-1,3-diamine hydrochloride

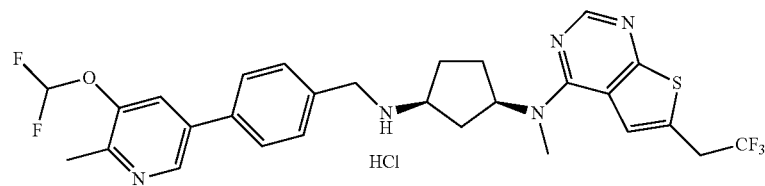 [SMILES: Cc1ncc(-c2ccc(CN[C@H]3CC[C@@H](N(C)c4ncnc5sc(CC(F)(F)F)cc45)C3)cc2)cc1OC(F)F ; Cl]

$^1$H-NMR (DMSO-D$_6$) δ: 1.88-2.12 (5H, m), 2.33-2.41 (1H, m), 3.29 (3H, s), 3.66 (1H, br s), 4.09 (2H, q, J = 11.1 Hz), 4.24 (2H, br s), 5.28 (1H, t, J = 8.8 Hz), 7.41 (1H, t, J = 73.8 Hz), 7.70 7.73 (3H, m), 7.88 (2H, d, J = 8.5 Hz), 7.92 (1H, s), 8.38 (1H, s), 8.73 (1H, d, J = 1.8 Hz), 9.25-9.46 (2H, m). MS (m/z): 578 (M + H)$^+$.

TABLE 2-17

Ex. 59

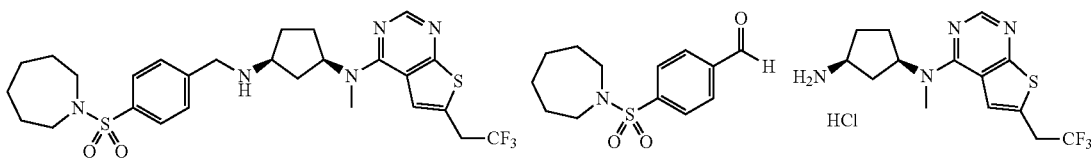

Reference Example D-93    Reference Example C-4 Step 2

(1R,3S)-N$^3$-{[4-(azepane-1-sulfonyl)phenyl]methyl)-N$^1$methyl-N$^1$-[6-(2,2,2-trifluoroethyl)thieno[2,3-d]pyrimidin-4-yl]cyclopentane-1,3-diamine hydrochloride

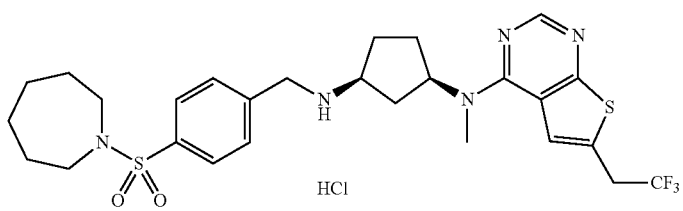 [SMILES: CN(c1ncnc2sc(CC(F)(F)F)cc12)[C@@H]1CC[C@H](NCc2ccc(S(=O)(=O)N3CCCCCC3)cc2)C1 ; Cl]

$^1$H-NMR (DMSO-D$_6$) δ: 1.48-1.51 (4H, m), 1.61-1.63 (4H, m), 1.90-2.03 (5H, m), 2.28-2.35 (1H, m), 3.20-3.21 (4H, m), 3.28 (3H, s), 3.62-3.64 (1H, m), 4.08-4.10 (2H, m), 4.24-4.27 (2H, m), 5.26-5.28 (1H, m), 7.72-7.87 (5H, m), 8.37 (1H, s), 9.47-9.61 (2H, m). MS (m/z): 582 (M + H)$^+$.

TABLE 2-17-continued

Ex. 60

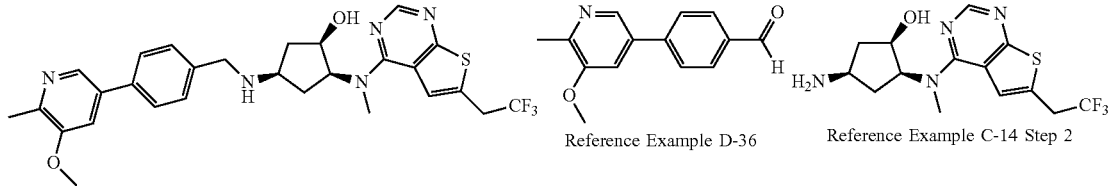

Reference Example D-36   Reference Example C-14 Step 2

(1R,2S,4R)-4-({[4-(5-methoxy-6-methylpyridin-3-yl)phenyl]methyl}
amino)-2-{methyl[6-(2,2,2-trifluoroethyl)thieno[2,3d]pyrimidin-4-yl]
amino}cyclopentan-1-ol

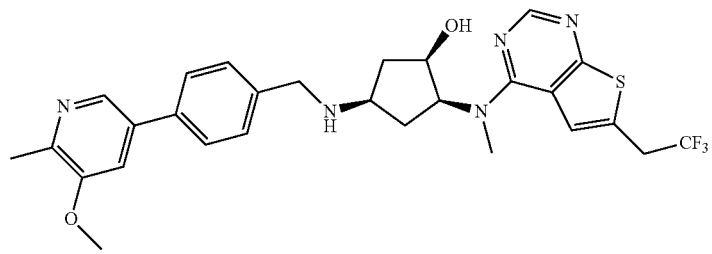 [SMILES: COc1cc(-c2ccc(CN[C@H]3C[C@@H](O)[C@@H](N(C)c4ncnc5sc(CC(F)(F)F)cc45)C3)cc2)cnc1C]

¹H-NMR (CDCl₃) δ: 1.59-2.16 (5H, m), 2.31-2.41 (1H, m), 2.51 (3H, s), 3.42-3.49 (1H, m), 3.55
(3H, s), 3.58-3.68 (2H, m), 3.87-3.94 (5H, m), 4.46-4.52 (1H, m), 5.08-5.17 (1H, m), 7.24-7.25
(1H, m), 7.40-7.44 (3H, m), 7.54-7.59 (2H, m), 8.29-8.31 (1H, m), 8.40 (1H, s). MS (m/z): 558 (M + H)⁺.
(1R,2S,4R)-4-({[4-(5-methoxy-6-methylpyridin-3-yl)phenyl]methyl}amino)-2-{methyl[6-(2,2,2-
trifluoroethyl)thieno[2,3-d]pyrimidin-4-yl]amino}cyclopentan-1-ol hydrochloride

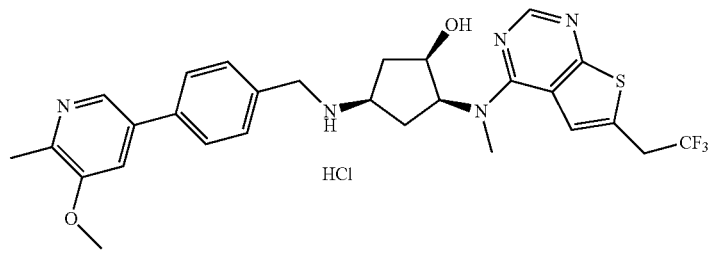 [SMILES: COc1cc(-c2ccc(CN[C@H]3C[C@@H](O)[C@@H](N(C)c4ncnc5sc(CC(F)(F)F)cc45)C3)cc2)cnc1C ; Cl]

¹H-NMR (DMSO-D₆) δ: 1.75-1.85 (1H, m), 2.08 (1H, q, J = 11.0 Hz), 2.24-2.43 (5H, m), 3.35
(3H, s), 3.41-3.47 (1H, m), 3.93 (3H, s), 4.08 (2H, q, J = 11.1 Hz), 4.25 (2H, br s), 4.37 (1H, br
s), 5.38-5.50 (1H, m), 6.20 (1H, d, J = 4.0 Hz), 7.60 (1H, s), 7.65-7.77 (3H, m), 7.85 (2H, d, J =
8.0 Hz), 8.33-8.40 (2H, m), 9.02 (1H, br s), 9.38 (1H, br s). MS (m/z): 558 (M + H)⁺.

TABLE 2-18

Ex. 61

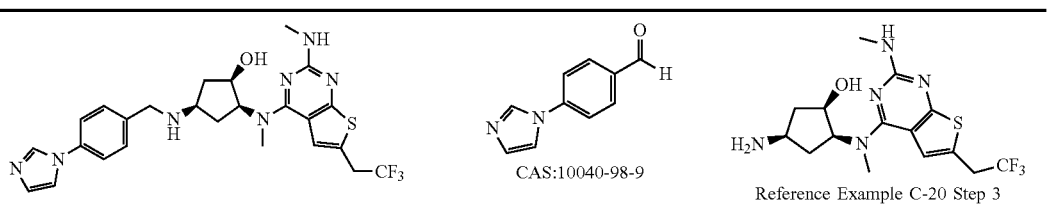

CAS:10040-98-9   Reference Example C-20 Step 3

(1R,2S,4R)-4-({[4-(1H-imidazol-1-yl)phenyl]methyl}amino)-
2-{methyl[2-(methylamino)-6-(2,2,2-trifluoroethyl)thieno
[2,3-d]pyrimidin-4-yl]amino}cyclopentan-1-ol hydrochloride

TABLE 2-18-continued

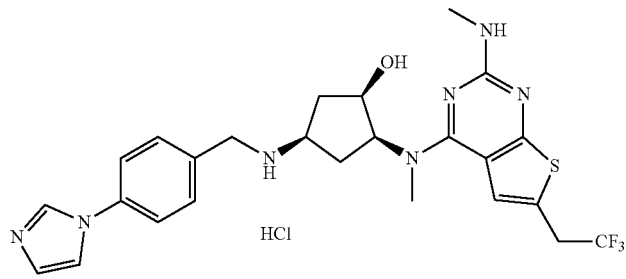 [SMILES: CNc1nc(N(C)[C@H]2C[C@@H](NCc3ccc(-n4ccnc4)cc3)C[C@H]2O)c2cc(CC(F)(F)F)sc2n1 ; Cl]

$^1$H-NMR (DMSO-D$_6$) δ: 1.77-1.84 (1H, m), 2.25-2.45 (3H, m), 2.77 (3H, d, J = 4.3 Hz), 3.35 (3H, s), 3.49-3.61 (1H, m), 3.89 (2H, q, J = 10.8 Hz), 4.20-4.30 (2H, m), 4.36-4.41 (1H, m), 4.73 4.82 (1H, m), 5.17 (1H, d, J = 4.3 Hz), 6.59-6.68 (1H, m), 7.30 (1H, s), 7.43 (1H, s), 7.73-7.82 (4H, m), 7.93 (1H, s), 8.63 (1H, s), 9.40 (2H, br s), MS (m/z): 532 (M + H)$^+$.

Ex. 62

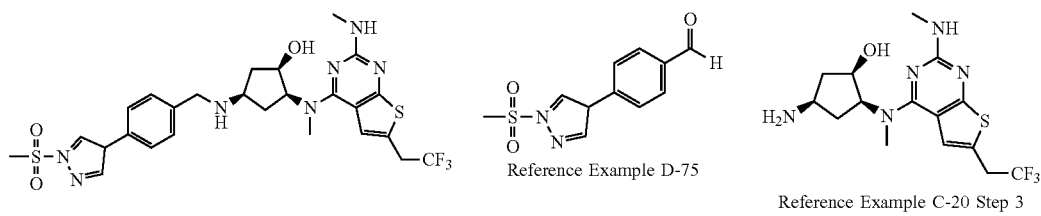

Reference Example D-75    Reference Example C-20 Step 3

(1R,2S,4R)-4[({4[1-(methanesulfonyl)-1H-pyrazol-4-yl]phenyl}methyl)amino]-2-{methyl[2-(methylamino)-6-(2,2,2-trifluoroethyl)thieno[2,3-d]pyrimidin-4-yl]amino}cyclopentan-1-ol hydrochloride

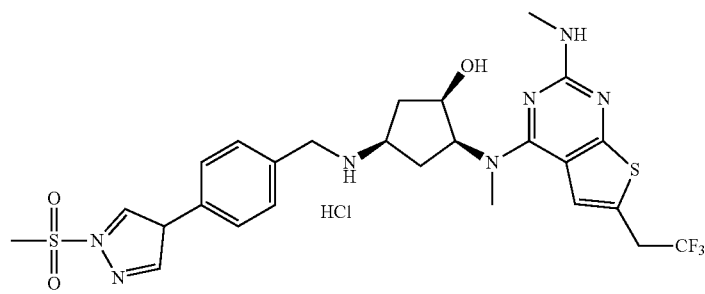

$^1$H-NMR (DMSO-D$_6$) δ: 1.85-1.88 (1H, m), 2.24-2.31 (1H, m), 2.40-2.44 (2H, m), 2.79 (3H, s), 3.35 (3H, s), 3.54-3.57 (4H, m), 3.82-3.85 (2H, m), 4.19-4.21 (2H, m), 4.37-4.39 (1H, m), 4.75-4.81 (1H, m), 5.00-5.02 (1H, m), 6.37 (1H, s), 7.38 (1H, s), 7.63 (2H, d, J = 8.3 Hz), 7.82 (2H, d, J = 8.3 Hz), 8.45 (1H, s), 8.75 (1H, s), 9.36-9.39 (2H, m). MS (m/z): 610 (M + H)$^+$.

TABLE 2-19

Ex. 63

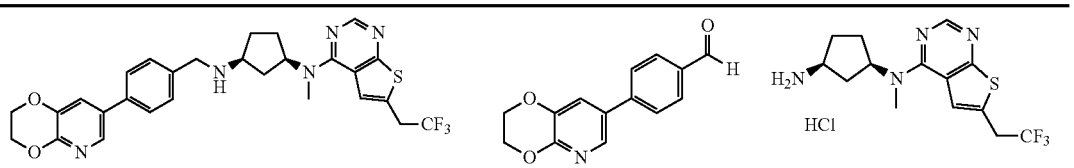

Reference Example D-42    Reference Example C-4 Step 2

(1R,3S)-N$^3$-{[4-(2,3-dihydro[1,4]dioxino[2,3-b]pyridin-7-yl)phenyl]methyl}-N$^1$-methyl-N$^1$-[6-(2,2,2-trifluoroethyl)thieno[2,3-d]pyrimidin-4-yl]cyclopentane-1,3-diamine hydrochloride TABLE 2-19-continued

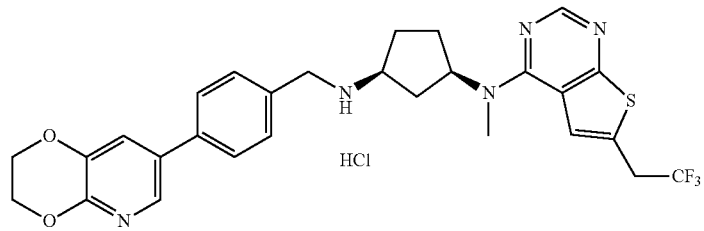 [SMILES: CN(c1ncnc2sc(CC(F)(F)F)cc12)[C@@H]1CC[C@H](NCc2ccc(-c3cnc4c(c3)OCCO4)cc2)C1 ; Cl]

$^1$H-NMR (DMSO-D$_6$) δ: 1.85-1.92 (1H, m), 1.96-2.13 (4H, m), 2.32-2.40 (1H, m), 3.29 (3H, 3.59-3.66 (1H, m), 4.09 (2H, q, J = 11.0 Hz), 4.20 (2H, t, J = 6.7 Hz), 4.29-4.32 (2H, m), 4.44-4.46 (2H, m), 5.23-5.30 (1H, m), 7.65 (2H, d, J = 8.0 Hz), 7.66 (1H, s), 7.73 (1H, s), 7.77 (2H J = 8.0 Hz), 8.13 (1H, d, J = 1.8 Hz), 8.38 (1H, s), 9.30-9.51 (2H, m). MS (m/z): 556 (M + HH)$^+$.

Ex. 64

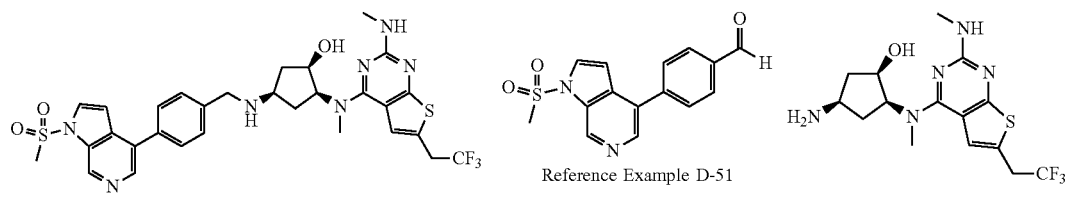

Reference Example D-51

Reference Example C-20 Step 3

(1R,2S,4R)-4[({4-[1-(methanesulfonyl)-1H-pyrrolo[2,3-c]pyridin-4yl]phenyl}methyl)amino]-2-{methyl[2-(methylamino)-6-(2,2,2trifluoroethyl)thieno[2,3-d]pyrimidin-4-yl]amino}cyclopentan-1-ol hydrochloride

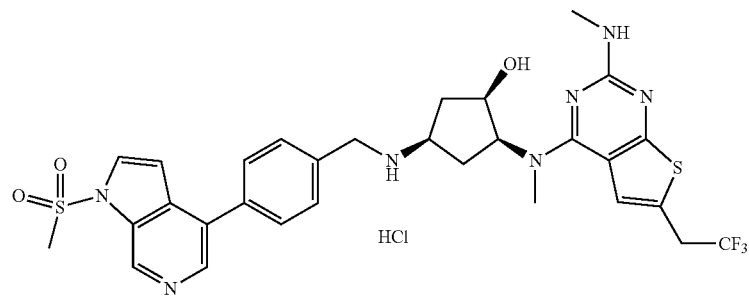 [SMILES: CNc1nc(N(C)[C@H]2C[C@@H](NCc3ccc(-c4cncc5c4ccn5S(C)(=O)=O)cc3)C[C@H]2O)c2cc(CC(F)(F)F)sc2n1 ; Cl]

$^1$H-NMR (DMSO-D$_6$) δ: 1.80-1.90 (1H, m), 2.31 (1H, dd, J = 12.3, 5.5 Hz), 2.38-2.49 (2H, m), 2.78 (3H, d, J = 4.3 Hz), 3.37 (3H, s), 3.53-3.64 (1H, m), 3.68 (3H, s), 3.90 (2H, q, J = 11.0 Hz), 4.30 (2H, br s), 4.40 (1H, br s), 4.80 (1H, br s), 5.17 (1H, br s), 6.62-6.73 (1H, m), 6.97 (1H J = 3.7 Hz), 7.45 (1H, s), 7.75-7.82 (4H, m), 7.96 (1H, d, J = 3.7 Hz), 8.57 (1H, s), 9.17 (1H, 9.41-9.52 (2H, m). MS (ra/z): 660 (M + H)$^+$.

TABLE 2-20

Ex. 65

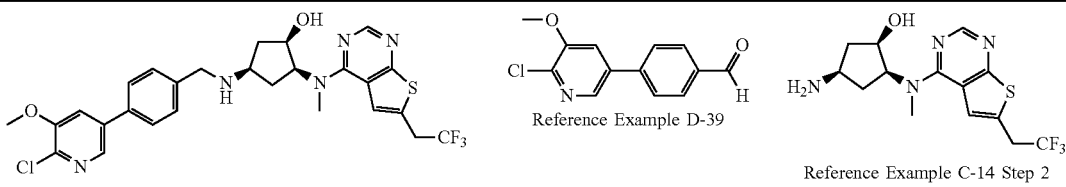

Reference Example D-39

Reference Example C-14 Step 2

(1R,2S,4R)-4({[4(6-chloro-5-methoxypyridin-3-yl)phenyl]methyl}amino)-2-{methyl[6-(2,2,2-trifluoroethyl)thieno[2,3d]pyrimidin-4-yl]amino}cyclopentan-1-ol TABLE 2-20-continued

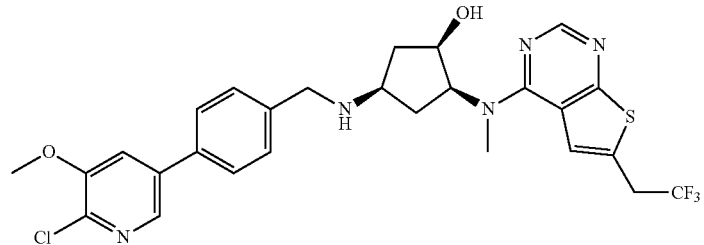

$^1$H-NMR (CDCl$_3$) δ: 1.87 (1H, d, J = 14.1 Hz), 1.97 (1H, ddd, J = 13.5, 9.2, 3.1 Hz), 2.03-2.11 (1H, m), 2.36 (1H, ddd, J = 13.5, 9.2, 6.1 Hz), 3.41-3.47 (1H, m), 3.55 (3H, s), 3.63 (2H, q, J = 10.0 Hz), 3.90 (2H, d, J = 3.7 Hz), 4.00 (3H, s), 4.48-4.51 (1H, m), 5.10 (1H, td, J = 9.2, 4.9 Hz), 7.35 (1H, d, J = 1.8 Hz), 7.40 (1H, s), 7.44 (2H, d, J = 8.0 Hz), 7.55 (2H, d, J = 8.0 Hz), 8.20 (1H, d, J = 1.8 Hz), 8.40 (1H, s).

(1R,2S,4R)-4-({[4-(6-chloro-5-methoxypyridin-3-yl)phenyl]methyl}amino)-2{methyl[6-(2,2,2-trifluoroethyl)thieno[2,3-d]pyrimidin-4-yl]amino}cyclopentan-1-ol hydrochloride

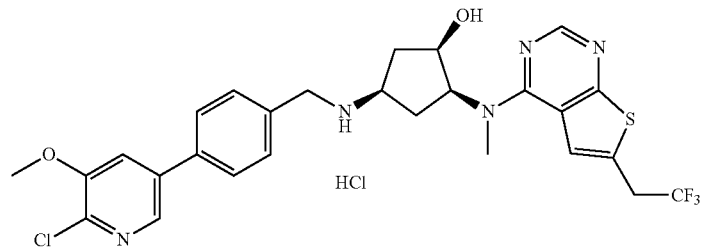 [SMILES: COc1cc(-c2ccc(CN[C@H]3C[C@@H](O)[C@@H](N(C)c4ncnc5sc(CC(F)(F)F)cc45)C3)cc2)cnc1Cl ; Cl]

$^1$H-NMR (DMSO-D$_6$) δ: 1.81-1.90 (1H, m), 2.26 2.34 (1H, m), 2.42 2.49 (2H, m), 3.44 (3H, s), 3.59 (1H, br s), 4.02 (3H, s), 4.09 (2H, q, J = 11.0 Hz), 4.26 (2H, br s), 4.35 (1H, br s), 4.90-4.99 (1H, m), 5.20 (1H, br s), 7.73-7.78 (3H, m), 7.84 (1H, d, J = 2.5 Hz), 7.91 (2H, d, J = 8.0 Hz), 8.35 (1H, d, J = 1.8 Hz), 8.36 (1H, s), 9.45-9.67 (2H, m). MS (m/z): 578 (M + H)$^+$.

Ex. 66

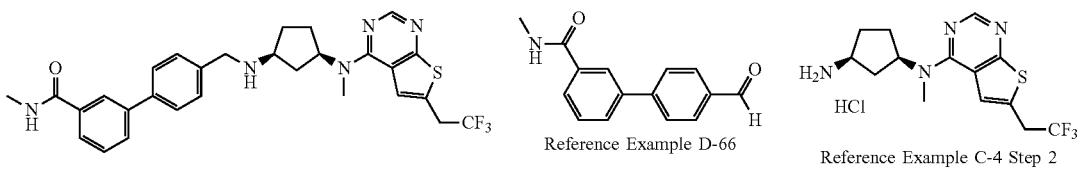

Reference Example D-66    Reference Example C-4 Step 2

N-methyl-4'-({[|(1S,3R)-3-{methyl[6-(2,2,2-trifluoroethyl)thieno[2,3-d]pyrimidin-4-yl]amino}cyclopentyl]amino}methyl)[1,1'-biphenyl]-3-carboxamide hydrochloride

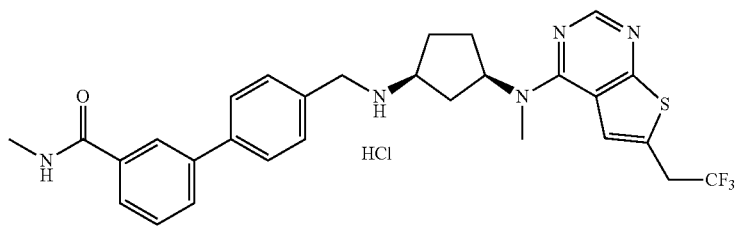 [SMILES: CNC(=O)c1cccc(-c2ccc(CN[C@H]3CC[C@@H](N(C)c4ncnc5sc(CC(F)(F)F)cc45)C3)cc2)c1 ; Cl]

1H-NMR (DMSO-D$_6$) δ: 1.89-1.91 (1H, m), 2.02-2.09 (4H, m), 2.34-2.41 (1H, m), 2.82 (3H, d, J = 4.9 Hz), 3.30 (3H, s), 3.63-3.66 (1H, m), 4.08-4.11 (2H, m), 4.21-4.24 (2H, m), 5.27-5.29 (1H, m), 7.57-7.58 (1H, m), 7.71-7.73 (3H, m), 7.85-7.86 (4H, m), 8.17 (1H, s), 8.38 (1H, s), 8.61-8.62 (1H, m), 9.43-9.56 (2H, m). MS (m/z): 554 (M + H)$^+$.

TABLE 2-21

Ex. 67

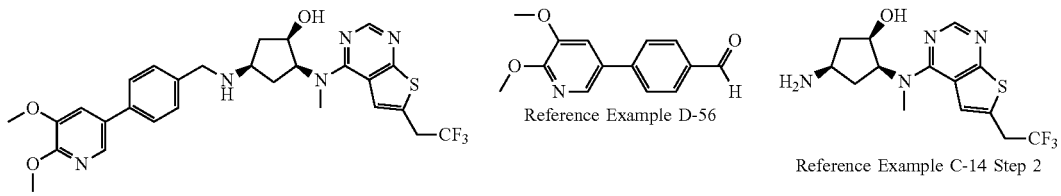

Reference Example D-56

Reference Example C-14 Step 2

(1R,2S,4R)-4-({[4(5,6-dimethoxypyridin-3yl)phenyl]
methyl}amino)-2-{methyl[6-(2,2,2-trifluoroethyl)thieno[2,3-d]
pyrimidin-4-yl]amino}cyclopentan-1-ol

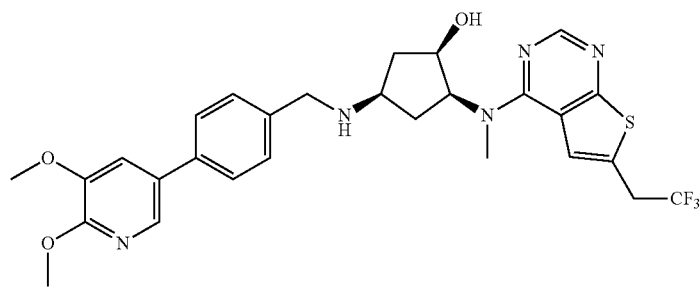

$^1$H-NMR (CDCl$_3$) δ:1.86-1.99 (2H, m), 2.01-2.08 (1H, m), 2.31-2.40 (1H, m), 3.43-3.48 (1H, m),
3.55 (3H, s), 3.63 (2H, q, J = 10.2 Hz), 3.89 (2H, d, J = 4.9 Hz), 3.95 (3H, s), 4.07 (3H, s), 4.47-4.50
(1H, m), 5.13 (1H, td, J = 9.8, 4.9 Hz), 7.24 (1H, d, J = 1.8 Hz), 7.40 (2H, d, J = 8.0 Hz),
7.41 (1H, s), 7.53 (2H, d, J = 8.0 Hz), 7.95 (1H, d, J = 1.8 Hz), 8.40 (1H, s).
(1R,2S,4R)-4-({[4-(5,6-dimethoxypyridin-3-yl)phenyl]methyl}amino)-2-{methyl[6-(2,2,2-
trifluoroethyl)thieno[2,3-d]pyrimidin-4-yl]amino}cyclopentan-1-ol hydrochloride

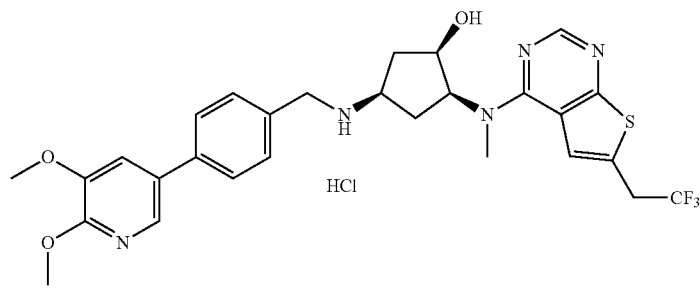 [SMILES: COc1cc(-c2ccc(CN[C@H]3C[C@@H](O)[C@@H](N(C)c4ncnc5sc(CC(F)(F)F)cc45)C3)cc2)cnc1OC]

$^1$H-NMR (DMSO-D$_6$) δ: 1.74-1.86 (1H, m), 2.25-2.47 (3H, m), 3.44 (3H, s), 3.57 (1H, br s), 3.90
(3H, s), 3.91 (3H, s), 4.09 (2H, q, J = 11.0 Hz), 4.23 (2H, br s), 4.33-4.39 (1H, m), 4.94 (1H, b rs),
5.20 (1H, br s), 7.57 (1H, d, J = 1.8 Hz), 7.63-7.70 (2H, m), 7.75 (1H, s), 7.80 (2H, d, J = 8.0
Hz), 8.06 (1H, d, J = 1.8 Hz), 8.36 (1H, s), 9.17-9.26 (2H, m). MS (m/z): 574 (M + H)$^+$.

Ex. 68

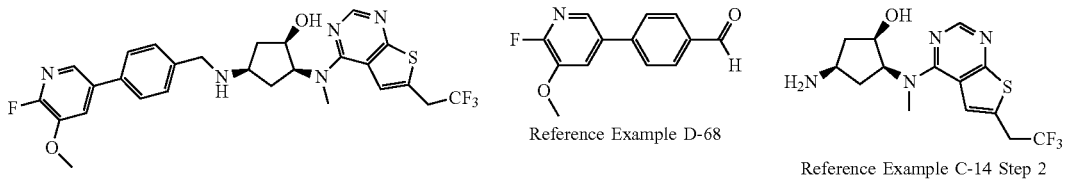

Reference Example D-68

Reference Example C-14 Step 2

(1R,2S,4R)-4-({[4-(6-fluoro-5-methoxypyridin-3-yl)phenyl]
methyl}amino)-2-{methyl[6-(2,2,2-trifluoroethyl)thieno[2,3-d]
pyrimidin-4-yl]amino}cyclopentan-1-ol hydrochloride TABLE 2-21-continued

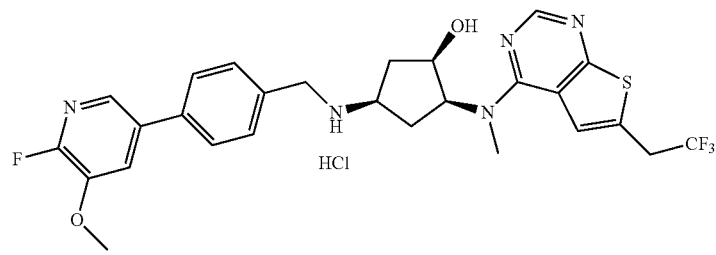 [SMILES: COc1cc(-c2ccc(CN[C@H]3C[C@@H](O)[C@@H](N(C)c4ncnc5sc(CC(F)(F)F)cc45)C3)cc2)cnc1F ; Cl]

¹H-NMR (DMSO-D₆) δ: 1.78-1.87 (1H, m), 2.25-2.36 (1H, m), 2.37-2.49 (2H, m), 3.44 (3H, s), 3.53-3.64 (1H, m), 4.00 (3H, s), 4.05-4.15 (2H, m), 4.22-4.31 (2H, m), 4.32-4.40 (1H, m), 4.88-4.99 (1H, m), 5.15-5.25 (1H, m), 7.68-7.74 (2H, m), 7.76 (1H, s), 7.85-7.90 (2H, m), 7.90-7.95 (1H, m), 8.07-8.10 (1H, m), 8.36 (1H, s), 9.30-9.50 (2H, m). MS (m/z) : 562 (M + H)⁺.

TABLE 2-22

Ex. 69

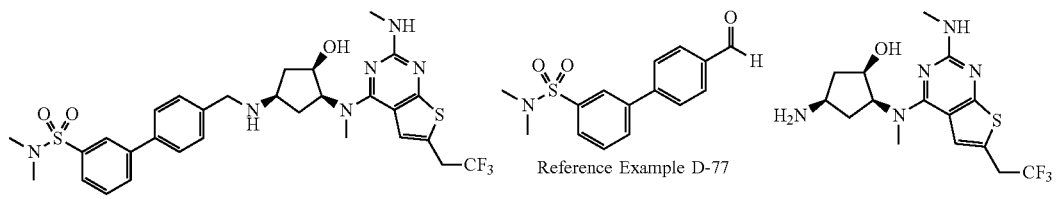

Reference Example D-77

Reference Example C-20 Step 3

4'-({[(1R,3R,4S)-3-hydroxy-4-{methyl[2-(methylamino)-6-(2,2,2-trifluoroethyl)thieno[2,3-d]pyrimidin-4-yl]amino}cyclopentyl]amino}methyl)-N,N-dimethyl[1,1'-biphenyl]-3-sulfonamide hydrochloride

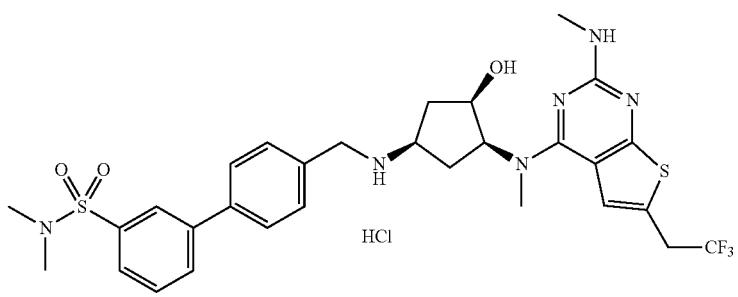 [SMILES: CNc1nc(N(C)[C@H]2C[C@@H](NCc3ccc(-c4cccc(S(=O)(=O)N(C)C)c4)cc3)C[C@H]2O)c2cc(CC(F)(F)F)sc2n1 ; Cl]

¹H-NMR (DMSO-D₆) δ: 1.87-1.90 (1H, m), 2.28-2.46 (3H, m), 2.69 (6H, s), 2.82 (3H, s), 3.38 (3H, s), 3.57-3.59 (1H, m), 3.85-3.88 (2H, m), 4.25-4.27 (2H, m), 4.40-4.41 (1H, m), 4.77 4.83 (1H, m), 7.43 (1H, s), 7.72-8.04 (8H, m), 9.41-9.43 (2H, m). MS (m/z): 649 (M + H)⁺.

Ex. 70

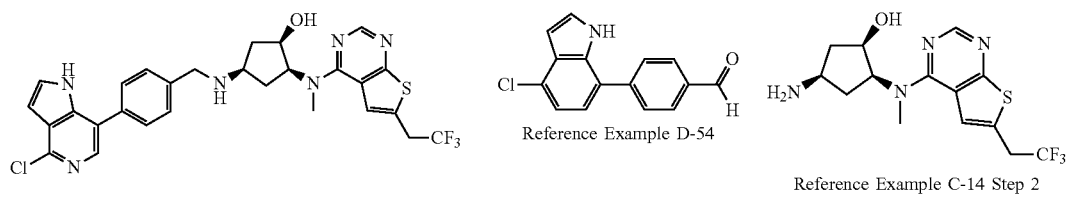

Reference Example D-54

Reference Example C-14 Step 2

(1R,2S,4R)-4-({[4-(4-chloro-1H-pyrrolo[3,2-c]pyridin-7-yl)phenyl]methyl}amino)-2-{methyl[6-(2,2,2-trifluoroethyl)thieno[2,3-d]pyrimidin-4-yl]amino}cyclopentan-1-ol hydrochloride TABLE 2-22-continued

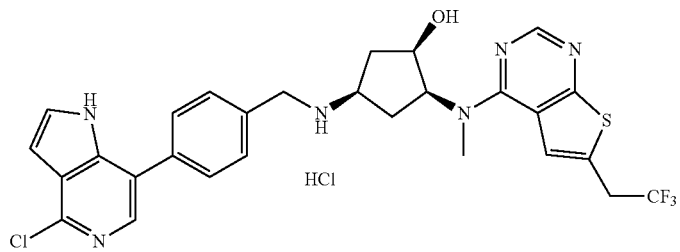 [SMILES: CN(c1ncnc2sc(CC(F)(F)F)cc12)[C@H]1C[C@@H](NCc2ccc(-c3cnc(Cl)c4cc[nH]c34)cc2)C[C@H]1O ; Cl]

HCl $^1$H-NMR (DMSO-D$_6$) δ: 1.83-1.88 (1H, m), 2.29-2.37 (1H, m), 2.43-2.49 (2H, m), 3.46 (3H, s), 3.61 (1H, br s), 4.10 (2H, q, J = 11.0 Hz), 4.31 (2H, br s), 4.36 (1H, br s), 4.90-5.01 (1H, m), 6.68 (1H, dd, J = 3.1, 1.8 Hz), 7.60 (1H, dd, J = 3.1, 2.5 Hz), 7.74-7.77 (1H, m), 7.77-7.79 (4H, m), 8.05 (1H, s), 8.38 (1H, s), 9.47-9.57 (2H, m), 12.03 (1H, s). MS (m/z): 587, 589 (M + H)$^+$.

TABLE 2-23

Ex. 71

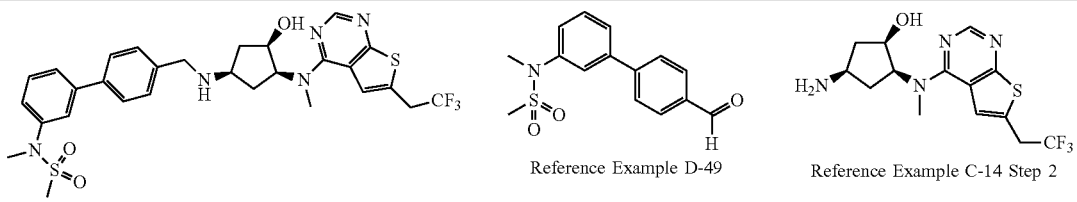

Reference Example D-49    Reference Example C-14 Step 2

N-[4'-({[(1R,3R,4S)-3-hydroxy-4-{methyl[6-(2,2,2-trifluoroethyl)thieno[2,3-d]pyrimidin-4-yl]amino}cyclopentyl]amino}methyl)[1,1'-biphenyl]-3-yl]-N-methylmethanesulfonamide

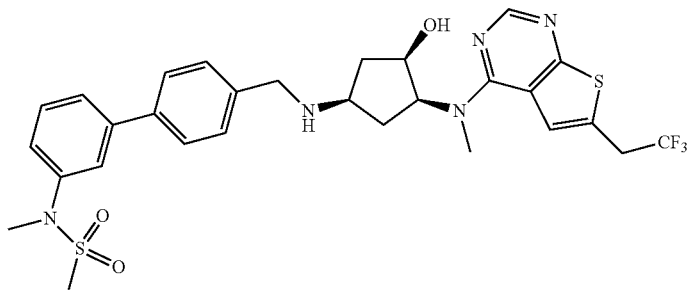 [SMILES: CN(c1ncnc2sc(CC(F)(F)F)cc12)[C@H]1C[C@@H](NCc2ccc(-c3cccc(N(C)S(C)(=O)=O)c3)cc2)C[C@H]1O]

$^1$H-NMR (CDCl3) δ: 1.82-2.11 (3H, m), 2.30-2.41 (1H, m), 2.89 (3H, s), 3.39 (3H, s), 3.41-3.49 (1H, m), 3.55 (3H, s), 3.58-3.68 (2H, m), 3.84-3.95 (2H, m), 4.44-4.52 (1H, m), 5.08-5.18 (1H, m), 7.33-7.38 (1H, m), 7.38-7.43 (3H, m), 7.44-7.50 (1H, m), 7.50-7.62 (4H, m), 8.40 (1H, s). MS (m/z): 620 (M + H)$^+$.
N-[4'-({[(1R,3R,4S)-3-hydroxy-4-{methyl[6-(2,2,2-trifluoroethyl)thieno[2,3-d]pyrimidin-4-yl]amino}cyclopentyl]amino}methyl)[1,1'-biphenyl]-3-yl]-N-methylmethanesulfonamide hydrochloride

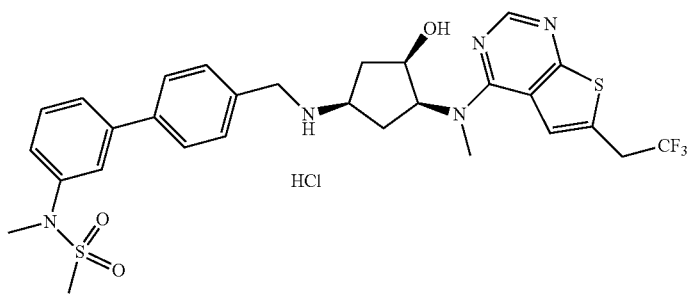 [SMILES: CN(c1ncnc2sc(CC(F)(F)F)cc12)[C@H]1C[C@@H](NCc2ccc(-c3cccc(N(C)S(C)(=O)=O)c3)cc2)C[C@H]1O ; Cl]

HCl $^1$H-NMR (DMSO-D$_6$) δ: 1.78-1.87 (1H, m), 2.27-2.34 (1H, m), 2.40-2.52 (2H, m), 3.00 (3H, s), 3.31 (3H, s), 3.44 (3H, s), 3.51-3.67 (1H, m), 4.02-4.15 (2H, m), 4.20-4.30 (2H, m), 4.33-4.40 (1H, m), 4.87-5.00 (1H, m), 5.08-5.34 (1H, m), 7.42-7.47 (1H, m), 7.50-7.56 (1H, m), 7.63-7.72 (4H, m), 7.74-7.82 (3H, m), 8.37 (1H, s), 9.28-9.49 (2H, m). MS (m/z): 620 (M + H)$^+$.

TABLE 2-24

Ex. 72

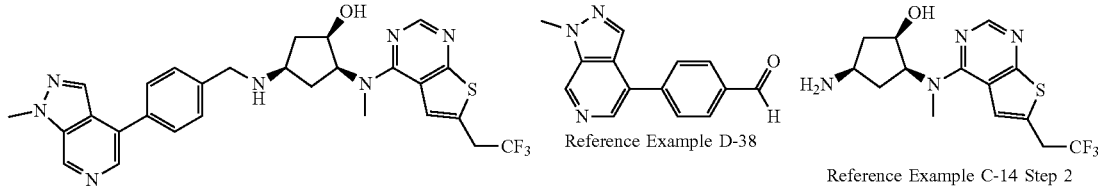

(1R,2S,4R)-4-({[4-(1-methyl-1H-pyrazolo[3,4-c]pyridin-4-yl)phenyl]
methyl}amino)-2-{methyl[6-(2,2,2-trifluoroethyl)thieno[2,3-d]
pyrimidin-4-yl]amino}cyclopentan-1-ol hydrochloride

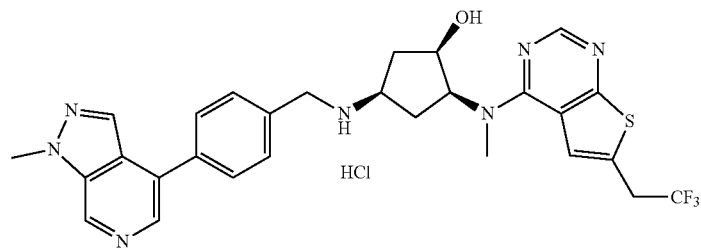 [SMILES: CN(c1ncnc2sc(CC(F)(F)F)cc12)[C@H]1C[C@@H](NCc2ccc(-c3cncc4c3cnn4C)cc2)C[C@H]1O ; Cl]

¹H-NMR (DMSO-D₆) δ: 1.76-1.87 (1H, m), 2.29-2.47 (3H, m), 3.45 (3H, s), 3.64 (1H, br s), 4.09 (2H, q, J = 11.0 Hz), 4.25 (3H, s), 4.31 (2H, br s), 4.38 (1H, br s), 4.91-5.00 (1H, m), 5.19-5.23 (1H, m), 7.75-7.80 (3H, m), 7.93 (2H, d, J = 8.0 Hz), 8.36 (1H, s), 8.37 (1H, s), 8.47 (1H, s), 9.21-9.41 (2H, m), 9.24 (1H, s). MS (m/z): 568 (M + H)⁺.

TABLE 2-25

Ex. 73

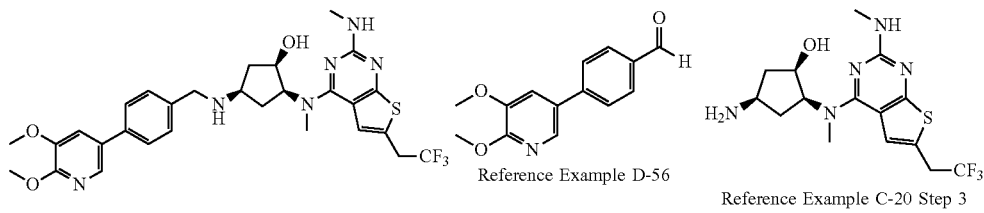

(1R,2S,4R)-4-({[4-(5,6-dimethoxypyridin-3-yl)phenyl]methyl}amino)-2-{methyl[2-(methylamino)-6-(2,2,2-trifluoroethyl)
thieno[2,3-d]pyrimidin-4-yl]amino}cyclopentan-1-ol

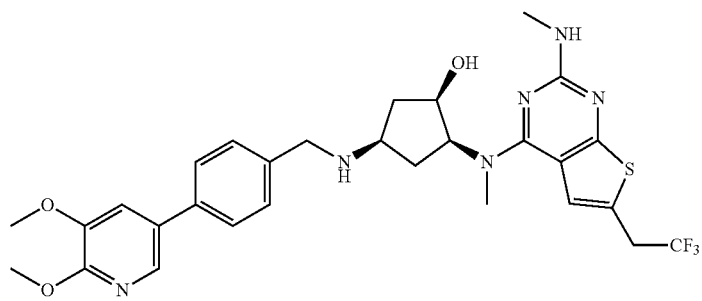 [SMILES: CNc1nc(N(C)[C@H]2C[C@@H](NCc3ccc(-c4cnc(OC)c(OC)c4)cc3)C[C@H]2O)c2cc(CC(F)(F)F)sc2n1]

¹H-NMR (CDCl₃) δ: 1.84 (1H, d, J = 14.1 Hz), 1.95-2.09 (2H, m), 2.31 (1H, ddd, J = 13.5, 9.2, 6.7 Hz), 2.96 (3H, d, J = 4.9 Hz), 3.36-3.43 (1H, m), 3.46 (3H, s), 3.51 (2H, q, J = 10.4 Hz), 3.88 (2H, d, J = 1.8 Hz), 3.95 (3H, s), 4.07 (3H, s), 4.46-4.50 (1H, m), 4.74 (1H, dt, J = 4.9, 4.9 Hz), 4.83-4.90 (1H, m), 7.18 (1H, s), 7.24 (1H, d, J = 1.8 Hz), 7.41 (2H, d, J = 8.6 Hz), 7.52 (2H, d, J = 8.6 Hz), 7.95 (1H, d, J = 1.8 Hz).
(1R,2S,4R)-4-({[4-(5,6-dimethoxypyridin-3-yl)phenyl]methyl}amino)-2-{methyl[2-
(methylamino)-6-(2,2,2-trifluoroethyl)thieno[2,3-d]pyrimidin-4-yl]amino}cyclopentan-1-ol hydrochloride

TABLE 2-25-continued

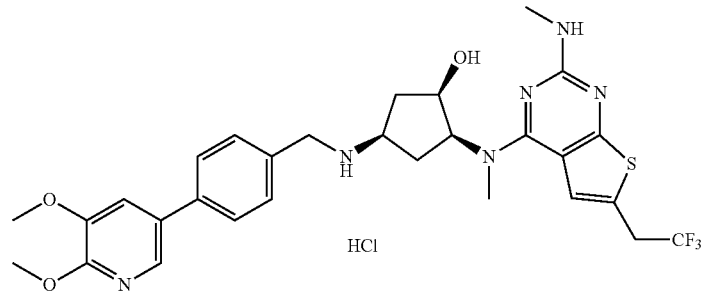 [SMILES: CNc1nc(N(C)[C@H]2C[C@@H](NCc3ccc(-c4cnc(OC)c(OC)c4)cc3)C[C@H]2O)c2cc(CC(F)(F)F)sc2n1 ; Cl]

¹H-NMR (DMSO-D₆) δ: 1.75-1.86 (1H, m), 2.20-2.46 (3H, m), 2.78 (3H, d, J = 4.3 Hz), 3.36 (3H, s), 3.38 (2H, q, J = 6.7 Hz), 3.48-3.62 (1H, m), 3.90 (3H, s), 3.91 (3H, s), 4.19-4.29 (2H, m), 4.39 (1H, br s), 4.72-4.83 (1H, m), 5.18 (1H, br s), 6.67-6.70 (1H, m), 7.44 (1H, s), 7.57 (1H, d, J = 2.5 Hz), 7.66 (2H, s), 7.81 (2H, d, J = 8.0 Hz), 8.06 (1H, d, J = 2.5 Hz), 9.21-9.36 (2H, m). MS (m/z): 603 (M + H)⁺.

TABLE 2-26

Ex. 74

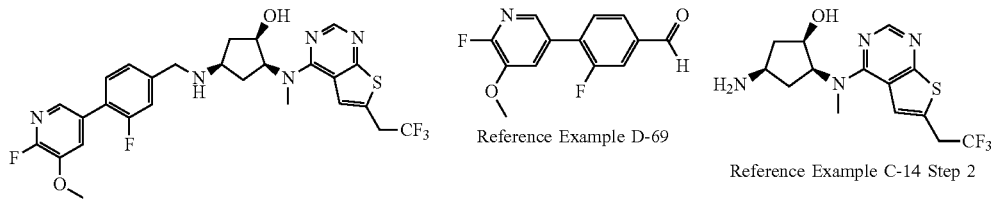

(1R,2S,4R)-4-({[3-fluoro-4-(6-fluoro-5-methoxypyridin-3-yl)phenyl]methyl}amino)-2-{methyl[6-(2,2,2-trifluoroethyl)thieno[2,3-d]pyrimidin-4-yl]amino}cyclopentan-1-ol hydrochloride

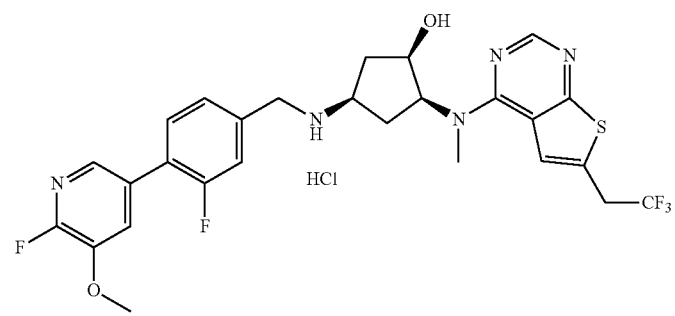 [SMILES: COc1cc(-c2ccc(CN[C@H]3C[C@@H](O)[C@@H](N(C)c4ncnc5sc(CC(F)(F)F)cc45)C3)cc2F)cnc1F ; Cl]

¹H-NMR (DMSO-D₆) δ: 1.79-1.86 (1H, m), 2.28 2.35 (1H, m), 2.41-2.48 (2H, m), 3.45 (3H, s), 3.56-3.62 (1H, m), 3.96 (3H, s), 4.09 (2H, q, J = 11.0 Hz), 4.25-4,32 (2H, m), 4.34-4.38 (1H, m), 4.90-4.98 (1H, m), 5.21 (1H, br s), 7.55-7.58 (1H, m), 7.67 (1H, d, J = 11.0 Hz), 7.73-7.79 (2H, m), 7.83 (1H, d, J = 11.0 Hz), 7.93 7.96 (1H, m), 8.36 (1H, s), 9.40-9.57 (2H, m). MS (m/z): 580 (M + H)⁺.

Ex. 75

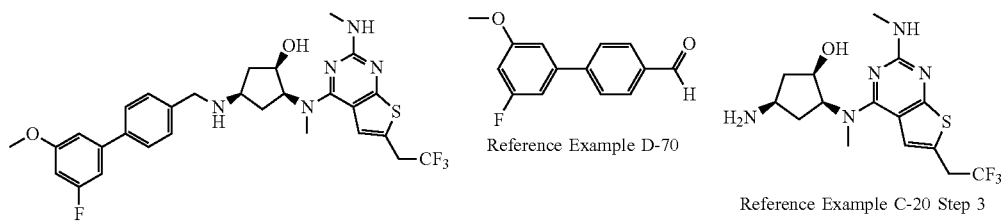

(1R,2S,4R)-4-{[(3'-fluoro-5'-methoxy[1,1'-biphenyl]-4-yl)methyl]amino}-2-{methyl[2-(methylamino)-6-(2,2,2-trifluoroethyl)thieno[2,3-d]pyrimidin-4-yl]amino}cyclopentan-1ol hydrochloride TABLE 2-26-continued

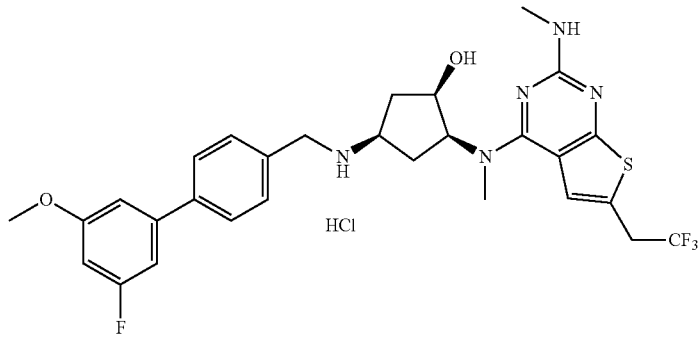 [SMILES: CNc1nc(N(C)[C@H]2C[C@@H](NCc3ccc(-c4cc(F)cc(OC)c4)cc3)C[C@H]2O)c2cc(CC(F)(F)F)sc2n1 ; Cl]

¹H-NMR (DMSO-D₆) δ: 1.76-1.87 (1H, m), 2.20-2.47 (3H, m), 2.74-2.82 (3H, m), 3.36 (3H, s), 3.48-3.62 (1H, m), 3.81-3.97 (2H, m), 3.85 (3H, s), 4.17-4.31 (2H, m), 4.34 4.43 (1H, m), 4.72-4.85 (1H, m), 5.11-5.22 (1H, m), 6.63-6.84 (1H, m), 6.84-6.90 (1H, m), 7.09-7.13 (1H, m), 7.13-7.18 (1H, m), 7.45 (1H, s), 7.64-7.70 (2H, m), 7.78-7.84 (2H, m), 9.27-9.54 (2H, m), MS (m/z): 590 (M + H)⁺.

TABLE 2-27

Ex. 76

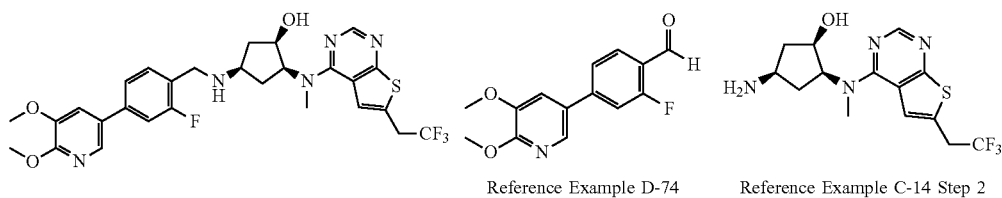

Reference Example D-74    Reference Example C-14 Step 2

(1R,2S,4R)-4-({[4-(5,6-dimethoxypyridin-3-yl)-2-fluorophenyl]methyl}amino)-2-{methyl[6-(2,2,2-trifluoroethyl)thieno[2,3-d]pyrimidin-4-yl]amino}cyclopentan-1-ol hydrochloride

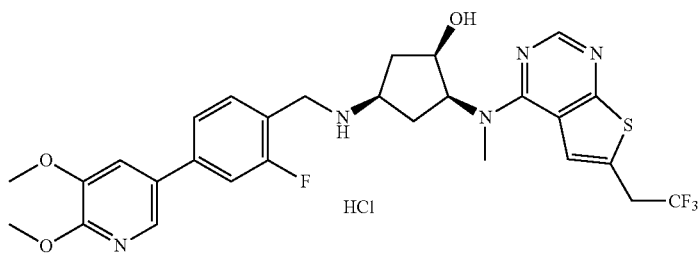 [SMILES: COc1cc(-c2ccc(CN[C@H]3C[C@@H](O)[C@@H](N(C)c4ncnc5sc(CC(F)(F)F)cc45)C3)c(F)c2)cnc1OC ; Cl]

¹H-NMR (DMSO-D₆) δ: 1.77-1.86 (1H, m), 2.29-2.37 (1H, m), 2.39-2.49 (2H, m), 3.44 (3H, s), 3.62-3.70 (1H, m), 3.90 (3H, s), 3.92 (3H, s), 4.09 (2H, q, J = 11.0 Hz), 4.28 (2H, t, J = 5.5 Hz), 4.36 (1H, br s), 4.92-5.01 (1H, m), 5.23 (1H, br s), 7.63 (1H, d, J = 1.8 Hz), 7.70 (1H, dd, J = 8.0, 1.8 Hz), 7.76 (2H, s), 7.77-7.80 (1H, m), 8.13 (1H, d, J = 2.5 Hz), 8.37 (1H, s), 9.38-9.56 (2H, m). MS (m/z): 592 (M + H)⁺.

Ex. 77

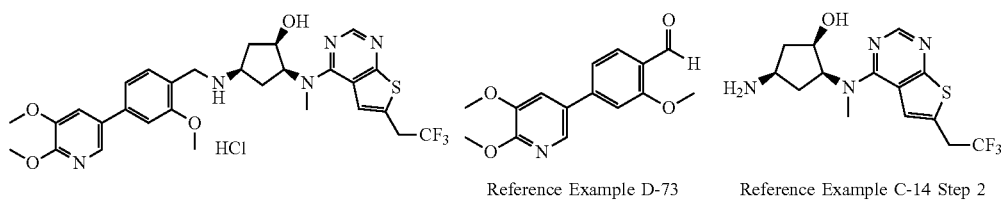

Reference Example D-73    Reference Example C-14 Step 2

(1R,2S,4R)-4-({[4-(5,6-dimethoxypyridin-3-yl)-2-methoxyphenyl]methyl}amino)-2-{methyl[6-(2,2,2-trifluoroethyl)thieno[2,3-d]pyrimidin-4-yl]amino}cyclopentan-1-ol hydrochloride TABLE 2-27-continued

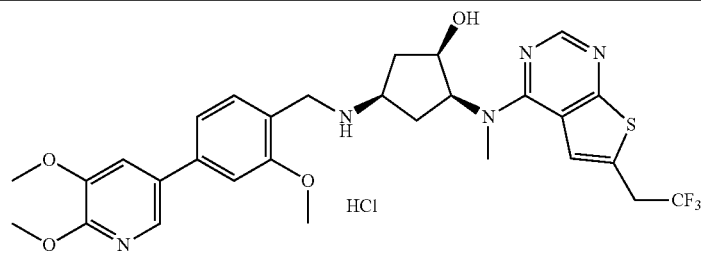

¹H-NMR (DMSO-D₆) δ: 1.84 (1H, ddd, J = 14.1, 6.7, 3.1 Hz), 2.27-2.36 (1H, m), 2.41-2.49 (2H, m), 3.45 (3H, s), 3.57-3.66 (1H, m), 3.91 (3H, s), 3.91 (3H, s), 3.98 (3H, s), 4.09 (2H, q, J = 11.0 Hz), 4.19 (2H, t, J = 5.5 Hz), 4.36 (1H, br s), 4.91-4.99 (1H, m), 5.26 (1H, br s), 7.35 (1H, dd, J = 8.0, 1.2 Hz), 7.37 (1H, d, J = 1.2 Hz), 7.58 (1H, d, J = 8.0 Hz), 7.58 (1H, s), 7.76 (1H, s), 8.10 (1H, d, J = 1.8 Hz), 8.37 (1H, s), 9.11-9.24 (2H, m). MS (m/z): 604 (M + H)⁺.

TABLE 2-28

Ex. 78

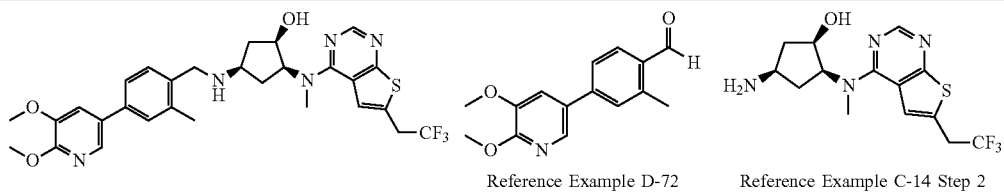

Reference Example D-72    Reference Example C-14 Step 2

(1R,2S,4R)-4-({[4-(5,6-dimethoxypyridin-3-yl)-2-methylphenyl]methyl}amino)-2-{methyl[6-(2,2,2-trifluoroethyl)thieno[2,3-d]pyrimidin-4-yl]amino}cyclopentan-1-ol hydrochloride

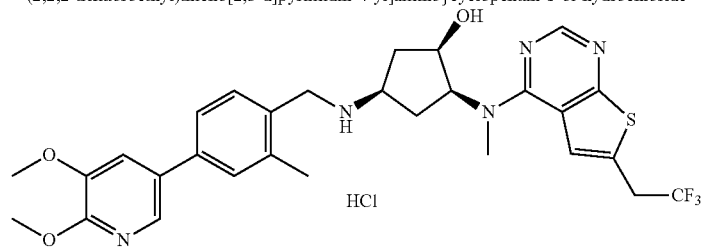

¹H-NMR (DMSO-D₆) δ: 1.83-1.90 (1H, m), 2.33-2.39 (1H, m), 2.41-2.48 (1H, m), 2.50 (3H, s), 2.52-2.60 (1H, m), 3.45 (3H, s), 3.72 (1H, br s), 3.90 (3H, s), 3.91 (3H, s), 4.10 (2H, q, J = 11.0 Hz), 4.22 (2H, t, J = 6.1 Hz), 4.35-4.40 (1H, m), 4.94-5.02 (1H, m), 5.10-5.27 (1H, m), 7.57 (1H, d, J = 1.8 Hz), 7.63 (2H, s), 7.65 (1H, s), 7.77 (1H, s), 8.05 (1H, d, J = 1.8 Hz), 8.38 (1H, s), 9.22-9.32 (1H, m), 9.38-9.44 (1H, m), MS (m/z): 588 (M + H)⁺.

Ex. 79

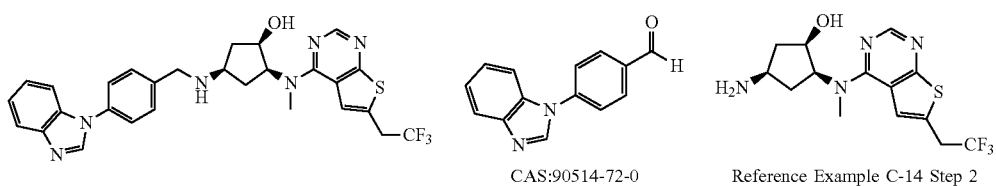

CAS:90514-72-0    Reference Example C-14 Step 2

(1R,2S,4R)-4-({[4-(1H-benzimidazol-yl)phenyl]methyl}amino)-2-{methyl[6-(2,2,2-trifluoroethyl)thieno[2,3-d]pyrimidin-4-yl]amino}cyclopentan-1-ol hydrochloride

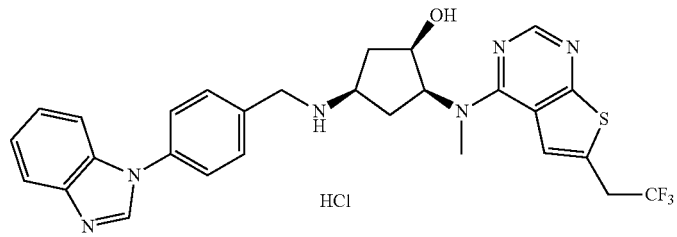 [SMILES: CN(c1ncnc2sc(CC(F)(F)F)cc12)[C@H]1C[C@@H](NCc2ccc(-n3cnc4ccccc43)cc2)C[C@H]1O ; Cl]

¹H-NMR (DMSO-D₆) δ: 1.83-1.93 (1H, m), 2.28-2.38 (1H, m), 2.43-2.57 (2H, m), 3.45 (3H, s), 3.56-3.71 (1H, m), 4.10 (2H, q, J = 11.0 Hz), 4.25-4.42 (3H, m), 4.91-5.03 (1H, m), 5.21 (1H, br s), 7.32-7.43 (2H, m), 7.66 (1H, d, J = 7.4 Hz), 7.73-7.93 (6H, m), 8.37 (1H, s), 8.70 (1H, s), 9.56 (1H, br s), 9.62 (1H, br s). MS: m/z 553 (M + H)⁺.

TABLE 2-29

Ex. 80

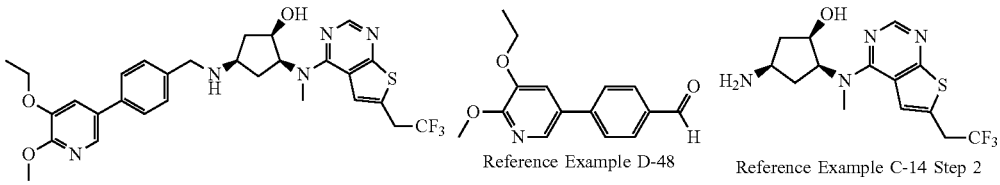

Reference Example D-48   Reference Example C-14 Step 2

(1R,2S,4R)-4-({[4-(5-ethoxy-6-methoxypyridin-3-yl)phenyl]methyl}amino)-2-{methyl[6-(2,2,2-trifluoroethyl)thieno[2,3-d]pyrimidin-4-yl]amino}cyclopentan-1-ol hydrochloride

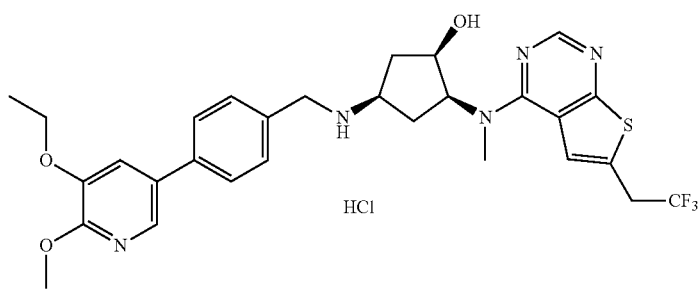 [SMILES: CCOc1cc(-c2ccc(CN[C@H]3C[C@@H](O)[C@@H](N(C)c4ncnc5sc(CC(F)(F)F)cc45)C3)cc2)cnc1OC ; Cl]

$^1$H-NMR (DMSO-D$_6$) δ: 1.35-1.40 (3H, m), 1.78-1.90 (1H, m), 2.26-2.37 (1H, m), 2.40-2.55 (2H, m), 3.44 (3H, s), 3.51-3.66 (1H, m), 3.91 (3H, s), 4.02-4.29 (6H, m), 4.31-4.39 (1H, m), 4.89-5.02 (1H, m), 5.04-5.34 (1H, m), 7.54-7.57 (1H, m), 7.65-7.70 (2H, m), 7.74-7.81 (3H, m), 8.04-8.07 (1H, m), 8.36-8.38 (1H, m), 9.35-9.57 (2H, m), MS (m/z): 588 (M + H)$^+$.

TABLE 2-30

Ex. 81

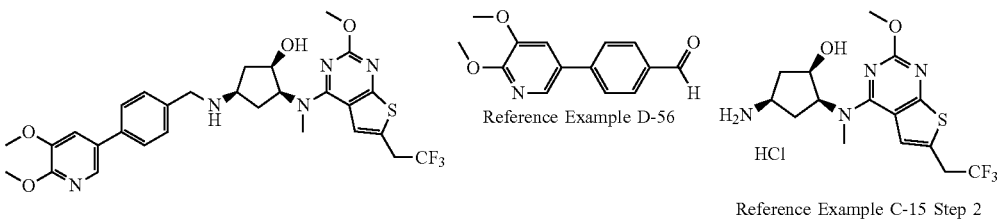

Reference Example D-56   Reference Example C-15 Step 2

(1R,2S,4R)-4-({[4-(5,6-dimethoxypyridin-3-yl)phenyl]methyl}amino)-2-{[2-methoxy-6-(2,2,2-trifluoroethyl)thieno[2,3-d]pyrimidin-4-yl](methyl)amino}cyclopentan-1-ol

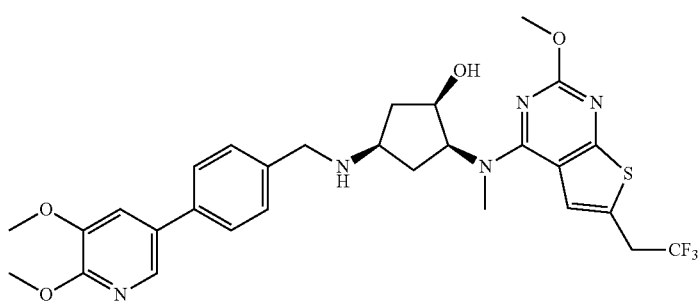 [SMILES: COc1nc(N(C)[C@H]2C[C@@H](NCc3ccc(-c4cnc(OC)c(OC)c4)cc3)C[C@H]2O)c2cc(CC(F)(F)F)sc2n1]

$^1$H-NMR (CDCl$_3$) δ: 1.84-1.97 (2H, m), 2.03-2.08 (1H, m), 2.32-2.35 (1H, m), 3.38-3.41 (2H, m), 3.52 (3H, s), 3.55-3.60 (2H, m), 3.88-3.88 (2H, m), 3.94 (6H, s), 4.06 (3H, s), 4.48-4.51 (1H, m), 5.04-5.13 (1H, m), 7.25-7.29 (2H, m), 7.40 (2H, d, J = 8.0 Hz), 7.52 (2H, d, J = 8.0 Hz), 7.95-7.95 (1H, m), MS (m/z): 604 (M + H)$^+$.

(1R,2S,4R)-4-({[4-(5,6-dimethoxypyridin-3-yl)phenyl]methyl}amino)-2-{[2-methoxy-6-(2,2,2-trifluoroethyl)thieno[2,3-d]pyrimidin-4-yl](methyl)amino}cyclopentan-1-ol hydrochloride

TABLE 2-30-continued

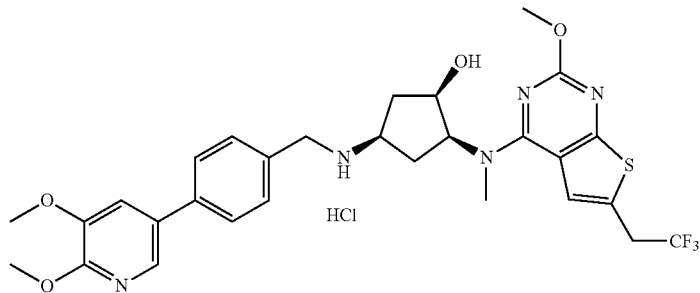 [SMILES: COc1nc(N(C)[C@H]2C[C@@H](NCc3ccc(-c4cnc(OC)c(OC)c4)cc3)C[C@H]2O)c2cc(CC(F)(F)F)sc2n1 ; Cl]

$^1$H-NMR (DMSO-D$_6$) δ: 1.85-1.88 (1H, m), 2.29-2.33 (1H, m), 2.42-2.45 (1H, m), 2.47-2.48 (1H, m), 3.41 (3H, s), 3.52-3.55 (1H, m), 3.84 (3H, s), 3.89-4.00 (8H, m), 4.22-4.24 (2H, m), 4.36-4.38 (1H, m), 4.82-4.88 (1H, m), 7.51-7.56 (2H, m), 7.67-7.77 (4H, m), 8.04 (1H, s), 9.38-9.44 (2H, m). MS (m/z): 604 (M + H)$^+$.

TABLE 2-31

Ex. 82

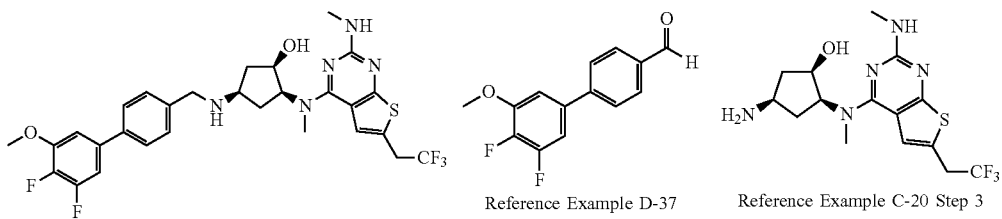

Reference Example D-37     Reference Example C-20 Step 3

(1R,2S,4R)-4-{[(3',4'-difluoro-5'-methoxy[1,1'-biphenyl]-4-yl)methyl]amino}-2-{methyl[2-(methylamino)-6-(2,2,2-trifluoroethyl)thieno[2,3-d]pyrimidin-4-yl]amino}cyclopentan-1-ol hydrochloride

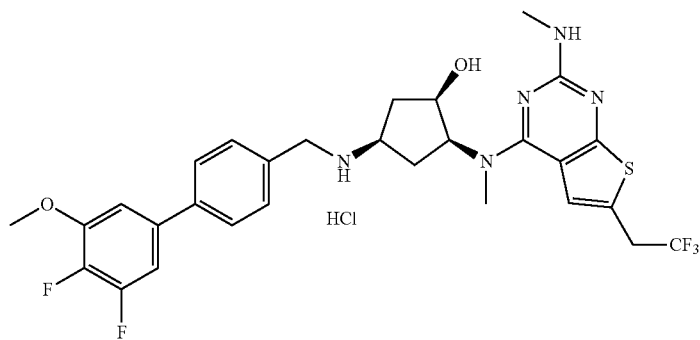 [SMILES: CNc1nc(N(C)[C@H]2C[C@@H](NCc3ccc(-c4cc(F)c(F)c(OC)c4)cc3)C[C@H]2O)c2cc(CC(F)(F)F)sc2n1 ; Cl]

$^1$H-NMR (DMSO-D$_6$) δ: 1.81-1.84 (1H, m), 2.30-2.43 (3H, m), 2.80 (3H, s), 3.37 (3H, s), 3.56-3.59 (1H, m), 3.85-3.87 (2H, m), 3.99 (3H, s), 4.24-4.26 (2H, m), 4.39-4.41 (1H, m), 4.79-4.80 (1H, m), 7.30-7.33 (2H, m), 7.41 (1H, s), 7.65 (2H, d, J = 8.3 Hz), 7.81 (2H, d, J = 8.3 Hz), 9.17-9.22 (2H, m). MS (m/z): 608 (M + H)$^+$.

Ex. 83

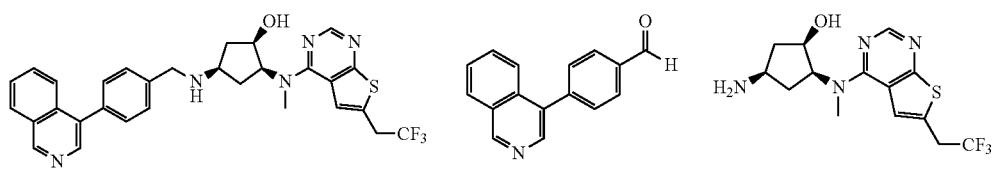

(1R,2S,4R)-4-({[4-(isoquinolin-4-yl)phenyl]methyl}amino)-2-{methyl[6-(2,2,2-trifluoroethyl)thieno[2,3-d]pyrimidin-4-yl]amino}cyclopentan-1-ol hydrochloride TABLE 2-31-continued

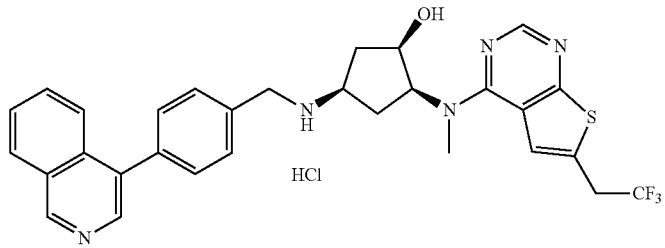 [SMILES: CN(c1ncnc2sc(CC(F)(F)F)cc12)[C@H]1C[C@@H](NCc2ccc(-c3cncc4ccccc34)cc2)C[C@H]1O ; Cl]

¹H-NMR (DMSO-D₆) δ: 1.83-1.92 (1H, m), 2.30-2.49 (2H, m), 2.52-2.59 (1H, m), 3.46 (3H, s), 3.66 (1H, br s), 4.10 (2H, q, J = 11.2 Hz), 4.33 (2H, br s), 4.38 (1H, br s), 4.93-5.02 (1H, m), 5.16-5.26 (1H, m), 7.67 (2H, d, J = 8.0 Hz), 7.76-7.83 (4H, m), 7.85-7.90 (2H, m), 8.30 (1H, d, J = 8.6 Hz), 8.37 (1H, s), 8.49 (1H, s), 9.39-9.55 (2H, m), 9.45 (1H, s). MS (m/z): 564 (M + H)⁺.

TABLE 2-32

Ex. 84

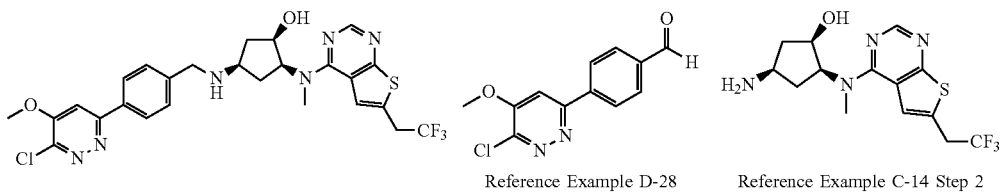

Reference Example D-28    Reference Example C-14 Step 2

(1R,2S,4R)-4-({[4-(6-chloro-5-methoxypyridazin-3-yl)phenyl]methyl}amino)-2-{methyl[6-(2,2,2-trifluoroethyl)thieno[2,3-d]pyrimidin-4-yl]amino}cyclopentan-1-ol

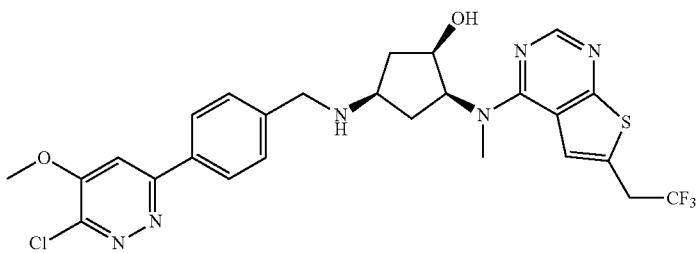 [SMILES: COc1cc(-c2ccc(CN[C@H]3C[C@@H](O)[C@@H](N(C)c4ncnc5sc(CC(F)(F)F)cc45)C3)cc2)nnc1Cl]

¹H-NMR (CDCl₃) δ: 1.85-1.92 (1H, m), 1.94-2.04 (1H, m), 2.06-2.13 (1H, m), 2.35 (1H, ddd, J = 14.9, 8.4, 5.4 Hz), 3.41-3.48 (1H, m), 3.54 (3H, s), 3.63 (2H, q, J = 10.2 Hz), 3.91 (1H, d, J = 13.5 Hz), 3.95 (1H, d, J = 13.5 Hz), 4.07 (3H, s), 4.48-4.52 (1H, m), 5.08 (1H, td, J = 9.7, 4.5 Hz), 7.22 (1H, s), 7.40 (1H, s), 7.46-7.51 (2H, m), 7.98-8.03 (2H, m), 8.40 (1H, s). MS (m/z): 579, 581 (M + H)⁺.

(1R,2S,4R)-4-({[4-(6-chloro-5-methoxypyridazin-3-yl)phenyl]methyl}amino)-2-{methyl[6-(2,2,2-trifluoroethyl)thieno[2,3-d]pyrimidin-4-yl]amino}cyclopentan-1-ol hydrochloride

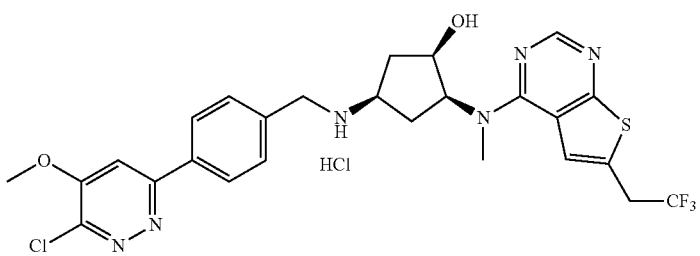 [SMILES: COc1cc(-c2ccc(CN[C@H]3C[C@@H](O)[C@@H](N(C)c4ncnc5sc(CC(F)(F)F)cc45)C3)cc2)nnc1Cl ; Cl]

¹H-NMR (DMSO-D₆) δ: 1.80-1.90 (1H, m), 2.26-2.36 (1H, m), 2.42-2.54 (2H, m), 3.44 (3H, s), 3.55-3.67 (1H, m), 4.09 (2H, q, J = 10.7 Hz), 4.13 (3H, s), 4.25-4.40 (3H, m), 4.90-5.00 (1H, m), 5.20 (1H, br s), 7.75 (1H, s), 7.79 (2H, d, J = 8.0 Hz), 7.92 (1H, s), 8.28 (2H, d, J = 8.0 Hz) 8.36 (1H, s), 9.47 (1H, br s), 9.54 (1H, br s). MS (m/z): 579, 581 (M + H)⁺.

TABLE 2-33

Ex. 85

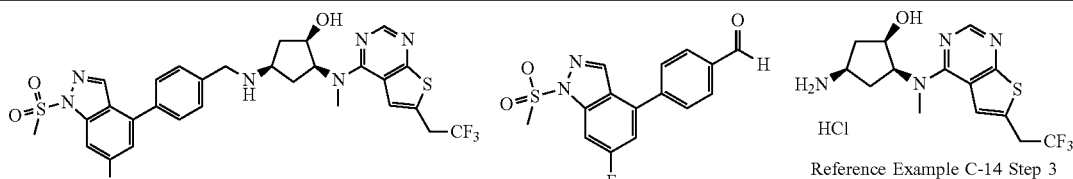

Reference Example D-41    Reference Example C-14 Step 3

(1R,2S,4R)-4-[({4-[6-fluoro-1-(methanesulfonyl)-1H-indazol-4-yl]phenyl}methyl)amino]-2-
{methyl[6-(2,2,2-trifluoroethyl)thieno[2,3-d]pyrimidin-4-yl]amino}cyclopentan-1-ol hydrochloride

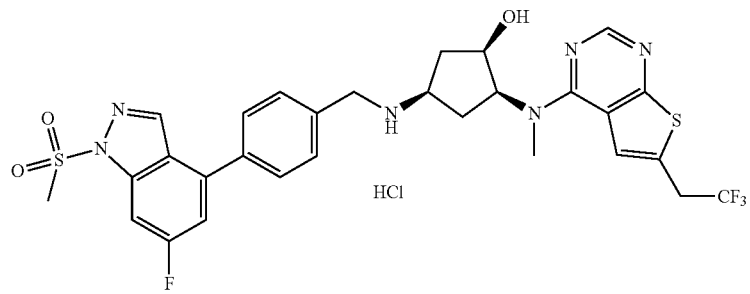 [SMILES: CN(c1ncnc2sc(CC(F)(F)F)cc12)[C@H]1C[C@@H](NCc2ccc(-c3cc(F)cc4c3cnn4S(C)(=O)=O)cc2)C[C@H]1O ; Cl]

$^1$H-NMR (DMSO-D$_6$) δ: 1.79-1.88 (1H, m), 2.29-2.36 (1H, m), 2.38-2.49 (2H, m), 3.45 (3H, s),
3.57 (3H, s), 3.60-3.68 (1H, m), 4.10 (2H, q, J = 11.2 Hz), 4.31 (2H, br s), 4.38 (1H, br s), 4.92-
5.01 (1H, m), 5.21 (1H, br s), 7.54 (1H, dd, J = 10.1, 2.1 Hz), 7.74 (1H, dd, J = 8.6, 2.5 Hz), 7.76
(1H, s), 7.78 (2H, d, J = 8.0 Hz), 7.88 (2H, d, J = 8.0 Hz), 8.37 (1H, s), 8.65 (1H, d, J = 1.2 Hz),
9.30-9.45 (2H, m). MS (m/z): 649 (M + H)$^+$.

Ex. 86

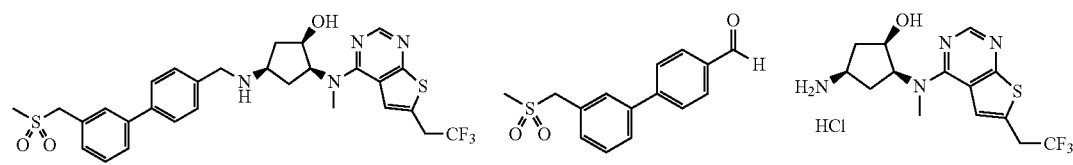

Reference Example D-44    Reference Example C-14 Step 3

(1R,2S,4R)-4-[({3'-[(methanesulfonyl)methyl][1,1'biphenyl]-4-yl}methyl)amino]-2-{methyl[6-
(2,2,2 trifluoroethyl)thieno[2,3-d]pyrimidin-4-yl]amino}cyclopentan-1-ol hydrochloride

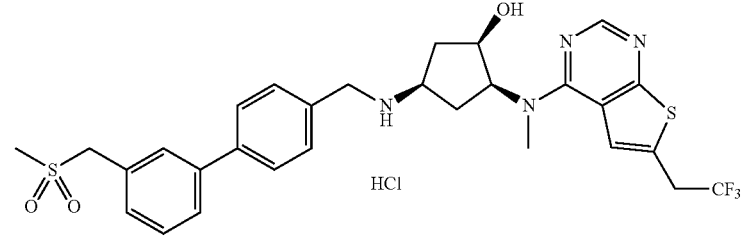 [SMILES: CN(c1ncnc2sc(CC(F)(F)F)cc12)[C@H]1C[C@@H](NCc2ccc(-c3cccc(CS(C)(=O)=O)c3)cc2)C[C@H]1O ; Cl]

$^1$H-NMR (DMSO-D$_6$) δ: 1.79-1.83 (1H, m), 2.27-2.47 (3H, m), 2.95 (3H, s), 3.44 (3H, s), 3.58-
3.61 (1H, m), 4.09 (2H, q, J = 11.0 Hz), 4.23-4.26 (2H, m), 4.34-4.37 (1H, m), 4.58 (2H, s), 4.94-
4.95 (1H, m), 5.18-5.21 (1H, m), 7.43-7.77 (9H, m), 8.36 (1H, s), 9.32-9.34 (2H, m). MS (m/z): 605 (M + H)$^+$.

TABLE 2-34

Ex. 87

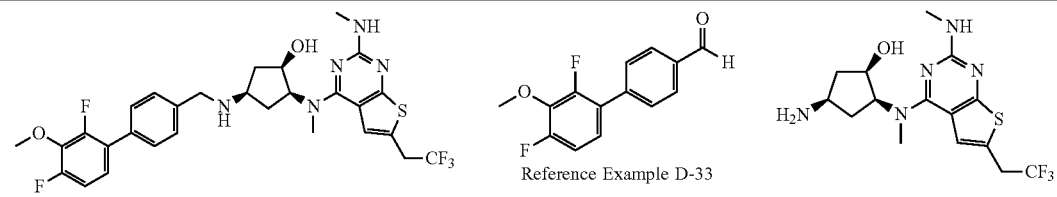

Reference Example D-33    Reference Example C-20 Step 3

(1R,2S,4R)-4-{[(2',4'-difluoro-3'-methoxy[1,1'-biphenyl]-4-yl)methyl]amino}-2-{methyl[2-
(methylamino)-6-(2,2,2-trifluoroethyl)thieno[2,3-d]pyrimidin-4-yl]amino}cyclopentan-1-ol hydrochloride TABLE 2-34-continued

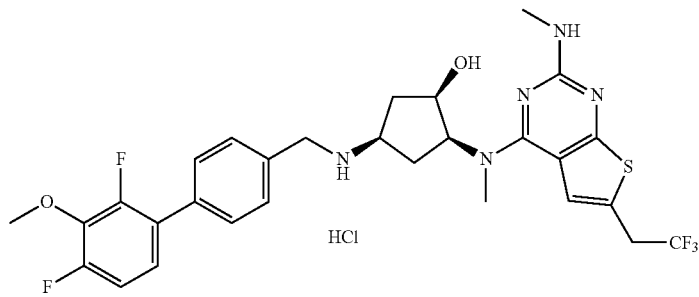 [SMILES: CNc1nc(N(C)[C@H]2C[C@@H](NCc3ccc(-c4ccc(F)c(OC)c4F)cc3)C[C@H]2O)c2cc(CC(F)(F)F)sc2n1 ; Cl]

¹H-NMR (DMSO-D₆) δ: 1.82-1.86 (1H, m), 2.27-2.33 (1H, m), 2.39-2.48 (2H, m), 2.81 (3H, s), 3.38 (3H, s), 3.55-3.58 (1H, m), 3.90-3.96 (5H, m), 4.24-4.26 (2H, m), 4.38-4.40 (1H, m), 4.79-4.82 (1H, m), 5.17-5.20 (1H, m), 7.23-7.30 (2H, m), 7.49 (1H, s), 7.60-7.62 (2H, m), 7.70-7.72 (2H, m), 9.46-9.52 (2H, m). MS (m/z): 608 (M + H)⁺.

Ex. 88

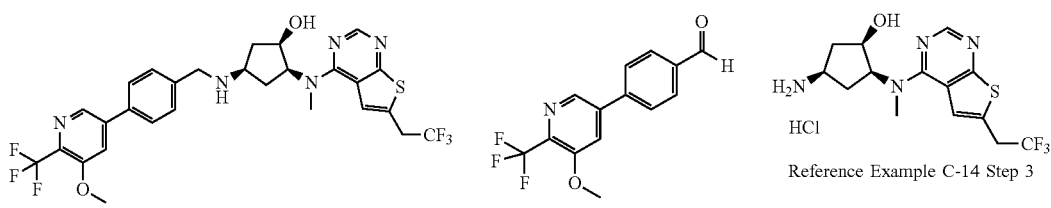

Reference Example D-47    Reference Example C-14 Step 3

(1R,2S,4R)-4-[({4-[5-methoxy-6-(trifluoromethyl)pyridin-3-yl]phenyl}methyl)amino]-2-{methyl[6-(2,2,2-trifluoroethyl)thieno[2,3-d]pyrimidin-4-yl]amino}cyclopentan-1-ol hydrochloride

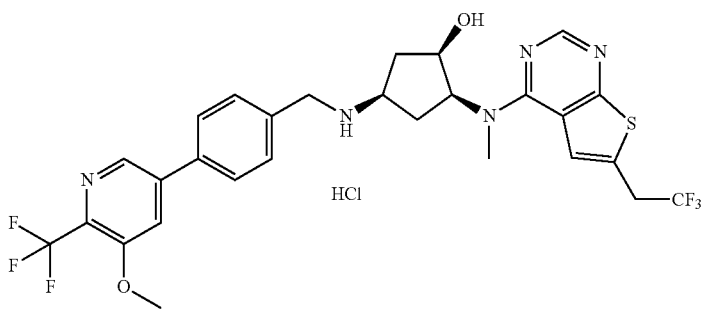 [SMILES: COc1cc(-c2ccc(CN[C@H]3C[C@@H](O)[C@@H](N(C)c4ncnc5sc(CC(F)(F)F)cc45)C3)cc2)cnc1C(F)(F)F ; Cl]

¹H-NMR (DMSO-D₆) δ: 1.81-1.90 (1H, m), 2.26 2.36 (1H, m), 2.40 2.55 (2H, m), 3.45 (3H, s), 3.53-3.65 (1H, m), 4.05 (3H, s), 4.05-4.15 (2H, m), 4.17-4.32 (2H, m), 4.32-4.38 (1H, m), 4.90-5.00 (1H, m), 5.05-5.39 (1H, m), 7.70 7.78 (3H, m), 7.84 7.90 (2H, m), 8.36 8.40 (2H, m), 8.81-8.85 (1H, m), 9.41-9.62 (2H, m). MS (m/z): 612 (M + H)⁺.

TABLE 2-35

Ex. 89

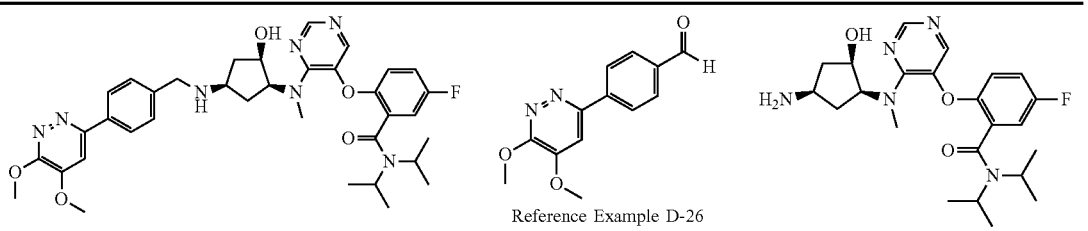

Reference Example D-26    Reference Example C-24 Step 2

2-[(4-{[(1S,2R,4R)-4-({[4-(5,6-dimethoxypyridazin-3-yl)phenyl]methyl}amino)-2-hydroxycyclopentyl](methyl)amino}pyrimidin-5-yl)oxy]-5-fluoro-N,N-di(propan-2-yl)benzamide hydrochloride TABLE 2-35-continued

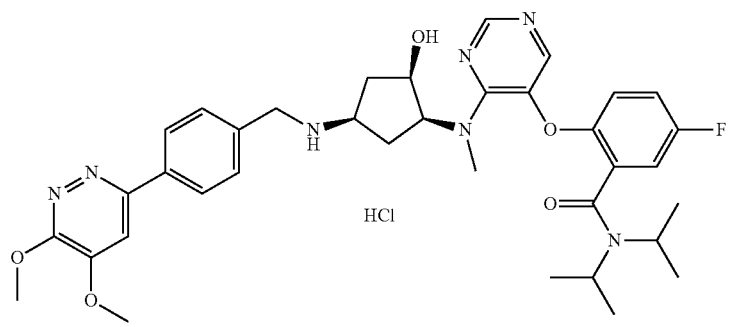 [SMILES: COc1cc(-c2ccc(CN[C@H]3C[C@@H](O)[C@@H](N(C)c4ncncc4Oc4ccc(F)cc4C(=O)N(C(C)C)C(C)C)C3)cc2)nnc1OC ; Cl]

¹H-NMR (DMSO-D₆) δ: 0.99-1.14 (6H, m), 1.24-1.48 (5H, m), 1.68-1.80 (1H, m), 2.06-2.23 (1H, m), 2.30-2.55 (2H, m), 3.22 (3H, s), 3.27-3.61 (3H, m), 3.68-3.80 (1H, m), 4.01 (3H, s), 4.07 (3H, s), 4.08-4.32 (3H, m), 4.48-4.66 (1H, m), 5.12-5.23 (1H, m), 6.79-6.91 (1H, m), 7.16-7.26 (2H, m), 7.64-7.73 (3H, m), 7.94-7.99 (1H, m), 8.15-8.22 (2H, m), 8.46 (1H, s), 9.20-9.47 (2H, m). MS (m/z): 674 (M + H)⁺.

Ex. 90

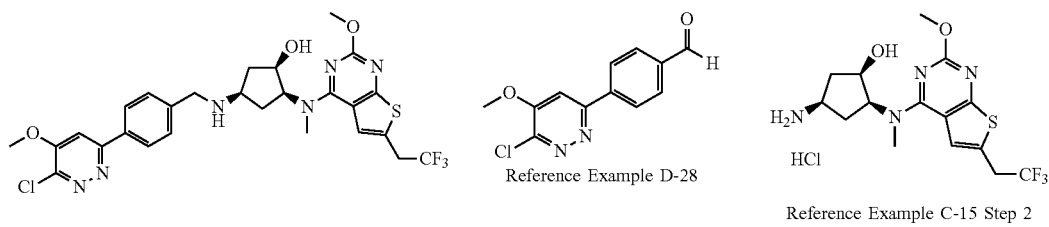

(1R,2S,4R)-4-({[4-(6-chloro-5methoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan1-ol hydrochloride

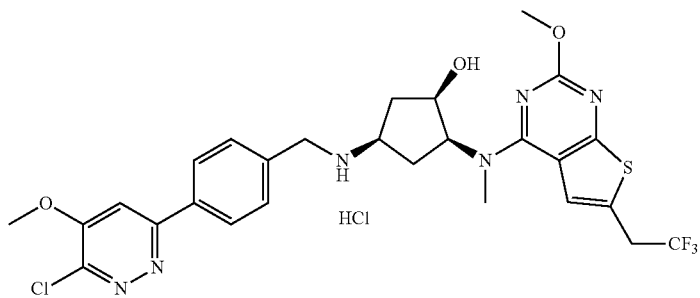 [SMILES: COc1nc(N(C)[C@H]2C[C@@H](NCc3ccc(-c4cc(OC)c(Cl)nn4)cc3)C[C@H]2O)c2cc(CC(F)(F)F)sc2n1 ; Cl]

¹H-NMR (DMSO-D₆) δ: 1.86-1.89 (1H, m), 2.29-2.35 (2H, m), 2.43-2.50 (2H, m), 2.50-2.53 (1H, m), 3.42 (3H, s), 3.85 (3H, s), 3.96 (2H, q, J = 11.0 Hz), 4.13 (3H, s), 4.28 4.31 (2H, m), 4.37-4.39 (1H, m), 4.82-4.88 (1H, m), 7.59 (1H, s), 7.78 (2H, d, J = 8.6 Hz), 7.87 (1H, s), 8.25 (2H, d, J = 8.6 Hz), 9.44-9.48 (2H, m). MS (m/z): 609, 611 (M + H)⁺.

TABLE 2-36

Ex. 91

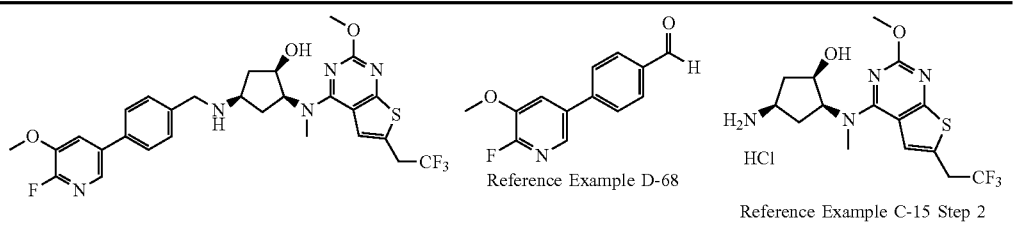

(1R,2S,4R)-4-({[4-(6-fluoro-5-methoxypyridin-3yl)phenyl]methyl}amino)-2{[2-methoxy6-(2,2,2-trifluoroethyl)thieno[2,3-d]pyrimidin-4-yl](methyl)amino}cyclopentan-1-ol hydrochloride TABLE 2-36-continued

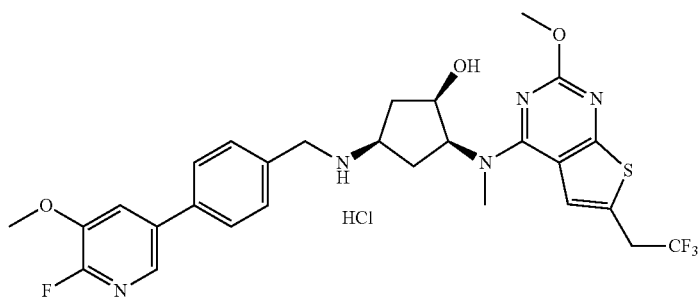 [SMILES: COc1nc(N(C)[C@H]2C[C@@H](NCc3ccc(-c4cnc(F)c(OC)c4)cc3)C[C@H]2O)c2cc(CC(F)(F)F)sc2n1 ; Cl]

¹H-NMR (DMSO-D₆) δ: 1.86-1.89 (1H, m), 2.30-2.33 (1H, m), 2.43-2.46 (2H, m), 3.42 (3H, s), 3.59-3.68 (1H, m), 3.85 (3H, s), 3.93-3.98 (5H, m), 4.24-4.26 (2H, m), 4.37-4.38 (1H, m), 4.82-4.88 (1H, m), 7.59 (1H, s), 7.72 (2H, d, J = 8.6 Hz), 7.84 (2H, d, J = 8.6 Hz), 7.88-7.90 (1H, m), 8.05-8.06 (1H, m), 9.43-9.47 (2H, m). MS (m/z): 592 (M + H)⁺.

Ex. 92

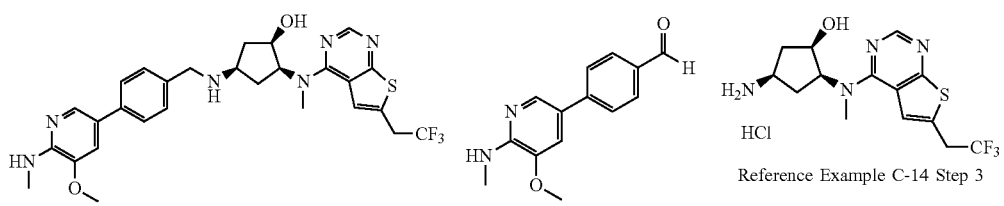

Reference Example D-79 Step 1    Reference Example C-14 Step 3

(1R,2S,4R)-4-[({4-[5-methoxy-6-(methylamino)pyridin-3-yl]phenyl}methyl)amino]-2-{methyl[6-(2,2,2-trifluoroethyl)thieno[2,3-d]pyrimidin-4-yl]amino}cyclopentan-1-ol hydrochloride

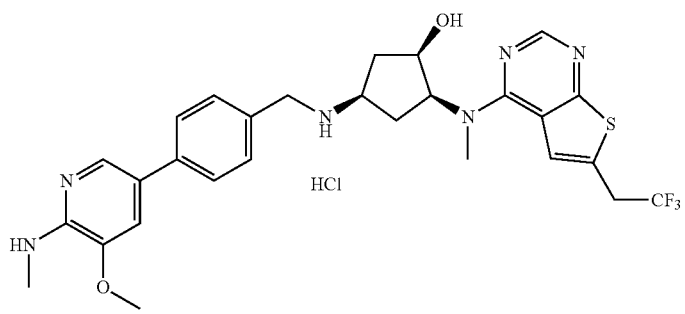 [SMILES: CNc1ncc(-c2ccc(CN[C@H]3C[C@@H](O)[C@@H](N(C)c4ncnc5sc(CC(F)(F)F)cc45)C3)cc2)cc1OC ; Cl]

¹H-NMR (DMSO-D₆) δ: 1.79-1.88 (1H, m), 2.25-2.36 (1H, m), 2.37-2.53 (2H, m), 2.85-2.91 (3H, m), 3.44 (3H, s), 3.50-3.64 (1H, m), 3.91 (3H, s), 4.00 4.30 (4H, m), 4.32-4.39 (1H, m), 4.88 4.99 (1H, m), 5.17-5.23 (1H, m), 6.18-6.74 (1H, m), 7.31-7.35 (1H, m), 7.59-7.66 (2H, m), 7.70-7.77 (3H, m), 7.96-8.00 (1H, m), 8.36 (1H, s), 9.31-9.53 (2H, m). MS (m/z): 573 (M + H)⁺.

TABLE 2-37

Ex. 93

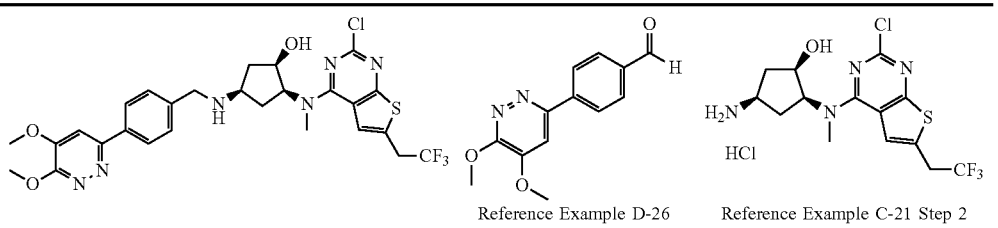

Reference Example D-26    Reference Example C-21 Step 2

(1R,2S,4R)-2-{[2-chloro-6-(2,2,2-trifluoroethyl)thieno[2,3-d]pyrimidin-4-yl](methyl)amino}-4-({[4-(5,6-dimethoxypyridazin-3-yl)phenyl]methyl}amino)cyclopentan-1-ol TABLE 2-37-continued

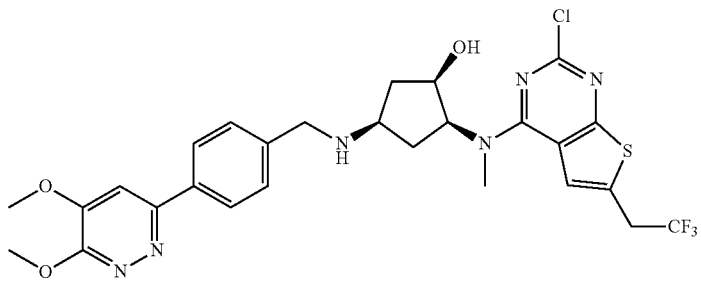 [SMILES: COc1cc(-c2ccc(CN[C@H]3C[C@@H](O)[C@@H](N(C)c4nc(Cl)nc5sc(CC(F)(F)F)cc45)C3)cc2)nnc1OC]

¹H-NMR (DMSO-D₆) δ: 1.49-1.52 (1H, m), 1.97-2.05 (1H, m), 2.12-2.18 (1H, m), 2.23-2.30 (1H, m), 3.08-3.10 (1H, m), 3.41 (3H, s), 3.813.84 (2H, m), 3.99 (3H, s), 4.00 4.05 (2H, m), 4.06 (3H, s), 4.29-4.31 (1H, m), 4.67-4.73 (2H, m), 7.49 (2H, d, J = 8.0 Hz), 7.55 (1H, s), 7.68 (1H, s), 8.02 (2H, d, J = 8.0 Hz). MS (m/z): 609, 611 (M + H)⁺.
(1R,2S,4R)-2-{[2-chloro-6-(2,2,2-trifluoroethyl)thieno[2,3-d]pyrimidin-4-yl](methyl)amino}-4-({[4-(5,6-dimethoxypyridazin-3-yl)phenyl]methyl}amino)cyclopentan-1-ol hydrochloride

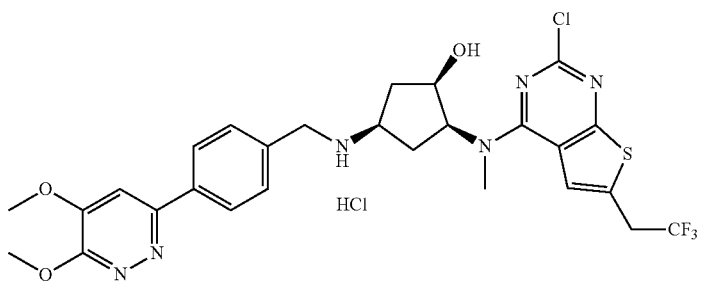 [SMILES: COc1cc(-c2ccc(CN[C@H]3C[C@@H](O)[C@@H](N(C)c4nc(Cl)nc5sc(CC(F)(F)F)cc45)C3)cc2)nnc1OC ; Cl]

¹H-NMR (DMSO-D₆) δ: 1.86-1.90 (1H, m), 2.37-2.44 (2H, m), 2.51-2.54 (1H, m), 3.44 (3H, s), 3.61-3.63 (1H, m), 4.01-4.10 (8H, m), 4.26-4.28 (2H, m), 4.36-4.38 (1H, m), 4.79-4.85 (1H, m), 7.63 (1H, s), 7.73 (3H, d, J = 8.6 Hz), 8.17 (2H, d, J = 8.6 Hz), 9.41-9.48 (2H, m). MS (m/z): 609, 611 (M + H)⁺.

TABLE 2-38

Ex. 94

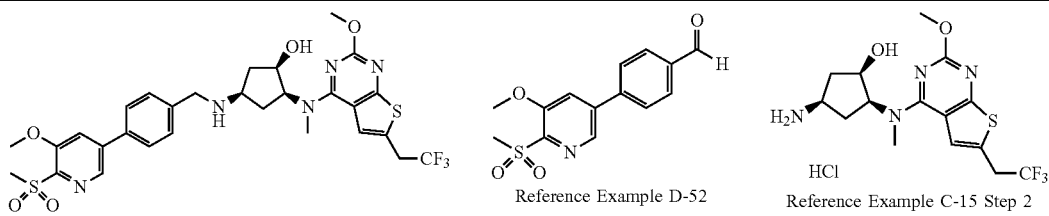

Reference Example D-52    Reference Example C-15 Step 2

(1R,2S,4R)-4-[({4-[6-(methanesulfonyl)-5-methoxypyridin-3-yl]phenyl}methyl)amino]-2-{[2-methoxy-6-(2,2,2-trifluoroethyl)thieno[2,3-d]pyrimidin-4-yl](methyl)amino}cyclopentan-1-ol hydrochloride

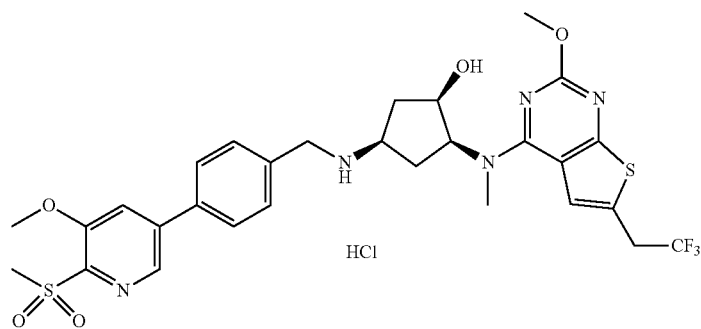 [SMILES: COc1nc(N(C)[C@H]2C[C@@H](NCc3ccc(-c4cnc(S(C)(=O)=O)c(OC)c4)cc3)C[C@H]2O)c2cc(CC(F)(F)F)sc2n1 ; Cl]

¹H-NMR (DMSO-D₆) δ: 1.75-1.88 (1H, m), 2.25-2.48 (3H, m), 3.34 (3H, s), 3.41 (3H, s), 3.55-3.64 (1H, m), 3.84 (3H, s), 4.00 (2H, q, J = 11.0 Hz), 4.09 (3H, s), 4.29 (2H, br s), 4.37 (1H, br s), 4.84 (1H, br s), 5.20 (1H, br s), 7.64 (1H, s), 7.73-7.80 (2H, m), 7.99 (2H, d, J = 8.0 Hz), 8.05 (1H, d, J = 1.8 Hz), 8.61 (1H, d, J = 1.8 Hz), 9.27-9.49 (2H, m). MS (m/z): 652 (M + H)⁺.

TABLE 2-39

Ex. 95

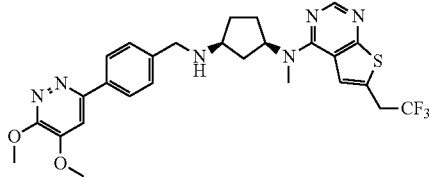 [SMILES: COc1cc(-c2ccc(CN[C@H]3CC[C@@H](N(C)c4ncnc5sc(CC(F)(F)F)cc45)C3)cc2)nnc1OC]
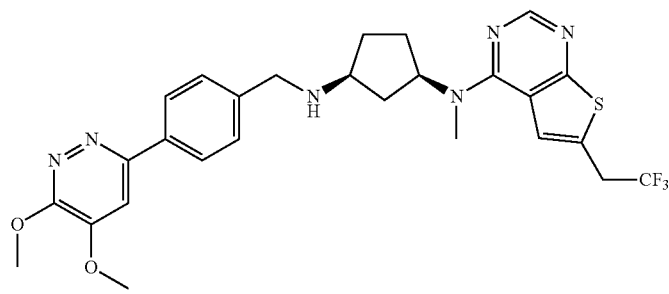 [SMILES: COc1cc(-c2ccc(CN[C@H]3CC[C@@H](N(C)c4ncnc5sc(CC(F)(F)F)cc45)C3)cc2)nnc1OC]

Reference Example D-26     Reference Example C-4 Step 2

(1R,3S)-N³-{[4-(5,6-dimethoxypyridazin-3-yl)phenyl]methyl}-N¹-methyl-N¹-[6-(2,2,2-trifluoroethyl)thieno[2,3-d]pyrimidin-4-yl]cyclopentane-1,3-diamine ¹H-NMR (CDCl₃) δ: 1.51-1.60 (1H, m), 1.65-1.71 (1H, m), 1.90-2.00 (3H, m), 2.26-2.33 (1H, m), 3.24-3.31 (1H, m), 3.32 (3H, s), 3.63 (2H, q, J = 10.0 Hz), 3.84-3.90 (2H, m), 4.03 (3H, s), 4.24 (3H, s), 5.30-5.39 (1H, m), 7.14 (1H, s), 7.35 (1H, s), 7.46 (2H, d, J = 8.6 Hz), 7.97 (2H, d, J = 8.6 Hz), 8.42 (1H, s).

(1R,3S)-N³-{[4-(5,6-dimethoxypyridazin-3-yl)phenyl]methyl}-N¹-methyl-N¹-[6-(2,2,2-trifluoroethyl)thieno[2,3-d]pyrimidin-4-yl]cyclopentane-1,3-diamine hydrochloride

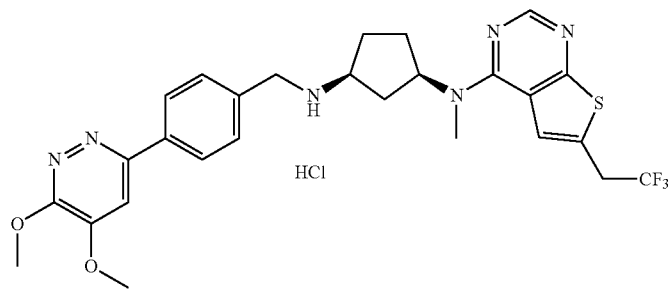 [SMILES: COc1cc(-c2ccc(CN[C@H]3CC[C@@H](N(C)c4ncnc5sc(CC(F)(F)F)cc45)C3)cc2)nnc1OC ; Cl]

¹H-NMR (DMSO-D₆) δ: 1.88-2.15 (5H, m), 2.33-2.41 (1H, m), 3.29 (3H, s), 3.61-3.70 (1H, m), 4.01 (3H, s), 4.05-4.15 (5H, m), 4.24-4.29 (2H, m), 5.25-5.32 (1H, m), 7.67 (1H, s), 7.71-7.74 (3H, m), 8.19-8.22 (2H, m), 8.38 (1H, s), 9.25-9.48 (2H, m). MS (m/z): 559 (M + H)⁺.

TABLE 2-40

Ex. 96

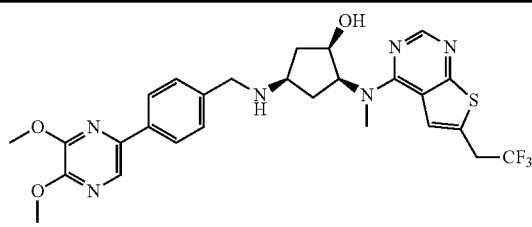
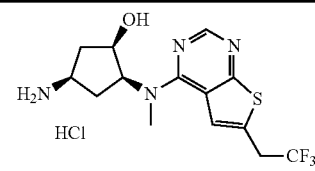

Reference Example D-46     Reference Example C-14 Step 3

(1R,2S,4R)-4-({[4-(5,6-dimethoxypyrazin-2-yl)phenyl]methyl}amino)-2-{methyl[6-(2,2,2-trifluoroethyl)thieno[2,3-d]pyrimidin-4-yl]amino}cyclopentan-1-ol hydrochloride TABLE 2-40-continued

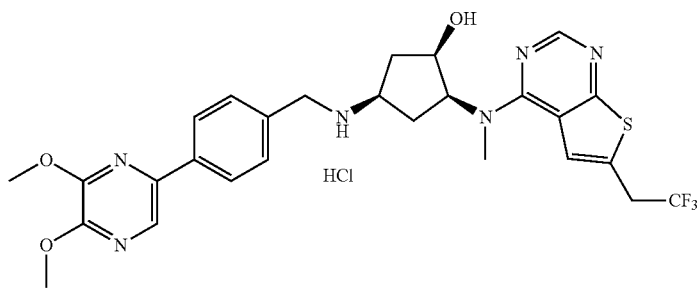 [SMILES: COc1ncc(-c2ccc(CN[C@H]3C[C@@H](O)[C@@H](N(C)c4ncnc5sc(CC(F)(F)F)cc45)C3)cc2)nc1OC ; Cl]

¹H-NMR (DMSO-D₆) δ: 1.70-1.82 (1H, m), 2.22-2.43 (2H, m), 3.43 (3H, s), 3.57 (1H, br s), 3.95 (3H, s), 4.00-4.15 (5H, m), 4.24 (2H, br s), 4.31-4.40 (2H, m), 4.87-4.99 (1H, m), 5.20 (1H, br s), 7.65 (2H, d, J = 8.5 Hz), 7.75 (1H, s), 8.10 (2H, d, J = 8.5 Hz), 8.36 (1H, s), 8.38 (1H, s), 9.24 (2H, br s). MS (m/z): 575 (M + H)⁺.

Ex. 97

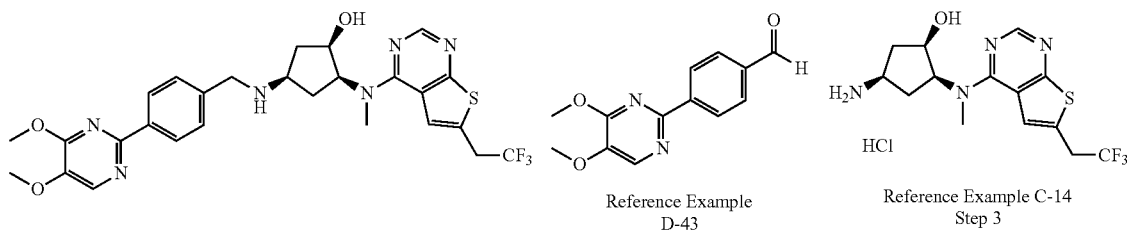

Reference Example D-43

Reference Example C-14 Step 3

(1R,2S,4R)-4-({[4-(4,5-dimethoxypyrimidin-2-yl)phenyl]methyl}amino)-2-{methyl[6-(2,2,2-trifluoroethyl)thieno[2,3-d]pyrimidin-4-yl]amino}cyclopentan-1-ol hydrochloride

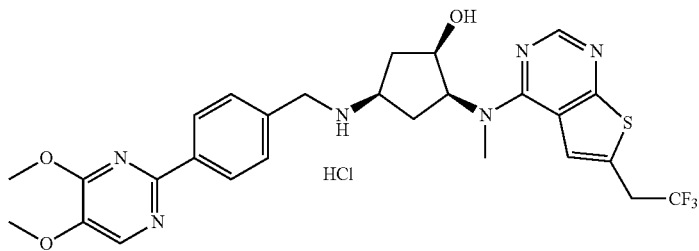 [SMILES: COc1cnc(-c2ccc(CN[C@H]3C[C@@H](O)[C@@H](N(C)c4ncnc5sc(CC(F)(F)F)cc45)C3)cc2)nc1OC ; Cl]

¹H-NMR (DMSO-D₆) δ: 1.74-1.81 (1H, m), 2.24-2.44 (3H, m), 3.44 (3H, s), 3.55-3.65 (1H, m), 3.92 (3H, s), 4.08 (3H, s), 4.09 (2H, q, J = 10.4 Hz), 4.27 (2H, br s), 4.37 (1H, br s), 4.89-4.98 (1H, m), 5.17-5.22 (1H, m), 7.67 (2H, d, J = 8.0 Hz), 7.75 (1H, s), 8.36 (2H, s), 8.36 (2H, d, J = 8.0 Hz), 9.15-9.27 (2H, m). MS (m/z): 575 (M + H)⁺.

TABLE 2-41

Ex. 98

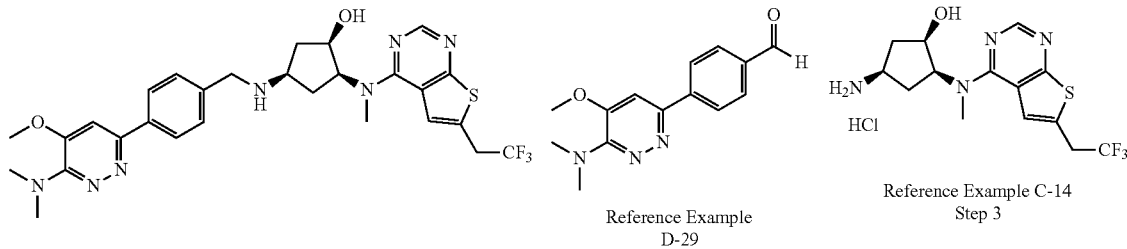

Reference Example D-29

Reference Example C-14 Step 3

(1R,2S,4R)-4-[({4-[6-(dimethylamino)-5-methoxypyridazin-3-yl]phenyl}methyl)amino]-2-{methyl[6-(2,2,2-trifluoroethyl)thieno[2,3-d]pyrimidin-4-yl]amino}cyclopentan-1-ol hydrochloride

TABLE 2-41-continued

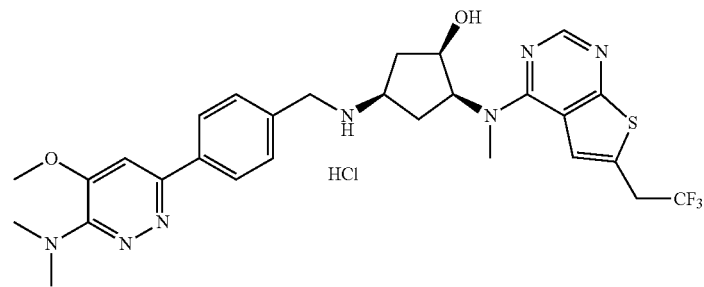 [SMILES: COc1cc(-c2ccc(CN[C@H]3C[C@@H](O)[C@@H](N(C)c4ncnc5sc(CC(F)(F)F)cc45)C3)cc2)nnc1N(C)C ; Cl]

¹H-NMR (DMSO-D₆) δ: 1.73-1.84 (1H, m), 2.23-2.46 (3H, m), 3.08 (6H, s), 3.44 (3H, s), 3.57-3.68 (1H, m), 4.03 (3H, s), 4.09 (2H, q, J = 11.0 Hz), 4.28 (2H, br s), 4.37 (1H, br s), 4.90-4.99 (1H, m), 5.21 (1H, br s), 7.54 (1H, s), 7.68-7.73 (2H, m), 7.75 (1H, s), 8.17 (2H, d, J = 8.6 Hz), 8.36 (1H, s), 9.15-9.33 (2H, m). MS (m/z): 588 (M + H)⁺.

Ex. 99

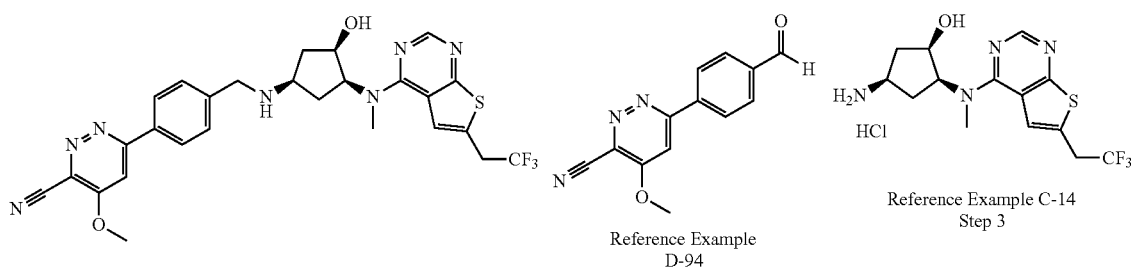

Reference Example D-94

Reference Example C-14 Step 3

6-[4-({[(1R,3R,4S)-3-hydroxy-4-{methyl[6-(2,2,2-trifluoroethyl)thieno[2,3-d]pyrimidin-4-yl]amino}cyclopentyl]amino}methyl)phenyl]-4-methoxypyridazine-3-carbonitrile hydrochloride

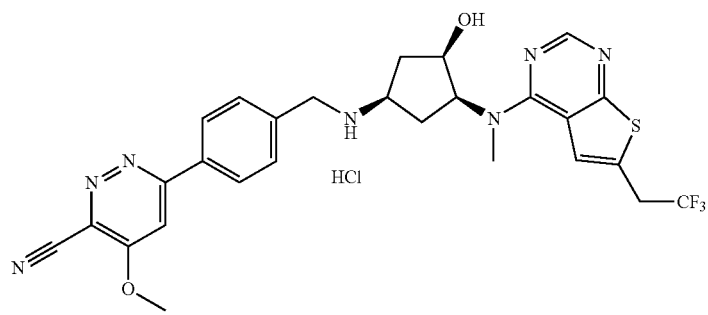 [SMILES: COc1cc(-c2ccc(CN[C@H]3C[C@@H](O)[C@@H](N(C)c4ncnc5sc(CC(F)(F)F)cc45)C3)cc2)nnc1C#N ; Cl]

¹H-NMR (DMSO-D₆) δ: 1.78-1.86 (1H, m), 2.27-2.34 (1H, m), 2.41-2.49 (2H, m), 3.44 (3H, s), 3.59-3.67 (1H, m), 4.09 (2H, q, J = 10.4 Hz), 4.19 (3H, s), 4.29-4.38 (3H, m), 4.91-4.99 (1H, m), 5.18-5.24 (1H, m), 7.75 (1H, s), 7.81 (2H, d, J = 8.0 Hz), 8.13 (1H, s), 8.36 (1H, s), 8.38 (2H, d, J = 8.0 Hz), 9.38 (2H, br s). MS (m/z): 570 (M + H)⁺.

TABLE 2-42

Ex. 100

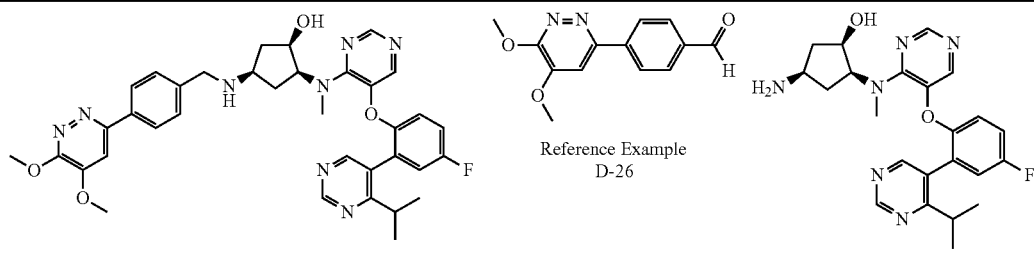

Reference Example D-26

Reference Example C-25 Step 3

(1R,2S,4R)-4-({[4-(5,6-dimethoxypyridazin-3-yl)phenyl]methyl}amino)-2-[(5-{4-fluoro-2-[4-(propan-2-yl)pyrimidin-5-yl]phenoxy}pyrimidin-4-yl)(methyl)amino]cyclopentan-1-ol hydrochloride TABLE 2-42-continued

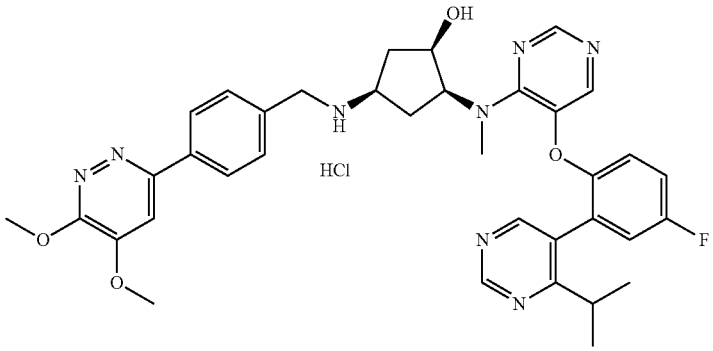

¹H-NMR (DMSO-D₆) δ: 1.07-1.16 (6H, m), 1.75-1.77 (1H, m), 2.14-2.16 (1H, m), 2.31-2.34 (2H, m), 3.03-3.06 (4H, m), 4.01 (3H, s), 4.07 (3H, s), 4.21-4.23 (3H, m), 4.48-4.51 (1H, m), 5.10-5.13 (1H, m), 7.00-7.03 (1H, m), 7.34-7.36 (1H, m), 7.42-7.44 (1H, m), 7.66 (1H, s), 7.71 (2H, d, J = 8.6 Hz), 7.98-8.00 (1H, m), 8.18 (2H, d, J = 8.6 Hz), 8.41 (1H, s), 8.67-8.72 (1H, m), 9.17 (1H, s), 9.37-9.44 (2H, m). MS (m/z): 667 (M + H)⁺.

Ex. 101

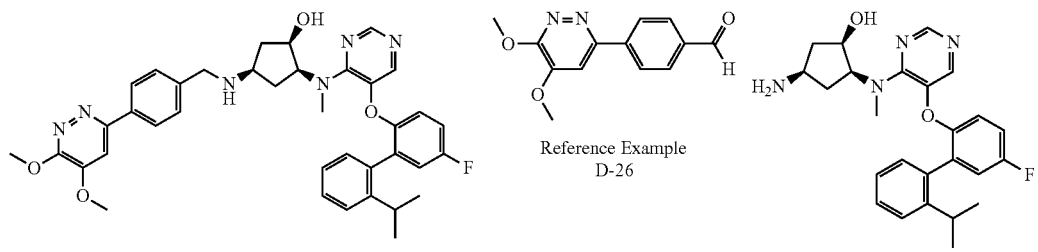

Reference Example D-26

Reference Example C-26 Step 2

(1R,2S,4R)-4-({[4-(5,6-dimethoxypyridazin-3-yl)phenyl]methyl}amino)-2-[(5-{[5-fluoro-2'-(propan-2-yl)[1,1'-biphenyl]-2-yl]oxy}pyrimidin-4-yl)(methyl)amino]cyclopentan-1-ol hydrochloride

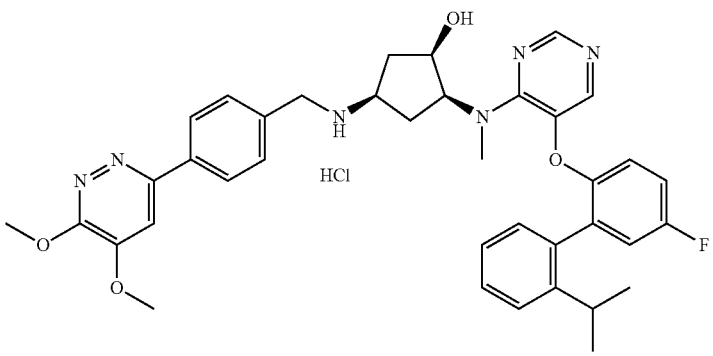 [SMILES: COc1cc(-c2ccc(CN[C@H]3C[C@@H](O)[C@@H](N(C)c4ncncc4Oc4ccc(F)cc4-c4ccccc4C(C)C)C3)cc2)nnc1OC ; Cl]

¹H-NMR (DMSO-D₆) δ: 1.09-1.12 (6H, m), 1.70-1.74 (1H, m), 2.10-2.13 (1H, m), 2.26-2.33 (2H, m), 2.79-2.82 (1H, m), 3.06 (3H, d, J = 6.1 Hz), 4.00 (3H, s), 4.07 (3H, s), 4.21-4.24 (3H, m), 4.40-4.47 (1H, m), 5.10-5.12 (1H, m), 6.94-6.97 (1H, m), 7.13-7.28 (4H, m), 7.34-7.40 (2H, m), 7.66 (1H, s), 7.70 (2H, d, J = 8.0 Hz), 7.86 (1H, d, J = 10.4 Hz), 8.19 (2H, d, J = 8.0 Hz), 8.37 (1H, d, J = 4.3 Hz), 9.30-9.33 (2H, m). MS (m/z): 665 (M + H)⁺.

TABLE 2-43

| Ex. 102 | 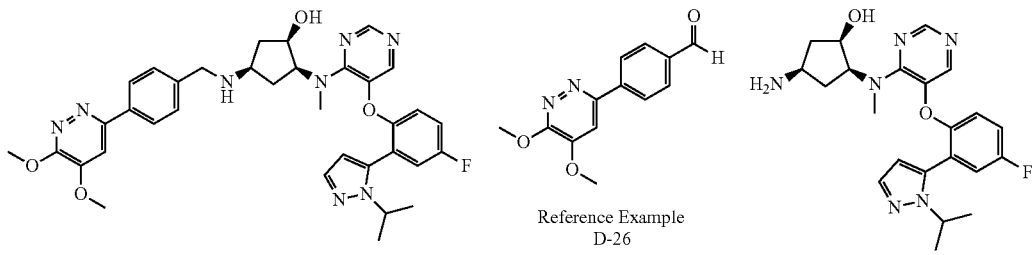 |

(1R,2S,4R)-4-({[4-(5,6-dimethoxypyridazin-3-yl)phenyl]methyl}amino)-2-[(5-{4-fluoro-2-[1-(propan-2-yl)-1H-pyrazol-5-yl]phenoxy}pyrimidin-4-yl)(methyl)amino]cyclopentan-1-ol hydrochloride

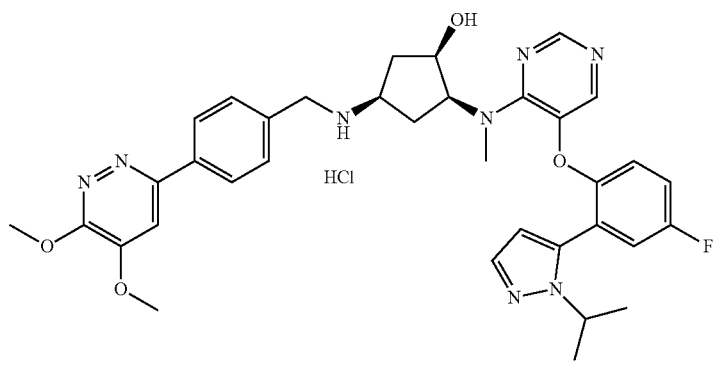 [SMILES: COc1cc(-c2ccc(CN[C@H]3C[C@@H](O)[C@@H](N(C)c4ncncc4Oc4ccc(F)cc4-c4ccnn4C(C)C)C3)cc2)nnc1OC ; Cl]

¹H-NMR (DMSO-D₆) δ: 1.31-1.34 (6H, m), 1.70-1.75 (1H, m), 2.04-2.17 (2H, m), 2.26-2.34 (2H, m), 3.08 (3H, s), 4.01 (3H, s), 4.07 (3H, s), 4.13-4.16 (1H, m), 4.22 (2H, s), 4.40-4.45 (2H, m), 5.13-5.16 (1H, m), 6.29 (1H, s), 6.98-6.99 (1H, m), 7.34-7.36 (2H, m), 7.53 (1H, s), 7.66 (1H, s), 7.70 (2H, d, J = 8.6 Hz), 8.06 (1H, s), 8.18 (2H, d, J = 8.6 Hz), 8.46 (1H, s), 9.33-9.39 (2H, m). MS (m/z): 655 (M + H)⁺.

| Ex. 103 | 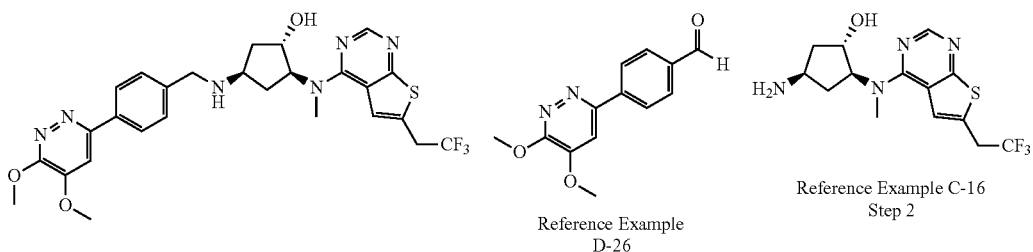 |

(1S,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol hydrochloride

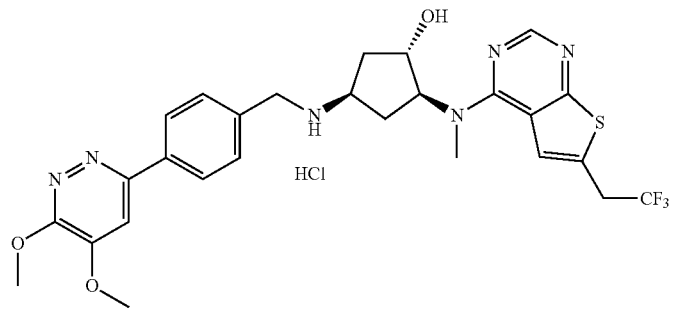 [SMILES: COc1cc(-c2ccc(CN[C@H]3C[C@H](O)[C@@H](N(C)c4ncnc5sc(CC(F)(F)F)cc45)C3)cc2)nnc1OC ; Cl]

¹H-NMR (DMSO-D₆) δ: 1.93-2.05 (2H, m), 2.24-2.32 (1H, m), 2.38-2.44 (1H, m), 3.30 (3H, s), 3.71-3.81 (1H, m), 4.00 (3H, s), 4.01-4.07 (2H, m), 4.08 (3H, s), 4.18-4.25 (2H, m), 4.49-4.56 (1H, m), 4.89-4.97 (1H, m), 5.01-5.13 (1H, m), 7.59 (1H, s), 7.71 (2H, d, J = 8.0 Hz), 7.72 (1H, s), 8.15 (2H, d, J = 8.0 Hz), 8.35 (1H, s), 9.32 (2H, br s). MS (m/z): 575 (M + H)⁺.

TABLE 2-44

Ex. 104

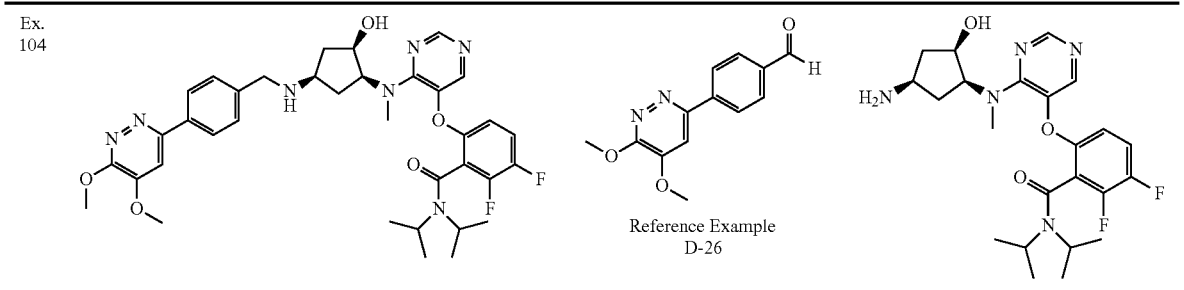

Reference Example D-26

Reference Example C-28 Step 2

6-[(4-{[(1S,2R,4R)-4-({[4-(5,6-dimethoxypyridazin-3-yl)phenyl]methyl}amino)-2-hydroxycyclopentyl](methyl)amino}pyrimidin-5-yl)oxy]-2,3-difluoro-N,N-di(propan-2-yl)benzamide hydrochloride

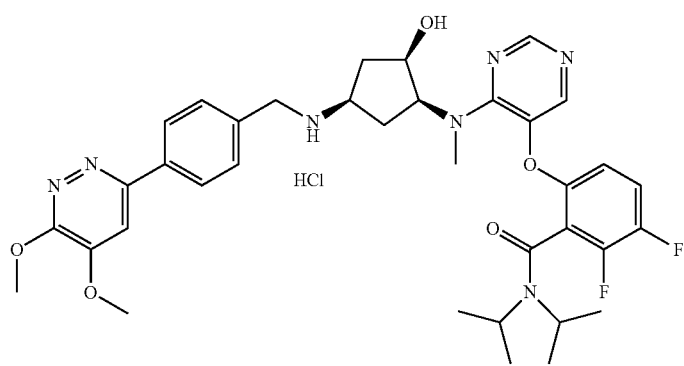 [SMILES: COc1cc(-c2ccc(CN[C@H]3C[C@@H](O)[C@@H](N(C)c4ncncc4Oc4ccc(F)c(F)c4C(=O)N(C(C)C)C(C)C)C3)cc2)nnc1OC ; Cl]

¹H-NMR (DMSO-D₆) δ: 1.04-1.45 (12H, m), 1.72-1.79 (1H, m), 2.04-2.20 (1H, m), 2.33-2.46 (2H, m), 3.19 (3H, s), 3.47-3.49 (2H, m), 3.59-3.64 (1H, m), 3.83-3.90 (1H, m), 4.00 (3H, s), 4.07 (3H, s), 4.24 (2H, s), 4.50-4.60 (1H, m), 5.16-5.18 (1H, m), 6.61-6.66 (1H, m), 7.40-7.45 (1H, m), 7.66 (1H, s), 7.69-7.72 (2H, m), 8.00-8.02 (1H, m), 8.16-8.18 (2H, m), 8.47 (1H, s), 9.40-9.42 (2H, m). MS (m/z): 692 (M + H)⁺.

Ex. 105

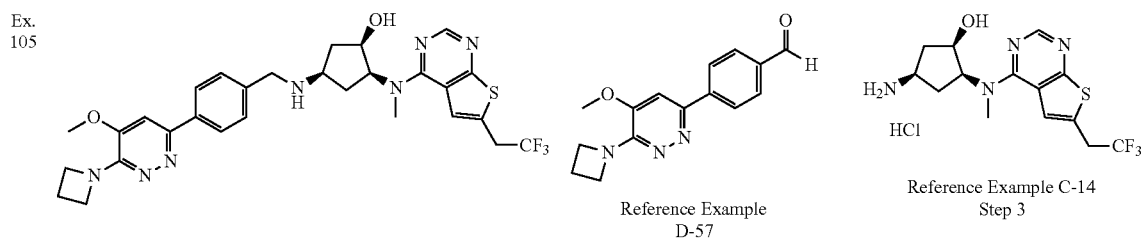

Reference Example D-57

Reference Example C-14 Step 3

(1R,2S,4R)-4-[({4-[6-(azetidin-1-yl)-5-methoxypyridazin-3-yl]phenyl}methyl)amino]-2-{methyl[6-(2,2,2-trifluoroethyl)thieno[2,3-d]pyrimidin-4-yl]amino}cyclopentan-1-ol hydrochloride

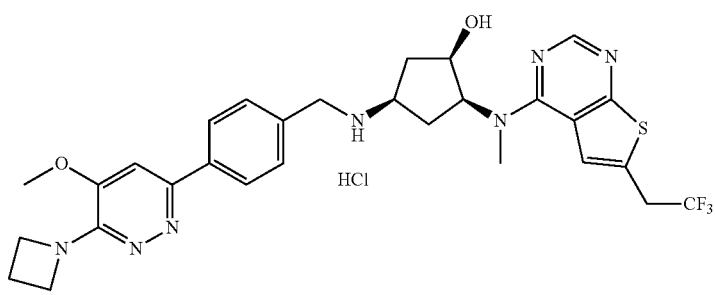 [SMILES: COc1cc(-c2ccc(CN[C@H]3C[C@@H](O)[C@@H](N(C)c4ncnc5sc(CC(F)(F)F)cc45)C3)cc2)nnc1N1CCC1 ; Cl]

¹H-NMR (DMSO-D₆) δ: 1.85-1.91 (1H, m), 2.29-2.37 (3H, m), 2.43-2.47 (2H, m), 3.44 (3H, s), 3.58-3.66 (1H, m), 3.93 (3H, s), 4.02 (2H, q, J = 10.9 Hz), 4.19 (4H, t, J = 7.3 Hz), 4.23-4.25 (2H, m), 4.36-4.40 (1H, m), 4.91-4.98 (1H, m), 5.02 (1H, br s), 7.35 (1H, s), 7.65-7.68 (3H, m), 8.09 (2H, d, J = 8.5 Hz), 8.33 (1H, s), 9.24 (2H, br s). MS (m/z): 600 (M + H)⁺.

TABLE 2-45

Ex. 106

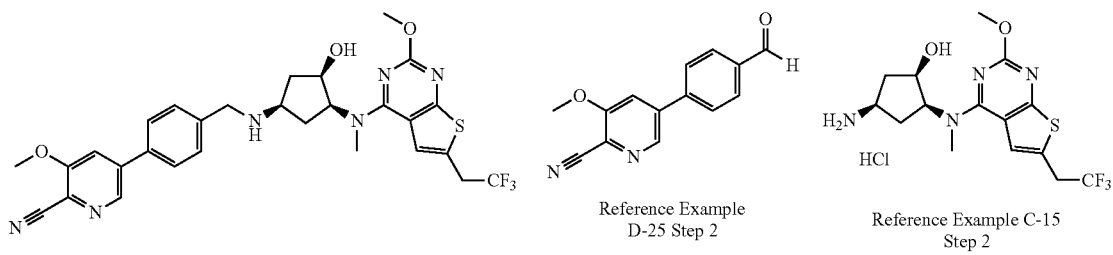

Reference Example D-25 Step 2

Reference Example C-15 Step 2

5-[4-({[(1R,3R,4S)-3-hydroxy-4-{[2-methoxy-6-(2,2,2-trifluoroethyl)thieno[2,3-d]pyrimidin-4-yl](methyl)amino}cyclopentyl]amino}methyl)phenyl]-3-methoxypyridine-2-carbonitrile hydrochloride

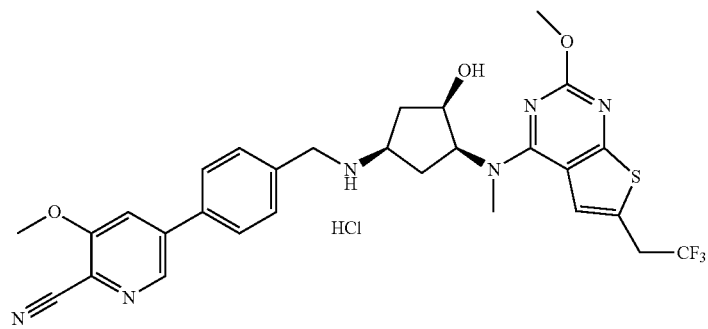 [SMILES: COc1nc(N(C)[C@H]2C[C@@H](NCc3ccc(-c4cnc(C#N)c(OC)c4)cc3)C[C@H]2O)c2cc(CC(F)(F)F)sc2n1 ; Cl]

$^1$H-NMR (DMSO-D$_6$, 80° C.) δ: 1.83-1.90 (1H, m), 2.29-2.36 (1H, m), 2.39-2.47 (2H, m), 3.42 (3H, s), 3.58-3.65 (1H, m), 3.85 (3H, s), 3.94 (2H, q, J = 11.0 Hz), 4.09 (3H, s), 4.24-4.31 (2H, m), 4.37-4.41 (1H, m), 4.81-4.88 (1H, m), 4.98-5.10 (1H, m), 7.57 (1H, s), 7.75 (2H, d, J = 8.6 Hz), 7.95 (2H, d, J = 8.6 Hz), 7.98 (1H, d, J = 1.8 Hz), 8.66 (1H, d, J = 1.8 Hz), 9.30 (2H, br s). MS (m/z): 599 (M + H)$^+$.

Ex. 107

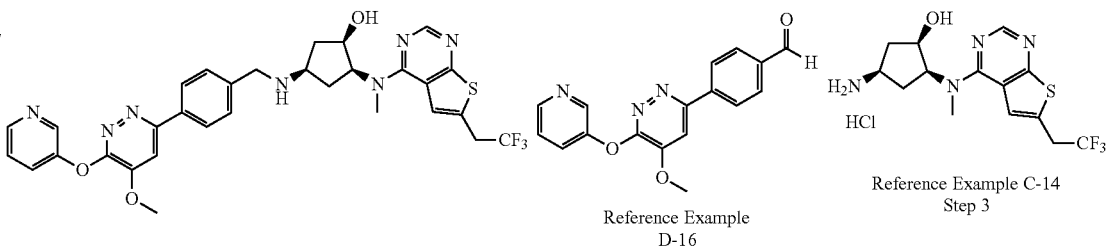

Reference Example D-16

Reference Example C-14 Step 3

(1R,2S,4R)-4-{[(4-{5-methoxy-6-[(pyridin-3-yl)oxy]pyridazin-3-yl}phenyl)methyl]amino}-2-{methyl[6-(2,2,2-trifluoroethyl)thieno[2,3-d]pyrimidin-4-yl]amino}cyclopentan-1-ol hydrochloride

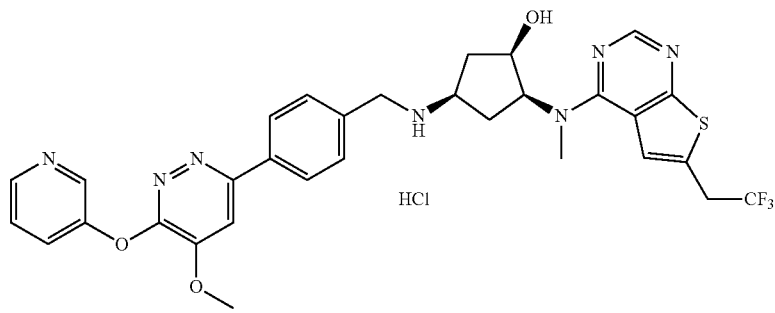 [SMILES: COc1cc(-c2ccc(CN[C@H]3C[C@@H](O)[C@@H](N(C)c4ncnc5sc(CC(F)(F)F)cc45)C3)cc2)nnc1Oc1cccnc1 ; Cl]

$^1$H-NMR (DMSO-D$_6$) δ: 1.82-1.88 (1H, m), 2.28-2.32 (1H, m), 2.40-2.45 (2H, m), 3.44 (3H, s), 3.60-3.63 (1H, m), 4.06-4.11 (5H, m), 4.27-4.29 (2H, m), 4.35-4.37 (1H, m), 4.93-4.95 (1H, m), 5.19-5.21 (1H, m), 7.53-7.57 (1H, m), 7.74-7.78 (4H, m), 7.90 (1H, s), 8.21 (2H, d, J = 8.6 Hz), 8.36 (1H, s), 8.50-8.51 (1H, m), 8.57-8.57 (1H, m), 9.35-9.42 (2H, m). MS (m/z): 638 (M + H)$^+$.

TABLE 2-46

Ex. 108

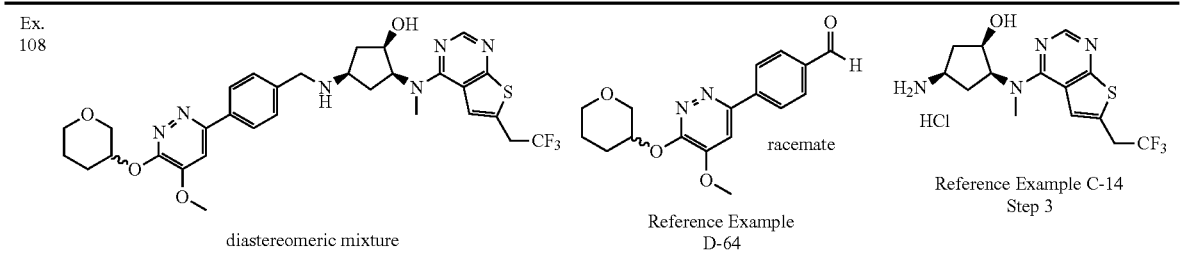

diastereomeric mixture / Reference Example D-64 / Reference Example C-14 Step 3

(1R,2S,4R)-4-{[(4-{5-methoxy-6-[(oxan-3-yl)oxy]pyridazin-3-yl}phenyl)methyl]amino}-2-
{methyl[6-(2,2,2-trifluoroethyl)thieno[2,3-d]pyrimidin-4-yl]amino}cyclopentan-1-ol
hydrochloride (diastereomer mixture)

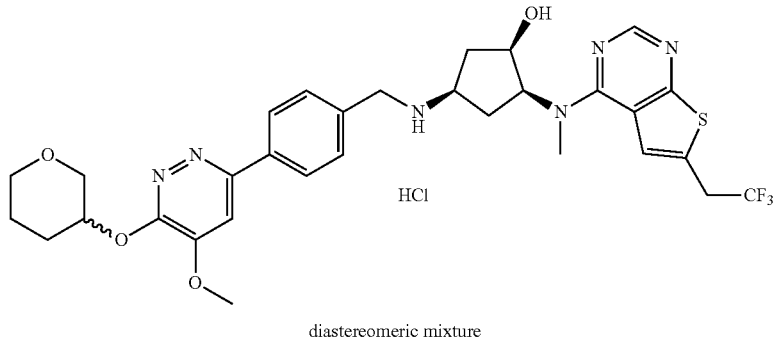 [SMILES: COc1cc(-c2ccc(CN[C@H]3C[C@@H](O)[C@@H](N(C)c4ncnc5sc(CC(F)(F)F)cc45)C3)cc2)nnc1OC1CCCOC1 ; Cl]

diastereomeric mixture $^1$H-NMR (DMSO-D$_6$) δ: 1.57-1.59 (1H, m), 1.81-1.91 (3H, m), 2.10-2.14 (1H, m), 2.29-2.35 (1H, m), 2.44-2.46 (1H, m), 2.52-2.53 (1H, m), 3.45 (3H, s), 3.54-3.69 (4H, m), 3.91-3.94 (1H, m), 4.00-4.07 (5H, m), 4.26-4.28 (2H, m), 4.36-4.38 (1H, m), 4.92-4.98 (1H, m), 5.23-5.28 (1H, m), 7.63 (1H, s), 7.72-7.73 (3H, m), 8.16 (2H, d, J = 8.0 Hz), 8.35 (1H, s), 9.39-9.46 (2H, m). MS (m/z): 645 (M + H)$^+$.

Ex. 109

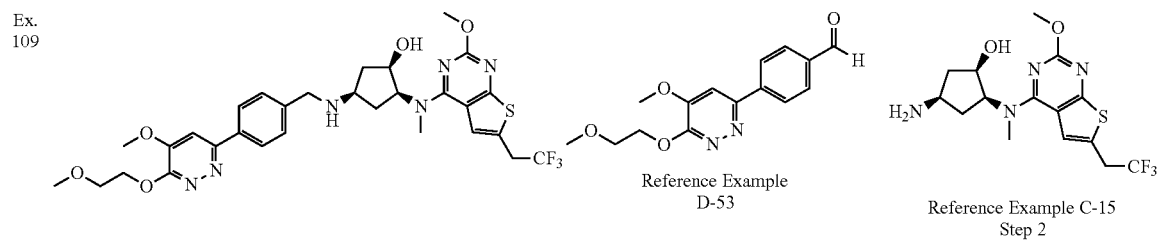

Reference Example D-53 / Reference Example C-15 Step 2

(1R,2S,4R)-4-[({4-[5-methoxy-6-(2-methoxyethoxy)pyridazin-3-yl]phenyl}methyl)amino]-2-
{[2-methoxy-6-(2,2,2-trifluoroethyl)thieno[2,3-d]pyrimidin-4-yl](methyl)amino}cyclopentan-
1-ol hydrochloride

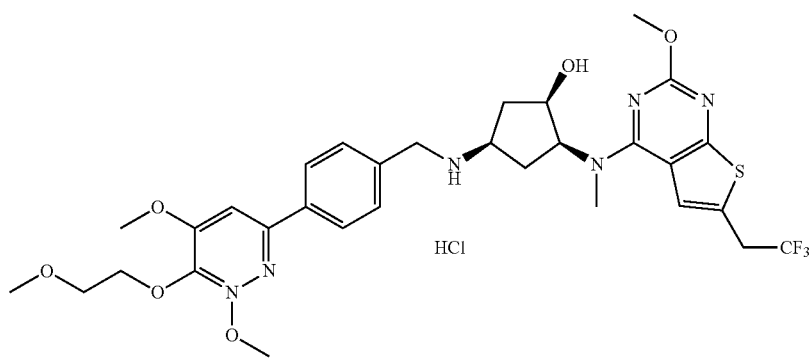

$^1$H-NMR (DMSO-D$_6$) δ: 1.74-1.84 (1H, m), 2.25-2.46 (3H, m), 3.32 (3H, s), 3.41 (3H, s), 3.57-3.64 (1H, m), 3.72-3.75 (2H, m), 3.84 (3H, s), 4.00 (2H, q, J = 10.4 Hz), 4.01 (3H, s), 4.28 (2H, br s), 4.38 (1H, br s), 4.57-4.60 (2H, m), 4.80-4.87 (1H, m), 5.20 (1H, br s), 7.64 (1H, s), 7.67 (1H, s), 7.70 (2H, d, J = 8.0 Hz), 8.20 (2H, d, J = 8.0 Hz), 9.15-9.32 (2H, m). MS (m/z): 649 (M + H)$^+$.

TABLE 2-47

| Ex. 110 | | |
|---|---|---|
| 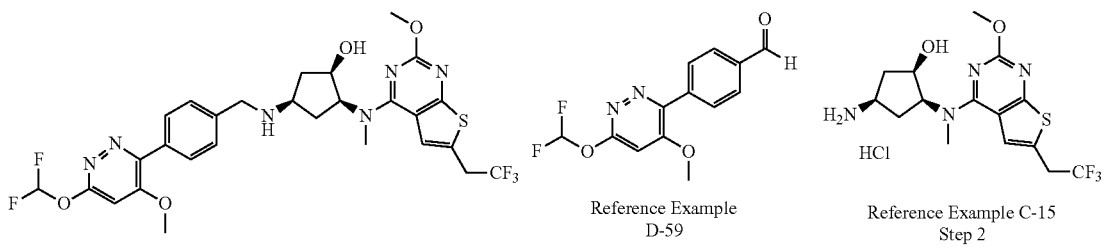 | Reference Example D-59 | Reference Example C-15 Step 2 |

(1R,2S,4R)-4-[({4-[6-(difluoromethoxy)-4-methoxypyridazin-3-yl]phenyl}methyl)amino]-2-{[2-methoxy-6-(2,2,2-trifluoroethyl)thieno[2,3-d]pyrimidin-4-yl](methyl)amino}cyclopentan-1-ol hydrochloride

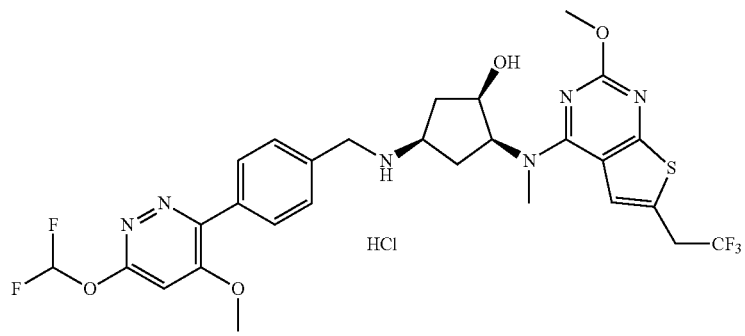 [SMILES: COc1nc(N(C)[C@H]2C[C@@H](NCc3ccc(-c4nnc(OC(F)F)cc4OC)cc3)C[C@H]2O)c2cc(CC(F)(F)F)sc2n1 ; Cl]

$^1$H-NMR (DMSO-D$_6$) δ: 1.81-2.08 (1H, m), 2.28-2.35 (1H, m), 2.42-2.45 (1H, m), 2.53-2.55 (1H, m), 3.41 (3H, s), 3.60-3.62 (1H, m), 3.85 (3H, s), 3.99-4.02 (5H, m), 4.26-4.28 (2H, m), 4.37-4.38 (1H, m), 4.84-4.86 (1H, m), 7.28 (1H, s), 7.78-8.01 (6H, m), 9.48-9.54 (2H, m). MS (m/z): 641 (M + H)$^+$.

| Ex. 111 | | |
|---|---|---|
| 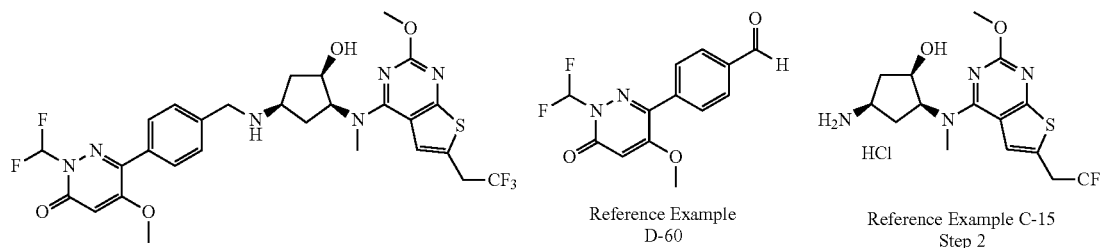 | Reference Example D-60 | Reference Example C-15 Step 2 |

2-(difluoromethyl)-6-[4-({[(1R,3R,4S)-3-hydroxy-4-{[2-methoxy-6-(2,2,2-trifluoroethyl)thieno[2,3-d]pyrimidin-4-yl](methyl)amino}cyclopentyl]amino}methyl)phenyl]-5-methoxypyridazin-3(2H)-one hydrochloride

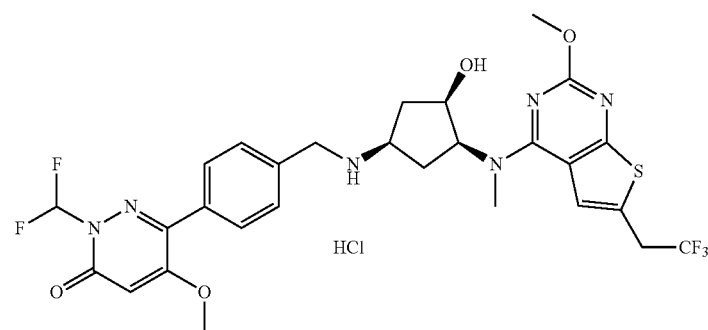

$^1$H-NMR (DMSO-D$_6$) δ:1.77-2.45 (4H, m), 3.41 (3H, s), 3.59-3.61 (1H, m), 3.84 (3H, s), 3.89 (3H, s), 3.98-4.01 (2H, m), 4.25-4.28 (2H, m), 4.36-4.39 (1H, m), 4.82-4.85 (1H, m), 5.18-5.20 (1H, m), 6.55 (1H, s), 7.63-7.73 (5H, m), 7.97 (1H, t, J = 58.3 Hz), 9.31-9.38 (2H, m). MS (m/z): 641 (M + H)$^+$.

TABLE 2-48

Ex. 112

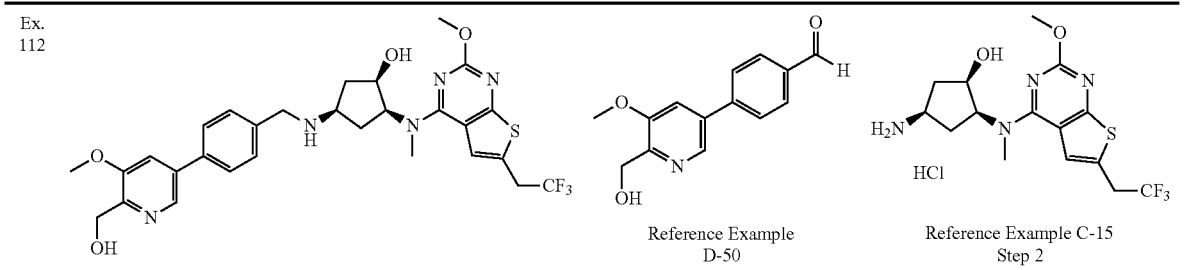

Reference Example D-50

Reference Example C-15 Step 2

(1R,2S,4R)-4-[({4-[6-(hydroxymethyl)-5-methoxypyridin-3-yl]phenyl}methyl)amino]-2-{[2-methoxy-6-(2,2,2-trifluoroethyl)thieno[2,3-d]pyrimidin-4-yl](methyl)amino}cyclopentan-1-ol hydrochloride

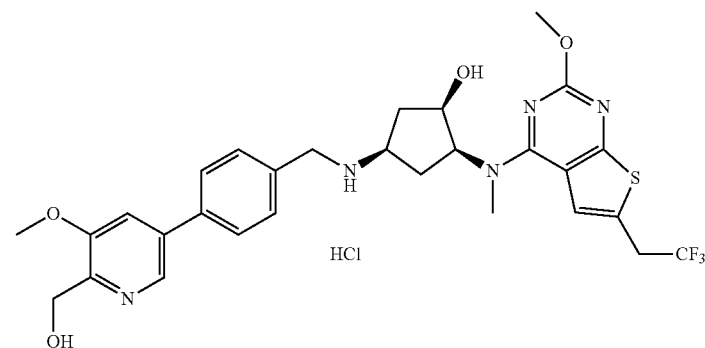 [SMILES: COc1nc(N(C)[C@H]2C[C@@H](NCc3ccc(-c4cnc(CO)c(OC)c4)cc3)C[C@H]2O)c2cc(CC(F)(F)F)sc2n1 ; Cl]

$^1$H-NMR (DMSO-D$_6$, 80° C.) δ: 1.84-1.91 (1H, m), 2.28-2.37 (1H, m), 2.39-2.50 (2H, m), 3.42 (3H, s), 3.56-3.68 (1H, m), 3.85 (3H, s), 3.94 (2H, q, J = 10.6 Hz), 3.94 (3H, s), 4.22-4.30 (2H, m), 4.36-4.42 (1H, m), 4.60 (2H, s), 4.81-4.88 (1H, m), 5.00-5.10 (1H, m), 7.57 (1H, s), 7.63 (1H, d, J = 1.8 Hz), 7.70 (2H, d, J = 7.4 Hz), 7.84 (2H, d, J = 8.6 Hz), 8.44 (1H, d, J = 1.8 Hz), 9.30 (2H, s). MS (m/z): 604 (M + H)$^+$.

Ex. 113

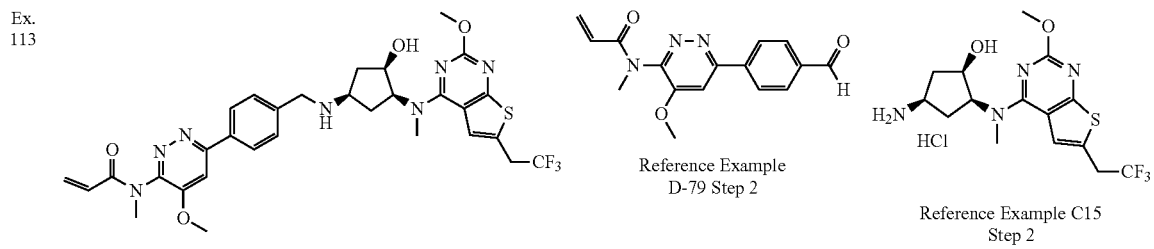

Reference Example D-79 Step 2

Reference Example C15 Step 2

N-{6-[4-({[(1R,3R,4S)-3-hydroxy-4-{[2-methoxy-6(2,2,2-trifluoroethyl)thieno[2,3-d]pyrimidin-4-yl](methyl)amino}cyclopentyl]amino}methyl)phenyl]-4-methoxypyridazin-3-yl}-N-methylprop-2-enamide hydrochloride

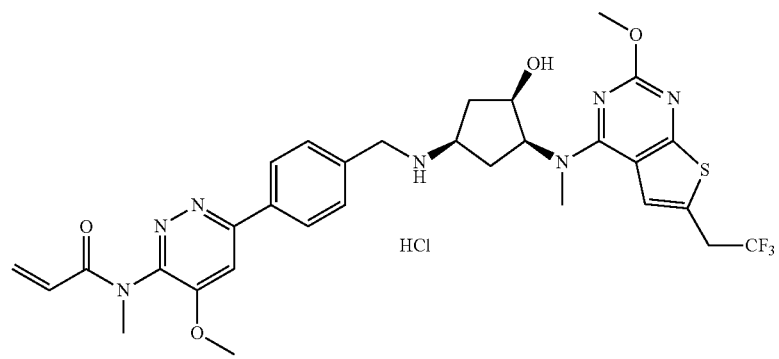 [SMILES: C=CC(=O)N(C)c1nnc(-c2ccc(CN[C@H]3C[C@@H](O)[C@@H](N(C)c4nc(OC)nc5sc(CC(F)(F)F)cc45)C3)cc2)cc1OC ; Cl]

$^1$H-NMR (DMSO-D$_6$) δ: 1.83-2.47 (4H, m), 3.42 (3H, s), 3.59-3.61 (1H, m), 3.85 (3H, s), 3.87 (3H, s), 3.94-3.97 (5H, m), 4.25-4.28 (2H, m), 4.36-4.38 (1H, m), 4.81-4.87 (1H, m), 5.09-5.12 (1H, m), 5.62 (1H, dd, J = 10.4, 1.8 Hz), 6.01 (1H, dd, J = 17.2, 1.8 Hz), 6.27 (1H, dd, J = 17.2, 10.4 Hz), 7.41 (1H, s), 7.59 (1H, s), 7.73 (2H, d, J = 8.3 Hz), 8.05 (2H, d, J = 8.3 Hz), 9.44-9.47 (2H, m). MS (m/z): 658 (M + H)$^+$.

TABLE 2-49

| Ex. 114 | 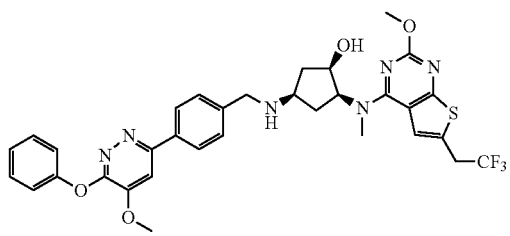 [SMILES: COc1nc(N(C)[C@H]2C[C@@H](NCc3ccc(-c4cc(OC)c(Oc5ccccc5)nn4)cc3)C[C@H]2O)c2cc(CC(F)(F)F)sc2n1] | 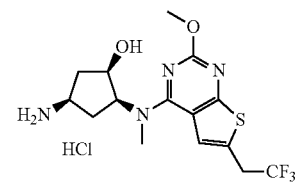 |
|---|---|---|
| | Reference Example D-96 | Reference Example C-15 Step 2 |

(1R,2S,4R)-4-({[4-(5-methoxy-6-phenoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol hydrochloride

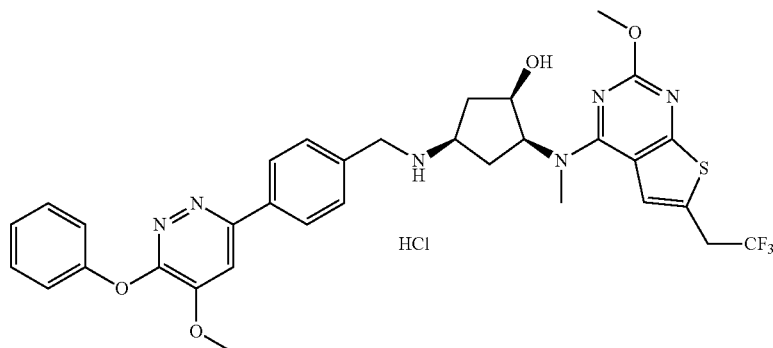

$^1$H-NMR (DMSO-D$_6$) δ: 1.83-2.46 (4H, m), 3.41 (3H, s), 3.58-3.61 (1H, m), 3.84 (3H, s), 3.98-4.01 (2H, m), 4.10 (3H, s), 4.27 (2H, s), 4.35-4.37 (1H, m), 4.83-4.84 (1H, m), 7.20-7.29 (3H, m), 7.44-7.49 (2H, m), 7.64 (1H, s), 7.76-7.78 (2H, m), 8.20 (2H, d, J = 8.6 Hz), 9.57-9.63 (2H, m). MS (m/z): 667 (M + H)$^+$.

| Ex. 115 | 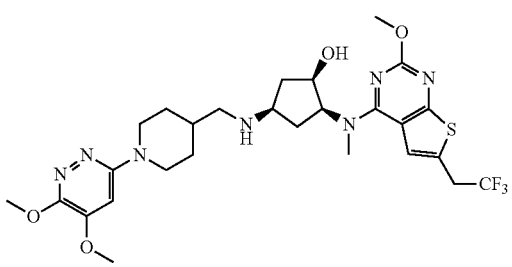 [SMILES: COc1nc(N(C)[C@H]2C[C@@H](NCC3CCN(c4cc(OC)c(OC)nn4)CC3)C[C@H]2O)c2cc(CC(F)(F)F)sc2n1] | 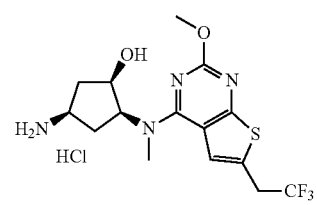 |
|---|---|---|
| | Reference Example D-90 Step 2 | Reference Example C-15 Step 2 |

(1R,2S,4R)-4-({[1-(5,6-dimethoxypyridazin-3-yl)piperidin-4-yl]methyl}amino)-2-{[2-methoxy-6-(2,2,2-trifluoroethyl)thieno[2,3-d]pyrimidin-4-yl](methyl)amino}cyclopentan-1-ol hydrochloride

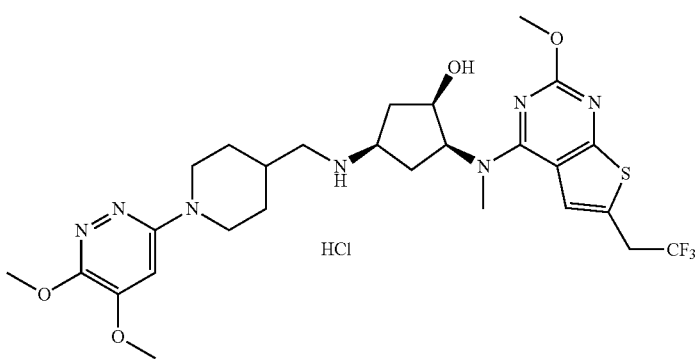 [SMILES: COc1nc(N(C)[C@H]2C[C@@H](NCC3CCN(c4cc(OC)c(OC)nn4)CC3)C[C@H]2O)c2cc(CC(F)(F)F)sc2n1 ; Cl]

$^1$H-NMR (DMSO-D$_6$) δ: 1.27-1.30 (2H, m), 1.74-2.47 (7H, m), 2.87-2.89 (4H, m), 3.40 (3H, s), 3.53-3.58 (1H, m), 3.84 (3H, s), 3.88 (3H, s), 3.89 (3H, s), 3.98-4.01 (2H, m), 4.22-4.25 (2H, m), 4.35-4.36 (1H, m), 4.81-4.82 (1H, m), 5.16-5.17 (1H, m), 6.86 (1H, s), 7.63 (1H, s), 8.93-9.02 (2H, m). MS (m/z): 612 (M + H)$^+$.

TABLE 2-50

Ex. 116

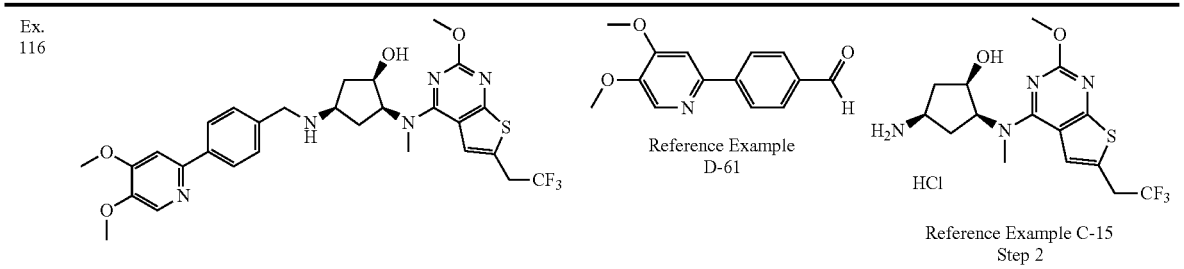

Reference Example D-61

Reference Example C-15 Step 2

(1R,2S,4R)-4-({[4-(4,5-dimethoxypyridin-2-yl)phenyl]methyl}amino)-2-{[2-methoxy-6-(2,2,2-trifluoroethyl)thieno[2,3-d]pyrimidin-4yl](methyl)amino}cyclopentan-1-ol hydrochloride

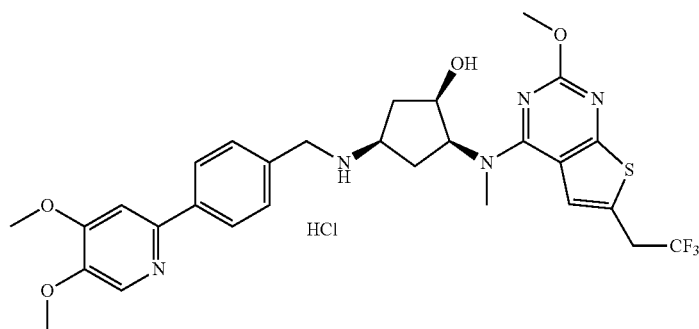

$^1$H-NMR (DMSO-D$_6$) δ: 1.79-2.08 (1H, m), 2.27-2.33 (1H, m), 2.40-2.46 (2H, m), 3.41 (3H, s), 3.58-3.60 (1H, m), 3.84 (3H, s), 3.91 (3H, s), 3.98-4.01 (5H, m), 4.24-4.26 (2H, m), 4.35-4.38 (1H, m), 4.82-4.85 (1H, m), 5.17-5.20 (1H, m), 7.62 (1H, s), 7.63 (1H, s), 7.69 (2H, d, J = 8.0 Hz), 8.15 (2H, d, J = 8.0 Hz), 8.27 (1H, s), 9.38-9.44 (2H, m). MS (m/z): 604 (M + H)$^+$.

Ex. 117

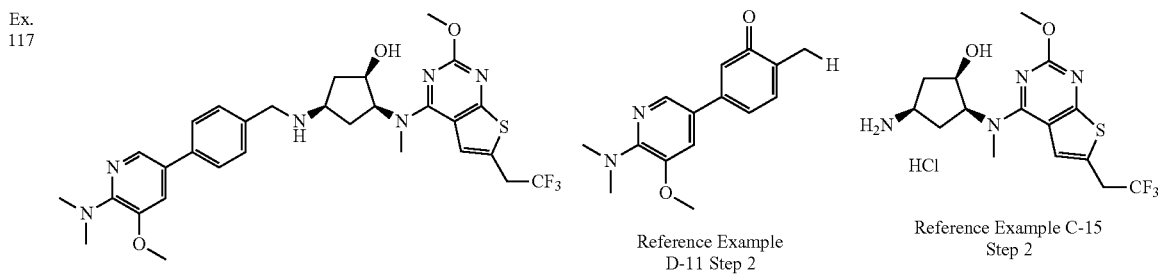

Reference Example D-11 Step 2

Reference Example C-15 Step 2

(1R,2S,4R)-4-[({4-[6-(dimethylamino)-5-methoxypyridin-3-yl]phenyl}methyl)amino]-2-{[2-methoxy-6-(2,2,2-trifluoroethyl)thieno[2,3-d]pyrimidin-4-yl](methyl)amino}cyclopentan-1-ol hydrochloride

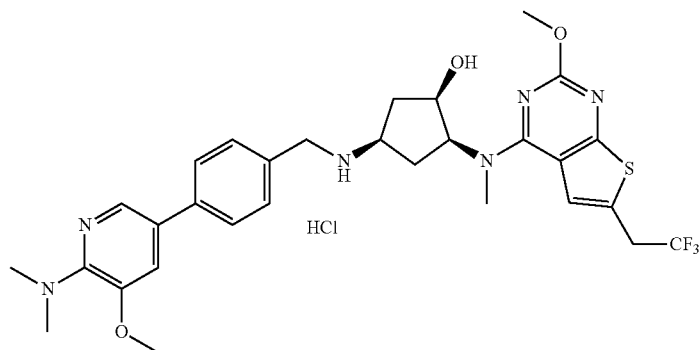 [SMILES: COc1nc(N(C)[C@H]2C[C@@H](NCc3ccc(-c4cnc(N(C)C)c(OC)c4)cc3)C[C@H]2O)c2cc(CC(F)(F)F)sc2n1 ; Cl]

$^1$H-NMR (DMSO-D$_6$) δ: 1.83-2.47 (4H, m), 2.99 (6H, s), 3.42 (3H, s), 3.58-3.61 (1H, m), 3.85 (3H, s), 3.90 (3H, s), 3.94-3.97 (2H, m), 4.21-4.23 (2H, m), 4.36-4.38 (1H, m), 4.81-4.88 (1H, m), 7.46 (1H, d, J = 1.8 Hz), 7.59 (1H, s), 7.65 (2H, d, J = 8.3 Hz), 7.75 (2H, d, J = 8.3 Hz), 8.10 (1H, d, J = 1.8 Hz), 9.36-9.42 (2H, m). MS (m/z): 617 (M + H)$^+$.

TABLE 2-51

| Ex. 118 | 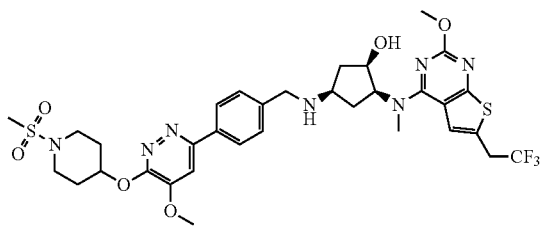 [SMILES: COc1nc(N(C)[C@H]2C[C@@H](NCc3ccc(-c4cc(OC)c(OC5CCN(S(C)(=O)=O)CC5)nn4)cc3)C[C@H]2O)c2cc(CC(F)(F)F)sc2n1] | 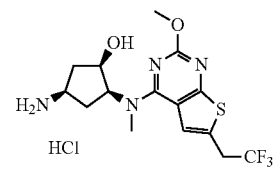 |
|---|---|---|
| | Reference Example D-62 | Reference Example C-15 Step 2 |

(1R,2S,4R)-4-({[4-(6-{[1-(methanesulfonyl)piperidin-4-yl]oxy}-5-methoxypyridazin-3-yl)phenyl]methyl}amino)-2-{[2-methoxy-6-(2,2,2-trifluoroethyl)thieno[2,3-d]pyrimidin-4-yl(methyl)amino}cyclopentan-1-ol hydrochloride

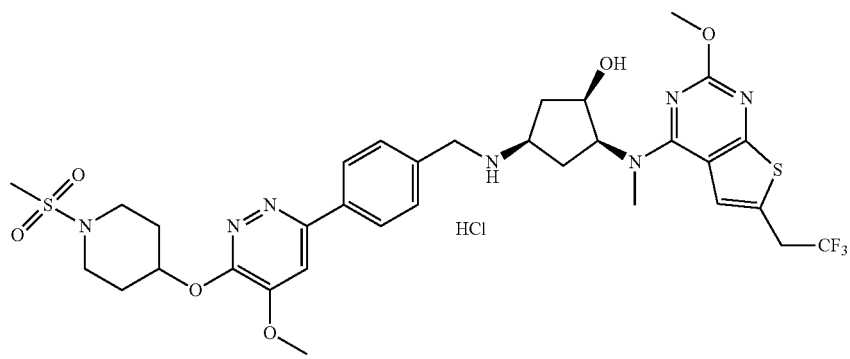 [SMILES: COc1nc(N(C)[C@H]2C[C@@H](NCc3ccc(-c4cc(OC)c(OC5CCN(S(C)(=O)=O)CC5)nn4)cc3)C[C@H]2O)c2cc(CC(F)(F)F)sc2n1 ; Cl]

$^1$H-NMR (DMSO-D$_6$) δ: 1.80-2.42 (8H, m), 2.93 (3H, s), 3.12-3.16 (2H, m), 3.36-3.47 (6H, m), 3.84 (3H, s), 3.97-4.01 (5H, m), 4.27-4.29 (2H, m), 4.37-4.38 (1H, m), 4.83-4.86 (1H, m), 5.34-5.40 (1H, m), 7.64 (1H, s), 7.70 (1H, s), 7.74 (2H, d, J = 8.3 Hz), 8.19 (2H, d, J = 8.3 Hz), 9.39-9.46 (2H, m) MS (m/z): 752 (M + H)$^+$.

| Ex. 119 | 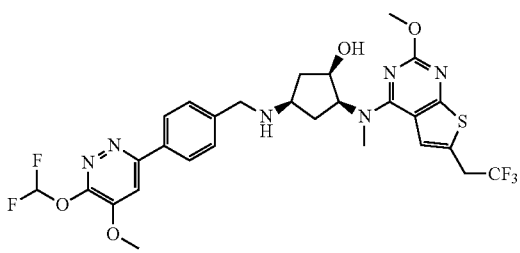 [SMILES: COc1nc(N(C)[C@H]2C[C@@H](NCc3ccc(-c4cc(OC)c(OC(F)F)nn4)cc3)C[C@H]2O)c2cc(CC(F)(F)F)sc2n1] | | |
|---|---|---|---|
| | | Reference Example D-58 | Reference Example C-15 Step 2 |

(1R,2S,4R)-4-[({4-[6-(difluoromethoxy)-5-methoxypyridazin-3-yl]phenyl}methyl)amino]-2-{[2-methoxy-6-(2,2,2-trifluoroethyl)thieno[2,3-d]pyrimidin-4-yl](methyl)amino}cyclopentan-1-ol hydrochloride

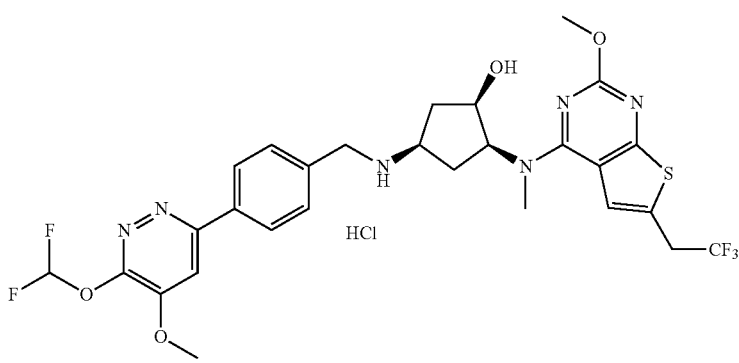 [SMILES: COc1nc(N(C)[C@H]2C[C@@H](NCc3ccc(-c4cc(OC)c(OC(F)F)nn4)cc3)C[C@H]2O)c2cc(CC(F)(F)F)sc2n1 ; Cl]

$^1$H-NMR (DMSO-D$_6$) δ: 1.73-1.83 (1H, m), 2.28-2.44 (2H, m), 3.42 (3H, s), 3.62 (1H, s), 3.84 (3H, s), 4.00 (2H, dd, J = 22.0, 11.0 Hz), 4.09 (3H, s), 4.30 (2H, s), 4.39 (1H, s), 4.84 (1H, br s), 5.20 (1H, d, J = 4.3 Hz), 7.63 (1H, s), 7.69-8.10 (4H, m), 8.24 (2H, d, J = 8.5 Hz), 9.27 (2H, br s). MS (m/z): 641 (M + H)$^+$.

TABLE 2-52

Ex. 120

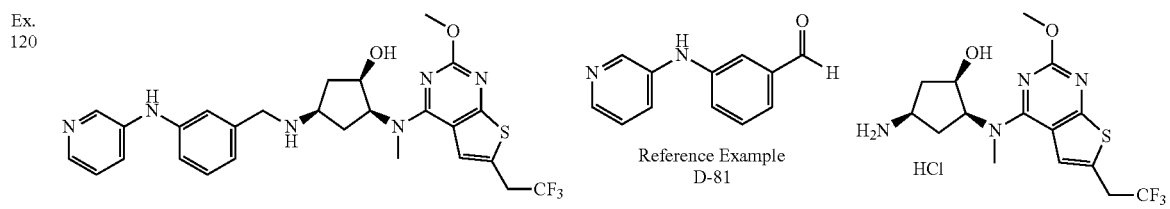

Reference Example D-81

Reference Example C-15 Step 2

(1R,2S,4R)-2-{[2-methoxy-6-(2,2,2-trifluoroethyl)thieno[2,3-d]pyrimidin-4-yl](methyl)amino}-4-[({3-[(pyridin-3-yl)amino]phenyl}methyl)amino]cyclopentan-1-ol hydrochloride

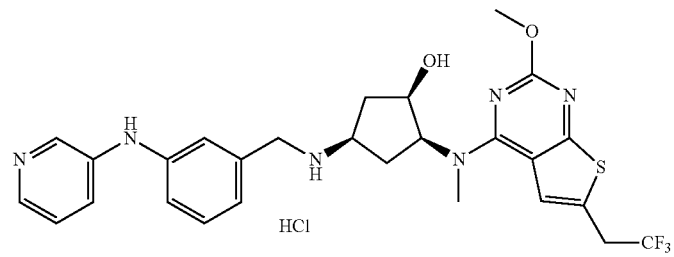 [SMILES: COc1nc(N(C)[C@H]2C[C@@H](NCc3cccc(Nc4cccnc4)c3)C[C@H]2O)c2cc(CC(F)(F)F)sc2n1 ; Cl]

$^1$H-NMR (DMSO-D$_6$) δ: 1.74-1.75 (1H, m), 2.04-2.08 (2H, m), 2.27-2.36 (1H, m), 3.40 (3H, s), 3.59 (1H, s), 3.84 (3H, s), 3.99 (2H, q, J = 11.0 Hz), 4.15 (2H, s), 4.37 (1H, s), 4.82 (1H, s), 5.18 (1H, s), 7.02-7.13 (2H, m), 7.29-7.40 (3H, m), 7.53-7.65 (2H, m), 8.10 (1H, d, J = 4.9 Hz), 8.46 (1H, d, J = 2.4 Hz), 9.15 (2H, br s). MS (m/z): 559 (M + H)$^+$.

Ex. 121

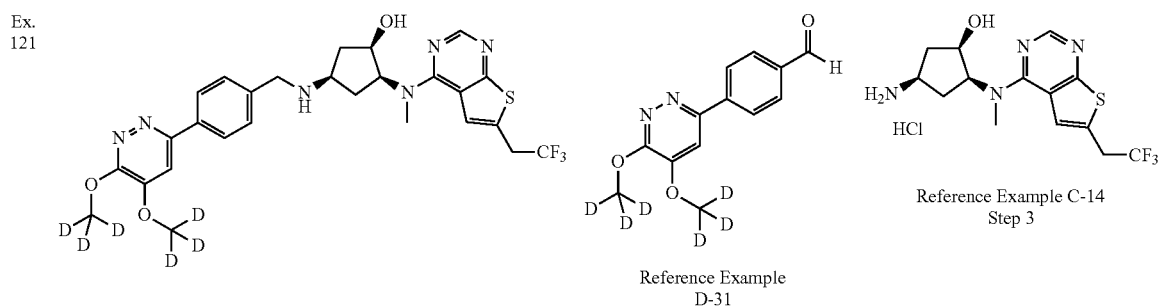

Reference Example D-31

Reference Example C-14 Step 3

(1R,2S,4R)-4-{[(4-{5,6-bis[($^2$H$_3$)methyloxy]pyridazin-3-yl}phenyl)methyl[amino}-2-{methyl[6-(2,2,2-trifluoroethyl)thieno[2,3-d]pyrimidin-4-yl]amino}cyclopentan-1-ol

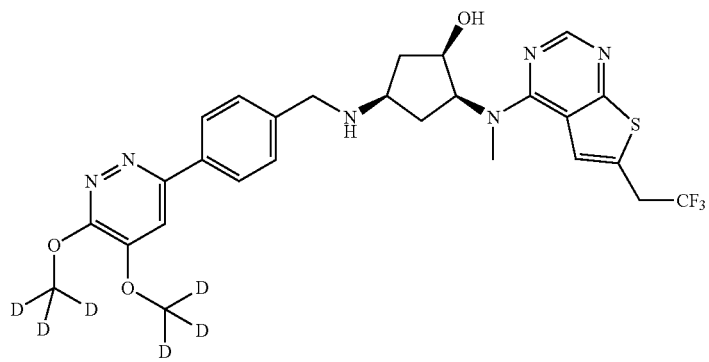 [SMILES: [2H]C([2H])([2H])Oc1cc(-c2ccc(CN[C@H]3C[C@@H](O)[C@@H](N(C)c4ncnc5sc(CC(F)(F)F)cc45)C3)cc2)nnc1OC([2H])([2H])[2H]]

$^1$H-NMR (CDCl$_3$) δ: 1.86-2.09 (3H, m), 2.34 (1H, ddd, J = 14.9, 8.2, 5.2 Hz), 3.42-3.47 (1H, m), 3.54 (3H, s), 3.63 (2H, q, J = 10.3 Hz), 3.87-3.95 (2H, m), 4.47-4.50 (1H, m), 5.11 (1H, td, J = 9.6, 4.7 Hz), 7.13 (1H, s), 7.41 (1H, s), 7.45 (2H, d, J = 7.9 Hz), 7.98 (2H, d, J = 7.9 Hz), 8.40 (1H, s). MS (m/z): 581 (M + H)$^+$.

TABLE 2-53

Ex. 122

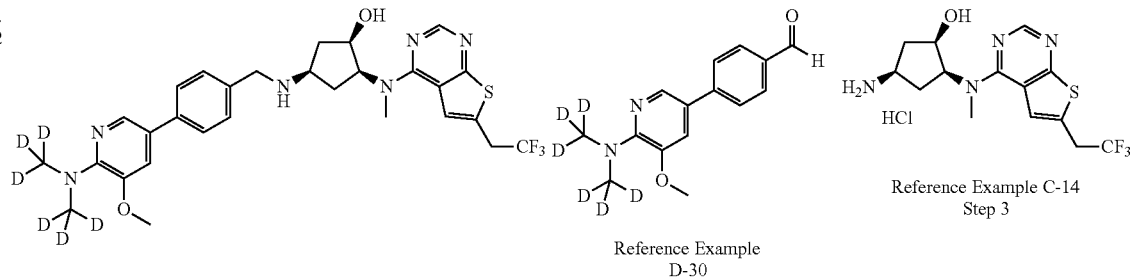

Reference Example D-30

Reference Example C-14 Step 3

(1R,2S,4R)-4-({[4-(6-{bis[($^2$H$_3$)methyl]amino}-5-methoxypyridin-3-yl)phenyl]methyl}amino)-2-{methyl[6-(2,2,2-trifluoroethyl)thieno[2,3-d]pyrimidin-4-yl]amino}cyclopentan-1-ol

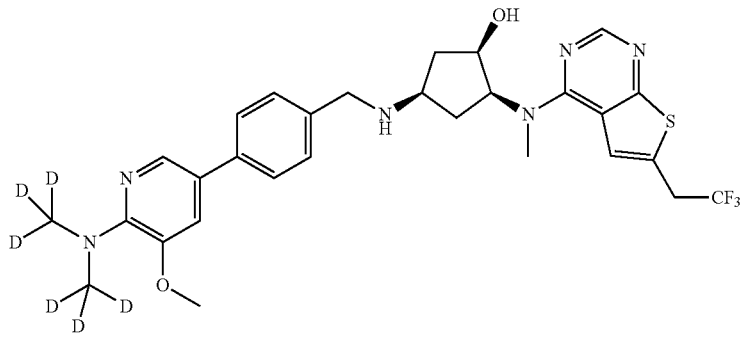 [SMILES: [2H]C([2H])([2H])N(c1ncc(-c2ccc(CN[C@H]3C[C@@H](O)[C@@H](N(C)c4ncnc5sc(CC(F)(F)F)cc45)C3)cc2)cc1OC)C([2H])([2H])[2H]]

$^1$H-NMR (CDCl$_3$) δ: 1.86-2.08 (3H, m), 2.31-2.38 (1H, m), 3.42-3.48 (1H, m), 3.54 (3H, s), 3.62 (2H, q, J = 10.3 Hz), 3.83-3.91 (2H, m), 3.92 (3H, s), 4.47-4.50 (1H, m), 5.13 (1H, td, J = 9.6, 4.5 Hz), 7.20 (1H, d, J = 1.9 Hz), 7.37-7.41 (3H, m), 7.53 (2H, d, J = 8.5 Hz), 8.09 (1H, d, J = 1.9 Hz), 8.39 (1H, s). MS (m/z): 593 (M + H)$^+$.

Ex. 123

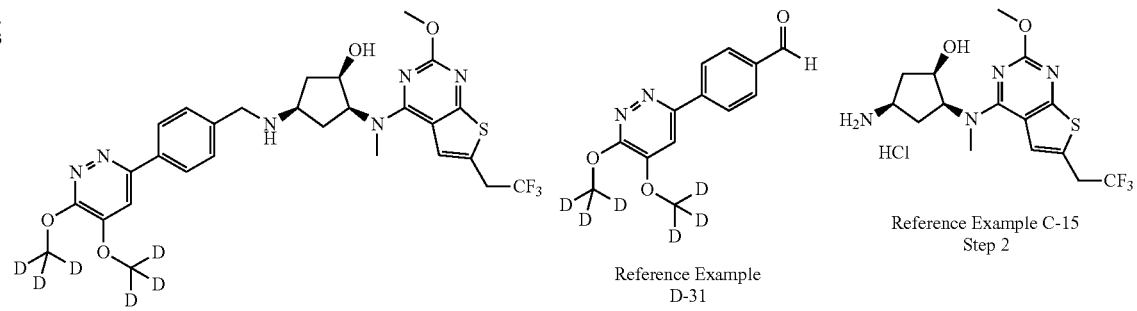

Reference Example D-31

Reference Example C-15 Step 2

(1R,2S,4R)-4-{[(4-{5,6-bis[($^2$H$_3$)methyloxy]pyridazin-3-yl}phenyl)methyl]amino}-2-{[2-methoxy-6-(2,2,2-trifluoroethyl)thieno[2,3-d]pyrimidin-4-yl](methyl)amino}cyclopentan-1-ol

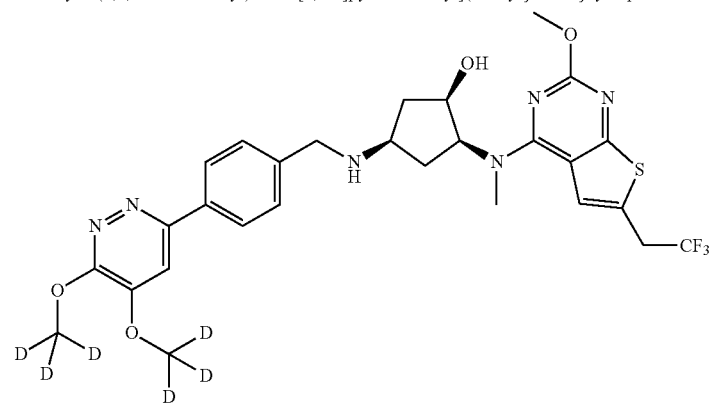

$^1$H-NMR (CDCl$_3$) δ: 1.85-2.06 (3H, m), 2.30-2.38 (1H, m), 3.41-3.46 (1H, m), 3.52 (3H, s), 3.57 (2H, q, J = 10.3 Hz), 3.86-3.94 (2H, m), 3.96 (3H, s), 4.47-4.50 (1H, m), 5.12 (1H, td, J = 9.4, 4.5 Hz), 7.13 (1H, s), 7.32 (1H, s), 7.44 (2H, d, J = 7.9 Hz), 7.98 (2H, d, J = 7.9 Hz). MS (m/z): 611(M + H)$^+$.

| Ex. 124 | 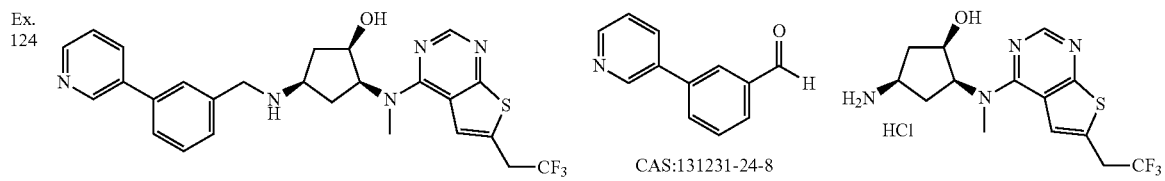 | | |
|---|---|---|---|
| | | CAS:131231-24-8 | Reference Example C-14 Step 3 |

(1R,2S,4R)-2-{methyl[6-(2,2,2-trifluoroethyl)thieno[2,3-d]pyrimidin-4-yl]amino}-4-({[3-(pyridin-3-yl)phenyl]methyl}amino)cyclopentan-1-ol hydrochloride

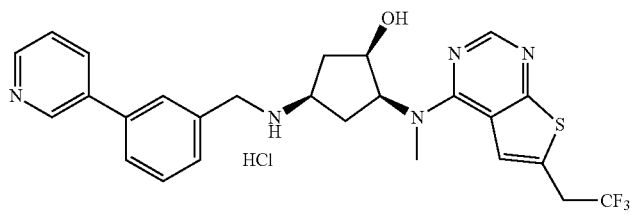 [SMILES: CN(c1ncnc2sc(CC(F)(F)F)cc12)[C@H]1C[C@@H](NCc2cccc(-c3cccnc3)c2)C[C@H]1O ; Cl]

¹H-NMR (DMSO-D₆)δ: 1.80-1.88 (1H, m), 2.27-2.35 (1H, m), 2.40-2.53 (2H, m), 3.44 (3H, s), 3.58-3.68 (1H, m), 4.06 (1H, d, J = 11.0 Hz), 4.11 (1H, d, J = 11.0 Hz), 4.23-4.39 (3H, m), 4.90-4.99 (1H, m), 5.19 (1H, s), 7.53-7.64 (3H, m), 7.75 (1H, s), 7.81 (1H, d, J = 8.0 Hz), 8.04 (1H, s), 8.16 (1H, dt, J = 8.0, 2.0 Hz), 8.36 (1H, s), 8.62 (1H, dd, J = 5.0, 2.0 Hz), 8.98 (1H, d, J = 2.0 Hz), 9.33-9.56 (2H, m). MS(m/z): 514 (M + H)⁺.

| Ex. 125 | 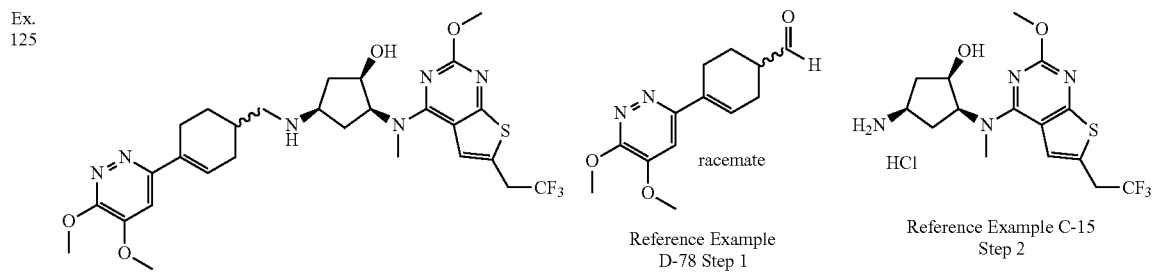 | | |
|---|---|---|---|
| | diastereomeric mixture | racemate Reference Example D-78 Step 1 | Reference Example C-15 Step 2 |

(1R,2S,4R)-4-({[4-(5,6-dimethoxypyridazin-3-yl)cyclohex-3-en-1-yl]methyl}amino)-2-{[2-methoxy-6-(2,2,2-trifluoroethyl)thieno[2,3-d]pyrimidin-4-yl](methyl)amino}cyclopentan-1-ol hydrochloride (diastereomer mixture)

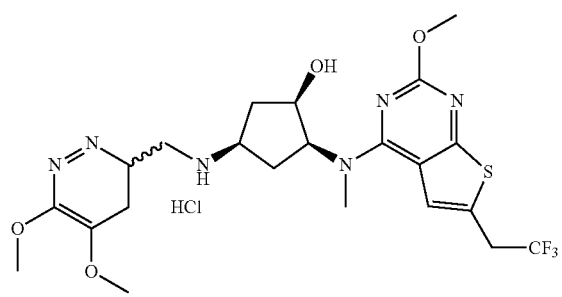

diastereomeric mixture

¹H-NMR (DMSO-D₆)δ: 1.37-1.49 (1H, m), 1.77-1.85 (1H, m), 2.03-2.16 (4H, m), 2.22-2.31 (1H, m), 2.37-2.48 (3H, m), 2.71-2.81 (1H, m), 2.91-3.02 (2H, m), 3.41(3H, s), 3.55-3.65 (1H, m), 3.85 (3H, s), 3.95-4.05 (8H, m), 4.33-4.38 (1H, m), 4.77-4.87 (1H, m), 6.76 (1H, s), 7.48 (1H, s), 7.64 (1H, s), 8.93-9.29 (2H, m). MS(m/z): 609 (M + H)⁺.

Example 126

(1S,3S,4S)—N¹-{[4-(5,6-dimethoxypyridazin-3-yl)phenyl]methyl}-4-methoxy-N³-[6-(2,2,2-trifluoroethyl)thieno[2,3-d]pyrimidin-4-yl]cyclohexane-1,3-diamine Hydrochloride Step 1 (1S,3S,4S)—N¹-{[4-(5,6-dimethoxypyridazin-3-yl)phenyl]methyl}-4-methoxy-N³-[6-(2,2,2-trifluoroethyl)thieno[2,3-d]pyrimidin-4-yl]cyclohexane-1,3-diamine

[Formula 426]

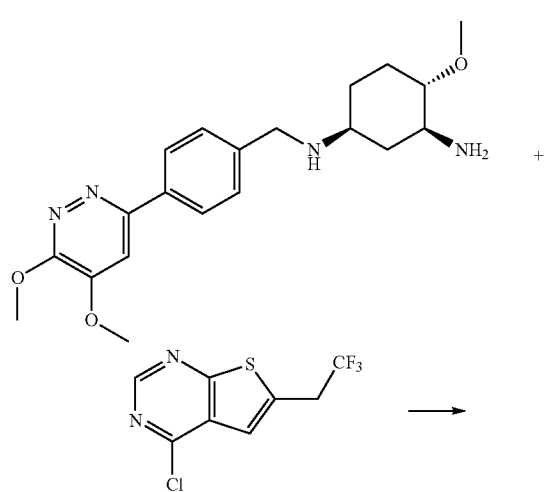

+

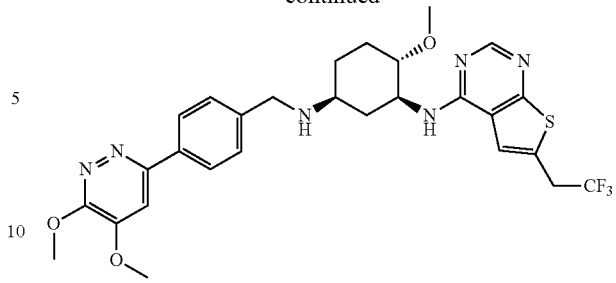

→

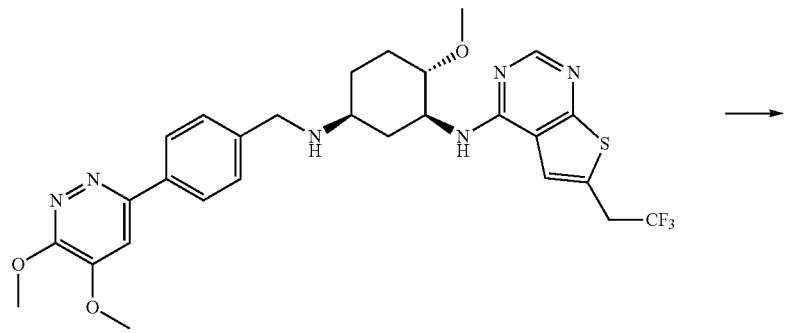

The title compound was obtained in the same manner as in Step 1 of Reference Example C-2, using the compound obtained in Step 2 of Reference Example E-3 and 4-chloro-6-(2,2,2-trifluoroethyl)thieno[2,3-d]pyrimidine produced according to the method described in a literature (cancer cell, 2015, 27, 589-602.).

$^1$H-NMR (CDCl$_3$) δ: 1.52-1.84 (4H, m), 1.97-2.13 (2H, m), 2.17-2.26 (1H, m), 3.15-3.21 (1H, m), 3.31-3.42 (2H, m), 3.46 (3H, s), 3.48-3.52 (1H, m), 3.92 (2H, s), 4.03 (3H, s), 4.25 (3H, s), 4.56-4.64 (1H, m), 6.52 (1H, s), 7.16 (1H, s), 7.47-7.51 (2H, m), 8.03-8.08 (2H, m), 8.08-8.25 (1H, m), 8.43 (1H, s).

MS (m/z): 589 (M+H)⁺.

Step 2 (1S,3S,4S)—N¹-{[4-(5,6-dimethoxypyridazin-3-yl)phenyl]methyl}-4-methoxy-N³-[6-(2,2,2-trifluoroethyl)thieno[2,3-d]pyrimidin-4-yl]cyclohexane-1,3-diamine Hydrochloride

[Formula 427]

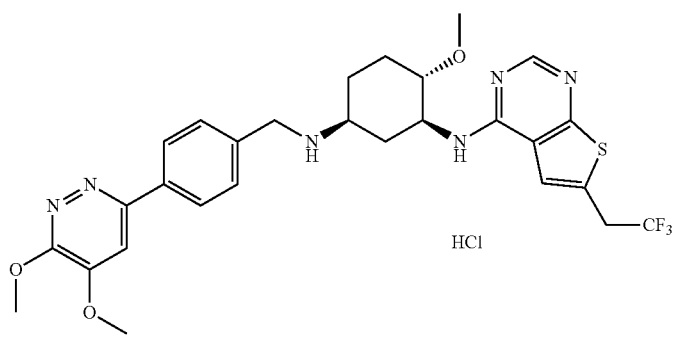

To a solution of the compound (0.143 g) obtained in the above Step 1 in ethanol (2.00 mL) was added 5N hydrochloric acid (0.0486 mL) at room temperature, and the solvent was evaporated under reduced pressure, and the residue was dried. The obtained residue was suspended in diethyl ether, and the resulting solid was collected by filtration, and dried to give the title compound (0.142 g).

$^1$H-NMR (DMSO-D6) δ: 1.19-1.34 (1H, m), 1.52-1.76 (2H, m), 2.20-2.34 (2H, m), 2.40-2.48 (1H, m), 3.26 (3H, s), 3.27-3.41 (2H, m), 4.01 (3H, s), 4.05-4.37 (5H, m), 4.07 (3H, s), 7.67-7.76 (4H, m), 8.14-8.20 (2H, m), 8.23-8.31 (1H, m), 8.36 (1H, s), 9.27-9.57 (2H, m).

MS (m/z): 589 (M+H)$^+$.

Example 127

(1R,3S,4R)—N$^1$-{[4-(5,6-dimethoxypyridazin-3-yl)phenyl]methyl}-4-methoxy-N$^3$-methyl-N$^3$-[6-(2,2,2-trifluoroethyl)thieno[2,3-d]pyrimidin-4-yl]cyclopentane-1,3-diamine Hydrochloride Step 1 (1R,3S,4R)—N$^1$-{[4-(5,6-dimethoxypyridazin-3-yl)phenyl]methyl}-4-methoxy-N$^3$-methyl-N$^3$-[6-(2,2,2-trifluoroethyl)thieno[2,3-d]pyrimidin-4-yl]cyclopentane-1,3-diamine

[Formula 428]

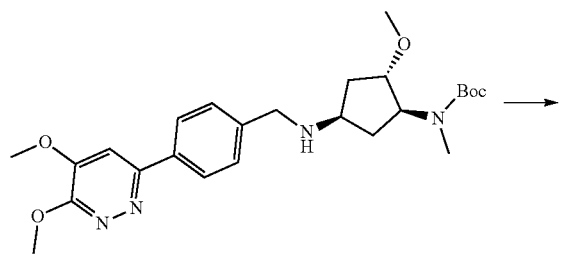

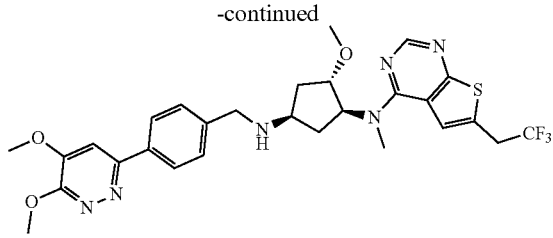

A mixture of the compound (0.638 g) obtained in Reference Example E-4, hydrogen chloride (4 mol/L, 1,4-dioxane solution, 13.5 mL) and dichloromethane (15.0 mL) was stirred at room temperature for 35 min, and concentrated. The residue was dried to give a solid (0.601 g). A mixture of the obtained solid, 4-chloro-6-(2,2,2-trifluoroethyl)thieno[2,3-d]pyrimidine (0.358 g) produced according to the method described in a literature (cancer cell, 2015, 27, 589-602), DIPEA (1.41 mL) and 2-propanol (20 mL) was stirred at 80° C. for 5 hr, and concentrated under reduced pressure, and the obtained residue was subjected to silica gel column chromatography (ethyl acetate/methanol to give the title compound (0.454 g) as a solid.

$^1$H-NMR (CDCl$_3$) δ: 1.67-1.74 (1H, m), 2.01-2.10 (1H, m), 2.20-2.34 (2H, m), 3.22 (3H, s), 3.22-3.28 (1H, m), 3.48 (3H, s), 3.63 (2H, q, J=10.2 Hz), 3.88-3.94 (2H, m), 4.00-4.04 (1H, m), 4.03 (3H, s), 4.24 (3H, s), 5.01-5.08 (1H, m), 7.14 (1H, s), 7.42 (1H, s), 7.48 (2H, d, J=7.9 Hz), 7.97 (2H, d, J=7.9 Hz), 8.40 (1H, s).

Step 2 (1R,3S,4R)—N$^1$-{[4-(5,6-dimethoxypyridazin-3-yl)phenyl]methyl}-4-methoxy-N$^3$-methyl-N$^3$-[6-(2,2,2-trifluoroethyl)thieno[2,3-d]pyrimidin-4-yl]cyclopentane-1,3-diamine Hydrochloride

[Formula 429]

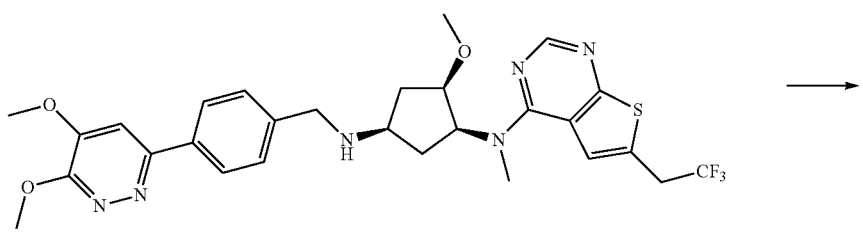

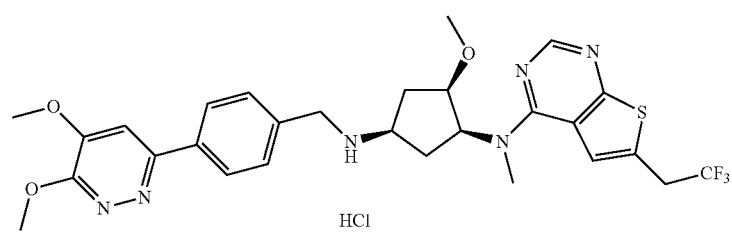

A mixture of the compound (0.454 g) obtained in the above Step 1, 1N hydrochloric acid (0.739 mL) and ethanol (3 mL) was stirred at room temperature for 5 min, and concentrated. Acetonitrile (10 mL) was added to the obtained residue, and the precipitated solid was collected by filtration, and dried to give the title compound (0.413 g) as a solid.

$^1$H-NMR (DMSO-D$_6$) δ: 1.88-1.95 (1H, m), 2.32-2.39 (2H, m), 2.46-2.49 (1H, m), 3.17 (3H, s), 3.41 (3H, s), 3.55-3.67 (1H, m), 3.99-4.04 (1H, m), 4.01 (3H, s), 4.07 (3H, s), 4.09 (2H, q, J=11.0 Hz), 4.25-4.30 (2H, m), 5.07-5.15 (1H, m), 7.67 (1H, s), 7.71 (2H, d, J=8.6 Hz), 7.77 (1H, s), 8.20 (2H, d, J=8.6 Hz), 8.39 (1H, s), 9.29 (2H, br s).

MS (m/z): 589 (M+H)$^+$.

Example 128

(1R,2S,4R)-4-({[(1s,4S)-4-(5,6-dimethoxypyridazin-3-yl)cyclohexyl]methyl}amino)-2-{[2-methoxy-6-(2,2,2-trifluoroethyl)thieno[2,3-d]pyrimidin-4-yl](methyl)amino}cyclopentan-1-ol Hydrochloride (1R,2S,4R)-4-({[(1r,4R)-4-(5,6-dimethoxypyridazin-3-yl)cyclohexyl]methyl}amino)-2-{[2-methoxy-6-(2,2,2-trifluoroethyl)thieno[2,3-d]pyrimidin-4-yl](methyl)amino}cyclopentan-1-ol Hydrochloride

[Formula 430]

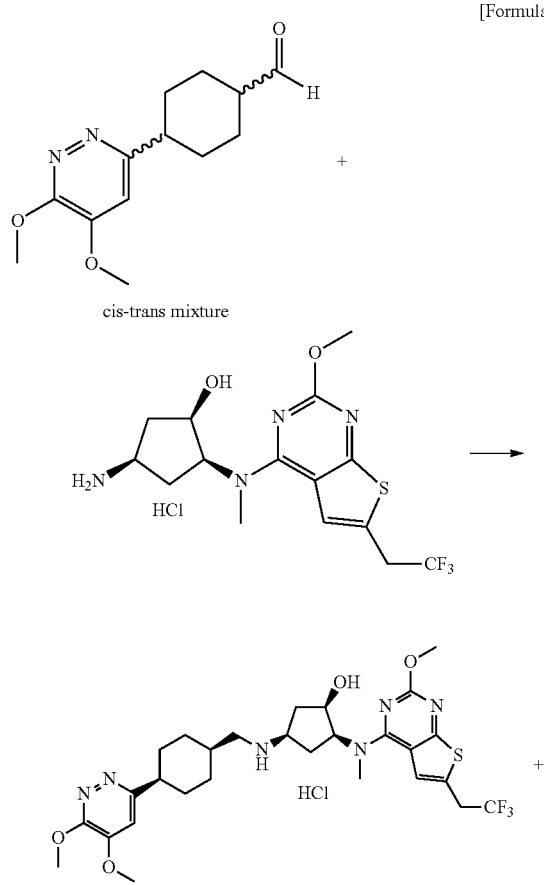

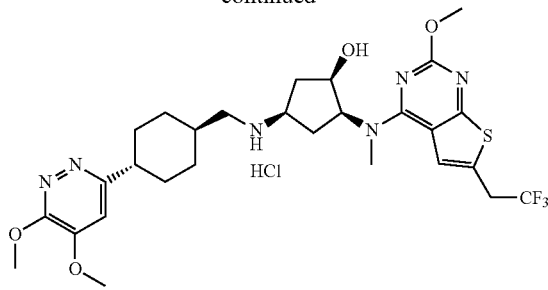

The compound (0.220 g) obtained in Step 2 of Reference Example C-15 was suspended in dichloromethane (5.3 mL), and DIPEA (0.371 mL) was added thereto. The mixture was stirred at room temperature for 1 hr. The compound (0.140 g) obtained in Step 2 of Reference Example D-78 and acetic acid (0.213 mL) were added thereto, and the mixture was stirred for 15 min. Sodium triacetoxyborohydride (0.384 g) was added to the mixture, and the mixture was stirred overnight at room temperature. Saturated aqueous sodium bicarbonate solution was added to the reaction solution, and the mixture was subjected to extraction operation. The organic layer was dried over anhydrous sodium sulfate, and the solvent was evaporated under reduced pressure. The residue was purified by silica gel chromatography (dichloromethane/methanol) to give a solid. The solid was purified by high-performance liquid chromatography (CHIRALPAK (registered trademark, Daicel Corporation) IG, mobile phase: n-hexane/ethanol) to give a free form of 128A (an earlier eluted component, 0.026 g) and a free form of 128B (a later eluted component 0.100 g), respectively as a solid.

the free form of 128A $^1$H-NMR (CDCl$_3$) δ: 1.68-2.08 (12H, m), 2.26-2.35 (1H, m), 2.68-2.74 (2H, m), 2.85-2.92 (1H, m), 3.35-3.42 (1H, m), 3.50 (3H, s), 3.54 (1H, d, J=10.5 Hz), 3.59 (1H, d, J=10.5 Hz), 3.93 (3H, s), 3.96 (3H, s), 4.16 (3H, s), 4.43 (1H, t, J=4.0 Hz), 5.12 (1H, td, J=10.0, 5.0 Hz), 6.61 (1H, s), 7.32 (1H, s).

MS (m/z): 611 (M+H)$^+$.

the free form of 128B $^1$H-NMR (CDCl$_3$) δ: 1.10-1.23 (2H, m), 1.57-2.09 (10H, m), 2.27-2.36 (1H, m), 2.57 (2H, d, J=7.0 Hz), 2.76 (1H, t, J=12.5 Hz), 3.32-3.38 (1H, m), 3.52 (3H, s), 3.54 (1H, d, J=10.5 Hz), 3.59 (1H, d, J=10.5 Hz), 3.92 (3H, s), 3.96 (3H, s), 4.15 (3H, s), 4.42-4.46 (1H, m), 5.10-5.18 (1H, m), 6.59 (1H, s), 7.32 (1H, s).

MS (m/z): 611 (M+H)$^+$.

The free form of 128A (25 mg) obtained in the above step was dissolved in ethanol (0.5 mL), 1N hydrochloric acid ethanol solution (41 μl) was added thereto, and the mixture was concentrated under reduced pressure. Ethyl acetate (1 mL) was added to the residue, and the precipitated solid was collected by filtration to give one compound (128A) (28 mg) of the title compounds, as a solid.

$^1$H-NMR (DMSO-D$_6$) δ: 1.60-2.12 (11H, m), 2.23-2.42 (2H, m), 2.85-3.10 (3H, m), 3.40 (3H, s), 3.53-3.64 (1H, m), 3.84 (3H, s), 3.92 (3H, s), 3.96-4.02 (5H, m), 4.34-4.40 (1H, m), 4.77-4.85 (1H, m), 5.14-5.20 (1H, m), 7.19 (1H, br s), 7.63 (1H, s), 8.87-8.60 (2H, m).

MS (m/z): 611 (M+H)$^+$.

Similarly, the free form of 128B (95.0 mg) was dissolved in ethanol (2 mL), 1N hydrochloric acid ethanol solution (0.160 mL) was added thereto, and the mixture was concentrated under reduced pressure. Ethyl acetate (2 mL) was added to the residue, and the precipitated solid was collected by filtration to give the other compound (128B) (0.103 g) of the title compounds, as a solid.

$^1$H-NMR (DMSO-D$_6$) δ: 1.10-1.24 (2H, m), 1.54-2.07 (9H, m), 2.22-2.44 (2H, m), 2.69-2.92 (3H, m), 3.40 (3H, s), 3.52-3.63 (1H, m), 3.85 (3H, s), 3.89 (3H, s), 3.94-4.04 (5H, m), 4.33-4.40 (1H, m), 4.77-4.87 (1H, m), 5.11-5.19 (1H, m), 7.09 (1H, br s), 7.62 (1H, s), 8.98-8.67 (2H, m).

MS (m/z): 611 (M+H)$^+$.

separation condition (analysis) CHIRALPAK (registered trademark, Daicel Corporation) IG, size 0.46 cm×25 cm, flow rate 1.0 mL/min, mobile phase n-hexane/ethanol=20/80, temperature 40° C.

the free form of 128A retention time 8.5 min, the free form of 128B retention time 11.7 min separation condition (preparative) CHIRALPAK (registered trademark, Daicel Corporation) IG, size 2 cm×25 cm, flow rate 15.0 mL/min, mobile phase n-hexane/ethanol=20/80, temperature 40° C.

the free form of 128A retention time 9.9 min, the free form of 128B retention time 12.2 min

Example 129

(1R,2S,4R)-4-({[4-(5-methoxypyridin-3-yl)phenyl]methyl}amino)-2-{methyl[6-(2,2,2-trifluoroethyl)thieno[2,3-d]pyrimidin-4-yl]amino}cyclopentan-1-ol Hydrochloride

[Formula 431]

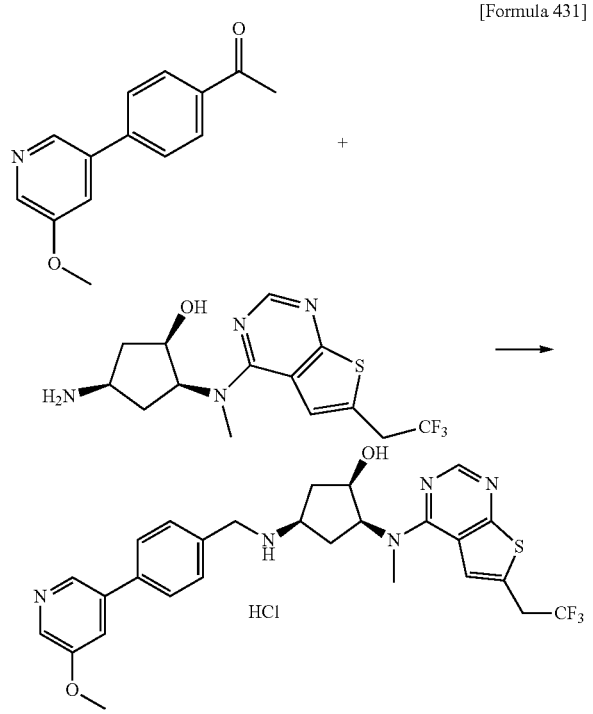

The title compound was obtained in the same manner as in Step 1 and Step 2 of Example 27, using the compound obtained in Step 2 of Reference Example C-14 and the compound obtained in Reference Example D-65.

$^1$H-NMR (DMSO-D$_6$) δ: 1.83-1.90 (1H, m), 2.28-2.34 (1H, m), 2.44-2.54 (2H, m), 3.44 (3H, s), 3.55-3.64 (1H, m), 3.93 (3H, s), 4.09 (2H, q, J=10.9 Hz), 4.23-4.28 (2H, m), 4.33-4.37 (1H, m), 4.91-4.99 (1H, m), 5.20 (1H, d, J=4.3 Hz), 7.67-7.69 (1H, m), 7.72-7.76 (3H, m), 7.86 (2H, d, J=7.9 Hz), 8.32 (1H, d, J=2.4 Hz), 8.36 (1H, s), 8.54 (1H, d, J=1.2 Hz), 9.52-9.64 (2H, m).

Example 130

(1R,3S)—N$^3$-{[4-(2-methoxy-1,3-thiazol-5-yl)phenyl]methyl}-N$^1$-methyl-N$^1$-[6-(2,2,2-trifluoroethyl)thieno[2,3-d]pyrimidin-4-yl]cyclopentane-1,3-diamine Hydrochloride

[Formula 432]

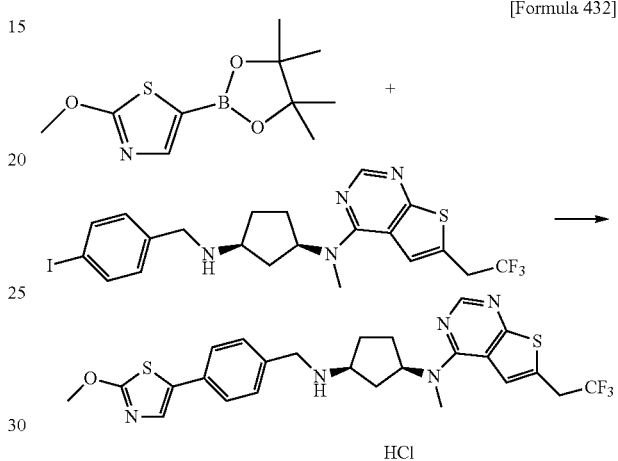

The title compound was obtained in the same manner as in Step 2 and Step 3 of Example 11, using the compound obtained in Step 1 of Example 11 and 2-methoxy-5-(4,4,5,5-tetramethyl-1,3,2-dioxaborolan-2-yl)thiazole.

$^1$H-NMR (DMSO-D$_6$) δ: 1.86-1.88 (1H, m), 1.95-2.09 (4H, m), 2.31-2.38 (1H, m), 3.29 (3H, s), 3.56-3.63 (1H, br m), 4.06-4.15 (7H, m), 5.24-5.29 (1H, br m), 7.51-7.54 (3H, m), 7.58 (2H, d, J=8.5 Hz), 7.74 (1H, s), 8.40 (1H, s), 9.35 (1H, br s), 9.48 (1H, br s), 11.57 (1H, d, J=2.4 Hz).

MS (m/z): 534 (M+H)$^+$.

Example 131

(1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol Succinate (1R,2S,4R)-4-({[4-(5,6-Dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol (25.8 g) obtained in the same manner as in Step 1 of Example 25 was suspended in 2-propanol (103 mL), and water (12.9 mL) was added thereto. Succinic acid (5.56 g) was added to the mixture, water (12.9 mL) was added thereto, and the mixture was stirred at room temperature for 4 hr. The insoluble substance was collected by filtration while washing with 2-propanol (150 mL), and dried to give the title compound (30.1 g) as crystals.

$^1$H-NMR (DMSO-D$_6$) δ: 1.50-1.58 (1H, m), 2.04-2.19 (2H, m), 2.27-2.35 (1H, m), 2.37 (4H, s), 3.14-3.24 (1H, m), 3.42 (3H, s), 3.88-3.94 (2H, m), 3.99 (3H, s), 4.05-4.11 (5H, m), 4.28-4.33 (1H, m), 4.80-4.90 (1H, m), 7.54 (2H, d, J=8.5 Hz), 7.61 (1H, s), 7.72 (1H, s), 8.08 (2H, d, J=8.5 Hz), 8.33 (1H, s).

MS (m/z): 575 (M+H)$^+$.

$[\alpha]_D^{20}$ −28.3 (c 1.00, DMSO)

elemental analysis found value. C, 53.62; H, 5.11; F, 8.27; N, 12.05; S, 4.58.

The powder X-RAY diffraction of the obtained crystal is shown in FIG. 1.

Table 3 shows peaks with a relative intensity of 35 or more when the maximum peak intensity is 100 in the diffraction pattern FIG. 1 of the powder X-RAY diffraction (CuKα, λ=1.54 angstroms, scanning speed=20°/min).

TABLE 3

| peak No. | 2θ | d value | relative intensity |
|---|---|---|---|
| 1 | 4.66 | 18.95 | 48 |
| 2 | 7.02 | 12.58 | 87 |
| 3 | 14.10 | 6.28 | 73 |
| 4 | 16.68 | 5.31 | 45 |
| 5 | 17.46 | 5.08 | 58 |
| 6 | 18.68 | 4.75 | 100 |
| 7 | 21.34 | 4.16 | 94 |
| 8 | 24.52 | 3.63 | 35 |
| 9 | 25.54 | 3.48 | 38 |
| 10 | 28.22 | 3.16 | 46 |

Example 132

(1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol Benzenesulfonate To (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol (200.31 mg) obtained in the same manner as in Step 1 of Example 25 and benzenesulfonic acid (57.89 mg) was added 80% hydrous acetone (1639 μL), and the mixture was stirred at room temperature about 24 hr. The precipitated solid was collected, and dried overnight at room temperature to give the title compound (220.45 mg) as crystals.

$^1$H-NMR (DMSO-D$_6$) δ: 1.72-1.79 (1H, m), 2.26-2.47 (3H, m), 3.44 (3H, s), 3.58-3.68 (1H, m), 4.01 (3H, s), 4.04-4.14 (5H. m), 4.26-4.42 (3H, m), 4.90-4.98 (1H, m), 5.22 (1H, d, J=4.0 Hz), 7.28-7.34 (3H, m), 7.57-7.61 (2H, m), 7.67 (1H, s), 7.69 (2H, d, J=8.5 Hz), 7.75 (1H, s), 8.20 (2H, d, J=8.5 Hz), 8.36 (1H, s), 8.98-9.17 (2H, m).

MS (m/z): 575 (M+H)$^+$.

elemental analysis found value. C, 50.24; H, 5.06; F, 7.64; N, 10.57; S, 8.21.

Figure 2:
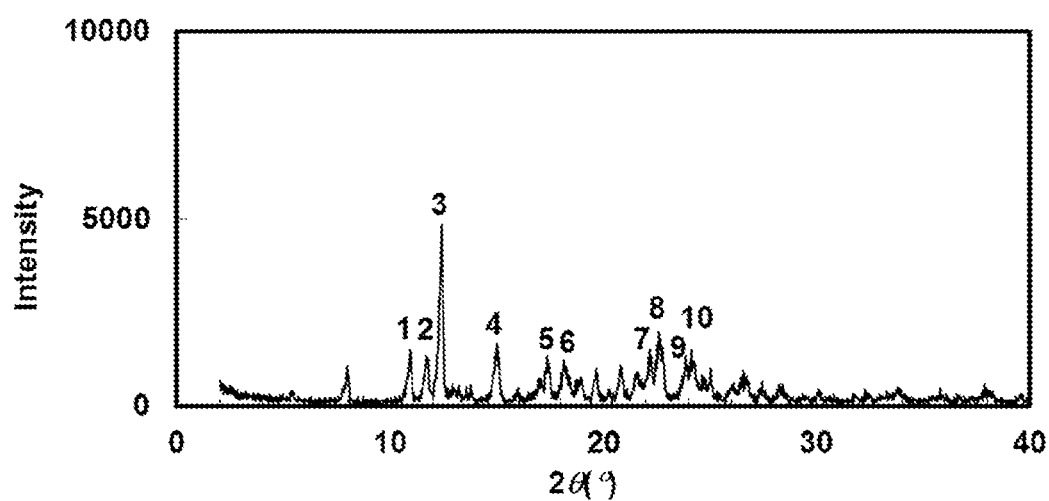
FIG. 2 is a powder X-ray diffraction diagram of the crystal obtained in Example 132. The vertical axis indicates the diffraction intensity (Intensity) in count/sec (cps) unit, and the horizontal axis indicates the value of the diffraction angle 2θ.

The powder X-RAY diffraction of the obtained crystal is shown in FIG. 2.

Table 4 shows peaks with a relative intensity of 24 or more when the maximum peak intensity is 100 in the diffraction pattern FIG. 2 of the powder X-RAY diffraction (CuKα, λ=1.54 angstroms, scanning speed=20°/min).

TABLE 4

| peak No. | 2θ | d value | relative intensity |
|---|---|---|---|
| 1 | 10.92 | 8.10 | 30 |
| 2 | 11.70 | 7.56 | 27 |
| 3 | 12.40 | 7.13 | 100 |
| 4 | 15.00 | 5.90 | 35 |
| 5 | 17.38 | 5.10 | 24 |

TABLE 4-continued

| peak No. | 2θ | d value | relative intensity |
|---|---|---|---|
| 6 | 18.16 | 4.88 | 22 |
| 7 | 22.18 | 4.00 | 30 |
| 8 | 22.62 | 3.93 | 35 |
| 9 | 23.86 | 3.73 | 26 |
| 10 | 24.20 | 3.67 | 24 |

Example 133

(1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol Maleate To (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol (300.14 mg) obtained in the same manner as in Step 1 of Example 25 and maleic acid (63.66 mg) was added 80% hydrous 2-propanol (5455 μL), and the mixture was stirred at 40° C. for about 24 hr. The precipitated solid was collected, and dried overnight at room temperature to give the title compound (304.38 mg) as crystals.

$^1$H-NMR (DMSO-D$_6$) δ: 1.71-1.79 (1H, m), 2.25-2.48 (3H, m), 3.45 (3H, s), 3.57-3.67 (1H, m), 4.01 (3H, s), 4.04-4.14 (5H, m), 4.25-4.41 (3H, m), 4.90-4.98 (1H, m), 5.15-5.27 (1H, m), 6.02 (2H, s), 7.68 (1H, s), 7.68 (2H, d, J=8.0 Hz), 7.75 (1H, s), 8.20 (2H, d, J=8.0 Hz), 8.37 (1H, s), 9.05 (2H, br s).

MS (m/z): 575 (M+H)$^+$.

elemental analysis found value. C, 53.61; H, 4.81; F, 8.25; N, 12.15; S, 4.67.

Figure 3:
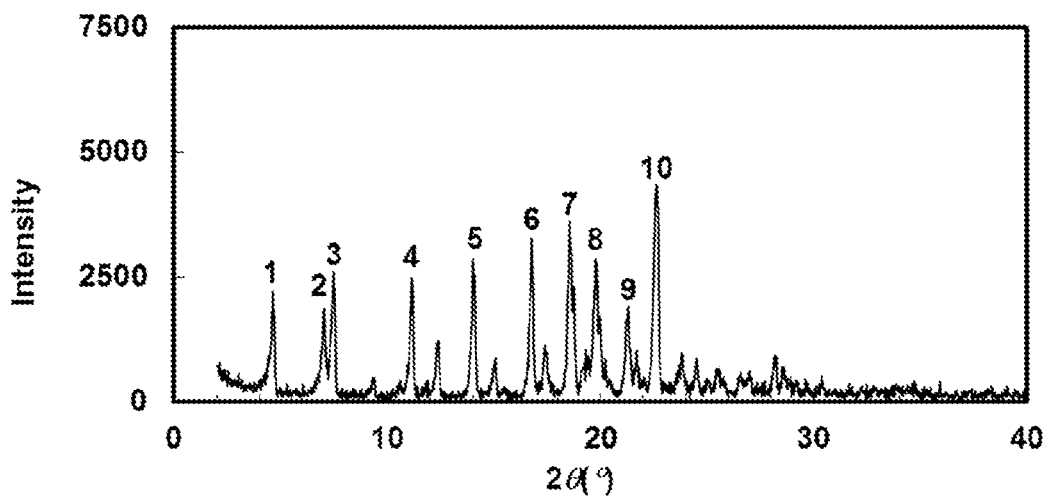
FIG. 3 is a powder X-ray diffraction diagram of the crystal obtained in Example 133. The vertical axis indicates the diffraction intensity (Intensity) in count/sec (cps) unit, and the horizontal axis indicates the value of the diffraction angle 2θ.

The powder X-RAY diffraction of the obtained crystal is shown in FIG. 3.

Table 5 shows peaks with a relative intensity of 42 or more when the maximum peak intensity is 100 in the diffraction pattern FIG. 3 of the powder X-RAY diffraction (CuKα, λ=1.54 angstroms, scanning speed=20°/min).

TABLE 5

| peak No. | 2θ | d value | relative intensity |
|---|---|---|---|
| 1 | 4.64 | 19.03 | 47 |
| 2 | 7.02 | 12.58 | 43 |
| 3 | 7.46 | 11.84 | 59 |
| 4 | 11.14 | 7.94 | 56 |
| 5 | 14.04 | 6.30 | 61 |
| 6 | 16.76 | 5.29 | 74 |
| 7 | 18.54 | 4.78 | 83 |
| 8 | 19.76 | 4.49 | 60 |
| 9 | 21.26 | 4.18 | 42 |
| 10 | 22.62 | 3.93 | 100 |

Example 134

(1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol Fumarate To the compound (200.38 mg) obtained in the same manner as in Step 1 of Example 25 and fumaric acid (42.50 mg) was added 80% hydrous 2-propanol (1638 µL), and the mixture was stirred at 40° C. for about 24 hr. The precipitated solid was collected, and dried overnight at room temperature to give the title compound (236.21 mg) as crystals.

$^1$H-NMR (DMSO-D$_6$) δ: 1.57-1.66 (1H, m), 2.14-2.22 (2H, m), 2.30-2.39 (1H, m), 3.21-3.31 (1H, m), 3.42 (3H, s), 3.97-4.01 (5H, m), 4.03-4.13 (5H, m), 4.28-4.33 (1H, m), 4.82-4.91 (1H, m), 6.55 (2H, s), 7.58 (2H, d, J=8.0 Hz), 7.62 (1H, s), 7.73 (1H, s), 8.10 (2H, d, J=8.0 Hz), 8.33 (1H, s).

MS (m/z): 575 (M+H)$^+$.

elemental analysis found value. C, 48.52; H, 5.31; F, 7.63; N, 10.89; S, 4.27.

Figure 4:
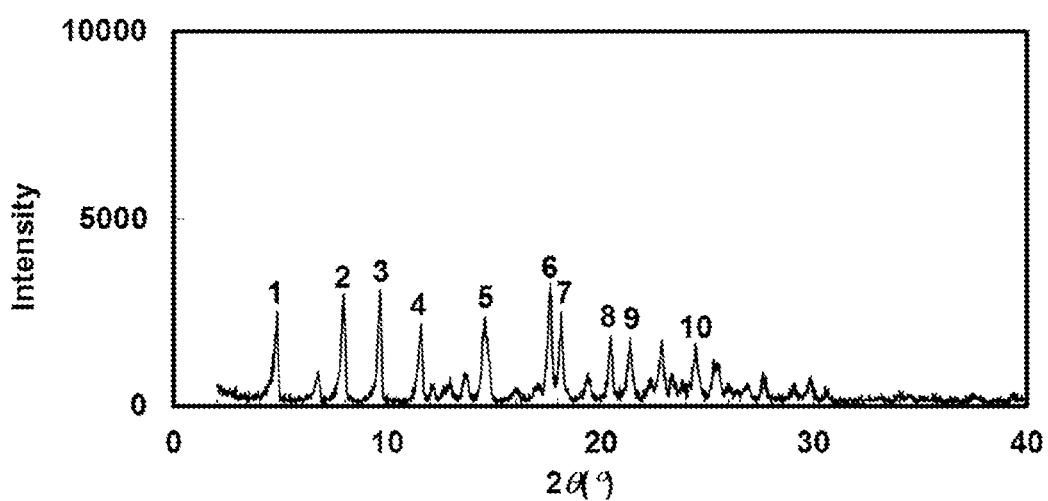
FIG. 4 is a powder X-ray diffraction diagram of the crystal obtained in Example 134. The vertical axis indicates the diffraction intensity (Intensity) in count/sec (cps) unit, and the horizontal axis indicates the value of the diffraction angle 2θ.

The powder X-RAY diffraction of the obtained crystal is shown in FIG. 4.

Table 6 shows peaks with a relative intensity of 51 or more when the maximum peak intensity is 100 in the diffraction pattern FIG. 4 of the powder X-RAY diffraction (CuKα, λ=1.54 angstroms, scanning speed=20°/min).

TABLE 6

| peak No. | 2θ | d value | relative intensity |
|---|---|---|---|
| 1 | 4.80 | 18.39 | 73 |
| 2 | 7.94 | 11.13 | 92 |
| 3 | 9.66 | 9.15 | 99 |
| 4 | 11.56 | 7.65 | 67 |
| 5 | 14.56 | 6.08 | 73 |
| 6 | 17.62 | 5.03 | 100 |
| 7 | 18.14 | 4.89 | 71 |
| 8 | 20.46 | 4.34 | 59 |
| 9 | 21.36 | 4.16 | 53 |
| 10 | 24.46 | 3.64 | 51 |

Example 135

Crystal of (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol To (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol (20.17 mg) obtained in the same manner as in Step 1 of Example 25 were added 2-propanol (81 µL) and water (323 µL), and the mixture was stirred at room temperature for about 24 hr. The obtained crystals were collected, and dried overnight at room temperature to give the title compound (13.89 mg).

elemental analysis found value. C, 53.01; H, 5.26; F, 8.97; N, 12.49; S, 4.84.

Figure 5:
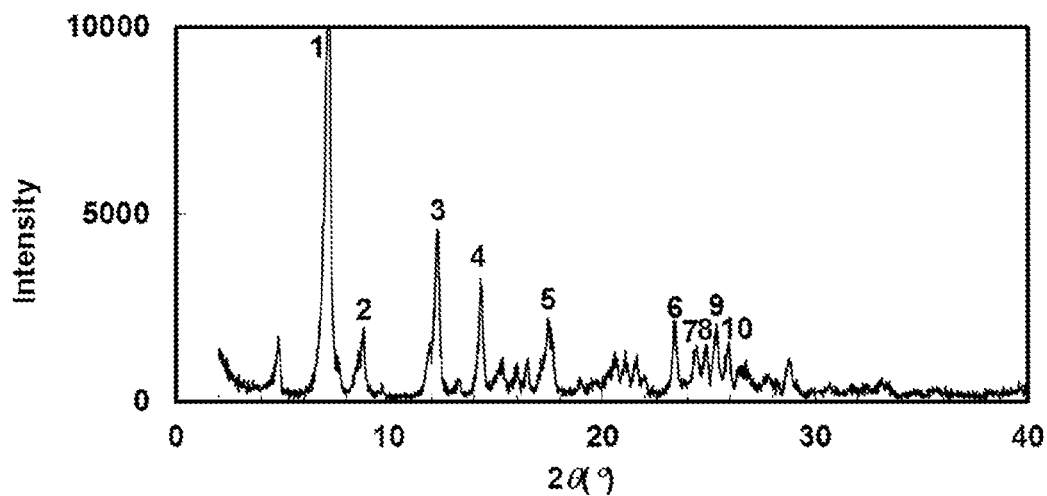
FIG. 5 is a powder X-ray diffraction diagram of the crystal obtained in Example 135. The vertical axis indicates the diffraction intensity (Intensity) in count/sec (cps) unit, and the horizontal axis indicates the value of the diffraction angle 2θ.

The powder X-RAY diffraction of the obtained crystal is shown in FIG. 5.

Table 7 shows peaks with a relative intensity of 12 or more when the maximum peak intensity is 100 in the diffraction pattern FIG. 5 of the powder X-RAY diffraction (CuKα, λ=1.54 angstroms, scanning speed=20°/min).

TABLE 7

| peak No. | 2θ | d value | relative intensity |
|---|---|---|---|
| 1 | 7.14 | 12.37 | 100 |
| 2 | 8.76 | 10.09 | 14 |

TABLE 7-continued

| peak No. | 2θ | d value | relative intensity |
|---|---|---|---|
| 3 | 12.26 | 7.21 | 38 |
| 4 | 14.30 | 6.19 | 25 |
| 5 | 17.52 | 5.06 | 16 |
| 6 | 23.40 | 3.80 | 15 |
| 7 | 24.40 | 3.65 | 12 |
| 8 | 24.86 | 3.58 | 12 |
| 9 | 25.34 | 3.51 | 16 |
| 10 | 25.90 | 3.44 | 13 |

Example 136

(1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol Fumarate To (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol (20.76 mg) obtained in the same manner as in Step 1 of Example 25 and fumaric acid (4.150 mg) was added 80% hydrous 2-propanol (415 µL), and the mixture was stirred at room temperature for about 24 hr. The precipitated solid was collected, and dried overnight at room temperature to give the title compound (22.13 mg) as crystals.

$^1$H-NMR (DMSO-D$_6$) δ: 1.55-1.63 (1H, m), 2.08-2.19 (2H, m), 2.28-2.37 (1H, m), 3.18-3.28 (1H, m), 3.39 (3H, s), 3.82 (3H, s), 3.92-4.03 (7H, m), 4.06 (3H, s), 4.29-4.34 (1H, m), 4.71-4.80 (1H, m), 6.55 (2H, s), 7.57 (2H, d, J=8.0 Hz), 7.61 (1H, br s), 7.62 (1H, s), 8.09 (2H, d, J=8.0 Hz).

elemental analysis found value. C, 50.58; H, 4.91; F, 7.58; N, 10.89; S, 4.15.

MS (m/z): 605 (M+H)$^+$.

Figure 6:
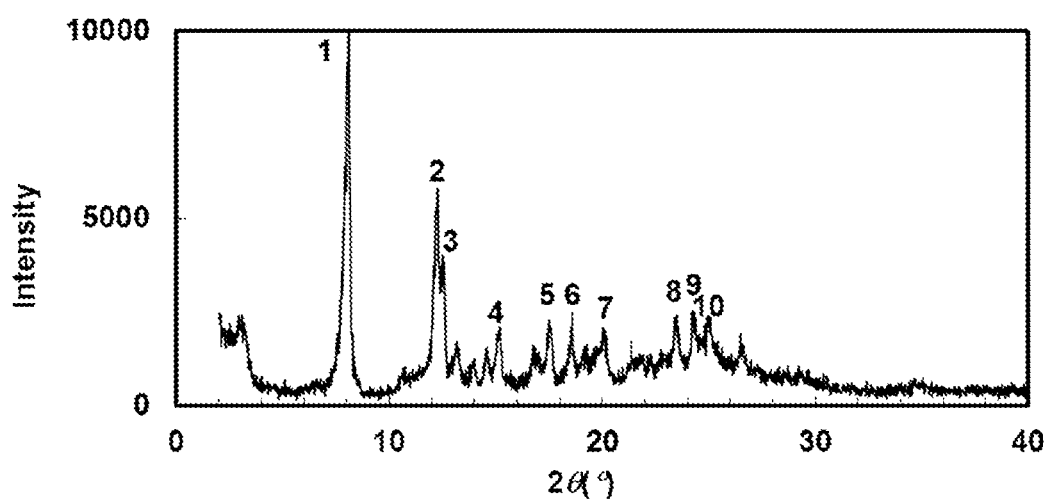
FIG. 6 is a powder X-ray diffraction diagram of the crystal obtained in Example 136. The vertical axis indicates the diffraction intensity (Intensity) in count/sec (cps) unit, and the horizontal axis indicates the value of the diffraction angle 2θ.

The powder X-RAY diffraction of the obtained crystal is shown in FIG. 6.

Table 8 shows peaks with a relative intensity of 20 or more when the maximum peak intensity is 100 in the diffraction pattern FIG. 6 of the powder X-RAY diffraction (CuKα, λ=1.54 angstroms, scanning speed=20°/min).

TABLE 8

| peak No. | 2θ | d value | relative intensity |
|---|---|---|---|
| 1 | 8.06 | 10.96 | 100 |
| 2 | 12.22 | 7.24 | 58 |
| 3 | 12.52 | 7.06 | 39 |
| 4 | 15.14 | 5.85 | 20 |
| 5 | 17.54 | 5.05 | 23 |
| 6 | 18.56 | 4.78 | 22 |
| 7 | 20.08 | 4.42 | 22 |
| 8 | 23.48 | 3.79 | 23 |
| 9 | 24.28 | 3.66 | 24 |
| 10 | 25.00 | 3.56 | 23 |

Example 137

(1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol Mucate To (1R,2S,4R)-4-({[4-(5,6-dimethoxypyridazin-3-yl)phenyl]methyl}amino)-2-{[2-methoxy-6-(2,2,2-trifluoroethyl)

thieno[2,3-d]pyrimidin-4-yl](methyl)amino}cyclopentan-1-ol (20.10 mg) obtained in the same manner as in Step 1 of Example 25 and mucic acid (7.421 mg) was added 80% hydrous 2-propanol (402 µL), and the mixture was stirred at room temperature for about 24 hr. The precipitated solid was collected, and dried overnight at room temperature to give the title compound (16.85 mg) as crystals.

$^1$H-NMR (DMSO-D$_6$) δ: 1.53-1.61 (1H, m), 2.06-2.21 (2H, m), 2.28-2.37 (1H, m), 3.17-3.27 (1H, m), 3.39 (3H, s), 3.72 (2H, s), 3.82 (3H, s), 3.92-4.03 (7H, m), 4.06 (3H, s), 4.14 (2H, s), 4.30-4.35 (1H, m), 4.71-4.81 (1H, m), 7.56 (2H, d, J=8.0 Hz), 7.61 (1H, s), 7.61 (1H, br s), 8.09 (2H, d, J=8.0 Hz).

MS (m/z): 605 (M+H)$^+$. elemental analysis found value. C, 46.77; H, 5.19; F, 6.71; N, 9.62; S, 3.61.

Figure 7:
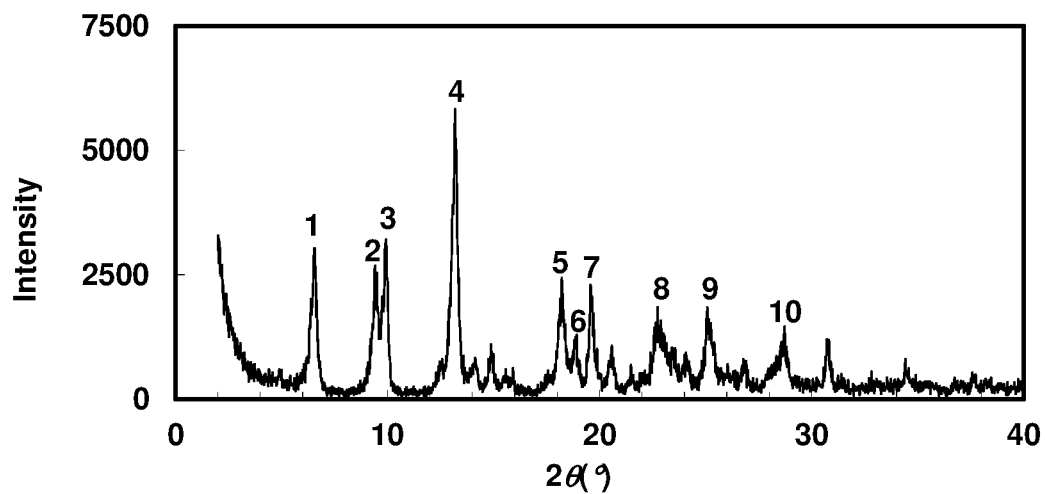
FIG. 7 is a powder X-ray diffraction diagram of the crystal obtained in Example 137. The vertical axis indicates the diffraction intensity (Intensity) in count/sec (cps) unit, and the horizontal axis indicates the value of the diffraction angle 2θ.

The powder X-RAY diffraction of the obtained crystal is shown in FIG. 7.

Table 9 shows peaks with a relative intensity of 22 or more when the maximum peak intensity is 100 in the diffraction pattern FIG. 7 of the powder X-RAY diffraction (CuKα, λ=1.54 angstroms, scanning speed=20°/min).

TABLE 9

| peak No. | 2θ | d value | relative intensity |
|---|---|---|---|
| 1 | 6.56 | 13.46 | 54 |
| 2 | 9.44 | 9.36 | 48 |
| 3 | 9.94 | 8.89 | 59 |
| 4 | 13.20 | 6.70 | 100 |
| 5 | 18.22 | 4.87 | 40 |
| 6 | 18.86 | 4.70 | 22 |
| 7 | 19.60 | 4.53 | 40 |
| 8 | 22.68 | 3.92 | 27 |
| 9 | 25.10 | 3.54 | 30 |
| 10 | 28.70 | 3.11 | 23 |

(1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol Adipate To (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol (19.68 mg) obtained in the same manner as in Step 1 of Example 25 and adipic acid (5.019 mg) was added 80% hydrous 2-propanol (394 µL), and the mixture was stirred at room temperature for about 24 hr. The precipitated solid was collected, and dried overnight at room temperature to give the title compound (19.75 mg) as crystals.

$^1$H-NMR (DMSO-D$_6$) δ: 1.44-1.53 (5H, m), 1.93-2.31 (7H, m), 3.01-3.10 (1H, m), 3.38 (3H, s), 3.76-3.86 (5H, m), 3.93-4.03 (5H, m), 4.05 (3H, s), 4.27-4.32 (1H, m), 4.68-4.78 (1H, m), 7.50 (2H, d, J=8.5 Hz), 7.59 (2H, br s), 8.05 (2H, d, J=8.5 Hz).

MS (m/z): 605 (M+H)$^+$.

elemental analysis found value. C, 50.67; H, 5.93; F, 7.28; N, 10.33; S, 3.98.

Figure 8:
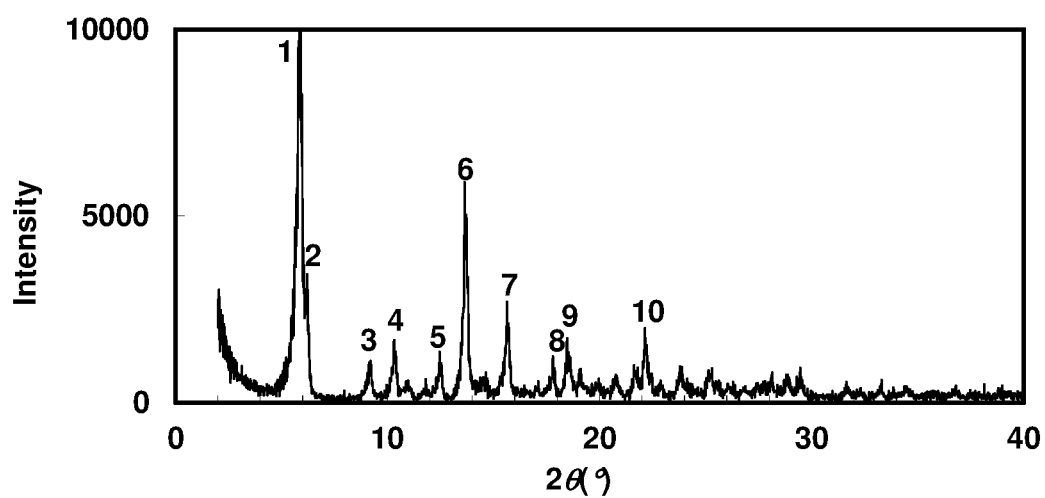
FIG. 8 is a powder X-ray diffraction diagram of the crystal obtained in Example 138. The vertical axis indicates the diffraction intensity (Intensity) in count/sec (cps) unit, and the horizontal axis indicates the value of the diffraction angle 2θ.

The powder X-RAY diffraction of the obtained crystal is shown in FIG. 8.

Table 10 shows peaks with a relative intensity of 10 or more when the maximum peak intensity is 100 in the diffraction pattern FIG. 8 of the powder X-RAY diffraction (CuKα, λ=1.54 angstroms, scanning speed=20°/min).

TABLE 10

| peak No. | 2θ | d value | relative intensity |
|---|---|---|---|
| 1 | 5.88 | 15.02 | 100 |
| 2 | 6.20 | 14.24 | 30 |
| 3 | 9.18 | 9.63 | 11 |
| 4 | 10.34 | 8.55 | 15 |
| 5 | 12.50 | 7.08 | 11 |
| 6 | 13.70 | 6.46 | 48 |
| 7 | 15.66 | 5.65 | 22 |
| 8 | 17.82 | 4.97 | 10 |
| 9 | 18.48 | 4.80 | 13 |
| 10 | 22.16 | 4.01 | 17 |

Example 139

(1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol Succinate To (1R,2S,4R)-4-({[4-(5,6-dimethoxypyridazin-3-yl)phenyl]methyl}amino)-2-{[2-methoxy-6-(2,2,2-trifluoroethyl)thieno[2,3-d]pyrimidin-4-yl](methyl)amino}cyclopentan-1-ol (20.27 mg) obtained in the same manner as in Step 1 of Example 25 was added 80% hydrous 2-propanol (368 µL), 1 mol/L aqueous succinic acid solution (81 µL) was added thereto, and the mixture was stirred at room temperature for about 24 hr. The precipitated solid was collected, and dried overnight at room temperature to give the title compound (14.41 mg) as crystals.

$^1$H-NMR (DMSO-D$_6$) δ: 1.50-1.58 (1H, m), 2.02-2.19 (2H, m), 2.26-2.34 (1H, m), 2.37 (4H, s), 3.13-3.23 (1H, m), 3.39 (3H, s), 3.82 (3H, s), 3.86-4.03 (7H, m), 4.06 (3H, s), 4.29-4.34 (1H, m), 4.70-4.80 (1H, m), 7.54 (2H, d, J=8.0 Hz), 7.61 (2H, br s), 8.08 (2H, d, J=8.0 Hz).

MS (m/z): 605 (M+H)$^+$.

$[\alpha]_D^{20}$ −43.6 (c 1.00, DMSO)

elemental analysis found value. C, 49.98; H, 5.30; F, 7.33; N, 10.73; S, 4.14.

Figure 9:
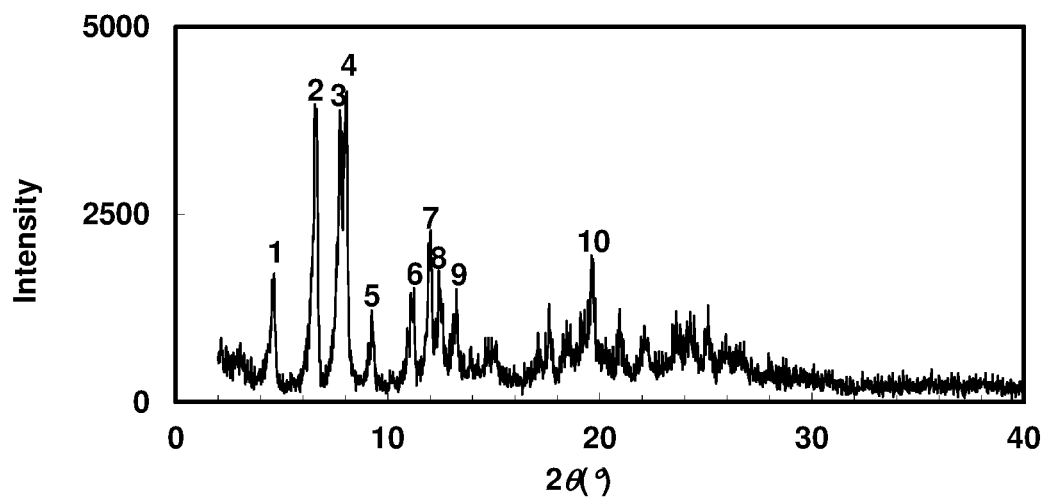
FIG. 9 is a powder X-ray diffraction diagram of the crystal obtained in Example 139. The vertical axis indicates the diffraction intensity (Intensity) in count/sec (cps) unit, and the horizontal axis indicates the value of the diffraction angle 2θ.

The powder X-RAY diffraction of the obtained crystal is shown in FIG. 9.

Table 11 shows peaks with a relative intensity of 26 or more when the maximum peak intensity is 100 in the diffraction pattern FIG. 9 of the powder X-RAY diffraction (CuKα, λ=1.54 angstroms, scanning speed=20°/min).

TABLE 11

| peak No. | 2θ | d value | relative intensity |
|---|---|---|---|
| 1 | 4.60 | 19.19 | 39 |
| 2 | 6.60 | 13.38 | 100 |
| 3 | 7.74 | 11.41 | 90 |
| 4 | 8.02 | 11.01 | 100 |
| 5 | 9.26 | 9.54 | 26 |
| 6 | 11.16 | 7.92 | 31 |
| 7 | 12.00 | 7.37 | 52 |
| 8 | 12.44 | 7.11 | 40 |
| 9 | 13.22 | 6.69 | 30 |
| 10 | 19.66 | 4.51 | 41 |

Formulation Example

Formulation Example 1 (Injection)

1.5% by weight of the Example compound is stirred in 10% by volume of propylene glycol, then the volume is adjusted to a predetermined value with water for injection, and the mixture is sterilized to give an injection.

Formulation Example 2 (Hard Capsule)

100 mg of the powdered Example compound, 128.7 mg of lactose, 70 mg of cellulose and 1.3 mg of magnesium stearate are mixed and passed through a 60 mesh sieve, and the resulting powder is put in 250 mg No. 3 gelatin capsules to give capsules.

Formulation Example 3 (Tablet)

100 mg of the powdered Example compound, 124 mg of lactose, 25 mg of cellulose and 1 mg of magnesium stearate are mixed and tableted with a tableting machine to give 250 mg of tablets per tablet. This tablet can be sugar-coated as needed.

Experimental Example

The pharmacological activity of the compound of the present invention was confirmed by the following tests.

[Experimental Example 1] Evaluation of Binding Inhibitory Activity Between Menin and MLL 10 μL of the reaction solution (50 mM Tris-HCl (pH7.5), 50 mM NaCl, 0.01% Triton X-100, 0.01% Bovine serum albumin, 3 mM TCEP) containing any of the compound of Examples 1 to 130, 1 nM menin (Flag tagged, Daiichi Sankyo RD Novare Co., Ltd.) and 10 nM biotinylated MLL1 peptide (1-46aa: Scrum Co., Ltd.) was added to a 384-well plate, and reacted at room temperature for minutes. Then, 10 μL of a mixed solution (10 μg/mL each) of Anti-FLAG AlphaLISA Acceptor beads (PerkinElmer Co., Ltd., AL112C) and Streptavidin-coated AlphaScreen Donor beads (PerkinElmer Co., Ltd., 6760002) was added thereto, and the mixture was reacted at room temperature for 1 hr. Then, the fluorescence signal by AlphaLISA (registered trademark, PerkinElmer Co., Ltd.) was measured using a plate reader (PerkinElmer Co., Ltd., EnVisionXcite). Based on the measured signals, the binding inhibitory rates of the compounds of Examples 1 to 130 at each concentration were calculated, and the obtained data was analyzed with the medical statistical analysis software GraphPad Prism (GraphPad Software, Inc.) to obtain the $IC_{50}$ values.

[Experimental Example 2] Evaluation of Cell Growth Inhibitory Activity

RPMI1640 medium supplemented with 10% FBS was used as a culture medium for each cells (MV-4-11, MOLM-13 cells, human AML cells, K562 cells, human CML cells). Each cell was purchased from American Type Culture Collection (ATCC). After diluting and preparing each drug (Example compound) with Freedom EVO 150 (Tecan Trading AG) (common ratio of 2, 10 concentrations from 10 mM or 5 mM to 20 μM or 10 μM), the drug was seeded at 40 nL/well using Echo555 (Labcyte Inc.) on a 384-well tissue culture plate (#3712, Corning Inc.) (final concentration 10 μM or 5 μM to 20 nM or 10 nM). The prepared drug-containing plate was stored at −30° C. until use, and thawed before use.

The suspension of each cells was prepared with 10% FBS RPMI1640 culture medium so as to be 1000 cells/mL (K562) or 10000 cells/mL (MV-4-11, MOLM-13), and seeded on the drug-containing plate (40 μL/well) (day 0). The cells were cultured for additional 3 or 7 days. ATP measurement reagent (CellTiter-Glo (registered trademark, Promega Corporation) 2.0 Assay, model number G9242, Promega Corporation) was added to each well at 10 μL/well, on the day of the drug addition (day 0) and 3 days (day 3) or 7 days (day 7) after the drug addition. After affixing a black sticker on the bottom surface, the mixture was stirred using a microplate mixing deaeration machine (model name, Weltornado FK-62, Sakaki Dengyo Co., Ltd.) (stirring conditions, revolution 9, rotation 7, time 12). The luminescence (cps) was measured using a luminescence detector of a microplate reader (model name EnVision 2102-0010, PerkinElmer Co., Ltd.) (N=4).

As an index of the cell growth inhibitory activity, the concentration ($GI_5$) that suppresses cell growth by 50% was calculated using EXCEL2010 (Microsoft Corporation). The cell growth of the drug-added group from day 0 to day 3 or day 7 was calculated as T/C %, when the cell growth of the drug-free group was considered as 100%. $GI_{50}$ was calculated by GROWTH function (exponential regression) using two concentrations sandwiching the concentration (T/C %=50%) that suppresses cell growth by 50%, and T/C %.

The results in Experimental Examples 1 and 2 are shown in Table 12-1 to Table 12-4.

TABLE 12-1

| Ex. No. | cell free $IC_{50}$ (nM) | $GI_{50}$ (μM) Day3 | | | $GI_{50}$ (μM) Day7 | | |
|---|---|---|---|---|---|---|---|
| | | K562 | MV4;11 | MOLM-13 | K562 | MV4;11 | MOLM-13 |
| 1 | 493.7 | 5.09 | 1.79 | NT | NT | NT | NT |
| 2 | 12.8 | 2.81 | 0.330 | NT | NT | NT | NT |
| 3 | 81.8 | 3.78 | 0.748 | NT | NT | NT | NT |
| 4 | 172.4 | 4.37 | 1.32 | NT | NT | NT | NT |
| 5 | 855.5 | >10.0 | 3.12 | NT | NT | NT | NT |
| 6 | 81.9 | >10.0 | 0.679 | NT | 6.89 | 0.439 | 1.10 |
| 7 | 150.7 | 1.67 | 1.36 | 1.69 | 0.95 | 0.908 | 1.82 |
| 8 | 8.8 | 2.73 | 0.408 | 0.87 | 1.44 | 0.201 | 0.592 |
| 9 | 22.2 | 2.95 | 0.585 | 1.61 | NT | NT | NT |
| 10 | 199.0 | >10.0 | >10.0 | >10.0 | NT | NT | NT |
| 11 | 63.9 | 6.66 | 1.30 | 3.28 | 3.82 | 0.711 | 1.19 |
| 12 | 33.8 | 6.72 | 0.702 | 2.72 | NT | NT | NT |
| 13 | 7.6 | 2.16 | 0.273 | 1.01 | NT | NT | NT |
| 14 | 27.4 | 2.23 | 0.655 | 1.48 | NT | NT | NT |
| 15A | 21.6 | >10.0 | 0.269 | 4.41 | NT | NT | NT |
| 15B | 402.8 | 5.42 | 1.88 | 3.15 | NT | NT | NT |
| 16 | 1868.0 | 7.43 | 5.18 | 6.04 | NT | NT | NT |

TABLE 12-1-continued

| Ex. No. | cell free IC₅₀ (nM) | GI₅₀ (µM) Day3 K562 | MV4;11 | MOLM-13 | GI₅₀ (µM) Day7 K562 | MV4;11 | MOLM-13 |
|---|---|---|---|---|---|---|---|
| 17A | 2262.0 | 8.66 | 2.25 | 3.29 | 5.27 | 1.58 | 3.35 |
| 17B | 13.3 | >10.0 | 0.170 | 5.00 | 7.25 | 0.118 | 0.310 |
| 18A | 10.3 | 5.70 | 0.260 | 2.83 | 5.01 | 0.131 | 0.448 |
| 18B | 182.2 | 5.18 | 2.16 | 3.08 | 4.71 | 1.47 | 3.97 |
| 19A | 33.5 | 5.51 | 0.489 | 3.20 | 5.39 | 0.295 | 0.906 |
| 19B | 1814.0 | 5.45 | 3.18 | 4.03 | 5.41 | 2.60 | 5.75 |
| 20A | 3.9 | 5.73 | 0.367 | 2.90 | 2.86 | 0.177 | 0.352 |
| 20B | 16.4 | 9.03 | 0.331 | 4.02 | 4.65 | 0.226 | 0.379 |
| 21 | 7.0 | 5.75 | 0.304 | 4.50 | 9.60 | 0.173 | 0.509 |
| 22 | 3.8 | 1.37 | 0.189 | 0.675 | 0.925 | 0.0971 | 0.262 |
| 23 | 2.8 | 1.55 | 0.106 | 0.594 | 0.586 | 0.0584 | 0.155 |
| 24 | 4.1 | 3.23 | 0.0609 | 0.873 | 2.57 | 0.0302 | 0.104 |
| 25 | 1.0 | >5.00 | 0.0253 | 0.224 | 3.47 | 0.0180 | 0.0400 |
| 26 | 3.8 | 2.74 | 0.121 | 1.39 | 1.93 | 0.0715 | 0.249 |

TABLE 12-2

| 27 | 1.3 | 3.37 | 0.0152 | 0.139 | 2.10 | 0.0123 | 0.0313 |
|---|---|---|---|---|---|---|---|
| 28 | 1163.0 | 6.31 | 5.34 | NT | NT | NT | NT |
| 29 | 463.6 | >10.0 | 1.26 | NT | 7.77 | 1.07 | 1.66 |
| 30 | 44.6 | 2.34 | 0.867 | NT | NT | NT | NT |
| 31 | 46.4 | >10.0 | 1.29 | NT | NT | NT | NT |
| 32 | 94.9 | 5.59 | 2.43 | NT | NT | NT | NT |
| 33 | 2419.0 | 6.44 | 5.22 | 4.82 | NT | NT | NT |
| 34 | 412.7 | 4.49 | 0.420 | 0.718 | 2.77 | 0.106 | 0.444 |
| 35 | 1222.0 | 6.97 | 4.34 | 5.72 | NT | NT | NT |
| 36 | 636.0 | >10.0 | 3.13 | 3.14 | NT | NT | NT |
| 37 | 700.8 | >10.0 | 5.21 | NT | NT | NT | NT |
| 38 | 1850.0 | >10.0 | 6.09 | >10.0 | NT | NT | NT |
| 39 | 2067.0 | >10.0 | 8.14 | >10.0 | NT | NT | NT |
| 40 | 265.5 | 5.53 | 2.62 | 4.54 | 4.16 | 2.16 | 4.33 |
| 41 | 471.6 | 2.67 | 2.46 | 2.54 | NT | NT | NT |
| 42 | 104.8 | 5.09 | 1.43 | 3.11 | 2.87 | 1.14 | 1.96 |
| 43 | 76.2 | 3.02 | 1.18 | 2.41 | 1.72 | 0.877 | 1.74 |
| 44 | 335.2 | 2.75 | 1.89 | 2.73 | 1.91 | 1.53 | 2.93 |
| 45 | 33.3 | 3.27 | 0.865 | 1.78 | 2.00 | 0.701 | 1.40 |
| 46 | 39.4 | 6.42 | 0.490 | 2.69 | NT | NT | NT |
| 47 | 97.2 | 6.20 | 0.704 | 2.22 | NT | NT | NT |
| 48 | 1417.0 | 3.45 | 1.77 | 2.21 | NT | NT | NT |
| 49 | 24.0 | 9.74 | 0.598 | 2.52 | 3.18 | 0.490 | 1.13 |
| 50 | 9.7 | 5.69 | 0.200 | 2.53 | 3.29 | 0.0812 | 0.330 |
| 51 | 10.1 | 3.20 | 0.137 | 1.24 | 2.06 | 0.0621 | 0.259 |
| 52 | 612.0 | 5.93 | 2.39 | 3.37 | NT | NT | NT |
| 53 | 17.7 | NT | NT | NT | 0.908 | 0.395 | 0.826 |
| 54 | 1.0 | 3.13 | 0.0669 | 1.33 | 2.18 | 0.0279 | 0.0579 |
| 55 | 9.8 | 1.90 | 0.149 | 0.614 | 1.32 | 0.0895 | 0.221 |
| 56 | 43.6 | 1.26 | 0.769 | 1.02 | 0.809 | 0.468 | 1.07 |
| 57 | 61.2 | 6.30 | 1.16 | 2.14 | 3.03 | 0.689 | 1.56 |
| 58 | 15.2 | 1.03 | 0.399 | 0.804 | 0.493 | 0.230 | 0.485 |
| 59 | 33.0 | 1.75 | 0.894 | 1.22 | 1.05 | 0.451 | 1.13 |
| 60 | 2.4 | 3.40 | 0.0776 | 0.614 | 2.39 | 0.0325 | 0.0807 |
| 61 | 1.9 | 6.25 | 0.110 | 0.974 | 5.74 | 0.0472 | 0.129 |

TABLE 12-3

| 62 | 2.0 | 2.69 | 0.113 | 1.06 | 2.59 | 0.0666 | 0.199 |
|---|---|---|---|---|---|---|---|
| 63 | 19.9 | 2.55 | 0.682 | 1.88 | 1.48 | 0.445 | 1.21 |
| 64 | 2.2 | 2.18 | 0.0563 | 0.358 | 1.67 | 0.0355 | 0.0933 |
| 65 | 2.5 | 2.85 | 0.0882 | 1.46 | 2.64 | 0.0557 | 0.143 |
| 66 | 6.7 | 1.61 | 0.286 | 0.978 | 0.865 | 0.177 | 0.540 |
| 67 | 2.1 | 4.00 | 0.0676 | 1.42 | 2.36 | 0.0440 | 0.130 |
| 68 | 1.7 | 4.93 | 0.0462 | 1.93 | 2.85 | 0.0207 | 0.0882 |
| 69 | 2.8 | 1.53 | 0.0382 | 0.630 | 1.41 | 0.0233 | 0.0637 |
| 70 | 3.8 | 2.57 | 0.0673 | 0.948 | 2.53 | 0.0351 | 0.111 |
| 71 | 0.6 | 2.80 | 0.285 | 0.964 | 1.77 | 0.157 | 0.469 |
| 72 | 10.7 | NT | NT | NT | 1.00 | 0.230 | 0.519 |
| 73 | 6.5 | NT | NT | NT | 0.723 | <0.0195 | 0.0389 |
| 74 | 6.5 | NT | NT | NT | 2.55 | 0.0455 | 0.122 |
| 75 | 17.2 | NT | NT | NT | 1.47 | 0.0571 | 0.194 |
| 76 | 8.6 | 4.80 | 0.183 | 1.70 | 2.70 | 0.0963 | 0.268 |
| 77 | 10.4 | 2.60 | 0.350 | 1.17 | 1.62 | 0.160 | 0.501 |
| 78 | 8.5 | 3.53 | 0.219 | 1.72 | 1.99 | 0.114 | 0.378 |
| 79 | 3.5 | 4.34 | 0.313 | 1.64 | 2.12 | 0.173 | 0.482 |
| 80 | 15.4 | 2.79 | 0.434 | 1.88 | 2.16 | 0.246 | 0.705 |
| 81 | 6.1 | 2.22 | 0.0544 | 0.569 | 1.61 | 0.0246 | 0.0943 |
| 82 | 22.8 | 1.41 | 0.112 | 0.521 | 1.33 | 0.0505 | 0.177 |
| 83 | 4.9 | 2.38 | 0.345 | 1.45 | 1.52 | 0.179 | 0.646 |
| 84 | 2.7 | 5.28 | 0.0235 | 0.652 | 3.39 | <0.0195 | 0.0455 |
| 85 | 4.0 | 2.04 | 0.137 | 0.742 | 0.921 | 0.0749 | 0.240 |
| 86 | 20.9 | 3.97 | 0.608 | 1.78 | 1.96 | 0.372 | 0.949 |
| 87 | 6.6 | 1.76 | 0.165 | 0.803 | 1.23 | 0.114 | 0.423 |
| 88 | 27.8 | 2.01 | 0.446 | 1.48 | 1.76 | 0.327 | 1.01 |
| 89 | 5.6 | >10.0 | 0.0761 | 7.18 | >10.0 | 0.0467 | 0.185 |
| 90 | 1.2 | 0.750 | <0.0195 | 0.324 | 0.636 | <0.0195 | 0.0364 |
| 91 | 1.3 | 0.769 | <0.0195 | 0.206 | 0.542 | <0.0195 | 0.0526 |
| 92 | 1.5 | 3.48 | 0.0891 | 0.826 | 2.79 | 0.0493 | 0.120 |
| 93 | 1.6 | 1.38 | 0.0552 | 0.659 | 1.41 | 0.0357 | 0.107 |
| 94 | 2.1 | 5.04 | 0.143 | 1.54 | 2.82 | 0.0751 | 0.227 |
| 95 | 1.2 | 5.08 | 0.0454 | 1.10 | 1.78 | 0.0239 | 0.0668 |
| 96 | 2.7 | 3.04 | 0.126 | 0.268 | 2.61 | 0.158 | 0.281 |

TABLE 12-4

| 97 | 3.9 | 3.21 | 0.295 | 0.852 | 2.46 | 0.187 | 0.285 |
|---|---|---|---|---|---|---|---|
| 98 | 1.9 | 5.57 | 0.109 | 0.411 | 2.10 | 0.0628 | 0.105 |
| 99 | 1.1 | 3.80 | 0.0626 | 0.187 | 1.84 | 0.0365 | 0.0562 |
| 100 | 2.5 | >10.0 | 0.0236 | 0.137 | 5.94 | <0.0195 | 0.0598 |
| 101 | 2.7 | 2.76 | 0.0563 | 0.216 | 2.03 | 0.0502 | 0.132 |
| 102 | 2.7 | >10.0 | 0.0393 | 0.258 | >10.0 | 0.0271 | 0.0742 |

TABLE 12-4-continued

| | | | | | | | |
|---|---|---|---|---|---|---|---|
| 103 | 1.4 | >10.0 | 0.028 | 0.13 | 8.00 | 0.032 | 0.073 |
| 104 | 6.3 | >5.00 | 0.097 | 0.70 | >5.00 | 0.066 | 0.187 |
| 105 | 8.0 | >5.00 | 0.156 | 1.63 | 3.37 | 0.129 | 0.285 |
| 106 | 0.7 | NT | NT | NT | 0.435 | 0.0248 | 0.0597 |
| 107 | 1.3 | NT | NT | NT | 4.91 | 0.0270 | 0.0647 |
| 108 | 1.3 | NT | NT | NT | >5.00 | 0.0234 | 0.0622 |
| 109 | 0.7 | NT | NT | NT | >5.00 | 0.0133 | 0.0312 |
| 110 | 2.1 | NT | NT | NT | 1.60 | 0.0763 | 0.253 |
| 111 | 42.3 | NT | NT | NT | 1.20 | 0.634 | 0.751 |
| 112 | 0.8 | NT | NT | NT | 2.56 | 0.0265 | 0.995 |
| 113 | 29.2 | NT | NT | NT | 1.66 | 0.0997 | 1.15 |
| 114 | 1.5 | NT | NT | NT | 1.94 | 0.0440 | 0.143 |
| 115 | 10.9 | NT | NT | NT | >5.00 | 0.222 | 0.974 |
| 116 | 1.0 | NT | NT | NT | 1.00 | 0.0133 | 0.0592 |
| 117 | 1.4 | NT | NT | NT | 1.56 | 0.0468 | 0.184 |
| 118 | 1.0 | NT | NT | NT | 2.70 | 0.0254 | 0.127 |
| 119 | 0.7 | NT | NT | NT | 0.859 | 0.0157 | 0.0637 |
| 120 | 5.8 | NT | NT | NT | 2.16 | 0.225 | 0.729 |
| 121 | 0.8 | NT | NT | NT | 0.894 | 0.0381 | 0.0495 |
| 122 | 1.7 | NT | NT | NT | 2.27 | 0.232 | 0.236 |
| 123 | 0.6 | NT | NT | NT | 1.69 | 0.0223 | 0.0284 |
| 124 | 182.1 | NT | NT | NT | 4.82 | 0.624 | 0.922 |
| 125 | 1.5 | NT | NT | NT | 3.75 | 0.0769 | 0.154 |
| 126 | 7.5 | >10.0 | 0.257 | 5.03 | 8.84 | 0.137 | 0.396 |
| 127 | 1.6 | 7.14 | 0.169 | 2.15 | 4.26 | 0.092 | 0.242 |
| 128A | 18.4 | NT | NT | NT | >5.00 | 0.728 | 1.451 |
| 128B | 6.6 | NT | NT | NT | >5.00 | 0.201 | 0.501 |
| 129 | 5.5 | 5.21 | 0.0968 | 1.25 | 2.74 | 0.0378 | 0.104 |
| 130 | 6.5 | 1.90 | 0.241 | 0.894 | NT | NT | NT |

NT: Not Tested.

NT: Not Tested.

[Experimental Example 3-1] Evaluation of Antitumor Activity in MV-4-11 Cell Subcutaneous Transplant Model MV-4-11 cells were transplanted subcutaneously to the right abdomen of female FOX CHASE SCIDC.B.17/Icr-scid/scidJcl mice at a ratio of $1\times10^7$ cells/head, and after 17 days, the mice were grouped into 6 animals per each group, based on the estimated tumor volume (major axis×minor axis×minor axis/2). MV-4-11 cells were purchased from ATCC. The female FOX CHASE SCID C.B.17/Icr-scid/scidJcl mice were purchased from Claire Japan. From the day after the grouping, the compound of Example 26 was orally administered on a schedule of once daily for 17 days everyday (qd×17), at a dose setting of 25, 50 or 100 mg/kg/day. The compound was administered as a suspension in 0.5% methylcellulose (MC). For the compound-free group, 0.5% MC was administered as a solvent. The estimated individual tumor volume was measured from the day of the grouping to 34 days after the transplantation (test end date).

[Experimental Example 3-2] Evaluation of Antitumor Activity in MV-4-11 Cell Subcutaneous Transplant Model MV-4-11 cells were transplanted subcutaneously to the right abdomen of female FOX CHASE SCID C.B.17/Icr-scid/scidJcl mice at a ratio of $1\times10^7$ cells/head, and after 17 days, the mice were grouped into 6 animals per each group, based on the estimated tumor volume (major axis×minor axis×minor axis/2). MV-4-11 cells were purchased from ATCC. The female FOX CHASE SCID C.B.17/Icr-scid/scidJcl mice were purchased from Claire Japan. From the day of the grouping, the compound of Example 25 or 27 was orally administered on a schedule of once daily for 18 days everyday (qd×18), at a dose setting of 12.5, 25, 50 or 100 mg/kg/day. The compound was administered as a suspension in 0.5% MC. For the compound-free group, 0.5% MC was administered as a solvent. The estimated individual tumor volume was measured from the day of the grouping to 34 days after the transplantation (test end date).

[Experimental Example 3-3] MV-4-11 Cell Evaluation of Antitumor Activity in MV-4-11 Cell Subcutaneous Transplant Model MV-4-11 cells were transplanted subcutaneously to the right abdomen of female FOX CHASE SCID C.B.17/Icr-scid/scidJcl mice at a ratio of $1\times10^7$ cells/head, and after 14 days, the mice were grouped into 6 animals per each group, based on the estimated tumor volume (major axis×minor axis×minor axis/2). MV-4-11 cells were purchased from ATCC. The female FOX CHASE SCID C.B.17/Icr-scid/scidJcl mice were purchased from Claire Japan. From the day after the grouping, the compound of Example 68, 25 or 27 was orally administered on a schedule of once daily for 17 days everyday (qd×17), at a dose setting of 25, 50 or 100 mg/kg/day. The compound was administered as a suspension in 0.5% MC. For the compound-free group, 0.5% MC was administered as a solvent. The estimated individual tumor volume was measured from the day of the grouping to 31 days after the transplantation (test end date).

[Experimental Example 3-4] Evaluation of Antitumor Activity in MV-4-11 Cell Subcutaneous Transplant Model MV-4-11 cells were transplanted subcutaneously to the right abdomen of female FOX CHASE SCID C.B.17/Icr-scid/scidJcl mice at a ratio of $1\times10^7$ cells/head, and after 15 days, the mice were grouped into 6 animals per each group, based on the estimated tumor volume (major axis×minor axis×minor axis/2). MV-4-11 cells were purchased from ATCC. The female FOX CHASE SCID C.B.17/Icr-scid/scidJcl mice were purchased from Claire Japan. From the day after the grouping, the compound of Example 60 or 67 was orally administered on a schedule of once daily for 16 days everyday (qd×16), at a dose setting of 25, 50 or 100 mg/kg/day. The compound was administered as a suspension in 0.5% MC. For the compound-free group, 0.5% MC was administered as a solvent. The estimated individual tumor volume was measured from the day of the grouping to 32 days after the transplantation (test end date).

The antitumor activities in MV4:11 cell subcutaneous transplant model in Experimental Examples 3-1 to 3-4 were calculated by the following formula on the end date of each test.

Tumor growth inhibitory rate %=(1−TVCt/TVCc)× 100

TVC=(Individual tumor volume on the test end date)− (Individual tumor volume on the grouping date)
TVCt: TVC mean value of the compound administration group
TVCc: TVC mean value of the compound-free group The results in Experimental Examples 3-1 to 3-4 are shown in Table 13.

TABLE 13

| Exp. Ex. | Ex. No. | Administration schedule | Dose mg/kg/day | Estimated tumor volume (test end date) Mean ± S.E. | Tumor growth inhibitory rate (%) |
|---|---|---|---|---|---|
| 3-1 | 0.5% MC | qd×17 | — | 1137 ± 114 | |
| | Ex. 26 | qd×17 | 25 | 250 ± 12 | 78.0 |
| | | qd×17 | 50 | 0 ± 0 | 100 |
| | | qd×17 | 100 | 0 ± 0 | 100 |
| 3-2 | 0.5% MC | qd×18 | — | 1383 ± 44 | |
| | Ex. 25 | qd×18 | 12.5 | 926 ± 86 | 33.0 |
| | | qd×18 | 25 | 250 ± 38 | 81.9 |
| | | qd×18 | 50 | 0 ± 0 | 100 |
| | | qd×18 | 100 | 0 ± 0 | 100 |
| | Ex. 27 | qd×18 | 25 | 335 ± 42 | 75.8 |
| | | qd×18 | 50 | 30 ± 8 | 97.8 |
| | | qd×18 | 100 | 0 ± 0 | 100 |
| 3-3 | 0.5% MC | qd×17 | — | 971 ± 21 | |
| | Ex. 68 | qd×17 | 25 | 1151 ± 142 | 0 |
| | | qd×17 | 50 | 559 ± 104 | 42 |
| | | qd×17 | 100 | 31 ± 23 | 97 |
| | Ex. 22 | qd×17 | 25 | 712 ± 82 | 27 |
| | | qd×17 | 50 | 9 ± 4 | 99 |
| | | qd×17 | 100 | 0 ± 0 | 100 |
| | Ex. 23 | qd×17 | 25 | 616 ± 86 | 37 |
| | | | 477 | | |
| | | qd×17 | 50 | 31 ± 10 | 97 |
| | | qd×17 | 100 | 0 ± 0 | 100 |
| 3-4 | 0.5% MC | qd×16 | — | 982 ± 103 | |
| | Ex. 60 | qd×16 | 25 | 558 ± 79 | 43 |
| | | qd×16 | 50 | 25 ± 11 | 97 |
| | | qd×16 | 100 | 0 ± 0 | 100 |
| | Ex. 67 | qd×16 | 25 | 896 ± 56 | 9 |
| | | qd×16 | 50 | 381 ± 59 | 61 |
| | | qd×16 | 100 | 0 ± 0 | 100 |

[Experimental Example 4] Evaluation of Cell Growth Inhibitory Activity (NPM1 Mutant)

MEM-alpha medium supplemented with 20% FBS was used as a culture medium for human AML cells, OCI-AML3 cells. The cells were purchased from Deutsche Sammlung von Mikroorganismen und Zellkulturen GmbH (DSMZ). After diluting and preparing each drug (each Example compound shown in Table 14) with Freedom EVO 150 (Tecan Trading AG) (common ratio of 4, 10 concentrations from 10 mM to 38 nM), the drug was seeded at 40 nL/well using Echo555 (Labcyte Inc.) on a 384-well tissue culture plate (#3712, Corning Inc.) (final concentration 10 μM to 0.038 nM). The prepared drug-containing plate was stored at −30° C. until use, and thawed before use.

The suspension of the cells was prepared with 10% FBS RPMI1640 culture medium so as to be 50000 cells/mL, and seeded on the drug-containing plate (40 μL/well) (day 0). The cells were cultured for additional 7 days. ATP measurement reagent (CellTiter-Glo (registered trademark, Promega Corporation) 2.0 Assay, model number G9242, Promega Corporation) was added to each well at 10 μL/well, on the day of the drug addition (day 0) and 7 days (day 7) after the drug addition. After affixing a black sticker on the bottom surface, the mixture was stirred using a microplate mixing deaeration machine (model name, Weltornado FK-62, Sakaki Dengyo Co., Ltd.) (stirring conditions, revolution 9, rotation 7, time 12). The luminescence (cps) was measured using a luminescence detector of a microplate reader (model name EnVision 2104-0010, PerkinElmer Co., Ltd.) (N=4).

As an index of the cell growth inhibitory activity, the concentration ($GI_{50}$) that suppresses cell growth by 50% was calculated using EXCEL2010 (Microsoft Corporation). The cell growth of the drug-added group from day 0 to day 7 was calculated as T/C %, when the cell growth of the drug-free group was considered as 100%. $GI_{50}$ was calculated by GROWTH function (exponential regression) using two concentrations sandwiching the concentration (T/C %=50%) that suppresses cell growth by 50%, and T/C %.

The results in Experimental Example 4 are shown in Table 14.

TABLE 14

| Ex. No. | $GI_{50}$ (nM) Day 7 |
|---|---|
| 22 | 217 |
| 25 | 39 |
| 27 | 24 |
| 116 | 46 |
| 119 | 33 |

[Experimental Example 5] Evaluation of Differentiation-Inducing Activity

The human MLL-AF9 fusion gene was introduced into cKit-positive mononuclear cells isolated from the myeloid of C57BL6 mouse, by retrovirus infection. MLL-AF9-overexpressing AML-like cells (MA9 cells) that acquired abnormal growth ability were established by liquid-culturing the cells after virus infection for a long period of time. Serum-free medium (GlutaMax, P/S, Stem Pro-34 medium containing 10 ng/ml mIL-3, ng/mL mSCF and 10 ng/mL human Oncostatin M) was used as a culture medium.

The suspension of the cells was prepared with the culture medium so as to be 12500 cells/mL, and seeded on a 6-well tissue culture plate at 2 mL/well, and then a drug (compound of Example 25, 27, 26 or 22) was added thereto at various concentrations (5 nM or 20 nM for the compounds of Examples 25 and 27, 150 nM or 300 nM for the compound of Example 26, and 50 nM or 100 nM for the compound of Example 22) (2 μL/well) (day 0). For the control group, DMSO was added thereto at a final concentration of 0.1% (2 μL/well) (day 0). After culturing for 7 days (day 7), the cells were collected, and blocked with 5% FBS/PBS containing 10% Mouse BD Fc Block (BD) for 10 minutes at room temperature, and then any of various antibodies (Gr-1-FITC or CD117 (cKit)-APC: Biolegend) was added thereto at a final concentration of 0.4 μg/sample, and the mixture was reacted on ice for 30 minutes. Then, dead cell staining dye DAPI (0.2 mg/mL) was added thereto at so as to be 1 g L/sample, and the reaction was carried out on ice for additional 2 minutes under shading. Then, the expression level of each surface antigen of the cells was measured by NovoCyte flow cytometer (LMS). The obtained data were analyzed by FlowJo software (Becton Dickinson), and the rate of each surface antigen-expressing cells in the living cells excluding dead cells was graphed.

Figure 10:
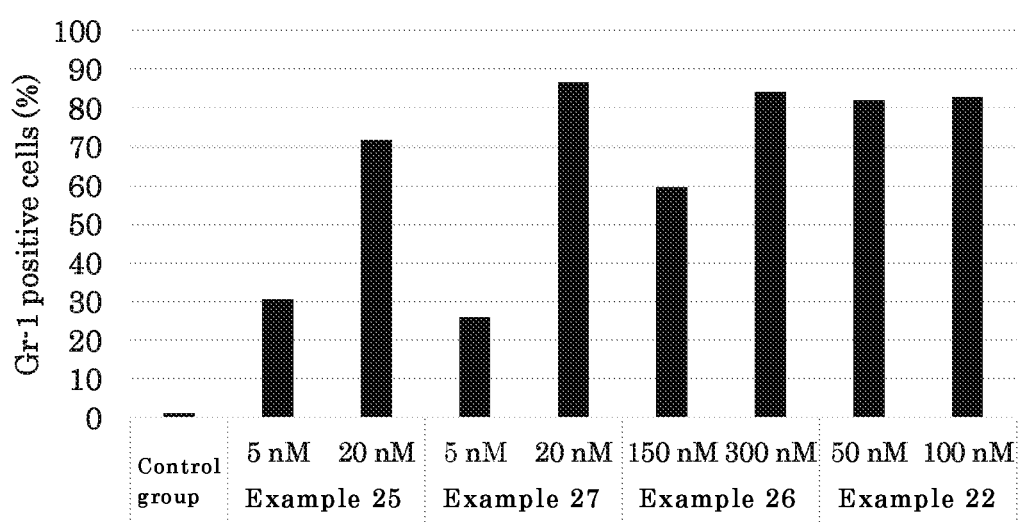
FIG. 10 is a graph showing the rate of the myeloid cell differentiation antigen Gr-1-expressing cells in living cells after treatment with the compound of Example 25, 27, 26 or 22 for 7 days. The vertical axis indicates the percentage of the myeloid cell differentiation antigen Gr-1-expressing cells in living cells, and the horizontal axis indicates each compound and concentration (nM) thereof.
Figure 11:
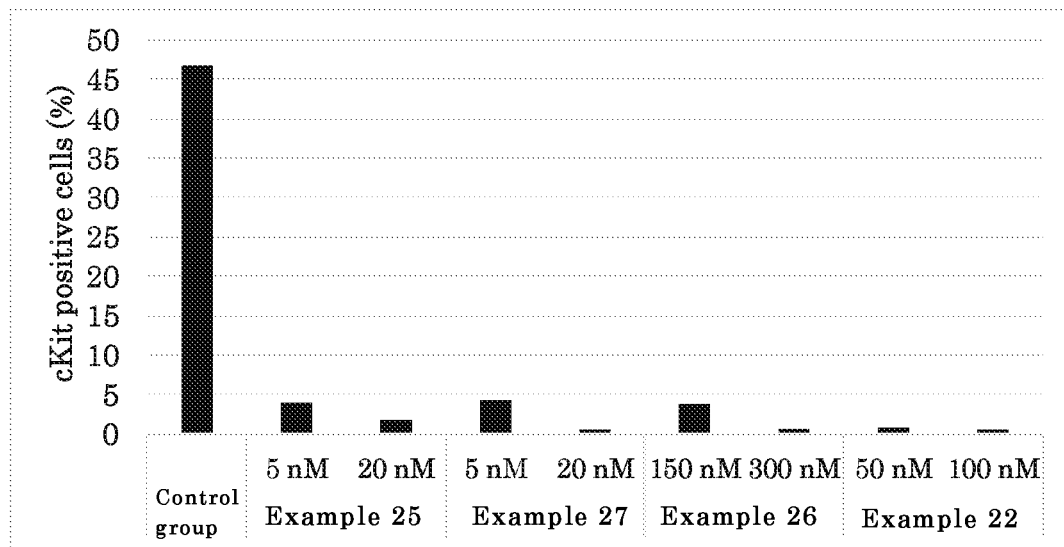
FIG. 11 is a graph showing the rate of the cKit-expressing cells in living cells after treatment with the compound of Example 25, 27, 26 or 22 for 7 days. The vertical axis indicates the percentage of the cKit-expressing cells in living cells, and the horizontal axis indicates each compound and concentration (nM) thereof.

The results in Experimental Example 5 are shown in FIG. 10 and FIG. 11.

FIG. 10 is a graph showing the rate of the myeloid cell differentiation antigen Gr-1-expressing cells in living cells after treatment with the compound of Example 25, 27, 26 or 22 for 7 days. The vertical axis indicates the percentage of the myeloid cell differentiation antigen Gr-1-expressing cells in living cells, and the horizontal axis indicates each compound and concentration (nM) thereof. Since each compound increased the rate of Gr-1-positive cells as compared with the control group, it was demonstrated that these compounds have a differentiation-inducing action of MA9 cells.

FIG. 11 is a graph showing the rate of the cKit-expressing cells in living cells after treatment with the compound of Example 25, 27, 26 or 22 for 7 days. The vertical axis indicates the percentage of the cKit-expressing cells in living cells, and the horizontal axis indicates each compound and concentration (nM) thereof. Each compound reduced the rate of cKit-positive cells as compared with the control group. cKit is involved in the control of survival/differentiation/growth of hematopoietic progenitor cells, and is particularly highly expressed in immature hematopoietic stem progenitor cells in myeloid cells. As is clear from the results of FIG. 10 and FIG. 11, it was demonstrated that these compounds induce the differentiation of MA9 cells and reduce the rate of hematopoietic stem progenitor cells.

[Experimental Example 6] Evaluation of Cell Growth Inhibitory Activity by Combined Use of 2 Drugs RPMI1640 medium supplemented with 10% FBS was used as a culture medium for MOLM-13 cells. The cells were purchased from the American Type Culture Collection (ATCC). The suspension of MOLM-13 cells was prepared with 10% FBS RPMI1640 culture medium so as to be 25000 cells/mL, and seeded (50 g L/well) on a 96-well plate (day 0). The solutions of the compound of Example 25 and any of various other drugs (AraC (Cytarabine), 5Aza (Azacitidine) or Venetoclax) were prepared using a culture solution (the compound of Example 25: common ratio of 4, 5 concentrations from the final concentration of 2500 nM, AraC: common ratio of 2, 3 concentrations from the final concentration of 200 nM, 5Aza: common ratio of 2, 3 concentrations from the final concentration of 10000 nM, Venetoclax: common ratio of 2, 3 concentrations from the final concentration of 156 nM), and each solution was added to each well at 25 μL/well, and the mixture was cultured for additional 7 days. On the day of the drug addition (day 0) and 7 days after the drug addition (day 7), ATP measurement reagent (CellTiter-Glo (registered trademark, Promega Corporation) 2.0 Assay, model number G9242, Promega Corporation) was added to each well at 50 μL/well. After stirring with a plate mixer for 2 minutes, the mixture was allowed to stand at room temperature for 10 minutes or longer. Then, the luminescence level of each well was measured with a plate reader (N=4, model name EnVision 2104 Multilabel Reader, PerkinElmer Co., Ltd.).

The cell growth (%) of the treatment group of the compound of Example 25 alone and the treatment group of the compound of Example 25 and the other drug, when the cell growth of the drug-free group was considered as 100%, from day 0 to day 7, were graphed for each drug using EXCEL 2010 (Microsoft Corporation).

Figure 12:
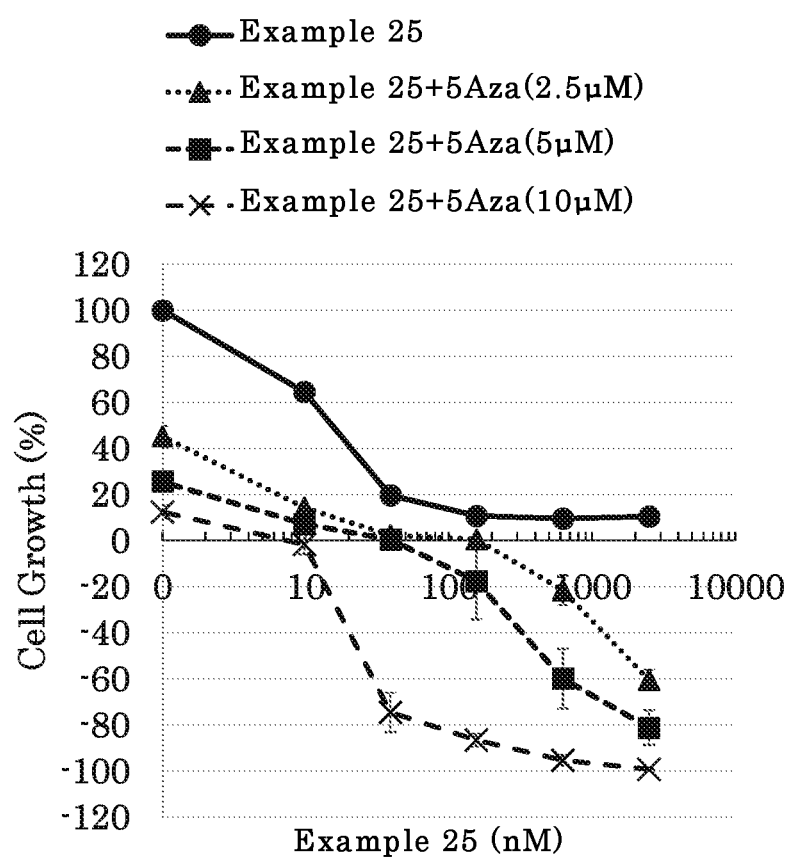
FIG. 12 is a graph showing the effects of the combined effect of the compound of Example 25 and 5Aza on the in-vitro growth of human AML cell line MOLM-13 cells. The vertical axis indicates the cell growth (%), and the horizontal axis indicates the concentration (nM) of the compound of Example 25. The symbol black circle indicates the compound of Example 25 alone, the symbol black triangle indicates the compound of Example 25+5Aza (2.5 μM), the symbol black square indicates the compound of Example 25+5Aza (5 μM), and the symbol x indicates the compound of Example 25+5Aza (10 μM). The error bar indicates SD.

FIG. 12 is a graph showing the effects of the combined effect of the compound of Example 25 and 5Aza on the in-vitro growth of human AML cell line MOLM-13 cells. The vertical axis indicates the cell growth (%), and the horizontal axis indicates the concentration (nM) of the compound of Example 25. The symbol black circle indicates the compound of Example 25 alone, the symbol black triangle indicates the compound of Example 25+5Aza (2.5 μM), the symbol black square indicates the compound of Example 25+5Aza (5 μM), and the symbol x indicates the compound of Example 25+5Aza (10 μM). The error bar indicates SD.

Figure 13:
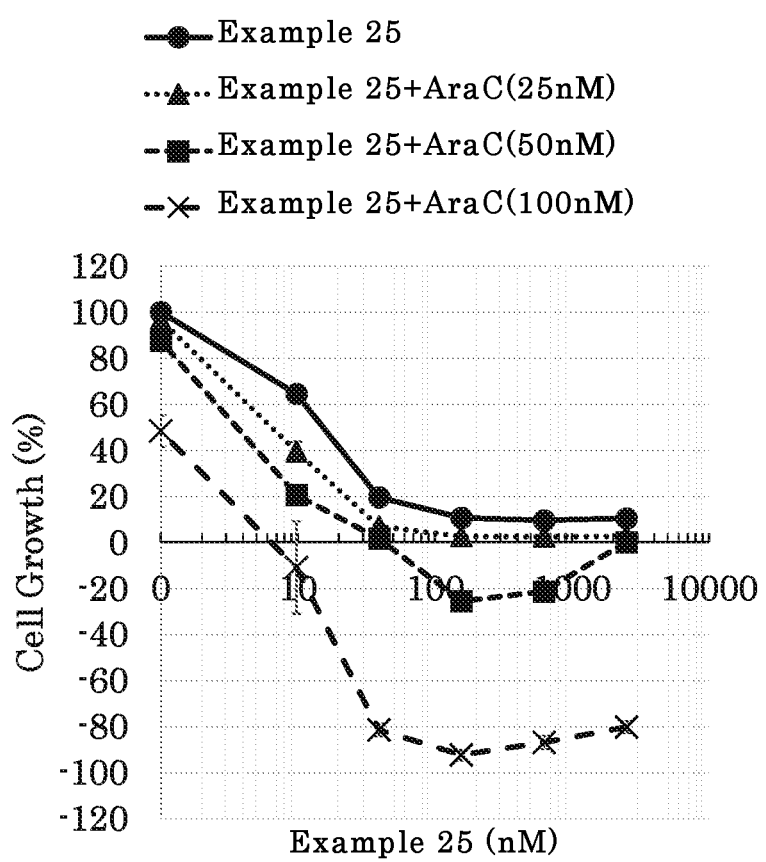
FIG. 13 is a graph showing the effects of the combined effect of the compound of Example 25 and AraC on the in-vitro growth of human AML cell line MOLM-13 cells. The vertical axis indicates the cell growth (%), and the horizontal axis indicates the concentration (nM) of the compound of Example 25. The symbol black circle indicates the compound of Example 25 alone, the symbol black triangle indicates the compound of Example 25+AraC (25 nM), the symbol black square indicates the compound of Example 25+AraC (50 nM), and the symbol x indicates the compound of Example 25+AraC (100 nM). The error bar indicates SD.

FIG. 13 is a graph showing the effects of the combined effect of the compound of Example 25 and AraC on the in-vitro growth of human AML cell line MOLM-13 cells. The vertical axis indicates the cell growth (%), and the horizontal axis indicates the concentration (nM) of the compound of Example 25. The symbol black circle indicates the compound of Example 25 alone, the symbol black triangle indicates the compound of Example 25+AraC (25 nM), the symbol black square indicates the compound of Example 25+AraC (50 nM), and the symbol x indicates the compound of Example 25+AraC (100 nM). The error bar indicates SD.

Figure 14:
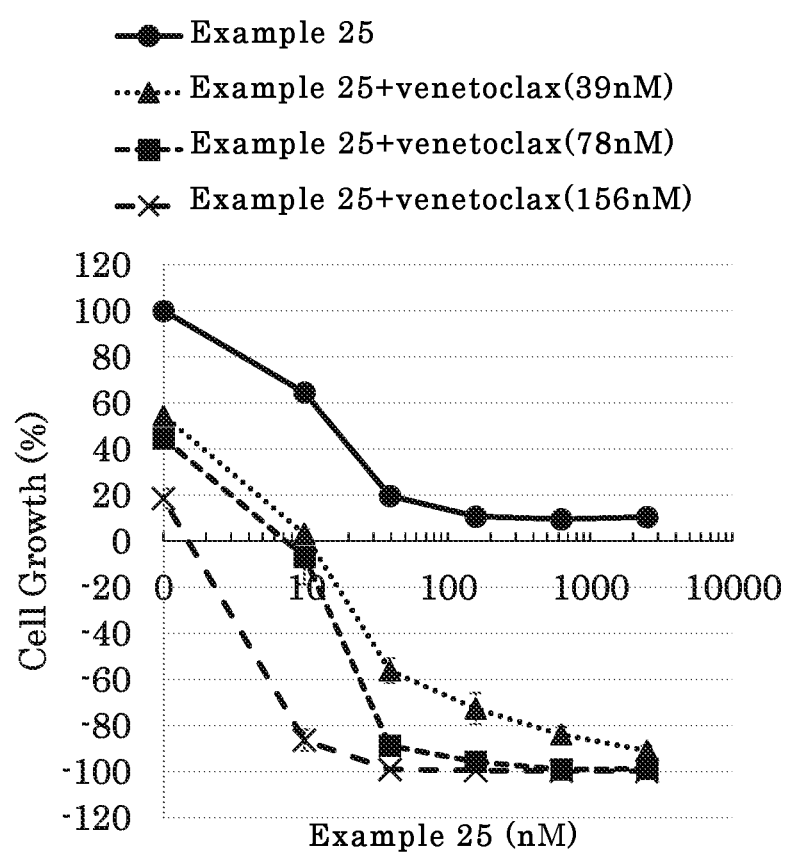
FIG. 14 is a graph showing the effects of the combined effect of the compound of Example 25 and Venetoclax on the in-vitro growth of human AML cell line MOLM-13 cells. The vertical axis indicates the cell growth, and the horizontal axis indicates the concentration (nM) of the compound of Example 25. The symbol black circle indicates the compound of Example 25 alone, the symbol black triangle indicates the compound of Example 25+Venetoclax (39 nM), the symbol black square indicates the compound of Example 25+Venetoclax (78 nM), and the symbol x indicates the compound of Example 25+Venetoclax (156 nM). The error bar indicates SD.

FIG. 14 is a graph showing the effects of the combined effect of the compound of Example 25 and Venetoclax on the in-vitro growth of human AML cell line MOLM-13 cells. The vertical axis indicates the cell growth, and the horizontal axis indicates the concentration (nM) of the compound of Example 25. The symbol black circle indicates the compound of Example 25 alone, the symbol black triangle indicates the compound of Example 25+Venetoclax (39 nM), the symbol black square indicates the compound of Example 25+Venetoclax (78 nM), and the symbol x indicates the compound of Example 25+Venetoclax (156 nM). The error bar indicates SD.

As is clear from these results, it was demonstrated that the combined use of the compound of Example 25 and any of various drugs enhanced the growth inhibitory effect of AML cells.

[Experimental Example 7] Evaluation of Cell Growth Inhibitory Activity

As a culture medium for each cells, RPMI1640 medium supplemented with 10% FBS (MOLM-13 cells (human AML cells)) or IMDM medium supplemented with 10% FBS (K562 cells (human CML cells), MV-4-11 cells (human AML cells)) was used.

The suspension of each cells was prepared with each culture medium so as to be 25000 cells/mL (K562, MOLM-13) or 50000 cells/mL (MV-4-11), and seeded on a 96-well plate (50 g L/well) (day 0). A solution of each concentration (MV-4-11 and MOLM-13: common ratio of 3, 9 concentrations from the final concentration of 1 μM, K562: common ratio of 3, 9 concentrations from the final concentration of 10 μM) of a drug (the compound of Example 131) or a growth medium containing 0.2% DMSO was added to each well at 50 μL/well, and the cells were cultured for additional 7 days.

On the day of the drug addition (day 0) and 7 days after the drug addition (day 7), ATP measurement reagent (CellTiter-Glo (registered trademark, Promega Corporation) 2.0 Assay, model number G9242, Promega Corporation) was added to each well at 100 μL/well. After stirring with a plate mixer for 2 minutes, the mixture was allowed to stand at room temperature for 10 minutes or longer. Then, the luminescence level of each well was measured with a plate reader (N=6, model name EnVision 2104 Multilabel Reader, PerkinElmer Co., Ltd.).

As an index of the cell growth inhibitory activity, the concentration ($GI_{50}$) that suppresses cell growth by 50% was calculated using EXCEL2010 (Microsoft Corporation). The cell growth of the drug-added group from day 0 to day 7 was calculated as T/C %, when the cell growth of the drug-free group (DMSO group) was considered as 100%. The concentration (T/C %=50%) that suppresses cell growth by 50% was calculated as $GI_{50}$ by Sigmoid Emax model. When analysis by the Sigmoid Emax model did not converge (K562 cells), $GI_{50}$ was calculated by linear regression using the cell viabilities in two concentrations sandwiching 50%. The $GI_{50}$ of the compound of Example 131 in this test was 1.97 nM in MV-4-11 cells, 10.1 nM in MOLM-13 cells, and 9110 nM in K562 cells.

INDUSTRIAL APPLICABILITY

Since the compound represented by the general formula (1) or a pharmaceutically acceptable salt thereof of the present invention exhibits an inhibitory action on the interaction between menin and an MLL protein, it can be used for the treatment and/or prophylaxis of diseases dependent on the interaction between menin and an MLL protein. Specifically, the compound represented by the general formula (1) or a pharmaceutically acceptable salt thereof of the present invention is useful for the treatment and/or prophylaxis of cancer or diabetes, preferably myelodysplastic syndrome, blood cancer, prostate cancer, breast cancer, hepatoma or pediatric glioma, more preferably leukemia.

The invention claimed is:

1. A compound which is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol or a pharmaceutically acceptable salt thereof.

2. The compound according to claim 1, which is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol succinate.

3. The compound according to claim 1, which is represented by the formula.

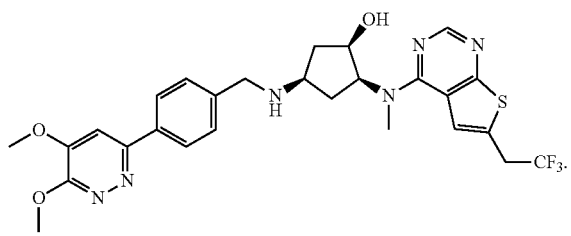 [SMILES: COc1cc(-c2ccc(CN[C@H]3C[C@@H](O)[C@@H](N(C)c4ncnc5sc(CC(F)(F)F)cc45)C3)cc2)nnc1OC]

4. The compound according to claim 1, which is benzenesulfonate, maleate, fumarate, or hydrochloride of (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol.

5. A crystal of the compound according to claim 2, wherein the compound is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol succinate, having at least five peaks at diffraction angles (2θ) selected from 4.66±0.2, 7.02±0.2, 14.10±0.2, 16.68±0.2, 17.46±0.2, 18.68±0.2, 21.34±0.2, 24.52±0.2, 25.54±0.2 and 28.22±0.2 in a powder X-ray diffraction diagram obtained through irradiation with copper Kα line (λ=1.54 angstroms).

6. A crystal of the compound according to claim 4, wherein the compound is (1R,2S,4R)-4-({[4-(5,6-dimethoxypyridazin-3-yl)phenyl]methyl}amino)-2-{methyl[6-(2,2,2-trifluoroethyl)thieno[2,3-d]pyrimidin-4-yl]amino}cyclopentan-1-ol maleate, having at least five peaks at diffraction angles (2θ) selected from 4.64±0.2, 7.02±0.2, 7.46±0.2, 11.14±0.2, 14.04±0.2, 16.76±0.2, 18.54±0.2, 19.76±0.2, 21.26±0.2 and 22.62±0.2 in a powder X-ray diffraction diagram obtained through irradiation with copper Kα line (λ=1.54 angstroms).

7. A pharmaceutical composition comprising the compound according to claim 1, or a pharmaceutically acceptable salt thereof, and a pharmaceutically acceptable carrier.

8. The pharmaceutical composition according to claim 7, wherein the pharmaceutically acceptable salt is selected from the group consisting of succinate, benzenesulfonate, maleate, fumarate, and hydrochloride.

9. A pharmaceutical composition comprising the compound according to claim 2 and a pharmaceutically acceptable carrier.

10. A pharmaceutical composition comprising the crystal according to claim 5 and a pharmaceutically acceptable carrier.

11. The pharmaceutical composition according to claim 9 further comprising one drug selected from the group consisting of Venetoclax, Azacitidine, and Cytarabine.

12. A method for the treatment of acute myelogenous leukemia (AML) or acute lymphocytic leukemia (ALL), the method comprising administering to a subject in need thereof a therapeutically effective amount of the compound according to claim 1, or a pharmaceutically acceptable salt thereof.

13. The method according to claim 12, wherein the pharmaceutically acceptable salt is selected from the group consisting of succinate, benzenesulfonate, maleate, fumarate, and hydrochloride.

14. The method according to claim 12, wherein the pharmaceutically acceptable salt is succinate.

15. The method according to claim 12, wherein the disease is acute lymphocytic leukemia (ALL).

16. The method according to claim 12, wherein the disease is acute myelogenous leukemia (AML).

17. The method according to claim 12, wherein the disease is acute myelogenous leukemia (AML) with NPM1 mutation.

* * * * *